(12) United States Patent
Geurtsen et al.

(10) Patent No.: US 12,233,121 B2
(45) Date of Patent: Feb. 25, 2025

(54) **METHODS OF PRODUCING BIOCONJUGATES OF *E. COLI* O-ANTIGEN POLYSACCHARIDES, COMPOSITIONS THEREOF, AND METHODS OF USE THEREOF**

(71) Applicants: Janssen Pharmaceuticals, Inc., Titusville, NJ (US); GlaxoSmithKline Biologicals S.A., Rixensart (BE)

(72) Inventors: Jeroen Geurtsen, Vleuten (NL); Pieter Jan Burghout, Pijnacker (NL); Eveline Marleen Weerdenburg, Uithoorn (NL); Jan Theunis Poolman, Vogelenzang (NL); Kellen Cristhina Fae, Mainz (DE); Patricia Ibarra Yon, Solothurn (CH); Darren Robert Abbanat, Cornwall, NY (US); Stefan Jochen Kemmler, Zurich (CH); Michael Thomas Kowarik, Zurich (CH); Manuela Mally, Watt (CH); Veronica Gambillara Fonck, Meilen (CH); Martin Edward Braun, Cham (CH); Maria Paula Carranza Sandmeier, Rudolfstetten (CH)

(73) Assignees: Janssen Pharmaceuticals, Inc., Titusville, NJ (US); GlaxoSmith Kline Biologicals S.A., Rixensart (BE)

( * ) Notice: Subject to any disclaimer, the term of this patent is extended or adjusted under 35 U.S.C. 154(b) by 6 days.

(21) Appl. No.: 17/938,454

(22) Filed: Oct. 6, 2022

(65) Prior Publication Data
US 2023/0190926 A1 Jun. 22, 2023

Related U.S. Application Data

(62) Division of application No. 16/822,403, filed on Mar. 18, 2020, now Pat. No. 11,491,220.

(60) Provisional application No. 62/819,762, filed on Mar. 18, 2019.

(51) Int. Cl.
| | | |
|---|---|---|
| *A61K 39/108* | (2006.01) | |
| *A61K 39/00* | (2006.01) | |
| *A61K 39/02* | (2006.01) | |
| *A61K 39/085* | (2006.01) | |
| *A61K 39/09* | (2006.01) | |
| *A61K 39/095* | (2006.01) | |
| *A61K 39/102* | (2006.01) | |
| *A61K 39/104* | (2006.01) | |
| *A61K 47/64* | (2017.01) | |

(52) U.S. Cl.
CPC ........ *A61K 39/104* (2013.01); *A61K 39/0258* (2013.01); *A61K 39/085* (2013.01); *A61K 39/092* (2013.01); *A61K 39/095* (2013.01); *A61K 39/102* (2013.01); *A61K 39/107* (2013.01); *A61K 47/646* (2017.08); *A61K 2039/6037* (2013.01); *A61K 2039/62* (2013.01)

(58) Field of Classification Search
None
See application file for complete search history.

(56) References Cited

U.S. PATENT DOCUMENTS

| | | |
|---|---|---|
| 3,700,612 A | 10/1972 | Fath |
| 5,057,540 A | 10/1991 | Kensil |
| 5,370,872 A | 12/1994 | Cryz |
| 6,331,415 B1 | 12/2001 | Cabilly |
| 6,858,211 B1 | 2/2005 | Szu |
| 9,700,612 B2 | 7/2017 | Kowarik |
| 9,849,169 B2 | 12/2017 | Nagy |
| 10,150,952 B2 | 12/2018 | Haas |
| 10,159,751 B2 | 12/2018 | Labovitiadi |
| 10,206,992 B2 | 2/2019 | Nagy |
| 10,441,647 B2 | 10/2019 | Kowarik |
| 10,525,145 B2 | 1/2020 | Labovitiadi |
| 10,577,592 B2 | 3/2020 | Haas |
| 10,583,185 B2 | 3/2020 | Poolman |
| 10,940,191 B2 | 3/2021 | Nagy |
| 10,940,192 B2 | 3/2021 | Kowarik |
| 11,015,177 B2 | 5/2021 | Haas |
| 11,033,633 B2 | 6/2021 | Labovitiadi |
| 11,446,370 B2 | 9/2022 | Geurtsen |

(Continued)

FOREIGN PATENT DOCUMENTS

| | | |
|---|---|---|
| CN | 1554759 | 12/2004 |
| CN | 101983070 | 3/2011 |

(Continued)

OTHER PUBLICATIONS

Moll et al. Infect. Immun. 53: 257-263, 1986, Abstract.*
Chorro et al. Microbiol. Spectrum 12: 1-15, 2024.*
DeBroy et al., "Comparison of O-Antigen Gene Clusters of All O-Serogroups of *Escherichia coli* and Proposal for Adopting a New Nomenclature for O-Typing," PLoS ONE 11(1): e0147434, Jan. 29, 2016, 13 pages.
Office Action issued Feb. 3, 2023 in corresponding Korean Patent Application No. 10-2019-7011812, 8 pages, with English Translation.

(Continued)

*Primary Examiner* — S. Devi
(74) *Attorney, Agent, or Firm* — Ice Miller LLP

(57) ABSTRACT

Methods of producing bioconjugates of O-antigen polysaccharides covalently linked to a carrier protein using recombinant host cells are provided. The recombinant host cells used in the methods described herein encode a particular oligosaccharyl transferase enzyme depending on the O-antigen polysaccharide bioconjugate to be produced. The oligosaccharyl transferase enzymes can be PglB oligosaccharyl transferase or variants thereof. Also provided are compositions containing the bioconjugates, and methods of using the bioconjugates and compositions described herein to vaccinate a subject against extra-intestinal pathogenic *E. coli*. (ExPEC).

8 Claims, 12 Drawing Sheets

Specification includes a Sequence Listing.

(56) References Cited

U.S. PATENT DOCUMENTS

| | | |
|---|---|---|
| 11,738,076 B2 | 8/2023 | Kowarik |
| 11,844,766 B2 | 12/2023 | Labovitiadi |
| 2002/0177170 A1 | 11/2002 | Luo |
| 2014/0038296 A1 | 2/2014 | Palsson |
| 2015/0238588 A1 | 8/2015 | Kowarik |
| 2018/0002679 A1 | 1/2018 | Haas |
| 2019/0078064 A1 | 3/2019 | Haas |
| 2020/0181586 A1 | 6/2020 | Haas |
| 2020/0316184 A1 | 10/2020 | Geurtsen |
| 2020/0353073 A1 | 11/2020 | Geurtsen |
| 2021/0004617 A1 | 1/2021 | Gouraud |
| 2021/0154286 A1 | 5/2021 | Kowarik |
| 2021/0275681 A1 | 9/2021 | Labovitiadi |
| 2022/0323576 A1 | 10/2022 | Geurtsen |
| 2023/0118878 A1 | 4/2023 | Geurtsen |

FOREIGN PATENT DOCUMENTS

| | | |
|---|---|---|
| CN | 105008539 | 10/2015 |
| CN | 105828839 | 8/2016 |
| EP | 2289911 | 3/2011 |
| EP | 3941516 A1 | 1/2022 |
| GB | 2220211 A | 1/1990 |
| JP | S62500173 | 1/1987 |
| JP | H10500102 A | 1/1998 |
| JP | 2004515450 A | 5/2004 |
| JP | 2007256214 | 10/2007 |
| JP | 2008539743 A | 11/2008 |
| JP | 2011514155 | 5/2011 |
| JP | 4791866 B2 | 10/2011 |
| JP | 2012525376 A | 10/2012 |
| JP | 2017507178 | 3/2017 |
| JP | 2018525423 A | 9/2018 |
| RU | 2189253 C1 | 9/2002 |
| WO | 8601806 A1 | 3/1986 |
| WO | 86001806 | 3/1986 |
| WO | 9303765 A1 | 3/1993 |
| WO | 9522563 | 8/1995 |
| WO | 9522563 A1 | 8/1995 |
| WO | 9523256 | 8/1995 |
| WO | 2001078787 A2 | 10/2001 |
| WO | 2003074679 | 9/2003 |
| WO | 2003074687 A1 | 9/2003 |
| WO | 2004078209 A1 | 9/2004 |
| WO | 2006119987 A2 | 11/2006 |
| WO | 2007109812 A2 | 9/2007 |
| WO | 2007109813 A1 | 9/2007 |
| WO | 2009036379 | 3/2009 |
| WO | 2009089396 A2 | 7/2009 |
| WO | 2009104074 | 8/2009 |
| WO | 2009104074 A2 | 8/2009 |
| WO | 2010105256 | 9/2010 |
| WO | 2010125565 A2 | 11/2010 |
| WO | 2011062615 | 5/2011 |
| WO | 2012009568 | 1/2012 |
| WO | 2012078482 A1 | 6/2012 |
| WO | 2013034664 A1 | 3/2013 |
| WO | 2014037585 A1 | 3/2014 |
| WO | 2014057109 A1 | 4/2014 |
| WO | 2014072405 | 5/2014 |
| WO | 2014102265 A1 | 7/2014 |
| WO | 2014111516 A1 | 7/2014 |
| WO | 2015052344 | 4/2015 |
| WO | 2015068129 | 5/2015 |
| WO | 2015117711 A1 | 8/2015 |
| WO | 2015124769 | 8/2015 |
| WO | 2015124769 A1 | 8/2015 |
| WO | 2016107818 A1 | 7/2016 |
| WO | 2016107819 A1 | 7/2016 |
| WO | 2017035181 A1 | 3/2017 |
| WO | 2018077853 A1 | 5/2018 |
| WO | 2019016187 A1 | 1/2019 |
| WO | 2020191082 | 9/2020 |
| WO | 2020191088 | 9/2020 |

OTHER PUBLICATIONS

DebRoy C, Fratamico PM, Yan X, Baranzoni G, Liu Y, et al. (2016) Correction: Comparison of O-Antigen Gene Clusters of All O-Serogroups of Escherichia coli and Proposal for Adopting a New Nomenclature for O-Typing. PLoS ONE 11(4): e0154551, Published: Apr. 27, 2016, 5 pages.

Sela-Culang et al. (Frontiers in Immunology, 2013 vol. 4, article 302, pp. 1-13).

Van Den Dobbelsteen Germie P J M et al, "Immunogenicity and safety of a tetravalent E. coli O-antigen bioconjugate vaccine in animal models", Vaccine, Elsevier, Amsterdam, NL, (20160706), vol. 34, No. 35, doi:10.1016/J.VACCINE.2016.06.067, ISSN 0264-410X, pp. 4152-4160, XP029644969.

Ihssen Julian et al., "Production of glycoprotein vaccines in Escherichia coli", Microbial Cell Factories,, (Aug. 11, 2010), vol. 9, No. 1, doi:10.1186/1475-2859-9-61, ISSN 1475-2859, p. 61, XP021077209.

Roland Stenutz et al, "The structures of Escherichia coli O-polysaccharide antigens", FEMS Microbiology Reviews, Elsevier, Amsterdam; NL, vol. 30, doi:10.1111/J.1574-6976.2006.00016.X, ISSN 0168-6445, (Jan. 1, 2006), pp. 382-403, (Feb. 9, 2006), XP007921666.

ClinicalTrials.gov archive, "History of Changes for Study: NCT03819049, A Study of Three Different Doses of VAC52416 (ExPEC10V) in Adults Aged 60 to 85 Years in Stable Health", https://clinicaltrials.gov/ct2/history/NCT03819049, Aug. 6, 2019 (v6), 6 pages.

Jansson et al., "Sturctural Studies of the O-Antigen Polysaccharide of Escherichia coli O4", Carbohydrate Research, 134 (1984) 283-291.

S. Muller-Loennies, et al., "Structural Analysis of Oligosaccharides from Lipopolysaccharide (LPS) of Escherichia coli K12 Strain W3100 Reveals a Link between Inner and Outer Core LPS Biosynthesis", The Journal of Biological Chemistry, Sep. 5, 2003, vol. 278, No. 36, pp. 34090-34101.

Saade, Elie, et al., "Characerization of Escherichia coli isolates potentially covered by ExPEC4V and ExPEC10V, that were collected from post-transrectal ultrasound-guided prostate needle biopsy," Vasccine, Elsevier, Amsterdam, NL, vol. 38, No. 33, Jun. 16, 2020 pp. 5100-5104.

Savita Jadhav et al, "Virulence Characteristics and Genetic Affinities of Multiple Drug Resistant Uropathogenic Escherichia coli from a Semi Urban Locality in India", PLOS ONE, (Jan. 1, 2011), vol. 6, No. 3, doi:10.1371/journal.pone.0018063, ISSN 1932-6203, p. e18063, XP055056608.

Schito et al., "The ARESC study: an international survey on the antimicrobial resistance of pathogens involved in uncomplicated urinary tract infections", Elsevier, International Journal of Antimicrobial Agents 34, pp. 407-413, 2009.

Seidl et al., "Tungsten-Induced Denaturation and Aggregation of Epoetin Alfa During Primary Packaging as a Cause of Immunogenicity," Pharm. Res., vol. 29, pp. 1454-1467 (2012).

Simone Cagnacci, et al., "European Emergence of Ciprofloxacin-Resistant Escherichia coli Clonal Groups O25:H4-ST131 and O15:K52:H1 Causing Community-Acquired Uncomplicated Cystitis", in the Journal of Clinical Microbiology, Aug. 2008, vol. 46, No. 8, pp. 2605-2612 (8 pgs.).

Stenutz Roland et al, "The structures of Escherichia coli O-polysaccharide antigens", FEMS Microbiology Reviews, (May 2006), vol. 30, No. 3, ISSN 0168-6445, pp. 382-403, XP007921666.

Stevenson et al., "Structure of the O antigen of Escherichia coli K-12 and the sequence of its rfb gene cluster," J. Bacteriol., vol. 176, No. 13, pp. 4144-4156 (1994).

Stoute et al., "A Preliminary Evaluation of a Recombinant Circumsporozoite Protein Vaccine Against Plasmodium Falciparum Malaria," New England Journal of Medicine, vol. 336, pp. 86-91 (1997).

Szijarto et al., "Bactericidal Monoclonal Antibodies Specific to the Lipopolysaccharide 0 Antigen from Multidrug-Resistant Escherichia coli Clone ST131-025b:H4 Elicit Protection in Mice," Antimicrobial Agents and Chemotherapy, Jun. 2015, vol. 59, No. 6, pp. 3109-3116, XP009187151.

(56) References Cited

OTHER PUBLICATIONS

Szijarto et al., "Diagnostic Potential of Monoclonal Antibodies Specific to the Unique O-Antigen of Multidrug-Resistant Epidemic *Escherichia coli* Clone ST131-025b:H4," Clinical and Vaccine Immunology, Jul. 2014, vol. 21, No. 7, p. 930-939.

Terai et al., "*Escherichia coli* Virulence Factors and Serotypes in Acute Bacterial Prostatitis," Int. Journal of Urology, vol. 4, No. 3, pp. 289-294 (1997).

Vajdos et al., "Comprehensive Functional Maps of the Antigen-binding Site of an Anti-ErbB2 Antibody Obtained with Shotgun Scanning Mutagenesis," J Mol. Biol. 2002, vol. 320(2), pp. 415-428.

Valéria Szijártó et al, "The rapidly emerging ESBL-producing *Escherichia coli*O25-ST131 clone carries LPS core synthesis genes of the K-12 type", FEMS Microbiology Letters, (Jul. 1, 2012), vol. 332, No. 2, doi:10.1111/j.1574-6968.2012.02585.x, ISSN 0378-1097, pp. 131-136, XP055056565.

Van Den Dobbelsteen et al., "Immunogenicity and safety of tetravalent *Escherichia coli* O-antigen bioconjugate vaccine In animal models," Vaccine, vol. 34, No. 35, pp. 4152-4160 (2016).

Wacker et al., "N-linked glycosylation in Campylobacter jejuni and its functional transfer into *Escherichia coli*," Science, vol. 298, No. 5599, pp. 1790-1793 (2002).

Wacker, M., et al., "Substrate specificity of bacterial oliogsaccharyltransferase suggests a common transfer mechanism for the bacterial and eukaryotic systems," PNAS, vol. 103, No. 18, pp. 7088-7093, May 2, 2006.

Written Opinion dated Dec. 21, 2018 in Int'l Application No. PCT/EP2017/077123, 8 pages.

Written Opinion issued Jun. 12, 2020 in PCT/US2020/023404, 6 pages.

Written opinion of the Int'l Searching Authority dated Jan. 24, 2018 in Int'l Application No. PCT/EP2017/077123, 6 pages.

Written Opinion of the International Preliminary Examining Authority dated Sep. 11, 2018 in PCT/EP2017/077123, 8 pages.

Written Opinion of the International Searching Authority dated Mar. 14, 2014, in connection with corresponding International Application No. PCT/EP2014/050895. 8 pages.

Yakubke et al., "Amino acids, peptides, proteins", MTR Publishers, 1985, 456 pages.

Int'l Search Report issued Jan. 24, 2018 in Int'l Application No. PCT/EP2017/077123, 6 pages.

International Search Report and Written Opinion for App. No. PCT/US2020/023415, dated Jun. 12, 2020, 21 pages.

International Search Report and Written Opinion issued in International Application No. PCT/EP2014/078709 dated May 12, 2015, 4 pages.

International Search Report issued in International Application No. PCT/EP2014/050895 dated Mar. 14, 2014. 2 pages.

International Search Report issued Jun. 12, 2020 in PCT/US2020/023404, 5 pages.

J. Wibbenmeyer et al., "Cloning, expression, and characterization of the Fab fragment of the anti-lysozyme antibody HyHEL-5", Biochimica et Biophysica Acta, 1999, vol. 1430, No. 2, pp. 191-202.

Jann et al., "Structural Comparison of the O6 Specific Polysaccharides From *Escherichia coli* O6:K2:H1, *Escherichia coli* O6:K13:H1, and *Escherichia coli* O6:K54:H10," Carbohydrate Research, vol. 263, No. 2, pp. 217-225 (1994).

Jansson et al., "Structural studies of the *Escherichia coli* O-antigen 6," Carbohydrate Research, vol. 131, No. 2, pp. 277-283 (1984).

Jansson et al., "Structural studies of the O-specific side-chains of the *Escherichia coli* O2 lipopolysaccharide," Carbohydrate Res., vol. 161, pp. 273-279 (1987).

Jeffrey Skolnick, et al., "From genes to protein structure and function: novel applications of computational approaches in the genomic era", in Tibtech, vol. 18, Jan. 2000, pp. 34-39 (6 pgs.).

Jiang et al., "Tungsten-Induced Protein Aggregation: Solution Behavior," Wiley InterScience, vol. 98, No. 12, pp. 1695-4710 (2009).

Johnson et al., "*Escherichia coli* sequence type ST131 as an emerging fluoroquinolone-resistant uropathogen among renal transplant recipients," Antimicrob Agents Chemother. vol. 54, No. 1, pp. 546-550 (2010).

Johnson et al., Extraintestinal Pathogenic *Escherichi coli*: "The other bad *E coli*", J Lab Clin Med., 139(3), pp. 155-162, 2002.

Josef Prassler, et al., "In vitro affinity maturation of HuCAL antibodies: complementarity determining region exchange and RapMat technology", in Immunotherapy, vol. 1, No. 4, 2009, pp. 571-583 (13 pgs.).

Kenne et al., "Structural studies of the *Escherichia coli* O-antigen 25," Carbohydrate Research, vol. 122, No. 2, pp. 249-256 (1983).

Kim et al., "Efficiency of a pneumococal Opsonophagocytic Killing Assay Improved by Multiplexing and by Colloring Colonies", Clinical and Dianostic laboratory Immunology, pp. 616-621, Jul. 2003.

Kohler et al., "What defines extraintestinal pathogenic *Escherichia coli*", Elsevier, International journal of Medical Microbiology 301, pp. 642-647, 2011.

Laurentin et al., "A Microtiter Modification of the anthrone-sulfuric acid colorimetric assay for glucose-based carbohydrates", Analytical Biochemistry, 315, pp. 143-145, 2003.

Lazar et al. (Mol. Cell. Biol., 8:1247-1252, 1988).

Lipsitch, "Bacterial vaccines and Serotype Replacement: Lessons from Haemophilus Influenzae and Prospects for *Streptococcus pneumonia*", Emerging Infectious Diseases, vol. 5, No. 3, May/Jun. 1999, 10 pages.

Lukac et al., "Toxoid of Pseudomonas aeruginosa exotoxin A generated by deletion of an active-site residue," Infect Immun, vol. 56, No. 12, pp. 3095-3098 (1988).

Marie-Paule Lefranc, et al., "IMGT, the international ImMunoGeneTics database", in Nucleic Acids Research, vol. 27, No. 1, 1999, pp. 209-212 (4 pgs.).

Mario F Feldman et al, "Engineering N-linked protein glycosylation with diverse O antigen lipopolysaccharide structures in *Escherichia coli*", Proceedings of the National Academy of Sciences, vol. 102, No. 8, pp. 3016-3021, (Feb. 9, 2005).

Molina-Lopez et al., "Drug resistance, serotypes, and phylogenetic groups among uropathogenic *Escherichia coli* including O25-ST131 in Mexico City," J Infect Dev Ctries, vol. 5, No. 12, pp. 840-849 (2011).

Mora A et al, "Emergence of clonal groups O1:HNM-D-ST59, O15:H1-D-ST393, O20:H34/HNM-D-ST354, O25b:H4-B2-ST131 and ONT:H21,42-B1-ST101 among CTX-M-14-producing *Escherichia coli* clinical isolates in Galicia, northwest Spain", International Journal of Antimicrobial Agents, Elsevier Science, Amsterdam, NL, vol. 37, No. 1, ISSN 0924-8579, (Jan. 1, 2011), pp. 16-21, (Dec. 13, 2010), XP027557799.

Myung-Hoon Lee, et al., "Expression and functional reconstitution of a recombinant antibody (Fab') specific for human apolipoprotein B-100", Journal of Biotechnology, 2003, vol. 101, pp. 189-198.

N. Woodford et al., "Multiresistant Gram-negative bacteria: the role of high-risk clones in the dissemination of antibiotic resistance", FEMS Microbiol Rev, 2011, vol. 35, No. 5, pp. 736-755.

Nadine C. Chien, et al., "Significant structural and functional change of an antigen-binding site by a distant amino acid substitution: Proposal of a structural mechanism", in Proc. Natl. Acad. Sci., vol. 86, Jul. 1989, pp. 5532-5536 (5 pgs.).

Neil S. Greenspan, et al., "Defining epitopes: It's not as easy as it seems", in Nature Biotechnology, vol. 17, Oct. 1999, pp. 936-937 (2 pgs.).

Notification Concerning Transmittal of International Preliminary Report on Patentability dated Aug. 18, 2016, in connection with corresponding international Application No. PCT/EP2014/078709 (7 pgs.).

D. Clermont et al, "Rapid detection of the O25b-ST131 clone of *Escherichia coli* encompassing the CTX-M-15-producing strains", Journal of Antimicrobial Chemotherapy, (Aug. 1, 2009), vol. 64, No. 2, doi:10.1093/jac/dkp194, ISSN 0305-7453, pp. 274-277, XP055056568.

Office Action dated Mar. 29, 2018 in Russian Patent Application No. 2015134413, with English translation. 12 pages.

(56) References Cited

OTHER PUBLICATIONS

Office Action dated Oct. 17, 2018 in corresponding Russian Application No. 2015134413/10(052839), 17 pages Including English-language translation.
Office Action issued Apr. 22, 2021 in corresponding Russian Patent Application No. 2019144146/10(085375), 9 pages, with English Translation.
Office Action issued on Aug. 23, 2018 in corresponding Russian Application No. 2016135962, 17 pages including English-language translation.
Office Action issued on Aug. 28, 2018 in corresponding Japanese Application No. 2015-553093; 12 pages including English-language translation.
Office Action issued on Oct. 4, 2018 in corresponding Japanese Application No. 2016-550556; 9 pages including English-language translation.
Pablo Umana, et al., "Engineeredglycoforms of an antineuroblastoma IgG1 with optimized antibody-dependent cellular cyto9toxic activity", in Nature Biotechnology, vol. 17, Feb. 1999, pp. 176-180 (5 pgs.).
Phan et al., "The serum resistome of a globally disseminated multidrug resistant uropathogenic *Escherichia coil* clone," PLOS Genetics, vol. 9, No. 10, pp. 1-18 (2013).
Pinayev et al., "The Cell Cultures", Information Gazette, 2010, Issue 26, St. Petersburg, 61 pages.
Pitout et al., "Extraintestinal Pathogenic *Escherichia coli*: An Update on Antimicrobial Resistance, Laboratory Diagnosis and Treatment," Expert Rev. Anti. Infect. Then, vol. 10, No. 10, pp. 1165-1176 (2012).
Poolman et al., "Extraintestinal Pathogenic *Escherichia coli*, a Common Human Pathogen: Challenges for Vaccine Development and Progress in the Field," Journal of Infectious Diseases, vol. 213, pp. 6-13 (2016).
Poolman, J.T., et al., "The history of pneumococcal conjugate vaccines development: dose selection," Expert Reviews Vaccines, vol. 12 (12), pp. 1379-1394 (2013).
Reschedko, G.K. et al, "*Escherichia coli* as a Nosocomial Pathogen in ICUs", Clinical microbiology and antimicrobial chemotherapy, 2011, vol. 13, No. 4, pp. 314-321.
Response to Austrian Office Action dated Mar. 12, 2019 in Austrian Patent Application No. 2018204437. 6 pages.
Royt A et al., "Hypervariable sequences of antigen-recognition centers enable binding of various antigens by antibodies", Immunology, Moscow, "Mir" Publishers 2000, 4 pages including English-language translation, abstract only.
Russian Office Action dated Apr. 24, 2018, in connection with corresponding RU Application No. 2016135962/10 (056446) (5 pgs.).
Russian Office Action dated Dec. 27, 2017, in connection with corresponding RU Application No. 2015134413/10 (052839) (18 pgs., including English translation).
Russo et al., "A killed, genetically engineered derivative of a wild-type extraintestinal pathogenic *E coli* strain is a caccine candidate", Elsevier, Vaccine 25, pp. 3859-3870, 2007.
Russo et al., "Medical and Exonomic impact of extraintestinal infections due to *Escherichia coli*: focus on an Increasingly important endemic problem", Elsevier, Microbes and Infection 5, pp. 449-456, 2003.
"Typhoid Vi Polysaccharide Vaccine Typhim VI," Sanofi Pasteur Inc., vol. 3., pp. 1-26 (Mar. 2014).
A. Cross et al, "Safety and Immunogenicity of a Polyvalent *Escherichia coli* Vaccine In Human Volunteers", Journal of Infectious Diseases. JID, Chicago, IL., (Oct. 1, 1994), vol. 170, No. 4, doi:10.1093/infdis/170.4.834, ISSN 0022-1899, pp. 834-840, XP055311603.
Abbanat et al., Poster presented at ASM's Interscience Conference of Antimicrobial Agents and Chemotherapy (ICAAC), Jun. 16-20, 2016, Boston, 1 page.
Amor et al., "Distribution of Core Oligosaccharide Types in Lipopolysaccharides from *Escherichia coli*," Infection and Immunity, Mar. 2000, p. 1116-1124.

Angela M. Giusti, et al., "Somatic diversification of S107 from an antiphosphocholine to an anti-DNA autoantibody is due to a single base change in its heavy chain variable region", in Proc. Natl. Acad. Sci., vol. 84, May 1987, pp. 2926-2930 (5 pgs.).
Angela Novais, et al., "Contribution of IncFII and Broad-Host IncA/C and IncN Plasmids to the Local Expansion and Diversification of Phylogroup B2 *Escherichia coli* ST131 Clones Carrying blaCTX-M-15 and qnrS1 Genes", in Antimicrobial Agents and Chemotherapy, vol. 56, No. 5, May 2012, pp. 2763-2766 (4 pgs.).
Arturo Casadevall, et al., "Immunoglobulin isotype influences affinity and specificity", in PNAS, vol. 109, No. 31, Jul. 31, 2012, pp. 12272-12273 (2 pgs.).
B. A. Rogers et al, "*Escherichia coli* O25b-ST131: a pandemic, multiresistant, community-associated strain", Journal of Antimicrobial Chemotherapy, (Jan. 1, 2011), vol. 66, No. 1, doi:10.1093/jac/dkq415, ISSN 0305-7453, pp. 1-14, XP055056619.
B.R. Brodeur et al., "Mouse-Human Myeloma Partners for the Production of Heterohybridomas", Monoclonal Antibody Production Techniques and Applications, Marcel Dekker, Inc., 1987, pp. 51-63.
Banerjee et al., "A new clone sweeps clean: the enigmatic emergence of *Escherichia coli* sequence type 131," Antimicrob Agents Chemother. vol. 58, No. 9, pp. 4997-5004 (2014).
Blanco et al., "Virulence factors and 0 groups of *Escherichia coli* isolates from patients with acute pyelonephritis, cystitis and asymptomatic bacteriuria," Eur. J. Epidemiol., vol. 12, No. 2, pp. 191-198 (1996).
Blanco et al., "Molecular epidemiology of *Escherichia coli* producing extended-spectrum {beta}-lactamases in Lugo (Spain): dissemination of clone O25b:H4-ST131 producing CTX-M-15," J. Antimicrob. Chemother., vol. 63, pp. 1135-1141 (2009).
Bowie et al. (Science, 1990, 247:1306-1310).
Brown et al., "Tolerance to Single, but Not Multiple, Amino Acid Replacements in Antibody Vh CDR2," The Journal of Immunology, 1996, 156: 3285-3291.
Burgess et al. (J. Cell Biol. 111:2129-2138, 1990).
Chris Galanos, et al., "Galactosamine-induced sensitization to the lethal effects of endotoxin", in Proc. Natl. Acad. Sci., vol. 76, No. 11, Nov. 1979, pp. 599-5943 (5 pgs.).
Claudia Sheedy, et al., "Isolation and affinity maturation of hapten-specific antibodies", in Biotechnolgy Advances 25, 2007, pp. 333-352 (20 pgs.).
Clermont et al., "The CTX-M-15-producing *Escherichia coli* diffusing clone belongs to a highly virulent B2 phylogenetic subgroup," J. Antimicrob. Chemother., vol. 61, No. 5, pp. 1024-1028 (2008).
Cristina Caldas, et al., "Humanization of the anti-CD18 antibody 6.7: an unexpected effect of a framework residue in binding to antigen", in Molecular Immunology, vol. 39, 2003, pp. 941-952 (12 pgs.).
Cryz et al., "Synthesis and Characterization of *Escherichia coli* O18 O-Polysaccharide Conjugate Vaccines," Infection and Immunity, Feb. 1990, p. 373-377.
Cryz S J et al, "Synthesis and characterization of a polyvalent *Escherichia coli* O-polysaccharide-toxin A conjugate vaccine", Vaccine, Elsevier Ltd, GB, (Jan. 1, 1995), vol. 13, No. 5, doi:10.1016/0264-410X(94)00009-C, ISSN 0264-410X, pp. 449-453, XP004057719.
D. Kozbor et al., "A Human Hybrid Myeloma for Production of Human Monoclonal Antibodies", The Journal of Immunology, Dec. 1984, vol. 133, No. 6, pp. 3001-3005.
Datsenko et al., "One-step inactivation of chromosomal genes in *Escherichia coli* K-12 using PCR products," PNAS, vol. 97, No. 12, pp. 6640-6645 (2000).
Debroy et al., "Detection of O antigens in *Escherichia coli*," Animal Health Research Reviews, vol. 12, No. 2, pp. 169-185 (2011).
Denka Seiken Co. Ltd.(Catalogue), Bacterial Antisera "Seiken", [Denka Seiken Co., Ltd, MSDS No. 200000-01, Feb. 16, 2010. 13 pages.
Duda et al., "The lipopolysaccharide of the mastitis isolate *Escherichia coli* strain 1303 comprises a novel O-antigen and the rare K-12 core type," Microbiology (2011), 157, 1750-1760, doi: 10.1099/mic.0.046912-0.

(56) References Cited

OTHER PUBLICATIONS

European Office Action dated Mar. 7, 2017, in connection with corresponding EP Application No. 14703783.2 (7 pgs.).
European Search Report issued in International Application No. 13151627.0 dated Mar. 28, 2013. 7 pages.
Extended European Search Report dated Jul. 16, 2014, in connection with corresponding EP Application No. 14154158.1 (5 pgs.).
Extended European Search Report dated Mar. 14, 2017, including the European Search Report and the European Search Opinion, in connection with corresponding EP Application No. 16201732.1 (10 pgs.).
Extended Search Report dated Sep. 10, 2021 in EP Application No. 21154782.3, 6 pages.
Extended Search Report dated Apr. 12, 2017 in EP Application No. 16195256.9, 8 pages.
Foxman, "Epidemiology of Urinary Tract Infections: Incidence, morbidity, and Economic Costs", The American Journal of Medicine, vol. 113(1A), 5S-13S, Jul. 2002.
Fratamico et al., "*Escherichia coli* serogroup O2 and O28ac O-antigen gene cluster sequences and detection of pathogenic *Escherichia coil* O2 and O28ac by PCR," Canadian Journal of Microbiology, vol. 56, No. 4, pp. 308-316 (2010).
Frenck, et al., "Safety and Immunogenicity of a vaccine for extraintestinal pathogenic *Escherichia coli* (Estella): a phase 2 randomised controlled trial," Lancet Infect. Dis. vol. 1, No. 6, pp. 631-640 (2019).
Fundin et al., "NMR analysis of the O-antigen polysaccharide from *Escherichia coli* strain F171," Magnetic Resonance In Chemistry, vol. 41, No. 3, pp. 202-205 (2003).
G. Kohler et al., "Continuous cultures of fused cells secreting antibody of predefined specificity", Nature, Aug. 7, 1975, vol. 256, pp. 495-497.
G. Peirano, et al., "Molecular characteristics of extended-spectrum B-lactamase-producing *Escherichia coli* from the Chicago area: high prevalence of ST131 producing CTX-M-15 in community hospitals", International Journal of Antimicrobial Agents, 2010, vol. 36, pp. 19-23.

G. Peirano, et al., "Molecular epidemiology of *Escherichia coli* producing CTX-M beta-lactamases: the worldwide emergence of clone ST131 O25:H4", in International Journal of Antimicrobial Agents, vol. 35, 2010, pp. 316-321 (7 pgs.).
Gabor Nagy et al., "Lipopolysaccharide: a tool and target in enterobacterial vaccine development", in Biological Chemistry, vol. 389, No. 5, Jan. 2008, 8 pgs. (XP055349068).
Gisele Peirano, et al., "Characteristics of *Escherichia coli* Sequence Type 131 Isolates That Produce Extended-Spectrum B-Lactamases: Global Distribution of the H30-Rx Sublineage", in Antimicrobial Agents and Chemotherapy, vol. 58, No. 7, Jul. 2014, pp. 3762-3767 (6 pgs.).
Glover et al., "Chemoenzymatic synthesis of Glycopeptides with PglB, a bacterial oligosaccharyl transferase from Campylobacter jejuni," Chemistry and Biology, Current Biology, vol. 12, No. 12, pp. 1311-1316 (2005).
Helen Miajlovic, et al., "Response of Extraintestinal Pathogenic *Escherichia coli* to Human Serum Reveals a Protective Role for Rcs-Regulated Exopolysaccharide", in Infection and Immunity, vol. 82, No. 1, Jan. 2014, pp. 298-305 (8 pgs.).
Ho et al., Preclinical Laboratory Evaluation of a Bivalent *Staphylococcus aureus* Saccharide-Exotoxin A Protein Conjugate Vaccine, Human vaccines, 2:3, pp. 89-98, May/Jun. 2006.
Huttner et al., "Safety, immunogenicity, and preliminary clinical efficacy of a vaccine against extraintestinal pathogenic *Escherichia coli* in women with a history of recurrent urinary tract infection: a randomised, single-blind, placebo-controlled phase 1b trial", Lancet Infect Dis., 2017, vol. 17, No. 5, pp. 528-537.
Ihssen et al., "Production of glycoprotein vaccines in *Escherichia coli*," Microbial Cell Factories, vol. 9, No. 61, pp. 1-13 (2010).
Int'l Preminary Report on Patentability dated Feb. 14, 2019 in Int'l Application No. PCT/EP2017/077123, 16 pages.
Int'l Search Report and Written Opinion dated Jul. 20, 2017 in Int'l Application No. PCT/US2016/048278, 9 pages.
Int'l Search Report and Written Opinion issued Jun. 15, 2015 in Int'l Application No. PCT/EP2015/053739, 10 pages.
Int'l Search Report and Written Opinion issued Oct. 27, 2016 in Int'l Application No. PCT/US2016/048278, 16 pages.

\* cited by examiner

Gel 2:

| Lane | Sample Name | gtrS | Amount loaded (µl) |
|---|---|---|---|
| 1 | Marker | NA | 5.0 |
| 2 | stGVXN4994 | Positive | 4.0 |
| 3 | OC24788 | Negative | 4.2 |
| 4 | OC24794 | Positive | 3.9 |
| 5 | OC9487 neg. control | Reduced | 4.1 |
| 6 | Marker | NA | 5.0 |

Gel 1:

| Lane | Sample Name | gtrS | Amount loaded (µl) |
|---|---|---|---|
| 1 | Marker | NA | 5.0 |
| 2 | A2625 | Negative | 4.0 |
| 3 | Y1382 | Positive | 3.8 |
| 4 | stGVXN4988 | Negative | 4.2 |
| 5 | E551 | Positive | 3.9 |
| 6 | OC24784 | Negative | 4.5 |
| 7 | OC24334 | Positive | 4.1 |
| 8 | OC24787 | Negative | 4.2 |
| 9 | stGVXN4983 | Positive | 3.9 |
| 10 | OC9487 neg. control | NA | 4.1 |
| 11 | Marker | NA | 5.0 |
| 12 | EMPTY | - | - |

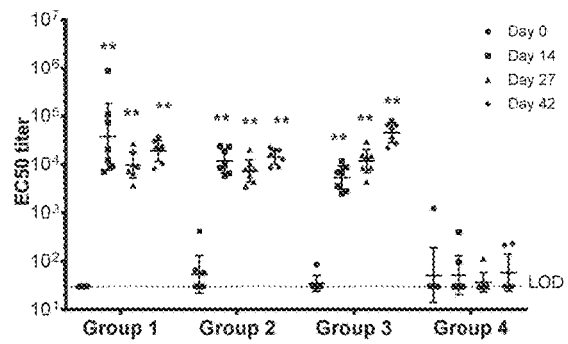
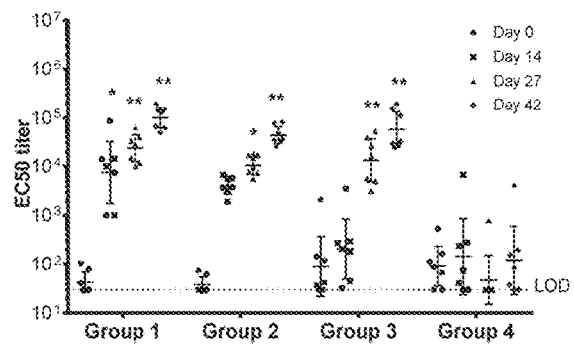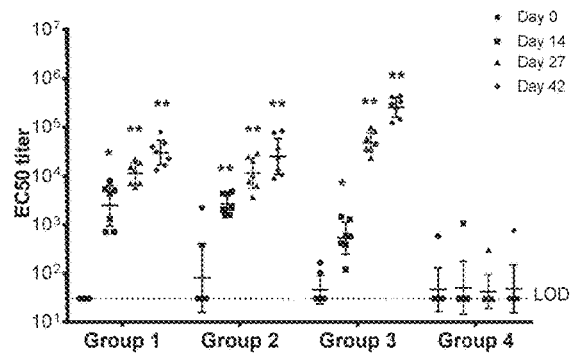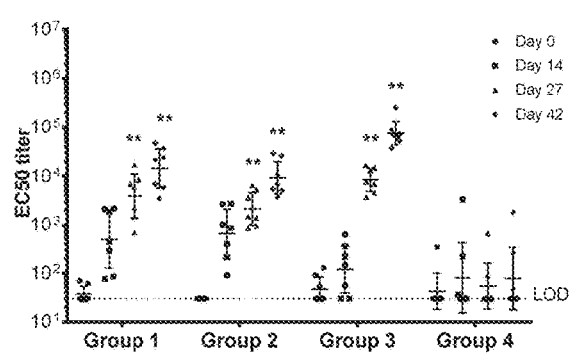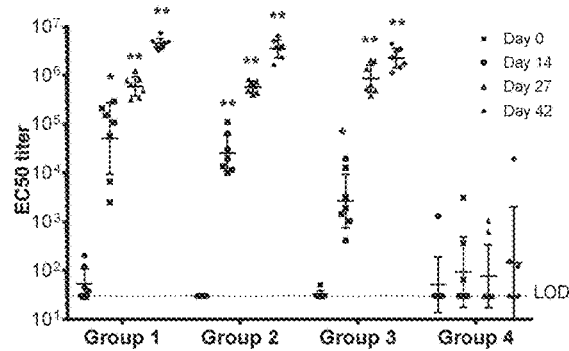
Fig. 8 - continued

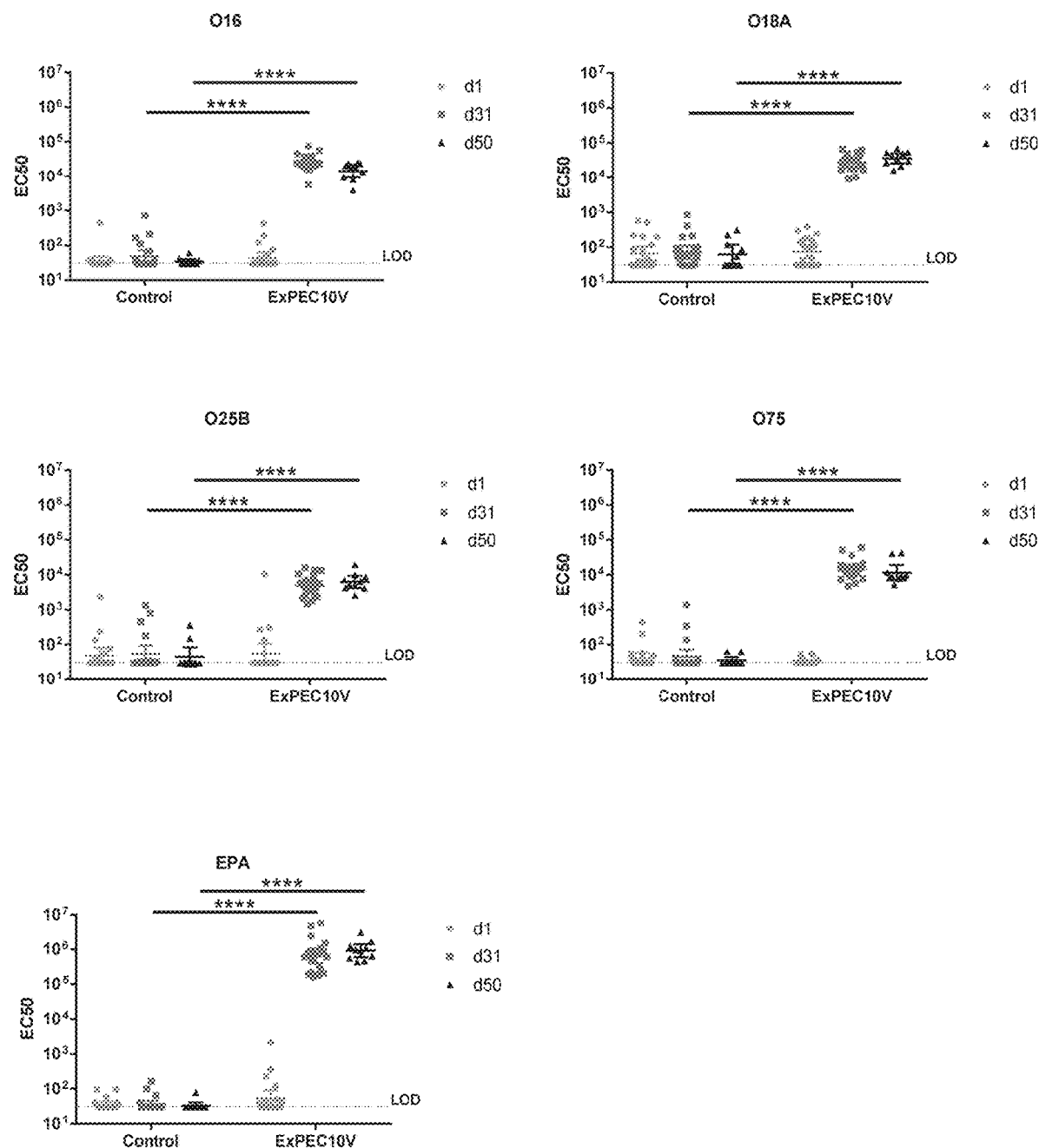
Fig. 9 - continued

METHODS OF PRODUCING BIOCONJUGATES OF E. COLI O-ANTIGEN POLYSACCHARIDES, COMPOSITIONS THEREOF, AND METHODS OF USE THEREOF

CROSS REFERENCE TO RELATED APPLICATION

This application is a divisional of U.S. patent application Ser. No. 16/822,403, filed on Mar. 18, 2020, allowed, which claims priority to U.S. Provisional Application No. 62/819,762 filed on Mar. 18, 2019, the disclosures of all of which are herein incorporated by reference in their entireties.

REFERENCE TO SEQUENCE LISTING SUBMITTED ELECTRONICALLY

The contents of the electronic sequence listing (004852_128US3.xml; Size: 152,000 bytes; and Date of Creation: Sep. 27, 2022) is herein incorporated by reference in its entirety.

BACKGROUND OF THE INVENTION

Extraintestinal pathogenic *Escherichia coli* (ExPEC) strains are normally harmless inhabitants of the human gastrointestinal tract, alongside commensal *E. coli* strains. ExPEC isolates cannot readily be distinguished from commensal isolates by serotype, although many clonal lineages are dominated by ExPEC, as defined by O-antigen, capsule and flagellar antigen serotypes (abbreviated as O:K:H, for example O25:K1:H4). In contrast to commensal *E. coli*, ExPEC strains express a broad array of virulence factors enabling them to colonize the gastrointestinal tract, as well as to cause a wide range of extraintestinal infections, which are associated with a significant healthcare cost burden due to hospitalization and death. Neonates, the elderly, and immunocompromised patients are particularly susceptible to ExPEC infection, including invasive ExPEC disease (IED).

ExPEC strains are the most common cause of urinary tract infections (UTI) and important contributors to surgical site infections and neonatal meningitis. The strains are also associated with abdominal and pelvic infections and nosocomial pneumonia, and are occasionally involved in other extraintestinal infections, such as osteomyelitis, cellulitis, and wound infections. All these primary sites of infection can result in ExPEC bacteremia. ExPEC is the most common cause of community-onset bacteremia and a major causative pathogen in nosocomial bacteremia and is found in about 17% to 37% of clinically significant blood isolates. Patients with an ExPEC-positive blood culture typically suffer sepsis syndrome, severe sepsis, or septic shock. Increasing resistance of ExPEC against first-line antibiotics including the cephalosporins, fluoroquinolones, and trimethoprim/sulfamethoxazole has been observed. The emergence and rapid global dissemination of ExPEC sequence type 131 (ST131) is considered a main driver of increased drug resistance, including multi-drug resistance. This clone is found in 12.5% to 30% of all ExPEC clinical isolates, exhibits mostly serotype O25b:H4, and shows high levels of resistance to fluoroquinolones, which is often accompanied by trimethoprim/sulfamethoxazole resistance and extended-spectrum beta-lactamases conferring resistance to cephalosporins.

The O-antigen comprises the immunodominant component of the cell wall lipopolysaccharide (LPS) in Gram-negative bacteria, including *E. coli*. There are currently >180 serologically unique *E. coli* O-antigens identified, with the vast majority of ExPEC isolates classified within less than 20 O-antigen serotypes. Full-length *E. coli* O-antigens are typically comprised of about 10 to 25 repeating sugar units attached to the highly conserved LPS core structure, with each component synthesized separately by enzymes encoded predominantly in the rfb and rfa gene clusters, respectively. Following polymerization of the O-antigen, the O-antigen polysaccharide backbone may be modified, typically through the addition of acetyl or glucose residues. These modifications effectively increase serotype diversity by creating antigenically distinct serotypes that share a common polysaccharide backbone, but differ in side branches. Genes encoding O-antigen modifying enzymes typically reside outside of the rfb cluster on the chromosome, and in some cases, these genes are found within lysogenic bacteriophages.

ExPEC isolates belonging to the O4 serogroup have been commonly identified in contemporary surveillance studies of U.S. and EU blood isolates. The structure of the O4 polysaccharide was determined as→2) α-L-Rha (1→6) α-D-Glc (1→3) α-L-FucNAc (1→3) β-D-GlcNAc (1→from an *E. coli* O4:K52 strain (Jann et al., Carbohydr. Res. (1993) v. 248, pp. 241-250). A distinct form of the O4 polysaccharide structure was determined for O4:K3, O4:K6 and O4:K12 strains, in which the structure above was modified by the addition of an α-D-Glc (1→3) linked to the rhamnose residue of the polysaccharide (Jann et al., 1993, supra), this form of the polysaccharide referred to herein below as 'glucosylated O4'. The enzymes responsible for the O-antigen modification within *E. coli* O4 strains were not identified.

Efforts toward the development of a vaccine to prevent ExPEC infections have focused on O-antigen polysaccharide conjugates. A 12-valent O-antigen conjugate vaccine was synthesized through extraction and purification of O-antigen polysaccharide and chemical conjugation to detoxified *Pseudomonas aeruginosa* exotoxin A and tested for safety and immunogenicity in a Phase 1 clinical study (Cross et al., J. Infect. Dis. (1994) v. 170, pp. 834-40). This candidate vaccine was never licensed for clinical use. A bioconjugation system in *E. coli* has been developed recently, in which the polysaccharide antigen and the carrier protein are both synthesized in vivo and subsequently conjugated in vivo through the activities of the oligosaccharyl transferase PglB, a *Campylobacter jejuni* enzyme, expressed in *E. coli* (Wacker et al., Proc. Nat. Acad. Sci. (2006) v. 103, pp. 7088-93). This N-linked protein glycosylation system is capable of the transfer of diverse polysaccharides to a carrier protein, allowing for straightforward methods to purify the conjugate.

Bioconjugation has been used successfully to produce conjugate polysaccharide for an *E. coli* four-valent O-antigen candidate vaccine (Poolman and Wacker, J. Infect. Dis. (2016) v. 213(1), pp. 6-13). However, the development of a successful ExPEC vaccine requires coverage of predominant serotypes, and the presence of further O-antigen modifications in subsets of ExPEC isolates presents a further challenge in covering isolates displaying unmodified and modified LPS. Moreover, efficiency of production of the multiple components for more complex vaccine compositions covering multiple serotypes becomes increasingly important, and hence there remains a need for improvements in production of individual bioconjugates of specific O-antigens.

BRIEF SUMMARY OF THE INVENTION

In view of increasing antibiotic resistance among ExPEC isolates and the presence of further O-antigen modifications among predominant O-serotypes, there is a need for improved prophylactic and therapeutic treatments for these infections. The invention satisfies this need by defining the genetic composition of contemporary clinical isolates, including identifying the genes encoding O-antigen modifying enzymes, thus allowing for the engineering of recombinant host cells capable of synthesizing bioconjugates of the O-antigens including bioconjugates comprising selected O-antigen modifications. In addition, in one aspect of the invention, host cells and methods for improved production of bioconjugates of specific O-antigens by using variants of oligosaccharyltransferase (OST) are provided, based on advantages of use of certain OST variants for bioconjugates of certain E. coli O-antigens in an unpredictable serotype-dependent manner. Use of such OST variants may in certain cases also affect the glycosylation pattern of the bioconjugate, e.g. by increasing the relative number of glycans coupled to the carrier protein as compared to bioconjugates produced using wild-type or other variants of the OST, and hence novel bioconjugates produced by such methods are also provided as an aspect of the invention.

In one aspect, provided is a method of preparing a bioconjugate of an E. coli $O_x$ antigen polysaccharide covalently linked to a carrier protein, the method comprising:
(i) providing a recombinant host cell comprising:
   a. a nucleotide sequence of an rfb gene cluster for the $O_x$-antigen polysaccharide;
   b. a nucleotide sequence encoding the carrier protein comprising at least one glycosylation site comprising a glycosylation consensus sequence having SEQ ID NO: 1, preferably having SEQ ID NO: 2; and
   c. a nucleotide sequence encoding an oligosaccharyl transferase $PglB_y$; and
(ii) culturing the recombinant host cell under conditions for production of the bioconjugate,
wherein:
when the $O_x$-antigen is O1A antigen polysaccharide, the $PglB_y$ comprises the amino acid mutations of N311V, K482R, D483H, and A669V;
when the $O_x$-antigen is glucosylated O4 antigen polysaccharide, the $PglB_y$ comprises the amino acid mutation N311V or the amino acid mutations Y77H and N311V, and the recombinant host cell further comprises a sequence encoding a glucosyltransferase GtrS having at least 80% identity to SEQ ID NO: 4 and being capable of modifying an E. coli O4 antigen polysaccharide by addition of glucose to produce the E. coli glucosylated O4 antigen polysaccharide, and nucleotide sequences encoding a translocase GtrA and a glycosyltransferase GtrB having at least 80% sequence identity to SEQ ID NOs: 7 and 8 respectively, wherein the translocase is capable of translocating bactoprenol linked glucose and the glycosyltransferase is capable of glucosylating bactoprenol;
when the $O_x$-antigen is O6A antigen polysaccharide, the $PglB_y$ comprises the amino acid mutations of N311V, K482R, D483H, and A669V;
when the $O_x$-antigen is O8 antigen polysaccharide, the $PglB_y$ comprises no amino acid mutations at positions 77, 80, 287, 289, 311, 482, 483 and 669;
when the $O_x$-antigen is O15 antigen polysaccharide, the $PglB_y$ comprises the amino acid mutations of N311V, K482R, D483H, and A669V;
when the $O_x$-antigen is O16 antigen polysaccharide, the $PglB_y$ comprises the amino acid mutations of Y77H, S80R, Q287P, K289R, and N311V;
when the $O_x$-antigen is O18A antigen polysaccharide, the $PglB_y$ comprises no amino acid mutations at positions 77, 80, 287, 289, 311, 482, 483 and 669; and
when the $O_x$-antigen is O75 antigen polysaccharide, the $PglB_y$ comprises the amino acid mutation of N311V,
wherein in each case the amino acid mutations are relative to the wild-type PglB having the amino acid sequence of SEQ ID NO: 6,
wherein the O1A, glucosylated O4, O6A, O8, O15, O16, O18A, and O75 antigen polysaccharides have the structures of Formulas (O1A), (O4-Glc+), (O6A), (O8), (O15), (O16), (O18A), and (O75), respectively, as shown in Table 1, and each n is independently an integer of 1 to 100, preferably 3 to 50, e.g. 5 to 40, e.g. 7 to 25, e.g. 10 to 20.

In one embodiment, the $O_x$-antigen is O1A antigen polysaccharide, the $PglB_y$ comprises the amino acid mutations of N311V, K482R, D483H, and A669V relative to wild-type PglB having the amino acid sequence of SEQ ID NO: 6.

In one embodiment, the $O_x$-antigen is glucosylated O4 antigen polysaccharide, and the $PglB_y$ comprises the amino acid mutation N311V relative to wild-type PglB having the amino acid sequence of SEQ ID NO: 6. In one embodiment, the $O_x$-antigen is glucosylated O4 antigen polysaccharide, and the $PglB_y$ comprises the amino acid mutations Y77H and N311V relative to wild-type PglB having the amino acid sequence of SEQ ID NO: 6. In embodiments wherein the $O_x$-antigen is glucosylated O4 antigen polysaccharide, the recombinant host cell preferably further comprises a sequence encoding a GtrS having at least 80% identity to SEQ ID NO: 4, and nucleotide sequences encoding a GtrA and a GtrB having at least 80% sequence identity to SEQ ID NOs: 7 and 8 respectively.

In one embodiment, the $O_x$-antigen is O6A antigen polysaccharide, the $PglB_y$ comprises the amino acid mutations of N311V, K482R, D483H, and A669V relative to wild-type PglB having the amino acid sequence of SEQ ID NO: 6.

In one embodiment, the $O_x$-antigen is O8 antigen polysaccharide, the $PglB_y$ comprises no amino acid mutations at positions 77, 80, 287, 289, 311, 482, 483 and 669 relative to wild-type PglB having the amino acid sequence of SEQ ID NO: 6.

In one embodiment, the $O_x$-antigen is O15 antigen polysaccharide, the $PglB_y$ comprises the amino acid mutations of N311V, K482R, D483H, and A669V relative to wild-type PglB having the amino acid sequence of SEQ ID NO: 6.

In one embodiment, the $O_x$-antigen is O16 antigen polysaccharide, the $PglB_y$ comprises the amino acid mutations of Y77H, S80R, Q287P, K289R, and N311V relative to wild-type PglB having the amino acid sequence of SEQ ID NO: 6.

In one embodiment, the $O_x$-antigen is O18A antigen polysaccharide, the $PglB_y$ comprises no amino acid mutations at positions 77, 80, 287, 289, 311, 482, 483 and 669 relative to wild-type PglB having the amino acid sequence of SEQ ID NO: 6, and preferably comprises the amino acid sequence of SEQ ID NO: 6.

In one embodiment, the $O_x$-antigen is O75 antigen polysaccharide, the $PglB_y$ comprises the amino acid mutation of N311V relative to wild-type PglB having the amino acid sequence of SEQ ID NO: 6.

In a particular aspect, provided is a method of preparing a bioconjugate of an E. coli $O_x$-antigen polysaccharide covalently linked to a carrier protein, the method comprising:

(i) providing a recombinant host cell comprising:
   a. a nucleotide sequence of an rfb gene cluster for the $O_x$-antigen polysaccharide;
   b. a nucleotide sequence encoding the carrier protein comprising at least one glycosylation site comprising a glycosylation consensus sequence having SEQ ID NO: 1, preferably having SEQ ID NO: 2; and
   c. a nucleotide sequence encoding an oligosaccharyl transferase $PglB_y$; and
(ii) culturing the recombinant host cell under conditions for production of the bioconjugate,
wherein the $PglB_y$ comprises the amino acid mutation N311V relative to the wild-type PglB having the amino acid sequence of SEQ ID NO: 6,
wherein the $O_x$-antigen is O1A antigen polysaccharide, glucosylated O4 antigen polysaccharide, O6A antigen polysaccharide, O15 antigen polysaccharide, O16 antigen polysaccharide, or O75 antigen polysaccharide, and when the $O_x$-antigen is glucosylated O4 antigen polysaccharide, the recombinant host cell further comprises a sequence encoding a glucosyltransferase GtrS having at least 80% identity to SEQ ID NO: 4 and being capable of modifying an *E. coli* O4 antigen polysaccharide by addition of glucose to produce the *E. coli* glucosylated O4 antigen polysaccharide, and nucleotide sequences encoding a translocase GtrA and a glycosyltransferase GtrB having at least 80% sequence identity to SEQ ID NOs: 7 and 8, respectively, wherein the translocase is capable of translocating bactoprenol linked glucose and the glycosyltransferase is capable of glucosylating bactoprenol, and
wherein the O1A, glucosylated O4, O6A, O15, O16, and O75 antigen polysaccharides have the structures of Formulas (O1A), (O4-Glc+), (O6A), (O15), (O16), and (O75), respectively, as shown in Table 1, and each n is independently an integer of 1 to 100, preferably 3 to 50, e.g. 5 to 40, e.g. 7 to 25, e.g. 10 to 20.

In certain embodiments, the method further comprises isolating the bioconjugate from the recombinant host cell.

In certain embodiments, the carrier protein is selected from the group consisting of detoxified Exotoxin A of *P. aeruginosa* (EPA), *E. coli* flagellin (FliC), CRM197, maltose binding protein (MBP), Diphtheria toxoid, Tetanus toxoid, detoxified hemolysin A of *S. aureus*, clumping factor A, clumping factor B, *E. coli* heat labile enterotoxin, detoxified variants of *E. coli* heat labile enterotoxin, Cholera toxin B subunit (CTB), cholera toxin, detoxified variants of cholera toxin, *E. coli* Sat protein, the passenger domain of *E. coli* Sat protein, *Streptococcus pneumoniae* Pneumolysin, Keyhole limpet hemocyanin (KLH), *P. aeruginosa* PcrV, outer membrane protein of *Neisseria meningitidis* (OMPC), and protein D from non-typeable *Haemophilus influenzae*.

In certain embodiments, the carrier protein is detoxified exotoxin A of *Pseudomonas aeruginosa* (EPA). Preferably, the EPA carrier protein comprises 1-10, preferably 2-4, more preferably 4, glycosylation sites. In certain embodiments, each glycosylation site comprises a glycosylation consensus sequence having SEQ ID NO: 2. In a particular embodiment, the EPA carrier protein comprises SEQ ID NO: 3.

In certain embodiments, the recombinant host cell is an *E. coli* cell, e.g., an *E. coli* K-12 strain, such as strain W3110.

In another aspect, provided is a bioconjugate produced by a method of preparing a bioconjugate of an $O_x$ antigen polysaccharide covalently linked to a carrier protein as described herein.

In another aspect, provided is a composition comprising such a bioconjugate. In some embodiments, a composition comprises at least 2, preferably at least 3, more preferably at least 5, still more preferably at least 7 of such bioconjugates.

In certain embodiments, a composition according to the invention comprises a bioconjugate of *E. coli* glucosylated O4 antigen polysaccharide covalently linked to a carrier protein, wherein the glucosylated O4 antigen polysaccharide has the structure of Formula (O4-Glc+) as shown in Table 1, and n is an integer of 1 to 100, preferably 3 to 50, e.g. 5 to 40, e.g. 7 to 25, e.g. 10 to 20. In certain embodiments, a composition according to the invention further comprises at least a bioconjugate of *E. coli* O25B antigen polysaccharide covalently linked to a carrier protein, wherein the O25B antigen polysaccharide has the structure of Formula (O25B) as shown in Table 1, and n is an integer of 1 to 100, preferably 3 to 50, e.g. 5 to 40, e.g. 7 to 25, e.g. 10 to 20. In certain embodiments, a composition according to the invention further comprises at least a bioconjugate of *E. coli* O2 antigen polysaccharide covalently linked to a carrier protein, wherein the O2 antigen polysaccharide has the structure of Formula (O2) as shown in Table 1, and n is an integer of 1 to 100, preferably 3 to 50, e.g. 5 to 40, e.g. 7 to 25, e.g. 10 to 20.

In certain embodiments, a composition of the invention comprises: (i) bioconjugate of *E. coli* O1A antigen polysaccharide covalently coupled to a carrier protein, (ii) bioconjugate of *E. coli* O2 antigen polysaccharide covalently coupled to a carrier protein, (iii) bioconjugate of *E. coli* glucosylated O4 antigen polysaccharide covalently coupled to a carrier protein, (iv) bioconjugate of *E. coli* O6A antigen polysaccharide covalently coupled to a carrier protein, (v) bioconjugate of *E. coli* O8 antigen polysaccharide covalently coupled to a carrier protein, (vi) bioconjugate of *E. coli* O15 antigen polysaccharide covalently coupled to a carrier protein, (vii) bioconjugate of *E. coli* O16 antigen polysaccharide covalently coupled to a carrier protein, (viii) bioconjugate of *E. coli* O25B antigen polysaccharide covalently coupled to a carrier protein, and (ix) bioconjugate of *E. coli* O75 antigen polysaccharide covalently coupled to a carrier protein, wherein the O1A, O2, glucosylated O4, O6A, O8, O15, O16, O25B, and O75 antigen polysaccharides have the structures of Formulas (O1A), (O2), (O4-Glc+), (O6A), (O8), (O15), (O16), (O25B), and (O75), respectively, as shown in Table 1, and each n is independently an integer of 1 to 100, preferably 3 to 50, e.g. 5 to 40, e.g. 7 to 25, e.g. 10 to 20. In certain embodiments, such a composition further comprises: (x) bioconjugate of *E. coli* O18A antigen polysaccharide covalently coupled to a carrier protein, wherein the O18A antigen polysaccharide has the structure of Formula (O18A) as shown in Table 1, and n is an integer of 1 to 100, preferably 3 to 50, e.g. 5 to 40, e.g. 7 to 25, e.g. 10 to 20. In certain embodiments, a composition of the invention is an immunogenic composition.

In other aspects, provided is a method of vaccination a subject against extra-intestinal pathogenic *E. coli* (ExPEC), comprising administering to the subject such a bioconjugate or composition as described herein. In yet other aspects, provided is such bioconjugate or composition as described herein for use in vaccination against extra-intestinal pathogenic *E. coli* (ExPEC).

In other aspects, provided are recombinant host cells for preparing a bioconjugate of an *E. coli* $O_x$ antigen polysaccharide covalently linked to a carrier protein, the recombinant host cell comprising:
   (a) a nucleotide sequence of an rfb gene cluster for the $O_x$-antigen polysaccharide;
   (b) a nucleotide sequence encoding the carrier protein comprising at least one glycosylation site comprising a glycosylation consensus sequence having SEQ ID NO: 1, preferably having SEQ ID NO: 2; and (c) a nucleotide sequence encoding an oligosaccharyl transferase $PglB_y$, wherein:

when the $O_x$-antigen is O1A antigen polysaccharide, the $PglB_y$ comprises the amino acid mutations of N311V, K482R, D483H, and A669V;

when the $O_x$-antigen is glucosylated O4 antigen polysaccharide, the $PglB_y$ comprises the amino acid mutation N311V or the amino acid mutations Y77H and N311V, and the recombinant host cell further comprises a sequence encoding a glucosyltransferase GtrS having at least 80% identity to SEQ ID NO: 4 and being capable of modifying an *E. coli* O4 antigen polysaccharide by addition of glucose to produce the *E. coli* glucosylated O4 antigen polysaccharide, and nucleotide sequences encoding a translocase GtrA and a glycosyltransferase GtrB having at least 80% sequence identity to SEQ ID NOs: 7 and 8 respectively, wherein the translocase is capable of translocating bactoprenol linked glucose and the glycosyltransferase is capable of glucosylating bactoprenol;

when the $O_x$-antigen is O6A antigen polysaccharide, the $PglB_y$ comprises the amino acid mutations of N311V, K482R, D483H, and A669V;

when the $O_x$-antigen is O6A antigen polysaccharide, the $PglB_y$ comprises the amino acid mutations of N311V, K482R, D483H, and A669V;

when the $O_x$-antigen is O15 antigen polysaccharide, the $PglB_y$ comprises the amino acid mutations of N311V, K482R, D483H, and A669V;

when the $O_x$-antigen is O16 antigen polysaccharide, the $PglB_y$ comprises the amino acid mutations of Y77H, S80R, Q287P, K289R, and N311V;

when the $O_x$-antigen is O18A antigen polysaccharide, the $PglB_y$ comprises no amino acid mutations at positions 77, 80, 287, 289, 311, 482, 483 and 669; and when the $O_x$-antigen is O75 antigen polysaccharide, the $PglB_y$ comprises the amino acid mutation of N311V, wherein in each case the amino acid mutations are relative to the wild-type PglB having the amino acid sequence of SEQ ID NO: 6, and wherein the O1A, glucosylated O4, O6A, O8, O15, O16, O18A, and O75 antigen polysaccharides have the structures of Formulas (O1A), (O4-Glc+), (O6A), (O8), (O15), (O16), (O18A), and (O75), respectively, as shown in Table 1, and each n is independently an integer of 1 to 100, preferably 3 to 50, e.g. 5 to 40, e.g. 7 to 25, e.g. 10 to 20.

In certain embodiments, such host cells are provided wherein the $O_x$-antigen is O1A antigen polysaccharide, and the $PglB_y$ comprises the amino acid mutations of N311V, K482R, D483H, and A669V relative to wild-type PglB having the amino acid sequence of SEQ ID NO: 6.

In certain embodiments, recombinant host cells of the invention are provided wherein the $O_x$-antigen is glucosylated O4 antigen polysaccharide, and the $PglB_y$ comprises the amino acid mutation N311V relative to wild-type PglB having the amino acid sequence of SEQ ID NO: 6. In certain embodiments, recombinant host cells of the invention are provided wherein the $O_x$-antigen is glucosylated O4 antigen polysaccharide, and the $PglB_y$ comprises the amino acid mutations Y77H and N311V relative to wild-type PglB having the amino acid sequence of SEQ ID NO: 6. In certain embodiments wherein the $O_x$-antigen is glucosylated O4 antigen polysaccharide, the recombinant host cell further comprises a sequence encoding a GtrS having the amino acid sequence of SEQ ID NO: 4, and nucleotide sequences encoding a GtrA and a GtrB having the amino acid sequences of SEQ ID NOs: 7 and 8, respectively.

In certain embodiments, recombinant host cells of the invention are provided wherein the $O_x$-antigen is O6A antigen polysaccharide, and the $PglB_y$ comprises the amino acid mutations of N311V, K482R, D483H, and A669V relative to wild-type PglB having the amino acid sequence of SEQ ID NO: 6.

In certain embodiments, recombinant host cells of the invention are provided wherein the $O_x$-antigen is O8 antigen polysaccharide, the $PglB_y$ comprises no amino acid mutations at positions 77, 80, 287, 289, 311, 482, 483 and 669 relative to wild-type PglB having the amino acid sequence of SEQ ID NO: 6.

In certain embodiments, recombinant host cells of the invention are provided wherein the $O_x$-antigen is O15 antigen polysaccharide, the $PglB_y$ comprises the amino acid mutations of N311V, K482R, D483H, and A669V relative to wild-type PglB having the amino acid sequence of SEQ ID NO: 6.

In certain embodiments, recombinant host cells of the invention are provided wherein the $O_x$-antigen is O16 antigen polysaccharide, the $PglB_y$ comprises the amino acid mutations of Y77H, S80R, Q287P, K289R, and N311V relative to wild-type PglB having the amino acid sequence of SEQ ID NO: 6.

In certain embodiments, recombinant host cells of the invention are provided wherein the $O_x$-antigen is O18A antigen polysaccharide, the $PglB_y$ comprises no amino acid mutations at positions 77, 80, 287, 289, 311, 482, 483 and 669 relative to wild-type PglB having the amino acid sequence of SEQ ID NO: 6.

In certain embodiments, recombinant host cells of the invention are provided wherein the $O_x$-antigen is O75 antigen polysaccharide, the $PglB_y$ comprises the amino acid mutation of N311V relative to wild-type PglB having the amino acid sequence of SEQ ID NO: 6.

In certain embodiments, recombinant host cells of the invention are provided wherein the carrier protein is selected from the group consisting of detoxified Exotoxin A of *P. aeruginosa* (EPA), *E. coli* flagellin (FliC), CRM197, maltose binding protein (MBP), Diphtheria toxoid, Tetanus toxoid, detoxified hemolysin A of *S. aureus*, clumping factor A, clumping factor B, *E. coli* heat labile enterotoxin, detoxified variants of *E. coli* heat labile enterotoxin, Cholera toxin B subunit (CTB), cholera toxin, detoxified variants of cholera toxin, *E. coli* Sat protein, the passenger domain of *E. coli* Sat protein, *Streptococcus pneumoniae* Pneumolysin, Keyhole limpet hemocyanin (KLH), *P. aeruginosa* PcrV, outer membrane protein of *Neisseria meningitidis* (OMPC), and protein D from non-typeable *Haemophilus influenzae*.

In certain embodiments, recombinant host cells of the invention are provided wherein the carrier protein is detoxified exotoxin A of *Pseudomonas aeruginosa* (EPA). In certain embodiments thereof, the EPA carrier protein comprises 1-10, preferably 2-4, more preferably 4, of the glycosylation sites. In certain embodiments, each glycosylation site comprises a glycosylation consensus sequence having SEQ ID NO: 2. In certain embodiments, the EPA carrier protein comprises SEQ ID NO: 3.

In certain embodiments, recombinant host cells of the invention are provided wherein the recombinant host cell is an *E. coli* cell, e.g. an *E. coli* K-12 strain, such as strain W3110.

In certain embodiments for the host cells and methods for preparing a bioconjugate of an *E. coli* glucosylated O4 antigen polysaccharide covalently linked to a carrier protein according to the invention, the rfb gene cluster for the E. coli O4 antigen polysaccharide comprises a sequence that encodes the enzymes that create the E. coli O4 antigen polysaccharide (Formula (O4-Glc−) in Table 1) and is at least 80%, e.g. at least 90%, e.g. at least 95%, e.g. at least 98% identical to SEQ ID NO: 9. In certain embodiments the rfb gene cluster comprises SEQ ID NO: 9.

In certain embodiments for the host cells and methods for preparing a bioconjugate of an E. coli glucosylated O4 antigen polysaccharide covalently linked to a carrier protein according to the invention, the glucosyl transferase that is capable of modifying the E. coli O4 antigen polysaccharide to produce the E. coli glucosylated O4 antigen polysaccharide has an amino acid sequence that has at least 90%, preferably at least 95%, preferably at least 98% sequence identity to SEQ ID NO: 4. In certain embodiments, the glucosyl transferase comprises SEQ ID NO: 4.

In certain embodiments for the host cells and methods for preparing a bioconjugate of an E. coli glucosylated O4 antigen polysaccharide covalently linked to a carrier protein according to the invention, the translocase is capable of translocating bactoprenol-linked glucose and has at least 90%, preferably at least 95%, preferably at least 98% sequence identity to SEQ ID NO: 7. In certain embodiments, the translocase comprises SEQ ID NO: 7.

In certain embodiments for the host cells and methods for preparing a bioconjugate of an E. coli glucosylated O4 antigen polysaccharide covalently linked to a carrier protein according to the invention, the glycosyltransferase is capable of glucosylating bactoprenol and has at least 90%, preferably at least 95%, preferably at least 98% sequence identity to SEQ ID NO: 8. In certain embodiments, the glycosyltransferase comprises SEQ ID NO: 8.

BRIEF DESCRIPTION OF THE FIGURES

The foregoing summary, as well as the following detailed description of the invention, will be better understood when read in conjunction with the appended drawings. It should be understood that the invention is not limited to the precise embodiments shown in the drawings.

In the drawings:

FIG. 4A shows serum antibody levels measured by ELISA at day 0, 14 and 42 post-immunization; individual titers (log 10 EC50 titer) and GMT±95% CI are shown; the grey dotted line indicates the threshold above which the dilution curves of the samples have a 4PL fitting; FIG. 4B shows the results of the opsonophagocytic (OPK) assay to determine the functionality of the antibodies in serum samples obtained at day 42 post-immunization with glucosylated O4 (O4-Glc+)-EPA bioconjugate (4.0 µg); Wilcoxon rank sum test and Bonferroni correction; *P<0.05, ***P<0.0001;

FIG. 10 shows the overall study design for a phase 1/2a clinical trial with ExPEC10V vaccine in humans.

DETAILED DESCRIPTION OF THE INVENTION

Figure 1:
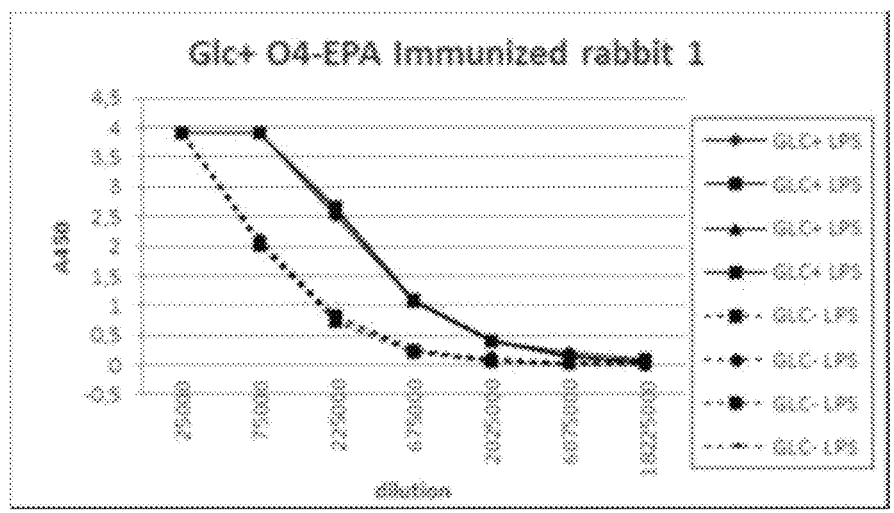
FIG. 1 shows ELISA IgG titers against unmodified (GLC−) or glucose-modified (GLC+) O4 LPS in sera from two rabbits immunized with Glc-modified O4 polysaccharide bioconjugate as described in Example 4; ELISA titers were determined in quadruplicate.
Figure 1:
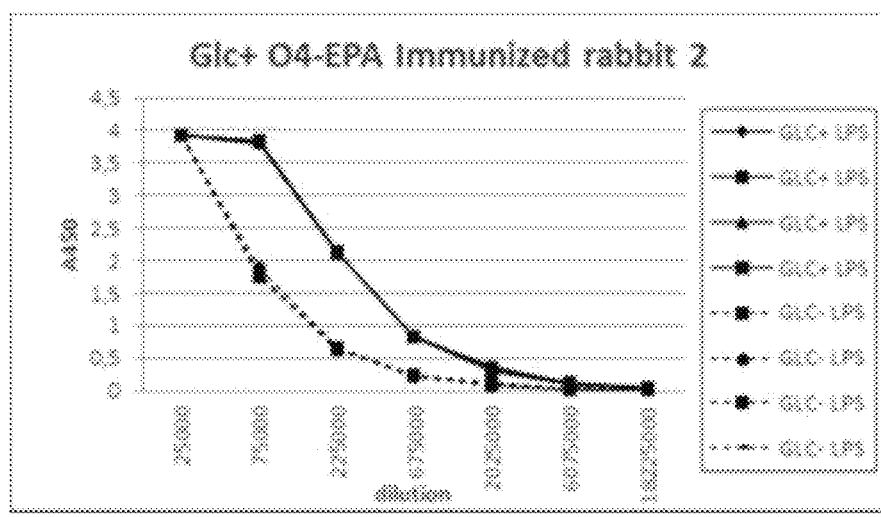

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the invention. Such discussion is not an admission that any or all of these matters form part of the prior art with respect to any inventions disclosed or claimed.

Unless defined otherwise, all technical and scientific terms used herein have the same meaning as commonly understood to one of ordinary skill in the art to which this invention pertains. Otherwise, certain terms used herein have the meanings as set forth in the specification.

It must be noted that as used herein and in the appended claims, the singular forms "a," "an," and "the" include plural reference unless the context clearly dictates otherwise.

Unless otherwise indicated, the term "at least" preceding a series of elements is to be understood to refer to every element in the series.

Those skilled in the art will recognize or be able to ascertain using no more than routine experimentation, many equivalents to the specific embodiments of the invention described herein. Such equivalents are intended to be encompassed by the invention.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or "including" or sometimes when used herein with the term "having".

When used herein "consisting of" excludes any element, step, or ingredient not specified in the claim element. When used herein, "consisting essentially of" does not exclude materials or steps that do not materially affect the basic and novel characteristics of the claim. Any of the aforementioned terms of "comprising," "containing," "including," and "having," whenever used herein in the context of an aspect or embodiment of the invention can be replaced with the term "consisting of" or "consisting essentially of" to vary scopes of the disclosure.

As used herein, the conjunctive term "and/or" between multiple recited elements is understood as encompassing both individual and combined options. For instance, where two elements are conjoined by "and/or," a first option refers to the applicability of the first element without the second. A second option refers to the applicability of the second element without the first. A third option refers to the applicability of the first and second elements together. Any one of these options is understood to fall within the meaning, and therefore satisfy the requirement of the term "and/or" as used herein. Concurrent applicability of more than one of the options is also understood to fall within the meaning, and therefore satisfy the requirement of the term "and/or."

The identification of an O-antigen structural modification, namely glucose branching, within the *E. coli* O4 serotype (Jann et al., 1993) presents a challenge to the discovery and development of a glycoconjugate vaccine targeting bacterial isolates within this serotype. The proportion of clinical contemporary O4 isolates expressing the unmodified (not having a glucose side-branch) and modified (having a glucose side-branch) forms of the O4 O-antigen is unknown. Obtaining information on this characteristic is critical for selecting the relevant antigenic structure. In addition, the extent to which vaccine induced antibodies elicited to one form of the O4 polysaccharide will cross-react with the other form has not been determined. Purification of O-antigen free from lipid A and subsequent chemical conjugation to a carrier protein is a lengthy and laborious process. Additionally, the purification, lipid A detoxification and chemical conjugation processes can result in loss of epitopes, antigen heterogeneity and reduced immunogenicity of the conjugated polysaccharide. Synthesis of glycoconjugates by bioconjugation can overcome these limitations of classical purification and chemical conjugation, but the in vivo synthesis of glucose-branched O4 O-antigen requires the activity of a polysaccharide branching enzyme, which lies outside of the rfb gene cluster. To date, the O-antigen modifying enzyme responsible for glucose-branching in O4 *E. coli* strains has not been identified. Cloning the O4 rfb gene cluster into the bioconjugation *E. coli* strain expressing PglB will not be sufficient to synthesize the glucose-branched O4 glycoconjugate, but rather would only produce non-glucose-branched O4 bioconjugates (the structure of the glycan thereof is shown in Formula (O4) in Table 1). As used herein, the terms "glucosylated O4", "glucose-branched O4", "O4 Glc+" and "Glc+O4" O-antigen refer to O4 O-antigen with a glucose side-branch, and the structure thereof is shown in formula (O4-Glc+) in Table 1.

Disclosed herein is the gene encoding the O-antigen modifying enzyme responsible for glucose branching of the *E. coli* O4 antigen polysaccharide. Also disclosed herein are host cells, e.g., recombinantly engineered host cells comprising nucleic acid encoding enzymes capable of producing bioconjugates comprising the glucosylated O4 antigen polysaccharide covalently bound to a carrier protein in vivo. Such host cells can be used to generate bioconjugates comprising the glucosylated O4 antigen linked to a carrier protein, which can be used in, e.g., the formulation of therapeutic and/or prophylactic compositions (e.g., vaccines). Further provided herein are compositions comprising bioconjugates of the glucosylated O4 antigen polysaccharide, alone or in combination with other *E. coli* antigens (e.g., O1, O2, O6, O8, O15, O16, O18, O25, and/or O75 antigen polysaccharides and subserotypes thereof). The compositions can be used in prophylactic and/or therapeutic methods, e.g., vaccination of hosts against infection with *E. coli*, and are useful in the generation of antibodies, which can be used, e.g., in therapeutic methods such as for immunization of subjects.

As used here, the terms "O-antigen," "O-antigen polysaccharide," "O-antigen saccharide," and "OPS" refer to the O-antigen of Gram-negative bacteria. Typically, an O-antigen is a polymer of immunogenic repeating polysaccharide units. In a particular embodiment, the terms "O-antigen," "O-antigen polysaccharide," and "OPS" refer to the O-antigen of *Escherichia coli*. Different serotypes of *E. coli* express different O-antigens. In *E. coli*, the gene products involved in O-antigen biogenesis are encoded by the rfb gene cluster.

As used herein, "rfb cluster" and "rfb gene cluster" refer to a gene cluster that encodes enzymatic machinery capable of synthesizing an O-antigen backbone structure. The term rfb cluster can apply to any O-antigen biosynthetic cluster, and preferably refers to a gene cluster from the genus *Escherichia*, particularly *E. coli*.

As used herein, the term "O1A" refers to the O1A antigen of *E. coli* (a subserotype of *E. coli* serotype O1). The term "O2" refers to the O2 antigen of *E. coli* (*E. coli* serotype O2). The term "O6A" refers to the O6A antigen of *E. coli* (a subserotype of *E. coli* serotype O6). The term "O8" refers to the O8 antigen of *E. coli* (*E. coli* serotype O8). The term "O15" refers to the O15 antigen of *E. coli* (*E. coli* serotype O15). The term "O16" refers to the O16 antigen of *E. coli* (*E. coli* serotype O16). The term "O18A" refers to the O18A antigen of *E. coli* (a subserotype of *E. coli* serotype O18). The term "O25B" refers to the O25B antigen from *E. coli* (a subserotype of *E. coli* serotype O25). The term "O75" refers to the O75 antigen of *E. coli* (*E. coli* serotype O75).

The structures of *E. coli* O-antigen polysaccharides referred to throughout this application are shown below in Table 1. A single repeating unit for each *E. coli* O-antigen polysaccharide is shown.

TABLE 1

Structures of *E. coli* O-antigen Polysaccharides

| *E. coli* O-antigen Polysaccharide | Structure of Repeating Unit[1] |
|---|---|
| Non-glucosylated O4 antigen polysaccharide (O4-Glc-) | [→2)-α-L-Rhap-(1→6)-α-D-Glcp-(1→3)-α-L-FucpNAc-(1→3)-β-D-GlcpNAc-(1→]$_n$ |
| Glucosylated O4 antigen polysaccharide (O4-Glc+) | α-D-Glcp<br>1<br>↓<br>3<br>[→2)-α-L-Rhap-(1→6)-α-D-Glcp-(1→3)-α-L-FucpNAc-(1→3)-β-D-GlcpNAc-(1→]$_n$ |
| O1A antigen polysaccharide (O1A) | [→3)-α-L-Rhap-(1→3)-α-L-Rhap-(1→3)-β-L-Rhap-(1→4)-β-D-GlcpNAc-(1→]$_n$<br>2<br>↑<br>↑<br>β-D-ManpNAc |
| O2 antigen polysaccharide (O2) | [→3)-α-L-Rhap-(1→2)-α-L-Rhap-(1→3)-β-L-Rhap-(1→4)-β-D-GlcpNAc-(1→]$_n$<br>2<br>↑<br>↑<br>α-D-Fucp3NAc |
| O6A antigen polysaccharide (O6) | [→4)-α-D-GalpNAc-(1→3)-β-D-Manp-(1→4)-β-D-Manp-(1→3)-α-D-GlcpNAc-(1→]$_n$<br>2<br>↑<br>↑<br>β-D-Glcp |
| O8 antigen polysaccharide (O8) | α-D-Manp3Me-(1→[3)-β-D-Manp-(1→2)-α-D-Manp-(1→2)-α-D-Manp-(1→]n |
| O15 antigen polysaccharide (O15) | [→2)-β-D-Galp-(1→3)-α-L-FucpNAc-(1→3)-β-D-GlcpNAc-(1→]$_n$ |

TABLE 1-continued

Structures of *E. coli* O-antigen Polysaccharides

| *E. coli* O-antigen Polysaccharide | Structure of Repeating Unit[1] |
|---|---|
| O16 antigen polysaccharide (O16) | [→2)-β-D-Galf-(1→6)-α-D-Glcp-(1→3)-α-L-Rhap-(1→3)-α-D-GlcpNAc-(1→]$_n$<br>         2<br>         ↑<br>         Ac |
| O18A antigen polysaccharide (O18A) | [→2)-α-L-Rhap-(1→6)-α-D-Glcp-(1→4)-α-D-Galp-(1→3)-α-D-GlcpNAc-(1→]$_n$<br>         3<br>         ↑<br>         ↑<br>         β-D-GlcpNAc |
| O25B antigen polysaccharide (O25B) | β-D-Glcp<br>1<br>↓<br>6<br>[→4)-α-D-Glcp-(1→3)-α-L-Rhap-(1→3)-β-D-GlcpNAc-(1→]$_n$<br>     3                 2<br>     ↑                 ↑<br>     ↑              Ac<br>     α-L-Rhap |
| O75 antigen polysaccharide (O75) | β-D-Manp<br>1<br>↓<br>4<br>[→3)-α-D-Galp-(1→4)-α-L-Rhap-(1→3)-β-D-GlcpNAc-(1→]$_n$ |

[1]Each n is independently an integer of 1 to 100, such as 1-50, 1-40, 1-30, 1-20, and 1-10, 3-50, 3-40, e.g. at least 5, such as 5-40, e.g. 7-30, e.g. 7 to 25, e.g. 10 to 20, but in some instances can be 1-2.

All monosaccharides described herein have their common meaning known in the art. Monosaccharides can have the D or L configuration. If D or L is not specified, the sugar is understood to have the D configuration. Monosaccharides are typically referred to by abbreviations commonly known and used in the art. For example, Glc refers to glucose; D-Glc refers to D-glucose; and L-Glc refers to L-glucose. Other common abbreviations for monosaccharides include: Rha, rhamnose; GlcNAc, N-acetylglucosamine; GalNAc, N-acetylgalactosamine; Fuc, fucose; Man, mannose; Man3Me, 3-O-methyl-mannose; Gal, galactose; FucNAc, N-acetylfucosamine; and Rib, ribose. The suffix "f" refers to furanose and the suffix "p" refers to pyranose.

The terms "RU," "repeat unit," and "repeating unit" as used with respect to an O-antigen refer to the biological repeat unit (BRU) of an O-antigen as it is synthesized in vivo by cellular machinery (e.g., glycosyltransferases). The number of RUs of an O-antigen may vary per serotype, and in embodiments of the invention typically varies from about 1-100 RUs, preferably about 1 to 50 RUs, such as 1-50 RUs, 1-40 RUs, 1-30 RUs, 1-20 RUs, and 1-10 RUs, and more preferably at least 3 RUs, at least 4 RUs, at least 5 RUs, such as 3-50 RUs, preferably 5-40 RUs, e.g. 7-25 RUs, e.g. 10-20 RUs. However, in some instances, the number of RUs of an O-antigen can be 1-2. The structure of each O-antigen that is specifically described herein is shown containing one RU with the variable "n" designating the number of RUs. In each O-antigen polysaccharide in a bioconjugate of the invention, n is independently an integer of 1-100, such as 1-50, 1-40, 1-30, 1-20, 1-10, preferably at least 3, more preferably at least 5, such as 3-50, preferably 5-40 (e.g. 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40), but in some instances can be 1-2. In some embodiments n is independently an integer of about 7-25, e.g. about 10-20. The values may vary between individual O-antigen polysaccharides in a composition, and are provided here as average values, i.e. if a bioconjugate is described herein as having an n that is independently an integer of 5-40, the composition contains a majority of O-antigen polysaccharides with 5-40 repeat units, but may also contain some O-antigen polysaccharides that have less than 5 repeat units or more than 40 repeat units.

The term "glycoconjugate" refers to a sugar or saccharide antigen (e.g., oligo- and polysaccharide)-protein conjugate linked to another chemical species, including but not limited to proteins, peptides, lipids, etc. Glycoconjugates can be prepared chemically, e.g., by chemical (synthetic) linkage of the protein and sugar or saccharide antigen. The term glycoconjugate also includes bioconjugates.

The term "bioconjugate" refers to a conjugate between a protein (e.g., a carrier protein) and a sugar or saccharide antigen (e.g., oligo- and polysaccharide) prepared in a host cell background, preferably a bacterial host cell, e.g. an E. coli host cell, wherein host cell machinery links the antigen to the protein (e.g., N-links). Preferably, the term "bioconjugate" refers to a conjugate between a protein (e.g., carrier protein) and an O-antigen, preferably an E. coli O-antigen (e.g., O1A, O2, glucosylated O4, O6A, O8, O15, O16, O18A, O25B, O75, etc.) prepared in a host cell background, wherein host cell machinery links the antigen to the protein (e.g., N-links). Because bioconjugates are prepared in host cells by host cell machinery, the antigen and protein are covalently linked via a glycosidic linkage or bond in a bioconjugate. Bioconjugates can be prepared in recombinant host cells engineered to express the cellular machinery needed to synthesize the O-antigen and/or link the O-antigen to the target protein. Bioconjugates, as described herein, have advantageous properties over chemically prepared glycoconjugates where the glycans are purified from bacterial cell walls and subsequently chemically coupled to a carrier protein, e.g., bioconjugates require fewer chemicals in manufacture and are more consistent in terms of the final product generated, and contain less or no free (i.e. unbound to carrier protein) glycan. Thus, in typical embodiments, bioconjugates are preferred over chemically produced glycoconjugates.

The term "about," when used in conjunction with a number, refers to any number within ±1, ±5 or ±10% of the referenced number.

The term "percent (%) sequence identity" or "% identity" describes the number of matches ("hits") of identical amino acids of two or more aligned amino acid sequences as compared to the number of amino acid residues making up the overall length of the amino acid sequences. In other terms, using an alignment, for two or more sequences the percentage of amino acid residues that are the same (e.g. 90%, 95%, 97% or 98% identity) may be determined, when the sequences are compared and aligned for maximum correspondence as measured using a sequence comparison algorithm as known in the art, or when manually aligned and visually inspected. The sequences which are compared to determine sequence identity may thus differ by substitution(s), addition(s) or deletion(s) of amino acids. Suitable programs for aligning protein sequences are known to the skilled person. The percentage sequence identity of protein sequences can, for example, be determined with programs such as CLUSTALW, Clustal Omega, FASTA or BLAST, e.g using the NCBI BLAST algorithm (Altschul S F, et al (1997), Nucleic Acids Res. 25:3389-3402).

For example, for amino acid sequences, sequence identity and/or similarity can be determined by using standard techniques known in the art, including, but not limited to, the local sequence identity algorithm of Smith and Waterman, 1981, Adv. Appl. Math. 2:482, the sequence identity alignment algorithm of Needleman and Wunsch, 1970, J. Mol. Biol. 48:443, the search for similarity method of Pearson and Lipman, 1988, Proc. Nat. Acad. Sci. U.S.A. 85:2444, computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al, 1984, Nucl. Acid Res. 12:387-395, preferably using the default settings, or by inspection. In certain embodiments, percent identity is calculated by FastDB based upon the following parameters: mismatch penalty of 1; gap penalty of 1; gap size penalty of 0.33; and joining penalty of 30, "Current Methods in Sequence Comparison and Analysis," Macromolecule Sequencing and Synthesis, Selected Methods and Applications, pp 127-149 (1988), Alan R. Liss, Inc.

Another example of a useful algorithm is the BLAST algorithm, described in: Altschul et al, 1990, J. Mol. Biol. 215:403-410; Altschul et al, 1997, Nucleic Acids Res. 25:3389-3402; and Karin et al, 1993, Proc. Natl. Acad. Sci. U.S.A. 90:5873-5787. A particularly useful BLAST program is the WU-BLAST-2 program which was obtained from Altschul et al, 1996, Methods in Enzymology 266:460-480. WU-BLAST-2 uses several search parameters, most of which are set to the default values.

An additional useful algorithm is gapped BLAST as reported by Altschul et al, 1993, Nucl. Acids Res. 25:3389-3402.

The term "Invasive Extraintestinal pathogenic *Escherichia coli* (ExPEC) disease (IED)" is defined herein as an acute illness consistent with systemic bacterial infection, which is microbiologically confirmed either by the isolation and identification of *E. coli* from blood or other normally sterile body sites, or by the isolation and identification of *E. coli* from urine in a patient with presence of signs and symptoms of invasive disease (systemic inflammatory response syndrome (SIRS), sepsis or septic shock) and no other identifiable source of infection.

Bioconjugates of *E. coli* Glucosylated O4 Antigen Polysaccharides

In one aspect, provided herein is a bioconjugate of an *E. coli* glucosylated O4 antigen polysaccharide covalently linked to a carrier protein. As used herein, the term "O4" refers to the O4 antigen from *E. coli* (*E. coli* serotype O4). O-antigen structural modification is known to exist within the *E. coli* O4 serotype. In particular, some O4 serotypes express a modified O-antigen having a branched glucose unit. As used herein, "glucosylated O4 antigen," "glucosylated O4 antigen polysaccharide, "O4-Glc+ antigen polysaccharide," and "O4-Glc+ antigen" refer to an O4 antigen (e.g., *E. coli* O4 antigen) having a glucose branch, in which D-glucose is linked to L-rhamnose in the repeating unit L-Rha→D-Glc→L-FucNAc→D-GlcNAc. In a particular embodiment, an *E. coli* glucosylated O4 antigen polysaccharide comprises the structure of formula (O4-Glc+), as shown in Table 1, wherein n is an integer of 1 to 100. In preferred embodiments, n is an integer of 3 to 50, e.g. 5 to 40, e.g. 7 to 25, e.g. 10 to 20.

*E. coli* O4 strains, independent of glucose branching status, carry a substantially identical rfb gene cluster encoding the genes responsible for production of the O4 antigen polysaccharide. However, in vivo synthesis of the modified O4 antigen having glucose branching requires the activity of a polysaccharide branching enzyme, which lies outside of the rfb gene cluster. To the best of the knowledge of the inventors, the identity of the polysaccharide branching enzyme responsible for glucose modification of the O4 antigen has remained unknown to date. Here, the inventors discovered the sequence of the polysaccharide branching enzyme responsible for glucose modification of the O4 antigen. Identification of this enzyme enables production of bioconjugates of the modified O4 antigen polysaccharide having glucose branching. The glucose modified form of the O4 antigen polysaccharide is present in predominant serotypes and can thus be used to provide an improved immune response, e.g for prophylactic or therapeutic use.

In particular, provided herein is the sequence of a gtrS gene encoding a glucosyltransferase enzyme specific for *E. coli* serotype O4 that glucosylates the O4 antigen. In general, the gtrA, gtrB, and gtrS genes encodes the enzymes responsible for O-antigen glucosylation. While the gtrA and gtrB genes in different serotypes are highly homologous and interchangeable, the gtrS gene encodes a serotype specific O-antigen glucosyl transferase. The gtrS gene of *E. coli* serotype O4 encodes the GtrS enzyme that modifies the O4 antigen by introducing glucose branching. Characterization of contemporary clinical *E. coli* isolates of the O4 serotype revealed the presence of gtrS in 78% of tested isolates, indicating that *E. coli* O4 antigen polysaccharide modified with the addition of a glucose residue is predominant in current infecting isolates.

In one embodiment, provided herein is a nucleic acid of a gtrS gene from *E. coli* serotype O4 encoding a GtrS glucosyltransferase comprising the amino acid sequence of SEQ ID NO: 4. In another embodiment, a gtrS nucleic acid encodes a GtrS protein from *E. coli* serotype O4 that is about 80%, 85%, 90%, 95%, 96%, 97%, 98%, 99%, or 100% identical to the amino acid sequence of SEQ ID NO: 4, preferably 98%, 99%, or 100% identical to the amino acid sequence of SEQ ID NO: 4. A GtrS protein that is at least 80% identical to the amino acid sequence of SEQ ID NO: 4 is capable of specifically glucosylating the *E. coli* O4 antigen polysaccharide to obtain a glucosylated O4 antigen having the structure of Formula (O4-Glc+) as shown in Table 1. One of ordinary skill in the art will be able to make mutated forms of the GtrS protein of SEQ ID NO: 4 having at least 80% sequence identity to SEQ ID NO: 4, and test such sequences for glucosylation activity of the *E. coli* O4 antigen in view of the present disclosure. Recombinant host cells comprising nucleic acid sequence encoding the glucosyl transferase gtrS gene of *E. coli* serotype O4, and use of the recombinant host cells in production of the glucose modified O4 antigen polysaccharides and bioconjugates thereof are described in greater detail below.

Sequences for gtrA and gtrB encoded proteins, which function as bactoprenol-linked glucose translocase (GtrA, flips the bactoprenol-linked glucose over the inner membrane to the periplasm) and bactoprenol glucosyl transferase (GtrB, links glucose to bactoprenol), respectively, may comprise amino acid sequences that are at least about 80% identical to SEQ ID NOs: 7 and 8, respectively. In certain embodiments, nucleic acid sequences encoding GtrA and GtrB proteins that are at least about 80%, 85%, 90%, 95%, 96%, 97%, 98%, 99%, or 100% identical to SEQ ID NOs: 7 and 8, respectively, and having bactoprenol-linked glucose translocase and bactoprenol glucosyl transferase activity, respectively, are also present in the host cells of the invention, that further comprise an O4-specific rfb locus, the O4-specific GtrS encoding sequence described above, an oligosaccharyl transferase as described herein, and a sequence encoding a carrier protein having one or more glycosylation consensus sequences as described herein, to produce bioconjugates of *E. coli* glucosylated O4 serotype (comprising glycan structure of Formula (O4-Glc+) in Table 1).

Bioconjugates of an *E. coli* glucosylated O4 antigen polysaccharide provided herein are covalently linked to a carrier protein, preferably by a glycosidic linkage. Any carrier protein known to those skilled in the art in view of the present disclosure can be used. Suitable carrier proteins include, but are not limited to, detoxified Exotoxin A of *P. aeruginosa* (EPA), *E. coli* flagellin (FliC), CRM197, maltose binding protein (MBP), Diphtheria toxoid, Tetanus toxoid, detoxified hemolysin A of *S. aureus*, clumping factor A, clumping factor B, *E. coli* heat labile enterotoxin, detoxified variants of *E. coli* heat labile enterotoxin, Cholera toxin B subunit (CTB), cholera toxin, detoxified variants of cholera toxin, *E. coli* Sat protein, the passenger domain of *E. coli* Sat protein, *Streptococcus pneumoniae* Pneumolysin, Keyhole limpet hemocyanin (KLH), *P. aeruginosa* PcrV, outer membrane protein of *Neisseria meningitidis* (OMPC), and protein D from non-typeable *Haemophilus influenzae*. Bioconjugation with various different carrier proteins containing the required consensus glycosylation sequence has been described, showing that a wide range of proteins can be glycosylated using this technology (see, e.g. WO 06/119987, WO 2015/124769, WO 2015/158403, WO 2015/82571, WO 2017/216286, and WO 2017/67964, together showing a wide variety of carrier proteins that were successfully used in bioconjugation).

In certain embodiments a carrier protein is modified, e.g., modified in such a way that the protein is less toxic and/or more susceptible to glycosylation. In a specific embodiment, the carrier proteins used herein are modified such that the number of glycosylation sites in the carrier proteins is maximized in a manner that allows for lower concentrations of the protein to be administered, e.g., in an immunogenic composition, particularly in its bioconjugate form.

Thus, in certain embodiments, the carrier proteins described herein are modified to include 1, 2, 3, 4, 5, 6, 7, 8, 9, 10 or more glycosylation sites than would normally be associated with the carrier protein (e.g., relative to the number of glycosylation sites associated with the carrier protein in its native/natural, i.e., “wild-type” state). Introduction of glycosylation sites into a carrier protein can be accomplished by insertion of a glycosylation consensus sequence anywhere in the primary structure of the protein by, e.g., adding new amino acids to the primary structure of the protein such that a glycosylation site is added in full or in part, or by mutating existing amino acids in the protein in order to generate a glycosylation site. One of ordinary skill in the art will recognize that the amino acid sequence of a protein can be readily modified using approaches known in the art, e.g., recombinant approaches that include modification of the nucleic acid sequence encoding the protein. In specific embodiments, glycosylation consensus sequences are introduced into specific regions of the carrier protein, e.g., surface structures of the protein, at the N or C termini of the protein, and/or in loops that are stabilized by disulfide bridges at the base of the protein. In some embodiments, a glycosylation consensus sequence can be extended by addition of lysine residues for more efficient glycosylation.

Exemplary examples of glycosylation consensus sequences that can be inserted into or generated in a carrier protein include Asn-X-Ser(Thr), wherein X can be any amino acid except Pro (SEQ ID NO: 1); and Asp(Glu)-X-

Asn-Z-Ser(Thr), wherein X and Z are independently selected from any amino acid except Pro (SEQ ID NO: 2).

In some embodiments, the *E. coli* glucosylated O4 antigen polysaccharide is covalently linked to an asparagine (Asn) residue in the carrier protein (e.g., N-linked), wherein the Asn residue is present in a glycosylation site comprising a glycosylation consensus sequence having SEQ ID NO: 1, more preferably having SEQ ID NO: 2. Typically, a carrier protein comprises 1-10 glycosylation sites, preferably 2 to 4 glycosylation sites, most preferably 4 glycosylation sites, such as 1-10, preferably 2-4, and more preferably 4 glycosylation sites each comprising a glycosylation consensus sequences having the amino acid sequence of SEQ ID NO: 1, and more preferably the amino acid sequence of SEQ ID NO: 2.

In particular embodiments, a carrier protein is a detoxified Exotoxin A of *P. aeruginosa*. For EPA, various detoxified protein variants have been described in literature and could be used as carrier proteins. For example, detoxification can be achieved by mutating and deleting the catalytically essential residues L552V and ΔE553 according to Lukac et al., 1988, *Infect Immun,* 56: 3095-3098, and Ho et al., 2006, *Hum Vaccin,* 2:89-98. As used herein, "EPA" refers to a detoxified Exotoxin A of *P. aeruginosa*. In those embodiments, wherein the carrier protein is EPA, an *E. coli* glucosylated O4 antigen polysaccharide can be covalently linked to an Asn residue in a glycosylation site comprising a glycosylation consensus sequence having SEQ ID NO: 1, and preferably covalently linked to an Asn residue in a glycosylation site comprising a glycosylation consensus sequence having SEQ ID NO: 2. Preferably, the EPA carrier protein comprises 1-10 glycosylation sites, preferably 2 to 4 glycosylation sites, most preferably 4 glycosylation sites, such as 1-10, preferably 2-4, and more preferably 4 glycosylation sites each comprising a glycosylation consensus sequence having the amino acid sequence of SEQ ID NO: 1, and more preferably the amino acid sequence of SEQ ID NO: 2.

In some embodiments, the EPA carrier protein comprises four glycosylation sites each comprising a glycosylation consensus sequence, for instance a glycosylation site comprising a glycosylation consensus sequence having SEQ ID NO: 2. As used herein, "EPA-4 carrier protein" and "EPA-4" refer to a detoxified Exotoxin A of *P. aeruginosa* carrier protein comprising four glycosylation sites each comprising a glycosylation consensus sequences having SEQ ID NO: 2. An exemplary preferred example of an EPA-4 carrier protein is EPA carrier protein comprising the amino acid sequence of SEQ ID NO: 3.

Compositions

In another aspect, provided herein is a composition comprising a bioconjugate of an *E. coli* glucosylated O4 antigen polysaccharide covalently linked to a carrier protein. The compositions provided herein can include any bioconjugate of an *E. coli* glucosylated O4 antigen polysaccharide covalently linked to a carrier protein (e.g., EPA) described herein.

In some embodiments, a composition is an immunogenic composition. As used herein, an "immunogenic composition" refers to a composition that can elicit an immune response in a host or subject to whom the composition is administered. Immunogenic compositions can further comprise a pharmaceutically acceptable carrier. In some embodiments, a composition is a pharmaceutical composition further comprising a pharmaceutically acceptable carrier. As used herein, a "pharmaceutically acceptable carrier" refers to a diluent, adjuvant, excipient or vehicle with which a composition is administered, and that is non-toxic and should not interfere with the efficacy of the active ingredient. For example, saline solutions and aqueous dextrose and glycerol solutions can also be employed as liquid carriers, particularly for injectable solutions. Suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Other examples of suitable pharmaceutically acceptable carriers are described in "Remington's Pharmaceutical Sciences" by E. W. Martin.

In one embodiment, a composition of the invention comprises the bioconjugates of the invention in a Tris-buffered saline (TBS) pH 7.4 (e.g. containing Tris, NaCl and KCl, e.g. at 25 mM, 137 mM and 2.7 mM, respectively). In other embodiments, the compositions of the invention comprise bioconjugates of the invention in about 10 mM $KH_2PO_4$/$Na_2HPO_4$ buffer at pH of about 7.0, about 5% (w/v) sorbitol, about 10 mM methionine, and about 0.02% (w/v) polysorbate 80. In other embodiments, the compositions of the invention comprise bioconjugates of the invention in about 10 mM $KH_2PO_4$/$Na_2HPO_4$ buffer at pH of about 7.0, about 8% (w/v) sucrose, about 1 mM EDTA, and about 0.02% (w/v) polysorbate 80 (see e.g. WO 2018/077853 for suitable buffers for bioconjugates of *E. coli* O-antigens covalently bound to EPA carrier protein).

In some embodiments, the compositions described herein are monovalent formulations, and contain one *E. coli* O-antigen polysaccharide, e.g., in isolated form or as part of a glycoconjugate or bioconjugate, such as the *E. coli* glucosylated O4 antigen polysaccharide. Also provided herein are compositions (e.g., pharmaceutical and/or immunogenic compositions) that are multivalent compositions, e.g., bivalent, trivalent, tetravalent, etc. compositions. For example, a multivalent composition comprises more than one antigen, such as an *E. coli* O-antigen, glycoconjugate, or bioconjugate thereof. In particular embodiments, multivalent compositions provided herein comprise a bioconjugate of an *E. coli* glucosylated O4 antigen polysaccharide, and at least one additional antigen.

In one embodiment, a composition (e.g., pharmaceutical and/or immunogenic composition) is a monovalent composition comprising a bioconjugate of an *E. coli* glucosylated O4 antigen polysaccharide covalently linked to a carrier protein as described herein.

In another embodiment, a composition (e.g., pharmaceutical and/or immunogenic composition) is a multivalent composition comprising an *E. coli* glucosylated O4 antigen polysaccharide covalently linked to a carrier protein as described herein, and at least one additional antigen.

In some embodiments, the additional antigen is antigen saccharide or polysaccharide, more preferably an *E. coli* O-antigen polysaccharide, such as *E. coli* O-antigens of one or more of the O1, O2, O6, O8, O15, O16, O18, O25, and O75 serotypes and subserotypes thereof. In some embodiments, each of the additional *E. coli* O-antigen polysaccharides is a glycoconjugate, meaning that the *E. coli* O-antigen polysaccharide is covalently linked to another chemical species, e.g., protein, peptide, lipid, etc., most preferably a carrier protein, such as by chemical or enzymatic methods. In preferred embodiments, each of the additional *E. coli* O-antigen polysaccharides is a bioconjugate in which the O-antigen polysaccharide is covalently linked to, e.g. a carrier protein, via a glycosidic bond enzymatically by host cell machinery. Compositions provided herein in certain embodiments can comprise 1-20 additional glycoconjugates, more preferably bioconjugates of *E. coli* O-antigen polysaccharides, such as 1, 2, 3, 4, 5, 6, 7, 8, 9, 10, 11, 12, 13, 14, 15, 16, 17, 18, 19 or 20 additional glycoconjugates or preferably bioconjugates of *E. coli* O-antigen polysaccharides. Other antigens can be included in the compositions provided herein, such as peptide, protein, or lipid antigens, etc.

In some embodiments, a composition (e.g., pharmaceutical and/or immunogenic composition) comprises a bioconjugate of an *E. coli* glucosylated O4 antigen polysaccharide, and at least one additional antigen polysaccharide selected from the group consisting of *E. coli* O1A antigen polysaccharide, *E. coli* O2 antigen polysaccharide, *E. coli* O6A antigen polysaccharide, *E. coli* O8 antigen polysaccharide, *E. coli* O15 antigen polysaccharide, *E. coli* O16 antigen polysaccharide, *E. coli* O18A antigen polysaccharide, *E. coli* O25B antigen polysaccharide, and *E. coli* O75 antigen polysaccharide. Preferably, each of the additional O-antigen polysaccharides is covalently linked to a carrier protein, and is more preferably a bioconjugate.

In one embodiment, an O1A antigen polysaccharide (e.g., in isolated form or as part of a glycoconjugate or bioconjugate) is used in a composition provided herein (e.g., in combination with a glucosylated O4 antigen polysaccharide or bioconjugate thereof). In a specific embodiment, the O1A antigen polysaccharide comprises the structure of formula (O1A) as shown in Table 1, wherein n is an integer of 1-100, preferably 3-50, e.g. 5-40, e.g. 7 to 25, e.g. 10 to 20. Preferably, the O1A antigen polysaccharide is part of a bioconjugate and is covalently linked to a carrier protein, e.g., EPA.

In one embodiment, an O2 antigen polysaccharide (e.g., in isolated form or as part of a glycoconjugate or bioconjugate) is used in a composition provided herein (e.g., in combination with a glucosylated O4 antigen polysaccharide or bioconjugate thereof). In a specific embodiment, the O2 antigen polysaccharide comprises the structure of formula (O2) as shown in Table 1, wherein n is an integer of 1-100, preferably 3-50, e.g. 5-40, e.g. 7 to 25, e.g. 10 to 20. Preferably, the O2 antigen polysaccharide is part of a bioconjugate and is covalently linked to a carrier protein, e.g., EPA.

In one embodiment, an O6A antigen polysaccharide (e.g., in isolated form or as part of a glycoconjugate or bioconjugate) is used in a composition provided herein (e.g., in combination with a glucosylated O4 antigen polysaccharide or bioconjugate thereof). In a specific embodiment, the O6A antigen polysaccharide comprises the structure of formula (O6A) as shown in Table 1, wherein n is an integer of 1-100, preferably 3-50, e.g. 5-40, e.g. 7 to 25, e.g. 10 to 20. Preferably, the O6A antigen polysaccharide is part of a bioconjugate and is covalently linked to a carrier protein, e.g., EPA.

In one embodiment, an O8 antigen polysaccharide (e.g., in isolated form or as part of a glycoconjugate or bioconjugate) is used in a composition provided herein (e.g., in combination with a glucosylated O4 antigen polysaccharide or bioconjugate thereof). In a specific embodiment, the O8 antigen polysaccharide comprises the structure of formula (O8) as shown in Table 1, wherein n is an integer of 1-100, preferably 3-50, e.g. 5-40, e.g. 7 to 25, e.g. 10 to 20. Preferably, the O8 antigen polysaccharide is part of a bioconjugate and is covalently linked to a carrier protein, e.g., EPA.

In one embodiment, an O15 antigen polysaccharide (e.g., in isolated form or as part of a glycoconjugate or bioconjugate) is used in a composition provided herein (e.g., in combination with a glucosylated O4 antigen polysaccharide or bioconjugate thereof). In a specific embodiment, the O15 antigen polysaccharide comprises the structure of formula (O15) as shown in Table 1, wherein n is an integer of 1-100, preferably 3-50, e.g. 5-40, e.g. 7 to 25, e.g. 10 to 20. Preferably, the O15 antigen polysaccharide is part of a bioconjugate and is covalently linked to a carrier protein, e.g., EPA.

In one embodiment, an O16 antigen polysaccharide (e.g., in isolated form or as part of a glycoconjugate or bioconjugate) is used in a composition provided herein (e.g., in combination with a glucosylated O4 antigen polysaccharide or bioconjugate thereof). In a specific embodiment, the O16 antigen polysaccharide comprises the structure of formula (O16) as shown in Table 1, wherein n is an integer of 1-100, preferably 3-50, e.g. 5-40, e.g. 7 to 25, e.g. 10 to 20. Preferably, the O16 antigen polysaccharide is part of a bioconjugate and is covalently linked to a carrier protein, e.g., EPA.

In one embodiment, an O18A antigen polysaccharide (e.g., in isolated form or as part of a glycoconjugate or bioconjugate) is used in a composition provided herein (e.g., in combination with a glucosylated O4 antigen polysaccharide or bioconjugate thereof). In a specific embodiment, the O18A antigen polysaccharide comprises the structure of formula (O18A) as shown in Table 1, wherein n is an integer of 1-100, preferably 3-50, e.g. 5-40, e.g. 7 to 25, e.g. 10 to 20. Preferably, the O18A antigen polysaccharide is part of a bioconjugate and is covalently linked to a carrier protein, e.g., EPA.

In one embodiment, an O25B antigen polysaccharide (e.g., in isolated form or as part of a glycoconjugate or bioconjugate) is used in a composition provided herein (e.g., in combination with a glucosylated O4 antigen polysaccharide or bioconjugate thereof). In a specific embodiment, the O25B antigen polysaccharide comprises the structure of formula (O25B) as shown in Table 1, wherein n is an integer of 1-100, preferably 3-50, e.g. 5-40, e.g. 7 to 25, e.g. 10 to 20. Preferably, the O25B antigen polysaccharide is part of a bioconjugate and is covalently linked to a carrier protein, e.g., EPA.

In one embodiment, an O75 antigen polysaccharide (e.g., in isolated form or as part of a glycoconjugate or bioconjugate) is used in a composition provided herein (e.g., in combination with a glucosylated O4 antigen polysaccharide or bioconjugate thereof). In a specific embodiment, the O75 antigen polysaccharide comprises the structure of formula (O75) as shown in Table 1, wherein n is an integer of 1-100, preferably 3-50, e.g. 5-40, e.g. 7 to 25, e.g. 10 to 20. Preferably, the O75 antigen polysaccharide is part of a bioconjugate and is covalently linked to a carrier protein, e.g., EPA.

In another embodiment, a composition (e.g., a pharmaceutical and/or immunogenic composition) comprises at least the *E. coli* O1A, O2, glucosylated O4, O6A and O25B antigen polysaccharides, preferably bioconjugates of the O1A, O2, glucosylated O4, O6A and O25B antigen polysaccharides covalently linked to a carrier protein, e.g., EPA (i.e., a pentavalent composition).

In a preferred embodiment, a composition (e.g., a pharmaceutical and/or immunogenic composition) comprises at least the *E. coli* O1A, O2, glucosylated O4, O6A, O8, O15, O16, O25B and O75 antigen polysaccharides, preferably bioconjugates of the O1A, O2, glucosylated O4, O6A, O8, O15, O16, O25B and O75 antigen polysaccharides covalently linked to a carrier protein, e.g., EPA (i.e., a 9-valent composition).

In another preferred embodiment, a composition (e.g., a pharmaceutical and/or immunogenic composition) comprises at least the *E. coli* O1A, O2, glucosylated O4, O6A, O8, O15, O16, O18A, O25B and O75 antigen polysaccharides, preferably bioconjugates of the O1A, O2, glucosylated O4, O6A, O8, O15, O16, O18A, O25B and O75 antigen polysaccharides covalently linked to a carrier protein, e.g., EPA (i.e., a 10-valent composition).

Also contemplated herein are compositions which optionally further comprise additional O-antigens (e.g., in isolated form, or as part of a glycoconjugate or bioconjugate) from other *E. coli* serotypes.

In some embodiments, each of the additional *E. coli* O1A, O2, O6A, O8, O15, O16, O18A, O25B, and/or O75 antigen polysaccharides is covalently linked to a carrier protein. The O-antigen polysaccharide can be linked to a carrier protein by chemical or other synthetic methods, or the O-antigen polysaccharide can be part of a bioconjugate, and is preferably part of a bioconjugate. Any carrier protein known to those skilled in the art in view of the present disclosure can be used. Suitable carrier proteins include, but are not limited to, detoxified Exotoxin A of *P. aeruginosa* (EPA), *E. coli* flagellin (FliC), CRM197, maltose binding protein (MBP), Diphtheria toxoid, Tetanus toxoid, detoxified hemolysin A of *S. aureus*, clumping factor A, clumping factor B, *E. coli* heat labile enterotoxin, detoxified variants of *E. coli* heat labile enterotoxin, Cholera toxin B subunit (CTB), cholera toxin, detoxified variants of cholera toxin, *E. coli* Sat protein, the passenger domain of *E. coli* Sat protein, *Streptococcus pneumoniae* Pneumolysin, Keyhole limpet hemocyanin (KLH), *P. aeruginosa* PcrV, outer membrane protein of *Neisseria meningitidis* (OMPC), and protein D from nontypeable *Haemophilus influenzae*. Preferably, the carrier protein is EPA.

In some embodiments, each of the additional *E. coli* O1A, O2, O6A, O8, O15, O16, O18A, O25B, and/or O75 antigen polysaccharides, particularly when part of a bioconjugate, is covalently linked to an asparagine (Asn) residue in the carrier protein, wherein the Asn residue is present in a glycosylation site comprising a glycosylation consensus sequence Asn-X-Ser(Thr), wherein X can be any amino acid except Pro (SEQ ID NO: 1), preferably wherein the Asn residue is present in a glycosylation site comprising a glycosylation consensus sequence Asp(Glu)-X-Asn-Z-Ser(Thr), wherein X and Z are independently selected from any amino acid except Pro (SEQ ID NO: 2). The carrier protein can comprise 1-10 glycosylation sites, preferably 2 to 4 glycosylation sites, most preferably 4 glycosylation sites, each comprising a glycosylation consensus sequence. In a particular embodiment, the carrier protein is EPA-4 carrier protein, for instance EPA-4 carrier protein comprising the amino acid sequence of SEQ ID NO: 3.

In a particular embodiment, provided herein is a composition (e.g., pharmaceutical and/or immunogenic composition) comprising: (i) a bioconjugate of an *E. coli* glucosylated O4 antigen polysaccharide covalently linked to a detoxified Exotoxin A of *P. aeruginosa* carrier protein comprising SEQ ID NO: 3 (EPA-4 carrier protein), wherein the *E. coli* glucosylated O4 antigen polysaccharide comprises the structure of Formula (O4-Glc+); (ii) a bioconjugate of an *E. coli* O1A antigen polysaccharide covalently linked to an EPA-4 carrier protein, wherein the *E. coli* O1A antigen polysaccharide comprises the structure of Formula (O1A); (iii) a bioconjugate of an *E. coli* O2 antigen polysaccharide covalently linked to an EPA-4 carrier protein, wherein the *E. coli* O2 antigen polysaccharide comprises the structure of Formula (O2); (iv) a bioconjugate of an *E. coli* O6A antigen polysaccharide covalently linked to an EPA-4 carrier protein, wherein the *E. coli* O6A antigen polysaccharide comprises the structure of Formula (O6A); (v) a bioconjugate of an *E. coli* O8 antigen polysaccharide covalently linked to an EPA-4 carrier protein, wherein the *E. coli* O8 antigen polysaccharide comprises the structure of Formula (O8); (vi) a bioconjugate of an *E. coli* O15 antigen polysaccharide covalently linked to an EPA-4 carrier protein, wherein the *E. coli* O15 antigen polysaccharide comprises the structure of Formula (O15); (vii) a bioconjugate of an *E. coli* O16 antigen polysaccharide covalently linked to an EPA-4 carrier protein, wherein the *E. coli* O16 antigen polysaccharide comprises the structure of Formula (O16); (viii) a bioconjugate of an *E. coli* O25B antigen polysaccharide covalently linked to an EPA-4 carrier protein, wherein the *E. coli* O25B antigen polysaccharide comprises the structure of Formula (O25B); and (ix) a bioconjugate of an *E. coli* O75 antigen polysaccharide covalently linked to an EPA-4 carrier protein, wherein the *E. coli* O75 antigen polysaccharide comprises the structure of Formula (O75), wherein each of the Formulas is provided in Table 1, and for each of the Formulas independently n is an integer of 1 to 100, e.g. 1 to 50, preferably 3 to 50, e.g. 5 to 40.

In a particular embodiment, said composition (e.g. pharmaceutical and/or immunogenic composition) further comprises: (x) a bioconjugate of an *E. coli* O18A antigen polysaccharide covalently linked to an EPA-4 carrier protein, wherein the *E. coli* O18A antigen polysaccharide comprises the structure of Formula (O18A) as shown in Table 1, wherein n for this structure is an integer of 1 to 100, e.g. 1 to 50, preferably 3 to 50, e.g. 5 to 40.

In some embodiments, a composition provided herein comprises a bioconjugate of an *E. coli* glucosylated O4 antigen polysaccharide, and at least a bioconjugate of an *E. coli* O25B antigen polysaccharide, wherein the bioconjugate of the *E. coli* O25B antigen polysaccharide is present in the composition at a concentration that is about 1.5 to 6 times, e.g. about 2 to 4 times higher, such as 1.5, 2, 3, 4, 5 or 6 times higher than the concentration of any of the other bioconjugates present in the composition.

In particular embodiments, a composition comprises bioconjugates of *E. coli* O1A, O2, glucosylated O4, O6A, O8, O15, O16, O25B, and O75 antigen polysaccharides, wherein the bioconjugates of O1A:O2:glucosylated O4:O6A:O8:O15:O16:O25B:O75 are present in a ratio (by weight of O-antigen polysaccharide) of 1:1:1:1:1:1:1:2:1, or 2:1:1:1:2:1:1:1:4:1.

In particular embodiments, a composition comprises bioconjugates of *E. coli* O1A, O2, glucosylated O4, O6A, O8, O15, O16, O18A, O25B, and O75 antigen polysaccharides, wherein the bioconjugates of O1A:O2:glucosylated O4:O6A:O8:O15:O16:O18A:O25B:O75 are present in a ratio (by weight of O-antigen polysaccharide) of 1:1:1:1:1:1:1:1:2:1, or 2:1:1:2:1:1:1:1:4:1.

In some embodiments, a composition provided herein comprises a bioconjugate of an *E. coli* glucosylated O4 antigen polysaccharide, and at least a bioconjugate of an *E. coli* O25B antigen polysaccharide, wherein the bioconjugate of the *E. coli* O25B antigen polysaccharide is present in the composition at a concentration of 2 to 50 μg/mL, preferably 8 to 40 μg/mL, more preferably 16-32 μg/mL, such as 16, 18, 20, 22, 24, 26, 28, 30, or 32 μg/mL. In such embodiments, the concentration of the bioconjugate of the *E. coli* O25B antigen polysaccharide is preferably about 1.5 to 6 times, e.g., about 2 to 4 times higher, such as 1.5, 2, 3, 4, 5, or 6 times higher than the concentration of any of the other bioconjugates present in the composition.

In certain embodiments, the compositions described herein (e.g., pharmaceutical and/or immunogenic compositions) comprise, or are administered in combination with, an adjuvant. The adjuvant for administration in combination with a composition described herein may be administered before (e.g. within 72 hours, 48 hours, 24 hours, 12 hours, 6 hours, 2 hours, 1 hour, 10 minutes), concomitantly with, or after (e.g. within 72 hours, 48 hours, 24 hours, 12 hours, 6 hours, 2 hours, 1 hour, 10 minutes) administration of said composition. As used herein, the term "adjuvant" refers to a compound that when administered in conjunction with or as part of a composition described herein augments, enhances and/or boosts the immune response to an E. coli O-antigen polysaccharide in a bioconjugate, but when the adjuvant compound is administered alone does not generate an immune response to the E. coli O-antigen polysaccharide in the bioconjugate. In some embodiments, the adjuvant enhances an immune response to an E. coli O-antigen polysaccharide in a bioconjugate thereof and does not produce an allergy or other adverse reaction. Adjuvants can enhance an immune response by several mechanisms including, e.g., lymphocyte recruitment, stimulation of B and/or T cells, and stimulation of macrophages.

Examples of suitable adjuvants include, but are not limited to, aluminum salts (alum) (such as aluminum hydroxide, aluminum phosphate, aluminum sulfate and aluminum oxide, including nanoparticles comprising alum or nanoalum formulations), calcium phosphate, monophosphoryl lipid A (MPL) or 3-de-O-acylated monophosphoryl lipid A (3D-MPL) (see e.g., United Kingdom Patent GB2220211, EP0971739, EP 1194166, U.S. Pat. No. 6,491,919), AS01, AS02, AS03 and AS04 (all GlaxoSmithKline; see e.g. EP1126876, U.S. Pat. No. 7,357,936 for AS04, EP0671948, EP0761231, U.S. Pat. No. 5,750,110 for AS02), MF59 (Novartis), imidazopyridine compounds (see WO2007/109812), imidazoquinoxaline compounds (see WO2007/109813), delta-inulin, STING-activating synthetic cyclic-dinucleotides (e.g. US20150056224), combinations of lecithin and carbomer homopolymers (e.g. U.S. Pat. No. 6,676,958), and saponins, such as QuilA and QS21 (see e.g. Zhu D and W Tuo, 2016, Nat Prod Chem Res 3: e113 (doi:10.4172/2329-6836.1000e113), Matrix M, Iscoms, Iscomatrix, etc, optionally in combination with QS7 (see Kensil et al., in Vaccine Design: The Subunit and Adjuvant Approach (eds. Powell & Newman, Plenum Press, N Y, 1995); U.S. Pat. No. 5,057,540). In some embodiments, the adjuvant is Freund's adjuvant (complete or incomplete). Other adjuvants are oil in water emulsions (such as squalene or peanut oil), optionally in combination with immune stimulants, such as monophosphoryl lipid A (see Stoute et al., N. Engl. J. Med. 336, 86-91 (1997)). Another adjuvant is CpG (Bioworld Today, Nov. 15, 1998). Further examples of adjuvants are liposomes containing immune stimulants such as MPL and QS21 such as in AS01E and AS01B (e.g. US 2011/0206758). Other examples of adjuvants are CpG (Bioworld Today, Nov. 15, 1998) and imidazoquinolines (such as imiquimod and R848). See, e.g., Reed G, et al., 2013, Nature Med, 19: 1597-1608. In certain embodiments, the adjuvant contains a toll-like receptor 4 (TLR4) agonist. TLR4 agonists are well known in the art, see e.g. Ireton G C and S G Reed, 2013, Expert Rev Vaccines 12: 793-807. In certain embodiments, the adjuvant comprises a TLR4 agonist comprising lipid A, or an analog or derivative thereof, such as MPL, 3D-MPL, RC529 (e.g. EP1385541), PET-lipid A, GLA (glycopyranosyl lipid adjuvant, a synthetic disaccharide glycolipid; e.g. US20100310602, U.S. Pat. No. 8,722,064), SLA (e.g. Carter D et al, 2016, Clin Transl Immunology 5: e108 (doi: 10.1038/cti.2016.63), which describes a structure-function approach to optimize TLR4 ligands for human vaccines), PHAD (phosphorylated hexaacyl disaccharide), 3D-PHAD (the structure of which is the same as that of GLA), 3D-(6-acyl)-PHAD (3D(6A)-PHAD) (PHAD, 3D-PHAD, and 3D(6A)PHAD are synthetic lipid A variants, see e.g. avantilipids.com/divisions/adjuvants, which also provide structures of these molecules), E6020 (CAS Number 287180-63-6), ONO4007, OM-174, and the like.

In certain embodiments, the compositions described herein do not comprise, and are not administered in combination with, an adjuvant.

In certain embodiments, the compositions described herein are formulated to be suitable for the intended route of administration to a subject. For example, the compositions (e.g., pharmaceutical and/or immunogenic) described herein can be formulated for subcutaneous, parenteral, oral, sublingual, buccal, intradermal, transdermal, colorectal, intraperitoneal, rectal administration, intravenous, intranasal, intratracheal, intramuscular, topical, transdermal, or intradermal administration. In a specific embodiment, a composition provided herein (e.g., pharmaceutical and/or immunogenic) is formulated for intramuscular injection.

Methods of Use

Bioconjugates and compositions provided herein can be used to induce antibodies against an E. coli glucosylated O4 antigen in a subject, and to vaccinate a subject against E. coli in particular extra-intestinal pathogenic E. coli (ExPEC). As used herein, "subject" means any animal, preferably a mammal, to whom will be or has been administered a bioconjugate or composition provided herein. The term "mammal" as used herein, encompasses any mammal. Examples of mammals include, but are not limited to, cows, horses, sheep, pigs, cats, dogs, mice, rats, rabbits, guinea pigs, non-human primates (NHPs) such as monkeys or apes, humans, etc. In certain embodiments, a subject is a human. A human subject may be of any age. In certain embodiments, a subject is a human of about two months to about 18 years old, e.g. of 1 year to 18 years old. In certain embodiments, a subject is a human of at least 18 years old. In certain embodiments, a subject is a human of 15 to 50 years old, e.g. 18 to 45 years old, e.g. 20 to 40 years old. In certain embodiments, a subject is a human male. In certain embodiments, a subject is a human female. In certain embodiments, a subject is immunocompromised. In certain embodiments, a subject is a human of at least 50 years, at least 55 years, at least 60 years, at least 65 years old. In certain embodiments, a subject is a human that is not older than 100 years, not older than 95 years, not older than 90 years, not older than 85 years, not older than 80 years, or not older than 75 years. In certain embodiments, a subject is a human of at least 60 years old, and not older than 85 years old. In certain embodiments, a subject is a human in stable health. In certain embodiments, a subject is a human adult of at least 60 and not more than 85 years old in stable health. In certain embodiments, a subject is a human that has a history of a urinary tract infection (UTI, i.e. a bacterial infection in the urethra, bladder, ureters, and/or kidneys), i.e. having had at least one UTI episode in his or her life. In certain embodiments, a subject is a human that has a history of UTI in the past twenty, fifteen, twelve, ten, nine, eight, seven, six, five, four, three, two or one years. In certain embodiments, a subject is a human that has a history of UTI in the past two years. In certain embodiments, a subject is a human subject that has a history of recurrent UTI, i.e. having had at least two UTIs in six months or at least three UTIs in one year. In certain embodiments, a subject is a human subject that has a history of recurrent UTI in the past two years. In certain embodiments, a subject is a human of 60 years or older in stable health. In certain embodiments, a subject is a human of 60 years or older that has a history of UTI in the past two years. In certain embodiments, a subject is a human of at least 60 years and less than 75 years old that has a history of UTI in the past two years. In certain embodiments, a subject is a human subject of 75 years or older that has a history of UTI in the past two years. In certain embodiments, a subject is a patient scheduled for undergoing elective urogenital and/or abdominal procedures or surgeries, e.g. transrectal ultrasound-guided prostate needle biopsy (TRUS-PNB).

In one aspect, provided herein is a method of inducing antibodies against an *E. coli* glucosylated O4 antigen in a subject, comprising administering to the subject any of the bioconjugates of an *E. coli* glucosylated O4 antigen covalently linked to a carrier protein described herein, or a composition comprising a bioconjugate of an *E. coli* glucosylated O4 antigen covalently linked to a protein, alone or further in combination with other *E. coli* O-antigen polysaccharides or glycoconjugates or bioconjugates thereof.

In certain embodiments, the antibodies induced, elicited or identified against an *E. coli* glucosylated O4 antigen have opsonophagocytic activity. In particular embodiments, the antibodies induced, elicited or identified are cross-reactive antibodies capable of mediating opsonophagocytic killing of both *E. coli* glucosylated and non-glucosylated O4 strains.

In certain embodiments, the antibodies induced, elicited or identified against an *E. coli* glucosylated O4 antigen specifically recognize unmodified and glucose modified O4 antigen polysaccharide. In certain embodiments, the antibodies induced, elicited or identified against an *E. coli* glucosylated O4 antigen specifically recognize *E. coli* of the O4 serotype. In certain embodiments, the antibodies induced by a bioconjugate of an *E. coli* glucosylated O4 antigen bind preferentially to glucosylated O4 antigen as compared to non-glucosylated O4 antigen.

Antibodies induced by the bioconjugates and compositions described herein can include immunoglobulin molecules and immunologically active portions of immunoglobulin molecules, i.e., molecules that contain an antigen binding site that specifically binds to an *E. coli* O-antigen polysaccharide, e.g., glucosylated O4 antigen polysaccharide.

Antibodies induced, elicited or identified using the bioconjugates or compositions provided herein can be used to monitor the efficacy of a therapy and/or disease progression. Any immunoassay system known in the art can be used for this purpose including, but not limited to, competitive and noncompetitive assay systems using techniques such as radioimmunoassays, ELISA (enzyme linked immunosorbent assays), electrochemiluminescence (ECL)-based immunoassays, "sandwich" immunoassays, precipitin reactions, gel diffusion precipitin reactions, immunodiffusion assays, immunoradiometric assays, fluorescent immunoassays, protein A immunoassays and immunoelectrophoresis assays. Several of these assays, e.g. ECL-based immunoassays, can be done in multiplex format, and typically multiplex assay formats are preferred.

Antibodies induced, elicited or identified using a bioconjugate of an *E. coli* glucosylated O4 antigen polysaccharide can be used to detect *E. coli* O4 strains, particularly glucosylated O4 strains, for example, from a plurality of *E. coli* strains and/or to diagnose an infection by an *E. coli* O4 or glucosylated O4 strain.

In another aspect, provided herein is a method of vaccinating a subject against *E. coli* (e.g. extra-intestinal pathogenic *E. coli*, ExPEC), comprising administering to the subject any of the bioconjugates of an *E. coli* glucosylated O4 antigen covalently linked to a carrier protein described herein, or a composition comprising a bioconjugate of an *E. coli* glucosylated O4 antigen covalent linked to a carrier protein, alone or further in combination with other *E. coli* O-antigens or glycoconjugates or bioconjugates thereof. One skilled in the art will understand that the subject will be vaccinated against *E. coli* strains whose O antigens or glycoconjugates or bioconjugates thereof are present in the composition administered. For example, administration of a composition comprising O1A, O2, glucosylated O4, O6A, and O25B antigen polysaccharides can be used to a vaccinate a subject against *E. coli* serotypes O1A, O2, O4, O6A, and O25B.

In certain embodiments, vaccination is for preventing an invasive ExPEC disease (IED), e.g., urosepsis, bacteremia, sepsis, etc. In certain embodiments, vaccination is to prevent or reduce the occurrence or severity of urinary tract infections. In certain embodiments, an IED can be hospital-acquired, e.g. in patients undergoing urogenital and/or abdominal procedures or surgeries. In certain embodiments, an IED can be healthcare-associated, e.g. in patients receiving health care for another condition, for instance via central lines, catheters, etc, e.g. in a hospital, ambulatory surgical center end-stage renal disease facility, long-term care facility, etc. In certain embodiments, the IED can be community-acquired, e.g. in a patient that was not recently exposed to healthcare risks.

In another aspect, provided herein is a method of inducing an immune response against *E. coli* (e.g., ExPEC) in a subject, comprising administering to the subject any of the bioconjugates of an *E. coli* glucosylated O4 antigen covalently linked to a carrier protein described herein, or a composition comprising a bioconjugate of an *E. coli* glucosylated O4 antigen covalently linked to a carrier protein, alone or further in combination with other *E. coli* O-antigens or glycoconjugates or bioconjugates thereof. In one embodiment, the subject has an *E. coli* (e.g., ExPEC) infection at the time of administration. In a preferred embodiment, the subject does not have an *E. coli* (e.g., ExPEC) infection at the time of administration.

In certain embodiments, the compositions and bioconjugates described herein can be administered to a subject to induce an immune response that includes the production of antibodies, preferably antibodies having opsonophagocytic activity. Such antibodies can be isolated using techniques known to one of skill in the art (e.g., immunoaffinity chromatography, centrifugation, precipitation, etc.).

The ability of the bioconjugates and compositions described herein to generate an immune response in a subject can be assessed using any approach known to those of skill in the art or described herein. In some embodiments, the ability of a bioconjugate to generate an immune response in a subject can be assessed by immunizing a subject (e.g., a mouse, rat, rabbit, or monkey) or set of subjects with a bioconjugate described herein and immunizing an additional subject (e.g., a mouse, rat, rabbit, or monkey) or set of subjects with a control (PBS). The subjects or set of subjects can subsequently be challenged with ExPEC and the ability of the ExPEC to cause disease (e.g., UTI, bacteremia, or other disease) in the subjects or set of subjects can be determined. Those skilled in the art will recognize that if the subject or set of subjects immunized with the control suffer(s) from disease subsequent to challenge with the ExPEC but the subject or set of subjects immunized with a bioconjugate(s) or composition thereof described herein suffer less from or do not suffer from disease, then the bioconjugate is able to generate an immune response in a subject. The ability of a bioconjugate(s) or composition thereof described herein to induce antiserum that cross-reacts with an O antigen from ExPEC can be tested by, e.g., an immunoassay, such as an ELISA (see e.g., Van den Dobbelsteen et al, 2016, Vaccine 34: 4152-4160), or an ECL-based immunoassay.

For example, the ability of the bioconjugates described herein to generate an immune response in a subject can be assessed using a serum bactericidal assay (SBA) or opsonophagocytic killing assay (OPK assay, or OPKA), which represents an established and accepted method that has been used to obtain approval of glycoconjugate-based vaccines. Such assays are well-known in the art and, briefly, comprise the steps of generating and isolating antibodies against a target of interest (e.g., an O antigen polysaccharide, e.g., *E. coli* glucosylated O4 antigen polysaccharide) by administering to a subject (e.g., a mouse, rat, rabbit, or monkey) a compound that elicits such antibodies. Subsequently, the bactericidal capacity of the antibodies can be assessed by, e.g., culturing the bacteria in question (e.g., *E. coli* of the relevant serotype) in the presence of the antibodies and complement and—depending on the assay—neutrophilic cells and assaying the ability of the antibodies to mediate killing and/or neutralization of the bacteria, e.g., using standard microbiological approaches. For an example of OPK assay for *E. coli* bioconjugate vaccines, see e.g. Abbanat et al, 2017, Clin. Vaccine Immunol. 24: e00123-17. An OPK assay can be performed in monoplex or multiplex format, of which multiplex format (e.g. testing multiple serotypes at the same time) is typically preferred. A multiplex OPK assay is sometimes referred to herein as 'MOPA'.

In some embodiments, the methods described herein comprise administering an effective amount of bioconjugates of an *E. coli* glucosylated O4 antigen covalently linked to a carrier protein described herein, or a composition comprising a bioconjugate of an *E. coli* glucosylated O4 antigen covalently linked to a carrier protein, alone or further in combination with other *E. coli* O-antigens or glycoconjugates or bioconjugates thereof. In one embodiment, an "effective amount" is an amount that vaccinates a subject against *E. coli* (e.g., ExPEC). In another embodiment, an "effective amount" is an amount that induces an immune response against *E. coli* (e.g., ExPEC) in a subject, such as an immune response including the production of antibodies, preferably antibodies having opsonophagocytic activity.

In particular embodiments, wherein a composition provided herein comprises a bioconjugate of an *E. coli* glucosylated O4 antigen polysaccharide and at least a bioconjugate of an *E. coli* O25B antigen polysaccharide, an effective amount of the *E. coli* O25B antigen polysaccharide is about 1.5 to 6 times, e.g. about 2 to 4 times higher, such as 1.5, 2, 3, 4, 5 or 6 times higher than the concentration of any of the other bioconjugates present in the composition. In such embodiments, an effective amount of the *E. coli* O25B antigen polysaccharide is for instance about 5 to 18 µg per administration, such as 5, 6, 7, 8, 9, 10, 11, 12, 13, 14, 15, 16, 17, 18 µg per administration.

In certain embodiments, a bioconjugate or composition according to the invention is administered to a subject once. In certain embodiments, a bioconjugate or composition according to the invention is administered to a subject more than once, e.g. in a prime-boost regimen. In certain embodiments, the time between two administrations is at least two weeks, at least one month, at least two months, at least three months, at least six months, at least one year, at least two years, at least five years, at least ten years, or at least fifteen years. In humans, a desired immune response can typically be generated by a single administration of a bioconjugate or composition according to the invention. In certain embodiments, a repeat administration after for instance ten years is provided.

Host Cells

Provided herein are host cells, e.g., prokaryotic host cells, capable of producing *E. coli* O antigens and bioconjugates comprising such *E. coli* O antigens. The host cells provided herein preferably are modified to comprise (e.g., through genetic engineering) one or more of the nucleic acids encoding host cell machinery (e.g., glycosyltransferases) used to produce *E. coli* O-antigen polysaccharides and/or bioconjugates thereof.

Any host cells known to those of skill in the art can be used to produce the *E. coli* O antigen polysaccharides described herein (e.g., *E. coli* glucosylated O4 antigen polysaccharide) and bioconjugates comprising the *E. coli* O antigen polysaccharides described herein (e.g., a bioconjugate of *E. coli* glucosylated O4 antigen polysaccharide) including archaea, prokaryotic host cells, and eukaryotic host cells. In a preferred embodiment, a host cell is a prokaryotic host cell. Exemplary prokaryotic host cells for use in production of the *E. coli* O antigen polysaccharides described herein and bioconjugates comprising the *E. coli* O antigen polysaccharides described herein include, but are not limited to, *Escherichia* species, *Shigella* species, *Klebsiella* species, *Xhantomonas* species, *Salmonella* species, *Yersinia* species, *Lactococcus* species, *Lactobacillus* species, *Pseudomonas* species, *Corynebacterium* species, *Streptomyces* species, *Streptococcus* species, *Staphylococcus* species, *Bacillus* species, and *Clostridium* species.

In a specific embodiment, the host cell used to produce the *E. coli* O antigen polysaccharides described herein and bioconjugates comprising the *E. coli* O antigen polysaccharides described herein is a prokaryotic host cell, and is preferably *E. coli*.

In certain embodiments, the host cells used to produce the *E. coli* O antigen polysaccharides and bioconjugates described herein are engineered to comprise heterologous nucleic acids, e.g., heterologous nucleic acids comprising rfb gene clusters of a desired O antigen serotype, heterologous nucleic acids that encode one or more carrier proteins and/or glycosyltransferases. In a specific embodiment, heterologous rfb genes, and/or heterologous nucleic acids that encode proteins involved in glycosylation pathways (e.g., prokaryotic and/or eukaryotic glycosylation pathways) can be introduced into the host cells described herein. Such nucleic acids can encode proteins including, but not limited to, oligosaccharyl transferases and/or glycosyltransferases.

Sequences of various genes and gene clusters encoding glycosyltransferases useful in making recombinant host cells that can, e.g., be used to prepare *E. coli* O antigen polysaccharides and bioconjugates thereof are described herein. Those skilled in the art will appreciate that due to the degeneracy of the genetic code, a protein having a specific amino acid sequence can be encoded by multiple different nucleic acids. Thus, those skilled in the art will understand that a nucleic acid provided herein can be altered in such a way that its sequence differs from a sequence provided herein, without affecting the amino acid sequence of the protein encoded by the nucleic acid.

Provided herein are host cells (e.g., recombinant host cells) for producing a bioconjugate of an *E. coli* glucosylated O4 antigen polysaccharide, O1A antigen polysaccharide, O2 antigen polysaccharide, O6A antigen polysaccharide, O8 antigen polysaccharide, O15 antigen polysaccharide, O16 antigen polysaccharide, O18A antigen polysaccharide, O25B antigen polysaccharide, or O75 antigen polysaccharide. The host cells provided herein comprise nucleic acids encoding enzymes (e.g., glycosyltransferases) capable of producing the *E. coli* 0 antigen polysaccharide. The host cells provided herein can naturally express nucleic acids capable of producing an O antigen of interest, or the host cells can be made to express such nucleic acids. In certain embodiments the nucleic acids are heterologous to the host cells and introduced into the host cells using genetic approaches known in the art. For example, the nucleic acids can be introduced into the host cell by genetic manipulation (e.g., the gene cluster is expressed on a plasmid or plasmids or integrated into the host cell genome (see, e.g., International Patent Application Publications WO 2014/037585, WO 2014/057109, WO 2015/052344).

In one embodiment, provided herein is a host cell (e.g., recombinant host cell) capable of producing a bioconjugate of an *E. coli* glucosylated O4 antigen polysaccharide covalently linked to a carrier protein. Such a host cell comprises, preferably by engineering a precursor cell, a nucleic acid sequence encoding a gtrS gene, which, to the best of the knowledge of the inventors, was identified herein for the first time as encoding a polysaccharide branching enzyme capable of transferring glucose to the *E. coli* O4 antigen (i.e., a glucosyltransferase specific to the *E. coli* O4 antigen polysaccharide), and particularly to L-Rha via an α-1,3-glycosidic linkage. An example of an amino acid sequence of such branching enzyme is provided in SEQ ID NO: 4. Other examples comprise amino acid sequences that are at least 80% identical thereto. Exemplary examples of nucleic acid sequence encoding gtrS genes specific to the *E. coli* O4 antigen polysaccharide include, but are not limited to, SEQ ID NO: 5, or degenerate nucleic acid sequences thereto that encode SEQ ID NO: 4, or nucleic acid sequences that encode functional O4-specific GtrS enzymes that have at least 80% identity to SEQ ID NO: 4.

In a specific embodiment, a host cell (e.g., recombinant host cell) capable of producing a bioconjugate of an *E. coli* glucosylated O4 antigen polysaccharide covalently linked to a carrier protein, comprises a nucleotide sequence encoding a glucosyl transferase having at least 80% sequence identity to SEQ ID NO: 4, such as about 80%, 85%, 90%, 91%, 92%, 93%, 94%, 95%, 95%, 97%, 98%, 99%, or 100% sequence identity to SEQ ID NO: 4. In view of the redundancy in the genetic code, one of ordinary skill in the art can make variants of nucleic encoding the amino acid sequences of glucosyl transferases, e.g., using codon optimized sequences, if desired.

In certain embodiments, a host cell (e.g., recombinant host cell) capable of producing a bioconjugate of an *E. coli* glucosylated O4 antigen polysaccharide covalently linked to a carrier protein, comprising a nucleotide sequence encoding a glucosyl transferase (GtrS) having at least 80% sequence identity to SEQ ID NO: 4, further comprises a nucleotide sequence encoding a bactoprenol-linked glucose translocase (GtrA) having at least 80% sequence identity to SEQ ID NO: 7, and a nucleotide sequence encoding a bactoprenol glucosyl transferase (GtrB) having at least 80% sequence identity to SEQ ID NO: 8. In certain embodiments, said nucleic acid sequences encode GtrA and GtrB proteins that are at least about 80%, 85%, 90%, 95%, 96%, 97%, 98%, 99%, or 100% identical to SEQ ID NOs: 7 and 8, respectively, and have bactoprenol-linked glucose translocase (SEQ ID NO: 7) and bactoprenol glucosyl transferase (SEQ ID NO: 8) activity, respectively. In view of the redundancy in the genetic code, one of ordinary skill in the art can make variants of nucleic encoding the amino acid sequences of bactoprenol-linked glucose translocases and of bactoprenol glucosyl transferases, e.g., using codon optimized sequences, if desired.

A host cell (e.g., recombinant host cell) capable of producing a bioconjugate of an *E. coli* glucosylated O4 antigen polysaccharide covalently linked to a carrier protein provided herein further comprises a nucleotide sequence of an rfb gene cluster for the *E. coli* O4 antigen polysaccharide. An example of an rfb gene cluster useful for production of the *E. coli* O4 antigen polysaccharide is provided herein as SEQ ID NO: 9. Another example can be found in GenBank, locus AY568960. Degenerate nucleic acid sequences encoding the same enzymes as encoded by this sequence, or sequences that encode enzymes that are at least 80% identical, preferably at least 85%, 90%, 91%, 92%, 93%, 94%, 95%, 96%, 97%, 98%, 99% identical, can also be used.

In a specific embodiment, provided herein is a host cell (e.g., a recombinant host cell, preferably a recombinant prokaryotic host cell, preferably a recombinant *E. coli* host cell) that produces glucosylated O4 antigen polysaccharide, wherein the host cell comprises gtrS, an rfb gene cluster for the *E. coli* O4 antigen polysaccharide, and nucleic acid encoding a carrier protein. Such host cells can be engineered using recombinant approaches to comprise one or more plasmids comprising the gtrS gene, the rfb gene cluster, and/or nucleic acid encoding a carrier protein, or to comprise some or all of the relevant genes such as gtrS, the rfb cluster and/or the nucleic acid encoding the carrier protein integrated into the host cell genome. In certain embodiments, the genes or gene clusters have been integrated into the genome of the host cell using homologous recombination. An advantage of integration of genes into the genome of the host cell is stability in the absence of antibiotic selection.

In another specific embodiment, provided herein is a host cell (e.g., a recombinant host cell, preferably a recombinant prokaryotic host cell) that produces glucosylated O4 antigen polysaccharide, wherein the host cell comprises GtrS (glucosyltransferase), as well as the enzymes encoded by the O4 rfb cluster. In certain embodiments, some or all of the aforementioned enzymes are heterologous to the host cell.

In other specific embodiments, provided herein is a host cell (e.g. a recombinant host cell, preferably a recombinant prokaryotic host cell) that produces *E. coli* glucosylated O4 antigen polysaccharide, preferably a bioconjugate of *E. coli* glucosylated O4 antigen polysaccharide, wherein the host cell further comprises a nucleotide sequence encoding an oligosaccharyl transferase and/or a nucleotide sequence encoding a carrier protein. In one specific embodiment, the oligosaccharyl transferase is heterologous to the host cell. In another specific embodiment, the carrier protein is heterologous to the host cell. Preferably, the host cell comprises a heterologous nucleotide sequence encoding a glucosyl transferase having at least 80% sequence identity to SEQ ID NO: 4. In preferred embodiments, the rfb genes of the O4 cluster are heterologous to the host cell. Preferably the sequence encoding the enzyme that is capable of introducing the branched glucose side chain to the O4 antigen, i.e. the gtrS gene (encoding a glucosyl transferase having at least 80% sequence identity to SEQ ID N0:4) is heterologous to the host cell. A nucleic acid is heterologous to the host cell if the same sequence is not naturally present in said host cell.

Heterologous nucleic acid can for instance be introduced in a parent cell by genetic engineering, e.g by transformation (e.g. chemical transformation or electroporation) and/or recombination. In certain embodiments, heterologous nucleic acid such as a desired rfb locus, gtrS coding sequence, carrier protein encoding sequence, and/or glycosyltransferase encoding sequence are integrated into the genome of the host cell, preferably a bacterial host cell, preferably an *E. coli* host cell. In preferred embodiments, the endogenous rfb locus and if applicable gtrS coding sequence have been inactivated, preferably deleted from the genome of the recombinant host cell as compared to a predecessor thereof, and preferably these are replaced by the desired heterologous rfb locus, and if applicable desired gtrS coding sequence, respectively. In certain embodiments the host cell is a K-12 of *E. coli* (as a non-limiting example, *E. coli* strain W3110 is a K-12 strain), or a B strain of *E. coli* (as a non-limiting example, *E. coli* strain BL21 is a B strain), or any other well-defined strain of *E. coli*, e.g. laboratory strains or production strains, in contrast to primary wild-type isolates. In preferred embodiments, the host cell is derived from *E. coli* that does not express O4 antigen or glucosylated O4 antigen, by introduction into such *E. coli* of the O4 rfb locus and the gtrS gene encoding a glucosyl transferase having at least 80% sequence identity to SEQ ID NO:4. Advantages of using well-characterized strains, such as *E. coli* K-12 or *E. coli* B, as precursors for host cells is the possibility to use a similar production process for different O-antigen bioconjugates, since the characteristics of the production strain are well-defined. Even though bioconjugates of different O-antigens will behave differently and expression processes can be optimized per production strain, at least the basic process for production of O-antigen bioconjugates will be more predictable using such well-defined precursor strains than when unknown strains such as wild-type isolates are used as precursors for production of host strains. This way, experience with production of earlier described *E. coli* O-antigen bioconjugates such as O1A, O2, O6A and O25B bioconjugates as described in for instance WO 2015/124769 and WO 2017/035181 can be used as basis to design production of other *E. coli* O-antigen bioconjugates. Unlike gtrS, the gtrA and gtrB genes are not serotype-specific, and in certain embodiments these are homologous to the host cell (e.g. *E. coli* K12 strain W3110 includes gtrA and gtrB genes that are capable of functioning together with the O4-serotype specific recombinantly introduced gtrS gene encoding a glucosyl transferase of SEQ ID NO: 4 or a glucosyl transferase that is at least 80% identical thereto, replacing the endogenous gtrS gene). In other embodiments, one or both of gtrA and gtrB genes (encoding GtrA and GtrB proteins that are at least about 80% identical to SEQ ID NOs: 7 and 8, respectively, and having bactoprenol-linked glucose translocase and bactoprenol glucosyl transferase activity respectively, are also recombinantly introduced in the host cell, for instance in case the host cell does not have endogenous gtrA and/or gtrB genes.

Also provided herein are host cells (e.g., recombinant host cells) capable of producing a bioconjugate of an *E. coli* O1A, O2, O6A, O8, O15, O16, O18A, O25B, or O75 antigen polysaccharide covalently linked to a carrier protein. Such host cells (e.g., recombinant host cells) comprise nucleotide sequence of an rfb gene cluster specific to the O-antigen polysaccharide. The rfb gene clusters can be isolated from wild-type *E. coli* strains, and combined with nucleic acids encoding an oligosaccharyl transferase (e.g., PglB) and carrier protein (e.g., EPA) within one host cell to obtain a recombinant host cell that produces the *E. coli* O-antigen of interest or bioconjugate thereof. For example, such host cells can be engineered using recombinant approaches to comprise one or more plasmids comprising the rfb gene cluster, oligosaccharyl transferase (e.g., PglB) and carrier protein (e.g., EPA) using bioconjugation technology such as that described in WO 2014/037585, WO 2009/104074, and WO 2009/089396. Preferably the host cells comprise the rfb gene clusters integrated into their genome. The nucleic acids encoding oligosaccharyl transferase, carrier protein, and where applicable gtrS gene, are in certain embodiments also integrated into the genome of the host cell. Heterologous or homologous gtrA and gtrB genes are in certain embodiments also integrated into the genome of the host cell.

Preparation of bioconjugates for O1A, O2, O6A and O25B antigens has been described in detail in WO 2015/124769 and WO 2017/035181. Examplary gene clusters for each *E. coli* O antigen (rfb loci) have been described in Iguchi A, et al, DNA Research, 2014, 1-7 (doi: 10.1093/dnares/dsu043), and in DebRoy C, et al, PLoS One. 2016, 11(1):e0147434 (doi: 10.1371/journal.pone.0147434; correction in: Plos One. 2016, 11(4):e0154551, doi: 10.1371/journal.pone.0154551). Nucleic acid sequences for the rfb clusters and amino acid sequences for proteins encoded therein can also be found in public databases, such as GenBank. Exemplary sequences for rfb clusters that can be used in production strains for bioconjugates with polysaccharide antigens of the serotypes disclosed herein, are also provided in SEQ ID NOs: 9 and 11-19. Thus, for each of the desired bioconjugates mentioned above, the respective rfb cluster can be introduced into a host cell, to obtain host cells with the specific rfb cluster for the desired O-antigen, as well as containing nucleic acid encoding oligosaccharyltransferase and carrier protein. For reasons indicated above, preferably the host cells are recombinant host cells, and preferably are derived from strains with relatively well-known characteristics, such as *E. coli* laboratory or production strains, e.g. *E. coli* K12 or *E. coli* BL21, etc. Preferably, the rfb clusters are heterologous to the host cell, e.g. introduced into a precursor cell of the host cell, and preferably integrated into the genome thereof. Preferably an original rfb gene cluster, if such was present in a precursor cell, has been replaced by the rfb gene cluster for the O-antigen of interest in the host cell, to enable production of bioconjugate of the O-antigen of interest. Preferably the oligosaccharyltransferase is heterologous to the host cell, and in certain embodiments nucleic acid encoding such oligosaccharyltransferase is integrated into the genome of the host cell.

Any of the host cells provided herein (e.g., recombinant host cells, preferably recombinant prokaryotic host cells) comprise nucleic acids encoding additional enzymes active in the N-glycosylation of proteins, e.g., the host cell provided herein can further comprise a nucleic acid encoding an oligosaccharyl transferase or nucleic acids encoding other glycosyltransferases.

The host cells provided herein comprise a nucleic acid that encodes an oligosaccharyl transferase. Oligosaccharyl transferases transfer lipid-linked oligosaccharides to asparagine residues of nascent polypeptide chains that comprise an N-glycosylation consensus motif. The nucleic acid that encodes an oligosaccharyl transferase can be native to the host cell, or can be introduced into the host cell using genetic approaches. In preferred embodiments, the oligosaccharyl transferase is heterologous to the host cell. *E. coli* does not naturally comprise an oligosaccharyl transferase, and hence if *E. coli* is used as a host cell for production of bioconjugates, a heterologous oligosaccharyl transferase is comprised in such host cell, e.g. upon introduction by genetic engineering. The oligosaccharyl transferase can be from any source known in the art in view of the present disclosure.

In certain embodiments, an alternative to an oligosaccharyl transferase with N-glycosyltransferase activity, such as an O-glycosyltransferase, e.g. as a non-limiting example PglL, can be used, in conjunction with its own, different, glycosylation consensus sequence in the carrier protein, as for instance described in WO 2016/82597. Other glycosyltransferases, such as O-glycosyltransferases, can thus also be used as an oligosaccharyltransferase according to the invention.

In certain preferred embodiments, the oligosaccharyl transferase is an oligosaccharyl transferase from *Campylobacter*. For example, in one embodiment, the oligosaccharyl transferase is an oligosaccharyl transferase from *Campylobacter jejuni* (i.e., pglB; see, e.g., Wacker et al., 2002, Science 298:1790-1793; see also, e.g., NCBI Gene ID: 3231775, UniProt Accession No. O86154). In another embodiment, the oligosaccharyl transferase is an oligosaccharyl transferase from *Campylobacter lari* (see, e.g., NCBI Gene ID: 7410986).

In specific embodiments, the oligosaccharyl transferase is PglB oligosaccharyl transferase from *Campylobacter jejuni*, including the natural (wild-type) protein or any variant thereof, such as those described in International Patent Application Publications WO 2016/107818 and WO 2016/107819. PglB can transfer lipid-linked oligosaccharides to asparagine residues in the consensus sequences SEQ ID NO: 1 and SEQ ID NO: 2. In particular embodiments, the PglB oligosaccharyl transferase comprises SEQ ID NO: 6, or a variant thereof. In certain embodiments one or more endogenous glycosylation consensus sequences in a wild-type PglB have been mutated to avoid PglB autoglycosylation, e.g. SEQ ID NO: 6 comprising the mutation N534Q. Examples of variant PglB oligosaccharyl transferases suitable for use in the recombinant host cells provided herein include the PglB oligosaccharyl transferase of SEQ ID NO: 6 comprising at least one mutation selected from the group consisting of N311V, K482R, D483H, A669V, Y77H, S80R, Q287P, and K289R. In one particular embodiment, a variant PglB oligosaccharyl transferase has SEQ ID NO: 6 comprising the mutation N311V. In another particular embodiment, a variant PglB oligosaccharyl transferase has SEQ ID NO: 6 comprising the mutations Y77H and N311V. In another particular embodiment, a variant PglB oligosaccharyl transferase has SEQ ID NO: 6 comprising the mutations N311V, K482R, D483H, and A669V. In another particular embodiment, a variant PglB oligosaccharyl transferase has SEQ ID NO: 6 comprising the mutations Y77H, S80R, Q287P, K289R, and N311V. It was found and described herein that certain PglB oligosaccharyl transferase variants give surprisingly improved yields in production of *E. coli* O-antigen bioconjugates of specific serotypes. The improved or optimal PglB variant for a given *E. coli* O-antigen was not predictable. The invention in certain aspects therefore also provides methods for producing bioconjugates of specific *E. coli* O-antigens, using specific PglB variants as the oligosaccharyl transferase. Further variants of PglB that are at least 80%, 85%, 90%, 91%, 92%, 93%, 94%, 95%, 96%, 97%, 98%, 99% identical to SEQ ID NO: 6 and still have oligosaccharyl transferase activity, preferably having one or more of the specific amino acids on the indicated positions disclosed in combination herein (e.g. 77Y, 80S, 287Q, 289K, 311N, 482K, 483D, 669A; or 311V; or 311V, 482R, 483H, 669V; or 77H, 80R, 287P, 289R, 311V; or 77H, 311V; etc) can also be used for production of bioconjugates.

In a specific embodiment, a host cell (e.g., recombinant host cell) capable of producing a bioconjugate of an *E. coli* glucosylated O4 antigen polysaccharide covalently linked to a carrier protein further comprises a nucleotide sequence encoding PglB oligosaccharyl transferase from *Campylobacter jejuni* having the amino acid sequence of SEQ ID NO: 6, or preferably SEQ ID NO: 6 comprising the mutation N311V, or more preferably SEQ ID NO: 6 comprising the mutations Y77H and N311V.

In other specific embodiments, a host cell (e.g., recombinant host cell) capable of producing a bioconjugate of an *E. coli* O1A, O6A, or O15 antigen polysaccharide covalently linked to a carrier protein further comprises a nucleotide sequence encoding PglB oligosaccharyl transferase from *Campylobacter jejuni* having the amino acid sequence of SEQ ID NO: 6, or preferably SEQ ID NO: 6 comprising the mutations N311V, K482R, D483H, and A669V.

In a specific embodiment, a host cell (e.g., recombinant host cell) capable of producing a bioconjugate of an *E. coli* O16 antigen polysaccharide covalently linked to a carrier protein further comprises a nucleotide sequence encoding PglB oligosaccharyl transferase from *Campylobacter jejuni* having the amino acid sequence of SEQ ID NO: 6, or preferably SEQ ID NO: 6 comprising the mutations Y77H, S80R, Q287P, K289R, and N311V.

In a specific embodiment, a host cell (e.g., recombinant host cell) capable of producing a bioconjugate of an *E. coli* O75 antigen polysaccharide covalently linked to a carrier protein further comprises a nucleotide sequence encoding PglB oligosaccharyl transferase from *Campylobacter jejuni* having the amino acid sequence of SEQ ID NO: 6, or preferably SEQ ID NO: 6 comprising the mutation N311V.

In a specific embodiment, a host cell (e.g., recombinant host cell) capable of producing a bioconjugate of an *E. coli* O8, O18A, O25B, or O2 antigen polysaccharide covalently linked to a carrier protein further comprises a nucleotide sequence encoding PglB oligosaccharyl transferase from *Campylobacter jejuni* having the amino acid sequence of SEQ ID NO: 6, preferably wherein SEQ ID NO: 6 comprises no amino acid mutations at positions 77, 80, 287, 289, 311, 482, 483, and 669.

In some embodiments, any of the host cells provided herein comprise a nucleic acid encoding a carrier protein, e.g., a protein to which the O-antigen polysaccharide(s) produced by the host cell glycosylation machinery can be attached to form a bioconjugate. The host cell can comprise a nucleic acid encoding any carrier protein known to those skilled in the art in view of the present disclosure including, but not limited to, detoxified Exotoxin A of *P. aeruginosa* (EPA), *E. coli* flagellin (FliC), CRM197, maltose binding protein (MBP), Diphtheria toxoid, Tetanus toxoid, detoxified hemolysin A of *S. aureus*, clumping factor A, clumping factor B, *E. coli* heat labile enterotoxin, detoxified variants of *E. coli* heat labile enterotoxin, Cholera toxin B subunit (CTB), cholera toxin, detoxified variants of cholera toxin, *E. coli* Sat protein, the passenger domain of *E. coli* Sat protein, *Streptococcus pneumoniae* Pneumolysin, Keyhole limpet hemocyanin (KLH), *P. aeruginosa* PcrV, outer membrane protein of *Neisseria meningitidis* (OMPC), and protein D from non-typeable *Haemophilus influenzae*.

In preferred embodiments, a host cell further comprises a nucleic acid encoding detoxified Exotoxin A of *P. aeruginosa* (EPA). Preferably, the EPA carrier protein comprises 1-10 glycosylation sites, preferably 2 to 4 glycosylation sites, most preferably 4 glycosylation sites, such as 1-10, preferably 2-4, and more preferably 4 glycosylation sites each comprising a glycosylation consensus sequence having the amino acid sequence of SEQ ID NO: 1, and more preferably having the amino acid sequence of SEQ ID NO: 2. In a specific embodiment, a host cell further comprises a nucleic acid encoding EPA-4 carrier protein comprising SEQ ID NO: 3.

In certain embodiments, the carrier proteins used in the generation of the bioconjugates by the host cells described herein comprise a "tag," i.e., a sequence of amino acids that allows for the isolation and/or identification of the carrier protein. For example, adding a tag to a carrier protein can be useful in the purification of that protein and, hence, the purification of conjugate vaccines comprising the tagged carrier protein. Exemplary tags that can be used herein include, without limitation, histidine (HIS) tags (e.g., hexa-histidine-tag, or 6×His-Tag), FLAG-TAG, and HA tags. In certain embodiments, the tags used herein are removable, e.g., removal by chemical agents or by enzymatic means, once they are no longer needed, e.g., after the protein has been purified. In other embodiments, the carrier protein does not comprise a tag.

In certain embodiments, the carrier proteins described herein comprise a signal sequence that targets the carrier protein to the periplasmic space of the host cell that expresses the carrier protein. In a specific embodiment, the signal sequence is from *E. coli* DsbA, *E. coli* outer membrane porin A (OmpA), *E. coli* maltose binding protein (MalE), *Erwinia carotovorans* pectate lyase (PelB), FlgI, NikA, or *Bacillus* sp. endoxylanase (XynA), heat labile *E. coli* enterotoxin LTIIb, *Bacillus* endoxylanase XynA, or *E. coli* flagellin (FlgI). In one embodiment, the signal sequence comprises SEQ ID NO: 10. A signal sequence may be cleaved off after translocation of the protein to the periplasm and may thus no longer be present in the final carrier protein of a bioconjugate.

In certain embodiments, additional modifications can be introduced (e.g., using recombinant techniques) into the host cells described herein. For example, host cell nucleic acids (e.g., genes) that encode proteins that form part of a possibly competing or interfering glycosylation pathway (e.g., compete or interfere with one or more heterologous genes involved in glycosylation that are recombinantly introduced into the host cell) can be deleted or modified in the host cell background (genome) in a manner that makes them inactive/dysfunctional (i.e., the host cell nucleic acids that are deleted/modified do not encode a functional protein). In certain embodiments, when nucleic acids are deleted from the genome of the host cells provided herein, they are replaced by a desirable sequence, e.g., a sequence that is useful for production of an O antigen polysaccharide or bioconjugate thereof.

Exemplary genes or gene clusters that can be deleted in host cells (and, in some cases, replaced with other desired nucleic acid sequences) include genes or gene clusters of host cells involved in glycolipid biosynthesis, such as waaL (see, e.g., Feldman et al., 2005, PNAS USA 102:3016-3021), the lipid A core biosynthesis cluster (waa), galactose cluster (gal), arabinose cluster (ara), colonic acid cluster (wc), capsular polysaccharide cluster, undecaprenol-p biosynthesis genes (e.g. uppS, uppP), und-P recycling genes, metabolic enzymes involved in nucleotide activated sugar biosynthesis, enterobacterial common antigen cluster (eca), and prophage O antigen modification clusters like the gtrABS cluster or regions thereof. In a specific embodiment, the host cells described herein are modified such that they do not produce any O antigen polysaccharide other than a desired O antigen polysaccharide, e.g., glucosylated O4 antigen polysaccharide.

In a specific embodiment, the waaL gene is deleted or functionally inactivated from the genome of a host cell (e.g., recombinant host cell) provided herein. The terms "waaL" and "waaL gene" refer to the O-antigen ligase gene encoding a membrane bound enzyme with an active site located in the periplasm. The encoded enzyme transfers undecaprenylphosphate (UPP)-bound O antigen to the lipid A core, forming lipopolysaccharide. Deletion or disruption of the endogenous waaL gene (e.g., ΔwaaL strains) disrupts transfer of the O-antigen to lipid A, and can instead enhance transfer of the O-antigen to another biomolecule, such as a carrier protein.

In another specific embodiment, one or more of the waaL gene, gtrA gene, gtrB gene, gtrS gene, and the rfb gene cluster is deleted or functionally inactivated from the original genome of a prokaryotic host cell provided herein.

In one embodiment, a host cell used herein is *E. coli* that produces a bioconjugate of glucosylated O4 antigen polysaccharide, wherein the waaL gene is deleted or functionally inactivated from the genome of the host cell, and a gtrS gene specific to *E. coli* O4 antigen polysaccharide is inserted. In certain embodiments for production strains for bioconjugates of the glucosylated O4 O-antigen, a gtrS gene encoding a glucosyl transferase having at least 80% sequence identity to SEQ ID NO. 4 is inserted in the place of a gtrS gene of the parent strain, so as to replace the gtrS gene in that parent strain with the one that is responsible for glucosylation of the O4 antigen. An example of such a parent strain is *E. coli* K-12 strain W3110. The gtrA and gtrB genes can be homologous to the parent strain, or alternatively one or both of these genes can be heterologous to the parent strain. Typically, and unlike the gtrS gene, these gtrA and gtrB genes are not specific for the O-antigen structure.

Also provided herein are methods of making recombinant host cells. Recombinant host cells produced by the methods described herein can be used to produce bioconjugates of *E. coli* O antigens. The methods comprise introducing one or more recombinant nucleic acid molecules into a cell to produce the recombinant host cell. Typically, the recombinant nucleic acid molecules are heterologous. Any method known in the art in view of the present disclosure can be used to introduce recombinant nucleic acid molecules into a host cell. Recombinant nucleic acids can be introduced into the host cells described herein using any methods known to those of ordinary skill in the art, e.g., electroporation, chemical transformation, by heat shock, natural transformation, phage transduction, and conjugation. In specific embodiments, recombinant nucleic acids are introduced into the host cells described herein using a plasmid. For example, the heterologous nucleic acids can be expressed in the host cells by a plasmid (e.g., an expression vector). In another specific embodiment, heterologous nucleic acids are introduced into the host cells described herein using the method of insertion into the genome as for instance described in International Patent Application Publication WO 2014/037585, WO 2014/057109, or WO 2015/052344.

In one embodiment, a method of making a recombinant host cell for producing a bioconjugate of an *E. coli* glucosylated O4 antigen polysaccharide covalently linked to a carrier protein comprises introducing one or more recombinant nucleic acid molecules into a cell, preferably an *E. coli* cell, to produce the recombinant host cell. In such embodiments, the recombinant nucleic acid molecules introduced into the cell include (i) a nucleotide sequence of an rfb gene cluster for the *E. coli* O4 antigen polysaccharide; (ii) a nucleotide sequence encoding a glucosyl transferase having at least 80% sequence identity to SEQ ID NO: 4, wherein the glucosyl transferase is capable of modifying the *E. coli* O4 antigen polysaccharide to produce the *E. coli* glucosylated O4 antigen polysaccharide; (iii) a nucleotide sequence encoding a carrier protein; and (iv) a nucleotide sequence encoding an oligosaccharyl transferase capable of covalently linking the *E. coli* glucosylated O4 antigen polysaccharide to the carrier protein to produce the bioconjugate. In preferred embodiments, the nucleotide sequence encoding a glucosyl transferase having at least 80% sequence identity to SEQ ID NO: 4 replaces the endogenous gtrS gene. Deleting the endogenous gtrS has the advantage that it will not interfere with generation of the glucosylated O4 antigen polysaccharide structure. In certain embodiments, the nucleotide sequence of the rfb gene cluster for the *E. coli* O4 antigen polysaccharide replaces the endogenous rfb gene cluster of the parent strain that is used to make the recombinant host cell. If the cell does not yet encode gtrA and/or gtrB genes, nucleotide sequences encoding a translocase (gtrA) and a glycosyltransferase (gtrB), having at least 80% identity to SEQ ID NOs: 7 and 8, respectively, can be introduced into the cell. If the cell already encodes gtrA and gtrB genes (such as for instance the case in *E. coli* K-12 strain W3110), there is no need to introduce or change these genes.

In a specific embodiment, the glucosyl transferase (gtrS specific for adding glucose branch to O4 antigen) has SEQ ID NO: 4.

In a specific embodiment, the oligosaccharyl transferase is PglB from *C. jejuni*. In one such embodiment, the oligosaccharyl transferase comprises the amino acid sequence of SEQ ID NO: 6. In another such embodiment, the oligosaccharyl transferase comprises the amino acid sequence of SEQ ID NO: 6 comprising the mutation N311V. In another such embodiment, the oligosaccharyl transferase comprises the amino acid sequence of SEQ ID NO: 6 comprising the mutations Y77H and N311V.

In another specific embodiment, the carrier protein comprises at least one glycosylation site comprising a glycosylation consensus sequence having SEQ ID NO: 1, preferably SEQ ID NO: 2. In another specific embodiment, the carrier protein is EPA, preferably EPA-4, such as EPA-4 comprising SEQ ID NO: 3.

*E. coli* strains that are used routinely in molecular biology as both a tool and a model organism can for instance be used as parents for host cells in certain embodiments according to the invention. Non-limiting examples include *E. coli* K12 strains (for example, such as W1485, W2637, W3110, MG1655, DH1, DH5a, DH10, etc.), B strains (e.g. BL-21, REL606, etc.), C strains, or W strains. In one particular embodiment, the host strain is derived from parent strain W3110. This strain can for instance be obtained from the *E. coli* Genetic Stock Center at Yale. For more information on *E. coli*, see e.g. Ecoliwiki.net.

Methods of Producing Conjugates and Bioconjugates

Also provided are methods of producing glycoconjugates of the *E. coli* O antigen polysaccharides described herein. Glycoconjugates, including bioconjugates, can be prepared in vitro or in vivo, e.g., using the recombinant host cells described herein for production.

In some embodiments, glycoconjugates can be prepared by chemical synthesis, i.e., prepared outside of host cells (in vitro). For example, an *E. coli* O antigen polysaccharide can be conjugated to carrier proteins using methods known to those of ordinary skill in the art, including by means of using activation reactive groups in the polysaccharide/oligosaccharide as well as the carrier protein. See, e.g., Pawlowski et al., 2000, *Vaccine* 18:1873-1885; and Robbins, et al., 2009, *Proc Natl Acad Sci USA* 106:7974-7978), the disclosures of which are herein incorporated by reference. Such approaches comprise extraction of antigenic polysaccharides/oligosaccharides from host cells, purifying the polysaccharides/oligosaccharides, chemically activating the polysaccharides/oligosaccharides, and conjugating the polysaccharides/oligosaccharides to a carrier protein.

In some embodiments, the host cells described herein can be used to produce bioconjugates comprising an *E. coli* O antigen polysaccharide covalently linked to a carrier protein. Methods of producing such bioconjugates using host cells are known in the art. See, e.g., WO 2003/074687 and WO 2006/119987. Such methods comprise culturing any of the recombinant host cells described herein under conditions for production of the bioconjugate. Bioconjugates can be isolated, separated, and/or purified from recombinant host cells using any method known in the art in view of the present disclosure. For example, bioconjugates can be purified by any method known in the art for purification of a protein, for instance, by chromatography (e.g., ion exchange, anionic exchange, affinity, and sizing column chromatography), centrifugation, differential solubility, or by any other standard technique for the purification of proteins. See, e.g., methods described in WO 2009/104074. Further, the bioconjugates can be fused to heterologous polypeptide sequences to facilitate purification. The actual conditions used to purify a particular bioconjugate will depend, in part, on factors such as net charge, hydrophobicity, and/or hydrophilicity of the bioconjugate, and will be apparent to those skilled in the art. Preparation of bioconjugates for O1A, O2, O6A, and O25B, as well as vaccine compositions comprising these, have for instance been described in WO 2015/124769 and in WO 2017/035181.

Also provided are bioconjugates produced by the methods described herein, i.e., using the recombinant host cells described herein.

In some embodiments, a method of preparing a bioconjugate of an *E. coli* O-antigen polysaccharide covalently linked to a carrier protein comprises: (i) providing a recombinant host cell comprising (a) nucleotide sequence of an rfb gene cluster for the O-antigen polysaccharide; (b) a nucleotide sequence encoding a carrier protein, preferably EPA, comprising at least one glycosylation site comprising a glycosylation consensus sequence having SEQ ID NO: 1, preferably SEQ ID NO: 2, and more preferably comprising four glycosylation sites each comprising a glycosylation consensus sequence having SEQ ID NO: 2; and (c) nucleotide sequence encoding an oligosaccharyl transferase, for instance PglB oligosaccharyl transferase or variant thereof.

In certain embodiments, *E. coli* O-antigen polysaccharides produced using the recombinant host cells described herein are covalently bound to the carrier protein at a particular polysaccharide to protein ratio by weight (w/w). This ratio of amount of O-antigen polysaccharide by weight covalently bound to the carrier protein by weight is referred to as the "glycan/protein ratio" or "polysaccharide/protein ratio" or "PS/protein ratio". In some embodiments, the O-antigen polysaccharide is covalently bound to the carrier protein at a polysaccharide to protein (w/w) ratio of about 1:20 to 20:1, preferably 1:10 to 10:1, more preferably 1:3 to 3:1. In certain non-limiting embodiments for bioconjugates described herein, glycan/protein ratio is about 0.1 to 0.5, such as 0.1, 0.15, 0.2, 0.25, 0.3, 0.35, 0.4, 0.45, or 0.5. In such embodiments, the weight ratio of the O-antigen polysaccharide: protein is about 1:10 to 1:2, such as 1:10:1:9:1:8, 1:7, 1:6, 1:5, 1:4, 1:3, or 1:2, depending on the particular O-antigen serotype. In certain embodiments the glycan/protein ratio is from about 0.15 to about 0.45. In general, a higher glycan/protein ratio of O-antigen polysaccharide to carrier protein is preferred, because a high amount of carrier protein can lead to immunological interference in some instances. Also, a higher glycan/protein ratio would help getting sufficient O-antigen polysaccharide dosed in the form of bioconjugate, while keeping the amount of carrier protein relatively low, which is especially beneficial for multivalent compositions where multiple serotypes are to be covered by the composition, e.g. compositions comprising bioconjugates from at least 4 different O-antigens, at least 5 different O-antigens, at least 6 different O-antigens, at least 7 different O-antigens, at least 8 different O-antigens, at least 9 different O-antigens, at least 10 different O-antigens, etc.

A glycan/protein ratio of a conjugate according to the invention can be determined by determining the protein amount and the glycan amount. Protein amount can be determined by measurement of UV absorbance at 280 nm (A280). Glycan amount can be determined based on ion chromatography with pulsed amperometric detection (IC-PAD) of a sugar in the repeat unit (e.g. of Man for O8 in Table 1, and of GlcNAc for the other glycans in Table 1), after which the structural information of the repeat unit can be used to calculate the total glycan amount (e.g. the repeat unit of O1A has a molar mass of 845 Da and one mole of such a repeat unit contains one mole of GlcNAc, enabling calculation of the total glycan amount when the amount of GlcNAc has been determined by IC-PAD).

In some embodiments, a bioconjugate of an *E. coli* O25B antigen polysaccharide covalently linked to a carrier protein produced using a recombinant host cell according to the cells and methods described herein has a certain degree of acetylation at position 2 of the L-Rh sugar. The degree of O-acetylation of O25B antigen polysaccharide in a bioconjugate is preferably at least 30%, preferably at least 50%, such as at least 50%, 55%, 60%, 65%, 70%, 75%, 80%, 85%, 90%, 95%, or 100%.

Similarly, the degree of O-acetylation of an *E. coli* O16 antigen polysaccharide in a bioconjugate is preferably at least 30%, preferably at least 50%, such as at least 50%, 55%, 60%, 65%, 70%, 75%, 80%, 85%, 90%, 95%, or 100%.

In specific embodiments, a method of preparing a bioconjugate of an O-antigen polysaccharide comprises providing a recombinant host cell comprising nucleic acid sequence encoding a particular oligosaccharyl transferase enzyme, particularly a PglB oligosaccharyl transferase or variant thereof, depending on the O-antigen polysaccharide bioconjugate to be produced. The particular oligosaccharyl transferase enzyme variant may impact the yield of bioconjugate produced by the host cell. Typically, a higher yield is preferred, since the yield will impact the costs for producing a specific bioconjugate, which is especially important for multivalent compositions comprising several different bioconjugates. In some embodiments, the method further comprises isolating the bioconjugate from the recombinant host cell.

In one particular embodiment, when the O-antigen is O1A, O6A, or O15 antigen polysaccharide, the PglB oligosaccharyl transferase comprises the amino acid mutations of N311V, K482R, D483H, and A669V, wherein the amino acid mutations are relative to the wild-type PglB having the amino acid sequence of SEQ ID NO: 6.

In another particular embodiment, when the O-antigen is glucosylated O4 antigen polysaccharide, the PglB oligosaccharyl transferase comprises the amino acid mutation N311V, or the amino acid mutations of Y77H and N311V, wherein the amino acid mutations are relative to the wild-type PglB having the amino acid sequence of SEQ ID NO: 6.

In another particular, embodiment, when the O-antigen is O16 antigen polysaccharide, the PglB oligosaccharyl transferase comprises the amino acid mutations of Y77H, S80R, Q287P, K289R, and N311V, wherein the amino acid mutations are relative to the wild-type PglB having the amino acid sequence of SEQ ID NO: 6.

In another particular embodiment, when the O-antigen is O75 antigen polysaccharide, the PglB oligosaccharyl transferase comprises the amino acid mutation of N311V, wherein the amino acid mutations are relative to the wild-type PglB having the amino acid sequence of SEQ ID NO: 6.

In another particular embodiment, when the O-antigen is O8, O18A, O25B, or O2 antigen polysaccharide, the PglB oligosaccharyl transferase comprises the amino acid sequence of SEQ ID NO: 6, wherein SEQ ID NO: 6 comprises no amino acid mutations at positions 77, 80, 287, 289, 311, 482, 483, and 669. In certain embodiments thereof, the PglB oligosaccharyl transferase comprises the amino acid sequence of SEQ ID NO: 6.

In some embodiments, the carrier protein is selected from the group consisting of detoxified Exotoxin A of *P. aeruginosa* (EPA), *E. coli* flagellin (FliC), CRM197, maltose binding protein (MBP), Diphtheria toxoid, Tetanus toxoid, detoxified hemolysin A of *S. aureus*, clumping factor A, clumping factor B, *E. coli* heat labile enterotoxin, detoxified variants of *E. coli* heat labile enterotoxin, Cholera toxin B subunit (CTB), cholera toxin, detoxified variants of cholera toxin, *E. coli* Sat protein, the passenger domain of *E. coli* Sat protein, *Streptococcus pneumoniae* Pneumolysin, Keyhole limpet hemocyanin (KLH), *P. aeruginosa* PcrV, outer membrane protein of *Neisseria meningitidis* (OMPC), and protein D from non-typeable *Haemophilus influenzae*.

In certain embodiments, the carrier protein is detoxified exotoxin A of *Pseudomonas aeruginosa* (EPA). Preferably, the EPA carrier protein comprises 1-10, preferably 2-4, more preferably 4 glycosylation sites. Preferably, each glycosylation site comprises a glycosylation consensus sequence having the amino acid sequence of SEQ ID NO: 2. In a specific embodiment, a host cell comprises a nucleic acid encoding EPA-4 carrier protein comprising SEQ ID NO: 3.

In certain embodiments, the recombinant host cell is an *E. coli* cell, e.g., an *E. coli* K-12 strain, such as strain W3110.

Also provided herein are bioconjugates of O-antigen polysaccharides produced using recombinant host cells encoding the oligosaccharyl transferase enzymes per the O-antigen/PglB oligosaccharyl transferase pairings indicated above. Also provided are compositions comprising such bioconjugates. In certain embodiments, a composition comprises at least 2, preferably at least 3, more preferably at least 5, still more preferably at least 7 of such bioconjugates.

In some embodiments, bioconjugates of O-antigen polysaccharides produced by recombinant host cells encoding the oligosaccharyl transferase enzymes per the O-antigen/PglB oligosaccharyl transferase pairings indicated above preferably have one or more of the preferred attributes described herein, e.g., glycan/protein ratio and/or amount or ratio of multi-glycosylated carrier protein.

EMBODIMENTS

Embodiment 1 is a method of preparing a bioconjugate of an E. coli $O_x$ antigen polysaccharide covalently linked to a carrier protein, the method comprising:
(i) providing a recombinant host cell comprising:
a. a nucleotide sequence of an rfb gene cluster for the $O_x$-antigen polysaccharide;
b. a nucleotide sequence encoding the carrier protein comprising at least one glycosylation site comprising a glycosylation consensus sequence having SEQ ID NO: 1, preferably having SEQ ID NO: 2; and
c. a nucleotide sequence encoding an oligosaccharyl transferase $PglB_y$; and
(ii) culturing the recombinant host cell under conditions for production of the bioconjugate;
wherein:
when the $O_x$-antigen is O1A antigen polysaccharide, the $PglB_y$ comprises the amino acid mutations of N311V, K482R, D483H, and A669V;
when the $O_x$-antigen is glucosylated O4 antigen polysaccharide, the $PglB_y$ comprises the amino acid mutation N311V or the amino acid mutations Y77H and N311V, and the recombinant host cell further comprises a sequence encoding a glucosyltransferase GtrS having at least 80% identity to SEQ ID NO: 4 and being capable of modifying an E. coli O4 antigen polysaccharide by addition of glucose to produce the E. coli glucosylated O4 antigen polysaccharide, and nucleotide sequences encoding a translocase GtrA and a glycosyltransferase GtrB having at least 80% sequence identity to SEQ ID NOs: 7 and 8 respectively, wherein the translocase is capable of translocating bactoprenol linked glucose and the glycosyltransferase is capable of glucosylating bactoprenol;
when the $O_x$-antigen is O6A antigen polysaccharide, the $PglB_y$ comprises the amino acid mutations of N311V, K482R, D483H, and A669V;
when the $O_x$-antigen is O8 antigen polysaccharide, the $PglB_y$ comprises no amino acid mutations at positions 77, 80, 287, 289, 311, 482, 483 and 669;
when the $O_x$-antigen is O15 antigen polysaccharide, the $PglB_y$ comprises the amino acid mutations of N311V, K482R, D483H, and A669V;
when the $O_x$-antigen is O16 antigen polysaccharide, the $PglB_y$ comprises the amino acid mutations of Y77H, S80R, Q287P, K289R, and N311V;
when the $O_x$-antigen is O18A antigen polysaccharide, the $PglB_y$ comprises no amino acid mutations at positions 77, 80, 287, 289, 311, 482, 483 and 669; and
when the $O_x$-antigen is O75 antigen polysaccharide, the $PglB_y$ comprises the amino acid mutation of N311V;
wherein in each case the amino acid mutations are relative to the wild-type PglB having the amino acid sequence of SEQ ID NO: 6, and
wherein the O1A, glucosylated O4, O6A, O8, O15, O16, O18A, and O75 antigen polysaccharides have the structures of Formulas (O1A), (O4-Glc+), (O6A), (O8), (O15), (O16), (O18A), and (O75), respectively, as shown in Table 1, and each n is independently an integer of 1 to 100, preferably 3 to 50, e.g. 5 to 40, e.g. 7 to 25, e.g. 10 to 20.

Embodiment 2 is the method of embodiment 1, wherein the $O_x$-antigen is O1A antigen polysaccharide, and the $PglB_y$ comprises the amino acid mutations of N311V, K482R, D483H, and A669V relative to wild-type PglB having the amino acid sequence of SEQ ID NO: 6.

Embodiment 3 is the method of embodiment 1, wherein the $O_x$-antigen is glucosylated O4 antigen polysaccharide, and the $PglB_y$ comprises the amino acid mutation N311V or the amino acid mutations Y77H and N311V relative to wild-type PglB having the amino acid sequence of SEQ ID NO: 6.

Embodiment 4 is the method of embodiment 3, wherein the recombinant host cell further comprises a sequence encoding a GtrS having the amino acid sequence of SEQ ID NO: 4, and nucleotide sequences encoding a GtrA and a GtrB having the amino acid sequences of SEQ ID NOs: 7 and 8, respectively.

Embodiment 5 is the method of embodiment 1, wherein the $O_x$-antigen is O6A antigen polysaccharide, and the $PglB_y$ comprises the amino acid mutations of N311V, K482R, D483H, and A669V relative to wild-type PglB having the amino acid sequence of SEQ ID NO: 6.

Embodiment 6 is the method of embodiment 1, wherein the $O_x$-antigen is O8 antigen polysaccharide, and the $PglB_y$ comprises no amino acid mutations at positions 77, 80, 287, 289, 311, 482, 483 and 669 relative to wild-type PglB having the amino acid sequence of SEQ ID NO: 6.

Embodiment 7 is the method of embodiment 1, wherein the $O_x$-antigen is O15 antigen polysaccharide, and the $PglB_y$ comprises the amino acid mutations of N311V, K482R, D483H, and A669V relative to wild-type PglB having the amino acid sequence of SEQ ID NO: 6.

Embodiment 8 is the method of embodiment 1, wherein the $O_x$-antigen is O16 antigen polysaccharide, and the $PglB_y$ comprises the amino acid mutations of Y77H, S80R, Q287P, K289R, and N311V relative to wild-type PglB having the amino acid sequence of SEQ ID NO: 6.

Embodiment 9 is the method of embodiment 1, wherein the $O_x$-antigen is O18A antigen polysaccharide, and the $PglB_y$ comprises no amino acid mutations at positions 77, 80, 287, 289, 311, 482, 483 and 669 relative to wild-type PglB having the amino acid sequence of SEQ ID NO: 6.

Embodiment 10 is the method of embodiment 1, wherein the $O_x$-antigen is O75 antigen polysaccharide, and the $PglB_y$ comprises the amino acid mutation of N311V relative to wild-type PglB having the amino acid sequence of SEQ ID NO: 6.

Embodiment 11 is a method of preparing a bioconjugate of an E. coli $O_x$ antigen polysaccharide covalently linked to a carrier protein, the method comprising:
(i) providing a recombinant host cell comprising:
(a) a nucleotide sequence of an rfb gene cluster for the $O_x$-antigen polysaccharide;
(b) a nucleotide sequence encoding the carrier protein comprising at least one glycosylation site comprising a glycosylation consensus sequence having SEQ ID NO: 1, preferably having SEQ ID NO: 2; and
(c) a nucleotide sequence encoding an oligosaccharyl transferase $PglB_y$; and
(ii) culturing the recombinant host cell under conditions for production of the bioconjugate, wherein the $PglB_y$ comprises the amino acid mutation N311V relative to the wild-type PglB having the amino acid sequence of SEQ ID NO: 6,
wherein the $O_x$-antigen is O1A antigen polysaccharide, glucosylated O4 antigen polysaccharide, O6A antigen polysaccharide, O15 antigen polysaccharide, O16 antigen polysaccharide, or O75 antigen polysaccharide, and when the $O_x$-antigen is glucosylated O4 antigen polysaccharide, the recombinant host cell further comprises a sequence encoding a glucosyltransferase GtrS having at least 80% identity to SEQ ID NO: 4 and being capable of modifying an *E. coli* O4 antigen polysaccharide by addition of glucose to produce the *E. coli* glucosylated O4 antigen polysaccharide, and nucleotide sequences encoding a translocase GtrA and a glycosyltransferase GtrB having at least 80% sequence identity to SEQ ID NOs: 7 and 8, respectively, wherein the translocase is capable of translocating bactoprenol linked glucose and the glycosyltransferase is capable of glucosylating bactoprenol, and wherein the O1A, glucosylated O4, O6A, O15, O16, and O75 antigen polysaccharides have the structures of Formulas (O1A), (O4-Glc+), (O6A), (O15), (O16), and (O75), respectively, as shown in Table 1, and each n is independently an integer of 1 to 100, preferably 3 to 50, e.g. 5 to 40, e.g. 7 to 25, e.g. 10 to 20.

Embodiment 12 is the method of any one of embodiments 1 to 11, further comprising isolating the bioconjugate from the recombinant host cell.

Embodiment 13 is the method of any one of embodiments 1 to 12, wherein the carrier protein is selected from the group consisting of detoxified Exotoxin A of *P. aeruginosa* (EPA), *E. coli* flagellin (FliC), CRM197, maltose binding protein (MBP), Diphtheria toxoid, Tetanus toxoid, detoxified hemolysin A of *S. aureus*, clumping factor A, clumping factor B, *E. coli* heat labile enterotoxin, detoxified variants of *E. coli* heat labile enterotoxin, Cholera toxin B subunit (CTB), cholera toxin, detoxified variants of cholera toxin, *E. coli* Sat protein, the passenger domain of *E. coli* Sat protein, *Streptococcus pneumoniae* Pneumolysin, Keyhole limpet hemocyanin (KLH), *P. aeruginosa* PcrV, outer membrane protein of *Neisseria meningitidis* (OMPC), and protein D from non-typeable *Haemophilus influenzae*.

Embodiment 14 is the method of embodiment 13, wherein the carrier protein is detoxified exotoxin A of *Pseudomonas aeruginosa* (EPA).

Embodiment 15 is the method of embodiment 14, wherein the EPA carrier protein comprises 1-10, preferably 2-4, more preferably 4, of the glycosylation sites.

Embodiment 16 is the method of embodiment 15, wherein each glycosylation site comprises a glycosylation consensus sequence having SEQ ID NO: 2.

Embodiment 17 is the method of embodiment 16, wherein the EPA carrier protein comprises SEQ ID NO: 3.

Embodiment 18 is the method of any one of embodiments 1-17, wherein the recombinant host cell is an *E. coli* cell, e.g. an *E. coli* K-12 strain, such as strain W3110.

Embodiment 19 is a bioconjugate produced by the method of any one of embodiments 1-18.

Embodiment 20 is a composition comprising a bioconjugate of embodiment 19.

Embodiment 21 is a composition comprising at least 2, preferably at least 3, more preferably at least 5, still more preferably at least 7 bioconjugates of embodiment 19.

Embodiment 22 is a composition of embodiment 20 or 21, comprising a bioconjugate of *E. coli* glucosylated O4 antigen polysaccharide covalently linked to a carrier protein, wherein the glucosylated O4 antigen polysaccharide has the structure of Formula (O4-Glc+) as shown in Table 1, and n is an integer of 1 to 100, preferably 3 to 50, e.g. 5 to 40, e.g. 7 to 25, e.g. 10 to 20.

Embodiment 23 is a composition of any one of embodiments 20 to 22, further comprising at least a bioconjugate of *E. coli* O25B antigen polysaccharide covalently linked to a carrier protein, wherein the O25B antigen polysaccharide has the structure of Formula (O25B) as shown in Table 1, and n is an integer of 1 to 100, preferably 3 to 50, e.g. 5 to 40, e.g. 7 to 25, e.g. 10 to 20.

Embodiment 24 is a composition of any one of embodiments 20 to 23, further comprising at least a bioconjugate of *E. coli* O2 antigen polysaccharide covalently linked to a carrier protein, wherein the O2 antigen polysaccharide has the structure of Formula (O2) as shown in Table 1, and n is an integer of 1 to 100, preferably 3 to 50, e.g. 5 to 40, e.g. 7 to 25, e.g. 10 to 20.

Embodiment 25 is a composition of any one of embodiments 20 to 24, comprising: (i) bioconjugate of *E. coli* O1A antigen polysaccharide covalently coupled to a carrier protein, (ii) bioconjugate of *E. coli* O2 antigen polysaccharide covalently coupled to a carrier protein, (iii) bioconjugate of *E. coli* glucosylated O4 antigen polysaccharide covalently coupled to a carrier protein, (iv) bioconjugate of *E. coli* O6A antigen polysaccharide covalently coupled to a carrier protein, (v) bioconjugate of *E. coli* O8 antigen polysaccharide covalently coupled to a carrier protein, (vi) bioconjugate of *E. coli* O15 antigen polysaccharide covalently coupled to a carrier protein, (vii) bioconjugate of *E. coli* O16 antigen polysaccharide covalently coupled to a carrier protein, (viii) bioconjugate of *E. coli* O25B antigen polysaccharide covalently coupled to a carrier protein, and (ix) bioconjugate of *E. coli* O75 antigen polysaccharide covalently coupled to a carrier protein, wherein the O1A, O2, glucosylated O4, O6A, O8, O15, O16, O25B, and O75 antigen polysaccharides have the structures of Formulas (O1A), (O2), (O4-Glc+), (O6A), (O8), (O15), (O16), (O25B), and (O75), respectively, as shown in Table 1, and each n is independently an integer of 1 to 100, preferably 3 to 50, e.g. 5 to 40, e.g. 7 to 25, e.g. 10 to 20.

Embodiment 26 is a composition of embodiment 25, further comprising: (x) bioconjugate of *E. coli* O18A antigen polysaccharide covalently coupled to a carrier protein, wherein the O18A antigen polysaccharide has the structure of Formula (O18A) as shown in Table 1, and n is an integer of 1 to 100, preferably 3 to 50, e.g. 5 to 40, e.g. 7 to 25, e.g. 10 to 20.

Embodiment 27 is a composition of any one of embodiments 20 to 26, wherein the composition is an immunogenic composition.

Embodiment 28 is a method of vaccinating a subject against *E. coli*, in particular extra-intestinal pathogenic *E. coli* (ExPEC), comprising administering to the subject the bioconjugate of embodiment 19, or the composition or immunogenic composition of any one of embodiments 20 to 27.

Embodiment 29 is the bioconjugate of embodiment 19, or the composition or immunogenic composition of any one of embodiments 20 to 27 for use in vaccination against extra-intestinal pathogenic *E. coli* (ExPEC).

Embodiment 30 is a recombinant host cell for preparing a bioconjugate of an *E. coli* $O_x$ antigen polysaccharide covalently linked to a carrier protein, the recombinant host cell comprising:

(a) a nucleotide sequence of an rfb gene cluster for the $O_x$-antigen polysaccharide;

(b) a nucleotide sequence encoding the carrier protein comprising at least one glycosylation site comprising a glycosylation consensus sequence having SEQ ID NO: 1, preferably having SEQ ID NO: 2; and (c) a nucleotide sequence encoding an oligosaccharyl transferase $PglB_y$;

wherein:

when the $O_x$-antigen is O1A antigen polysaccharide, the $PglB_y$ comprises the amino acid mutations of N311V, K482R, D483H, and A669V;

when the O$_x$-antigen is glucosylated O4 antigen polysaccharide, the PglB$_y$ comprises the amino acid mutation N311V or the amino acid mutations Y77H and N311V, and the recombinant host cell further comprises a sequence encoding a glucosyltransferase GtrS having at least 80% identity to SEQ ID NO: 4 and being capable of modifying an *E. coli* O4 antigen polysaccharide by addition of glucose to produce the *E. coli* glucosylated O4 antigen polysaccharide, and nucleotide sequences encoding a translocase GtrA and a glycosyltransferase GtrB having at least 80% sequence identity to SEQ ID NOs: 7 and 8 respectively, wherein the translocase is capable of translocating bactoprenol linked glucose and the glycosyltransferase is capable of glucosylating bactoprenol;

when the O$_x$-antigen is O6A antigen polysaccharide, the PglB$_y$ comprises the amino acid mutations of N311V, K482R, D483H, and A669V;

when the O$_x$-antigen is O8 antigen polysaccharide, the PglB$_y$ comprises no amino acid mutations at positions 77, 80, 287, 289, 311, 482, 483 and 669;

when the O$_x$-antigen is O15 antigen polysaccharide, the PglB$_y$ comprises the amino acid mutations of N311V, K482R, D483H, and A669V;

when the O$_x$-antigen is O16 antigen polysaccharide, the PglB$_y$ comprises the amino acid mutations of Y77H, S80R, Q287P, K289R, and N311V;

when the O$_x$-antigen is O18A antigen polysaccharide, the PglB$_y$ comprises no amino acid mutations at positions 77, 80, 287, 289, 311, 482, 483 and 669; and when the O$_x$-antigen is O75 antigen polysaccharide, the PglB$_y$ comprises the amino acid mutation of N311V;

wherein in each case the amino acid mutations are relative to the wild-type PglB having the amino acid sequence of SEQ ID NO: 6, and wherein the O1A, glucosylated O4, O6A, O8, O15, O16, O18A, and O75 antigen polysaccharides have the structures of Formulas (O1A), (O4-Glc+), (O6A), (O8), (O15), (O16), (O18A), and (O75), respectively, as shown in Table 1, and each n is independently an integer of 1 to 100, preferably 3 to 50, e.g. 5 to 40, e.g. 7 to 25, e.g. 10 to 20.

Embodiment 31 is the recombinant host cell of embodiment 30, wherein the O$_x$-antigen is O1A antigen polysaccharide, and the PglB$_y$ comprises the amino acid mutations of N311V, K482R, D483H, and A669V relative to wild-type PglB having the amino acid sequence of SEQ ID NO: 6.

Embodiment 32 is the recombinant host cell of embodiment 30, wherein the O$_x$-antigen is glucosylated O4 antigen polysaccharide, and the PglB$_y$ comprises the amino acid mutation N311V or the amino acid mutations Y77H and N311V relative to wild-type PglB having the amino acid sequence of SEQ ID NO: 6.

Embodiment 33 is the recombinant host cell of embodiment 32, wherein the recombinant host cell further comprises a sequence encoding a GtrS having the amino acid sequence of SEQ ID NO: 4, and nucleotide sequences encoding a GtrA and a GtrB having the amino acid sequences of SEQ ID NOs: 7 and 8, respectively.

Embodiment 34 is the recombinant host cell of embodiment 30, wherein the O$_x$-antigen is O6A antigen polysaccharide, and the PglB$_y$ comprises the amino acid mutations of N311V, K482R, D483H, and A669V relative to wild-type PglB having the amino acid sequence of SEQ ID NO: 6.

Embodiment 35 is the recombinant host cell of embodiment 30, wherein the O$_x$-antigen is O8 antigen polysaccharide, and the PglB$_y$ comprises no amino acid mutations at positions 77, 80, 287, 289, 311, 482, 483 and 669 relative to wild-type PglB having the amino acid sequence of SEQ ID NO: 6.

Embodiment 36 is the recombinant host cell of embodiment 30, wherein the O$_x$-antigen is O15 antigen polysaccharide, and the PglB$_y$ comprises the amino acid mutations of N311V, K482R, D483H, and A669V relative to wild-type PglB having the amino acid sequence of SEQ ID NO: 6.

Embodiment 37 is the recombinant host cell of embodiment 30, wherein the O$_x$-antigen is O16 antigen polysaccharide, and the PglB$_y$ comprises the amino acid mutations of Y77H, S80R, Q287P, K289R, and N311V relative to wild-type PglB having the amino acid sequence of SEQ ID NO: 6.

Embodiment 38 is the recombinant host cell of embodiment 30, wherein the O$_x$-antigen is O18A antigen polysaccharide, and the PglB$_y$ comprises no amino acid mutations at positions 77, 80, 287, 289, 311, 482, 483 and 669 relative to wild-type PglB having the amino acid sequence of SEQ ID NO: 6.

Embodiment 39 is the recombinant host cell of embodiment 30, wherein the O$_x$-antigen is O75 antigen polysaccharide, and the PglB$_y$ comprises the amino acid mutation of N311V relative to wild-type PglB having the amino acid sequence of SEQ ID NO: 6.

Embodiment 40 is the recombinant host cell of any one of embodiments 30 to 39, wherein the carrier protein is selected from the group consisting of detoxified Exotoxin A of *P. aeruginosa* (EPA), *E. coli* flagellin (FliC), CRM197, maltose binding protein (MBP), Diphtheria toxoid, Tetanus toxoid, detoxified hemolysin A of *S. aureus*, clumping factor A, clumping factor B, *E. coli* heat labile enterotoxin, detoxified variants of *E. coli* heat labile enterotoxin, Cholera toxin B subunit (CTB), cholera toxin, detoxified variants of cholera toxin, *E. coli* Sat protein, the passenger domain of *E. coli* Sat protein, *Streptococcus pneumoniae* Pneumolysin, Keyhole limpet hemocyanin (KLH), *P. aeruginosa* PcrV, outer membrane protein of *Neisseria meningitidis* (OMPC), and protein D from non-typeable *Haemophilus influenzae*.

Embodiment 41 is the recombinant host cell of any one of embodiments 30-40, wherein the carrier protein is detoxified exotoxin A of *Pseudomonas aeruginosa* (EPA).

Embodiment 42 is the recombinant host cell of embodiment 41, wherein the EPA carrier protein comprises 1-10, preferably 2-4, more preferably 4, of the glycosylation sites.

Embodiment 43 is the recombinant host cell of embodiment 42, wherein each glycosylation site comprises a glycosylation consensus sequence having SEQ ID NO: 2.

Embodiment 44 is the recombinant host cell of embodiment 43, wherein the EPA carrier protein comprises SEQ ID NO: 3.

Embodiment 45 is the recombinant host cell of any one of embodiments 30 to 44, wherein the recombinant host cell is an *E. coli* cell, e.g. an *E. coli* K-12 strain, such as strain W3110.

Embodiment 46 is a bioconjugate according to embodiment 19, wherein the bioconjugate is a bioconjugate of *E. coli* glucosylated O4 antigen polysaccharide covalently linked to a carrier protein.

Embodiment 47 is a bioconjugate according to embodiment 46, wherein the carrier protein is an EPA carrier protein comprising SEQ ID NO: 3.

Embodiment 48 is a bioconjugate according to embodiment 46 or 47, wherein the glucosylated O4 antigen polysaccharide has the structures of Formula (O4-Glc+) as shown in Table 1, and n is an integer of 5 to 40.

Embodiment 49 is a composition comprising a bioconjugate according to any one of embodiments 46-48.

Embodiment 50 is a composition according to embodiment 49, further comprising one or more conjugates each comprising an *E. coli* antigen polysaccharide covalently coupled to a carrier protein.

Embodiment 51 is a composition according to embodiment 50, wherein the one or more conjugates comprise *E. coli* antigen polysaccharide of one or more of the following *E. coli* serotypes: O1A, O2, O6A, O8, O15, O16, O18A, O25B, and O75, wherein the O1A, O2, O6A, O8, O15, O16, O25B, and O75 antigen polysaccharides have the structures of Formulas (O1A), (O2), (O6A), (O8), (O15), (O16), (O18A), (O25B), and (O75), respectively, as shown in Table 1, and each n is independently an integer of 1 to 100, preferably 3 to 50, e.g. 5 to 40, e.g. 7 to 25, e.g. 10 to 20.

Embodiment 52 is a composition according to embodiment 51, comprising conjugates of *E. coli* serotypes: O1A, O2, O6A, O8, O15, O16, O18A, O25B, and O75.

Embodiment 53 is a composition according to embodiment 52, wherein each of the conjugates is a bioconjugate.

EXAMPLES

The following examples of the invention are to further illustrate the nature of the invention. It should be understood that the following examples do not limit the invention and the scope of the invention is to be determined by the appended claims.

Example 1: Epidemiological Data of *E. coli* Infections

To determine the O-serotype distribution of bacteremia-causing *E. coli*, global surveillance studies were performed. Between 2011 and 2017, more than 3200 *E. coli* bloodstream isolates were collected from patients ≥60 years of age hospitalized in countries within North America, Europe, the Asia-Pacific region, and South America. Each strain was analyzed for O antigen serotype using classical agglutination techniques and sequence-based O-genotyping. See Table 2.

Isolated human blood samples were analyzed to determine the identity of pathogens therein and their antibiotic resistance patterns. *E. coli* isolates were obtained from the samples following the analysis. *E. coli* identity was verified by MALDI-TOF MS. Further analysis on the *E. coli* isolates was performed using an antisera-based agglutination assay to determine their O-antigen serotype (DebRoy et al. (2011) Animal health research reviews/Conference of Research Workers in Animal Diseases 12, 169-185). Isolates un-typeable by the agglutination method, were further analyzed by whole-genome sequencing followed by O-genotyping based on O-serotype specific wzy and wzx gene sequences.

TABLE 2 distribution of the most common bacteremia-associated *E. coli* O-serotypes from a collection of 3217 blood isolates collected globally between 2011 and 2017, based on O-serotyping by agglutination plus O-genotyping of isolates un-typeable by agglutination. Subjects were hospitalized in the following countries: USA, Canada, Argentina, Brazil, UK, Germany, Spain, Italy, The Netherlands, France, Japan, Thailand, South Korea and Australia.

| O-serotype | Prevalence n (%) |
|---|---|
| O25 | 737 (22.9%) |
| O2 | 268 (8.3%) |
| O6 | 261 (8.1%) |
| O1 | 255 (7.9%) |
| O75 | 145 (4.5%) |
| O15 | 110 (3.4%) |
| O8 | 104 (3.2%) |
| O16 | 103 (3.2%) |
| O4 | 96 (3.0%) |
| O18 | 91 (2.8%) |

Stratification of on geographical location in the global set of bacteremia-associated *E. coli* showed a prevalence of the top 10 O-serotypes independent of location, suggesting these to be the predominant O-serotypes globally associated with bacteremia-causing *E. coli*.

In the global set of bacteremia-associated multi-drug resistant *E. coli* isolates (n=345), i.e. those strains that are resistant to at least three classes of clinically relevant antimicrobial drugs, the prevalence of the top 10 O-serotypes is 75.4%.

All information from epidemiology analysis taken together, the 10 predominant O-serotypes could cover an estimated 60-80% of *E. coli*-associated bacteremia infections, assuming coverage of subportions of the un-typeable strains.

A multivalent vaccine covering a significant proportion of bacteremia-causing *E. coli* serotypes would be very useful. The O-serotypes of Table 2 would thus be good candidates for an O-antigen based multivalent vaccine. Such a vaccine could beneficially be prepared using bioconjugation technology.

One of the serotypes in the top-10 (Table 2) is O4. It would thus be beneficial to prepare a bioconjugate vaccine that includes O-antigen polysaccharide of *E. coli* serotype O4 coupled to a carrier protein.

Example 2: Characterization of Contemporary O4 Clinical Isolates for Genes Encoding O-Antigen Modifying Enzymes Two variants of *E. coli* O4 antigen polysaccharide have been described (see, e.g. Jann B, et al., 1993, Carbohydr. Res. 248: 241-250), one having an unbranched structure (structure shown as (O4-Glc−) in Table 1) and another variant substituted with an additional glucose side-branch (structure shown as (O4-Glc+) in Table 1). The proportion in which these two variants are found in contemporary clinical isolates was not known. Although both variants react with O4 antisera, it was also not known whether immunological differences between these variants exist. Moreover, an enzyme responsible for attaching the glucose side-branch to generate the (O4-Glc+) antigen polysaccharide was hitherto not identified, and a putative coding sequence thereof is likely residing outside the O4 rfb gene cluster.

A set of 32 agglutination-confirmed *E. coli* O4 clinical isolates originally isolated during the period of 2011-2012 from subjects in the United States and the European Union were subjected to whole genome sequence analysis. Extracted rfb gene cluster sequences from the 32 sequenced O4 isolates were aligned with those of the reference strain and compared at the nucleotide level. Except for some naturally occurring single nucleotide polymorphisms, the characterized isolates all displayed an rfb cluster that was identical to the O4 reference strain, indicating that *E. coli* O4 strains, independent of their Glc-branching status, carry an identical rfb gene cluster. Thus, to generate the *E. coli* O4-Glc+ antigen polysaccharide, a gene with unknown sequence that encodes an *E. coli* O4-specific branching enzyme and that must reside somewhere outside of the *E. coli* O4 rfb gene cluster is likely needed. The sequence of this unknown gene needs to be identified and employed if one wants to produce bioconjugates with the *E. coli* O4-Glc+ antigen polysaccharides in a strain that would otherwise only produce bioconjugates with *E. coli* O4-Glc- antigen polysaccharides.

The whole-genome sequence data were then analyzed for the presence of genes outside of the rfb gene cluster that may encode O-antigen modifying enzymes. Homologs of gtrAB in *Shigella flexneri* were first identified in *E. coli* O4. An open reading frame downstream of gtrAB in *E. coli* was then putatively identified as the *E. coli* O4-specific gene gtrS, that could encode the putative *E. coli* O4 specific branching enzyme GtrS responsible for adding a glucose branch to the *E. coli* O4 antigen.

The amino acid sequence of the O4 specific GtrS enzyme is provided as SEQ ID NO: 4. An exemplary nucleic acid sequence encoding this protein is provided as SEQ ID NO: 5.

Of the characterized *E. coli* O4 isolates, approximately 80% were found to carry the here identified gtrS gene (26 out of 32). Prevalence of the *E. coli* O4-specific gtrS sequence was also determined by PCR using sequence specific primers in an independent set of 20 agglutination-confirmed *E. coli* O4 clinical isolates isolated during the period of 2014-2016 from subjects in the United States and the European Union. This analysis demonstrated that 17 out of 20 isolates carried the O4 gtrS sequence, which corresponds to a prevalence of 85%.

Example 3: Cloning of O4 gtrS into *E. coli* W3110, Production and Structural Confirmation of Glc-Modified O4 Bioconjugates To test whether bioconjugates comprising O4-antigen polysaccharide modified with a branching glucose could be prepared, *E. coli* O4-antigen EPA bioconjugate production strains with the putative branching enzyme were constructed. For this, the endogenous O16-gtrS gene was substituted by the putative O4-gtrS gene (SEQ ID NO: 5, see Example 2) and the O16 rfb cluster was replaced with the O4 rfb cluster in *E. coli* strain W3110 ΔwzzE-wecG ΔwaaL ΔwbbI-J-K by homologous recombination. Alternatively, in some strains, the O4 rfb cluster was encoded on a plasmid.

Subsequently, plasmids encoding a detoxified exotoxin A of *Pseudomonas aeruginosa* (EPA) carrier protein (a variant either having 2 or 4 consensus glycosylation sites, referred to as 'EPA-2' and 'EPA-4', respectively), and oligosaccharyl transferase PglB were introduced into the strains. O4-EPA bioconjugates modified with Glc were produced by growing the *E. coli* production strains in bioreactor cultures, and induction of PglB and EPA expression by IPTG and arabinose, respectively. The O4-EPA bioconjugates were extracted from the biomass periplasmic extract.

To confirm the detailed polysaccharide composition and linkage of the O4-EPA bioconjugates, multiple NMR experiments were performed on the bioconjugates having EPA-4 carrier protein (data not shown). The assignments obtained agreed with literature published (Jansson, P. E., et al., 1984, Carbohydr. Res. 134(2): 283-291; Jann B, et al., 1993, Carbohydr. Res. 248: 241-250). The 1D spectrum recorded at 313K showed a large HOD signal and small sharp signals from the O4 pentasaccharide RU with five anomeric, two NAc and two H6 signals (Rha and FucNAc).

The 1D proton assignments were confirmed by use of 2D proton-proton and proton-carbon correlation NMR experiments. First, 2D TOCSY (120 ms) experiments demonstrated the expected cross peaks from H1 and H6 (for Rha and FucNAc) for the O4 pentasaccharide RU and small peaks from the terminal RU and EPA. In the methyl region, TOCSY showed cross peaks from H6 to H1 for α-Rha and H6 to H5 for α-FucNAc for the O4 RU. Other peaks observed were from EPA amino acids and terminal Rha (tRha). Second, a carbon NMR spectrum contained well-dispersed and diagnostic single peaks for the O4 RU. The carbons were profiled indirectly through the attached protons by use of the HSQC experiment. The HSQC-DEPT experiment gave inverted peaks for CH2 groups. The HSQC gave cross peaks for the O4 pentasaccharide RU [5 anomeric, ring, two N-acetyl and two methyl (Rha & FucNAc)] groups as well as EPA amino acids in characteristic regions. Each of the proton/carbon pairs for the O4 could be assigned based on the proton assignments and literature.

The structural characterization experiments thus confirmed that Glc-branched O4 bioconjugates (comprising polysaccharide antigen structures as indicated by Formula (O4-Glc+) in Table 1) could be produced, using the putative *E. coli* O4-gtrS gene identified in Example 2.

Example 4: Immunogenicity of a Glc-Branched O4 Bioconjugate in Rabbits

Glc-modified O4 bioconjugates (i.e. having glycans with the structure of Formula (O4-Glc+) as shown in Table 1) were used for rabbit immunization by applying a speedy-rabbit protocol (Eurogentec). Sera from immunized rabbits were analyzed by ELISA for anti-O4 IgG titers against purified O4 lipopolysaccharide (LPS) with (Glc+; i.e. containing glucosylated O4 polysaccharide) or without Glc-branching (Glc-; i.e. containing non-glucosylated O4 polysaccharide). Immunization with the bioconjugate resulted in high IgG titers in both rabbits (FIG. 1). In both cases, antibody titers induced by the O4 bioconjugate were higher against Glc+ LPS as compared to Glc- LPS.

Figure 2:
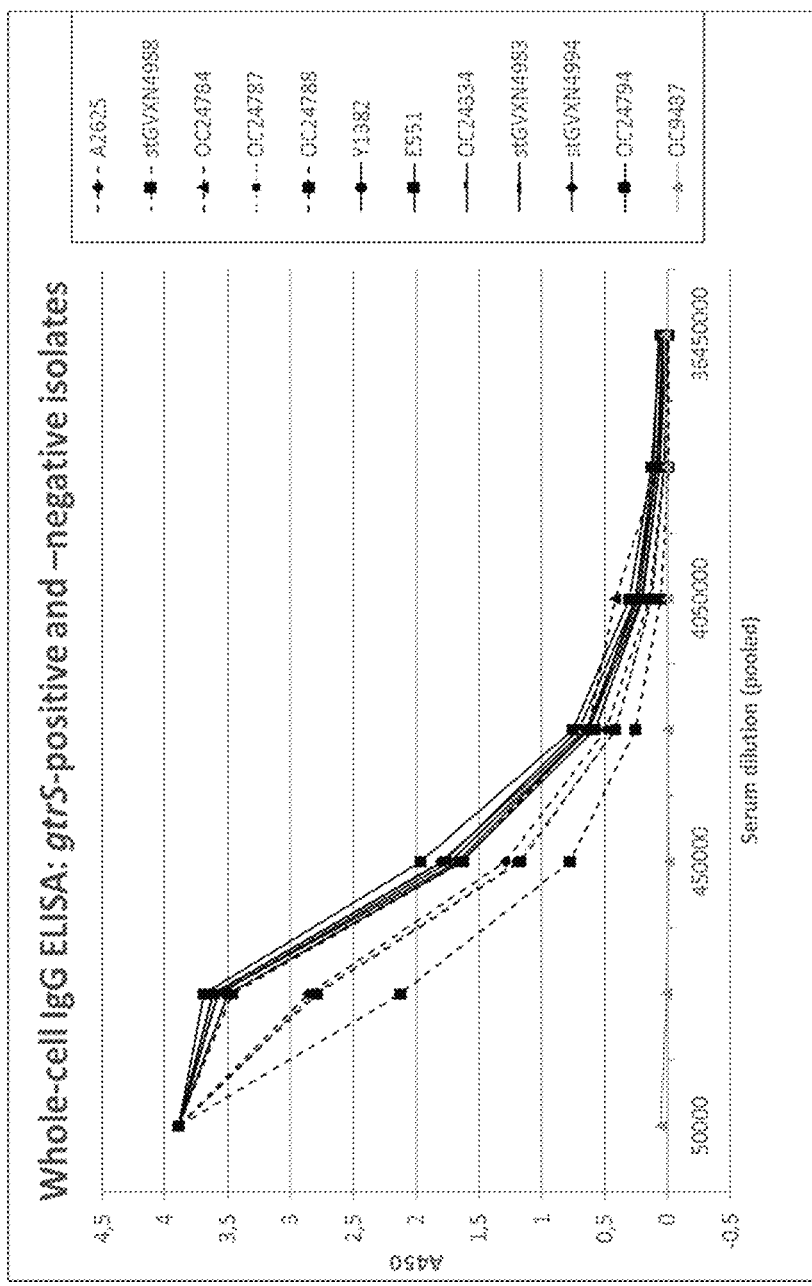
FIG. 2 shows IgG titers in whole cell ELISAs with pooled sera from rabbits immunized with a Glc-modified O4 bioconjugate against E. coli O4 isolates with characterized gtrS status as described in Example 4; the following isolates were gtrS-negative: A2625, stGVXN4988, OC24784, OC24787 and OC24788; the following isolates were gtrS-positive: Y1382, E551, OC24334, stGVXN4983, stGVXN4994 and OC24794; the negative control strain OC9487 (ATCC 35383; serotype O75) was also included.

Sera were also pooled and used in whole cell ELISA studies with test sets of *E. coli* O4 isolates with characterized gtrS status. Five gtrS-negative (no Glc-branching) and six gtrS-positive (Glc-branching) *E. coli* O4 isolates and a negative control strain were tested. Pooled sera from rabbits immunized with a Glc-modified O4 bioconjugate contained high titers of IgG specifically recognizing the tested O4 isolates (FIG. 2). In concordance with the LPS ELISA, all tested O4 isolates were recognized by the immune sera. The gtrS-positive isolates displayed an overall higher binding than the gtrS-negative isolates (FIG. 2). In particular, the following isolates were gtrS-positive: Y1382, E551, OC24334, stGVXN4983, stGVXN4994 and OC24794, and the following isolates were gtrS-negative: A2625, stGVXN4988, OC24784, OC24787, and OC24788. Immune sera did not bind the negative control strain of a non-related O-serotype, *E. coli* OC9487 (ATCC 35383).

The profiles of LPS extracted from the test set of gtrS-positive and -negative isolates in silver-stained polyacrylamide gels did not reveal marked differences between isolates expressing unmodified and modified forms of the O4 antigen confirming that the observed differences are not explained by quantitative differences in LPS expression levels (data not shown).

Figure 3:
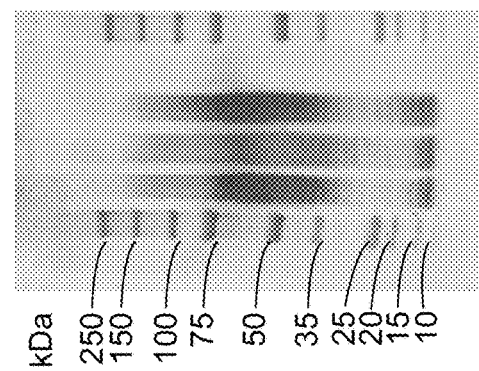
FIG. 3 shows Western blots of LPS extracted from gtrS-positive and -negative O4 isolates probed with pooled sera from rabbits immunized with modified O4 polysaccharide.
Figure 3:
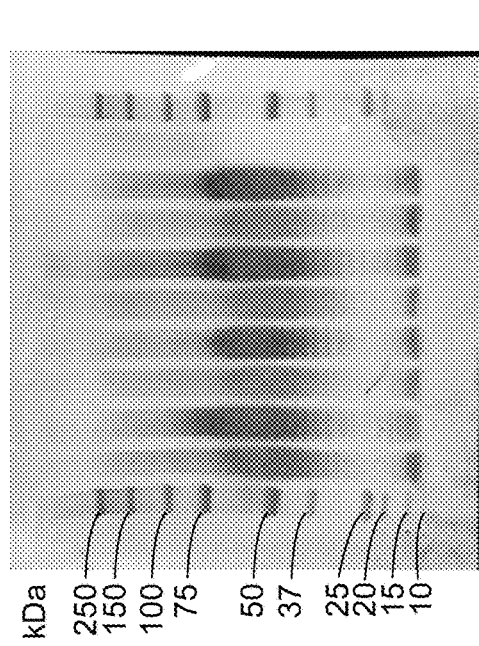

Western blots of extracted LPS using pooled immune sera were performed to assess recognition of O4 O-antigen by IgGs elicited in response to immunization with a Glc-modified O4 bioconjugate. Binding of both modified and unmodified O4 LPS by IgGs from modified O4 immunized rabbits was observed and included specific recognition of LPS bands spanning a wide range of sizes, including high molecular weight LPS bands (FIG. 3).

In the further experiments below, when reference is made to 'O4' bioconjugate or production strains or 'EcoO4', the bioconjugate or production strain of Glc-branched O4 (having glycan structure (O4-Glc+) in Table 1) is meant, unless specifically indicated otherwise (the terms 'O4' and 'O4-Glc+' are thus used interchangeably for bioconjugates or production strains in those experiments).

Example 5: Immunogenicity of a Glc-Branched O4 Bioconjugate in Rats

Sprague Dawley rats were immunized intramuscularly 3 times with formulation buffer or (O4-Glc+)-EPA bioconjugate (i.e. bioconjugate of glucosylated O4 antigen polysaccharide covalently coupled to EPA carrier protein; carrier protein was EPA-2 as described in Example 3 above) at 3 different doses (0.04 µg, 0.40 µg or 4.0 µg). Serum antibody levels were measured by ELISA at day 0, 14 and 42 post-immunization.

Figure 4A:
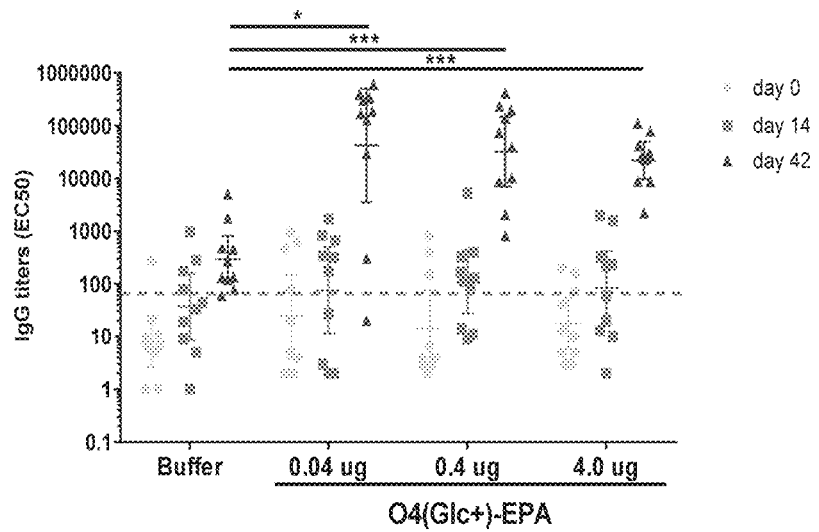
FIGS. 4A and 4B show antibody responses induced by glucosylated O4 (O4-Glc+)-EPA bioconjugates.
Figure 4B:
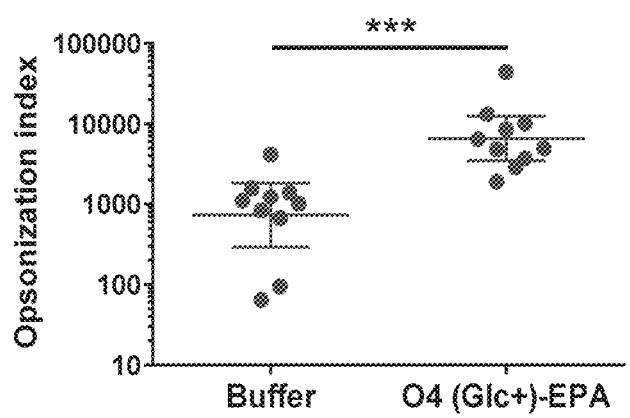

Immunization with 0.04 µg, 0.40 µg and 4.00 µg of (O4-Glc+)-EPA bioconjugate induced significant increase in the levels of IgG antibodies at day 42 post-immunization when compared to formulation buffer (FIG. 4A). The antibodies induced by (O4-Glc+)-conjugate were functional, i.e., capable of mediating killing of (O4-Glc+) *E. coli* strain (FIG. 4B).

Figure 5:
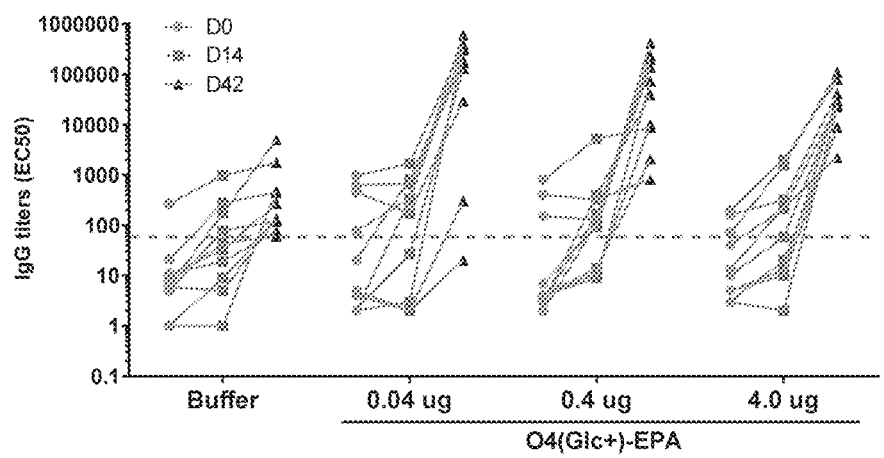
FIG. 5 shows the boost effect of glucosylated O4 (O4 Glc+)-EPA bioconjugate in Sprague Dawley rats immunized at 3 different doses as described in Example 4; serum antibody levels were measured by ELISA at day 0, 14 and 42 post-immunization; individual titers (log 10 EC50 titer) are shown for each animal; the lines between the data points connect IgG titers for each animal in time; the grey dotted line indicates the threshold above which the dilution curves of the samples have a 4PL fitting; statistical analysis was performed with Wilcoxon signed-rank test and Bonferroni correction for multiple comparisons (day 14 vs day 0, P=0.012 for 4.0 µg/dose; day 42 vs day 0, P=0.006 for all doses; day 42 vs day 14, P=0.006 for all doses)

Antibody levels induced by 0.04 µg, 0.40 µg and 4.0 µg of (O4-Glc+)-EPA bioconjugate were significantly increased at day 42 as compared to those detected at baseline (day 42 vs day 0, P=0.006 for all doses) and at day 14 post-immunization (day 42 vs day 14, P=0.006 for all doses) (FIG. 5). In the group that received 4.0 µg of bioconjugate, titers were also significantly increased at day 14 compared to day 0, indicating that a single dose of 4.0 µg of (O4-Glc+)-EPA bioconjugate induces significant increase in IgG titers (day 14 vs day 0, P=0.012). The significant increase in IgG titers observed between day 14 and 42, for all three concentrations of bioconjugate tested showed that a third dose of (O4-Glc+)-EPA bioconjugate is able to boost antibody responses (FIG. 5).

Figure 6:
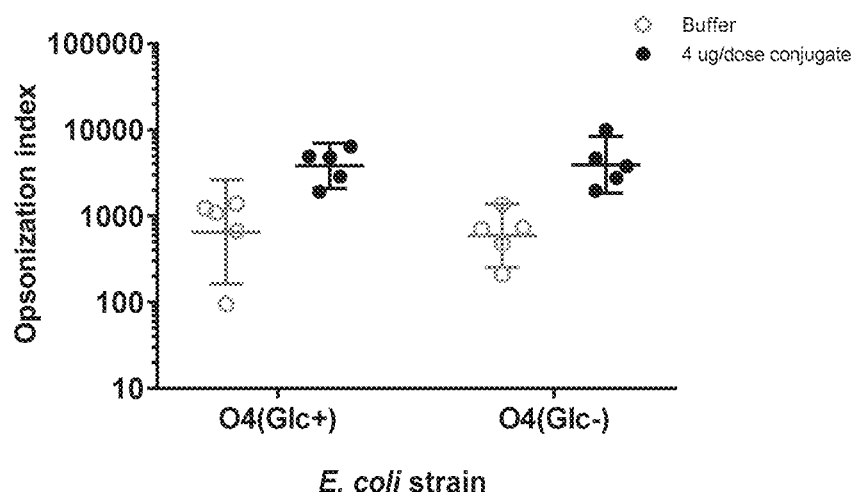
FIG. 6 shows the functionality of antibodies induced by O4-Glc+-EPA bioconjugate; Sprague Dawley rats were immunized intramuscularly 3 times with formulation buffer or O4(Glc+)-EPA bioconjugate at 4.00 µg/dose; functionality of the antibodies was determined by opsonophagocytic killing assay (OPKA) using O4(Glc+) and O4(Glc−) E. coli strains; individual opsonic titers (O1) and GMT±95% CI are shown.

Functionality of antibodies induced by O4-Glc+-EPA conjugate in the rats immunized intramuscularly 3 times with formulation buffer or the bioconjugate at 4.00 µg/dose was determined by opsonophagocytic killing assay (OPKA) using O4(Glu+) and O4(Glu−) *E. coli* strains. The antibodies induced by (O4-Glc+)-EPA bioconjugate were functional, i.e., capable of mediating killing of an (O4-Glc+) *E. coli* strain (FIG. 4B, FIG. 6). Notably, antibodies induced by (O4-Glc+)-EPA bioconjugate were capable of mediating killing of both (O4-Glc+) and (O4-Glc−, i.e. having glycans with structure of Formula (O4-Glc−) in Table 1, i.e. O4 polysaccharide without Glc-branching) *E. coli* strains (FIG. 6).

In conclusion, antibodies induced by O4-Glc+-EPA bioconjugate are cross-reactive and capable of mediating killing of *E. coli* O4 strains with and without glucose branching.

Example 6: Production Strains for *E. coli* O-Antigen Bioconjugates and Resulting Bioconjugate Products In addition to (O4-Glc+)-EPA bioconjugates prepared as described above, nine (9) other bioconjugates were produced. In particular, the additionally produced bioconjugates included *E. coli* O1A-EPA bioconjugate, O2-EPA bioconjugate, O6A-EPA bioconjugate, O8-EPA bioconjugate, O15-EPA bioconjugate, O16-EPA bioconjugate, O18A-EPA bioconjugate, O25B-EPA bioconjugate, and O75-EPA bioconjugate. The chemical structures of the glycans of these conjugates can be seen in the respective Formulas in Table 1. A composition comprising the 10 bioconjugates is referred to herein as 'ExPEC10V'. A composition comprising the O1A-EPA, O2-EPA, O6A-EPA and O25B-EPA bioconjugates is referred to as 'ExPEC4V' (and was previously described in for instance WO 2015/124769 and WO 2017/035181).

*Escherichia coli* W3110 Parental Strain

The non-pathogenic *E. coli* K12 strain W3110 was used as the parental strain for the construction of all ten production strains. The *E. coli* K12 strain W3110 was obtained from the *Coli* Genetic Stock Center (Yale University, New Haven (Conn.), USA, product number CGSC #4474). Its relevant genotype was previously described (*E. coli* W3110, F-, lambda-, IN(rrnD-rrnE)1, rph-1) and its genomic sequence was previously published (Hayashi K, et al., 2006, Mol. Syst. Biol. 2006.0007 (doi:10.1038/msb4100049). The *E. coli* W3110 strain was genetically modified to enable production of each of the *E. coli* O-antigen bioconjugates (Table 3).

Bioconjugate Production Strains

The "ExPEC4V" and "ExPEC10V" compositions both comprise the O2-EPA and O25B-EPA bioconjugates from the same production strains. The "ExPEC4V" composition comprises the O1A-EPA bioconjugate from the stGVXN4411 or stLMTB10217 production strains, while the "ExPEC10V" composition comprises the O1A-EPA bioconjugate from the stLMTB10217 production strain. The "ExPEC4V" composition comprises the O6A-EPA bioconjugate from the stGVXN4112 production strain, while the "ExPEC10V" composition comprises the O6A-EPA bioconjugate from the stLMTB10923 production strain. Furthermore, the "ExPEC10V" composition comprises the O4-EPA (i.e. (O4-Glc+)-EPA), O8-EPA, O15-EPA, O16-EPA, O18A-EPA, and O75-EPA bioconjugates from production strains that are not used for "ExPEC4V". Different production strains could vary in the plasmids for expression of the EPA carrier protein and/or the oligosaccharyl transferase PglB, as indicated below. An overview of several production strains is given in Table 3 below.

TABLE 3

Overview of genetic engineering of E. coli production strains for
O-antigen bioconjugates for ExPEC4V and ExPEC10V vaccine compositions

| Serotype | Strain name | Genomic mutations | | | Plasmids | |
| --- | --- | --- | --- | --- | --- | --- |
| | | rfb gene cluster | waaL | gtrABS | pglB | epa |
| O1A (ExPEC4V) | stGVXN4411 | Δrfb::O1A rfb upecGVXN_032 | ΔwaaL | — | pGVXN970 | PGVXN1076 |
| O1A (ExPEC4V; ExPEC10V) | stLMTB10217 | Δrfb::O1A rfb upecGVXN_032 | ΔwaaL | — | pGVXN1221 | PGVXN1076 |
| O2 | stGVXN4906 | Δrfb::O2 rfb upecGVXN_116 | ΔwaaL | — | pGVXN971 | pGVXN1076 |
| O4 | BVEC-L-00684 | Δrfb::O4 rfb CCUG11450 | ΔwaaL | ΔgtrS::gtrS O4 | pGVXN1217 | pGVXN1076 |
| O6A (ExPEC4V) | stGVXN4112 | Δrfb::O6A rfb CCUG11309 | ΔwaaL | — | pGVXN114 | pGVXN659 |
| O6A (ExPEC10V) | stLMTB10923 | Δrfb::O6A rfb CCUG11309 | ΔwaaL | — | pGVXN1221 | pGVXN1076 |
| O8 | stLMTB11734 | Δrfb::O8 rfb E2420 | ΔwaaL | ΔgtrABS | pGVXN970 | pGVXN1076 |
| O15 | stLMTB11738 | Δrfb::O15 rfb OC24891 | ΔwaaL | ΔgtrABS | pGVXN1221 | pGVXN1076 |
| O16 | stLMTB11739 | Δrfb::O16 rfb OC24208 | ΔwaaL | ΔgtrABS | pGVXN2381 | pGVXN1076 |
| O18A | BVEC-L-00559 | Δrfb::O18A rfb OC24255 | ΔwaaL | ΔgtrABS | pGVXN970 | pGVXN1076 |
| O25B | stGVXN4459 | Δrfb::O25B rfb upecGVXN_138 | ΔwaaL | ΔgtrABS | pGVXN970 | pGVXN1076 |
| O75 | stLMTB11737 | Δrfb::O75 rfb CCUG31 | ΔwaaL | ΔgtrABS | pGVXN1217 | pGVXN1076 |

O-Antigen Biosynthesis (Rfb) Gene Cluster

In all E. coli O-antigen production strains, the naturally occurring E. coli W3110 genomic O16::IS5-antigen biosynthesis (rfb) gene cluster was replaced by the selected O-antigen-specific biosynthesis clusters from E. coli strains of the selected serotype, encoding for the serotype-specific O-antigen structures (see Table 1 for these O-antigen structures). The ten donor rfb clusters were selected or confirmed after whole-genome analysis of E. coli blood isolates. Replacement of the W3110 O16::IS5 rfb gene cluster, which is defective in O-antigen biosynthesis, has been achieved in a single homologous recombination event. In case of the O16 and O18A rfb gene clusters, the donor DNA recombined via the flanking gnd and rmlCA genes, while the rfb gene cluster for the other strains recombined via the flanking gnd and galF genes. Sequences of the rfb clusters in the production strains are provided in SEQ ID NOs: 9 and 11-19.

O-Antigen Ligase (waaL) Gene

All E. coli O-antigen production strains carry an artificially introduced deletion of the E. coli W3110 genomic O-antigen ligase encoded by the waaL gene. In the ΔwaaL strains the transfer of the O-antigen to lipid A is disrupted, which instead directs transfer of the O-antigen to the carrier protein to increase product yield.

O-Antigen Glucosylation (gtrABS) Genes

In the E. coli O8, O15, O16, O18A, O25B, and O75 production strains the E. coli W3110 genomic gtrABS genes, which are responsible for O16 O-antigen glucosylation, have been deleted. While the gtrA and gtrB genes in different serotypes are highly homologous and interchangeable, the gtrS gene encodes a serotype-specific O-antigen glycosyl transferase. In E. coli W3110 GtrS can transfer a glucose (Glc) residue to the GlcNAc sugar in the α-L-Rha-(1→3)-D-GlcNAc motif of the E. coli O16 O-antigen. In the E. coli O1A, O2 and O6A production strains no deletion or replacement of the gtrABS gene has occurred. These O-antigens miss the α-L-Rha-(1→3)-D-GlcNAc motif that is the natural substrate for E. coli O16 gtrS. In the E. coli O4 production strain, the W3110 gtrS gene has been replaced with the E. coli O4 gtrS gene to accommodate proper glucosylation of the E. coli O4 O-antigen.

Oligosaccharyl Transferase PglB

All E. coli O-antigen production strains expressed a variant of the C. jejuni glycosyl transferase PglB, which can transfer the O-antigen onto an amino acid consensus sequence on a carrier protein by N-glycosylation. PglB has broad substrate recognition, but due to low product yields several production strains were prepared expressing a PglB variant having modified substrate specificities, which resulted in improved product yield (see e.g. WO 2016/107818, WO 2016/107819). The pglB gene was placed behind an Isopropyl β-D-1-thiogalactopyranoside (IPTG) inducible promoter on a plasmid. Table 4 below lists the PglB variants encoded by the plasmids used for production of the E. coli O-antigen production strains for the bioconjugates for the ExPEC4V and ExPEC10V compositions described above. Further plasmids with variation in vector backbone, antibiotic resistance marker, and/or alternative PglB variants have also been tested successfully for bioconjugate production.

TABLE 4

PglB and EPA plasmids used in *E. coli* O-antigen Production Strains

| Plasmid name | Gene | Description[1] |
|---|---|---|
| pGVXN114 | PglB | *C. jejuni* codon usage; SpR |
| pGVXN970 | pglB | *E. coli* codon usage optimized; SpR |
| pGVXN971 | pglB$^{N534Q}$ | *E. coli* codon usage optimized; The natural glycosylation site of PglB was inactivated; SpR |
| pGVXN1217 | pglB$^{N311V}$ | *E. coli* codon usage optimized; Substrate optimized PglB; SpR |
| pGVXN1221 | pglB$^{N311V, K482R, D483H, A669V}$ | *E. coli* codon usage optimized; Substrate optimized PglB; SpR |
| pGVXN2381 | pglB$^{Y77H, S80R, Q287P, K289R, N311V}$ | *E. coli* codon usage optimized; Substrate optimized PglB; SpR |
| pGVXN659 | EPA-4 | EPA with four bioconjugation sites; AmpR |
| pGVXN1076 | EPA-4 | EPA with four bioconjugation sites; KanR |

[1]SpR, spectinomycin resistant;
AmpR, ampicillin resistant;
KanR, kanamycin resistant Carrier Protein (EPA)

All *E. coli* O-antigen production strains expressed a genetically detoxified *P. aeruginosa* ADP-ribosyltransferase toxoid (EPA) as a carrier protein for the O-antigen. The EPA toxoid differs from wild-type EPA toxin in two residues: Leu552 was changed to Val and Glu553 (in the catalytic domain) was deleted. Glu553 deletions were reported to significantly reduce toxicity. In addition to the detoxification mutation, four (EPA-4) consensus N-glycosylation site motifs were introduced. The epa gene was placed behind a L-Arabinose (Ara) inducible promoter on a plasmid (Table 4). Table 4 is limited to the plasmids used in production strains for bioconjugates used in the "ExPEC4V" and "ExPEC10V" compositions described above. Plasmids with variation in vector backbone, antibiotic resistance marker, and/or EPA variants, e.g. varying in the number of consensus N-glycosylation site motifs (e.g. having two such motifs, EPA-2), have also been tested successfully for bioconjugate production.

Example 7: Optimizing the Oligosaccharyltransferase for Generation of Bioconjugates with Glucosylated O4 (O4-Glc+) Antigen Yield optimization for bioconjugate production can be achieved by modification of the *C. jejuni* oligosaccharyl transferase PglB, which can lead to a more efficient or higher degree of N-glycosylation of the O-antigen of interest to the EPA carrier protein. In an *E. coli* strain for production of bioconjugate with glucosylated O4 (O4-Glc+)O-antigen polysaccharide, such optimization strategy was applied and resulted in an (O4-Glc+)-specific optimized PglB variant improving bioconjugate product yield.

In this approach, an O4-Glc+O-antigen polysaccharide producing strain containing an EPA-expression plasmid was transformed with a variety of different PglB expression plasmids, each of which contained different amino acid substitutions in the PglB protein, altering substrate specificity. Bioconjugate production level and profile of each strain was assessed at shake-flask level in osmotic shock experiments, and readout was performed by capillary electrophoresis immunoassays on the periplasmic extract using O4-Glc+-specific monoclonal antibodies.

Figure 7:
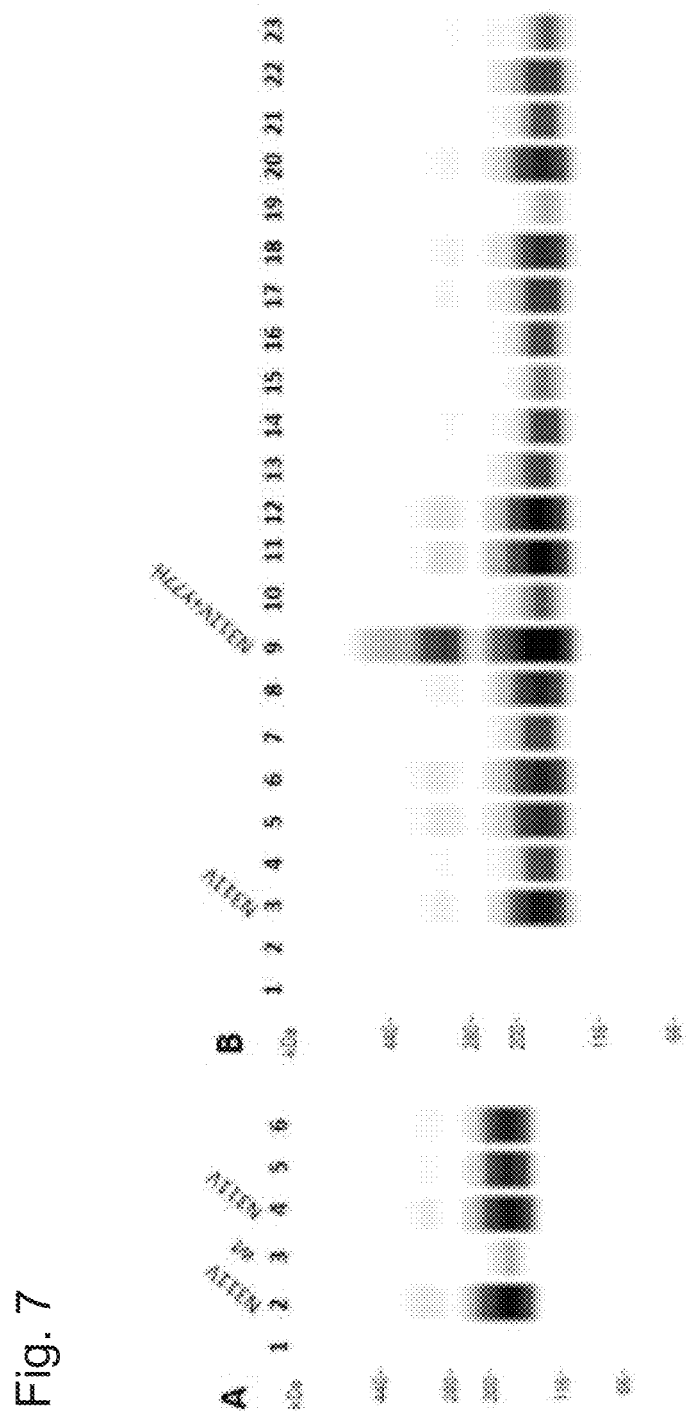
FIG. 7 shows capillary electrophoresis readout of PglB screen visualizing O4-Glc+ bioconjugate production for each tested strain in a blot-like image, using monoclonal antibodies to detect O4-Glc+ bioconjugate in the periplasmic fraction. Mono-glycosylated product approximately 180 kDa, di-glycosylated product approximately 320 kDa and tri-glycosylated product approximately 450 kDa. A) First screening round. Wt PglB in lane 3, N311V-PglB in lanes 2 and 4, empty control strain in lane 1 and other PglB variants in lanes 5 and 6. B) Second screening round. N311V PglB in lane 3, N311V+Y77H PglB in lane 9, empty control strain in lanes 1 and 2, other PglB variants in remaining lanes.

One of the tested PglB variants containing an N311V amino acid substitution was found to improve product yield of glucosylated O4 bioconjugates significantly (FIG. 7A).

In a further improvement where the N311V PgB-variant was further modified, an Y77H amino acid substitution further enhanced O4-Glc+-specific product yield and showed an increased degree of di- and tri-glycosylated product compared to the N311V PglB-variant, where other modifications were found to be neutral or had a negative effect on product yield (FIG. 7B). Plasmid pLMTB4008 (SpR) encodes *E. coli* codon usage optimized, (O4-Glc+)-substrate optimized, PglB variant with mutations Y77H and N311V.

The PglB variant with optimized substrate specificity for O4-Glc+O-antigen polysaccharide, containing N311V and Y77H amino acid substitutions relative to wild-type (wt) *C. jejuni* glycosyl transferase PglB, was found to double bioconjugate yield compared to the first round optimized PglB-N311V variant.

Similarly using screens, the most optimal yielding PglB variants were also determined for *E. coli* O-antigen bioconjugate production of the of the other nine serotypes in the ExPEC10V composition.

For bioconjugates having the O1A, O6A, or O15 antigen polysaccharide, PglB with amino acid mutations N311V, K482R, D483H, and A669V was found to give the highest yields.

For bioconjugates having the O2, O8, O18A, or O25B antigen polysaccharide, wild-type PglB (i.e. not having amino acid mutations at positions 77, 80, 287, 289, 311, 482, 483 and 669) was found to give the highest yields.

For bioconjugates having the O16 antigen polysaccharide, PglB with amino acid mutations Y77H, S80R, Q287P, K289R, and N311V was found to give the highest yields.

For bioconjugates having the O75 antigen polysaccharide, PglB with amino acid mutation N311V was found to give the highest yields.

It can be seen from these results that the optimal PglB variant is different for different O-antigens, and that the optimal PglB variant for producing a bioconjugate with a given O-antigen polysaccharide is unpredictable.

Example 8: Bioconjugates of O-Antigens from 10 *E. coli* Serotypes and their Quality Attributes O-glycan residues of the target O-antigens are structurally diverse and have variable repeating units. The specificity and affinity of the glycosyl transferase PglB is linked to the glycan structure. Thus, making a bioconjugate that has the desired quality attributes, e.g., purity, glycan/protein ratio, etc., is a challenging, non-straightforward, task. The right combination of PglB and EPA carrier protein determines the yield and may influence glycosylation efficiency. By optimizing the PglB and carrier proteins, bioconjugates having the desired quality attributes were produced. It may be also important to maintain a lower threshold value of total carrier protein, particularly when one or more O-antigen bioconjugates are combined together and administered in a single composition or vaccine, because very high amounts of carrier protein may lead to immunological interference. In order to avoid such a phenomenon, conjugates having a higher glycan/protein ratio are preferred. Hence, for ExPEC10V vaccine, bioconjugates with at least comparable (to the previously described ExPEC4V vaccine that has been subject to clinical trials) glycosylation ratio were developed.

The bioconjugates were each produced by culturing the respective host cells (Example 6, Table 3) in bioreactors (10 L and/or 200 L volumes) and expression of the bioconjugates, following methods previously described. Each drug substance was manufactured batch-wise by bacterial fed-batch fermentation to generate biomass containing the expressed bioconjugates of the corresponding polysaccharide serotype. Cells were cultured and induced with IPTG and arabinose. The bioconjugates were isolated from the periplasm of the cells in the bioreactor cultures by osmotic shock followed by chromatographic purification. This process was performed for each of the 10 bioconjugates.

The E. coli O-antigen bioconjugates thus prepared that are drug substances (DSs) for ExPEC10V and ExPEC4V showed comparable critical quality attributes: (1) process-related purity (measured by RP-HPLC) was higher than 95%, (2) polysaccharide/protein ratio ranged between about 0.1-0.5, mostly between 0.15 and 0.45, (3) bacterial endotoxin (Ph. Eur. 2.2.3) was less than 0.5 EU/µg polysaccharide. The average length of the individual polysaccharide chains was typically between about 10-20 repeating units (measured using high resolution SDS-PAGE).

The structures of the polysaccharide repeat units were confirmed (by NMR and MS/MS of the conjugates, intact or trypsin-digested) to be the ones shown in the Formulas for the corresponding serotypes in Table 1, for all ten bioconjugates that are DSs for the ExPEC10V composition described above.

The O18 serotype had the lowest yields of bioconjugate production amongst the ten serotypes of which bioconjugates were made for the ExPEC10V composition.

ExPEC10V drug product (DP) comprises a mixture of the ten monovalent DSs described above.

Example 9: Toxicology of ExPEC10V Vaccine

A single-dose pilot toxicity and local tolerance study (non-GLP) with ExPEC10V was conducted in female NZW rabbits. One group (n=2) received an intramuscular (IM) injection (on Day 0) of the control (saline), and a second group (n=4) received an IM injection of ExPEC10V at 105.6 µg total polysaccharide (PS)/dose (9.6:9.6:9.6:9.6:9.6:9.6: 9.6:9.6:19.2:9.6 µg PS per dose, for respectively O-serotypes O1A, O2, O4, O6A, O8, O15, O16, O18A, O25B and O75) using a dosing volume of 0.6 mL (176 µg PS/mL). Necropsy was performed on Day 2.

There were no mortalities observed. In addition, there were no vaccine-related effects noted for clinical observations (including injection site effects using Draize scoring), body weight, food consumption, and body temperature. Histopathologically, there were no vaccine-related changes observed at the administration site or draining (iliac) lymph node. A minimal increase in germinal center formation in the spleen was observed in one out of four treated animals (Day 2), and was considered a normal, immunological response to the injected vaccine. Overall, the administration of a single IM dose of ExPEC10V to female rabbits was well-tolerated.

Example 10: Immunogenicity of ExPEC10V Blended Formulation in Rabbits

An ExPEC4V vaccine (comprising bioconjugates of E. coli O1A, O2, O6A, and O25B serotypes) has previously been shown to be immunogenic for these four serotypes in rats, rabbits, and humans (see e.g. WO 2015/124769; WO 2017/035181; Huttner et al, 2017, Lancet Infect Dis, http://dx.doi.org/10.1016/S1473-3099(17)30108-1; R W Frenck Jr, et al, abstract 5587, ASM Microbe 2018). The novel bioconjugates of the invention having the E. coli glucosylated O4 serotype were shown to be immunogenic in Examples 4 and 5 above. Immunogenicity of the bioconjugates of E. coli serotypes O8, O15, O16, O18A, and O75 (all having EPA-2 as carrier protein in this experiment) when separately administered (monovalent) to rats confirmed that also each of these bioconjugates was immunogenic, since ELISA data indicated that each of these bioconjugates could elicit high levels of E. coli O-antigen specific antibodies (not shown).

Immunogenicity of the 10-valent vaccine that contained a mixture of the 10 bioconjugates as described above was also tested. New Zealand White (NZW) rabbits (female, 12-16 weeks old) received 3 intramuscular immunizations with ExPEC10V or saline administered 2 weeks apart (Table 5; administration at days 0, 14, and 27). The 10 polysaccharides that are part of the ExPEC10V vaccine used in these experiments were conjugated to the carrier protein EPA containing 4 sites of glycosylation (EPA-4). The vaccine was formulated in 3 different doses: Group 1 ('high dose'): 8 ug/dose of O1A, O2, O6A, O4, O8, O15, O16, O18 and O75 and 16 ug/dose of O25B; Group 2 ('medium dose'): 4 ug/dose of O2, O4, O8, O15, O16, O18 and O75, 8 ug/dose of O1A and O6A and 16 ug/dose of O25B; Group 3 ('low dose'): 0.4 ug/dose of O2, O4, O8, O15, O16, O18 and O75, 0.8 ug/dose of O1A and O6A and 1.6 ug/dose of O25B. Animals from the control group (Group 4) received only saline (0.9% (w/v) sodium chloride solution) (Table 5).

Antibody responses were evaluated at day 0 (pre-immunization) and days 14, 27 and 42 post-immunization. Serum antibody levels induced by each of the bioconjugates included in the vaccine and the carrier protein EPA were measured by ELISA (total IgG), using type-specific LPS as coating material. The antibody titers were reported as EC50 values that correspond to the half maximal effective concentration based on duplicates of 12-step titration curves plotted in a 4-parameter logistic nonlinear regression model. Functional activity was determined by OPK.

TABLE 5

Description of experimental groups.

| Experimental groups | Dosing (µg/PS) O1A:O2:O6A:O25B:O4:O8:O15:O16:O18A:O75 | Sample size |
|---|---|---|
| Group 1 (high dose) | 8:8:8:16:8:8:8:8:8:8 | 7 |

TABLE 5-continued

Description of experimental groups.

| Experimental groups | Dosing (μg/PS) O1A:O2:O6A:O25B:O4:O8:O15:O16:O18A:O75 | Sample size |
|---|---|---|
| Group 2 (medium dose) | 8:4:8:16:4:4:4:4:4:4 | 7 |
| Group 3 (low dose) | 0.8:0.4:0.8:1.6:0.4:0.4:0.4:0.4:0.4:0.4 | 7 |
| Group 4 (control) | 0.9% (w/v) sodium chloride solution | 7 |

Figure 8:
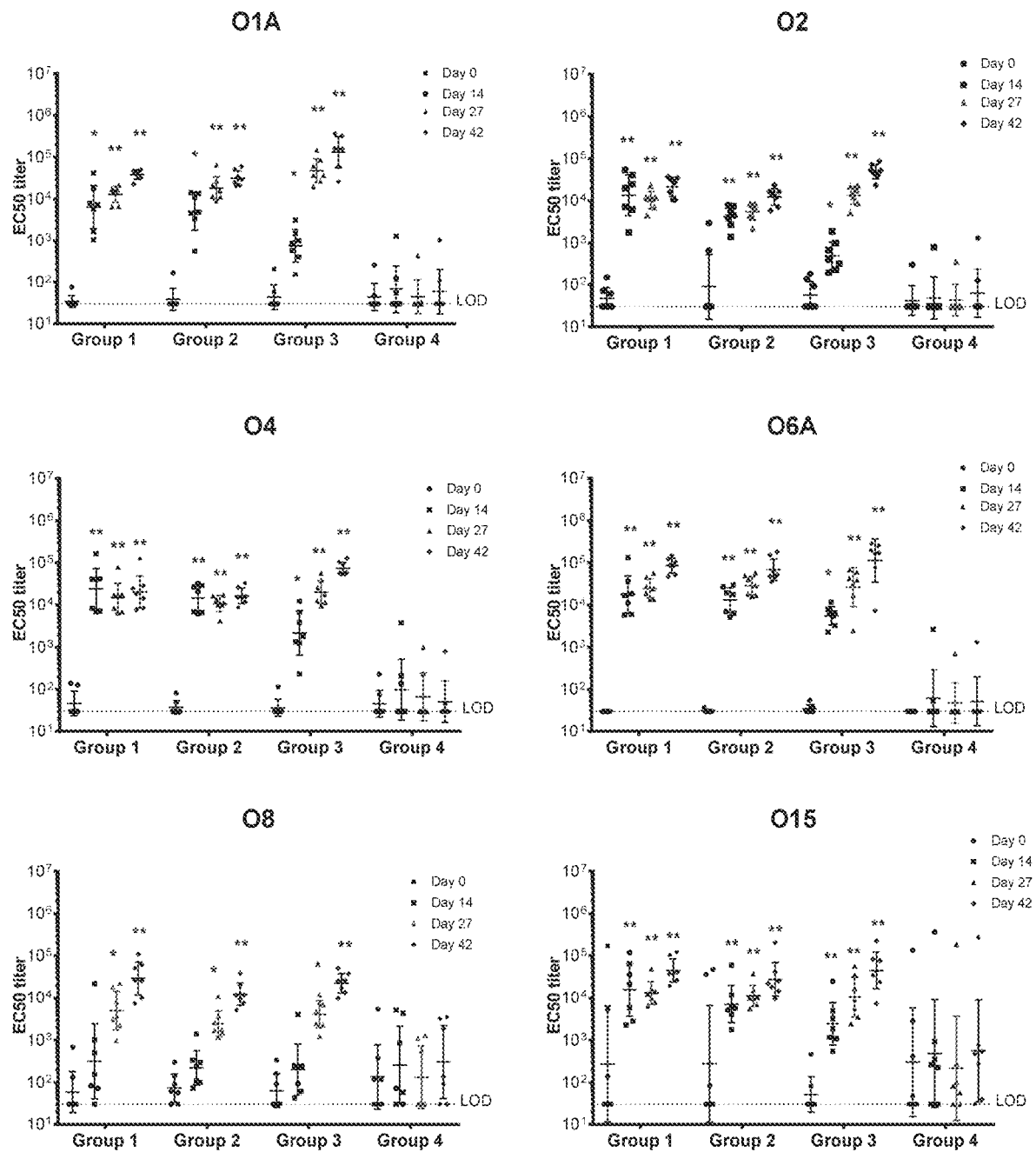
FIG. 8 shows antibody responses induced by ExPEC10V vaccine in New Zealand White rabbits. Animals received 3 intramuscular immunizations with ExPEC10V or saline administered 2 weeks apart. ExPEC10V vaccine was administered at 3 different concentrations (group 1: high dose, group 2: medium dose and group 3: low dose, Table 11) and a control group received only saline (group 4, 0.9% (w/v) sodium chloride solution). Antibody levels were measured by ELISA at day 0 (pre-vaccination) and days 14, 27 and 42 (post-vaccination). Individual titers (EC50 titer) and geometric mean titers (GMT)+95% CI are shown. Wilcoxon Rank Sum test with Bonferroni correction for multiple comparisons. Comparisons ExPEC10V vaccinated animals (group 1, 2 and 3) versus saline control (group 4). *p≤0.05, p≤0.01; *p≤0.001; ****p≤0.0001. LOD: limit of detection.

Results are shown in FIG. 8 and summarized in Table 6.

TABLE 6

Summary of *E. coli* O-antigen specific antibody responses induced by ExPEC10V in NZW rabbits.

| ExPEC10V dose | O1A | O2 | O6A | O25B | O4 | O8 | O15[#] | O16 | O18A | O75 |
|---|---|---|---|---|---|---|---|---|---|---|
| Antibody responses day 14 post-vaccination ||||||||||| 
| High | * | ** | ** | * | ** | ns | ** | ** | * | ns |
| Mid | * | ** | ** | ** | ** | ns | ** | ** | ns | ns |
| Low | * | * | * | * | * | ns | ** | ** | ns | ns |
| Antibody responses day 27 post-vaccination ||||||||||
| High | ** | ** | ** | ** | ** | * | ** | ** | ** | ** |
| Mid | ** | ** | ** | ** | ** | * | ** | ** | * | ** |
| Low | ** | ** | ** | ** | ** | * | ** | ** | ** | ** |
| Antibody responses day 42 post-vaccination ||||||||||
| High | ** | ** | ** | ** | ** | ** | ** | ** | ** | ** |
| Mid | ** | ** | ** | ** | ** | ** | ** | ** | ** | ** |
| Low | ** | ** | ** | ** | ** | ** | ** | ** | ** | ** |

Serotype-specific antibody responses in which p values were statistically significant are shown by asterisks.
Serotype-specific antibody responses in which p values were not statistically significant are designated as ns.
Wilcoxon Rank Sum test with Bonferroni correction for multiple comparisons.
Comparisons ExPEC10V vaccinated animals (Group 1, 2 and 3) versus saline control (Group 4).
* $p \leq 0.05$,
** $p \leq 0.01$.
[#]P values were statistically significant after excluding an outlier animal from the control group (sensitivity analysis).

The high dose of ExPEC10V (Group 1) induced significantly higher IgG antibody levels at all time-points investigated (Days 14, 27 and 42 post-immunization) when compared to saline control for O1A, O2, O4, O6A, O16, O18A and O25B (FIG. 8, Table 6). Significantly higher antibody titers induced by O8 and O75 conjugates when compared to saline control were observed at Days 27 and 42 post-immunization (FIG. 8, Table 6).

The medium dose of ExPEC10V (Group 2) and the low dose (Group 3) induced significantly higher antibody levels at all time-points investigated (Days 14, 27 and 42 post-immunization) when compared to saline control for O1A, O2, O4, O6A, O16 and O25B (FIG. 8, Table 6). Significantly higher antibody titers induced by O8, O18A and O75 conjugates when compared to saline control were observed at Days 27 and 42 post-immunization suggesting that the boost dose in rabbits increases the response to these O-serotypes (FIG. 8, Table 6).

For O15 conjugates, sensitivity analysis omitting an outlier animal from the control group showed that all three doses of ExPEC10V vaccine induced a significant increase in antibody responses when compared to saline control at Days 14, 27 and 42 post-immunization (FIG. 8, Table 6).

Antibodies induced by the carrier protein EPA were significantly higher than EPA antibody titers in the saline-treated (control) group for the three doses of ExPEC10V tested (high, medium and low) at all time points investigated (Days 14, 27 and 42) (FIG. 8).

Between dose comparisons (not shown) showed that at Day 14 post-vaccination, the high dose of ExPEC10V induced significantly higher antibody responses when compared to the low dose for most of the conjugates tested (O1A, O2, O4, O6A, O15, O16, O18A and O25B). The medium dose of ExPEC10V also induced significantly higher antibody responses compared to the low dose for O1A, O2, O4, O18A, O25B and O75. For O8 conjugate, all three formulations of ExPEC10V induced similar levels of antibodies at Day 14 post-vaccination.

The low dose of ExPEC10V induced a significant increase in antibody responses at Day 42 post vaccination (after a prime and two boost doses) when compared to the high and medium doses of ExPEC10V for O1A, O2, O4, O16, O25B and O75 conjugates. These findings are in line with other experiences with conjugate vaccines, where for instance no clear relationship between dose and the magnitude of the antibody response to primary vaccination was observed in infants vaccinated with pneumococcal conjugate vaccine (Poolman J T, et al. Expert Rev Vaccines. 2013, 12(12):1379-94).

There were no significant differences between the three doses of ExPEC10V tested at Day 42 post-vaccination for O6A, O8 and O15 conjugates. For the O18A conjugate, the high dose of ExPEC10V induced a significantly higher antibody response when compared to the medium dose at Day 42 post-vaccination.

For the carrier protein (EPA), the high and medium dose of ExPEC10V induced significantly higher antibody responses when compared to the low dose at day 14 post-vaccination. The high dose of the vaccine also induced significantly higher antibody responses when compared to the low dose at day 42 post-vaccination.

In conclusion, the three formulations of ExPEC10V (high, medium and low), administered via intramuscular injection on Days 0, 14, 27 are immunogenic in rabbits.

So far, functional antibodies capable of killing E. coli strains induced by this vaccine in rabbits were shown for serotypes O1A, O2, O4, O6A, O15, O16 and O25B.

In a further experiment, a GMP batch of the ExPEC10V vaccine (see Example 8 above for production) was prepared and injected into NZW rabbits as part of a toxicology study (Table 7). In this study, NZW rabbits (males and females) received 3 intramuscular injections (0.6 mL) of the ExPEC10V vaccine (day 1, 15 and 29) and a control group received 0.9% (w/v) sodium chloride solution (saline). Each dose of the vaccine contained 9.6 µg polysaccharide (PS) for serotypes O1A, O2, O4, O6A, O8, O15, O16, O18A and O75 and 19.2 µg PS for serotypes O25B, corresponding to 105.6 µg total PS (176 µg total PS/mL) and 382.8 µg of total EPA (638 µg EPA/mL). IgG titers against O-antigens and carrier protein (EPA) were determined from samples collected during the pre-treatment period (day 1) and days 31 and 50 post-immunization.

Figure 9:
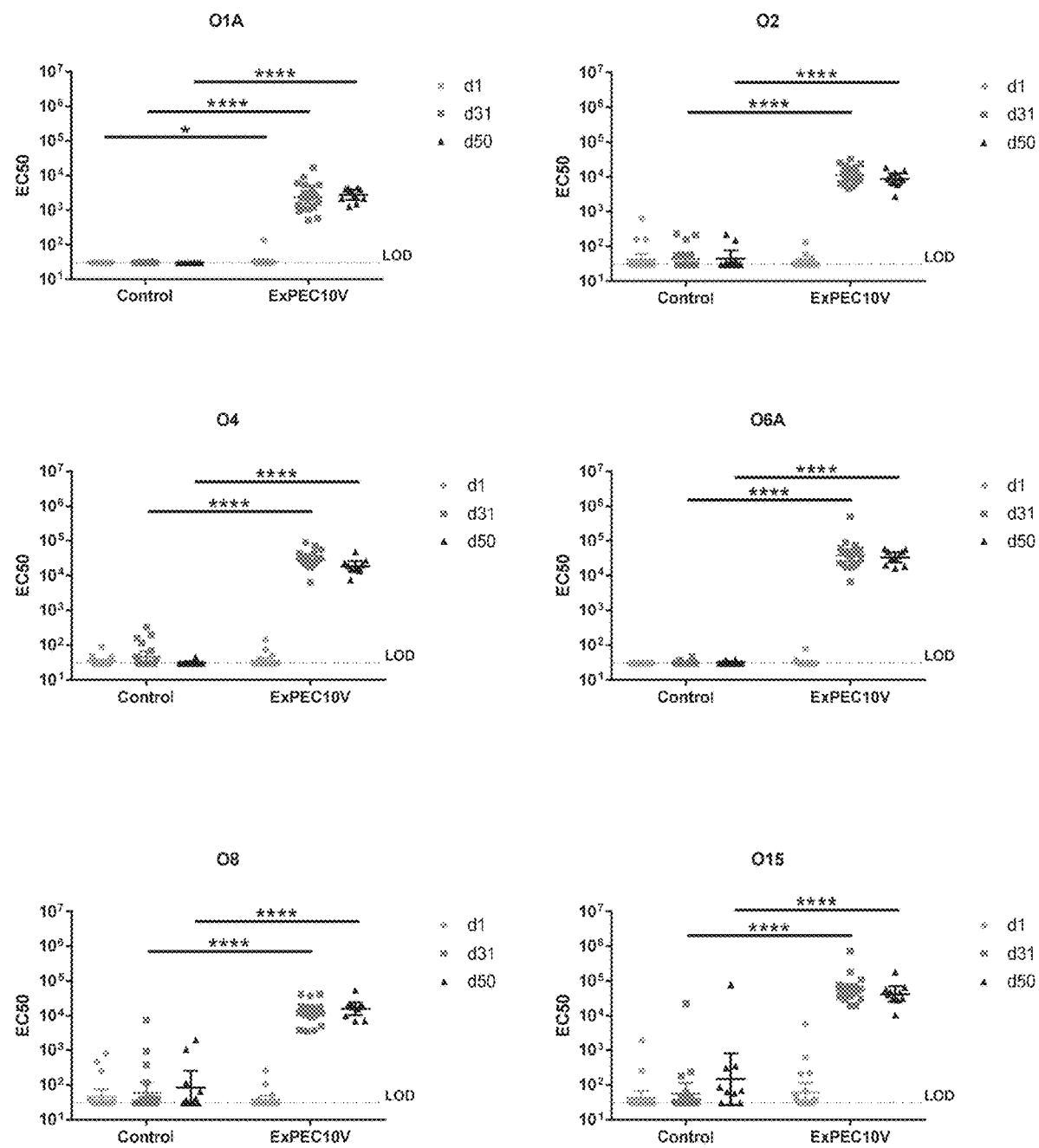
FIG. 9 shows antibody responses induced by ExPEC10V. New Zealand White rabbits received 3 intramuscular immunizations with ExPEC10V (105.6 µg total polysaccharide) or 0.9% w/v sodium chloride solution (control). IgG titers were determined by ELISA at day 1 (pre-immunization, n=20/group), day 31 (post-immunization, n=20/group) and day 50 (post-immunization, n=10/group). Plots show individual titers and geometric mean±95% confidence interval for each group. Differences in IgG titers between the ExPEC10V and control group were analyzed using a Tobit model with a likelihood ratio test. P-values≤0.05 were considered significant. *P≤0.05, ****P≤0.0001.

A significant increase in antibody responses against all O-antigens and the carrier protein EPA were observed at day 31 and 50 post-vaccination in the group that received ExPEC10V when compared to the control group that received only saline (FIG. 9, Table 8). For O1A serotype, a significantly higher antibody response was also observed at day 1 (baseline) when vaccinated animals were compared with the controls. These results suggest that some animals were pre-exposed to E. coli or have antibodies that cross-react with O1A-LPS.

Since the mechanism of action of conjugate vaccines in the prevention of invasive disease is not expected to be affected by antibiotic resistance mechanisms, it is believed that ExPEC10V vaccine provides protection against IED caused by drug-resistant- and drug-susceptible O1A, O2, O4, O6A, O8, O15, O16, O18A, O25B and O75 serotypes.

There is preceding clinical experience with ExPEC4V, an earlier vaccine candidate which comprised a subset of four of the E. coli O-antigen conjugates (O1A, O2, O6A and O25B) also found in ExPEC10V. Based on the results from four clinical studies (two completed phase 1 studies, one completed phase 2 study and an ongoing phase 2 study), ExPEC4V was well-tolerated by the study participants and no vaccine-related safety signals were observed at doses up to 16 µg polysaccharide (PS) per serotype (O1A, O2, O6A and O25B). Most adverse events (AEs) were Grade 1 and 2, very few Grade 3 AEs were reported. Late-onset solicited local AEs (AEs which start after Day 5 post-vaccination) were observed mainly with the higher doses of ExPEC4V. In each study, the ExPEC4V vaccine was shown to be immunogenic, demonstrating a dose-dependent vaccine immune response, and O-antigen specific Immunoglobulin G (IgG) titer increases, as measured by enzyme-linked immunosorbent assay (ELISA). Functional activity of the antibodies was demonstrated with an ExPEC4V-optimized opsonophagocytic killing assay (OPKA). Co-analysis of ELISA and OPKA test results showed correlation between the assay responses (Pearson correlation coefficients ≥0.61

TABLE 7

Experimental groups and ExPEC10V dose used in NZW rabbits.

| Groups | Treatment | Dose | Dosing days | Main (day 31) (males/females) | Recovery (day 50) (males/females) |
|---|---|---|---|---|---|
| 1 | control | 0 | 1, 15, 29 | 10 | 10 |
| 2 | ExPEC10V | 105.6 µg PS* | 1, 15, 29 | 10 | 10 |

*Each dose (0.6 mL dosing volume) contains 9.6:9.6:9.6:9.6:9.6:9.6:9.6:9.6:19.2:9.6 µg polysaccharide (PS) for serotypes O1A, O2, O4, O6A, O8, O15, O16, O18A, O25B, O75, respectively (176 µg total PS/mL). Each dose contains 382.8 µg EPA protein (638 µg EPA/mL).

TABLE 8

Immunogenicity of ExPEC10V in NZW rabbits as part to a toxicology study.

| Treatment | Antibody responses day 14 post-vaccination | | | | | | | | | |
|---|---|---|---|---|---|---|---|---|---|---|
| ExPEC10V | O1A | O2 | O6A | O25B | O4 | O8 | O15 | O16 | O18A | O75 |
| Day 31 | **** | **** | **** | **** | **** | **** | **** | **** | **** | **** |
| Day 50 | **** | **** | **** | **** | **** | **** | **** | **** | **** | **** |

Antibody responses induced by ExPEC10V. Serotypes in which a significant increase in antibody responses was observed in the vaccine group compared to control are shown by asterisks. Tobit model with a likelihood ratio test.
**** P ≤ 0.0001.

Example 11: Phase 1/2a Trial with the ExPEC10V Vaccine in Humans

At present, there is no vaccine available to prevent IED. The serotypes comprising the ExPEC10V vaccine (O1A, O2, O4, O6A, O8, O15, O16, O18A, O25B and O75) were selected to address invasive disease caused by the majority of clinically relevant ExPEC strains that also represent the majority of ExPEC isolates causing antimicrobial resistant IED, including ST131. The selected serotypes are representative for the ten prevalent ExPEC O-serotypes causing bloodstream infections in the older population and responsible for approximately 70% of bloodstream infections caused by ExPEC.

and ≥0.48 for Day 30 and Day 360, respectively in a Phase 2 clinical trial [study 4V-BAC2001]), substantiating the use of ELISA as a primary measure of ExPEC4V antibody titers and to predict functional antibody activity. Analysis of the immunogenicity data has demonstrated the durability of the immune response through three years after vaccination with ExPEC4V. It has now also been observed that sera from humans vaccinated with ExPEC4V and that had high titers of serotype-specific opsonophagocytic antibodies, when passively transferred into mice that were subsequently intraperitoneally challenged with E. coli strains of O25B or O2 serotype, were able to mediate protection in vivo (not shown). Hence, ExPEC4V-specific opsonophagocytic human antibodies mediate bacterial killing in vivo, which is in line with other conjugate vaccines in which the proposed mechanism of protection is by induction of opsonophagocytic antibodies that mediate bacterial killing.

ExPEC10V includes a total often serotypes and increases coverage from about 50% (ExPEC4V) to approximately 70% of bloodstream infections caused by ExPEC in adults aged 60 years and older. Based on the clinical experience with ExPEC4V, and on the pre-clinical data for ExPEC10V as discussed in the examples above, it is expected that administration of ExPEC10V will induce immune responses to E. coli serotypes O1A, O2, O4, O6A, O8, O15, O16, O18A, O25B and O75 also in humans.

A randomized, observer-blind, first-in-human phase 1/2a study to evaluate the safety, reactogenicity, and immunogenicity of three different doses of the ExPEC10V vaccine is conducted in humans aged 60 to 85 years in stable health (study 10V-BAC1001). The study design includes 2 cohorts: A total of 1,004 participants are enrolled in the study with 404 participants (100 participants/ExPEC10V dose) aged ≥60 to ≤85 years in stable health in Cohort 1 and an additional of 600 participants aged ≥60 years in stable health with a history of UTI in the past 5 years in Cohort 2.

ExPEC10V is a 10-valent vaccine candidate in development for the prevention of invasive extraintestinal pathogenic *Escherichia coli* (ExPEC) disease (IED) in adults 60 years of age and older. ExPEC10V consists of the O-antigen polysaccharides (PSs) of the ExPEC serotypes O1A, O2, O4, O6A, O8, O15, O16, O18A, O25B and O75 separately bioconjugated to the carrier protein, a genetically detoxified form of exotoxin A (EPA) derived from *Pseudomonas aeruginosa*, and its production has been described above. The O4 PS is the glucosylated form, having the structure of Formula (O4-Glc+) in Table 1.

Objectives and Endpoints

COHORT 1—Phase 1/2a observer-blind period with open-label long-term follow-up period (N=404):

| Objectives | Endpoints |
|---|---|
| Primary | |
| To evaluate the safety and reactogenicity of different doses of ExPEC10V in participants ≥60 to ≤85 years of age | Solicited local and systemic adverse events (AEs) collected for 14 days post-vaccination (from Day 1 to Day 15) Unsolicited AEs collected from the administration of the study vaccine until 29 days post-vaccination (from Day 1 to Day 30) Serious adverse events (SAEs) collected from the administration of the study vaccine until Day 181 |
| To evaluate the dose-dependent immunogenicity of ExPEC10V on Day 15 in participants ≥60 to ≤85 years of age | Antibody titers for ExPEC10V, as determined by multiplex electrochemiluminescent (ECL)-based immunoassay and multiplex opsonophagocytic assay (MOPA) on Day 15 |
| Secondary | |
| To evaluate the correlation between multiplex ECL-based immunoassay (total antibody) and MOPA (functional antibody) serum titers on Day 15 | Antibody titers for ExPEC10V, as determined by multiplex ECL-based immunoassay and MOPA on Day 15 |
| To evaluate the dose-dependent immunogenicity of ExPEC10V on Days 30 and 181 in participants ≥60 to ≤85 years of age | Antibody titers for ExPEC10V, as determined by multiplex ECL-based immunoassay and MOPA on Days 30 and 181 |
| To evaluate, in the long-term follow-up (LTFU) period, the safety of the ExPEC10V dose selected for further clinical development based on the Day 30 primary analysis in participants ≥60 to ≤85 years of age | SAEs related to the study vaccine or study procedures collected from Day 182 until the end of the study |
| To evaluate, in the LTFU period, the immunogenicity of the ExPEC10V dose selected for further clinical development based on the Day 30 primary analysis | Antibody titers for ExPEC10V, as determined by multiplex ECL-based immunoassay and MOPA at Year 1 (Day 366), Year 2 (Day 731) and Year 3 (Day 1096) |

COHORT 2—Double-blind period with double-blind long-term follow-up period (N=600):

| Objectives | Endpoints |
|---|---|
| Primary | |
| To evaluate the safety and reactogenicity of the selected dose of ExPEC10V in participants ≥60 years of age with a history of UTI in the past 5 years | Solicited local and systemic AEs collected for 14 days post-vaccination (from Day 1 to Day 15) Unsolicited AEs collected from the administration of the study vaccine until |

-continued

| Objectives | Endpoints |
|---|---|
| To evaluate the immunogenicity of the selected dose of ExPEC10V on Day 30 in participants ≥60 years of age with a history of UTI in the past 5 years | 29 days post-vaccination (from Day 1 to Day 30) SAEs collected from the administration of the study vaccine until Day 181 Antibody titers for ExPEC10V, as determined by multiplex ECL-based immunoassay and MOPA on Day 30 |
| Secondary | |
| To evaluate the correlation between multiplex ECL-based immunoassay (total antibody) and MOPA (functional antibody) serum titers on Day 30 in participants ≥60 years of age with a history of UTI in the past 5 years | Antibody titers for ExPEC10V, as determined by multiplex ECL-based immunoassay and MOPA on Day 30 |
| To evaluate the immunogenicity of the selected dose of ExPEC10V on Days 15 and 181 in participants ≥60 years of age with a history of UTI in the past 5 years | Antibody titers for ExPEC10V, as determined by multiplex ECL-based immunoassay and MOPA on Days 15 and 181 |
| To evaluate, in the LTFU period, the safety of the selected dose of ExPEC10V in participants ≥60 years of age with a history of UTI in the past 5 years | SAEs related to the study vaccine or study procedures collected from Day 182 until the end of the study |
| To evaluate, in the LTFU period, the immunogenicity of the selected dose of ExPEC10V in participants ≥60 years of age with a history of UTI in the past 5 years | Antibody titers for ExPEC10V, as determined by multiplex ECL-based immunoassay and MOPA at Year 1 (Day 366), Year 2 (Day 731), and Year 3 (Day 1096) |
| Exploratory | |
| To evaluate the effect of ExPEC10V on the intestinal (stool) microbiome by metagenomic analyses | Metagenomics of stool samples from a selected subset of participants to evaluate the effect of ExPEC10V on: Prevalence of pathogens (eg, *Clostridium difficile*) in the intestinal flora Prevalence of ExPEC10V serotypes in the intestinal flora |

Overall Design

This is a randomized, multicenter, interventional study including two cohorts.

Figure 10A:
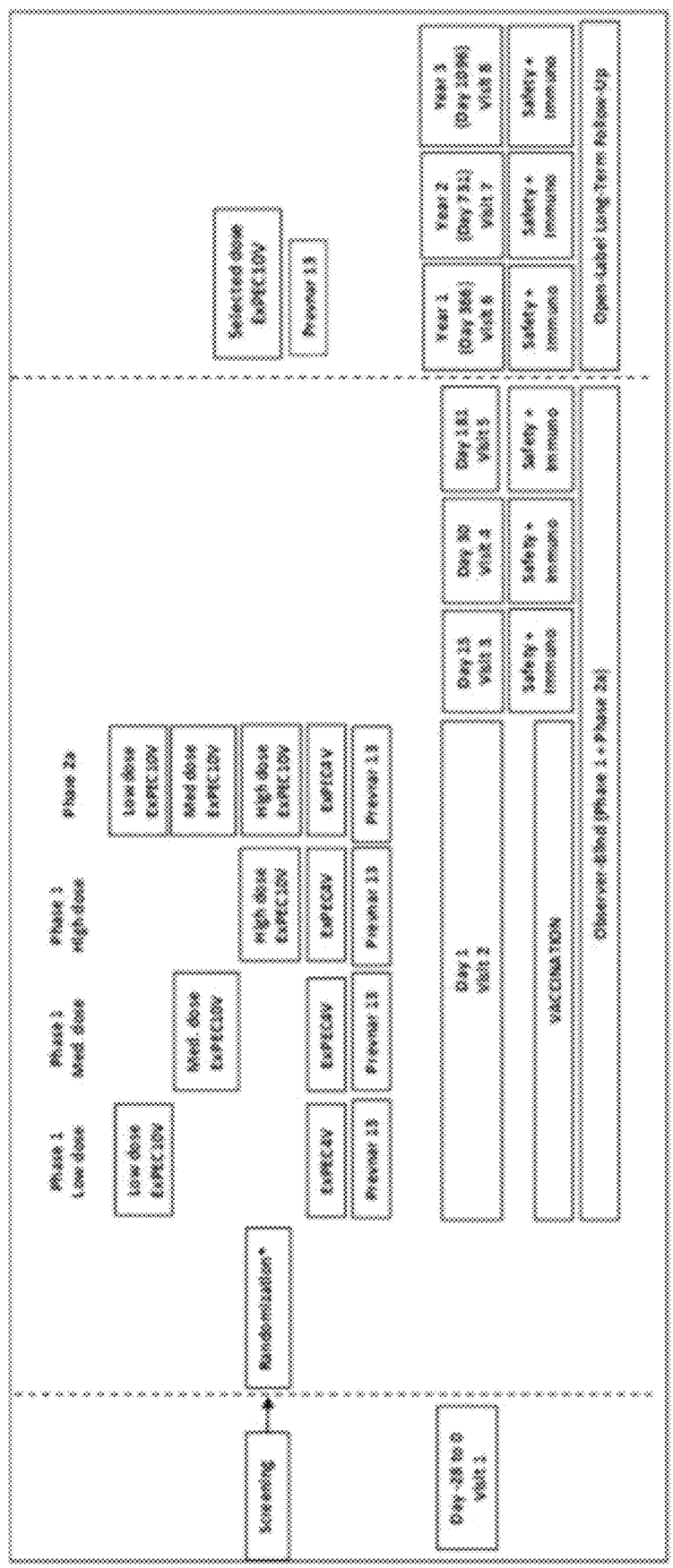
FIG. 10A shows the overall study design for Cohort 1.

For Cohort 1, the study has an observer-blind, active-controlled design, and a total of 404 adult participants aged ≥60 to ≤85 years in stable health with or without a history of UTI are included. The study design for Cohort 1 is comprised of three periods: a maximum of 28-day screening period, an observer-blinded 181-day follow-up period with vaccination on Day 1 and an open-label LTFU period which lasts from Day 182 until 3 years (Day 1096) post-vaccination (FIG. 10A). Only participants from the ExPEC10V selected dose group (approximately 100 participants) and participants from the Prevnar 13 group progress to the LTFU period. The end of Cohort 1 is the last participant's Year 3 visit (Day 1096).

Figure 10B:
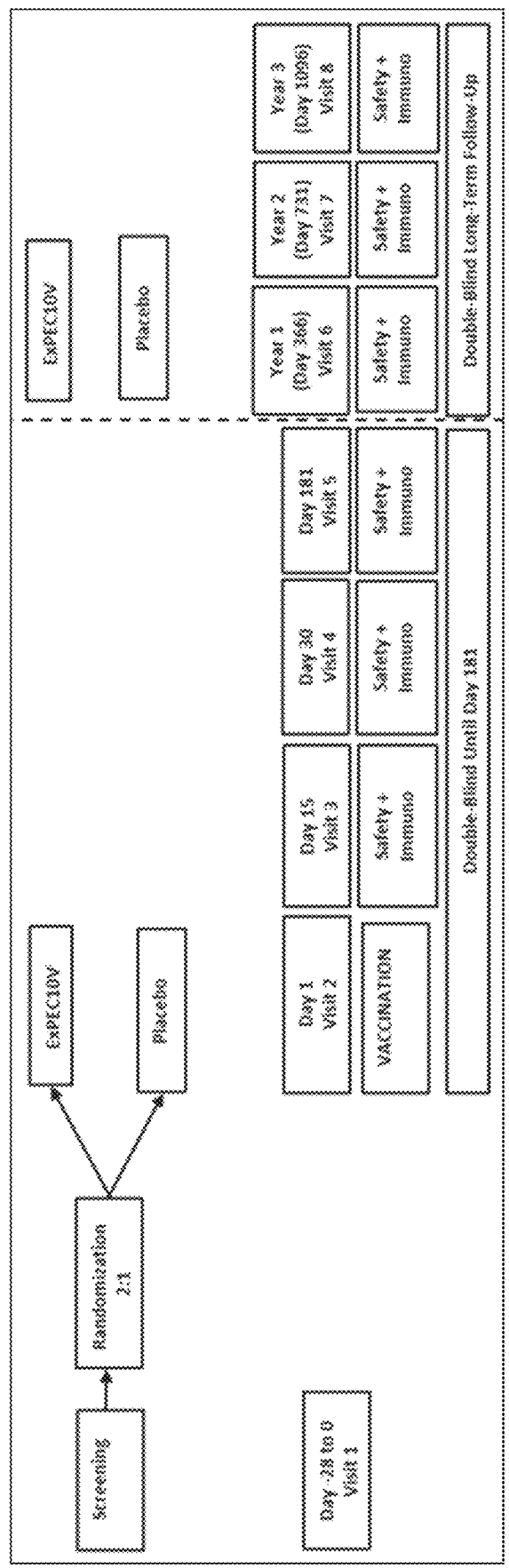
FIG. 10B shows the overall study design for Cohort 2. See Example 11 for details.

For Cohort 2, the study has a double-blind, placebo-controlled design, and a total of 600 adult participants aged ≥60 years in stable health with a history of UTI in the past 5 years is included. Enrollment commences after completion of the Phase 1/2a primary analysis and ExPEC10V dose selection from Cohort 1. The study design for Cohort 2 is comprised of three periods: a maximum 28-day screening period, a double-blind 181-day follow-up period with vaccination on Day 1, and a double-blind LTFU period which lasts from Day 182 until 3 years (Day 1096) post-vaccination (FIG. 10B). All participants in Cohort 2 progress to the LTFU period. The end of study is the last participant's Year 3 visit (Day 1096) in Cohort 2.

Cohort 1: Phase 1

In Phase 1 of Cohort 1, a total of 84 participants are enrolled in a staggered approach following stepwise dose-escalating procedures with safety evaluations in place before progressing from one step to the next. An internal Data Review Committee (DRC) is commissioned for this study to review the physical examination data (baseline as well as targeted), baseline demographic data and the 14-day post-vaccination safety data (including solicited local and systemic AEs, unsolicited AEs, SAEs, clinical laboratory data and vital signs) of these 84 Phase 1 participants. In this phase of the study, participants were enrolled and randomized in six steps:

Step 1: Four sentinel participants were enrolled and randomized; two participants in the ExPEC10V low dose group (Table 11), and one participant each in the ExPEC4V and Prevnar 13 groups.

Step 2: Twenty-four participants were enrolled and randomized; 18 participants in the ExPEC10V low dose group (Table 11), and three participants each in the ExPEC4V and Prevnar 13 groups.

Step 3: Four sentinel participants were enrolled and randomized; two participants in the ExPEC10V medium dose group (Table 11), and one participant each in the ExPEC4V and Prevnar 13 groups.

Step 4: Twenty-four participants were enrolled and randomized; 18 participants in the ExPEC10V medium dose group (Table 11), and three participants each in the ExPEC4V and Prevnar 13 groups.

Step 5: Four sentinel participants were enrolled and randomized; two participants in the ExPEC10V high dose group (Table 11), and one participant each in the ExPEC4V and Prevnar 13 groups.

Step 6: Twenty-four participants were enrolled and randomized; 18 participants in the ExPEC10V high dose group (Table 11), and three participants each in the ExPEC4V and Prevnar 13 groups.

All participants received a single intramuscular (IM) injection of either ExPEC10V (1 of 3 doses), ExPEC4V or Prevnar 13 on Day 1 per the assigned study vaccination groups. The four sentinel participants at each of Steps 1, 3 and 5 were contacted by telephone 24 hours post-vaccination to collect safety information. The blinded 24-hour post-vaccination safety data in each group of four sentinel participants were reviewed by the principal investigator (PI), study responsible physician (SRP) and sponsor medical lead (SML). Randomization of additional participants for the next step was halted until this Day 2 sentinel safety evaluation was completed.

In the absence of any clinically significant findings, an additional 24 participants (for Steps 2, 4, and 6) were enrolled and randomized to one of three study vaccination groups (Table 11) to receive a single IM injection of either ExPEC10V (1 of 3 doses), ExPEC4V or Prevnar 13 on Day 1.

After vaccination of an additional 24 participants at each dose level (low dose in Step 2, medium dose in Step 4, and high dose in Step 6), 14-day post-vaccination safety data of all 28 (4+24) participants at each dose level was reviewed by the DRC before progressing to the next dose level or Phase 2a.

Cohort 1: Phase 2a

Based on acceptable safety and reactogenicity (in the absence of any safety concerns or any events meeting a specific study pausing rule) as determined by DRC after the review of 14-day post-vaccination safety data for the initial 84 participants, the remaining 320 participants from Cohort 1 are randomized and dosed in Phase 2a of the study. These additional 320 participants were enrolled and randomized in parall in a ratio of 2:2:2:1:1 to one of the five study vaccination groups to receive a single IM injection of either ExPEC10V (1 of 3 doses), ExPEC4V or Prevnar 13 on Day 1 (Table 11).

In addition to performing the 14-day safety review for the initial 84 participants, the DRC also evaluates safety data of Cohort 1 over the course of the study and review any events that meet a specific study vaccination pausing rule or any other safety issue that may arise.

For Cohort 1, the primary analysis occurs when all participants have completed the Day 30 visit (Visit 4) or have discontinued earlier. The final analysis occurs when all participants have completed the Day 181 visit or have discontinued earlier. For participants progressing to the open-label long-term follow-up (LTFU) period (ExPEC10V selected dose group and Prevnar 13 group), yearly follow-up analyses include safety and immunogenicity data (multiplex ECL-based immunoassay and MOPA) collected up to the time of the visit at Year 1 (Day 366), Year 2 (Day 731) and Year 3 (Day 1096) after vaccination.

Cohort 2

In Cohort 2, the safety, reactogenicity, and immunogenicity of the selected dose of ExPEC10V (based on the primary analysis results of Cohort 1) is evaluated in participants aged ≥60 years in stable health with a history of UTI in the past 5 years. For Cohort 2, the study has a double-blind, placebo-controlled design, and a total of 600 participants are enrolled and randomized in parallel in a 2:1 ratio (400 participants in the ExPEC10V group and 200 in the placebo group).

All participants receive a single IM injection of either the selected dose of ExPEC10V or placebo on Day 1 per the assigned study vaccination groups (Table 11).

For Cohort 2, the primary analysis includes safety and immunogenicity data and occurs when all participants have completed the Day 30 visit (Visit 4) or have discontinued earlier. The final analysis occurs when all participants have completed the Day 181 visit or have discontinued earlier. For all participants, yearly follow-up analyses include safety and immunogenicity data (multiplex ECL-based immunoassay and MOPA) collected up to the time of the visit at Year 1 (Day 366), Year 2 (Day 731), and Year 3 (Day 1096) after vaccination.

A stool sample analysis is performed in a selected subset of participants to evaluate the effect of ExPEC10V on the prevalence of pathogens (eg, *Clostridium difficile*) and ExPEC10V serotypes in the intestinal flora using metagenomics.

Number of Participants

A total of 1004 participants is enrolled in the study; 404 participants in Cohort 1 and 600 participants in Cohort 2.

Intervention Groups

Description of Interventions

ExPEC10V: *E. coli* bioconjugate vaccine in phosphate buffered solution containing O-antigen PS of ExPEC serotypes O1A, O2, O4, O6A, O8, O15, O16, O18A, O25B and O75 separately bioconjugated to the EPA carrier protein. Single 0.5 mL IM (deltoid) injection of one of the three doses of ExPEC10V on Day 1.

ExPEC4V: *E. coli* bioconjugate vaccine in saline buffer solution containing O-antigen PS of ExPEC serotypes O1A, O2, O6A, O25B (4:4:4:8 µg PS/ExPEC serotypes) separately bioconjugated to the EPA carrier protein. Single 0.5 mL IM (deltoid) injection of ExPEC4V on Day 1.

Prevnar 13: Sterile suspension of saccharides of the capsular antigens of *Streptococcus pneumoniae* serotypes 1, 3, 4, 5, 6A, 6B, 7F, 9V, 14, 18C, 19A, 19F, and 23F, individually linked to non-toxic Diphtheria CRM197 protein. Single 0.5 mL IM (deltoid) injection on Day 1, supplied in a single-dose prefilled syringe.

Placebo: normal saline. Single 0.5 mL IM (deltoid) injection of placebo on Day 1.

The ExPEC study intervention materials are described in Table 9.

TABLE 9

| | BAC1001MV ExPEC Study Vaccines | | | | | | | | | | | |
|---|---|---|---|---|---|---|---|---|---|---|---|---|
| Study Arm | O1A (µg) | O2 (µg) | O4 (µg) | O6A (µg) | O8 (µg) | O15 (µg) | O16 (µg) | O18A (µg) | O25B (µg) | O75 (µg) | EPA (µg) | PS (Total) (µg) |
| Low dose ExPEC10V | 4 | 4 | 4 | 4 | 4 | 4 | 4 | 4 | 8 | 4 | 160 | 44 |

TABLE 9-continued

BAC1001MV ExPEC Study Vaccines

| Study Arm | O1A (µg) | O2 (µg) | O4 (µg) | O6A (µg) | O8 (µg) | O15 (µg) | O16 (µg) | O18A (µg) | O25B (µg) | O75 (µg) | EPA (µg) | PS (Total) (µg) |
|---|---|---|---|---|---|---|---|---|---|---|---|---|
| Medium dose ExPEC10V | 8 | 4 | 4 | 8 | 4 | 4 | 4 | 4 | 16 | 4 | 221 | 60 |
| High dose ExPEC10V | 8 | 8 | 8 | 8 | 8 | 8 | 8 | 8 | 16 | 8 | 320 | 88 |
| ExPEC4V | 4 | 4 | — | 4 | — | — | — | — | 8 | — | 72 | 20 |

EPA = a genetically detoxified form of exotoxin A derived from *Pseudomonas aeruginosa*;
PS = polysaccharide ExPEC4V consists of the O-antigen polysaccharides (PSs) of the ExPEC serotypes O1A, O2, O6A, and O25B separately bioconjugated to the EPA carrier protein.
ExPEC10V consists of the O-antigen polysaccharides (PSs) of the ExPEC serotypes O1A, O2, O4, O6A, O8, O15, O16, O18A, O25B and O75 separately bioconjugated to the EPA carrier protein.
Dose is based on PS only.
The EPA (µg) are measured values.

ExPEC10V is composed of 10 monovalent drug substances (DSs). For this clinical study, 2 different concentrations (medium and high) of drug product (DP) are produced (Table 10). A third (low) concentration is obtained in the clinic by diluting the high concentration 1:1 with dilution buffer, which is the same as the formulation buffer. Each DP is formulated in Sodium/Potassium phosphate buffer at pH 7.0 (0.02% [w/w] Polysorbate 80, 5% [w/w] sorbitol, 10 mM methionine).

TABLE 10

Composition of ExPEC10V vaccine for phase 1/2a clinical study

| Ingredient Active[a] | Amount (µg/mL)[a] | | |
|---|---|---|---|
| | Low Concentration[b] | Medium Concentration | High Concentration |
| O-antigen polysaccharide | | | |
| EcoO1A | 8 | 16 | 16 |
| EcoO2 | 8 | 8 | 16 |
| EcoO4 | 8 | 8 | 16 |
| EcoO6A | 8 | 16 | 16 |
| EcoO8 | 8 | 8 | 16 |
| EcoO15 | 8 | 8 | 16 |
| EcoO16 | 8 | 8 | 16 |
| EcoO18A | 8 | 8 | 16 |
| EcoO25B | 16 | 32 | 32 |
| EcoO75 | 8 | 8 | 16 |
| Carrier protein | | | |
| EPA | 320 | 441 | 640 |
| Excipients | | | |
| $KH_2PO_4$ | 6.19 mM | | |
| $Na_2HPO_4$ | 3.81 mM | | |
| Sorbitol | 5% (w/w) | | |
| Methionine | 10 mM | | |
| Polysorbate 80 | 0.02% (w/w) | | |

EPA = genetically detoxified *P. aeruginosa* exotoxin A used as carrier protein
[a] The active ingredient is a biologically synthesized conjugate composed of the PS antigen and a carrier protein (EPA); the dose is calculated on the PS moiety only.
[b] The "low concentration" is obtained in the clinic by diluting the "high concentration" 1:1 with dilution buffer Safety Evaluations Key safety assessments include solicited local and systemic AEs, unsolicited AEs, SAEs, physical examinations, vital sign measurements, and clinical laboratory tests.

Immunogenicity Evaluations

Key immunogenicity assessments of collected sera include the assessment of ExPEC10V and ExPEC4V serotype-specific total IgG antibody levels elicited by the vaccine as measured by a multiplex ECL-based immunoassay, and ExPEC10V and ExPEC4V serotype-specific functional antibodies as measured by an opsonophagocytic killing assay (OPKA) in multiplex format (MOPA). Immunogenicity assessments of pneumococcal antibody titers elicited by Prevnar 13 are not performed.

The levels of serum antibodies induced by ExPEC10V are measured by a multiplex electrochemiluminescent (ECL)-based immunoassay. This assay combines high binding carbon electrodes in a multi-spot 96-well format microplate that is coated with different *E. coli* O-LPS antigens or the carrier protein EPA. The levels of antigen-specific antibodies present in serum samples are detected using a secondary antibody (anti-human IgG) labeled with SULFO-TAG. The SULFO-TAG emits light in the presence of electrical stimulation at an intensity that increases proportionally to the amount of bound IgG antibodies. This assay was qualified according to International Conference on Harmonisation (ICH) recommendations.

The levels of functional antibodies induced by ExPEC10V are measured by a multiplex opsonophagocytic assay (MOPA). Briefly, heat-inactivated serum samples are serially diluted and incubated with different *E. coli* strains that are specifically resistant to different types of antibiotics. After that, human complement and phagocytic cells (HL60) are added to the reaction and, after a second incubation period, an aliquot of the reaction mix is transferred to different PVDF hydrophilic membrane filter plates containing media supplemented with specific antibiotic that selectively allow growth of a strain that is resistant to that particular antibiotic. After overnight grown, the colony forming units (CFUs) are counted to determine the number of surviving bacteria. This assay was qualified according to ICH recommendations.

For ExPEC10V serotype antibodies as measured by multiplex ECL-based immunoassay and MOPA, and EPA as measured by multiplex ECL-based immunoassay only, the following measures of immunogenicity are evaluated and tabulated by the study vaccination groups, for all immunogenicity time points:
- proportion of participants with a ≥2-fold and ≥4-fold increase in serum antibody titers from Day 1 (pre-vaccination)
- geometric mean titer (GMT)
- GMR: fold change from baseline, calculated from the post-baseline/baseline value.

For the LTFU period, descriptive summaries of immunogenicity are provided for each serotype.

Dose selection for later phases considers the totality of the evidence available at the time of the primary analysis of Cohort 1 (Day 30 results).

TABLE 11

Cohort 1: Vaccination Schedule

| Study Vaccination Group | Vaccination on Day 1 | Phase 1 | | | | | | Phase 2a Step 7 Additional Phase 2a Participants | Total |
|---|---|---|---|---|---|---|---|---|---|
| | | Step 1 Sentinel participants (Low dose) | Step 2 Additional participants (Low dose) | Step 3 Sentinel participants (Medium dose) | Step 4 Additional participants (Medium dose) | Step 5 Sentinel participants (High dose) | Step 6 Additional participants (High dose) | | |
| G1 | Low dose ExPEC10V* | 2 | 18 | | | | | 80 | 100 |
| G2 | Medium dose ExPEC10V* | | | 2 | 18 | | | 80 | 100 |
| G3 | High dose ExPEC10V* | | | | | 2 | 18 | 80 | 100 |
| G4 | ExPEC4V** | 1 | 3 | 1 | 3 | 1 | 3 | 40 | 52 |
| G5 | Prevnar 13*** | 1 | 3 | 1 | 3 | 1 | 3 | 40 | 52 |
| Total | | 4 | 24 | 4 | 24 | 4 | 24 | 320 | 404 |

*ExPEC10V consists of the O-antigen polysaccharides (PSs) of the ExPEC serotypes O1A, O2, O4, O6A, O8, O15, O16, O18A, O25B and O75 separately bioconjugated to the carrier protein, a genetically detoxified form of exotoxin A (EPA) derived from *Pseudomonas aeruginosa*.
**ExPEC4V consists of the O-antigen polysaccharides (PSs) of the ExPEC serotypes O1A, O2, O6A, and O25B separately bioconjugated to the carrier protein, a genetically detoxified form of exotoxin A (EPA) derived from *Pseudomonas aeruginosa*.
***Prevnar 13, Pneumococcal 13-valent conjugate vaccine (Diphtheria CRM197 protein) is a sterile suspension of saccharides of the capsular antigens of *Streptococcus pneumoniae* serotypes 1, 3, 4, 5, 6A, 6B, 7F, 9V, 14, 18C, 19A, 19F, and 23F, individually linked to non-toxic Diphtheria CRM197 protein.

TABLE 11

Cohort 2: Vaccination Schedule

| Study Vaccination Group | Vaccination on Day 1 | Total |
|---|---|---|
| G6 | ExPEC10V$^a$ | 400 |
| G7 | Placebo | 200 |
| Total | | 600 |

$^a$ExPEC10V consists of the O-antigen polysaccharides (PSs) of the ExPEC serotypes O1A, O2, O4, O6A, O8, O15, O16, O18A, O25B, and O75 separately bioconjugated to the carrier protein, a genetically detoxified form of exotoxin A (EPA) derived from *Pseudomonas aeruginosa*.

The randomization ratio for the participants enrolled in Cohort 2 of the study is 2:1 (ExPEC10V:Placebo). The ExPEC10V dose used in Cohort 2 is based on the primary analysis (Day 30) results of Cohort 1.

Status

Enrollment and vaccination of Cohort 1 of the study described above was completed. The study is ongoing in a blinded manner. Based on ongoing review of the safety data, no major safety issues were identified, and the ExPEC10V vaccine has an acceptable safety profile.

The analysis of the immunogenicity of the Cohort 1 clinical samples is ongoing in a blinded fashion. The ECL data were 100% Acceptance Quality Limits (AQL) checked and uploaded for data management. Analysis of the MOPA samples is ongoing. Data unblinding and statistical analysis is performed by using a clinical research organization (CRO).

The Cohort 2 vaccinations are started once the ExPEC10V dose for that Cohort has been identified based on the finalized primary analysis of the Day 30 results from Cohort 1.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the present description.

SEQUENCES

```
SEQ ID NO: 1 (Glycosvlation consensus sequence)
Asn-X-Ser(Thr), wherein X can be any amino acid except Pro SEQ ID NO: 2 (Optimized glycosvlation consensus sequence)
Asp(Glu)-X-Asn-Z-Ser(Thr), wherein X and Z are independently selected from any amino acid except Pro SEQ ID NO: 3 (EPA carrier protein comprising 4 glycosylation consensus sequences (EPA-4))
G SGGGDQNATG SGGGKLAEEA FDLWNECAKA CVLDLKDGVR SSRMSVDPAI ADTNGQGVLH YSMVLEGGND
ALKLAIDNAL SITSDGLTIR LEGGVEPNKP VRYSYTRQAR GSWSLNWLVP IGHEKPSNIK VFIHELNAGN
QLSHMSPIYT IEMGDELLAK LARDATFFVR AHESNEMQPT LAISHAGVSV VMAQAQPRRE KRWSEWASGK
VLCLLDPLDG VYNYLAQQRC NLDDTWEGKI YRVLAGNPAK HDLDIKDNNN STPTVISHRL HFPEGGSLAA
LTAHQACHLP LEAFTRHRQP RGWEQLEQCG YPVQRLVALY LAARLSWNQV DQVIRNALAS PGSGGDLGEA
IREQPEQARL ALTLAAAESE RFVRQGTGND EAGAASADVV SLTCPVAKDQ NRTKGECAGP ADSGDALLER
NYPTGAEFLG DGGDVSFSTR GTQNWTVERL LQAHRQLEER GYVFVGYHGT FLEAAQSIVF GGVRARSQDL
DAIWRGFYIA GDPALAYGYA QDQEPDARGR IRNGALLRVY VPRWSLPGFY RTGLTLAAPE AAGEVERLIG
HPLPLRLDAI TGPEEEGGRV TILGWPLAER TVVIPSAIPT DPRNVGGDLD PSSIPDKEQA ISALPDYASQ
PGKPPREDLK LGSGGGDQNA T
```

-continued

SEQUENCES

SEQ ID NO: 4 (O4 GtrS amino acid sequence)
MNNLIMNNWCKLSIFIIAFILLWLRRPDILTNAQFWAEDSVFWYKDAYENGFLSSLTTPRNGYFQTVSTFI
VGLTALLNPDYAPFVSNFFGIMIRSVIIWFLFTERFNFLTLTTRIFLSIYFLCMPGLDEVHANITNAHWYL
SLYVSMILIARNPSSKSWRFHDIFFILLSGLSGPFIIFILAASCFKFINNCKDHISVRSFINFYLRQPYAL
MIVCALIQGTSIILTFNGTRSSAPLGFSFDVISSIISSNIFLFTFVPWDIAKAGWDNLLLSYFLSVSILSC
AAFVFVKGTWRMKVFATLPLLIIIFSMAKPQLTDSAPQLPTLINGQGSRYFVNIHIAIFSLLCVYLLECVR
GKVATLFSKIYLTILLFVMGCLNFVITPLPNMNWREGATLINNAKTGDVISIQVLPPGLTLELRKK SEQ ID NO: 5 (Example O4 gtrS nucleic acid sequence)
ATGAATAATTTAATTATGAATAACTGGTGTAAATTATCTATATTTATTATTGCATTTATTTTGCTATGGCT
TAGAAGGCCGGATATACTCACAAACGCACAATTTTGGGCAGAAGATTCCGTTTTCTGGTATAAGGACGCCT
ATGAGAACGGATTCTTAAGTTCACTAACAACGCCTAGGAATGGGTATTTCCAGACTGTTTCTACATTTATA
GTTGGTCTGACTGCTTTATTAAATCCAGATTATGCACCTTTTGTTTCTAATTTTTTTGGCATAATGATTCG
CTCAGTAATTATATGGTTTTTATTTACAGAAAGATTCAACTTCCTCACATTGACTACTAGGATTTTCTTAT
CTATTTATTTTCTATGCATGCCTGGATTGGATGAAGTTCATGCAAATATAACAAATGCACATTGGTATTTG
TCATTATATGTATCAATGATCCTGATAGCTCGCAATCCAAGTTCAAAATCATGGAGGTTTCATGATATATT
CTTTATCTTGCTATCCGGGCTCAGTGGCCCATTTATAATTTTCATTTTAGCAGCTTCATGCTTTAAATTTA
TAAATAATTGTAAAGATCATATTAGTGTAAGATCTTTCATAAATTTCTACTTGCGTCAGCCATACGCATTA
ATGATTGTTTGCGCTTTAATTCAAGGAACTTCTATAATTCTAACTTTCAATGGCACACGTTCCTCAGCACC
GCTAGGATTCAGTTTTGATGTGATTTCGTCTATTATATCATCGAATATTTTTTATTTACATTTGTCCCAT
GGGATATTGCAAAGGCTGGGTGGGATAATTTACTGTTATCTTATTTTTGTCTGTTTCGATTTTGTCGTGT
GCGGCCTTTGTTTTGTTAAAGGTACGTGGCGAATGAAAGTATTTGCAACTTTACCATTGCTAATTATAAT
ATTTTCAATGGCAAAACCACAATTGACAGACTCGGCACCTCAATTGCCAACACTTATTAATGGGCAAGGTT
CAAGATACTTCGTAAATATACATATTGCGATATTCTCTTTGCTATGTGTTTACTTACTTGAGTGCGTCAGG
GGGAAAGTGGCAACTTTATTTTCCAAAATATACTTAACAATTTTGCTATTCGTGATGGGATGTTTGAATTT
TGTTATCACCCCACTCCCAAACATGAACTGGAGGGAAGGTGCTACTTTGATTAATAATGCAAAAACTGGTG
ATGTCATTTCGATTCAAGTGCTACCACCTGGCCTAACACTTGAACTAAGGAAAAAATAA SEQ ID NO: 6 (Example PglB sequence ('wild-type'))
MLKKEYLKNPYLVLFAMIILAYVFSVFCRFYWVWWASEFNEYFFNNQLMIISNDGYAFAEGARDMIAGFHQ
PNDLSYYGSSLSALTYWLYKITPFSFESIILYMSTFLSSLVVIPTILLANEYKRPLMGFVAALLASIANSY
YNRTMSGYYDTDMLVIVLPMFILFFMVRMILKKDFFSLIALPLFIGIYLWWYPSSYTLNVALIGLFLIYTL
IFHRKEKIFYIAVILSSLTLSNIAWFYQSAIIVILFALFALEQKRLNFMIIGILGSATLIFLILSGGVDPI
LYQLKFYIFRSDESANLTQGFMYFNVNQTIQEVENVDLSEFMRRISGSEIVFLFSLFGFVWLLRKHKSMIM
ALPILVLGFLALKGGLRFTIYSVPVMALGFGFLLSEFKAIMVKKYSQLTSNVCIVFATILTLAPVFIHIYN
YKAPTVFSQNEASLLNQLKNIANREDYVVTWWDYGYPVRYYSDVKTLVDGGKHLGKDNFFPSFALSKDEQA
AANMARLSVEYTEKSFYAPQNDILKTDILQAMMKDYNQSNVDLFLASLSKPDFKIDTPKTRDIYLYMPARM
SLIFSTVASFSFINLDTGVLDKPFTFSTAYPLDVKNGEIYLSNGVVLSDDFRSFKIGDNVVSVNSIVEINS
IKQGEYKITPIDDKAQFYIFYLKDSAIPYAQFILMDKTMFNSAYVQMFFLGNYDKNLFDLVINSRDAKVFK
LKI SEQ ID NO: 7 (example gtrA amino acid sequence; E. coli W3110 yfdG. GenBank: BAA16209.1)
MLKLFAKYTSIGVLNTLIHWVVFGVCIYVAHTNQALANFAGFVVAVSFSFFANAKFTFKASTTTMRYMLYV
GFMGTLSATVGWAADRCALPPMITLVTFSAISLVCGFVYSKFIVFRDAK SEQ ID NO: 8 (example gtrB amino acid sequence -E. coli W3110 yfdH. GenBank: BAA16210.1)
MKISLVVPVFNEEEAIPIFYKTVREFEELKSYEVEIVFINDGSKDATESIINALAVSDPLVVPLSFTRNFG
KEPALFAGLDHATGDAIIPIDVDLQDPIEVIPHLIEKWQAGADMVLAKRSDRSTDGRLKRKTAEWFYKLHN
KISNPKIEENVGDFRLMSRDVVENIKLMPERNLFMKGILSWVGGKTDIVEYVRAERIAGDTKFNGWKLWNL
ALEGITSFSTFPLRIWTYIGLVVASVAFIYGAWMILDTIIFGNAVRGYPSLLVSILFLGGIQMIGIGVLGE
YIGRTYIETKKRPKYIIKRVKK SEQ ID NO: 9 (example O4 rfb locus nucleotide sequence - O4-EPA production strain BVEC-L-
00684f)
ATGACGAATTTAAAAGCAGTTATTCCTGTAGCGGGTCTCGGGATGCATATGTTGCCTGCCACTAAGGCGAT
ACCCAAAGAGATGCTACCAATCGTCGACAAGCCAATGATTCATACATTGTTGACGAGATTGTGGCTGCAG
GGATCAAAGAAATCCTCCTGGTAACTCACGCGTCCAAGAACGCGGTCGAAAACCACTTCGACACCTCTTAT
GAGTTAGAATCACTCCTTGAGCAGCGCGTGAAGCGTCAACTGCTGGCGGAAGTACAGTCCATCTGTCCGCC
GGGCGTGACCATTATGAACGTGCGTCAGGGCGAACCTTTAGGTTTAGGCCACTCCATTTTGTGTGCGCGAC
CTGCCATTGGTGACAACCCATTTGTCGTGGTACTGCCAGACGTTGTGATCGACGATGCCAGCGCCGACCCG
CTACGTTACAACCTTGCTGCCATGATTGCACGTTTCAACGAAACGGGCCGCAGCCAGGTGCTGCAAAACG
TATGCCGGGTGACCTCTCTGAATACTCCGTCATCCAGACTAAAGAGCCGCTGGACCGTGAGGGTAAAGTCA
GCCGCATTGTTGAATTTATCGAAAAACCGGATCAGCCGCAGACGCTGGACTCAGACATCATGGCCGTAGGT
CGCTATGTGCTTTCTGCCGATATTTGGCCGGAACTGGAACGTACTCAGCCTGGTGCATGGGACGTATTCA
GCTGACTGATGCTATTGCCGAGCTGGCGAAAAAACAATCCGTTGATGCAATGCTGATGACCGGCGACGATT
ACGACTGCGGCAAAAAAATGGGCTATATGCAGGCGTTTGTGAAGTATGGCCTACGCAACCTGAAAGAAGGG
GCGAAGTTCCGTAAAGGTATTGAGAAGCTGTTAAGCGAATAATGAAAATCTGACCGGATGTAACGGTTGAT
AAGAAAATTATAACGGCAGTGAAAATTCGCAGCAAAGTAATTTGTTGCGAATCTTCCTGCCGTTGTTTTA
TATAAACCATCAGAATAACAACGAGTTAGCAGTAGGGTTTTATTCAAAGTTTTCCAGGATTTTCCTTGTTT
CCAGAGCGGATTGGTAAGACAATTAGCGTTTGAATTTTTCGGGTTTAGCGCGAGTGGGTAACGCTGCHAC
ATCATAGGCATGCATGCAGTGCTCTGGTAGCTGTAAAGCCAGGGGCGGTAGCGTGCATTAATACCTCTATT
AATCAAACTGAGAGCCGCTTATTTCACAGCATGCTCTGAAGTAATAATGGAATAAATTAAGTGAAAATACTT
GTTACTGGTGGCGCAGGATTTATTGGTTCAGCTGTAGTTCGTCACATTATAAATAATACGCAGGATAGTGT
TGTTAATGTCGATAAATTAACGTACGCCGGAAACCGGGAATCACTTGCTGATGTTTCTGATTCTGAACGCT
ATGTTTTTGAACATGCGGATATTTGCGATGCACCTGCAATGGCACGGATTTTTGCTCAGCATCAGCCGGAT
GCAGTGATGCACCTGGCTGCTGAAAGCCATGTTGACCGTTCAATTACAGGCCCTGCGGCATTTATTGAAAC

| SEQUENCES |
|---|
| CAATATTGTTGGTACTTATGTCCTTTTGGAAGCCGCTCGCAATTACTGGTCTGCTCTTGATAGCGACAAGA |
| AAAATAGCTTCCGTTTTCATCATATTTCTACTGACGAAGTATATGGTGATTTGCCTCATCCTGACGAGGTA |
| AATAATACAGAAGAATTACCCTTATTTACTGAGACAACAGCTTACGCGCCAAGCAGCCCTTATTCCGCATC |
| CAAAGCATCCAGCGATCATTTAGTCCGCGCGTGGAAACGTACCTATGGTTTACCGACCATTGTGACTAATT |
| GCTCTAACAATTATGGTCCTTATCATTTCCCGGAAAAATTGATTCCATTGGTTATTCTCAATGCTCTGGAA |
| GGTAAAGCATTACCTATTTATGGTAAAGGGGATCAAATTCGCGACTGGCTGTATGTTGAAGATCATGCGCG |
| TGCGTTATATACCGTCGTAACCGAAGGTAAAGCGGGTGAAACTTATAACATTGGTGGGCACAACGAAAAGA |
| AAAACATAGATGTAGTGCTCACTATTTGTGATTTGCTGGATGAGATTGTACCGAAAGAGAAATCTTATCGT |
| GAGCAAATCACTTATGTTGCCGATCGTCCGGGACACGATCGCCGTTATGCGATTGATGCTGAGAATATTGG |
| TCGCGAATTGGGATGGAAACCACAGGAAACGTTTGAGAGCGGGATTCGGAAGACAGTGGAATGGTATCTGT |
| CCAATACAAAATGGGTTGATAATGTGAAAAGTGGTGCCTATCAATCGTGGATTGAAGAGAACTATGAGGGC |
| CGCCAGTAATGAATATCCTCCTTTTTGGCAAAACAGGGCAGGTAGGTTGGGAACTACAGCGTGCTCTGGCA |
| CCTCTGGGTAACTTGATTGCTCTTGATGTTCATTCCACTGATTATTGTGGCGATTTCAGTAACCCCGAAGG |
| TGTGGCTGAAACCGTCAAAAAAATTCGCCCAGATGTTATTGTTAATGCTGCTGCTCATACCGCGGTAGATA |
| AGGCTGAGTCAGAACCAGAATTTGCACAATTACTCAATGCGACCAGCGTTGAAGCAATTGCAAAAGCGGCT |
| AATGAAGTTGGGGCTTGGGTAATTCATTACTCAACTGACTACGTCTTCCCTGGAAATGGCGACATGCCATG |
| GCTCGAGACTGATGTAACCGCTCCGCTCAATGTTTATGGCAAAACCAAATTGGCTGGAGAAAGAGCATTAC |
| AAGAACATTGCGCAAAGCATCTTATTTTCCGTACCAGCTGGGTATATGCAGGTAAAGGAAATAACTTTGCC |
| AAAACAATGTTACGTCTGGCAAAGAGCGCGAAGAACTGGCTGTGATAAACGATCAGTTTGGCGCACCAAC |
| AGGTGCTGAATTGCTGGCTGATTGCACCGCTCATGCCATTCGCGTGGCATTAAAAAAACCAGAAGTTGCTG |
| GCTTGTACCATCTGGTAGCAAATGGCACAACAACCTGGCACGATTACGCCGCGCTAGTATTCGAAGAAGCC |
| CGTAAAGCAGGGATTGACCTTGCACTTAACAAACTCAACGCCGTACCAACAACGGCTTATCCTACTCCAGC |
| CCGCCGTCCTCATAATTCTCGCCTCAATACCGAAAAGTTTCAGCAGAACTTTGCGCTTGTCTTGCCTGACT |
| GGCAGGTGGGCGTGAAACGTATGCTCAACGAATTATTTACGACTACGGCCAATTTAACAAATTTTTGCATCT |
| CGCTCATGATGCCAGAGCGGGATGAATTAAAAGGAATGGTGAAATGAAAACGCGTAAAGGTATTATTCTGG |
| CTGGTGGTTCCGGCACTCGTCTTTATCCTGTGACGATGGCAGTGAGTAAACAACTGCTGCCGATTTATGAT |
| AAGCCGATGATTTATTATCCGTTTCAACGCTTATGTTAGCGGGTATTCGCGATATTCTTATTATCAGTAC |
| GCCACAGGATACACCGCGTTTCCAACAATTGTTGGGGGACGGGAGTCAGTGGGGCTTAATCTACAGTATA |
| AAGTACAACCGAGTCCGGATGGCCTGGCGCAAGCGTTTATTATTGGTGAAGACTTTATTGGTGGTGATGAT |
| TGTGCACTCGTACTTGGCGATAATATCTTCTATGGACACGACTTGCCGAAATTAATGGAAGCTGCTGTTAA |
| CAAAGAAATCGGTGCAACGGTATTTGCTTATCACGTCAATGATCCTGAACGTTATGGTGTCGTGGAGTTTG |
| ATAATAACGGTACTGCAATTAGCCTGGAAGAAAAACCGCTGGAACCAAAAAGTAACTATGCGGTTACTGGG |
| CTTTATTTCTATGACAATGATGTTGTAGAAATGGCGAAAAACCTTAAGCCTTCTGCCCGTGGCGAACTGGA |
| AATTACCGTATATTAACCGTATTTATATGGAGCAGGGACGTTTGTCTGTCGCTATGATGGGCGTGGTTATG |
| CCTGGTTGGATACTGGTACACATCAAAGTCTTATTGAAGCAAGTAACTTCATTGCCACCATTGAAGAGCGT |
| CAGGGATTAAAGGTATCTTGCCCGGAAGAGATTGCTTACCGTAAAGGGTTTATTGATGCTGAGCAGGTGAA |
| AGTATTAGCCGAACCGCTGAAGAAAAATGATTATGGTCAGTATCTGCTAAAAATGATTAAAGGTTATTAAT |
| AAAATGAACGTAATTAAAACTGAAATTCCTGATGTGCTGATTTTTGAACCAAAAGTTTTTGGTGATGAACG |
| TGGCTTCTTTTTTGAGAGTTTTAACCAGAAAGTATTTGAAGAAGCTGTAGGACGGAAGGTTGAATTTGTTC |
| AGGATAACCATTCTAAGTCTAAAATAAATGTATTGCGTGGGATGCATTACAAACACAAAATACTCAAGGA |
| AAACTGGTTCGGGTAATTTCTGGTTCAGTATATGATGTTGCCGTAGATTTAAGAGAAAAATCAAAGACATT |
| TGGCAAATGGGTGGGTGTAGAATTATCTGGGAATAATAAAAGACAATTGTGGATCCCCGAAGGTTTTGCCC |
| ATGGTTTTTATGTGTTGGAGGAGAATACCGAATTTGTTTATAAATGTACCGATACTTATAACCCTGCTCAT |
| GAACACACATTGCTATGGAATGATCCAACTATCAATATAAGTTGGCCAATCATACAAAACTGCAAGCCAAT |
| TATTTCTGAAAAAGATGCTAATGGACATCTTTTTTCACATAAAACCTATTTCTGAAATGCAATATTATGAG |
| TTTAATTAGAAACAGTTTCTATAATATTGCTGGTTTTGCTGTGCCGACATTAGTTGCAGTCCCTGCTTTGG |
| GGATTCTTGCCAGGCTGCTTGGACCGGAGAATTTTGGACTTTTCACACTAGCATTCGCTTTGATAGGATAT |
| GCAAGTATTTTCGACGCCGGGATTAGTCGAGCTGTAATCAGAGAAATCGCTCTTTATCGAGAAAGTGAAAA |
| AGAGCAAATACAAATTATTTCGACAGCAAGTGTAATCGTACTATTCTTAGGGGTGGTTGGGTGTGCTTTGT |
| TTTATTTTAGTAGTAATAAAGTTGTTGAGTTATTGAATGTTAGTTCCGTTTATATTGAAACAGCAGTGCGT |
| GCATTCTCTGTTATTTCATTTATAATACCTGTGTATCTGATTAACCAGATTTGGCTTGGTTATCTGGAAGG |
| GCTAGAAAAATTGCAAATATAAATGTTCAGAGAATGATTTCTAGCACAAGCTTGGCTATATTACCAGTGA |
| TATTTTGTTATTACAATCCCTCGTTGCTTTATGCTATGTATGGGTTGGTGTTGGGCGTGTGATTTCATTT |
| TTGATTAGCGCAATAATTTGTCGAGATATTATTCTTAAAAGTAAACTTTACTTTAATGTGGCAACTTGCAA |
| TCGTCTTATCTCTTTTGGTGGATGGATAACAGTTAGTAATATCATAAGCCCAATCATGGCATATTTCGACC |
| GCTTTATCATCTCTCATATTATGGGGGCTTCGAGAATTGCATTTTATACAGCGCCCTCAGAGGGTGTATCA |
| AGGTTAATTAATATCCCATATGCTTTGGCAAGAGCTCTATTTCCTAAATTGGCATATAGCAATAATGATGA |
| TGAACGAAAAAATTACAACTACAGAGCTACGCAATTATAAGCATTGTATGTCTACCCATAGTTGTTATTG |
| GTGTCATTTTTGCCTCATTCATAATGACAACATGGATGGGACCTGATTATGCCTTAGAAGCAGCAACTATC |
| ATGAAAATACTTCTTGCTGGTTTTTCTTTAACTCTTTAGCGCAAATACCTTATGCATACTTGCAATCTAT |
| CGGAAAGTCAAAAATTACCGCATTTGTGCATCTCATAGAACTTGCGCCATACTTATTATTATTGTATTACT |
| TCACAATGCATTTCGGCATAATTGGCACGGCAATCGCTTGGTCACTTAGAACATTTTGTGATTTTGTTATA |
| CTACTTTCGATATCGAGAAGAAATGATTGCGGTTGATATTGCGCTTGCAACCTACAATGGTGCTAATTTT |
| ATTCGGCAACAGATTGAATCTATCCAGAAACAAACTTATAGAAATTGGCGTCTTATAATAAGTGATGATAA |
| CTCGAGTGATGATACTGTTGATATTATTAAGGATATGATGTCTAACGACAGTCGTATCTATTTGGTAGGAA |
| ATAAAAGACAAGGAGGGGTTATTCAGAACTTTAATTATGCTCTTTCACAAAACACATCTGAAATTGTGTTA |
| CTATGTGACCAGGATGACATTTGGCCGGAGGAGCGTCTGGAAATTCTTATAGATAAATTTAAGGCCTTGCA |
| GCGTAATGATTTTGTTCCGGCAATGATGTTTACTGATTTGAAATTAGTAGACGAAAATAATTGTTTGATTG |
| CAGAAAGTTTTTATCGAACGAATAATATTAATCCACAAGATAATCTGAAAAATAATAATCTTCTCTGGCGT |
| TCAACGGTATATGGCTGTACTTGCATCATGAATAAGAAACTTGTTGATATTGCATTGCCTATACCTACATA |
| TGCACATATGCATGATCAATGGTTGGCTATTTAGCGAAGCAATATTGGTAACATTTTTTATTTCGACTATG |
| CGTCTGTTCGTTATAGGCAACATTCTACAAATGTTGTTGGTGGTAGAAATAAAACGCCATTTCAAAAATTT |
| AATTCCATACAAAAAAACCTAAAAAGGATTAATTTGCTAGTGGATAGAACTGTTGCTTTAATTAAATCAAA |
| TAACGATTTCTATCAGGGAATAAAATGGAAAATAAAATTGATTACTTAAAATTTGGAGTGAATGAAGTAT |
| TACCTTATCTTTTAAAGGAAACAAGAAAGTTTTTTCACTTTGTGTATTAATTAGTTTGGCATTACAAAAA |
| TGATATATTTATTATTTTTTTTGCACTGTTTATGATCTGTACGTTTTAACACACAGGCGACAGGCATTA |
| TATGTTGTATCTGCGTTAGTATTTCTTTTTTTGGCTTTAACCTATCCATCAGGAGGGGACTGGATAGGTTA |

| SEQUENCES |
|---|
| TTTTCTCCATTATGACTGCATGGTTAATGAGCAGTGTAATAATGGTTTTATAATGTTTGAACCTGGATATG |
| AATTAATTGTTTCCTTATTTGGATATTTGGGATTTCAGACAATTATTATTTTTATAGCCGCTGTAAATGTA |
| ATTCTAATATTAAATTTTGCAAAGCATTTTGAAAACGGAAGTTTTGTTATTGTTGCGATAATGTGCATGTT |
| CCTTTGGAGTGTTTATGTTGAGGCGATTAGACAGGCTCTGGCCTTATCTATAGTTATATTTGGGATTCATT |
| CTCTTTTTTTGGGTAGAAAAAGGAAATTTATAACATTAGTATTATTTGCGTCAACTTTCCATATAACTGCT |
| TTGATTTGTTTTCTTCTAATGACTCCTCTATTTTCAAAGAAATTAAGCAAGATAATAAGTTATAGCCTATT |
| AATTTTCAGTAGCTTCTTTTTCGCTTTTTCTGAAACCATATTAAGTGCACTCCTTGCAATTTTGCCAGAAG |
| GATCCATTGCCAGTGAAAAATTAAGTTTTTACTTAGCAACCGAGCAATACAGGCCACAGTTATCTATTGGG |
| AGTGGCACTATTCTTGACATTATACTTATTTTTCTGATATGTGTAAGTTTTAAACGAATAAAGAAATATAT |
| GCTCGCTAATTATAATGCTGCAAATGAGATATTGCTTATTGGTTGCTGTCTTTATATTTCTTTCGGTATTT |
| TTATCGGGAAAATGATGCCAGTTATGACTCGCATTGGTTGGTATGGTTTTCCATTTGTTATAGTACTTCTT |
| TATATTAACTTGGGTTATTCAGAATATTTTAAGAGGTATATAAATAAAAGAGGGTGTGGGTATAGCAAATT |
| ATTAATTGCTTTTTATTTTTTGCTACAAATTTTGCGACCATTAACATATGATTATAGCTATTATAATATAA |
| TGCACCAGGATACTTTGCTGAATAGGTTTGATGCATTAGATGATGCATCATTAAGACAATCAGCGAAGAGA |
| AAATGTTTCGATTTGGGAAAGATAGGATATGGTTTCTTATGTAGTATATAATATCCTGCATTCATTCGGAT |
| AATTTCCTATGGAAGTGTCCTTTGCTCTGTCTGTCCTCATTTGTTGAAATTTTATGTTAATAAGAAGCTTT |
| AGATAACCACTTAGGAACTGTATGTTTGATCTGTCCAAAAATTATATTATTGTAAGTGCGACGGCGCTGGC |
| TTCCGGAGGTGCATTAACTATATTAAAGCAATTTATAAAACATGCATCACAAAATTCAAATGACTATATTA |
| TGTTTGTATCTGCGGGATTGGAGTTGCCGGTCTGTGATAACATCATTTACATAGAAAACACACCAAAAGGA |
| TGGTTGAAAAGAATATATTGGGATTGGTTCGGTTGTCGGAAGTTTATCTCGGAACATAAGATTAACGTTAA |
| GAAAGTAATTTCTCTACAAAATTCCAGTTTGAATGTTCCTTACGAACAGATTATTTACTTGCACCAGCCAA |
| TTCCTTTTAGTAAAGTTGATTCTTTTTTAAAAAATATCACATCCGATAACGTAAAGCTTTTTTTATATAAA |
| AAGTTTTATTCCTATTTTATATTTAAATATGTGAATGCCAATACAACCATCGTAGTGCAAACGAATTGGAT |
| GAAAAAGGAGTGCTGGAGCAATGTGATAAAATTAGTACCGAAAGGGTCCTTGTTATAAAACCTGATATCA |
| AAGCATTTAATAATACTAATTTTGATGTAGATATGGATGTATCTGCAAAAACACTCTTATATCCAGCGACA |
| CCACTTACCTATAAAAATCATTTGGTCATTCTGAAGGCGTTGGTTATTTAAAGAAAAGTATTTTATAGA |
| TGATCTGAAATTCCAAGTGACTTTTGAAAAGAATAGGTACAAAAATTTTGATAAGTTTGTGCAATTAAATA |
| ACTTAAGCAAAAACGTTGATTATCTCGGCGTTCTTTCATACTCGAACTTGCAAAAAAAATATATGGCGGCA |
| TCTTTAATCGTTTTTCCTAGCTATATCGAATCATATGGGTTACCACTCATCGAAGCTGCTAGTTTAGGAAA |
| AAAAATCATTAGTAGTGATCTTCCTTATGCCCGGGATGTTTTAAAGGATTATAGCGGCGTAGATTTTGTAA |
| TTTACAATAATGAAGATGGCTGGGCTAAGGCGTTGTTTAATGTTTTAAATGGCAATTCGAAGCTCAATTTT |
| AGGCCTTATGAAAAAGATAGTCGTTCATCTTGGCCACAGTTCTTCTCTATTTTGAAATAAGGTGTATTATG |
| TTTAATGGTAAAATATTGTTAATTACTGGTGGTACGGGGTCTTTCGGTAATGCTGTTCTAAGACGTTTTCT |
| TGACACTGTATATCAAAGAAATACGTATTTTTTCCCGGGATGAAAAAAACAAGATGACATGAGGAAAAAAT |
| ATAATAATCCGAAACTTAAGTTCTATATAGGTGATGTTCGCGACTATTCGAGTATCCTCAATGCTTCTCGA |
| GGTGTTGATTTTATTTATCATGCTGCAGCTCTGAAGCAAGTACCTTCCTGCGAATTCCACCCAATGGAAGC |
| TGTAAAAACGAATGTTTTAGGTACGGAAAACGTACTGGAAGCGGCAATAGCTAATGGAGTTAGGCGAATTG |
| TATGTTTGAGTACAGATAAAGCTGTATATCCTATCAATGCAATGGGTATTTCCAAAGCGATGATGGAAAAA |
| GTAATGGTAGCAAAATCGCGCAATGTTGACTGCTCTAAAACGGTTATTTGCGGTACACGTTATGGCAATGT |
| AATGGCATCTCGTGGTTCAGTTATCCCCATTATTTGTCGATCTGATTAAATCAGGTAGACCAATGACGATAA |
| CAGACCCTAATATGACTCGTTTCATGATGACTCTCGAAGCGTCTGTTGATTTGGTTCTTTACGCATTTGAA |
| CATGGCAATAATGGTGATATTTTTGTCCAAAAGGCACCTGCGGCTACCATCGAAACGTTGGCTATTGCACT |
| CAAAGAATTACTTAATGTAAACCAACACCCTGTAAATATAATCGGCACCCGACACGGGGAAAAACTGTACG |
| AAGCGTTATTGAGCCGAGAGGAAATGATTGCAGCGGAGGATATGGGTGATTATTATCGTGTTCCACCAGAT |
| CTCCGCGATTTGAACTATGGAAATATGTGGAACATGGTGACCGTCGTATCTCGGAAGTGGAAGATTATAA |
| CTCTCATAATACTGATAGGTTAGATGTTGAGGGAATGAAAAAATTACTGCTAAAACTTCCTTTTATCCGGG |
| CACTTCCGGTCTGGTGAAGATTATGAGTTGGATTCATAATATGAAAATTTTAGTTACTGGCGCTGCAGGGTT |
| TATCGGTCGAAATTTGGTATTCCGGCTTAAGGAAGCTGGATATAACGAACTCATTACGATAGATCGTAACT |
| CTTCTTTGGCGGATTTAGAGCAGGGACTTAAGCAGGCAGATTTTATTTTTTCACCTTGCTGGGGTAAATCGT |
| CCCGTGAAGGAGTGTGAATTTGAAGAGGGAAATAGTAATCTAACTCAACAGATTGTTGATATCCTGAAAAA |
| AAACAATAAAAATACTCCTATCATGCTGAGTTCTTCCATCCAGGCTGAATGTGATAACGCTTATGGAAAGA |
| GTAAAGCAGCTGCGGAAAAAATCATTCAGCAGTATGGGAAACGACAAACGCTAAATATTATATTTATCGC |
| TTGCCGAATGTATTCGGTAAGTGGTGTCGACCAAATTATAACTCCTTTATAGCAACTTTCTGCCATCGCAT |
| TGCAAATGATGAAGCTATTACAATTAATGATCCTTCAGCAGTTGTAAATCTGGTGTATATAGATGACTTTT |
| GTTCTGACATATTAAAGCTATTAGAAGGAGCGAACGAAACTGGTTACAGGACATTTGGTCCAATTTATTCT |
| GTTACTGTTGGTGAAGTGGCACAATTAATTTACCGGTTTAAAGAAAGTCGCCAAACATTAATCACCGAAGA |
| TGTAGGTAATGGATTTACACGTGCATTGTACTCAACATGGTTAAGTTACCTGTCTCCTGAACAGTTTGCGT |
| ATACGGTTCCTTCTTATAGTGATGACAGAGGGGTATTCTGTGAAGTATTGAAAACGAAAAACGCGGGCCAG |
| TTTTCGTTCTTTTACTGCGCATCCAGGAATTACTCGGGGTGGTCATTATCATCATTCCAAAAATGAGAAATT |
| TATTGTCATCCGAGGAAGTGCTTGTTTCAAATTTGAAAATATTGTCACGAGTGAACGATATGAACTTAATG |
| TTTCCTCTGATGATTTTAAAATTGTTGAAACAGTTCCGGGATGGACGCTAAATCATTACTAAATAATGGCTCG |
| GATGAGCTAGTTGTTATGCTTTGGGCAAATGAAATATTTAATCGTTCTGAACCAGATACTATAGCCGAGAGT |
| TTTATCGTGAAAAAATTGAAAGTCATGTCGGTTGTTGGGACTCGTCCAGAAATTATTCGACTCTCGCGTGT |
| CCTTGCAAAATTAGATGAATATTGTGACCACCTTATTGTTCATACCGGGCAAAACTACGATTATGAACTGA |
| ATGAAGTTTTTTCAAAGATTTGGGTGTTCGCAAACCTGATTATTTTCTTAATGCCGCAGGTAAAAATGCA |
| GCGAGACATTGGACAAGTTATCATTAAAGTTGATGAGGTCCTTGAACAGGAAAACACAGAGCCCATGTT |
| AGTACTTGGCGATACTAACTCCTGTATTTCAGCAATACCAGCAAAGCGTCGAAGAATTCCGATCTTCCATA |
| TGGAGGCTGGGAATCGTTGTTTTGACCAACGCGTACCGGAAGAAACTAACAGAAAAATAGTTGATCATACC |
| GCTGATATCAATATGACATATAGTGATATCGCGCGTGAATATCTTCGGCTGAAGGTGTACCAGCCGATAG |
| AATTATTAAAACCGGTAGCCCAATGTTTGAAGTACTCACTCATTATATGCCGCAGATTGATGGTTCCGATG |
| TACTTTCTCGCCTGAATTTAACACCTGGGAATTTCTTTGTGGTAAGTGCCCACAGAGAAGAAATGTTGAT |
| ACCCCTAAACAACTTGTGAAACTGGCGAATATACTTAATACCGTGGCTGAAAAATATGATGTCCCGGTAGT |
| TGTTTCTACTCATCCTCGCACTCGTAACCGCATCAACGAAAACGGTATTCAATTCCATAAAAATATCTTGC |
| TTCTTAAGCCATTAGGATTTCACGATTACAACCATCTGCAAAAAAATGCACGTGCTGTTTTATCGGATAGT |
| GGGACTATTACAGAAGAGTCCTCCATTATGAACTTCCCTGCACTCAATATACGAGAAGCGCACGAACGCCC |
| GGAAGGCTTCGAAGAAGGGCAGTAATGATGGTCGGTCTTGAATCTGATCGCGTTTTACAGGCATTAGAAA |
| TTATTGCAACACAGCCTCGTGGAGAAGTACGCTTACTTCGTCAGGTTAGTGACTATAGCATGCCAAATGTT |

-continued

SEQUENCES

TCAGATAAAGTTCTGCGTATTATCCATTCATATACTGACTACGTTAAACGGGTTGTCTGGAAGCAATACTA
ATGAAACTTGCATTAATCATTGATGATTATTTGCCCCATAGCACACGCGTTGGGGCTAAAATGTTTCATGA
GTTAGGCCTTGAATTACTGAGCAGAGGCCATGATGTAACTGTAATTACGCCTGACATCTCATTACAAGCAA
TTTATTCTATTAGTATGATTGATGGTATAAAGGTTTGGCGTTTCAAAAGTGGACCTTTAAAGGATGTAGGT
AAGGCTAAACGTGCCATAAATGAAACTCTTTTATCTTTTCGCGCATGGCGCGCATTTAAGCACCTCATTCA
ACATGATACATTTGATGGTATCGTTTATTATTCCCCCTCTATTTTTTGGGGCGACTTGGTTAAAAAAATAA
AACAACGATGCCAGTGCCCAAGCTATCTGATCCTAAGGGATATGTTTCCACAGTGGGTCATTGATGCAGGT
ATGTTGAAAGCCGGTTCACCAATTGAAAAATATTTTAGGTATTTTGAAAAAAAGTCATATCAGCAGGCTGG
CCGGATAGGGGTAATGTCTGATAAGAATCTTGAGATATTTCGCCAGACCAATAAAGGTTATCCGTGTGAAG
TTTTACGTAATTGGGCCTCAATGACTCCTGTGTCTGCCAGCGATGATTATCATTCACTTCGTCAAAAATAC
GATCTAAAAGATAAAGTCATTTTTTTCTATGGCGGTAATATTGGGCATGCTCAGGATATGGCAAACTTAAT
GCGCCTTGCGCGTAATATGATGCGTTATCATGATGCTCATTTCCTGTTTATAGGGCAGGGTGATGAAGTTG
AGCTGATAAAATCTCTTGCTGCAGAATGGAATTTAACTAATTTCACTCATCTACCTTCAGTGAACCAGGAA
GAGTTTAAATTAATTTTATCTGAAGTTGATGTCGGCCTGTTCTCCCTTTCATCTCGCCATTCTTCACATAA
TTTCCCCGGAAAATTACTAGGGTATATGGTTCAATCAATCCCGATCCTTGGGAGTGTGAATGGCGGCAATG
ATTTAATGGATGTAATTAATAAGCACAGAGCCGGTTTCATTCATGTTAATGGTGAAGATGATAAACTGTTT
GAATCTGCACAATTGCTTCTTAGTGATTCAGTTTTAAGAAAACAGCTAGGTCAGAACGCTAATGTGTTGTT
AAAGTCTCAATTTTCGGTTGAATCGGCGGCACATACTATCGAAGTCCGACTGGAGGCTGGAGAATGCGTTT
AGTTGATGACAATATTCTGGATGAACTTTTTCGCACTGCAGCAAATTCTGAACGTTTGCGCGCTCATTATT
TATTGCACGCATCTCATCAGGAGAAGGTTCAACGTTTACTTATTGCATTTGTACGCGACAGCTATGTTGAA
CCCCATTGGCATGAGTTACCGCATCAGTGGGAAATGTTTGTCGTCATGCAAGGGCAATTAGAAGTTTGTTT
GTATGAGCAAAATGGTGAGATCCAAAAACAGTTTGTTGTTGGAGACGGTACGGGAATAAGCGTCGTGGAAT
TTTCCCCAGGAGATATACATAGTGTCAAATGCCTGTCACCAAAAGCCCTTATGTTGGAGATAAAGGAGGGG
CCATTTGACCCACTCAAAGCTAAGGCTTTTTCTAAGTGGTTATAGGGCGATACACCACCGTTTATTCTTCT
ATCTTATTCTATACATGCTGGGTTACCATCTTAGCTTCTTCAAGCCGCGCAACCCCGCGGTGACCACCCCT
GACAGGAGTAGCTAGCATTTGACCACCCCTGACAGGATTAGCTAGCATATGAGCTCGAGGATATCTACTGT
GGGTACCCGGGATCCGTGTAGGCTGGAGCTGCTTCGAAGTTCCTATACTTTCTAGAGAATAGGAACTTCGG
AATAGGAACTAAGGAGGATATTCATAT

SEQ ID NO: 10 (example signal sequence for EPA carrier protein)
MKKIWLALAG LVLAPSASA SEQ ID NO: 11 (example O1A rfb locus nucleotide sequence - O1A-EPA production strain stGVXN4411 and stLMTB10217)
ATGACGAATTTAAAAGCAGTTATTCCTGTAGCGGGTCTCGGGATGCATATGTTGCCTGCCACTAAGGCGAT
ACCCAAAGAGATGCTACCAATCGTCGACAAGCCAATGATTCAGTACATTGTTGACGAGATTGTGGCTGCAG
GGATCAAAGAAATCCTCCTGGTAACTCACGCGTCCAAGAACGCGGTCGAAAACCACTTCGACACCTCTTAT
GAGTTAGAATCACTCCTTGAGCAGCGCGTGAAGCGTCAACTGCTGGCGGAAGTACAGTCCATCTGTCCGCC
GGGCGTGACCATTATGAACGTGCGTCAGGGCGAACCTTTAGGTTTAGGCCACTCCATTTTGTGTGCGCGAC
CTGCCATTGGTGACAACCCATTTGTCGTGGTACTGCCAGACGTTGTGATCGACGATGCCAGCGCCGACCCG
CTACGTTACAACCTTGCTGCCATGATTGCACGTTTCAACGAAACGGGCCGCAGCCAGGTGCTGGCAAAACG
TATGCCGGGTGACCTCTCTGAATACTCCGTCATCCAGACTAAAGAGCCGCTGGACCGTGAGGGTAAAGTCA
GCCGCATTGTTGAATTTATCGAAAAACCGGATCAGCCGCAGACGCTGGACTCAGACATCATGGCCGTAGGT
CGCTATGTGCTTTCTGCCGATATTTGGCCGGAACTGGAACGTACTCAGCCTGGTGCATGGGGACGTATTCA
GCTGACTGATGCTATTGCCGAGCTGGCGAAAAAACAATCCGTTGATGCAATGCTGATGACCGGCGACAGTT
ACGACTGCGGCAAAAAAATGGGCTATATGCAGGCGTTTGTGAAGTATGGCCTACGCAACCTGAAAGAAGGG
GCGAAGTTCCGTAAAGGTATTGAGAAGCTGTTAAGCGAATAATGAAAATCTGACCGGATGTAACGGTTGAT
AAGAAAATTATAACGGCAGTGAAAATTCGCAGCAAAAGTAATTTGTTGCGAATCTTCCTGCCGTTGTTTTA
TATAAACCATCAGAATAACAACGAGTTAGCAGTAGGGTTTTATTCAAAGTTTTCCAGGATTTTCCTTGTTT
CCAGAGCGGATTGGTAAGACAATTAGCGTTTGAATTTTTCGGGTTTAGCGCGAGTGGGTAACGCTCGTCAC
ATCATAGGCATGCATGCAGTGCTCTGGTAGCTGTAAAGCCAGGGGCGGTAGCGTGCATTAATACCTCTATT
AATCAAACTGAGAGCCGCTTATTTCACAGCATGCTCTGAAGTAATATGGAATAAATTAAGCTAGCGTGAAG
ATACTTGTTACTAGGGGCGCAGGATTTATTGGTTCTGCTGTAGTTCGTCACATTATAAATAATACGCAGGA
TAGTGTTGTTAATGTCGATAAATTAACGTACGCCGGAAACCTGGAATCACTTGCTGATGTTTCTGACTCTG
AACGCTATGTTTTTGAACATGCGGATATTTGCGATGCTGCTGCAATGGCGCGGATTTTTGCTCAGCATCAG
CCGGATGCAGTGATGCACCTGGCTGCTGAAAGCCATGTGGATCGTTCAATTACAGGCCCTGCGGCATTTAT
TGAAACCAATATTGTTGGTACTTATGTCCTTTTGGAAGCGGCTCGCAATTACTGGTCTGCTCTTGATGGCG
ACAAGAAAAATAGCTTCCGTTTTCATCATATTTCTACTGACGAAGTCTATGGTGATTTGCCTCATCCTGAC
GAAGTAAATAATAAAGAACAATTACCCCTCTTTACTGAGACGACAGCTTACGCGCCTAGTAGTCCTTATTC
CGCATCAAAAGCATCCAGCGATCATTTAGTCCGCGCGTGGAAACGTACCTATGGTTTACCGACTATTGTGA
CTAACTGTTCGAATAACTACGGTCCTTATCACTTTCCGGAAAAATTGATTCCACTAGTAATTCTTAATGCT
CTGGAAGGTAAGGCATTACCTATTTATGGCAAAGGGGATCAAATTCGTGACTGGCTGTATGTTGAAGATCA
TGCGCGTGCGTTATATACCGTAGTTACTGAAGGTCAAGCGGGTGAAACCTATAACATTGGCGGACACAACG
AAAAGAAAAACATCGATGTTGTGCTGACTATTTGTGATTTGTTGGACGAGATAGTCCCGAAAGAGAAATCT
TATCGTGAGCAAATTACTTATGTTGCTGATCGCCCAGGGCATGATCGCCGTTATGCGATTGATGCTGAGAA
GATTGGTCGCGAATTGGGATGGAAACCACAGGAAACGTTTGAGAGTGGGATTCGTAAAACGGTGGAATGGT
ATTTGGCTAATGCAAAATGGGTTGATAATGTGAAAAGTGGTGCCTATCAATCGTGGATTGAACAGAACTAT
GAGGGCCGCCAGTAATGAATATCCTCCTTTTTGGCAAAACAGGGCAGGTAGGTTGGGAACTACAGCGTGCT
CTGGCACCTCTGGGTAATTTGATTGCTCTTGATGTTCACTCCACTGATTACTGTGGTGATTTTAGTAACCC
TGAAGGTGTGGCTGAAACAGTCAAAAGAATTCGACCTGATGTTATTGTTAATGCTGCGGCTCACACCGCAG
TAGATAAGGCTGAGTCAGAACCCGAATTTGCACAATTACTCAATGCGACTAGCGTTGAATCAATTGCAAAA
GCGGCAAATGAAGTTGGGGCTTGGGTAATTCATTACTCAACTGACTACGTATTCCCTGGAAATGGCGACAC
GCCATGGCTGGAGATGGATGCAACCGCACCGCTAAATGTTTACGGTGAAACCAAGTTAGCTGGAGAAAAAG
CATTACAAGAGCATTGTGCGAAGCACCTAATTTTCCGTACCAGCTGGGTCTATGCAGGTAAAGGAAATAAT
TTCGCCAAAACGATGTTGCGTCTGGCAAAAGAGCGTGAAGAACTAGCCGTTATTAATGATCAGTTTGGTGC
GCCAACAGGTGCTGAACTGCTGGCTGATTGTACGGCACATGCCATTCGTGTCGCACTGAATAAACCGGATG
TCGCAGGCTTGTACCATTTGGTAGCCAGTGGTACCACAACCTGGTACGATTATGCTGCGCTGGTTTTTGAA

| SEQUENCES |
|---|
| GAGGCGCGCAATGCAGGCATTCCTCTTGCACTCAACAAGCTCAACGCAGTACCAACAACTGCCTATCCTAC |
| ACCAGCTCGTCGTCCACATAACTCTCGCCTTAATACAGAAAAATTTCAGCAGAATTTTGCGCTTGTATTGC |
| CTGACTGGCAGGTTGGTGTGAAACGCATGCTCAACGAATTATTTACGACTACAGCAATTTAATAGTTTTTG |
| CATCTTGTTCGTGATGGTGGAGCAAGATGAATTAAAAGGAATGATGAAATGAAAACGCGTAAAGGTATTAT |
| TTTAGCGGGTGGTTCTGGTACTCGTCTTTATCCTGTGACTATGGTCGTCAGTAAACAGCTATTACCTATAT |
| ATGATAAACCGATGATCTATTATCCGCTTTCTACACTGATGTTAGCGGGTATTCGCGATATTCTGATTATT |
| AGTACGCCACAGGATACTCCTCGTTTTCAACAACTGCTGGGTGACGGTAGCCAGTGGGGCCTGAATCTTCA |
| GTACAAAGTGCAACCGAGTCCGGATGGTCTTGCGCAGGCATTTATTATCGGTGAAGAGTTTATTGGTGGTG |
| ATGATTGTGCTTTGGTACTTGGTGATAATATCTTCTACGGTCACGACCTGCCTAAGTTAATGGATGCCGCT |
| GTTAACAAAGAAAGTGGTGCAACGGTATTTGCCTATCACGTTAATGATCCTGAACGCTATGGTGTCGTTGA |
| GTTTGATAAAAACGGTACGGCGATCAGCCTGGAAGAAAAACCGCTACAACCAAAAAGTAATTATGCGGTAA |
| CCGGGCTTTATTTTTATGATAACGACGTTGTCGAAATGGCGAAAAATCTTAAGCCTTCTGCCCGCGGTGAA |
| CTGGAAATTACCGATATTAACCGTATCTATATGGAACAAGGGCGTTTATCTGTTGCCATGATGGGGCGTGG |
| TTATGCGTGGTTAGACACGGGGACACATCAGAGCCTGATTGAGGCAAGCAACTTTATTGCAACAATTGAAG |
| AGCGTCAGGGGCTGAAAGTTTCCTGCCCGGAAGAAATTGCTTACCGTAAAGGGTTTGTTGATGCTGAGCAG |
| GTGAAAGTATTAGCTGAACCTCTGAAAAAAAATGCTTATGGTCAGTATCTGCTGAAAATGATTAAAGGTTA |
| TTAATAAAATGAACGTAATTAAAACAGAAATTCCTGATGTACTGATTTTTGAACCGAAAGTTTTTGGTGAT |
| GAGCGTGGTTTCTTTTTTGAGAGCTTTAACCAGAAGGTTTTTGAGGAAGCTGTAGGCCGCAAAGTTGAATT |
| TGTTCAGGATAACCATTCGAAGTCTAGTAAAGGTGTTTTACGCGGGCTGCATTATCAGTTGGAACCTTATG |
| CACAAGGAAAATTGGTGCGTTGCGTTGTCGGTGAAGTTTTTGACGTAGCTGTTGATATTCGTAAATCGTCA |
| TCGACTTTTGGCAAATGGGTTGGGGTGAATTTATCTGCTGAGAATAAGCGGCAATTGTGGATTCCTGAGGG |
| ATTTGCACATGGTTTTTTAGTGCTGAGTGAGACGGCGGATTTTTGTATAAGACGACAAATTATTATCATC |
| CTCAGAGTGATAGAGGAATAAAATGGGATGATCCAAGCATCAATATTTCATGGCCAGTCGATTCACAAGTG |
| CTGCTATCAGCTAAAGATAATAAGCATCCTCCATTAACAAAGATTGAAATGTATAGTTAAGATCACGATAA |
| ATCTTGGAAGGGTTGCAAAATTGAATAAAATAGTGAGCAAAAGTGAAATAAGGAACGTAATCCACAATGCT |
| GGCTATATGATGATTACTCAGATAGCTTTATATGTTGCACCATTATTTATACTGAGTTATCGTTAAAAAC |
| ACTGGGGGTTGCACAGTTTGGTAATTATGCCTTAATACTATCAATCGTTGCATATTTACAGATTATAACGG |
| ATTATGGTTTTTCTTTTAGTGCAAGTCGTGCGATCTCACAGAATAGCAGGAGTTTACAAAAAGCACTTTTAGT |
| ATTTATCTGTCAACTATGACTATCAAGTTGGCGATATGCGCTTTCTTATTCTTATTGCTCATGCTATTTTT |
| AAATCTTTTGCCTGTGCAAGCTGAATTAAAACAAGGAATATTATATGGATATCTTCTTGTAATAGGAAATA |
| CTTTCCAACCACAATGGTTTTTCCAAGGTATCGAAAAATTAAAAATCATAGCCCTTTCTAATGTTATATCA |
| AGATGCGCCGCGTGTTTACTTGTATTTATCTATGTGAGGAATAGCGAGGATTTACAAAAAGCACTTTTAGT |
| ACAGTCACTTCCATTAGTAATTTCTGCGATTGGATTAAATATATTTATATTGAAATATATCAATATTATTT |
| TTCCGGAAAAAAATTATTTAAGGTAATTTTAAAAGAAGGTAAGGATTTTTTTCTTGCATCACTTTATTCT |
| GTTATTCTCAATAATAGTGGCATTTTTCTATTAGGGATTTTTACTAATCCTGTTATTGTTGGTGTATATGC |
| CGCCGCTGAAAAGATAGTCAAGGCCGTATTGTCGCTATTTACACCACTGACGCAAGCTATATATCCTTATA |
| ATTGTCGTAAGTTTTCACTATCCGTATTTGACGGCATTGAGGCAGCAAAAAAAACTGGTATACCAATTATA |
| ATTTTAGCATTTATAGCTGCTGTTATCGTTGCAATTACCTTACCTGTTGCAATCGACTATCTTAATTTTCC |
| AAAAGAAACAATTTTTGTAGGTCAAATATTAAGTGCATGGATCTTTTTTGGTGTTCTTAATAATGTATTCG |
| GCATTCAGATATTGAGTGCATCAGGAAGAAGTAAAATATATAGGTAGGATGGTATTCGTATCAGCGCTTATA |
| ACATTACTTTTGATTACTCTATTATTGCAGTTTTGTAACGCCACTGGAGTGGCATGTGCAATATTATTGGG |
| TGAAATGTTCTTATCAATATTGTTACTTAAGCGATATAAAAAATAATTTAAGGAATAGTTATGAAGAAGT |
| TATTATTAGTGTTCGGTACTAGGCCTGAAGCAATAAAGATGGCCTCTATCATTGAATTATTAAAAAAAGAT |
| TGTAGATTCGAATATAAATATGTGTGACAGGCCAACATAAAGAGATGCTTGATCAAGTTATGCAAGTATT |
| TGATGTTAAACCTGATTATAATTTACGGATTATGCAGCCTGGGCAAACATTAGTATCTATAGCAACAAATA |
| TACTCTCACGGTTAAGTGAAGTTTTAATTATAGAAAAGCCAGATATTATACTTGTGCATGGGGATACAACG |
| ACTACCCTTGCTGCTACTTTAGCTGGGTATTACCACCAAATAAAAGTTTGTCATGTGGAAGCAGGATTAAG |
| AACAGGGGATATTTACTCTCCTTGGCCTGAAGAGGGCAATCGTAAAGTTACAGGGGCATTAGCATGTATTC |
| ATTTCGCCCCAACAGAGAGATCAAAAGATAATCTCCTGAGGGAGGAGGGCAAAGTAAATAATATATTTGTA |
| ACGGGTAATACCGTCATCGACTCTTTATTTATTGCAAAAGATATCATAGATAATGACCCTAATATAAAGAA |
| CGCTTTACATAATAAATTTAATTTTCTTGATAAAAGCCGACGAGTAGTACTTATAACAGGTCATCGAAGAG |
| AAAATTTCGGGAAAGGTTTTGAAGATATATGCTTTGCAATAAAGGAATTAGCTTTCATTTATCCTAATGTA |
| GATTTTATTTATCCGGTGCATCTTAATCCCAATGTAATGGAACCAGTACATCGTATATTAGATAATATATG |
| TAATATTTACCTTATTGAGCCCTTGGATTATTTGCCTTTTGTTTATTAATGAATGAGTCATATTTAATAT |
| TGACTGATTCAGGGGGGATACAAGAAGAAGCGCCTTCGTTAGGTAAACCGGTTTGGTTATGCGTGATACT |
| ACTGAACGCCCTGAGGCGGTTGAGGCTGGTACTGTTGTATTAGTGGGACTTCTAAGATAAAATAGTAAA |
| TAAAGTAACGGAGCTATTAAACAATGCTGATATCTACAATGCTATGTCTCTGTTACATAATCCATATGGCG |
| ATGGAACAGCTGCTCAAAAAATTCTTAATGTGCTCGCCCAAGAGCTAATTTAATTTAAGCTAAAAATATGT |
| TATTAATTATTGCTGATTATCCAAACGAAATGAATATGCGCGAGGGAGCTATGCAACGAATAGATGCGATA |
| GACTCTCTCATTCGAGATCGCAAGCGAGTGTATTTGAATATTTCATTCAAAAAGCATCTAGTTCGCTCAAA |
| TAGTTCCTTTAATAATGTTATAGTTGAAAATCTAAATGCAATTATTCACGAAACATCATAAAACAGTACA |
| TGCAAAAATCAACAACTATATATGTTCATTCTGTTTATAATTTATTAAAGGTTATAACGCTCATTGATCTA |
| AAAAAAACAATTCTTGATATACATGGTGTTGTACCGGAAGAACTTTTGGCAGATAATAAAAAATTACTTAG |
| TAAAGTATATAACATGGTGGAAAAAAAAGGTGTCCTTGGATGCAAAAAATTAATACACGTCAGTACAGAAA |
| TGCAAAAACACTATGAAGCAAAATATGGAGTAAACTTGGCTGAAAGGTCAATAGTGCTCCCGATTTTGAA |
| TATAAAAATATAACCCAATCGCAAAACAAATGGACAGAAAATAAAACGTATCTATCTTGGAGGATT |
| ACAAACATGGCAAAATATTGATAAAATGATTCAAGTTTGTGATGACACAGTGATAAACAATGAAGCAGGTA |
| AGTATGAATTCAACTTTTTCATCCCACAGAGTAACTTGGAAGGGTTTATAGATAAATATTCGTTAAAATTA |
| CATAATATCAATGCTAATGCATCTACGCTATCACGTGATGAAGTAATTCCCTTTCTAAAAGAATGTCATAT |
| TGGTTTTGTATTGCGCGATGATATAATAGTAAACAGAGTTGCGTGCCCTACAAAATTGGTTGAATATTTAG |
| AGTGTGGTGTCGTTCCAGTTGTGCTCTCCCCACTTATAGGTGATTTTTATTCGATGGGGATAATAACATT |
| ACTACAGAGGAAATGGCTAACAGAAGTATAAGTTTGTTGGATCTTGAAAAAATGGCTGCACATAATTTACA |
| AATTTTGACTTCTTATCAGAAGAGAACCTACAAGGCACAGAAAGAACTTATTGCTCAACTGTGCTGAATTT |
| TTTACATATATAAAATTATGTAAGCATATCGCGGGTCAGGTAATTGTATGCGTATCAAATATAAAGATAAC |
| GGTTATATATTATGTTTCTATTATGTTTCATTTGAGCTACTTAGTTTTACTCAAATCTGACTACTTTCC |
| TGCTGATTTTCTGCCATATACAGAAATATACGATGGGACATACGGAGAAATCAATAATATATTGAGCCTGCCT |
| TTTTATATTTAACACGGTTGTTTCATTATTTAAATTTCCCCTATATATTTTTTGCAATGTTAGTTTGTGCC |

| SEQUENCES |
|---|
| TTATGTTTAAGTTGGAAAATAAAATATGCAAGAAAAATAATTAAAGATAGTTATATATATTTGTTCTTGTA
TGTATATGTATCATTTTATGTGTTTTTGCATGAAATGACTCAATTGCGCATAGCAATTGCAGTCACTATGT
GCTATGTGTCGGTTTATTATTACTTTTATAAAAATTGTATTAAACATGCACTGCCATGGATGGTGTTGGCT
ATTTTGTTTCATTACAGCGCCTTGCTTTTATTTATGTCATTATTTATATACAGTTATAGGAGGTTATTAAT
AGTAATTATAGGGTTTGTAATATGTATGAGCTTTTTAAACGTGTATGCAGATACAATTGCACTATATTTGC
CAAATGAAAAAATAGTAAATTATTTATATAGTATTTCATCATCATTAGACAATAGAAATGATTTGGCAATA
TTCAACCTGAATAATATAATATTTTTATCAATATTTATTTTGATCTTTTATCTTAGCCGATATATAAAATT
AAATGATAATGAGGCGAAGTTTATTAAGTATGTGCAATGTTCAGGAATATTAGCCTTTTGTATTTTCTTTC
TGGCTAGTGGAGTCCCGGTCATTGCTTATCGAACTGCAGAGTTGCTGCGAATATTTATCCGATGGCTTTA
GTATTAATCCTTTCGCATATAAAAAATAATAATATGCGTTATTTTATTGCAGTCATTATAGTTATCCTTTC
AGGCTTAATGTTGTTTATAACACTAAGGGCTGTATCAATAGTTGGTCAAGGATTATAAAATGAATGTTGCT
ATTTTGTTGTCTACGTATAATGGCGAAAAATATTTAGAGGAACAACTGGATTCATTGCTGCTTCAAAGTTA
TCAGGATTTTGTAGTGTATATCCGTGATGACGGATCATCTGATAGAACTGTAAATATAATAAACCAATACG
TAATGAAAGATAACAGATTTATTAACGTGGGTAATTCAGAAAATCTTGGTTGTGCTGCTTCGTTTATTAAT
TTATTAAGAAATGCTTCAGCCGATATTTATATGTTTTGTGACCAAGATGATTATTGGCTTCCGAATAAATT
ACAGCGTGCTGTGGATTATTTTTCGGCTATTGATCCTTTACAACCTACCTTGTATCATTGCGATCTAAGCG
TTGTTGATGAAAAACTTAATATTATACAAAATTCATTTTTGCAGCATCAGAAAATGTCAGCGTATGATTCA
ATGAGAAAAAATAATCTTTTCATACAAAATTTTGTTGTTGGTTGTTCATGTGCTGTTAATGCTTCACTTGC
GGAATTTGTTCTTTCGCGAATTGGAGAGCAGCATGTAAAAATGATAGCTATGCATGACTGGTGGTTAGCCG
TGACTGCAAAACTTTTTGGTCGAATCCATTTTGATAATACTCAAACGATTCTTTATCGACAACATCAGGGC
AATGTATTAGGTGCAAAATCATCAGGTATGATGCGTTTTATTCGATTAGGATTAAATGGGCAAGGGATTTC
GCGAGTAGTATCTTTTAGAAAAAAGTTTGTGCGCAAAATAAGCTTCTTTTAGATGTCTATGATAAAGATT
TAAATCTTGAGCAAAAAAATCTATCAGGCTTGTAATTGAGGGCCTTAAAGAGAACTCTTCAATTGCTGAC
CTTTTAAAATGTTTCTATCATGGTAGCTATATGCAAGGTTTTAAACGTAATCTTGCCTTAATATATTCAGT
TCTTTACACAAAAAAAAGAAGATAGTGTATCCTTATGAAAAAAATTGCTATTATCGGTACTGTTGGCATAC
CAGCATCATATGGCGGATTTGAAACATTAGTTGAAAATTTAACAAGATACAATTCCTCGGGAGTTGAATAT
AATGTTTTTTGTTCATCGTTTCACTACAAATCCCACCAAAAAAAACATAATGGGGCCCGTTTAATTTATAT
TCCGCTTAAAGCCAATGGATGGCAGAGCATTGCGTATGACATAATTTCGTTAGCATATTCTATTTTTTTGA
AGCCTGATGTGATTCTGATTTTAGGGGTTTCTGGTTGTTCATTTTTGCCTTTCTTCAAACTCTTAACACGC
GCTAAGTTTATTACTAATATTGATGGCCTGGAATGGCGAAGAGATAAATGGAATTCAAAAGTGAAACGTTT
CTTAAAATTTTCAGAAAAAATCGCAGTTCAATATTCGGATGTCGTTATTACGGATAATGAGGCAATTTCTG
AGTACGTTTTTAACGAGTATAATAAAGATAGCCGAGTTATTGCCTATGGAGGGGATCATGCATGGTTAAAT
ACTGAGGATGTATTTACAACAAGAAATTATAAAAGCGATTACTACCTTTCTGTATGTCGTATCGAACCCGA
AAACAATGTAGAATTAATTTTAAAAACATTTTCAAAGCTAAAATATAAAATAAAATTTATTGGAAATTGGA
ATGGCAGCGAGTTTGGAAAGAAACTTAGGCTGCATTATTCTAACTATCCAAATATTGAAATGATTGATCCG
ATTTATGATCTTCAACAATTATTTCACTTACGAAATAATTGCATAGGATATATACATGGTCATTCGGCTGG
AGGAACAAACCCTTCTTTAGTCGAGGCAATGCATTTTAGTAAACCTATATTTGCATATGATTGTAAGTTTA
ATAGGTACACTACTGAAATGAAGCATGTTATTTTTCTAATGAATCTGACCTCGCAGAGAAAATCATAATG
CATTGTGAGCTATCATTAGGTGTCTCTGGCACGAAAATGAAAGAAATTGCTAACCAGAAATACACTTGGAG
ACGAATAGCAGAAATGTATGAGGATTGCTATTAACTCTGTTAAACTTCAAATCTTTTACAATATATGGCAT
GACTATAAGCGCCATTAATTGTTTTTCAAGCCGCTCTCGCGGTGACCACCCCCTGACAGGGGATCCGTGTAG
GCTGGAGCTGCTTGAAGTTCCTATACTTTCTAGAGAATAGGAACTTCGGAATAGGAACTAAGGAGGATAT
TCATATGGATAAAGCCGTAAGCATATAAGCATGGATAAGCTATTTATACTTTAATAAGTACTTTGTATACT
TATTTGCGAACATTCCAGGCCGCGAGCATTCAGCGCGGTGATCACACCTGACAGGAGTATGTAATGTCCAA
GCAACAGATCGGCGTAGTCGGTATGGCAGTGATGGGAGCCAACCTTGCGCTCAACATCGAAAGCCGTGGTT
ATACCGTCTCTATTTTCAACCGTTCCCGTGAGAAGACGGAAGAAGTGATTGCCGAAAATCCAGGCAAGAAA
CTGGTTCCTTACTATACGGTGAAAGAGTTTGTCGAATCTCTGGAAACGCCTCGTCGCATCCTGTTAATGGT
GAAAGCAGGTGCAGGCACGGATGCTGCTATTGATTCCCTCAAACCATATCTCGATAAAGGAGACATCATCA
TTGATGTGGTAACACCTTCTTCCAGGACACTATTCGTCGTAACGTTTGAGCTTTCAGCAGAGGGCTTTAAC
TTCATCGGTACCGGTGTTTCTGGCGGTGAAGAGGGGGCGCTGAAAGGTCCTTCTATTATGCCTGGTGGCCA
GAAAGAAGCCTATGAATTGGTAGCACCGATCCTGACCAAAATCGCCGCCGTAGCTGAAGACGGTGAACCAT
GCGTTACCTATATTGGTGCCGATGGCGCAGGTCACTATGTGAAGATGGTTCACAACGGTATTGAATACGGC
GATATGCAGCTGATTGCTGAAGCCTATTCTCTGCTTAAAGGTGGCTGAACCTCACCAACGAAGAACTGGC
GCAGACCTTTACCGAGTGGAATAACGGTGAACTGAGCAGTTACCTGATCGACATCACCAAAGATATCTTCA
CCAAAAAAGATGAAGACGGTAACTACCTGGTTGATGTGATCCTGGATGAAGCGGCTAACAAAGGTACCGGT
AAATGGACCAGCCAGAGCGCGCTGGATCTCGGCGAACCGCTGTCGCTGATTACCGAGTCTGTGTTTGCACG
TTATATCTCTTCTGAAAGATCAGCGTGTTGCCGCATCTAAAGTTTCTCTGGTCCGCAAGCACAGCCAG
CAGGCGACAAGGCTGAGTTCATCGAAAAAGTTCGTCGTGCGCTGTATCTGGGCAAAATCGTTTCTTACGCC
CAGGGCTTCTCTCAGCTGCGTGCTGCGTCTGAAGAGTACAACTGGGATCTGAACTACGGCGAAATCGCGAA
GATTTTCCGTGCTGGCTGCATCATCCGTGCGCAGTTCCTGCAGAAAATCACCGATGCTTATGCCGAAATC
CACAGATCGCTAACCTGTTGCTGGCTCCGTACTTCAAGCAAATTGCCGATGACTACCAGCAGGCGCTGCGT
GATGTCGTTGCTTATGCAGTACAGAACCGTGATTCCGGTTCCGACCCTTCTCCGCAGCGGTTGCCTATTACGA
CAGCTACCGTGCTGCTGTTCTGCCTGCGAACCTGATCCAGGCACAGCGTGACTATTTTGGTGCGCATACTT
ATAAGCGTATCGATAAAGAAGGTGTGTTCCATACCGAATGGCTGGATTAA |

SEQ ID NO: 12 (example O2 rfb locus nucleotide sequence - O2-EPA production strain stGVXN4906)
ATGACGAATTTAAAAGCAGTTATTCCTGTAGCGGGTCTCGGGATGCATATGTTGCCTGCCACTAAGGCGAT
ACCCAAAGAGATGCTACCAATCGTCGACAAGCCAATGATTCAGTACATTGTTGACGAGATTGTGGCTGCAG
GGATCAAAGAAATCCTCCTGGTAACTCACGCGTCCAAGAACGCGGTCGAAAACCACTTCGACACCTCTTAT
GAGTTAGAATCACTCCTTGAGCAGCGCGTGAAGCGTCAACTGCTGGCGGAAGTACAGTCCATCTGTCCGCC
GGGCGTGACCATTATGAACGTGCGTCAGGGCGAACCTTTAGGTTTAGGCCACTCCATTTTGTGTGCGCGAC
CTGCCATTGGTGACAACCCATTTGTCGTGGTACTGCCAGACGTTGTGATCGACGATGCCAGCGCCGACCCG
CTACGTTACAACCTTGCTGCCATGATTGCACGTTTCAACGAAACGGGCCGCAGCCAGGTGCTGGCAAAACG
TATGCCGGGTGACCCTCTCTGAATACTCCGTCATCCAGACTAAAGAGCCGCTGGACCGTGAGGGTAAAGTCA
GCCGCATTGTTGAATTTATCGAAAAACCGGATCAGCCGCAGACGCTGGACTCAGACATCATGGCCGTAGGT
CGCTATGTGCTTTCTGCCGATATTTGGCCGGAACTGGAACGTACTCAGCCTGGTGCATGGGGACGTATTCA
GCTGACTGATGCTATTGCCGAGCTGGCGAAAAAACAATCCGTTGATGCAATGCTGATGACCGGCGACAGTT

| SEQUENCES |
|---|
| ACGACTGCGGCAAAAAAATGGGCTATATGCAGGCGTTTGTGAAGTATGGCCTACGCAACCTGAAAGAAGGG |
| GCGAAGTTCCGTAAAGGTATTGAGAAGCTGTTAAGCGAATAATGAAAATCTGACCGGATGTAACGGTTGAT |
| AAGAAAATTATAACGGCAGTGAAAATTCGCAGCAAAAGTAATTTGTTGCGAATCTTCCTGCCGTTGTTTTA |
| TATAAACCATCAGAATAACAACGAGTTAGCAGTAGGGTTTTATTCAAAGTTTTCCAGGATTTTCCTTGTTT |
| CCAGAGCGGATTGGTAAGACAATTAGCGTTTGAATTTTTCGGGTTTAGCGCGAGTGGGTAACGCTCGTCAC |
| ATCATAGGCATGCATGCAGTGCTCTGGTAGCTGTAAAGCCAGGGGCGGTAGCGTGCATTAATACCTCTATT |
| AATCAAACTGAGAGCCGCTTATTTCACAGCATGCTCTGAAGTAATATGGAATAAATTAAGTGAAAATACTT |
| GTTACTGGTGGCGCAGGATTTATTGGTTCAGCTGTAGTTCGTCACATTATAAATAATACGCAGGATAGTGT |
| TGTTAATGTCGATAAATTAACGTACGCCGGAAACCGGGAATCACTTGCTGATGTTTCTGATTCTGAACGCT |
| ATGTTTTTGAACATGCGGATATTTGCGATGCACCTGCAATGGCACGGATTTTTGCTCAGCATCAGCCGGAT |
| GCAGTGATGCACCTGGCTGCTGAAAGCCATGTTGACCGTTCAATTACAGGCCCTGCGGCATTTATTGAAAC |
| CAATATTGTTGGTACTTATGTCCTTTTGGAAGCCGCTCGCAATTACTGGTCTGCTCTTGATAGCGACAAGA |
| AAAATAGCTTCCGTTTTCATCATATTTCTACTGACGAAGTCTATGGTGATTTGCCTCATCCAGATGAAGTA |
| AATAATACAGAAGAATTACCCTTATTTACTGAGACGACAGCTTACGCGCCAAGCAGCCCTTATTCCGCATC |
| CAAAGCATCCAGCGATCATTTAGTCCGCGCATGGAAACGTACGTATGGTTTACCGACCATTGTGACTAATT |
| GCTCGAACAACTATGGTCCGTATCACTTCCCGGAAAAGCTTATTCCATTGGTTATTCTTAATGCACTGGAA |
| GGTAAGGCATTACCTATTTATGGCAAAGGGGATCAAATTCGCGACTGGTTGTATGTAGAGGATCATGCTCG |
| TGCGTTATATACCGTCGTAACCGAAGGTAAAGCGGGTGAAACTTATAACATTGGCGGACACAACGAAAAGA |
| AAAACATCGATGTTGTGCTGACTATTTGTGATTTGTTGGATGAGATTGTACCGAAAGAGAAATCTTATCGT |
| GAGCAAATTACTTATGTTGCTGATCGCCCAGGGCATGATCGCCGTTATGCCGATAAAATTAG |
| CCGCGAATTGGGCTGGAAACCACAGGAAACGTTTGAGAGCGGGATTCGCAAAACGGTGGAATGGTATCTGG |
| CTAATACAAATTGGGTTGAGAATGTGAAAAGCGGTGCTTATCAGTCATGGATCGAACAAAACTATGAGGGC |
| CGTCAGTAATGAATATCCTGCTTTTCGGCAAAACAGGGCAGGTGGGTTGGGAACTGCAGCGTGCTCTGGCG |
| CCGCTGGGTAATCTGATCGCTCTTGATGTTCACTCCACTAATTATTGTGGAGATTTCAGCAACCCCGAAGG |
| TGTGGCAGAAACCGTCAAAAAAATTCGTCCTGACGTTATTGTTAATGCTGCTGCTCACACTGCAGTAGATA |
| AAGCAGAATCAGAACCGGATTTCGCACAATTACTTAACGCGACAAGCGTCGAAGCGATTGCAAAAGCTGCT |
| AATGAAGTCGGGGCCTGGGTTATACACTACTCTACTGATTATGTTTTCCCAGGCAGTGGTGACGCGCCATG |
| GCTGGAAACGGATGCAACAGCACCGCTAAATGTTTACGGTGAAACAAAATTAGCTGGGGAAAAGGCATTAC |
| AAGAACATTGCGCAAAGCATCTTATTTTCCGTACCAGCTGGGTATACGCTGGTAAAGGAAATAACTTTGCT |
| AAAACGATGTTGCGTTTGGCAAAAGAACGCGAAGAACTGGCTGTGATAAACGATCAGTTTGGCGCACCAAC |
| AGGTGCTGAATTGCTGGCTGATTGCACCGCTCATGCCATTCGCGTGGCATTAAAAAAACCAGAAGTCGCTG |
| GCTTGTACCATCTGGTAGCAAGTGCACAACAACCTGGCACGATTGTCTGCGCTGGTTTTTGAAGAGGCG |
| CGCAAAGCAGGGATTAATCTTGCACTTAACAAACTTAACGCCGTGCCAACAACGGCCTATCCCACACCAGC |
| CCGTCGACCCCATAACTCTCGCCTCAATACAGAAAAGTTTCAGCAGAACTTTGCGCTTGTCTTGCCTGACT |
| GGCAGGTGGGCGTGAAACGTATGCTCAACGAATTATTTACGACTACGGCAATTTAACAAATTTTTGCATCT |
| CGCTCATGATGCCAGAGCGGGATGAATTAAAAGGAATGGTGAAATGAAAACGCGTAAAGGTATTATTCTGG |
| CTGGTGGTTCCGGCACTCGTCTTTATCCTGTGACGATGGCAGTGAGTAAACAATTGCTGCCGATTTATGAT |
| AAGCCGATGATTTATTATCCGCTTTCAACGCTTATGTTAGCGGGTATTCGCGATATTCTTATTATTAGTAC |
| GCCACAGGATACACCGCGTTTCCAACAATTATTGGGGACGGGAGCCAGTGGGGTCTTAATCTACAGTATA |
| AAGTACAACCGAGTCCGGATGGCCTGGCGCAAGCGTTTATTATTGGCGAAGACTTTATTGGTGGTGATGAT |
| TGTGCACTCGTACTTGGCGATAATATCTTCTATGGACACGACTTGCCGAAATTGATGGAAGCTGCTGTTAA |
| CAAAGAAAGCGGTGCAACGGTATTTGCTTATCACGTTAATGATCCTGAACGCTATGGTGTCGTGGAGTTTG |
| ATAATAACGGTACGGCAATTAGCCTGGAAGAAAAACCGCTGGAGCCAAAAAGCAACTATGCGGTTACTGGG |
| CTTTATTTCTATGACAATGACGTTGTGGAAATGGCTAAAAACCTTAAGCCTTCTGCCCGTGGCGAACTGGA |
| AATTACCGATATTAACCGTATTTATATGGAACAAGGACGTTTGTCTGTAGCCATGATGGGGCGTGGCTATG |
| CATGGTTGGATACAGGGACGCATCAAAGCCTTATTGAAGCAAGTAACTTCATTGCAACAATTGAAGAGCGT |
| CAGGGATTAAAGGTATCTTGCCCGGAAGAGATTGCTTACCGTAAAGGGTTTATTGATGCCGAGCAGGTGAA |
| AGTATTAGCCGAACCGCTTATCAAGAATCAATATGGTCAATATTTGCTGAAAATGATCAGCGAATAGTATA |
| TGGGAACTCAATGATGGATATTAAATTAATCTCTTTGCAAAAACATGGGGATGAGCGCGGTGCATTAATTG |
| CTCTTGAAGAGCAACGAAATATACCTTTCGAAGTCAAAAGAATATATTACATACTTGAGACTCTTAATGGA |
| GTAAGACGCGGATTTCATGCGCACAAGGTTACTCGTCAGTTAGCTATTGTAGTCAAGGGAGCTTGTAAATT |
| TCATCTGGATAATGGTAAAGAAACAAAGCAGGTGGAACTTAATGATCCAACAATTGCGTTGCTGATAGAAC |
| CCTATATATGGCATGAAATGTATGATTTTAGTGATGATTGTGTGCCTTGTAATTGCGGATGATTTCTAT |
| AAAGAGTCTGATTATATCCGCAATTATGATGATTTTATTAGAAGAGTAAATTCAATTGAGAATTCATAAGC |
| TAAGTGACGTCCAGACAACATCAATTGGTGATGGAACAACTATCTGGCAGTTTGTTGTGATACTAAAAGGT |
| GCTGTAATTGGTAATAATTGCAACATCTGTGCAAATACCTTAATTGAAAATAACGTTGTAATTGGTAACAA |
| TGTCACAGTCAAAAGCGGTGTGTATATTTGGGATGGCGTTAAAATAGAGGATAATGTTTTTATTGGTCCTT |
| GTGTAGCATTTACAAATGATAAGTATCCTCGCTCTAAAGTCTATCCTGATGAATTTTTGCAAACAATAATA |
| CGCAAAGGAGCATCAATAGGTGCTAACGCAACCATCCTGCCAGGAATTGAAATTGGTGAAAAAGCAATCGT |
| TGGTGCGGGAGTGTTGTAACCAAAAATGTACCGCCATGCGCAATAGTAGTAGGTAATCCAGCTCGATTTA |
| TTAAATGGTAGAGGATAATGAATAAAATTGATTTTTTAGATCTTTTTGCAATTAACCAGCGACAGCACAA |
| AGAATTAGTCTCTGCGTTTAGTAGGGTGCTAGATTCTGGTTGGTATATCATGGGCGAAGAACTTGAGCAGT |
| TCGAGAAAGAGTTCGCAGAATACTGTGGAGTTAAGTATTGCATTGGTGTAGCAAATGGCCTTGATGCGTTG |
| ATACTAGTATTGAGGGCATGGAAAGAACTTGGCTATCTTGAAGACGGTGACGAGGTATTAGTACCGGCAAA |
| TACATATATTGCTTCTATTCTTGCTATAACAGAGAACAAACTTGTTCCTGTTCTTGTTGAACCAGATATAG |
| AAACTTATAATATTAATCCTGCTTTAATTGAAAATTACATTACGGAAAAAACTAAAGCAATTATTACCGGTT |
| CACTTATATGGTCTATTGTGCAATATGCCAGAAATTAGTGCAATCGCCAGAAAATATAATCTGTTGATTCT |
| TGAAGATTGTGCACAAGCACATGGTGCAATACGTGATGGTCGCAAAGCTGGAGCTTGGGGGATGCTGCAG |
| GATTTAGTTTTTATCCAGGAAAAAAACCTTGGAGCTTTGGGGATGCGGGAGCTGTTACTACAAATAATGCA |
| GAATTATCCTCAACTATAAAAGCTTTGCGAAATTATGGGTCACATAAGAAATATGAAATATTTATCAGGG |
| ATTGAATAGTCGATTGGATGAACTGCAAGCAGCCTTATTGCGTGTGAAAAATCCATTACCGGAAGATA |
| CTGCGATTCGGCAAAGGATTGCTGAAAAATATATTCGTGAAATAAAAAACCCTGCGATTACGTTACCAGTG |
| TACGAAGGCCAAGGTGCGCATGTTTGGCATTTATTTGTAGTAAGAATCGCTAATCGTGAAAATTCCAGTC |
| ATACTTATTAGAGAAGGGTATCAAAACCTTAATTCACTATCCATTACCACCCCATAAGCAGCAAGCATATC |
| AAAATATGTCTAGCCTTAGCCTTCCAATTACTGAGCAAATTCATGATGAAGTCATTTCTTTACCTATAAGT |
| CCGGTAATGAGTGAAGATGATGTCAATTATGTAATCAAAATGGTCAATGATTACAAGTAATGAAAAAATTT |
| CTTCAGGTAACTATATTATCCGCTATCTATACATTCATTAAAATGATTGCGGGTTTTATCATCGGTAAGGT |

| SEQUENCES |
|---|
| AGTAGCAATTTATACAGGGCCATCAGGGGTAGCAATGCTTGGCCAAGTGCAAAGTTTAATCACAATAGTTG |
| CAGGTACTACCTCTGCACCTGTAAGCACAGGCCTTGTTCGATATACTGCGGAAAATTGGCAAGAAGGACAA |
| GAAGCATGCGCGCCATGGTGGCGCGCATGCTTAAGGGTTACTCTGTTTTTATTCTTGCTTATTATTCCCGT |
| TGTTATTATATTGTCGAAAAATATTAGTGAGTTACTTTTTAGCGATGGACAATACACATGGTTAATCATTT |
| TCGCATGTTGTATATTGCCATTCTCCATTATAAATACATTGATCGCTTCAGTTTTAAATGGTCAACAATTT |
| TATAAGCAATATATATTGGTTGGGATGTTTTCTGTATTCATTTCTACTATGTTTATGATTTTGTTGATTGT |
| AGCTTATAATCTTAAAGGTGCATTGATTGCCACAGCTATAAATAGTGCTATTGCTGGTCTTGTATTGGTTT |
| TATTTTGTCTCAATAAATCTTGGTTTAGATTTAAATATTGGTGGGGTAAAACGGATAAAGACAAAATTATA |
| AAAATTATTCATTATACTCTGATGGCTCTGGTTTCTGTTATCTCCATGCCTACAGCATTGATGTGTATTAG |
| AAAAATATTGATTGCTAAAACTGGTTGGGAGGATGCAGGGCAATGGCAGGCCGTATGGAAGATATCTGAGG |
| TTTATCTTGGTGTTGTGACAATTGCTTTGTCAACATATTTCTTACCAAGATTGACAATTATAAAAACAAGT |
| TTCCTTATAAAAAAGAAGTAAATAGTACTATATTATACATAATATCTATTACTTCATTCATGGCGTTGAG |
| TATCTATTTATTCCGCGATTTGGTAATAACAGTTTTATTTACTGAACAGTTTCGCTCAGCTCGTGAATTAT |
| TTTTATTACAACTTATAGGGGATGTAATAAAAATTGCTGGGTTTCTTTATGCATACCCTCTTCAAAGTCAG |
| GGGCATACTAAACTATTCATCAGTTCAGAAGTGATTTTTTCTATGCTCTTTATCATTACCACCTATATTTT |
| TGTTGTAAATTATGGAGTACATGGTGCTAACATAAGTTATGTCATTACATATAGTTTATATTTTGTGTTTG |
| CATTTGTGTTTACTAATTTTATTAATGTTAGAAGAAATAATTAAAAACAGAGGTTGAATTTTGAAAATAAT |
| TATACCTGTCTTAGGATTTGGCAGGGCTGGTGGTGAAAGAGTTCTTTCTAAGCTGGCAACTGAATTGATGA |
| ATTATGGACATGATGTAAGTTTTGTTGTTCCAGATAATAGAACTAATCCATATTATGCTACCACAGCAAAA |
| ATTGTCACGAGTAAATCTAGTCAAAACCGTGTAAAAATATTGAGAATCATTAAAAATTACTATAATCTGTG |
| GCGTAAATGCATAGAGTTAAATCCTGATGCTGTAGTTGCTAGTTTTCATTTGACTGCCTATCTTGTCGCAT |
| TATTACCAATCACCCGTCGTAAGAAATATTATTATATTCAGGCGTATGAAGTTAATTTTTTTGATAATATA |
| ATATGGAAATTAATAGCGGGTTTAACATATTATTTACCGCTTAAAAAAATACTAAATAGTCCTAATTTGCT |
| TCCTCATAAACATGATGATTTTATAGGAGTAGTTCCTGCAGGAGTAGATTTAAACGTTTTCTATCCGAAAC |
| CATCAAATAGGTTATTAAATGGTCACACATCAATAGGGATTATTGGTAGAAAAGAGAAGCACAAAGGAACT |
| AGCGAAATTATTTCAGTATTGTGTTCACTGGAAAATAAAGCTGGAATTATAATCAATATTGCGATCTATCT |
| TGAAGAAGTTGATAAGCAGCGTTTAATCGCTGCCGGGTTTCAGGTTAATTTTTTTCCGATTACTTCTGATT |
| TAGAATTGGCATCCTTTTATCGAAGCAATGACATCATGATTGCTGTTGGGTTAATTGAAGATGGCGCTTTC |
| CATTATCCTTGTGCTGAATCAATGGCTTGTGGTTGTCTTGTTATTTCAAATTATGCGCCACTTACTGAAAC |
| TAACAGTGTACTTAAATTAGTCAAGTTTGATGCTTGCAAACTTGGTGAAGCAATTAATCTTTGTCTCAATC |
| TTGACCTAGAAGAAAAAGCAAAGAAATCCAATCTAATATTTCTGTGTTGAATAAATATGACTGGAAAATT |
| GTTGGTGAAACTTTCAATAGTTTATTGTTAGATGCAAATAAATAGTATACGTTGATGGGGAAAATATGAAT |
| ATTGTTAAAACTGATATTCCAGATCTGATCGTTCTTGAACCAAAAGTGTTTAGTGATGAACGCGGCTTTTT |
| TATGGAGAGTTATAATCAGATTGAATTTGAGAAGGCAATAGGAAGGCACGTAAATTTTGTTCAGGATAATC |
| ATTCAAAATCTAGTAAAGGCGTACTACGTGGGTTGCATTATCAATTAGCACCGTATGCACAGGCTAAATTA |
| GTTCGATGTGTTGTAGGTCAGGTATTTGATGTTGCTGTTGATCTTAGAAAAAATTCACCAACGTTCAAAAA |
| ATGGTTTGGAATAACCCTTTCCGCAGAAAATAAACGACAATTATGGATACCCGAAGGATTTGCTCATGGTT |
| TCTTGGTGACCAGTGATGAAGCTGAGTTCATTTATAAGACAACTAACTACTATGCTCCTGGTCATCAGCAA |
| GCAATTATTTACAATGATCCTATTTTAAACATCGATTGGCCTTTCTGCAGTAGTGCTCTGTCATTATCACA |
| AAAAGATCAAGAAGCAAAATTATTTTCAGAATTATTGGACAGTGAACTGTTCTAATAAAGTGTGCCACCTT |
| ATCCGTCTGAAGGATAGGTGGTTGCTTATATTTTTTGAGTATGTTTGTATAATGACAGAAAATAGTCCGA |
| AATATAAACACGATAAAAGCTTAATAAGTTTTATCTACTTATTTTTTATATTTACACTTATTGTAGGCTTT |
| ATTATCGCAAATACCCAGTTTTTGGGGCGAAGTAGAGACTATGATAATTATATACAGATCTTTTCTGGTAA |
| AGAAGGGGAGGGGGTTCTTGAATTATTTTATCGCGGATTGATGTTAATAACGACCAGCTATGAAACTATCA |
| TTTTTATAATTTTAACATGTTCTTTTTTTATAAAGGCAAGGTTTCTGCTAACTATTCGCGTAATTTTTCA |
| GGCTTGACCTTATTCTTTATTTATTATGCAAGCGTTGCACTTTGGGTTTTAAGATTATACTCAATTCAGAAA |
| TGGTCTATGTATTTCCATTTTAATGTTTTCCGTATACTATTTATTTATAAATAAACCGACTTATTTTTATT |
| TCTCGGTATTATGTGCAATTGCAACTCATTGGTCTGCTTTGCCTTTTTTGCTTTTATATCCTTTTGTCTAT |
| TCAACAAAAATAAGACGCCTTGGTTATTTTTGTTTCAGTATTCTTTGTTTTTGATTGCGATCTCAGGAGAGG |
| AAAAGAGATCATATCTTTTATAAGAAATTTTGGAGTGGGACAAAAAATAGGAAATGAAGCTGGTGTAAATT |
| TAATAAATTCATTATCCCTTACCGCTATTTCCTGGTTTATTATTAGTTACATATCAAGCATTGGAAATGAA |
| AGGAGAAATTTAAGGCTTTTCTTTTGTTATGGTGTCATGCAATACGTGACTTTTAGCCTTTTCTCTCTACC |
| TGTTATGGCTTTCCGTATTTTGGAAATGTATTTTTTCCTTATGCTAACCATTGGGGTGTTTATTAAGCAAA |
| AAAAGAATTATTATTTTATTTTTTGCAAAGTGTTAATTTTATTGTATCTAACATACTATTATCATATGGTC |
| TTTGGAGTGATTAATGTGTAAGGCTAAGGTGTTGGCTATAATTGTTACTTACAACCCGGAAATTATTCGAT |
| TGACGGAATGTATTAACTCTTTAGCCCCACAAGTTGAGAGAATAATTCTTGTAGATAATGGCTCAAATAAT |
| AGTGATTTGATAAAAAATATCAGTATTAATAACCTTGAAATTATTTACTTTCGGAAAACAAAGGCATTGC |
| ATTTGCTCAGAACCATGGTGTTAAGAAGGGCCTGGAAGCAAAAGAGTTTGACTATTTATTTTCTCAGATC |
| AGGATACTTGCTTTCCTAGCGATGTTATTGAAAAACTTAAGAGTACATTTACGAAAAATAATAAAAAAGGT |
| AAAAATGTTGCTTGTGCTTCTCCTTTTTTTAAAGACCATCGTTCAAATTATATGCATCCGTCAGTCAGCCT |
| AAATATTTTACGAGTACAAAAGTTATATGTAGTGAAGTAGCGATGATCTTTATCCCTCGCATGTTATTG |
| CTTCTGGGATGTTAATGTCTCGTGAAGCATGGCGCGTCGTCGGACCATTTTGTGAAAAACTCTTTATAGAC |
| TGGGTTGATACAGAATGGTGTTGGCGTGCATTAGCTAATAATATGATTATTGTTCAGACACCATCAGTCAT |
| CATTTCTCATGAACTTGGGTATGGGCAGAAAATTTTGCTGGTCGATCTGTTACAATACATAATTCTTTCA |
| GAATTTTTATAAAATACGCAATGCAATATACTTAATGCTGCATTCAAATTATAGCTTCAAGTATCGTTAT |
| CATGCTTTTTTCATGCGACAAAGAATGTGTATTTGAAATTTTATATTCGAAAGAAAATTAAATTCACT |
| GAAGGTTTGTTTTAAAGCTGTACGTGATGGTATGTTCAATAATTTTTAATACGAAAATAGTTAGGCTCAAG |
| GTGTTTAAATGGAAGAAAATAATATGAAGACGGTCGCTGTAGTTGGCACAGTGGGTGTTCCTGCTTGTTAT |
| GGTGGGTTCGAATCACTTGTTCAGAATCTAATTGATTATCAATCTGATGGTATACAATATCAGATATTTTG |
| CTCTTCAAAAAAATATGATAAAAAATTTAAAAATTATAAAAATGCAGAATTAATCTATTTGCCGATAAATG |
| CCAATGCGTCTCTAGCATAATTTATGATATTATGTGTTTAATTATTTGTTTATTCAAAAGGCCAGATGTT |
| GTTTTAATATTGGGGGTGTCTGGTTGTTTATTTCTACCAATTTATAAACTATTTTCAAAATCAAAGATTAT |
| TGTCAATATTGATGGGCTTGAATGGCGTAGAAATAAATGGGAACGTTTGCTAAGAAATTTCTTAAAAATAT |
| CTGAGGCGATATCTATTAGAATAGCTGATATTATCATTTCAGATAATCAAGCAATAGCTGATTATGTGGAA |
| AATAAGTACAAGAAAAAAGTGTAGTTATAGCTTATGGCGGAGATCATGCCACTAATCTTAGTACACCGAT |
| AGACAATGATCAAAAAAAAGAAGGTTATTTTTGGGGCTTTGTAGGATAGAGCCTGAGAATAATATAGAAA |
| TGATTCTGAATGCCTTCATTAATACAGATAAAAAAAATTAAATTTATGGGTAATTGGGATAACAGCGAGTAT |

```
GGACGCCAGCTAAAAAAATATTATTCAAACTATCCAAATATCACCCTACTAGAACCTAACTATAATATTGA
AGAGCTTTATAAACTAAGAAAAAATTGTCTTGCATACATTCATGGACACTCGGCTGGTGGAACAAACCCTT
CTTTAGTTGAAGCGATGCATTTTAATATTCCTATTTTTGCTTTCGATTGTGACTTTAATCGTTACACAACT
AACAATTTAGCTCATTACTTTAATGATTCTGAACAACTTAGCTTATTAGCAGAAAGTTTGTCTTTTGGAAA
TCTTAAATGTCGAGTATTAGATTTAAAAAATTATGCTGAAGATATGTATAACTGGAGGCATATAGCTGCTA
TGTATGAATCTATTTATTAAACGCATTAACAATAATATAATTGACCTTATATAGCAGGGAAAGATCACGTA
ACGCTGCGGCGCGCCGATCCCCATATGAATATCCTCCTTAGTTCCTATTCCGAAGTTCCTATTCTTTCTAG
AGAATAGGAACTTCGGAATAGGAACTAAGGAGGATATTCATATGGATAAAGCCGTAAGCATATAAGCATGG
ATAAGCTATTTATACTTTAATAAGTACTTTGTATACTTATTTGCGAACATTCCAGGCCGCGAGCATTCAGC
GCGGTGATCACACCTGACAGGAGTATGTAATGTCCAAGCAACAGATCGGCGTAGTCGGTATGGCAGTGATG
GGACGCAACCTTGCGCTCAACATCGAAAGCCGTGGTTATACCGTCTCTATTTTCAACCGTTCCCGTGAGAA
GACGGAAGAAGTGATTGCCGAAAATCCAGGCAAGAAACTGGTTCCTTACTATACGGTGAAAGAGTTTGTCG
AATCTCTGGAAACGCCTCGTCGCATCCTGTTAATGGTGAAAGCAGGTGCAGGCACGGATGCTGCTATTGAT
TCCCTCAAACCATATCTCGATAAAGGAGACATCATCATTGATGGTGGTAACACCTTCTTCCAGGACACTAT
TCGTCGTAATCGTGAGCTTTCAGCAGAGGGCTTTAACTTCATCGGTACCGGTGTTTCTGGCGGTGAAGAGG
GGGCGCTGAAAGGTCCTTCTATTATGCCTGGTGGCCAGAAAGAAGCCTATGAATTGGTAGCACCGATCCTG
ACCAAAATCGCCGCCGTAGCTGAAGACGGTGAACCATGCGTTACCTATATTGGTGCCGATGGCGCAGGTCA
CTATGTGAAGATGGTTCACAACGGTATTGAATACGGCGATATGCAGCTGATTGCTGAAGCCTATTCTCTGC
TTAAAGGTGGCCTGAACCTCACCAACGAAGAACTGGCGCAGACCTTTACCGAGTGGAATAACGGTGAACTG
AGCAGTTACCTGATCGACATCACCAAAGATATCTTCACCAAAAAAGATGAAGACGGTAACTACCTGGTTGA
TGTGATCCTGGATGAAGCGGCTAACAAAGGTACCGGTAAATGGACCAGCCAGAGCGCGCTGGATCTCGGCG
AACCGCTGTCGCTGATTACCGAGTCTGTGTTTGCACGTTATATCTCTTCTCTGAAAGATCAGCGTGTTGCC
GCATCTAAAGTTCTCTCTGGTCCGCAAGCACAGCCAGCAGGCGACAAGGCTGAGTTCATCGAAAAAGTTCG
TCGTGCGCTGTATCTGGGCAAAATCGTTTCTTACGCCCAGGGCTTCTCTCAGCTGCGTGCTGCGTCGAAG
AGTACAACTGGGATCTGAACTACGGCGAAATCGCGAAGATTTTCCGTCGGCTGCATCATCCGTGCGCAG
TTCCTGCAGAAAATCACCGATGCTTATGCCGAAAATCCACAGATCGCTAACCTGTTGCTGGCTCCGTACTT
CAAGCAAATTGCCGATGACTACCAGCAGGCGCTGCGTGATGTCGTTGCTTATGCAGTACAGAACGGTATTC
CGGTTCCGACCTTCTCCGCAGCGGTTGCCTATTACGACAGCTACCGTGCTGCTGTTCTGCCTGCGAACCTG
ATCCAGGCACAGCGTGACTATTTTGGTGCGCATACTTATAAGCGTATCGATAAAGAAGGTGTGTTCCATAC
CGAATGGCTGGATTAA

SEQ ID NO: 13 (example O6A rfb locus nucleotide sequence - O6A-EPA production strain
stGVXN4112 and stLMTB10923)
ATGACGAATTTAAAAGCAGTTATTCCTGTAGCGGGTCTCGGGATGCATATGTTGCCTGCCACTAAGGCGAT
ACCCAAAGAGATGCTACCAATCGTCGACAAGCCAATGATTCAGTACATTGTTGACGAGATTGTGGCTGCAG
GGATCAAAGAAAATCCTCCTGGTAACTCACGCGTCCAAGAACGCGATGTCGAAAATCCACTTCGACACCTCTTAT
GAGTTAGAATCACTCCTTGAGCAGCGCGTGAAGCGTCAACTGCTGGCGGAAGTACAGTCCATTTGCCCGCC
GGGCGTGACAATTATGAACGTGCGTCAGGGCGAACCTTTAGGTTTGGGCCACTCCATTTTATGTGCACGAC
CTGCCATTGGTGACAATCCATTTGTCGTGGTGCTGCCAGACGTTGTGATCGACGACGCCAGCGCCGACCCG
CTGCGCTACAACCTTGCTGCCATGATTGCGCGCTTCAACGAAACGGGCCGCAGCCAGGTGCTGGCAAAACG
TATGCCGGGTGACCTCTCTGAATACTCTGTCATCCAGACCAAAGAGCCGCTGGACCGCGAAGGTAAAGTCA
GCCGCATTGTTGAATTCATCGAAAAACCGGATCAGCCGCAGACGCTGGACTCAGACATCATGGCCGTTGGT
CGCTATGTGCTTTCTGCCGATATTTGGCCGGAACTTGAACGCACTCAGCCTGGTGCATGGGGGCGTATTCA
GCTGACTGATGCCATTGCCGAACTGGCGAAAAACAGTCCGTTGATGCCATGCTGATGACCGGCGACAGCT
ACGACTGCGGTAAAAAAATGGGTTATATGCAAGCGTTCGTGAAGTATGGACTACGCAACCTCAAAGAAGGG
GCGAAGTTCCGTAAAGGGATTGAGAAGCTGTTAAGCGAATAATGAAAATCTGACCGGATGTAACGGTTGAT
AAGAAAATTATAACGGCAGTGAAGATTAGCGGCGAAAGTAATTTGTTGCGAATTTTCCTGCCGTTGTTTTA
TATAAACAATCAGAATAACAACGACTTAGCAATAGGATTTTCGTCAAAGTTTTCCAGGATTTTCCTTGTTT
CCAGAGCGGATTGGTAAGACAATTAGCATTTGAATTTTACGGGTTTAGCGCGAGTGGGTAACGCTCGTCAC
ATCGTAGACATGCATGCAGTGCTCTGGTAGCTGTAAAGCCAGGGGCGGTAGCGTGCTGAAATTATAAAGTC
ATTCTTATAGAACATCGCATTTCAATAATATAATTACACCTAAATGAATAGGATACAACGTGTGCACAATT
ATTTAAGGCTTAAAGATAAAATAAAAAACGTATTTTAGGGTTGTATATATTGCAGTTATTTAATTATATC
GCGCCATTGGTAATTATCCCTATCCTGATAAAATATATTGGGTTGGGGGAATATGGGGAATTGGTCTATAT
TACATCTCTATTTATCAAATAGTGGCTTTGATTATTGATTTTGGCTTTACTTACACAGGACCTGTGGTTGCTG
CGAGACATAGATGTGAGACCCAAATTTACAGCGCTATTACTCAATAGTTGTTCTTTTAAAATCATTGCTT
TTTATAATTGCATTAACATGTGTATTTTTATTGTGCAGATTAAATATAGTCCACTTGTCATTTTTTGGGTT
TTTGTCAATTTTTCTATGCACTATTGGTAATATATTATCGCCCAATTGGTTTTTGCAGGGGATTGGTCATT
TTAAAAAACTTTCATACTCACAAGTAATAGTGAGAATAACATTGTTTATCATACTTCTTGTTTATGTCTGT
AGTGGCGGAGATAATGTTTTTATCCTAAGTTTTTTGCAAAATGCAACATTACTCATATGCTGTATATACTT
ATGGCCAAATATTCATATTAGCCATGTTGTTCATCTTAAACCTAATGAATGCATTGTGGAATTTAAGAAGG
CAGGAAATGTTTTTATTGGCGTAATAGGTACGATTGGTTACAAGGTCTAATTCCTGTGTTAATTGGAAAC
CTTTGCGGTAATACGAGTCTTGGTGTTTTTTCAATCGTTCAAAAAATGACAACAGCATGTCAAAGTCTAAT
TAATCCAATATCACAGTATATGTTATCTCAAGTTTCAGAAATTAAACCTCAAGATAAACTGTTTTATTATA
GAATTAAAAAAAGTTTTTTTGTGCATTTAACAATTAGCATAATTGCATGTTTATGTTATATGGGTTAGGG
CAATATGTGGCGACTTTTATAGGTAAAGTTGACGTTTCATTTGTTATTATTTTATTTGCGTCAATAATTAC
CATTTTTTCATCTTTAAATAATGTCCTTGGTATACAGTTTCTTATACCGACAGATAATGAAATATAAAATACTAC
GAAGTATAAATGTTATGGCGGGAATTATTGTTGTTAGTTTGTCCTGGCTGTTAATATCACGCTTTGACATT
CTGGGGGGGTTTTATTAAACCTAATTGGTGAGTTTCTTGTATTCAGTATGCTAGCTTTATTGCCCATCG
AAAGTGGGGAGCGAGAGTATAATGAAAGTGAAGGCGGTTCCTGCTATTACATTCTATTTAAGTTTAATGCT
GACAATTTTAGTGTTACTGTTTGGTAATGAACCAAATAAATCACAATATATCCTTGTTATAGCAACGATAA
CAGTTTTTTATATCGCATATATCACTAATAAAATAACTTCTCCGGCCAGCCTTCTCGTTATATATCATCTTTT
GTGTTTTTAGGTTGTCGCCCTTTATTATCTTTGTTTGCAAACATGATTATAGGATTGCCGATTGGTTTAT
TGAAGGATATATGGATGACGATGTGATTTGGCTAACTATGCTATAACACTAATGTATTATGGTTATACAT
TGGGACTAATTCTATGCAAAAATACTGAAAAATTTATCCGCATGGTCCTTATCCTGAAAAACAATTGCTA
AAAATAAAGTTTCTTTTGACTTTATTTTTTCTGGGTTCGATAGGTATGGTTGAAAGGGATATTCTTTTT
TAACTTTATAGAATCTAATAGTTATGTTGATATTTATCAATCAAATATAACAACGCCAATAGGTTATGATT
TTCTATCTTATTTATTTTTATTGTTCTTTTTTCCTTATATGTGCGTTTCATATACAGTTCAGAACAAATAAA
```

| SEQUENCES |
|---|
| AAATTTCTTTTTATTGCGATATGCATTGCTGCATTTAGCACCTTGAAGGGTAGTCGTAGTGAAGCTATAAC |
| GTTTCTTTTAACGGTTACATGTATATATTTTAATGAAGTAAAGACAAGAAACTTACGTCTGCTGATTACAA |
| TGATTTTTGTTTTTAGCGTCATTTTTGTGATTAGTGAATTTATCTCAATGTGGCGCACTGGAGGGAGTTTT |
| TTTCAATTAATGCAGGGTAATAATCCTGTTATAAACTTTGTATACGGCATGGGAGTATCATATCTTTCCAT |
| TTATCAATCAGTAAAACTACAACTATTGTCAGGGGGATATAATGTTACCTATCTATTCAGCCAGTTAATAA |
| TAACTTGCTCGTCAATATTTAATGTCAAATTGAGCTTGCCGGAAATAAGCTATAGCCATTTGGCCTCATAC |
| ACAGCAAACCCAGAACTATATAATCTTGGGTTCGGACTTGGGGGGAGTTATTTAGCAGAATCGTTTTTAGC |
| ATTTGGTCTGATTGGATGTTTCATTATACCCTTTTTACTTTTACTTAATTTAAATGTATTGGAAAAATATA |
| CAAAAAACAAACCAATTATATATTTTGTTTATTATAGTGTGTTGCCACCTATATTATTCACACCAAGAGAG |
| ACTTTGTTCTATTTCTTCCCCTATCTTGTCAAAAGTATATTTGTTGCTTTTTAGTTACATTATACATCCA |
| GTATAAAAAGGATTGACCAAAATGTCAGAAAAAAATGTCAGCATAATAATCCCAAGTTATAACAGGGCTCA |
| TATTCTTAAGGAGGTCATACCAAGTTATTTTCAGGATGAGACTTTAGAGGTTATAGTTATCAATGATGGAT |
| CAACAGATAATACAAATAGTGTATTAGCTGAACTGAAGGAAAAATATTCTCAGTTAGTTATTTTAGAAAAT |
| GAAACGAATAAAAACAGATGTATTCTAAAAACCGAGGGATTGAAATAGCCAAAGGGAAATATATTTTTT |
| TGGTGATGATGACTCTTACCTCTTACCCGGTGTTATATCTCGGTTATTGGCTACAAAATATGAGACAGGCG |
| CTGATGTAATCGGCGCAAGAATACTTTATATGAATAATAACGAGAAAACAATTGAAGATTGCATAAATCGA |
| CATAAAAAAGAGGGGCGTTTTGTTAGTGATCTAAATAGATTGGATTTTAGTTATACATGTGATTTGGACCA |
| TCCGATTGAATGTTTTTATGCACAGCCTTTTGTTCTAGCTGAAAGGGAACTAATATCGAAATATCGATTTG |
| ATATATCTTATACGGGAAACTGCTATCGTGAGGAAACTGATTTCATGCTATCTCTATTTATTAAAAATAAA |
| AAATTTATATATGATTCAAAGGCTTTGTTAATAAATTTACCTCCAAGAAAAACGACGGGAGGGGCAAGAAC |
| AGCTAATCGATTAAAATATCATTACGAAAGTTGCATAAATAATTATAGATTTTTAAAAAAATATAATGATA |
| ATTTGAATCTTCTTTCAGGACAAAAGCATGCTATATTTTACCGACAGTGTCAATTCGTTCTGCTAAAAATG |
| AAGTCGTTTATCGGAAGTTTTTAAAATGATTATATATATCGCCGCGTATAATGGTTCAGGAGGGCAAGGT |
| GGGGTGGAAAGGGTTGTTGCCCAACAATGTAACATTCTTAAAAATTTGGGGGTTAAAGTCATTATACTTGA |
| TAAAACATACTTCAAAATTTCTAACAAAATTCGTAACAAAAAAATACAAGTAGCACTTTATCCAATATTAG |
| TTTCTCTTTATTTAACCTTACAAAAATTACGTGGCGTGACGTTTAAAGTTATTGCACATGGCTATTGTTCT |
| CCTTTTTATAGGAATGACATCTTAATAGCTCATGGCAATATGAAATGTTATTTTCAAACAGTCATGAATAA |
| AAAACCTAATCGGTTGTCTGGCAGTGGTCTTTTATCTTTCTATGAGCGTTGGGCTGGAGCATTTTCAAAAA |
| ATATCTGGGCTGTTTCAAATAAGGTTAAAAGTGAATGGAATGAGCTTTACAATATTAATTCACATAAAATC |
| AAAGTTGTTCGAAATTTTATAAATCTTGCACAATTTGATTACACTGATGTTAATGAAGCAGAATATGTGAC |
| ATTTGTCGGGCGATTGGAAAAAGGAAAAGGAATAGATGATCTGTATTACATATGTAAAAATCTGCCAGATA |
| CTTCCTTCCATTTAGTTTCAAGTATTCCCGCCCCACAAAATTTTGCTTCGCTAAATAATGTTCTGACCAGC |
| ATTGCTGTCCCCTATGCGAAAATGCCAGAAATATTTAAGAAATCCAGAGTACTTATTTTACCGTCCTATTA |
| TGAAGGATATGAGCTGGTTACTATTGAAGCGCTATGCTGTGGTTGCCCTGTGATAGGCTATAATGTTGGTG |
| CAATTAGAGAGTTGTATGCAGAAAGTTTTCCTGGCGTATTTATTGCCAATAATAAAGAAGATTTAGCACAA |
| GTAGCCTACAAATTAATTAGTCTTGATAATGAAAAATATTATCATTTGAGACAAACTATTTATAGCAAGCG |
| TGAGCTTTTTTCTGAAGAGAGATATGCGGAAATTTTAACGGCGGCATTTAATGAAAAAAAATAAGAAACTC |
| TGTCTCATTTCAATTAACTCATATAATGAACTTACCGGAGGAGGAGTATATTTACGTACGCTTGTTAGTTT |
| TCTACAAAAACAGAATGTTAATTTAACACTTATTGATAAAAAATCCTCAGGTAAACTATTCGAAGACAATA |
| CTTTTCAACATATATCATTTATTAAAGGTAAACGTCAGGATATAATATCCAGGCTTTTTTTTATACCATCA |
| TTTTATGTCCCTTATATTTTCTCAATAATTAAAATTTTACGGAAGCAAGATATTCTTGCTTTTCACAACTC |
| TCGGCTTGGATTGTTATGTCTGCTTTTTAGAATACTCATGCCCCACAAAAGATCATATTGTTTACGGATA |
| ACTTCGAATATGACTTAATAAGACAAAAAGATAAAAACATAACTACTTTTATTGAAAAATTAATTGTTTAT |
| CTCAATGAATTTATCGGGCTTAAGAATTCAGATTTAGTTAGCTATATTACCCGGCAAGATAAAAATGCAAT |
| GGATAAATTTTATGGGATTAAAAAAAGCAGAAATTTAATTCTCCCTGTGATATTTAGTAGAGAAAAACCAA |
| CTGATGTATTGTCAGCTCACTTTATTAATGAGTATAATCGATTGAATAATGATAATAGGAAAAAAGTAGTA |
| TTTACTGCATCTTTTGATTTTTTCCAAATATAGATGCTGCCAACTATGTTTTAAATGCAGCAAAGTCTAA |
| TAATGATTATTGCTATATTTTGGCAGGTAGGAAAAGTACTACTTTGAATCTTCCTGATTTGGATAATTTAT |
| TTTTTTTCGATAATCTATCTAATAGTGAAATGTCATATTTATTTCTGTGATGTTTTTTATTCTCCT |
| ATAGTTTTAGGAAGTGGAATGAAAACAAAAATTGCAGAAGCACTATCATATGGATTATATATTTATGCGAC |
| AGAGCATTCCTTAATCGGCTATGATGAAATTATACACAATAAGGAGTGTGTTAAAAAAATCTCACATTTGG |
| ATGAGGAATTTCCTAAAGATTTCAAGATGAAAAGTATCAATAAACAGCTAATAATGTCTTATCAGCAAAAA |
| TATTATTCACATTATCGGTTTAATGGCCATGAACTTGATATAATAAATTTTGACGATTAGTTAGTGGAGAT |
| ATAATATGAACATATTAGTAACTGGTGGTGCTGGATATATCGGATCTCATACGGCTATTGAATTACTGAAT |
| GCAGGTCATGAGATTATCGTTCTGGACAATTTCAGTAATGCTTCATACAAGTGTATCGAAAAATAAAAGA |
| AATTACTCGACGTGATTTTATAACAATTACTGGAGATGCTGGGTGTAGGAAGACACTCTCCGCTATTTTCG |
| AGAAACACGCCATAGATATAGTTATTCATTTTGCTGGCTTTAAATCTGTTCAGAGTCTAAAAGTGAAACCC |
| TTAAAGTATTACCAGAATAATGTTGGAGTGACCATTACTTTATTACAGGTAATGGAAGAGTACAGAATTAA |
| AAAATTTATCTTTAGTTCATCTGCGACAGTCTATGGTGAACCAGAGATAATTCCAATTCCAGAAACAGCTA |
| AAATTGGAGGAACTACGAATCCATATGGCACATCGAAGTATTTTGTTGAAAAAATTCTAGAGGATGTTAGT |
| TCCACGGGAAAACTGGATATAATTTGCTTGAGATATTTAATCCTGCGGTGCTCATTCTAGTGGTAAAAT |
| AGGTGAGGCTCCATCTGGTATCCCTAATAATCTTGTTCCTTATTTATTGGATGTTGCGAGTGGTAAACGTG |
| ATAAATTATTTATTTATGGCAATGATTACCCTACTAATGATGGAACAGGTGTAAGGGATTTTATTCATGTT |
| GTTGACTTAGCGAAAGGTCATTTGGCTGCAATGAATTATTTAAGTATCAATTCGGGATATAATATCTTTAA |
| TCTTGGTACAGGAAAAGGTTATTCGGTACTTGAATTAATCACTACATTTGAAAAATTAACAAACATTAAGG |
| TCAATAAATCTTTTATAGAGAAGGGCAGGGGATGTTGCGTCTTGTTGGGCTGACAGATAAAGCTAAT |
| TCTTTATTGGACTGGCAAGCCGAACAAACTCTAGAACAGATGTTATTGGACTCGTGGCGTTGGAAAAAAAA |
| TTATCCAGACGGATTCTGAATATAAAAGGTTTCAGTTTTATGAATCAATCAGAGCAGAGAAAAAAAATACT |
| GGTTCTTACACCTCGCTTTCCCTACCCTGTCATTGGAGGGGATAGATTAAGAGTCTATATGTTATGTAAAG |
| AACTTTCCAAAAAATATGATCTTATTCTTCTGAGCTTATGTGATCAACCACTAGAACTTGAAATAAATATA |
| AATGACTCGGTCTTCAAAGAAATTCATCGTGTCTATCTACCAAAATATAAATCATATTATAATGTATTAAA |
| AGCTTTGGTTACGCAAAAACCGTTGCAAATTGCTTATTATCAATCGGACACATTTAAGAATAAATACAATA |
| AATTAATTAAACAATGCGATGCAGTATTTTGTCATCTGATAAGAGTTGCTGATTATGTTAAGGATACAGAC |
| AAGTTCAAAATTCTTGATATGACAGATGCAATATCTTTGAATTACAGTCGCGTTAAAAAATTAGCAAGTAA |
| AAAAGTTTGCGTGCAATTATTTATTCTCTGGAACAAAAAAGATTAGAATCATATGAACGTTCTGTGGCGA |
| ATCTTTTGATTTGACCACTTTATTTCATCCGTAGACCGTGACTATCTCTACCCTAATCTGGGCAGTAAT |
| ATCCATATAGTCAATAATGGGGTTGATACATCAGCCTTGAGATATATAAAAAGAGAAATAAAAATCGATAA |

-continued

| SEQUENCES |
|---|
| GCCTGTGGAACTTATATTTATCGGAAATATGTATTCTTTACAAAATATGGATGCTGCAAAACATTTTGCTA |
| AGAATATTTTACCTTGCTTGTATGATGAGTTTAATATTATTTTTAAAGTGATTGGTAAGATCTCAGAAACT |
| AATAAAAATATATTAAATTCATTTAAAAATACAATTGCTTTAGGTACTGTTGATGATATCAATTCTTCCGC |
| TTCTACAGGGCATATAGGTATATGTCCTGTTCGTCTTGGAGCAGGCGTACAAAATAAAATTCTTGAATACA |
| TGGCTTTAGGTTTACCATGTATTACATCTAGCATTGGTTATGAAGGTATTAATGCAAATCAGGTAGCGAA |
| ATTTTTGTTGCAGATACAGTAGAGCAATATAAAAACGTACTAAGAGAAATAATTTACGATTATAATCGTTA |
| TACTGAAGTGGCTGAAAATGCCCGTAGTTTTGTAGAAAATAATTTTTCTTGGGAATCAAAAGTTGCCAATT |
| TAATGAATACATTAGATGAGAAATTATATGAACAATAATAAAATTATTACACCTATCATTATGGCTGGTGG |
| TTCAGGCAGTCGGTTGTGGCCACTATCAAGAATTCTCTATCCGAAACAATTTCTTAGCCTAATCGGTAGTC |
| ATACCATGCTTCAAACAACGGCTAATCGTCTGGATGGTTTGGATTGTACCAACCCTTATGTCATTTGTAAT |
| GAACAATACCGCTTTATAGTTGCTGAACAGCTTAGAAAAATCGATAGATTGACTTCAAAGAATATCATCCT |
| TGAGCCTGTTGGGCGTAACACTGCCCCTGCAATTGCATTAGCGGCGTTGCTGATGTCTAAGTCTGATAAAA |
| GTGCAGATGATCTTATGCTCGTACTGGCTGCAGATCACGTTATACACGATGAAGAAAATTTTGTAACGCT |
| GTTAGATCGGCAATTCCATACGCTGCTGATGGGAAATTGGTAACATTTGGTATAATTCCAGACAAAGCAGA |
| AACTGGTTATGGTTATATACATCGAGGACAATATATTAATCAGGAAGATTCGGATGCATTTATAGTGTCAT |
| CATTTGTTGAAAAGCCAAATCATGAGACAGCCACTAAATATCTTGCTTCCGGTGAGTATTATTGGAATAGC |
| GGTATGTTTTTGTTTAGTGCAAATCGTTATATAGAGGAACTTAAACAATTTCGGCCTGATATTTTATCCGC |
| TTGTGAAAAAGCAATTGCTTCAGCGAACTTTGACCTTGATTTTGTGCGTTTAGATGAAAGTTCTTTCTCTA |
| AGTGCCCTGAAGAATCAATTGATTACGCTGTAATGGAAAAAACAAAGACGCAATTGTTATTCCAATGGAT |
| GCTGGCTGGAGTGATGTCGGTTCATGGTCTTCTCTTTGGGAAATTAATGATAAAGACTCAGACGGCAACGT |
| AATAGTTGGGGATATTTTCTCTCATGAAACAAAGAATTCTTTCATATATATGCCGAATCGGGAATTGTTGCTA |
| CAGTTGGAGTGGAAAATTTAGTTGTTGTCCAAACAAAGGATGCTGTTCTTGTCTCAGAGAGAAATAAAGTT |
| CAGGATGTAAAGAAAATAGTAGAACAAATTAAAAATTCAGGTCGTAGCGAGCATTATGTTCATCGCGAAGT |
| ATATCGTCCTTGGGGTAAATATGATTCCATTGACACAGGGGAGCGTTATCAGGTCAAACGTATAACAGTAA |
| ATCCTGGTGAAGGACTTTCTTTACAAATGCACCATCATAGGGCAGAACATTGGATCATAGTTTCTGGAACT |
| GCAAGGGTGACTATAGGTTCTGAAACTAAGATTCTTAGCGAAAATGAATCTGTTTACATACCTCTTGGTGT |
| AATACACTGCTTGGAAAATCCAGGGAAAATTCCTCTTGATTTAATTGAAGTTCGTTCTGGATCTTATTTAG |
| AAGAAGACGATGTTATCCGTTTTCAGGACCGATATGGTCGTAGCTAAATTTTTGATAATGTAACGTTAGTA |
| GAAGAGCGCTAATATTTTTAGTTAATCTGTAATAAGTATTATTTGTTTAAGGTATATCATGTCGAGTTTAC |
| CCTGCTTTAAAGCCTATGATATTCGCGGGAAATTAGGCGAAGAACTGAATGAAGATATTGCCTGGCGCATT |
| GGTCGCGCTTATGGCGAATTTCTCAAACCGAAAACCATTGTGTTAGGCGGTGACGTCCGACTCACCAGCGA |
| AACCTTAAAACTGGCGCTGGCGAAGGGGTTACAGGATGCGGGCGTCGATGTGCTGGATATTGGCAGTGCCG |
| GCACCGAAGAGATCTATTTCGCCACGTTCCATCTCGGCGTGGATGGCGGCATCGAAGTTACCGCCAGCCAT |
| AACCCGATGGATTACAACGGCATGAAACTGGTGCGCGAAGGGGCTCGCCCGATCAGCGGTGATACCGGACT |
| GCGCGACATCCAGCGTCTGGCAGAAGCCAACGACTTTCCTCCCGTTGATGAAACCAAACGCGGTCGCTATC |
| AGCAAATCAATCTGCGTGACGCTTACGTTGATCACCTGTTCGGTTATATCAACGTCAAAAACCTCACGCCG |
| CTCAAGCTGGTGATTAACTCCGGGAACGGCGCGGCGGGTCCGGTGGTGACGCCATTGAAGCCCGCTTTAA |
| AGCCCTCGGCGCACCCGTGGAATTAATCAAAGTGCACAACACGCCGGACGGCAATTTCCCCAACGGTATTC |
| CTAACCCGCTACTGCCGGAATGTCGCGACGACACCCGCAATGCGGTCATCAAACACGGCGCGGATATGGGC |
| ATTGCCTTTGATGGCGATTTTGACCGCTGTTTCCTGTTTGACGAAAAGGGCAGTTTATTGAGGGCTACTA |
| CATTGTCGGCCTGCTGGCAGAAGCGTTCCTCGAAAAAAATCCCGGCGCGAAGATCATCCACGATCCACGTC |
| TCTCCTGGAACACCGTTGATGTGGTGACTGCCGCAGGCGGCACCCGTGGTAATGTCGAAAACCGGACACGCC |
| TTTATTAAAGAACGTATGCGCAAGGAAGACGCTATCTACGGTGGCGAAATGAGCGCCCACCATTACTTCCG |
| TGATTTCGCTTACTGCGACAGCGGCATGATCCCGTGGCTGCTGGTCGCCGAACTGGTGTGCCTGAAAGGAA |
| AAACGCTGGGCGAACTGGTGCGCGACCGGATGGCAGCGTTTCCGGCAAGCGGTGAGATCAACAGCAAACTG |
| GCACACCCCGTTGAGGCGATTAACCGCGTGGAACAGCACTTTAGCCGCGAGGCGCTGGCGGTGGATCGCAC |
| CGATGGCATCAGCATGACCTTTGCCGACTGGCGCTTTAACCTGCGCTCCTCTAACACCGAACCGGTGGTGC |
| GGTTGAATGTGGAATCGCGCGGCGATGTACCGCTGATGGAAGAAAAGACAAAACTTATCCTTGAGTTACTG |
| AACAAGTAATTCAGTAATTTCATATAAATGGGTTTTAAAAAACGGAAAAGATGAGATATCCGGTGTGGTAT |
| ATCCAAGGTAATGCTATTCAGTATCTCTATGAGTGAGTTAACATCTATACCACATTTAAGCCGCACACTTC |
| GGGATCCCCATATGAATATCCTCCTTAGTTCCTATTCCGAAGTTCCTATTCTTTCTAGAGAATAGGAACTT |
| CGGAATAGGAACTAAGGAGGATATTCATATGGATAAAGCCGTAAGCATATAAGCATGGATAAGCTATTTAT |
| ACTTTAATAAGTACTTTGTATACTTATTTGCGAACATTCCAGGCCGCAGGATCAGCGCGGTGATCACAC |
| CTGACAGGAGTATGTAATGTCCAAGCAACAGATCGGCGTAGTCGGTATGGCAGTGATGGGACGCAACCTTG |
| CGCTCAACATCGAAAGCCGTGGTTATACCGTCTCTATTTTCAACCGTTCCCGTGAGAAGACGGAAGAAGTG |
| ATTGCCGAAAATCCAGGCAAGAAACTGGTTCCTTACTATACGGTGAAAGAGTTTGTCGAATCTCTGGAAAC |
| GCCTCGTCGCATCCTGTTAATGGTGAAAGCAGGTGCAGGCACGGATGCTGCTATTGATTCCCTCAAACCAT |
| ATCTCGATAAAGGAGACATCATCATTGATGGTGGTAACACCTTCTTCCAGGACACTATTCGTCGTAATCGT |
| GAGCTTTCAGCAGAGGGCTTTAACTTCATCGGTACCGGTGTTTCTGGCGGTGAAGAGGGGGCGCTGAAAGG |
| TCCTTCTATTATGCCTGGTGGCCAGAAAGAAGCCTATGAATTGGTAGCACCGATCCTGACCAAAATCGCCG |
| CCGTAGCTGAAGACGGTGAACCATGCGTTACCTATATTGGTGCCGATGGCGCAGGTCACTATGTGAAGATG |
| GTTCACAACGGTATTGAATACGGCGATATGCAGCTGATTGCTGAAGCCTATTCTCTGCTTAAAGGTGGCCT |
| GAACCTCACCAACGAAGAACTGGCGCAGACCTTTACCGAGTGGAATAACGGTGAACTGAGCAGTTACCTGA |
| TCGACATCACCAAAGATATCTTCACCAAAAAAGATGAAGACGGTAACTACCTGGTTGATGTGATCCTGGAT |
| GAAGCGGCTAACAAAGGTACCGGTAAATGGACCAGCCAGAGCGCGCTGGATCTCGGCGAACCGCTGTCGCT |
| GATTACCGAGTCTGTGTTTGCACGTTATATCTCTTCTCTGAAAGATCAGCGTGTTGCCGCATCTAAAGTTC |
| TCTCTGGTCCGCAAGCACAGCCAGCAGGCGACAAGGCTGAGTTCATCGAAAAAGTTCGTCGTGCGCTGTAT |
| CTGGGCAAAATCGTTTCTTACGCCCAGGGCTTCTCTCAGCTGCGTGCTGCATCACCGTTCCTGCAGAAAA |
| TCTGAACTACGGCGAAATCGCGAAGATTTTCCGTGCTGGCTGCATCATCCGTGCGCAGTTCCTGCAGAAAA |
| TCACCGATGCTTATGCCGAAAATCCACAGATCGCTAACCTGTTGCTGGCTCCGTACTTCAAGCAAATTGCC |
| GATGACTACCAGCAGGCGCTGCGTGATGTCGTTGCTTATGCAGTACAGAACGGTATTCCGGTTCCGACCTT |
| CTCCGCAGCGGTTGCCTATTACGACAGCTACCGTGCTGCTGTTCTGCCTGCGAACCTGATCCAGGCACAGC |
| GTGACTATTTTGGTGCGCATACTTATAAGCGTATCGATAAGAAGGGTGTGTTCCATACCGAATGGCTGGAT |
| TAA |

SEQ ID NO: 14 (example O8 rfb locus nucleotide sequence - O8-EPA production strain stLMTB11734)
ATGACGAATTTAAAAGCAGTTATTCCTGTAGCGGGTCTCGGGATGCATATGTTGCCTGCCACTAAGGCGAT
ACCCAAAGAGATGCTACCAATCGTCGACAAGCCAATGATTCAGTACATTGTTGACGAGATTGTGGCTGCAG
GGATCAAAGAAATCCTCCTGGTAACTCACGCGTCCAAGAACGCGGTCGAAAACCACTTCGACACCTCTTAT
GAGTTAGAATCACTCCTTGAGCAGCGCGTGAAGCGTCAACTGCTGGCGGAAGTACAGTCCATCTGTCCGCC
GGGCGTGACCATTATGAACGTGCGTCAGGGCGAACCTTTAGGTTTAGGCCACTCCATTTTGTGTGCGCGAC
CTGCCATTGGTGACAACCCATTTGTCGTGGTACTGCCAGACGTTGTGATCGACGATGCCAGCGCCGACCCG
CTACGTTACAACCTTGCTGCCATGATTGCACGTTTCAACGAAACGGGCCGCAGCCAGGTGCTGGCAAAACG
TATGCCGGGTGACCTCTCTGAATACTCCGTCATCCAGACTAAAGAGCCGCTGGACCGTGAGGGTAAAGTCA
GCCGCATTGTTGAATTTATCGAAAAACCGGATCAGCCGCAGACGCTGGACTCAGACATCATGGCCGTAGGT
CGCTATGTGCTTTCTGCCGATATTTGGCCGGAACTGGAACGTACTCAGCCTGGTGCATGGGGACGTATTCA
GCTGACTGATGCTATTGCCGAGCTGGCGAAAAAACAATCCGTTGATGCAATGCTGATGACCGGCGACAGTT
ACGACTGCGGCAAAAAAATGGGCTATATGCAGGCGTTTGTGAAGTATGGCCTACGCAACCTGAAAGAAGGG
GCGAAGTTCCGTAAAGGTATTGAGAAGTCGTTAAGCGAATAATGAAAATCTGACCGGATGTAACGGTTGAT
AAGAAAATTATAACGGCAGTGAAAATTCGCAGCAAAAGTAATTTGTTGCGAATCTTCCTGCCGTTGTTTTA
TATAAACCATCAGAATAACAACGAGTTAGCAGTAGGGTTTTATTCAAAGTTTTCCAGGATTTTCCTTGTTT
CCAGAGCGGATTGGTAAGACAATTAGCGTTTGAATTTTTCGGGTTTAGCGCGAGTGGGTAACGCTCGTCAC
ATCATAGGCATGCATGCAGTGCTCTGGTAGCTGTAAAGCCAGGGGCGGTAGCGTGCATTAATACCTCTATT
AATCAAACTGAGAGCCGCTTATTTCACAGCATGCTCTGAAGTAATATGGAATAAATTAAGCTAGCGATCGC
TTAAGATCTAGGATTTCATTATGTTACTTCCTGTAATTATGGCTGGTGGTACCGGCAGTCGTCTCTGGCCG
ATGTCACGCGAGCTTTATCCGAAACAGTTCCTCCGCCTGTTCGGCAGAACTCCATGCTGCAGGAAACCAT
CACCCGACTCTCGGGCCTTGAAATCCATGAACCGATGGTCATCGTAACGAAGAGCACCGCTTCCTGGTGG
CTGAACAGCTACGCCAGCTCAATAAGCTGTCGAATAATATTATTCTTGAGCCGGTCGGGCGCAACACCGCC
CCGGCCATCGCCCTGGCAGCCCTTCAGGCCACCCGCGACGGCGACGACCCGCTGATGCTGGTTCTCGCCGC
TGACCATATCATCAATAACCAGTCGGCCTTCCACGACGCCATCCGGGTCGCCGAGCAGTATGCTGATGAAG
GTCATCTGGTCACCTTCGGTATCGTGCCGAATGCCCCGGAAACTGGCTACGGTTACATTCAGCGCGGCGTG
GCGCTCACCGATAGTGCCCATTCCGCGTACCAGGTGGCCCGCTTTGTGGAGAAGCCGGATCGCGAGCGCGC
CGAGGCTTACCTCGCCTCCGGGGAGTACTACTGGAACAGCGGCATGTTTATGTTCCGCGCCAAGAAATACC
TCATCGAGCTGGCCAAATACCGTCCGGATATCCTGGAAGCCTGCCAGGCTGCGGTGAATGCCGCCGATAAT
GGCAGCGATTTCATCAATATCCCGCATGATATTTTCTGCGAGTGCCCGGATGAGTCCGTGGACTATGCCGT
TATGGAGAAAACCGCCGATGCGGTGGTGGTCGGTCTCGATGCTGACTGGAGCGACGTCGGCTCCTGGTCCG
CACTATGGGAGGTCAGCCCGAAAGACGAGCAGGGCAATGTCCTCAGCGGTGACGCGTGGGTACACAACAGC
GAAAACTGCTACATCAACAGCGACGAGAAGCTAGTGGCGGCCATTGGCGTAGAGAATCTGGTGATTGTCAG
CACTAAGGACGCCGTGCTGGTGATGAATCGCGAGCGTTCCCAGGACGTGAAGAAGGCGGTCGAGTTCCTCA
AGCAGAACCAGCGCAGCGAGTACAAGCGCCACCGTGAGATTTACCGCCCTGGGGCCGTTGCGACGTAGTG
GTCCAGACCCCGCGCTTCAACGTCAACCGCATCACGGTGAAACAGGCGGTGCCTTCTCGATGCAGATGCA
CCACCATCGCGCCGAGCATTGGGTTATTCTCGCCGGCACCGGTCAGGTGACTGTCAACGGTAAGCAGTTCC
TGTTGTCCGAGAACCAGTCCACCTTTATTCCGATTGGCGCCGAGCACTGCCTGGAAAACCCTGGCTGTATT
CCGCTGGAAGTGCTGGAGATCCAGTCGGGGGCGTACCTTGGCGAGGACGACATTATTCGTATTAAAGACCA
GTATGGTCGTTGCTAATTATTTTCGGGACAAGACGCAGAATGACACAGTTAACTTGTTTTAAAGCTTATGA
CATCCGTGGTGAACTGGGTGAGGAACTGAACGAGGACATCGCCTACCGTATCGGTCGCGCCTACGGCGAAT
TTCTGAAACCCGGGAAGATAGTGGTGGGGGCGATGTGCGCCTCACAAGCGAGTCGCTGAAGCTGGCGCTG
GCCCGCGGGTTAATGGACGCCGGTACCGACGTGCTGGACATCGGCCTGGCGTGCTGAGCGGTACCGAAGAGATTTACTT
TGCCACCTTCCACCTTGGGGTAGATGGTGGCATCGAGGTGACCGCGAGCCACAATCCTATGAACTACAACG
GCATGAAGCTGGTGCGCGAGAATGCGAAGCCCATCAGCGGCGACACCGGCCTGCGGGATATCCAGCGCCTG
GCGGAGGAAAACCAGTTCCCGCCAGTGGACCCGGCGCGTCGCGGGACCCTGAGCAAGATATCGGTACTGAA
GGAGTATGTTGACCATCTGATGAGCTACGTGGACTTCTCGAACTTCACCCGTCCACTGAAGTTGGTGGTGA
ACTCCGGAAACGGGGCTGCGGGGCACGTGATTGATGAGGTGGAGAAACGCTTCGCGGCGGCTGGGGTGCCG
GTAACCTTTATCAAGGTGCATCACCAGCCGGATGGCCATTTCCCTAACGGTATCCCGAATCCGCTGCTGCC
GGAGTGCCGCCAGGATACCGCCGACGCGGTGCGCGAGCATCAGGCCGACATGGGGATTGCCTTTGACGGCG
ACTTCGATGCTGCTTCCTGTTCGATGACGAAGCTTCGTTTATCGAGGGGTATTACATTGTCGGCCTGCTG
GCTGAGGCGTTCCTGCAGAAGCAGCCGGGAGCGAAAATCATTCACGACCCGCGCTTGACGTGGAACACGGT
AGACATCGTGACCCGCAACGGCGGCCAGCCGGTGATGTCGAAGACGGGGCATGCGTTCATCAAGGAGCGGA
TGCGTCAGGAAGACGCTATCTACGGCGGGGAGATGAGTGCGCACCATTACTTCCGCGATTTCGCCTACTGC
GATAGCGGGATGATCCCGTGGCTGCTGGTGGCGGAGCTGCTGTGTCTGAACAGCTCGCTGAAATCGCT
GGTGGCGGACCGCCAGAAGGCGTTCCCTGCGTCGGGAGAGATCAACCGCAAGCTAAGTAATGCTGCTGAGG
CGATCGCCCGCATCCGGGCGCAGTATGAGCCGGCGGCTGCACACATCGACACAACGACGGGATCAGTATT
GAATACCCTGAATGGCGCTTTAACCTGCGCACGTCTAACACCGAGCCGGTGGTGCGTCTGAACGTTGAGTC
CAGAGCTGATGTGGCGCTTATGAATGAAAAAACGACCGAGCTGTTACACCTGTTAAGCGGGAATAAGGTG
AGAGATTTACTAACGACGATTTATCGTTATCGGGGATTTATCTGGAGACAGTGTTAAACGTGATTTTCAGGC
ACGCTATCAAACTAGTATGCTGGGCGCACTATGGCTCGTTTTACAACCGCTCTCTATGATTCTGGTCTATA
CCCTGGTTTTTCCGAGGTGATGAAGGCAAGAATGCCCGATAATACCGGGTCGTTTGCCTATAGTATTTAT
CTCTGTTCCGGGGTACTGACCTGGGGATTATTACTGAGATGCTGGATAAAGGTCAGAGCGTATTTATTAA
CAATGCTAATCTGATCAAGAAACTCAGTTTTCCGAAAATCTGTCTGCCGATCATCGTGACGTTATCGGCGG
TGCTAAATTTCGCGATTATTTTCAGTCTGTTTCTAATTTTTATCATTGTCACCGGTAACTTCCCCGGCTGG
CTCTTTCTCGGTGATACCGGTCCTGCTTTTGCAGATCCTGTTTGCCGGTGGGCTGGGGATGATCCTTGG
TGTCATGAACGTCTTTTTCAGGGATGTGGGGCAACTGGTTGGCGTTGCGCTGCAATTCTGGTTTTGGTTCA
CACCCATTGTTTATGTACTGAATTCATTACCTGCATGGGCAAAAAATCTGATGATGTATAACCCGATGACT
CGGATCATGCAATCTTATCAGTCCATCTTCGCCTATCATCTGGCCCCCAACTGGTATTCGTCATGGCCAGT
ATTGGCTCTCGCCATTATTTTCTGCGTCATCGGTTTCAGGATGTTCCGCAAGCATGCGGCGGATATGGTG
ATGAATTATAATGAGTTATATCAGAGTAAATAATGTCGGTAAGGCGTATCGCCAGTATCACTCAAAGACCG
GGAGACTGATCGAATGGTTATCCCCTCTGAATACCAAACGCCATAATTTGAAATGGATCCTCCGCGATATT
AATTTCGAAGTCGCTCCGGGCGAGGCTGTCGGTATTATCGGTATCAACGGTGCAGGCAAGAGTACCCCTGCT
TAAACTCATAACCGGGACGTCCAGGCCGACGACTGGAGAAATTGAAATCTCCGGACGTGTCGCTGCATTAC
TCGAATTGGGGATGGGGTTTCATTCTGATTTCACTGGTCGGCAGAATGTTTATATGTCTGGGCAACTGTTG

| SEQUENCES |
|---|
| GGGTTATCGTCAGAGAAAATAACTGAACTGATGCCGCAAATTGAAGAGTTTGCTGAGATTGGGGACTATAT |
| CGATCAACCTGTGCGCGTCTACTCCAGTGGGATGCAAGTTCGATTAGCTTTTAGTGTAGCGACGGCTATCC |
| GTCCTGATGTGCTAATTATCGATGAGGCATTATCTGTTGGGGATGCATATTTCCAGCATAAAAGCTTTGAG |
| CGTATTCGAAAATTTCGTCAGGAAGGGACCACGCTGTTGCTGGTATCCCATGATAAACAAGCGATCCAAAG |
| CATTTGCGACCGGGCCATTTTATTGAATAAAGGCCAAATTGAAATGGAAGGTGAACCTGAAGCAGTGATGG |
| ATTATTACAATGCTCTTCTGGCCGATAAACAAAATCAGTCCATTAAACAAGTTGAGCATAATGGTAAAACG |
| CAAACTGTTTCAGGCACTGGTGAGGTGACTATCTCTGAGGTTCATCTTCTCGATGAACAGGGCAATGTGAC |
| TGAATTTGTTTCGGTAGGGCATCGTGTCAGCTTGCAGGTCAACGTTGAGGTCAAGGACGATATTCCTGAGC |
| TTGTTGTCGGATATATGATTAAGGATCGACTTGGGCAGCCGATTTTCGGGACCAATACGTACCATCTCAAT |
| CAGACACTCACCTCCCTGAAAAAAGGAGAAAAGCGTTCGTTCTTATTTTCTTTCGATGCGAGATTGGGGGT |
| TGGCTCCTATTCTGTCGCTGTCGCGTTGCATACTTCCAGTACGCACCTCGGCAAAAACTATGAATGGCGCG |
| ATCTGGCCGTGGTATTCAACGTCGTTAACACGGAACAACAAGAGTTTGTCGGCGTGTCCTGGTTGCCGCCT |
| GAACTGGAGATTCTTAATGGGTTCGTCGTTTTATCGTTCATTTGAAGAACGACACAGAGGTTCGGTTGAA |
| GAAATCAAGCGCCGCTTGAGTTTTTATTTACCTTTTCTTGCAGGTCTGAAGGACATTTATCCTGATGGCGT |
| GATTGCGGATATTGGTTGCGGACGTGGCGAATGGTTGGAGATCCTGACTGAAAATGGCATTGCGAACATCG |
| GCGTCGATCTCGATGATGGCATGCTGGCGCGCGCCAGGGAGGCCGGACTGAATGTGCAGAAAATGGATTGT |
| CTGCAGTTTTTGCAAAGTCAGGCGGATCAGAGCCTGATAGCGTTGACCGGTTTTCATATTGCTGAGCATTT |
| GCCGTTTGAGGTCCTGCAGCAACTCGCCATGCATACCCTACGGGTGCTGAAACCAGGTGGTTTGCTGATCC |
| TCGAAACGCCGAACCCGGAGAATGTAAGCGTCGGCACCTGTTCATTTTATATGGATCCAACGCATAATCAT |
| CCTCTGCCACCGCCACTGCTTGAGTTTTTACCTATTCATTATGGTTTTACCCGAGCAATTACCGTTCGTCT |
| GCAGGAAAAAGAGGTTCTTCAATCTCCGGATGCAGCCGTTAATTTGGTCGATGTACTCAAAGGGGTGAGCC |
| CCGACTACAGCATCATTGCTCAGAAAGCAGCGCCAACAGATATTCTTGAACGCTTTGACACCCTGTTTACC |
| CAGCAGTACGGTCTGACGCTGGATGCTCTGAGCAACCGTTACGATGCGATTTTGCGCCAACAGTTTTCGTC |
| CGTTGTCTCACGGCTGGAGACGTTGAACCAAACCTATATGCAACAGATAAGCCAAATGTCAGAGACTATTC |
| AGACGTTGCAAGGTGAGGTTGACGATCTGAGTCATGTCATCGATCAGAACCATCAGCTTCATCAGCAAATG |
| GCGGATTTACATAACAGTCGTTCATGGCGTATTACTCAACCACTACGCTGGTTGTCTTTGCAACGTCAATT |
| ATTACGTCAGGAAGGGGCTAAAGTGCGAGCCCGTAGGGCTGGGAAAAAAATATTGCGCAAAGGGATGGCGC |
| TCTCGCTGGTCTTTTTCCATCGTTACCCTAAGTCTAAGGTTTATCTGTTTAAGGTTCTGAGAAAAACTGGC |
| TGCTATACATTGCTACAACGTTTGTTCCAACGCGTAATGCTGGTGCAATCTGACACGATGATGATGCAGTC |
| CAGAAGATATGATGTGGGTACTGAAGAAATGACAAGTCGCGCGATGAGTATTTATAACGAATTAAAAAATA |
| AAAATACGGAGAAATAACGATGCGTATTGTCATAGATTTACAAGGCGCACAGACGGAAAGCCGCTTTCGTG |
| GCATCGGTCGTTATAGTATCGCAATCGCCAGAGGCATAATCAGAAATAACGCCGGCATGAGATTTTCATC |
| GCGCTATCCGCCATGCTGGATGAGTCGATTGCAAATATTAAGGCGCAATTTGCCGATCTCCTGCCGGCAGA |
| AAATATAGTCGTATGGCATGCCGTAGGCCCTGTTCGTGCGATGGACCAAGGTAATGAATGGCGTCGGGAGA |
| GCGCAGAACTGATTCGGGAAGCGTTTCTTGAATCATTGTGTCCAGATGTCGTTTTCATTACGAGTTTGTTT |
| GAAGGTCATGTCGACGATGCGGCTACATCGGTACACAAATTTAGTCGTCAGTATAAAGTAGCCGTACTGCA |
| CCACGATCTTATCCCCCTCGTGCAGGCGGAAACCTATCTGCAGGACGATGTATACAAACCCTACTATTTAC |
| AGAAAGTTGAGTGGTTAAAAAACGCTGACCTTTTGTTGACTAACTCTGCTTATACCGCACAGGAAGCGATC |
| GAGCATCTGCATTTACAGGGCGATCATGTGCAGAATATTGCAGCCGCAGTCGATTCTCAGTTTTGTATGGC |
| GGAGGTGGCAGCGAGCGAAAAAGAGACCGTCCTTGGCCATTACGGTTATTCAGCGCGAGTTCATGTTGTATG |
| CGCCCGGAGGATTTGACTCAAGGAAAAACTTTAAACGGTTGATTGAGGCCTATGCCGGGCTCAGTGATGCC |
| TTACGTCGCAGTCATCAACTGGTCATCGTCAGTAAGCTTTCCATCGGTGATCGTCAGTATCTGGAATCCCT |
| TGCGTCAGGTAATGGTTTACAGCAGGGCGAACTGGTACTCACTGGTTATGTGCCGGAAGATGAGCTGATCC |
| AGCTCTATCGCCTATGTAAGCTGTTCATCTTTGCTTCACTACATGAAGGTTTTGGGTTGCCGGTTCTGGAA |
| GCAATGTCGTGCGGTGCGCCGGTGATTGGCTCAAATGTCACCAGTATTCCTGAAGTCATCGGTAATCCTGA |
| GGCATTATTCGACCCGTATTCTGTCTCTTCCATGAGGGATAAGATCGCGCAATGTTTGACTGATGATACCT |
| TCCTCGCGCGTCTGAAAGAAATGGCGCAGCAGCAAGCGCGTAATTTCTCTTGGGATAAAGCTGCGGTGACT |
| GCTCTGGAAGCTTTCGAAAAGATCGCGGTAGAAGACACCGGTACTGCGCAGGTTTTGCCTGAAGCTTTGAT |
| TCAGAAGATCCTTGCTATCTCACAAGGGCAGCCAGATGACCGCGATCTGCGCTTGTGCGCAACAGCCATTG |
| ATTACAATCTGAAAACGGCAGAACTTTATCAAATCGACGATAAATCGCTGAACTGGCGTGTGGAAGGCCCA |
| TTCGATAGCTCATATAGTCTGGCGTTGGTCAACCGCGAATTTGCCCGGGCACTCTCAGCCGATGGTGTAGA |
| GGTTTTATTGCATTCCACTGAAGGACCAGGTGATTTTGCCCCAGATGCCTCGTTTATGGCACAGTCGGAAA |
| ATAGTGATCTTCTGGCATTTTATAATCAATGTCAGACCCGCAAGAGTAACGAAAAGATAGATATATTATTAGC |
| AGAAATATCTATCCACCGCGGGTTACCAAAATGGATGCCAAAGTAAAATTCCTTCATTGTTATGCTTGGGA |
| AGAAACGGGCTTTCCGCAACCGTGGATCAATGAATTTAATCGGGAACTTGACGGAGTGCTGTGTACTTCGG |
| AACATGTTCGTAAAATACTGATTGATAACGGACTGAATGTGCCCGCATTTGTTGTTGGCAATGGCTGTGAC |
| CATTGGCTCAATATCCCAGCCGAGACGACAAAAGATGTGGATCACGAACATTCCGTTTCCTGCACGTCCTC |
| TTCTTGTTTCCCACGCAAAGGGATACAGGCAATGCTTCAGGCTTGGGGGAAGGCGTTCACTCGTCGTGACA |
| ATGTTATCTTAATCATTAAGACTTTTAACAATCCGCACAATGAAATTGACGCATGGCTGGCTCAGGCCCAG |
| GCTCAATTCATAGACTATCCCAAAGTTGAAGTGATCAAAGAGGATATGTCAGCCACCGAGCTTAAAGGGCT |
| TTATGAAAGCTGTGATGTTTTGGTTGCTCCAGGTTGCGCTGAAGGCTTTGGTTTACCTATTGCTGAAGCAA |
| TGCTGAGTGGGCTACCGGCTATCGTCACCCAATTGGAGCGGGCAACTTGATTTTGTTAATTCACAAAATTCA |
| TGGCTGGTTGACTATCAGTTCACTCGGGTAAAAACGCACTTTGGTCTGTTTTCCTCAGCCTGGGCCAGTGT |
| GGATATTGACAACTTAACAGATGCATTAAAAGCGGCAGCCTCAACCGATAAATCAGTGCTGCGTGACATGG |
| CCAATGCTGGTCGCGAGCTTCTTCTGCAGCAGTTTACCTGGAAAGCGGTGGCTGATCGTTCTTGCCAGGCG |
| GTCAAGACTCTGCGTGCGCATATTGATATTGCACAGCATCGGGCGCCAATTGCTGGGTGACGACCTGGAA |
| CACGAAATGTGGGATCGCAACCTATTCCCAGCATCTGGTGGAAAGCGCACCTCATGGCGCGGATGTTGTTT |
| TTGCTCCCCAGGTCAGCGCTGGCGATCTTGTGTGTGCAGACGAAGAGTTTGTACTTCGCAACTGGATTGTA |
| GGTAAAGAGAGCAACTATCTGGAAAACCTCCAGCCACACATTGATGCTCTGAGACTCGATGTCATTGTGAT |
| CCAATTCAACTATGGATTCTTTAATCATCGAGAACTGTCGGCGTTTATTCGTCGCCAGCATGACGCCGGTC |
| GTTCAGTTGTTATGACGATGCATCAACTGTGGATCGCTGGAAAAAAGAGCCGAGCTGGAATTTCGTCTT |
| GCTGAAATGAAAGAGGCGCTGGCACTTTGCGACCGGTTGTTGGTGCATTCGATTGCCGATATGAACCGCCT |
| TAAAGATTTAGGCTTAACTGCGAATGTTGCTTTATTCCCGCACGGTGTTATCAACTACTCCGCAGCGAGCG |
| TCACACGTCAACAGCAGTCTTTACCGCTAATTGCGAGCTATGCCTTCTGCTTACCGCATAAGGGCCTGATG |
| GAACTAGTAGAATCCGTCCATAGACTCAAGCAAGCCGGTAAACCGGTTCGTTTACGACTGGTGAACGCAGA |
| GTATCCTGTTGGGGAGTCACGCGATCTGGTGGCAGAGCTTAAAGCTGCTGCTCAGCCGGTTAGGTGTTACCG |
| ATCTGATTGAGATGCATAATGATTTCCTACCTGATGCGGAGAGTCTGCGGTTGCTTTCAGAAGCCGATCTT |

| SEQUENCES |
|---|
| CTGATTTTTGCTTATCAGAATACTGGGGAGTCTGCTAGCGGGCGGTACGTTATGGTATGGCGACTCAAAA
ACCTGTTGCGGTAACGCCCCTGGCGATATTTGATGATTTGGACGATGCCGTCTTTAAATTTGATGGATGCA
GCGTCGATGATATCAGTCAGGGGATTGACCGGATCCTGAATTCCATCCGTGAACAGAACTCTTGGGCAACC
AGGACTCAACAACGTGCCGATGCATGGCGGGAACAACATGATTATCAAGCTGTTTCACGCCGTCTGGTTAA
TATGTGTCAAGGCTTAGCTAAAGCTAAATATTTTAAATAAAAATATCTCTTGTATTTTTTGCCTTTGAA
TACAAGAGGGGTTAGATAATGTGTCATTTATTATGAAAATTATTTTTGCTACTGAGCCAATTAAATACCCA
TTAACGGGCATCGGTCGGTATTCCCTGGAGCTGGTTAAGCGGCTGGCGGTCGCCCGCGAAATTGAAGAATT
AAAGCTATTTCACGGTGCGTCGTTTATAGAACAGATCCCTTTGGTGGAGAATAAAAGCGATACCAAAGCCA
GCAATCATGGTCGTCTGTCGGCGTTTCTACGCCGACAGACGCTGTTGATTGAGGCTTATCGCTTGCTGCAT
CCGCGGCGCCAGGCGTGGGCATTGCGCGACTATAAGGATTATATCTACCATGGCCCCAATTTTTATCTGCC
GCATAAACTGGAACGCGCCGTGACCACGTTTCATGACATATCCATTTTTACCTGCCCGGAATATCATCCAA
AAGATCGGGTTCGCTATATGGAGAAGTCCCTGCATGAGAGTCTGGATTCGGCAAAGCTGATCCTGACCGTT
TCTGATTTCTCGCGCAGTGAAATTATCCGCTTGTTCAACTATCCGGCGGAGCGGATCGTAACCACCAAGCT
AGCCTGCAGCAGTGACTATATCCCACGCAGCCCGGCAGAGTGTCTGCCGGTACTGCAGAAATATCAGCTGG
CGTGGCAGGCCTACGCGCTATATATCGGCACTATGGAGCCACGTAAAAATATCCGAGGCCTGCTGCATGCC
TATCAGCTGCTACCGATGGAGATCCGCATGCGCTATCCGCTAATCCTTAGCGGCTATCGCGGCTGGGAAGA
CGATGTGCTGTGGCAGTAGTCGAGCGCGGTACTCGGGAAGGCTGGATCCGTTACCTCGGATATGTTCCGG
ATGAAGACCTGCCGTATCTGTACGCAGCGGCCAGAGTCTTTGTTTATCCCTCCTTCTACGAGGGATTCGGT
TTACCTATTCTTGAAGCGATGTCTTGCGGTGTGCCGGTAGTATGCTCCAATGTCACCTCTTTGCCTGAGGT
TGTTGGCGATGCCGGCCTCGTTGCCGATCCTAATGATATAGACCGATTAGCGCGCAAATTTTGCAGAGCC
TGCAAGATGATAGCTGGCGGGAAATCGCCACCGCGCGCGGTCTTGCTCAGGCGAAACAGTTTTCGTGGGAG
AACTGTGCGACACAGACCATTAACGCCTATAAATTACTCTAAGGGTGTCAGTTGAGAGTTCTACACGTCTA
TAAGACTTACTATCCCGATACCTACGCGGTATTGAGCAGGTCATTTATCAGCTAAGTCAGGGCTGCGCCC
GCCGGGAATCGCAGCCGATGTTTTCACTTTTAGCCCGGACAAAGATACAGGTCCTGTCGCTTACGAAGAT
CATCGGGTCATTTATAATAAACAGCTTTTTGAAATTGCCTCCACGCCGTTTTCGCTGAAAGCGTTAAAGCG
TTTTAAGCTGATTAAAGATGACTACGATATCATCAACTACCATTTTCCGTTTCCCTTTATGGATATGCTGC
ATCTTTCGGCGCGGCCTGACGCCAGGACTGTGGTGACCTATCACTCTGATATAGTGAAACAAAACGGTTA
ATGAAGCTGTACCAGCCGCTGCAGGAGCGATTTCTCAGCGGCGTAGATTGCATCGTTGCCTCGTCGCCCAA
TTACGTGGCTTCCAGCCAGACCCTGAAAAAATATCTGGATAAAACGGTGGTGATCCCGTTTGGTCTGGAGC
AGCAGGACGTGCAGCACGATCCGCAGAGGGTCGCGCACTGGCGGGAAACTGTCGGCGATAAGTTCTTTCTC
TTCGTCGGCACTTTCCGCTACTACAAAGGGCTGCATATTCTGATGGATGCCGCTGAGCGTAGCCGACTGCC
AGTGGTGGTTGTAGGGGCGGGCCGCTGGAATCGGAAGTGCGGCGTGAAGCGCAGCAGCGCGGGCTGAGCA
ATGTGATGTTTACCGGCATGCTCAACGACGAAGATAAGTACATTCTCTTCCAGCTCTGCCGGGGCGTGGTA
TTCCCCTCGCATCTGCGCTCTGAGGCGTTTGGCATTACGTTATTGGAAGGCGCACGCTTTGCAAGGCCGCT
GATCTCTTGCGAGATCGGTACAGGTACCTCTTTCATTAACCAGGACAAAGTGAGTGGTTGCGTGATTCCGC
CGAATGATAGCCAGGCGCTGGTGGAGGCGATGAATGAGCTCTGGAATAACGAGGAAACCTCCAACCGCTAT
GGCGAAAACTCGCGTCGTCGTTTTGAAGAGATGTTTACTGCCGACCATATGATTGACGCCTATGTCAATCT
CTACACTACATTGCTGGAAAGCAAATCCTGAGCGGCCGCGAGCTCGTCGACTCGAGGATCCGTGTAGGCTG
GAGCTGCTTCGAAGTTCCTATACTTTCTAGAGAATAGGAACTTCGGAATAGGAACTAAGGAGGATATTCAT
ATGGATAAAGCCGTAAGCATATAAGCATGATAAGCTATTTATACTTTAATAAGTACTTTGTATACTTATT
TGCGAACATTCCAGGCCGCGAGCATTCAGCGCGGTGATCACACCTGACAGGAGTATGTAATGTCCAAGCAA
CAGATCGGCGTAGTCGGTATGGCAGTGATGGGACGCAACCTTGCGCTCAACATCGAAAGCCGTGGTTATAC
CGTCTCTATTTTCAACCGTTCCCGTGAGAAGACGGAAGAAGTGATTGCCGAAAATCCAGGCAAGAAACTGG
TTCCTTACTATACGGTGAAAGAGTTTGTCGAATCTCTGGAAACGCCTCGTCGCATCCTGTTAATGGTGAAA
GCAGGTCGCAGGCACGGATGCTGCTATTGATTCCCTCAAACCATATCTCGATAAAGGAGACATCATCATTGA
TGGTGGTAACACCTTCTTCCAGGACACTATTCGTCGTAATCGTGAGCTTTCAGCAGAGGGCTTTAACTTCA
TCGGTACCGGTGTTTCTGGCGGTGAAGAGGGGGCGCTGAAAGGTCCTTCTATTATGCCTGGTGGCCAGAAA
GAAGCCTATGAATTGGTAGCACCGATCCTGACCAAAATCGCCGCCGTAGCTGAAGACGGTGAACCATGCGT
TACCTATATTGGTGCCGATGGCGCAGGTCACTATGTGAAGATGGTTCACAACGGTATTGAATACGGCGATA
TGCAGCTGATTGCTGAAGCCTATTCTCTGCTTAAAGGTGGCCTGAACCTCACCAACGAAGAACTGGCGCAG
ACCTTTACCGAGTGGAATAACGGTGAACTGAGCAGTTACCTGATCGACATCACCAAAGATATCTTCACCAA
AAAAGATGAAGACGGTAACTACCTGGTTGATGTGATCCTGGATGAAGCGGCTAACAAAGGTACCGGTAAAT
GGACCAGCCAGAGCGCGCTGGATCTCGGCGAACCGCTGTCGCTTATTACCGAGTCTGTGTTTGCACGTTAT
ATCTCTTCTCTGAAAGATCAGCGTGTTGCCGCATCTAAAGTTCTCTCTGGTCCGCAAGCACAGCCAGCAGG
CGACAAGGCTGAGTTCATCGAAAAAGTTCGTCGTGCGCTGTATCTGGGCAAAATCGTTTCTTACGCCCAGG
GCTTCTCTCAGCTGCGTGCTGCGTCTGAAGAGTACAACTGGGATCTGAACTACGGCGAAATCGCGAAGATT
TTCCGTGCTGGCTGCATCATCCGTGCGCAGTTCCTGCAGAAATATCGCGATGACTACCAGCAGGCGTGCGATG
TCGTTGCTTATGCAGTACGAACGGTATTCCGGTTCCGACCTTCTCCGCAGCGGTTGCCTATTACGACAGC
TACCGTGCTGCTGTTCTGCCTGCGAACCTGATCCAGGCACAGCGTGACTATTTTGGTGCGCATACTTATAA
GCGTATTGATAAAGAAGGTGTGTTCCATACCGAATGGCTGGATTAA |

SEQ ID NO: 15 (example O15 rfb locus nucleotide sequence - O15-EPA production strain stLMTB11738)
ATGACGAATTTAAAAGCAGTTATTCCTGTAGCGGGTCTCGGGATGCATATGTTGCCTGCCACTAAGGCGAT
ACCCAAAGAGATGCTACCAATCGTCGACAAGCCAATGATTCATACATTGTTGACGAGATTGTGGCTGCAG
GGATCAAAGAAATCCTCCTGGTAACTCACGCGTCCAAGAACGCGGTCGAAACCACTTCGACACCTCTTAT
GAGTTAGAATCACTCCTTGAGCAGCGCGTGAAGCGTCAACTGCTGGCGGAAGTACAGTCCATCTGTCCGCC
GGGCGTGACCATTATGAACGTGCGTCAGGGCGAACCTTTAGGTTTAGGCCACTCCATTTTGTGTGCGCGAC
CTGCCATTGGTGACAACCCATTTGTCGTGGTACTGCCAGACGTTGTGATCGACGATGCCAGCGCCGACCCG
CTACGTTACAACCTTGCTGCCATGATTGCACGTTTCAACGAAACGGGCCGCACCAGGTGCTGGCAAAACG
TATGCCGGGTGACCTCTCTGAATACTCCGTCATCCGACATAAAGAGCCGCTGGACCGTGAGGGTAAAGTCA
GCCGCATTGTTGAATTTATCGAAAAACCGGATCAGCCGCAGACGCTGGACTCAGACATCATGGCCGTAGGT
CGCTATGTGCTTTCTGCCGATATTTGGCCGGAACTGGAACGTACTCAGCCTGGTGCATGGGGACGTATTCA
GCTGACTGATGCTATTGCCGAGCTGGCGAAAAAACAATCCGTTGATGCAATGCTGATGACCGGCGACAGTT
ACGACTGCGGCAAAAAATGGGCTATATGCAGGCGTTTGTGAAGTATGGCCTACGCAACCTGAAAGAAGGG
GCGAAGTTCCGTAAAGGTATTGAGAAGCTGTTAAGCGAATAATGAAAATCTGACCGGATGTAACGGTTGAT

| SEQUENCES |
|---|
| AAGAAAATTATAACGGCAGTGAAAATTCGCAGCAAAAGTAATTTGTTGCGAATCTTCCTGCCGTTGTTTTA |
| TATAAACCATCAGAATAACAACGAGTTAGCAGTAGGGTTTTATTCAAAGTTTTCCAGGATTTTCCTTGTTT |
| CCAGAGCGGATTGGTAAGACAATTAGCGTTTGAATTTTTCGGGTTTAGCGCGAGTGGGTAACGCTCGTCAC |
| ATCATAGGCATGCATGCAGTGCTCTGGTAGCTGTAAAGCCAGGGGCGGTAGCGTGCATTAATACCTCTATT |
| AATCAAACTGAGAGCCGCTTATTTCACAGCATGCTCTGAAGTAATATGGAATAAATTAAGCTAGCATGAGC |
| AAAACTAAACTAAATGTTCTTTACCTTGCAATAAGTCAGGGTGCCAATTACCTACTGCCATTATTAATTTT |
| TCCTTATCTTGTTAGAGTCATTGGTGTATCGAATTTTGGTGATCTGAGTTTTTCATTGATAACTATACAAG |
| TGTTGTTAATGGTTGTTGAATATGGTTTTGGATATAGTGGGACAAGAGAAATAGCACTAAATAACGATAAA |
| AAATACCATTCTGAATTTTTTGCGGTGTGGTGCTTGCTCGTTTTATATTAATGCTAATTGCAGCTATAAT |
| ACTCATAATACTCTGTTTTTTTATGTTTTAACGACGTTAAGTCTTTGTTATGTGTTGGTTTTCTGTCCG |
| TAATTGCAGGTGTTTTCAATCCAAATTGGTTTTTGCAAGGTAAGGAAATGATGAGTGTGATGGCTGTGCTG |
| TCACTATTTTCACGAGGCATAGCAGTCGTTGCAGTTTATCTAATTATAAAACCCGCAACGCCGATGTACAT |
| CAGTGCCTTATTATTGAGCATGCCATATATTTTGTATTCATTCTGTGGCGTTGCCTACTTACTTATTATCA |
| AGGAGATTTTTTATGTAGGCCACCGATAAAGAAAATTCAAGTAATTTTAAAAAATGGATTTCATTTTTT |
| TGTTCAACACTTGCGACTAGTGCATACACAATGTTGACCCCTCTTGTATTGGGTGGCGTATCTGGAAAGTT |
| TGATGTAGGCATCTTTAACTCAGCTAACATGATCAAACAAGGTTTGGCTGGACTTGCATCACCATTAGTCC |
| AAGCTTTTTATCCAAGAATTAACATTTTGCAAAGAGAGAATCCATATATTGCAAACTTAAAATCTAGAATG |
| ATTCTTAAATACTTGCTTGTTTTTACATGGCTTTAGCAATACCATTTTTACTTTTTGCCAACCAATTATC |
| ATTATTAATATTCGGCATGAAAGGTGAAGTAATTGCAGGTGCAATGCAATTAATGACATTGCTTCCTATAT |
| TCATAGGTTTTAATACAGTTGTCGGGTTACTTGTATTAGTACCTAATGGGTGCAAAAACAGTATTTCAAA |
| TCTATTTTCCTAGGAACTATTACTTGTTTAAGCATAGTTTATCCAGCATGTAAATATTATGGAGCAACGGG |
| TGCGATTGTGAGTCTTATTGTAGCTGAAATTTTCGTTGGCATGGGAATGCTTAAACAATTCATTAAAGTAA |
| ATAAAACCGTATGTAGGCCTCATAAATTATGAATATCTCGGTAATAATATCTGTTTGGAAACGCCCAGTTC |
| AATTAGAATTGATTCTCTCTGAGCTCGATTCTCAGGCTAAAGACAATAGTCTACACCTAGAAGTAATTGTT |
| TCCGATAGTCATAGTGGTAAAGAAATTGATGATGTAGTTGCTGATAATATTCATAAAAAGAAAAATATTAA |
| TATTATCCATCAACATACTAAAAATATACTCTCCGCTAAGCGCAATTTCGGAGCATCCCTAGCCCATGGGG |
| ATTATTTAATATTTCTTGATGATGATTGTATACCCGCAAGTGGATATATATCATCGTTGCTGAACTATTTA |
| AAAAAAATGAATAGTAAAAGCGTTTTATGTGGGGAAGTTAGATTCGAAAATGAACTCATTGAGACCAGCAA |
| TTACTATCGCTACAGGAACTCTTTACACCCTAAGTTTAGTGATAGTCCTGATATCTCTATGAATGCCTGGA |
| CTTTTGTCGCAATGAATTGTGTTCTTGATAGAAAGGCATTTTCATCAGGTATAGTTTCATATAATGAAAAT |
| TTTATTGGTTATGGTTGTGAAGATCATGAGTTTGGGTGGCAACTTGAAAAAAATGACTTCAAAATTATTTT |
| TGCTGATTTTAAAATATTACATCACGATACACAGTGGCGATATGAAGGATATACAAAAAAAATTCGTGCTA |
| CAGCACGTGATGGTATGAATGTATTAAGCAAAGTAAGGCCTGAAATGTTTTCTACTAATAAAAATTATTC |
| CTAGTTGAGAAAATATTTAGTAAACACAAAACGTTTAGTAAAATATGCCAATCAATATTTTTCAATAAATT |
| TATTTTTAAAAAAATAATACAATTTTTAAAAAAAACAGATGCAAATAAAAAACTCTATTTCCCAATTCTTT |
| ACAGATATGTGTTGATTTCGGCATATATACATGGTATTGGAGAGCGTGGCACCTCAAAAACAGATGATTTG |
| CTTAAGAACTGGTATATATAGATGATGCTATCTTCATTTATTAAGACATTTGTATGGAAGGTAAAAAACAA |
| TGAAGTATAATGCATTGATGGCTTTTTTATTATTTTTGTTGTTTTTTTAGATTGTCGCTGATAATACCT |
| TTCTTATATTTGGCATTTATTCCTGCATTTTTGGTATTATGTATTTAGTGCGTAATTTATGATTACTAT |
| GGGCAATGGATTGGTATCTATAGATCGTAAAAATTTGTTGCTGTTATCTATATTCATAATTATTTTTAT |
| TTTGTTTGGTTTTCGATTTGTTTCAAAAAAAGCCATTCTTTTTCAAAGTTATTTTACCGTTAGATTATTTATG |
| TTGTTTTTATTTTCATTTGTTCCTGCGTATTATTTAGTAAATAGATTCATAAAGGGTGACTTGAAATTAAT |
| GGAGCGAATATTAGTGTATTCTCTCTGGGTTCAAATAGTTATTTTTTTGGTATGTATATAAGTCCAGAGT |
| TAAAAAGATTGTTATATACTTTCTTTGGTATGTCTGACTCTGTTAATCTTTGGGAACAAAATGCTAAAGTA |
| AGAGGATTTGGGTTGTCGGGTGAAATAAATTTCATGACACCATTTTTGATGATCTATATGTCATTTTTAT |
| GATGAAAAGGCGTTATGCTTTAATTACTTTAATTTGTCTGACTCAAATCGTAAATTCTAACATGGCTGTGA |
| TTGCAGCCATTATTGGTATCGGTTGCTCTAGACTTAATATTAATATAAAAATTGCAACAGTATTGATTTTG |
| GGAGTTTTAGTTTATAGCTTAGGAGCGGTGTTCTTTCCTCGATTTTATGATGAGTTCGTTTCTGGAGATGG |
| CACAAGAACTCTGGATATCTTATTACAGCAACATGTGTTTGTTGGTAATTTAGATTTTTTAATATTA |
| TATTTGGATTACAGCAAAACATATCTTCATCAATCCCCGATATTAAACAAAGTTCGGATATGGGCTGGGTT |
| ATACTGTTTAATTACGGTGGGTTAACATTTATTACACTCTTTTTATTTTTAATCTTTACTATTTCTATTGC |
| GACATTTGGAATGACATATCAAGCAATTATATGGATGTTAATTGGGATAATTTTCAATACCAAAGGTTTAG |
| TTTTAGGATCTAACGGCTATTTCTTTCTATCTTTTATATATATTGTTTTGAATAGAGTAACACTTAGTAGA |
| CAGAGTTCAATTACTAATAAGTTAGGTCAAGTAAGTAAATAGCTTCCAGAGTATATTTGTCAATGATTTGA |
| GGTTCGGTTATTATGTTTTCATCTAAAACACTGTTAATTACTGGTGGTACTGGCTCTTTCGGGAATGCTGT |
| ATTAAATAGATTTCTTGATACAGATATTGCAGAAATCCGTATATTTAGTCGTGATGAAAAAAAACAAGATG |
| ATATGCGGAAAAAATACAATAATCAAAAATTAAAGTTCTATATTGGTGATGTCAGAGATTACCGTAGTATT |
| TTGAATGCGACTCGCGGTGTTGATTTTATATATCATGCAGCGGCACTTAAGCAAGTTCCATCATGTGAATT |
| TCATCCTATGGAAGCCGTTAAAACTAATATCCTTGGTACGGAAATGTTCTTGAAGCAGCTATAGCGAATG |
| AAGTGAAGAGGGTTGTATGCCTAAGTACTGATAAAGCTGTATACCCGATTAACGCAATGGGTATTTCAAAA |
| GCTATGATGGAAAAGGTCATGGTCGCGAAATCCCGTAATGTTGATCGCAATAAAACAGTAATATGTGGTAC |
| CCGTTATGGGAATGTTATGGCATCTCGCGGTTCAGTTATTCCATTATTTGTTGATCTTATTAGAGCGGGCA |
| AGCCACTCACAATAACTGATCCTAATATGACCCGCTTTATGATGACTCTTGAGGATGCGGTAGATTAGTT |
| CTTTATGCGTTTGAACATGGTAATAATGGTGATATCTTTGTGCAAAAAGCACCTGCAGCAACTATTGACAC |
| ATTAGCTATTGCTTTAAAGGAATTACTAAATGTTCCTGACCATCCGGTAAATGTCATTGGAACGCGTCATG |
| GCGAGAAATTATATGAAGCTCTACTTAGTCGTGAGGAAATGATCGCTGCTAGATATGGGCGATTATTAC |
| CGTGTCCCGCCAGATCTTCGTGACCTTAATTATGGCAAATATGTTGAGCAAGGTGATAGCCGAATATCTGA |
| AATAGAAGATTATAACTCTCATAATACTCAACGGTTAGATGTTGAAGGCATGAAAGAGCTCTTGCTAAAAT |
| TAGCCTTTATTCGAGCAATTCGTCTGGTGAAAAATATAATCTGGATTCATGATATGAAAATATTAGTTAC |
| TGGTGCAAATGGTTTTATTGGTCGTAATTTATGTTTGAGGCTTGAGGAACTTGGTTATAAAGATCTTATTA |
| GAATTGATCGAGAATCAACGAAGCAAGATCTTGAACAAGGCTTACAGGATGCCGCGATTTTATTTATCACTTA |
| GCTGGTATCAATAGACCTAAGACTGATGATGAGTTTATTTCTGGAAACAGTGATTTAACAAAGCATATAGT |
| TGAGTATCTCCTTTCTATTGGTAAGAATACACCAATTATGCTAAGTTCTTCGATACAAGCTGAACTTAATA |
| ATGCTTATGGGGTTAGCAAAGCTGTAGCTGAAAGCTATGTCGAAAAATATGCTGCTAGTGGTTCTTCG |
| TATTATATTTTCAGATATCCAAACGTTTTGGTAAATGGTGTAAGCCAAACTATAATTCTTTTATAGCAAC |
| TTTTTGCTACAATATTTCCAATGATATTGAGATTACTATCAATGATGCAGCAGCGCCAGTCAATCTGGTCT |
| ATATTGATGATGTTTGTACTGATGCTATAGCTCTTCTCTCTGGGACGGTTGAAAGTGGATATAAAGTTGTT |

| SEQUENCES |
|---|
| GCACCAATTTATTCAACAACAGTTGGTGAAGTTGCAGAATTAATTTATAGCTTCAAAAATAGCCGTTCCAC |
| CCTGATCACAGAGGCTGTCGGGGCGGGATTTACCCGTGCATTGTATTCTACATGGCTGAGTTATTTACCAG |
| CAGAGAAGTTTGCGTACAAGGTACCTTTTTATGGGGATGCCCGCGGAGTCTTTTGTGAGATGTTGAAAACG |
| CCTTCAGCGGGGCAGTTTTCATTTTTTACTGCTCACCCTGGTATTACGCGTGGCGGACATTACCATCACAG |
| TAAAAATGAGAAGTTTTTGGTCATTCGAGGTCAGGCATGCTTTAAATTTGAACATGTGATTACCGGTGAGC |
| GATATGAACTGAAAGTTTCATCGGGTGAGTTTAAGATTGTTGAAACAGTTCCTGGTTGGACACATGACATT |
| ACAAATATTGGAACTGATGAATTAATAGTCATGCTCTGGGCAAATGAAATTTTCAACCGTGATGAGCCCGA |
| TACTATTGCGAGACCTCTATAATGAAAAAATTAAAAGTTATGTCTGTTGTTGGAACCCGTCCTGAGATTAT |
| CCGTTTGTCGAGGGTTCTTGCTAAGTTTGATGAATACTGCGAGCATATTATTGTCCATACTGGTCAAAATT |
| ATGATTACGAATTAAATGAAGTGTTCTTCAATGACTTGGGTGTTCGAAAACCTGATTATTTTTAAATGCA |
| GCGGGTAAAAATGCGGCGGAAACCATTGGTCAGGTTATTATTAAGGTAGATGAAGTATTAGAAATCGAAAA |
| ACCTGAAGCAATACTGGTATTGGGCGATACGAATTCATGTATTTCTGCCATTCCGGCCAAACGCCGTAAAG |
| TGCCTATATTTCATATGGAAGCAGGTAACCGTTGTTTCGATCAACGCGTGCCTGAAGAAACCAACAGACGT |
| ATTGTTGACCATACGGCTGATATCAATATGACCTACAGTGATATTGCTCGTAATATCTCTTGGCTGAAGG |
| TATCCCAGCTGATCGGATCATAAAAACTGGTAGCCCTATGTTTGAGGTTCTTTCATATTATATGCCCCAAA |
| TTGATGGTTCAGATGTGCTATCGCGTTTGAATCTACAGTCTGGTGAGTTTTTTGTAGTAAGTGCGCATCGT |
| GAAGAGAATGTTGATTCTCCAAAACAGCTCGTAAAGCTTGCGAACATTCTAAATACTGTTGCTGAAAAATA |
| TAATCTTCCAGTTATTGTCTCCACACACCCAAGGACACGTAACCGAATCCGTGAGCAAGGAATTGAATTTC |
| ATTCAAATATAAATCTACTGAAACCATTGGGTTTCCATGATTATAACCACTTGCAGAAGAACTCACGAGCT |
| GTGCTTTCAGATAGCGGTACTATCACTGAAGAGTCATCCATCATGAATTTCCCAGCGGTAAACATCCGGGA |
| AGCGCATGAGCGTCCGAAGGCTTTGAGGAAGCATCCGTCATGATGGTGGGGTTAGAGTGTGAACGCGTAT |
| TACAAGCGCTGGATATTCTGGCAACACAACCGCGAGGTGAAGTCCGTCTTTTACGTCAGGTTAGTGATTAC |
| AGCATGCCAAATGTGTCGGATAAAGTTGTCAGAATTGTTCACTCTTACAGATTATGTTAAGAGAGTCGT |
| CTGGAAAGAATATTGATGAAACTTGCTTTAATCATAGATGATTACCTGCCCAACAGTACTCGTGTTGGTGC |
| AAAAAATGTTTCATGAACTTGCTCAAGAATTTATCCAGCGTGGGCACGATGTTACGGTAATTACTCCTGGTA |
| CGGGCATGCAAGAAGAGATTTCTTTTGATACCTTTCAGGGGGTAAAAACATGGCGTTTTAAAAGCGGGCCG |
| CTCAAGGATGTAAGTAAAATTCAGCGAGCGGTCAATGAAACGCTTTTGTCCTATCGGCGTGGAAAGCCAT |
| CAAAAAATGGGTAAAAAAAGAGACCTTTGAGGGGGTGATTTATTATTCACCTTCCATATTCTGGGGGCCTT |
| TAGTTAAAAAAATTAAAGCTCGTTGCCAATGTCCTGCTTATCTTATTTTAAGAGATATGTTTCCACAATGG |
| GTAATTGATGCAGGAATGCTTAATGCTGGTTCCCAATAGAACGCTACTTTCGTCTTTTTGAAAAAATATC |
| TTATCGTCAGGCAAATCGTATTGGACTTATGTCTGATAAGAATCTTGATGTTTTCGGAAAGATAATAAAG |
| GCTATCCGTGCGAAGTTTTGCGTAATTGGGCATCCCTAACACCAACGATCATACCCAAGGATTATATACCA |
| CTACGTAAGCGACTTGGCCTAGAGGATAAAACCATTTTCTTCTATGGTGGAAACATAGGTCATGCACAGGA |
| CATGACAAACTTGATGCGACTTGTGAGAAACATGGCAGCATATCCTCAAGCTCATTTCCTATTTATTGGCC |
| AGGGGGATGAAGTTGAATTAATTAATTCATTAGCATCTGAGTGGGCATTGACGAATTTCACCTATTTGCCC |
| TCGGTTAACCAAGATGAATTTAAGTTCATTTTGTCGGAAATGGATTCGGCTTGTTTTCTCTTTCCGCTAG |
| ACACTCTTCCCATAATTTTCCTGGTAAGTTATTAGGCTATATGGTTCAGTCGCTACCTATTTAGGTAGCG |
| TAAATGCCGGAAATGATTTGCTCGACATTGTCAATCAAAATAATGCGGGATTAATCCATGTCAATGGTGAG |
| GACGATAAATTATGTCAATCTGCGCTATTAATGTTGCATGATATTGATGTGCGCCGGCAACTTGGTTCGGG |
| GGCGAATATATTGTTGAAAGAACAATTCTCCGTTGAGTCTGCGGCACAGACGATAGAAATGAGGTTGGAGG |
| CATGCAATGCGATTAATTGATAATGACCAACTCGACGAATTATATGATCAAGCCGGGCAATCGGAACGTTT |
| ACGTTCCCACCTTATGATGCACGGCTCGCATCAAGAAAAGGTACAGCGTTTACTTATTGCATTAGTAAAGG |
| GCAGCTATGTTGAACCGCATTATCACGAACTTCCTCATCAGTGGGAAATGTTCATTGTTATGGAGGGGCAA |
| CTTCAGGTTTGTTTGTATGGTAGAAATGGTGAGGTTATAAAGCAATTTATAGCAGGAGATAATACTGGAAT |
| GAGCATTGTGGAGTTTTCTCCGGGCGATATACACAGTGTCGAATGCCTATCTCCGCGTGCTCTTATGGTGG |
| AAGTTAAGGAGGGGCCATTTGACCCTTCTTTTGCAAAATCGTTCGTGTGAGCGGCGCGAGCTCGTCGACT |
| CGAGGATCCGTGTAGGCTGGAGCTGCTTGAAGTTCCTATACTTTCTAGAGAATAGGAACTTCGGAATAGG |
| AACTAAGGAGGATATTCATATGGATAAAGCCGTAAGCATATAAGCATGGATAAGCTATTTATACTTTAATA |
| AGTACTTTGTATACTTATTTGCGAACATTCCAGGCCGCAGCATTCAGCGCGGTGATTCACACCTGACAGGA |
| GTATGTAATGTCCAAGCAACAGATCGGCTAGTCGGTATGGCAGTGATGGGACGCAACCTTGCGCTCAACA |
| TCGAAAGCCGTGGTTATACCGTCTCTATTTTCAACCGTTCCCGTGAGAAGACGGAAGAAGTGATTGCCGAA |
| AATCCAGGCAAGAAACTGGTTCCTTACTATACGGTGAAAGAGTTTGTCGAATCTCTGGAAACGCCTCGTCG |
| CATCCTGTTAATGGTGAAAGCAGGTGCAGGCACGGATGCTGCTATTGATTCCCTCAAACCATATCTCGATA |
| AAGGAGACATCATCATTGATGGTGGTAACACCTTCTTCCAGGACACTATTCGTCGTAATCGTGAGCTTTCA |
| GCAGAGGGCTTTAACTTCATCGGTACCGGTGTTTCTGGCGGTGAAGAGGGGGCGCTGAAAGGTCCTTCTAT |
| TATGCCTGGTGGCCAGAAAGAAGCCTATGAATTGGTAGCACCGATCCTGACCAAAATCGCCGCCGTAGCTG |
| AAGACGGTGAACCATGCGTTACCTATATTGGTGCCGATGGCGCAGGTCACTATGTGAAGATGGTTCACAAC |
| GGTATTGAATACGGCGATATGCAGCTGATTGCTGAAGCCTATTCTCTGCTTAAAGGTGGCCTGAACCTCAC |
| CAACGAAGAACTGGCGCAGACCTTTACCGAGTGGAATAACGGTGAACTGAGCAGTTACCTGATCGACATCA |
| CCAAAGATATCTTCACCAAAAAGATGAAGACGGTAACTACCTGGTTGATGTGATCCTGGATGAAGCGGCT |
| AACAAAGGTACCGGTAAATGGACCAGCCAGAGCGCGCTGGATCTCGGCGAACCGTCGCTGATTACCGA |
| GTCTGTGTTTGCACGTTATATCTCTTCTCTGAAAGATCAGCGTGTTGCCGCATCTAAAGTTCTCTCTGGTC |
| CGCAAGCACAGCCAGCAGGCGACAAGGCTGAGTTCATCGAAAAGTTCGTCGTGCGCTGTATCTGGGCAAA |
| ATCGTTTCTTACGCCCAGGGCTTCTCTCAGCTGCGTGCTGCGTCTGAAGAGTACAACTGGGATCTGAACTA |
| CGGCGAAATCGCGAAGATTTTCCGTGCTGGCTGCATCATCCGTGCGCAGTTCCTGCAGAAAATCACCGATG |
| CTTATGCCGAAAATCCACAGATCGCTAACCTGTTGCTGGCTCCGTATTTCAAACAAATTGCCGATGACTAC |
| CAGCAGGCGCTGCGTGATGTCGTTGCTTATGCAGTACAGAACGGCATTCCGGTTCCGACCTTCTCCGCAGC |
| GGTTGCCTATTACGACAGCTACCGTGCTGCTGTTCTGCCTGCGAACCTGATCCAGGCACAGCGTGACTATT |
| TTGGTGCGCATACTTATAAGCGTATTGATAAAGAAGGTGTGTTCCATACCGAATGGCTGGATTAA |

SEQ ID NO: 16 (example O16 rfb locus nucleotide sequence - O16-EPA production strain stLMTB11739)
```
ATGACGAATTTAAAAGCAGTTATTCCTGTAGCGGGTCTCGGGATGCATATGTTGCCTGCCACTAAGGCGAT
ACCCAAAGAGATGCTACCAATCGTCGACAAGCCAATGATTCAGTACATTGTTGACGAGATTGTGGCTGCAG
GGATCAAAGAAATCCTCCTGGTAACTCACGCGTCCAAGAACGCGGTCGAAAACCACTTCGACACCTCTTAT
GAGTTAGAATCACTCCTTGAGCAGCGCGTGAAGCGTCAACTGCTGGCGGAAGTACAGTCCATCTGTCCGCC
GGGCGTGACCATTATGAACGTGCGTCAGGGCGAACCTTTAGGTTTAGGCCACTCCATTTTGTGTGCGCGAC
```

| SEQUENCES |
|---|
| CTGCCATTGGTGACAACCCATTTGTCGTGGTACTGCCAGACGTTGTGATCGACGATGCCAGCGCCGACCCG |
| CTACGTTACAACCTTGCTGCCATGATTGCACGTTTCAACGAAACGGGCCGCAGCCAGGTGCTGGCAAAACG |
| TATGCCGGGTGACCTCTCTGAATACTCCGTCATCCAGACTAAAGAGCCGCTGGACCGTGAGGGTAAAGTCA |
| GCCGCATTGTTGAATTTATCGAAAAACCGGATCAGCCGCAGACGCTGGACTCAGACATCATGGCCGTAGGT |
| CGCTATGTGCTTTCTGCCGATATTTGGCCGGAACTGGAACGTACTCAGCCTGGTGCATGGGGACGTATTCA |
| GCTGACTGATGCTATTGCCGAGCTGGCGAAAAAACAATCCGTTGATGCAATGCTGATGACCGGCGACAGTT |
| ACGACTGCGGCAAAAAATGGGCTATATGCAGGCGTTTGTGAAGTATGGCCTACGCAACCTGAAAGAAGGG |
| GCGAAGTTCCGTAAAGGTATTGAGAAGCTGTTAAGCGAATAATGAAAATCTGACCGGATGTAACGGTTGAT |
| AAGAAAATTATAACGGCAGTGAAATTCGCAGCAAAAGTAATTTGTTGCGAATCTTCCTGCCGTTGTTTTA |
| TATAAACCATCAGAATAACAACGAGTTAGCAGTAGGGTTTTATTCAAAGTTTTCCAGGATTTTCCTTGTTT |
| CCAGAGCGGATTGGTAAGACAATTAGCGTTTGAATTTTTCGGGTTTAGCGCGAGTGGGTAACGCTCGTCAC |
| ATCATAGGCATGCATGCAGTGCTCTGGTAGCTGTAAAGCCAGGGGCGGTAGCGTGCATTAATACCTCTATT |
| AATCAAACTGAGAGCCGCTTATTTCACAGCATGCTCTGAAGTAATATGGAATAAATTAAGTGAAAATACTT |
| GTTACTGGTGGCGCAGGATTTATTGGTTCAGCTGTAGTTCGTCACATTATAAATAATACGCAGGATAGTGT |
| TGTTAATGTCGATAAATTAACGTACGCCGGAAACCGGGAATCACTTGCTCGATGTTTCTGATTCTGAACGCT |
| ATGTTTTTGAACATGCGGATATTTGCGATGCACCTGCAATGGCACGGATTTTTGCTCAGCATCAGCCGGAT |
| GCAGTGATGCACCTGGCTGCTGAAAGCCATGTTGACCGTTCAATTACAGGCCCTGCGGCATTTATTGAAAC |
| CAATATTGTTGGTACTTATGTCCTTTTGGAAGCCGCTCGCAATTACTGGTCTGCTCTTGATAGCGACAAGA |
| AAAATAGCTTCCGTTTTCATCATATTTCTACTGACGAAGTCTATGGTGATTTGCCTCATCCAGATGAAGTA |
| AATAATACAGAAGAATTACCCTTATTTACTGAGACGACAGCTTACGCGCCAAGCAGCCCTTATTCCGCATC |
| CAAAGCATCCAGCGATCATTTAGTCCGCGCGTGGAAACGTACATATGGTTTACCGACAATTGTGACTAATT |
| GCTCGAACAACTATGGTCCTTATCATTTCCCGGAAAAGCTTATTCCACTGGTTATTCTTAATGCACTGGAA |
| GGTAAGGCATTACCTATTTATGGCAAAGGAGATCAGATCCGCGACTGGTTGTATGTTGAAGATCATGCGCG |
| TGCGTTATATACCGTCGTAACCGAAGGTAAAGCGGGTGAAACTTATACATTGGTGGGCACAACGGAAAAGA |
| AAAACATCGATGTAGTGCTCACTATTTGTGATTTGCTGGATGAGATTGTACCGAAAGAGAAATCTTATCGT |
| GAGCAAATCACTTATGTTGCTGATCGTCCGGGACACGATCGCCGCTATGCTATTGATGCTGAGAAGATTGG |
| TCGCGCATTGGGATGGAAACCACAGGAAACGTTTGAGAGCGGGATTCGTAAAACGGTGGAATGGTACCTGT |
| CCAATACAAAATGGGTTGATAATGTGAAAAGTGGTGCCTATCAATCGTGGATTGAACAGAACTATGAGGGC |
| CGCCAGTAATGAATATCCTCCTTTTTGGCAAAACAGGGCAGGTAGGTTGGGAACTACAGCGTGCTCTGGCA |
| CCTTTGGGTAATTTGATTGCTTTTGATGTTCACTCTACTGATTATTGCGGTGATTTTAGTAATCCTGAAGG |
| TGTAGCTGAAACCGTAAGAAGCATTCGGCCGGATATTATTGTCAATGCAGCCGCTCACACCGCAGTAGACA |
| AAGCAGATCAGAACCGGAGTTTGCACAATTAATTAACGCAACAGTCGAAGCGATTGCGAAAGCAGCA |
| AATGAAGTTGGAGCCTGGGTTATCCATTACTCGACTGATTACGTCTTCCCTGGAAATGGCGATATGCCATG |
| GCTGGAGACGGATGCAACCGCACCACTAAATGTTTACGGTGAAACCAAGTTAGCCGGAGAAAAGCGTTAC |
| AGGAATATTGCGCGAAGCATCTTATTTTCCGGACCAGCTGGGTCTATGCAGGAAAAGGAAATAACTTCGCC |
| AAAACGATGTTACGTCTGGCAAAAGAGCGTGAAGAATTAGCGGTTATTAACGATCAGTTTGGTGCGCCAAC |
| AGGTGCTGAACTGCTGGCTGATTGTACAGCACATGCCATTCGTGTCGCACTGAATAAACCGGATGTCGCAG |
| GCTTGTACCATTTGGTAGCCAGTGGTACCACAACCTGGTACGATTATGCTGCGCTGGTTTTTGAAGAGGCG |
| CGCAAAGCAGGCATTCCCCTTGCACTCAACAAGCTCAACGCAGTACCAACAACAGCCTATCCTACACCAGC |
| TCGTCGTCCACATAACTCTCGCCTTAATACAGAAAAATTTCAGCAGAACTTTGCGCTTGTCTTGCCTGACT |
| GGCAGGTTGGCGTGAAACGAATGCTCAATGAATTATTTTACGACTACAGCAATTTAATAGTTTTTGCATCTT |
| GTTCGTGATGGTGGAGCAAGATGAATTAAAAGGAATGATGAAATGAAAATGCGTAAAGGTATTATTTTAGC |
| GGGTGGTTCTGGTACACGTCTTTATCCTGTGACTATGGCTGTCAGTAAACAGCTATTACCTATTTATGATA |
| AACCGATGATCTATTACCCGCTCTCTACACTGATGTTGGCGGGTATTCGCGATATTTTGATTATCAGTACA |
| CCTCAGGATACTCCTCGTTTTCAACAATTGCTGGGTGACGGTAGCCAGTGGGGCCTGAATCTTCAGTACAA |
| AGTGCAACCTAGCCCAGATGGCCTCGCGCAGGCATTTATCATCGGTGAAGAGTTTATTGGTGGTGATGATT |
| GTGCTTTGGTTCTTGGTGATAATATCTTTTACGGTCACGATCTGCCGAAGCTAATGAGGCCGCTGTTAAC |
| AAAGAAAGTGGTGCAACGGTATTTGCCTATCACGTTAATGATCCAGAACGCTATGGTGTCGTTGAGTTTGA |
| TAAAAACGGTACGGCAATCAGTCTGGAAGAAAAACCGTTAGAACCAAAGAGTAATTACGCCGTTACAGGTC |
| TGTACTTTTATGATAACGACGTGGTTCAGATGGCGAAAAACTTGAAGCCGTCTGCACGTGGTGAGTTAGAA |
| ATTACAGATATTAACCGTATTTATCTTGAGCAGGGACGTCTGTCTGTCGCGATGATGGGGCGTGGCTACGC |
| GTGGCTGGACACGGGGACTCATCAGAGTCTGATAGAAGCAAGTAATTTTATTGCGACAATTGAAGAGCGCC |
| AGGGATTGAAGGTTTCCTGTCCTGAAGAGATTGCATTTCGTAAAGGTTTTATTGATGTTGAGCAAGTAAGA |
| AAATTAGCTGTACCACTAATAAAGAATAATTATGGGCAGTATCTTTATAAAATGACGAAGGATTCAAATTA |
| ATGAATGTGATTAGAACTGAAATTGAAGATGTGCTAATTCTGGAGCCAAGAGTATTTGGTGATGATAGAGG |
| TTTCTTTTATGAGAGCTTTAATCAATCAGCATTTGAACATATTCTAGGCTATCCGGTCAGCTTTGTTCAAG |
| ACAATCACTCACGTTCATCAAAAAATGTACTCAGAGGCCTTCACTTTCAACGCGGCAGGTACGCACAAGAT |
| AAACTTGTACGCTGCACTCATGGAGCAGTTTTTGATGTTGCTGTTGATATTCGACCCAATTCGGTATCCTT |
| TGGTAAATGGGTTGGTGTTCTGCTTTCAGCTGATAATAAGCAGCAGTTGTGGATACCAAAAGGGTTTGCTC |
| ATGGCTTTTTGGTTCTGTCTGATATCGCTGAATTTCAATATAAAACTACAAACTATTATCATCCTGAAAGC |
| GATTGTGGAATATGTTGGAATGATGAACGCATTGCAATTGATTGGCCCCAAACATCAGGGTTAATCCTTTC |
| GCCAAAAGATGAAAGGCTCTTTACGTTAGATGAGCGTTATCAGATTAAAATTAATTGCATGAATACGAATAA |
| ATTATCTTTAAGAAGAACGTTATATATCGGCTGTCGTTCAAGGTAGCAATTATCTTTTACCATTGCTTA |
| CATTTCCATATCTTGTAAGAACACTTGGTCCTGAAAATTTCGGTATATTCGGTTTTTGCCAAGCGACTATG |
| CTATATATGATAATGTTTGTTGAATATGGTTTCAATCTCACAGCAACTCAGAGTATTGCCAAAGCAGCAGA |
| TAGTAAAGATAAAGTAACGTCTATTTTTTGGGCGGTGATATTTTCAAAAATAGTTCTTATCGTCATTACAT |
| TGATTTCTTAACGTCGATGACCTTGCTTGTTCCTGAATATAACAAGCATGCCGTAATTATATGGTCGTTT |
| GTTCCTGCATTAGTCGGGAATTTAATCTACCCTATCGGCTGTTTCAGGGAAAAGAAAAATGAAATGGCT |
| GACTTTAAGTAGTATTTTATCCCGCTTGGCTATTATCCCTCTAACATTTATTTTTGTGAACACAAAGTCAG |
| ATATAGCAATTGCCGGTTTTATTCAGTCAAGTGCAAATCTGGTTGCTGGAATTATTGCACTAGCTATCGTT |
| GTTCATTGAAGGTTGGTTAAAGTTACGCTATCATTACACATATGGCGTCGATCTTTAGCAGACAGCGGTTT |
| TCATGTTTTTATTTCCACATCTGCTATTAGTTTATATTCTACGGGAATAGTTATTATCCTGGGATTTATAT |
| CTGGACCAACGTCCGTAGGGAATTTTAATGCGGCCAATACTATAAGAAACGCGCTTCAAGGGCTATTAAAT |
| CCTATCACCCAAGCAATATACCCAAGAATATCAAGTACGCTTGTTCTTAATCGTGTGAAGGGTGTGATTTT |
| AATTAAAAAATCATTGACCTGCTTGAGTTTGATTGGTGGTGCTTTTTCATTAATTCTGCTCTTGGGTGCAT |
| CTATACTAGTAAAAATAAGTATAGGGCCGGGATATGATAATGCAGTGATTGTGCTAATGATTATATCGCCT |
| CTGCCTTTTCTTATTTCATTAAGTAATGTCTATGGCATTCAAGTTATGCTGACCCATAATTATAAGAAAGA |

| SEQUENCES |
|---|
| ATTCAGTAAGATTTTAATCGCTGCGGGTTTGTTGAGTTTGTTGTTGATTTTTCCGCTAACAACTCTTTTTA |
| AAGAGATTGGTGCAGCAATAACATTGCTTGCAACAGAGTGCTTAGTTACGTCACTCATGCTGATGTTCGTA |
| AGAAATAATAAATTACTGGTTTGCTGAGGATTTTATGTACGATTATATCATTGTTGGTTCTGGTTTGTTTG |
| GTGCCGTTTGTGCGAATGAGTTAAAAAAGCTAAACAAAAAGTTTTAGTGATTGAGAAAAGAAATCATATC |
| GGTGGAAATGCGTACACAGAGGACTGTGAGGGTATCCAGATTCATAAATATGGTGCACATATTTTTCATAC |
| CAATGATAAATATATATGGGATTACGTTAATGATTTAGTAGAATTTAATCGTTTTACTAATTCTCCACTGG |
| CGATTTATAAAGACAAATTATTCAACCTTCCTTTTAATATGAATACTTTCCACCAAATGTGGGGAGTTAAA |
| GATCCTCAAGAAGCTCAAAATATCATTAATGCTCAGAAAAAAAGTATGGTGACAAGGTACCTGAAAATTT |
| GGAGGAGCAGGCGATTTCATTAGTTGGGGAGGACTTATACCAAGCATTGATAAAGGGTTATACGGAGAAGC |
| AGTGGGGAAGAAGTGCAAAAGAATTGCCTGCATTTATTATTAAGCGAATCCCAGTGAGATTTACGTTTGAT |
| AACAATTATTTTCCGATCGCTATCAAGGTATTCCGGTGGGAGGCTACACTAAGCTTATTGAAAAAATGCT |
| TGAAGGTGTGGACGTAAAATTAGGCATTGATTTTTTGAAAGACAAAGATTCTCTAGCGAGTAAAGCCCATA |
| GAATCATCTACACTGGACCCATTGATCAGTACTTCGACTATAGGTTTGGAGCGTTAGAATATCGCTCTTTA |
| AAATTTGAGACGGAACGCCATGAATTTCCAAACTTCCAAGGGAATGCAGTAATAAATTTCACTGATGCTAA |
| TGTACCATATACCAGAATAATTGAGCATAAACATTTTGACTATGTTGAGACAAAGCATACGGTTGTTACAA |
| AAGAATATCCATTAGAGTGGAAAGTTGGCGACGAACCCTACTATCCAGTTAATGATAATAAAAACATGGAG |
| CTTTTTAAGAAATATAGAGAGTTAGCTAGCAGAGAAGACAAGGTTATATTTGGCGGGCGTTTGGCCGAGTA |
| TAAATATTATGATATGCATCAAGTGATATCTGCCGCTCTTTATCAAGTGAAAAATATAATGAGTACGGATT |
| AATGATCTATCTTGTAATTAGTGTCTTTCTCATTACAGCATTTATCTGTTTATATCTTAAGAAGGATATAT |
| TTTATCCAGCCGTATGCGTTAATATCATCTTCGCACTGGTCTTATCTGTTTGGGATATGAAATAACGTCAGATATA |
| TATGCTTTTCAGTTAAATGACGCTACGTTGATTTTTCTACTTTGCAATGTTTTGACATTTACCCTGTCATG |
| TTTATTGACGGAAAGTGTATTAGATCTAAATATCAGAAAGTCAATAATGCTATTTATAGCATACCATCGA |
| AGAAAGTGCATAATGTAGGCTTGTTAGTTATTTCTTTTTCGATGATATATATATGCATGAGGTTAAGTAAC |
| TACCAGTTCGGGACTAGCTTACTTAGCTATATGAATTTGATAAGGATGCTGATGTTGAAGACACATCAAG |
| AAATTTCTCAGCATACATGCAGCCAATCATTCTAACTACTTTTGCTTTATTTATTTGGTCTAAAAAATTTA |
| CTAATACAAAGGTAAGTAAAACATTTACTTTACTTGTTTTATTGTATTCATCTTTGCAATTATACTGAAT |
| ACTGGTAAGCAAATTGTCTTTATGGTTATCATCTCTTATGCATTCATCGTAGGTGTTAATAGAGTAAAACA |
| TTATGTTTATCTTATTACAGCTGTAGGTGTTCTATTCTCCTTGTATATGCTCTTTTTACGTGGACTGCCTG |
| GGGGGATGGCATATTATCTATCCATGTATTTGGTCAGCCCTATAATCGCGTTTCAGGAGTTTTATTTTCAG |
| CAAGTATCTAACTCTGCCAGTTCTCATGTCTTTTGGTTTTTTGAAAGGCTGATGGGGCTATTAACAGGTGG |
| AGTCTCTATGTCGTTGCATAAAGAATTTGTGTGGGTGGGTTTGCCAACAAATGTTTATACTGCTTTTTCGG |
| ATTATGTTTATATTTCCGCGGAGCTAAGCTATTTGATGATGGTTATTCATGGCTGTATTTCAGGTGTTTTA |
| TGGAGATTGTCTCGAAATTACATATCTGTGAAAATATTTTATTCATATTTTATTTATACCTTTTCTTTCAT |
| TTTTTATCATGAAAGCTTCATGACTAATATTAGCAGTTGGATACAAATAACTCTTTGTATCATAGTATTCT |
| CTCAATTTCTTAAGGCCCAGAAAATAAAGTGAAAATGTATTTTTGAATGATTTAAATTTCTCTAGACGCG |
| ATGCTGGATTTAAAGCAAGAAAAGATGCACTGGACATTGCTTCAGATTATGAAAACATTTCTGTTGTTAAC |
| ATTCCTCTATGGGGTGGAGTAGTCCAGAGAATTATTAGTTCTGTTAAGCTTAGTACATTTCTCTGCGGTCT |
| TGAAAATAAAGATGTTTTAATTTTCAATTTCCCGATGGCCAAACCATTTTGGCATATATTGTCATTCTTTC |
| ACCGCCTTCTAAAATTTAGAATAGTACCTCTGATTCATGATATTGATGAATTAAGAGGAGGAGGGGGTAGT |
| GATTCTGTGCGGCTTGCTACCTGTGATATGGTCATAAGTCACAATCCACAAATGACAAAGTACCTTAGTAA |
| ATATATGTCTCAGGATAAAATCAAAGACATAAAAATATTTGATTACCTCGTCTCATCTGATGGGAGCATC |
| GAGATGTTACGGATAAGCAACGAGGGGTCATATATGCTGGCAACCTTTCTAGGCATAAATGTTCTTTCATA |
| TATACTGAAGGATGCGATTTTACTCTCTTTGGTGTCAACTATGAAAATAAAGATAATCCTAAATATCTTGG |
| AAGTTTTGATGCTCAATCTCCGGAAAAGATTAACCTCCCAGGCATGCAATTTGGACTCATTTGGGATGGAG |
| ATTCTGTCGAAACCTGTAGTGGTGCCTTTGGCGACTATTTAAAGTTTTAATAACCCTCATAAGACATCTCTT |
| TATCTTTCAATGGAACTTCCAGTATTTATATGGGATAAAGCCGCCCTTGCGGATTTCATTGTAGATAATAG |
| AATAGGATATGCAGTGGGATCAATCAAAGAAATGCAAGAGATTGTTGACTCCATGACAATAGAAACTTATA |
| AGCAAATTAGTGAGAATACAAAAATTATTTCTCAGAAAATTCGAACAGGAAGTTACTTCAGGGATGTTCTT |
| GAAGAGGTGATCGATGATCTTAAAACTCGCTAAACGATATGGTCTCTGTGGTTTTATTCGGCTTGTTAGAG |
| ATGTCTTATTGACTCGTGTATTTTACCGGAACTGTAGAATTATTCGATTTCCCTGCTATATTCGCAATGAT |
| GGTAGCATTAATTTTGGTGAAAATTTCACAAGTGGAGTCGGTCTCAGGCTGGATGCATTTGGACGTGGCGT |
| GATTTTTTTTCCGATAATGTGCAAGTTAACGACTATGTTCATATCGCCTCAATTGAGAGCGTTACGATAG |
| GTCGGGATACGCTTATTGCAAGTAAAGTATTTATTACCGATCATAATCACGGTTCCTTTAAGCACTCTGAT |
| CCAATGAGTTCGCCAAATATACCTCCAGACATGCGCACGTTGGAATCTTCAGCTGTTGTAATTGGCCAGAG |
| GGTTTGGTTGGGTGAGAATGTGACGGTTTGCCTGGAACAATTATTGGTAATGGAGTCGTAGTCGGCGCCA |
| ATTCTGTTGTTAGAGGTTCTATTCCCGAAAATACTGTCATTGCGGGAGTACCAGCAAAAATCATAAAGAAA |
| TACAATCATGAGACCAAATTATGGGAAAAAGCATAGTCGTTGTTTCGTGGTCAATTTTACCACTGGCGGT |
| CCATTTACCATTTTGAAAAAATTTTTGGCAGCAACTAATAATAAAGAAAATGTCAGTTTTATCGCATTAGT |
| CCATTCTGCTAAAGAGTTAAAAGAAAGTTATCCATGGGTTAAATTCATTGAGTTTCCTGAGGTTAAAGGGT |
| CGTGGCTAAAACGTTTGCACTTTGAATATGTAGTTTGTAAAAAACTTTCAAAAGAGCTGAATGCTACGCAT |
| TGGATTTGTCTGCATGATATTACGGCCAATGTCGTCACTAAAAAAAGATATGTGTATTGTCATAACCCTGC |
| CCCTTTTTATAAAGGAATTTTATTCCGTGAAATTCTTATGGAGCCTAGCTTTTTCTTATTTAAAATGCTAT |
| ACGGGCTGATATATAAAATAAACATTAAAAAAAATACTGCAGTGTTTGTTCAACAATTCTGGATGAAAGAA |
| AAATTTATCAAGAAATATTCTATAAATAACATCATTGTCAGTCGGCCAGAAATTAAATTATCTGATAAAAG |
| CCAACTTACTGATGATGATTCTCAATTTAAGAATAACCCTTCTGAGTTGACAATATTTTACCCTGCTGTTC |
| CACGAGTATTTAAAAATTACGAGCTTATTATTAGTGCAGCAAGGAATTGAAAGAACAATCCAATATTTAAA |
| TTTCTGCTTACTATCAGTGGTACAGAAAATGCGTATGCAAAATATATTATCAGTCTTGCAGAAGGACTGGA |
| TAATGTTCATTTCCTCGGGTACTTGGATAAAGAAAAAATCGATCATTGTTATAATATTTCAGATATAGTTT |
| GTTTTCCCTCTAGGTTAGAAACATGGGGATTGCCGTTGTCTGAGGCTAAAGAGCGAGGTAAGTGGGTATTA |
| GCATCAGATTTCCCATTTACTAGAGAAACTCTTGGTAGTTATGAAAGAAAGCTTTTTTTGATTCTAATAA |
| CGATGACATGTTAGTTAAACTTATTATTGACTTCAAAAAAGGTAACCTCAAAAAGATATCTCTGATGCAA |
| ATTTCATTTATCGTAATGAAAATGTATTAGTTGGGTTTGATGAACTAGTTAATTTTATTACTGAAGAACAT |
| TGAAATGGTATATATAATAATCGTTTCCCACGGACATGAAGACTACATCAAAAAATTACTGAAAATCTTA |
| ATGCTGACGATGAGCACTACAAGATTATCGTACGCGACAACAAAGACTCTCTATTATTGAAACAAATATGC |
| CAGCATTATGCAGGCCTGGACTATATTAGTGGAGGTGTATACGGCTTTGGTCATAATAATAATATTGCGGT |
| GGCGTATGTAAAGGAAAAATATAGACCCGCAGATGATGATTACATTTTGTTTTTGAATCCCGATATCATCA |
| TGAAGCATGATGATTTGCTGACATATATTAAATATGTCGAAAGTAAGCGTTATGCTTTTAGTACATTATGC |

| SEQUENCES |
|---|
| CTGTTCCGAGATGAAGCGAAATCTTTACATGATTATTCCGTAAGAAAATTTCCTGTGCTTTCTGATTTTAT<br>TGTGTCATTTATGTTAGGGATTAATAAAACAAAAATTCCTAAAGAAAGTATCTATTCTGATACGGTTGTTG<br>ATTGGTGCGCAGGATCATTTATGCTGGTACGTTTTTCAGATTTTGTGCGTGTAAATGGCTTCGATCAAGGT<br>TACTTTATGTACTGTGAAGATATTGACCTGTGCTTGAGGCTTAGCCTGGCTGGTGTCAGACTTCATTATGT<br>TCCCGCTTTTCATGCGATACATTATGCTCATCATGACAATCGAAGTTTTTTTTCAAAAGCCTTCAGATGGC<br>ACTTAAAAAGTACTTTTAGATATTTAGCCAGAAAACGTATTTTATCAAATCGCAACTTTGATCGAATTTCA<br>TCAGTTTTTCACCCGTAAGAGCTCGGTACCCGGGCCTAGGGTGTAGGCTGGAGCTGCTTCGAAGTTCCTAT<br>ACTTTCTAGAGAATAGGAACTTCGGAATAGGAACTAAGGAGGATATTCATATCCGTCGACGGCGGCCGCCC<br>TGCAGGCATGCAAGCTTGATCCATATGGATCGCTAGCTTAATTAAATAAAGCCGTAAGCATATAAGCATGG<br>ATAAGCTATTTATACTTTAATAAGTACTTTGTATACTTATTTGCGAACATTCCAGGCCGCGAGCATTCAGC<br>GCGGTGATCACACCTGACAGGAGTATGTAATGTCCAAGCAACAGATCGGCGTAGTCGGTATGGCAGTGATG<br>GGACGCAACCTTGCGCTAACATCGAAAGCCGTGGTTATACCGTCTCTATTTTCAACCGTTCCCGTGAGAA<br>GACGGAAGAAGTGATTGCCGAAAATCCAGGCAAGAAACTGGTTCCTTACTATACGGTGAAAGAGTTTGTCG<br>AATCTCTGGAAACGCCTCGTCGCATCCTGTTAATGGTGAAAGCAGGTGCAGGCACGGATGCTGCTATTGAT<br>TCCCTCAAACCATATCTCGATAAAGGGAGACATCATCATTGATGGTGGTAACACCTTCTTCCAGGACACTAT<br>TCGTCGTAATCGTGAGCTTTCAGCAGAGGGCTTTAACTTCATCGGTACGGGTGTTTCTGGCGGTGAAGAGG<br>GGGCGCTGAAAGGTCCTTCTATTATGCCTGGTGGCCAGAAAGAAGCCTATGAATTGGTAGCACCGATCCTG<br>ACCAAAATCGCCGCCGTAGCTGAAGACGGTGAACCATGCGTTACCTATATTGGTGCCGATGGCGCAGGTCA<br>CTATGTGAAGATGGTTCACAACGGTATTGAATACGGCGATATGCAGCTGATTGCTGAAGCCTATTCTCTGC<br>TTAAAGGTGGCCTGAACCTCACCAACGAAGAACTGGCGCAGACCTTTACCGAGTGGAATAACGGTGAACTG<br>AGCAGTTACCTGATCGACATCACCAAAGATATCTTCACCAAAAAAGATGAAGACGGTAACTACCTGGTTGA<br>TGTGATCCTGGATGAAGCGGCTAACAAAGGTACGGGTAAATGGACCAGCCAGAGCGCGCTGGATCTCGGCG<br>AACCGCTGTCGCTGATTACCGAGTCTGTGTTTGCACGTTATATCTCTTCTCTGAAAGATCAGCGTGTTGCC<br>GCATCTAAAGTTCTCTCTGGTCCGCAAGCACAGCCAGCAGGCGACAAGGCTGAGTTCATCGAAAAAGTTCG<br>TCGTGCGCTGTATCTGGGCAAAATCGTTTCTTACGCCCAGGGCTTCTCTCAGCTGCGTGCTGCGTCGAAG<br>AGTACAACTGGGATCTGAACTACGGCGAAATCGCGAAGATTTTCCGTCGTGGCTGCATCATCCGTGCGCAG<br>TTCCTGCAAAAAATCACCGATGCTTATGCCGAAAATCCACAGATCGCTAACCTGTTGCTGGCCTCCGTACTT<br>CAAGCAAATTGCCGATGACTACCAGCAGGCGCTGCGTGATGTCGTTGCTTATGCAGTACAGAACGGTATTC<br>CGGTTCCGACCTTCTCCGCAGCGGTTGCCTATTACGACAGCTACCGTGCTGCTGTTCTGCCTGCGAACCTG<br>ATCCAGGCACAGCGTGACTATTTTGGTGCGCATACTTATAAGCGTATTGATAAAGAAGGTGTGTTCCATAC<br>CGAATGGCTGGATTAA |

SEQ ID NO: 17 (example O18A rfb locus nucleotide seauence - O18A-EPA production strain BVEC-L-00559)
ATGACGAATTTAAAAGCAGTTATTCCTGTAGCGGGTCTCGGGATGCATATGTTGCCTGCCACTAAGGCGAT
ACCCAAAGAGATGCTACCAATCGTCGACAAGCCAATGATTCAGTACATTGTTGACGAGATTGTGGCTGCAG
GGATCAAAGAAATCCTCCTGGTAACTCACGCGTCCAAGAACGCGGTCGAAAACCACTTCGACACCTCTTAT
GAGTTAGAATCACTCCTTGAGCAGCGCGTGAAGCGTCAACTGCTGGCGGAAGTACAGTCCATCTGTCCGCC
GGGCGTGACCATTATGAACGTGCGTCAGGGCGAACCTTTAGGTTTAGGCCACTCCATTTTGTGTGCGCGAC
CTGCCATTGGTGACAACCCATTTGTCGTGGTACTGCCAGACGTTGTGATCGACAGTGCCAGCGCCGACCG
CTACGTTACAACCTTGCTGCCATGATTGCACGTTTCAACGAAACGGGCCGCAGCCAGGTGCTGGCAAAACG
TATGCCGGGTGACCTCTCTGAATACTCCGTCATCCAGACTAAAGAGCCGCTGGACCGTGAGGGTAAAGTCA
GCCGCATTGTTGAATTTATCGAAAAACCGGATCAGCCGCAGACGCTGGACTCAGACATCATGGCCGTAGGT
CGCTATGTGCTTTCTGCCGATATTTGGCCGGAACTGGAACGTACTCAGCCTGGTGCATGGGGACGTATTCA
GCTGACTGATGCTATTGCCGAGCTGGCGAAAAAACAATCCGTTGCTGCAATGCTGATGACCGGCGACAAGTT
ACGACTGCGGCAAAAAAATGGGCTATATGCAGGCGTTTGTGAAGTATGGCCTACGCAACCTGAAAGAAGGG
GCGAAGTTCCGTAAAGGTATTGAGAAGCTGTTAAGCGAATAATGAAAATCTGACCGGATGTAACGGTTGAT
AAGAAAATTATAACGGCAGTGAAAATTCGCAGCAAAGTAATTTGTTGCGAATCTTCCTGCCGTTGTTTTA
TATAAACATCAGAATAACAACGAGTTAGCAGTAGGGTTTTATTCAAAGTTTTCCAGGATTTTCCTTGTTT
CCAGAGCGGATTGGTAAGACAATTAGCGTTTGAATTTTTCGGGTTTAGCGCGAGTGGGTAACGCTCGTCAC
ATCATAGGCATGCATGCAGTGCTCTGGTAGCTGTAAAGCCAGGGGCGGTAGCGTGCATTAATACCTCTATT
AATCAAACTGAGAGCCGCTTATTTCACAGCATGCTCTGAAGTAATATGGAATAAATTAAGTGAAAATACTT
GTTACTGGTGGCGCAGGATTTATTGGTTCAGCTGTAGTTCGTCACATTATAAATAATACGCAGGATAGTGT
TGTTAATGTCGATAAATTAACGTACGCCGGAAACCGGGAATCACTTGCTGATGTTTCTGATTCTGAACGCT
ATGTTTTTGAACATGCGGATATTTGCGATGCACCTGCAATGGCACGGATTTTTGCTCAGCATCAGCCGGAT
GCAGTGATGCACCTGGCTGCTGAAAGCCATGTTGACCGTTCAATTACAGGCCCTGCGGCATTTATTGAAAC
CAATATTGTTGGTACTTATGTCCTTTTGGAAGCCGCTCGCAATTACTGGTCTGCTCTTGATAGCGACAAGA
AAAATAGCTTCCGTTTTCATCATATTTCTACTGACGAAGTCTATGGTGATTTGCCTCATCCAGATGAAGTA
AATAATACAGAAGAATTACCCTTATTTACTGAGACGACAGCTTACGCGCAAGCAGCCCTTATTCCGCATC
CAAAGCATCCAGCGATCATTTAGTCCGCGCGTGGAAACGTACATATGGTTTACCGACAATTGTGACTAATT
GCTCGAACAACTATGGTCCTTATCATTTCCCGGAAAAGCTTATTCCACTGGTTATTCTTAATGCACTGGAA
GGTAAGGCATTACCTATTTATGGCAAAGGAGATCAGATCCGCGACTGGTTGTATGTTGAAGATCATGCGCG
TGCGTTATATACCGTCGTAACCGAAGGTAAAGCGGGTGAAACTTATAACATTGGTGGGCACAACGAAAAGA
AAAACATCGATGTAGTGCTCACTATTTGTGATTTGCTGGATGAGATTGTACCGAAAGAGAAATCTTATCGT
GAGCAAATCACTTATGTTGCTGATCGTCCGGGACACGATCGCCGCTATGCTATTGATGCTGAGAAGATTGG
TCGCGCATTGGGATGGAAACCACAGGAAACGTTTGAGAGCGGGATTCGTAAAACGGTGGAATGGTACCTGT
CCAATACAAAATGGGTTGATAATGTGAAAAGTGGTGCCTATCAATCGTGGATTGAACAGAACTATGAGGGC
CGCCAGTAATGAATATCCTCCTTTTTGGCAAAACAGGGCAGGTAGGTTGGGAACTACAGCGTGCTCTGGCA
CCTTTGGGTAATTTGATTGCTTTTGATGTTCACTCTACTGATTATTGCGGTGATTTTAGTAATCCTGAAGG
TGTAGCTGAAACCGTAAGAAGCATTCGGCCGGATATTATTGTCAATGCAGCCGCTCACACCGCAGTAGACA
AAGCAGAATCAGAACCGGAGTTTGCACAATTAATTAACGCACAACAAGATGCACAAGACGATTGCGAAAGCAGCA
AATGAAGTTGGAGCCTGGGTTATCCATTACTCGACTGATTACGTCTTCCCTGGAAATGGCGATATGCCATG
GCTGGAGACGGATGCAACCGCACCACTAAATGTTTACGGTGAAACCAAGTTAGCGGAGAAAAAGCGTTAC
AGGAATATTGCGCGAAGCATCTTATTTTCCGGACCAGCTGGGTCTATGCAGGAAAAGGAAATAACTTCGCC
AAAACGATGTTACGTCTGGCAAAGAGCGTGAAGAATTAGCGGTTATTAACGATCAGTTTGGTGCGCCAAC
AGGTGCTGAACTGCTGGCTGATTGTACAGCACATGCCATTCGTGTCGCACTGAATAAACCGGATGTCGCAG
GCTTGTACCATTTGGTAGCCAGTGGTACCACAACCTGGTACGATTATGCTGCGCTGGTTTTTGAAGAGGCG -continued

| SEQUENCES |
|---|
| CGCAAAGCAGGCATTCCCCTTGCACTCAACAAGCTCAACGCAGTACCAACAACAGCCTATCCTACACCAGC |
| TCGTCGTCCACATAACTCTCGCCTTAATACAGAAAAATTTCAGCAGAACTTTGCGCTTGTCTTGCCTGACT |
| GGCAGGTTGGCGTGAAACGAATGCTCAATGAATTATTTACGACTACAGCAATTTAATAGTTTTTGCATCTT |
| GTTCGTGATGGTGGAGCAAGATGAATTAAAAGGAATGATGAAATGAAAATGCGTAAAGGTATTATTTTAGC |
| GGGTGGTTCTGGTACACGTCTTTATCCTGTGACTATGGCTGTCAGTAAACAGCTATTACCTATTTATGATA |
| AACCGATGATCTATTACCCGCTCTCTACACTGATGTTGGCGGGTATTCGCGATATTTTGATTATCAGTACA |
| CCTCAGGATACTCCTCGTTTTCAACAATTGCTGGGTGACGGTAGCCAGTGGGGCCTGAATCTTCAGTACAA |
| AGTGCAACCTAGCCCAGATGGCCTCGCGCAGGCATTTATCATCGGTGAAGAGTTTATTGGTGGTGATGATT |
| GTGCTTTGGTTCTTGGTGATAATATCTTTTACGGTCACGATCTGCCGAAGCTAATGGAGGCCGCTGTTAAC |
| AAAGAAAGTGGTGCAACGGTATTTGCCTATCACGTTAATGATCCAGAACGCTATGGTGTCGTTGAGTTTGA |
| TAAAAACGGTACGGCAATCAGTCTGGAAGAAAAACCGTTAGAACCAAAGAGTAATTACGCCGTTACAGGTC |
| TGTACTTTTATGATAACGACGTGGTTCAGATGGCGAAAAACTTGAAGCCGTCTGCACGTGGTGAGTTAGAA |
| ATTACAGATATTAACCGTATTTATCTTGAGCAGGGACGTCTGTCTGTCGCGATGATGGGGCGTGGCTACGC |
| GTGGCTGGACACGGGGACTCATCAGAGTCTGATAGAAGCAAGTAATTTTATTGCGACAATTGAAGAGCGCC |
| AGGGATTGAAGGTTTCCTGTCCTGAAGAGATTGCATTTCGTAAAGGTTTTATTGATGTTGAGCAAGTAAGA |
| AAATTAGCTGTACCACTAATAAAGAATAATTATGGGCAGTATCTTTATAAAATGACGAAGGATTCAAATTA |
| ATGAATGTGATTAGAACTGAAATTGAAGATGTGCTAATTCTGGAGCCAAGAGTATTTGGTGATGATAGAGG |
| TTTCTTTTATGAGAGCTTTAATCAATCAGCATTTGAACATATTCTAGGCTATCCGGTCAGCTTTGTTCAAG |
| ACAATCACTCACGTTCATCAAAAAATGTACTCAGAGGCCTTCACTTTCAACGCGGCGAGTACGCACAAGAT |
| AAACTTGTACGCTGCACTCATGGAGCAGTTTTTGATGTTGCTGTTGATATTCGACCCAATTCGGTATCCTT |
| TGGTAAATGGGTTGGTGTTCTGCTTTCAGCTGATAATAAGCAGCAGTTGTGGATACCAAAAGGGTTTGCTC |
| ATGGCTTTTTGGTTCTGTCTGATATCGCTGAATTTCAATATAAAACTACAAACTATTATCATCCTGAAAGC |
| GATTGTGGAATATGTTGGAATGATGAACGCATTGCAATTGATTGGCCCCAAACATCAGGGTTAATCCTTTC |
| GCCAAAAGATGAAAGGCTCTTTACGTTAGATGAGCTTATCAGATTAAAATTAATTGCATGAGGCCGGCCTT |
| AAGGAGGACTAGTCCCGGCGCGCCATGAGTTTAATCAAAAACAGTTTTTGGAACCTTTGCGGGTATGTACT |
| TCCAGCTATTGTGACACTACCAGCTTTGGGTATTATGGGGCGAAAATTAGGCCCAGAATTATTTGGTGTAT |
| TCACTTTGGCATTAGCTGTTGTGGGTTATGCAAGCATTTTTGATGCAGGCCTTACTCGCGCAGTGATACGA |
| GAAGTCGCAATTGAAAAAGATAATGAAGAAATAAGTTGAAAATTATTTCTTCAGCGACAGTTGTAATTAT |
| TTATTTGAGTTTGGCCGCCTCACTCTTATTATTTTTTTTAGTGGTCATATCGCATTGCTACTGAACATTA |
| GTGAGACTTTTTTTCATAATGTAAGTGTCTCGCTTAAAATTCTCGCAGCATCCATACCATTATTTTTGATT |
| ACTCAAATATGGTTGTCAATTTTAGAAGGTGAAGAAAGATTTGGTTTACTTAATATCTACAAATCAATTAC |
| GGGAGTGATATTGCAATCTCACCGGCATTATTTATACTTATTAAACCCTCTTTGATGTATGCGATAATAG |
| GCTTAGTTCTAGCAAGGTTTTTATGTTTTATTTTGGCTTTTATAATTTGTCACGATAAAGTGCTTAAAGCT |
| AAACTAACAATCGATATACCAACAATTAAAGATTGTTTATGTTCGGTGGTTGGATTACAGTAAGTAATAT |
| CATCAGCCCTGTGCTATCATATTTTGATAGGTTTATTGTTTCAAATCAACTTGGGGCTGCTAATGTTGCTT |
| TTTATACTGCACCATCAGAAATTATTTCTCGGCTTAGTATAATTCCAGGTGCGTTTTCAAGAGCCTTATTT |
| CCAAGATTAGCTAATGCAAATAATTCCGCTGAAAGATATAAAACGAAAAGATTAATTACAATTTCACTTTT |
| AATAATCATCACCCCTATTTTTTGTATTGGCGTGTTATTTTCAGAGAAGATAATGGTTTTATGGATGGGGG |
| CATCATTTTTTGGTGAGCCTGGTTTGGTATTATCAATATTACTGATTGGCTTTATTTTTAATGGATTGGCA |
| CAAGTACCATTTGCCAGTATTCAATCCCGAGGTCATGCTAAGATAACTGCATTTGTTCATCTCTTAGAGTT |
| GTTTCCTTATTTATTACTTTTATTTTACCTCATAAAAGCACATGGGGTTGTTGGCGCGGGTATTGCGTGGT |
| CAGTGAGGATGATAGTAGATTATATAGCATTAAGTCTTTTGGACGGTAAGTATATTAATAAATAAAATTCA |
| AAATGCAAGTTAATAACTCATGGCTTTATTTGGGTAGGTGACAATTTATAATGATATATATATTAACTTTA |
| ACTCTTCTTCTAGTTATAGCCATAATGTTTTCTCTTCTCGGCACAAAAAGTAGGATCACATCTCCATTACC |
| TTTGCATTTTTTACCATGGTTACTAACTTTAATTGTCGGGATAAGTAATTACGATCAATTTTACAGAGTTA |
| ATGAAAGAAGCTTTTACTCTTTGTTGATTTGGTTTACAGTTATTTTTATATTTTATTTCATAGGGGAACTG |
| GTTAATTATAAACGTGAAAATATAAATGTTTATTATGGTCTTTCACATATTAAATATGAATGTAAAAAATA |
| TTGGATCATTGTCATCCCAATTTCATTATATACCATTTTCGAAATATATATGGTTGGTATGGGGGGAGCAG |
| ATGGATTCTTTCTCAATTTACGTCTTGCAAATACATTGGAGGGCTATACGGGTAAAAAATTTATCTTAATG |
| CCTGCTGTATATCCTCAATGATGGCTATGTTCGCAATTGTTTGTCTAACAAAAACTTCCAAATTAAATAA |
| ATACTCCATTTATTTCTGGATGTTTTTGTATTGTATTGGCACAATGGGAAATTTTCAATATTAACGCCAA |
| TATTGACATATTTAATTATTTATGACTTCAAACATAGATTAAAAGTAAAAAAACAATAAAGTTTACATTG |
| TTGATAATTATATTAGCTTTAACTTTGCATTTTACACGTATGGCTGAGAATGACCACTCAACATTTTTATC |
| TATTTTAGGGCTCTATATTTATTCACCAATAATTGCTTTAGGCCAGTTGAATGAAGTAAATAGTAGTCATT |
| TTGGTGAGTATACGTTTAGATTCATATATGCTATAACTAATAAATTGGCCTTATTAAAGAATTGCCAGTA |
| AATACTATTCTTGACTATTCATACGTTCCTGTACCAACAAATGTATATACTGACTTCAACCATTTTACCA |
| GGATTTTGGTTATACTGGCATCATATTTGGAGCAGTATTATACGGACTAATATATGTGAGTTTATACACGG |
| CCGGTGTTCGTGGAAATAATACACAGGCATTACTGATTTACGCATTGTTTTCAGTTAGCAGTGCAACGCT |
| TTCTTCGCTGAAACGCTAGTAACGAATTTAGCTGGAAATGTGATGTTAGTATTATGTACCATCTTACTATG |
| GCGATTTACAGTAATATGCAAACCAGTACAGTAACCATTCTAATGGCCACCTACAATGGCGAGGCCTTCAT |
| CAAAAATCAGATTTTGTCACTACAACAACAAACATTTTCTAACTGGCGGTTATTTATTCAGGATGATGGGT |
| CTACAGACAATACTATATCTATAATAAAAAACTTCCAAAAATCTGACTCCAGAATTCGGCTAGTTGATGAT |
| AATTTGAAAGGTCAAGGTCAGGAAAAAATTTTTTATCGCTGATAAAGTACAGCGAGACAGATTATACAAT |
| TTATTGTGACCAAGATGATATTTGGTTAGAAAACAAAATATTTGAATTAGTAAAGTATGCAAATGAAATTA |
| AATTGAATGTATCAGATGCGCCTTCGCTAGTTTATGCTGATGGCTATGCTTATATGGATGGTGAGGGTACA |
| ATCGATTTTTCTGGGATATCTAACAATCATCGCTGATCAATTAAAAGGATTTTCTTTTTTTTAATGGTGGATA |
| CCAAGGATGTTCTATTATGTTCAATCGTGCAATGACCAAATTTCTTCTGAATTATCGAGGATTTGTATATC |
| TACATGACGATATCACAACATTAGCTGCATACGCTCTTGGTAAAGTTTATTTTCTCCCGAAATACCTTATG |
| TTATATAGACAGCACACGAATGCGGTAACTGGTATCAAAACATTCCGCAATGGATTGACTTCTAAATTTAA |
| ATCACCAGTAAACTATCTTTTATCACGAAAACATTATCAGGTAAAAAATCTTTTTTTGAATGTAACAGCT |
| CTATCTTATCAGAGACGAATAAAAAAGTTTTTTGGATTTTATTTTGTGAATCAAATAATAATTTT |
| ACAGATTTTTTAAGTTATGGCGAGGTGGGTTTAGATTAAAATAACAGTAGAACTAAATTATTATTAAAATT |
| CTTAATACGGAGAAATTTAGCGAATGATTTCAATACTTACACCTACTTTTAATCGGCAACATACTTTATC |
| AAGGCTATTCAATTCTCTTATATTACAAACTGATAAAGATTTTGAGTGGATAATAATTGATGATGGTAGTA |
| TAGATGCAACAGCGGTACTTGTAGAAGATTTTAGAAAAAAATGTGATTTTGACTTGATTATTGCTATCAG |
| GAAAATAATGGTAAGCCCATGCTTTAAACGCTGGTGTTAAAGCTTGTAGAGGCGATTATATCTTTATTGT |
| TGACAGTGATGATGCACTAACTCCCGATGCCATAAAATTAATTAAAGAATCAATACATGATTGCTTATCTG |

| SEQUENCES |
|---|
| AGAAGGAAAGTTTCAGCGGAGTCGGTTTTAGAAAAGCATATATAAAAGGGGGGATTATTGGTAATGATTTA
AATAATTCTTCAGAACATATATACTATTTAAATGCGACTGAGATTAGCAATTTAATAAATGGTGATGTTGC
ATATTGTTTTAAAAAAGAAAGTTTGGTAAAAAATCCATTCCCCCGTATAGAAGATGAAAATTTGTTCCAG
AATTATATATTTGGAATAAAATAACTGACAAGGCGAAGATTCGATTTAACATAAGCAAAGTTATATATCTT
TGTGAGTATCTTGATGATGGTCTTTCTAAAAATTTCCATAACCAGCTTAAAAAATACCCAAAGGGGTTTAA
GATTTATTACAAAGATCAAAGAAAACGAGAGAAAACTTATATAAAAAAAACAAAGATGCTAATTAGATATT
TGCAATGTTGTTATTATGAGAAAATAAAATGAAAATACTATTTGTCATTACAGGTTTAGGCCTTGGAGGTG
CTGAGAAGCAGGTTTGTCTTTTAGCTGATAAATTAAGTTTAAGCGGGCACCATGTAAAGATTATTTCACTT
GGACATATGTCTAATAATAAAGTCTTTCCTAGCGAAAATAATGTTAATGTCATTAATGTAAATATGTCAAA
AAACATTTCTGGAGTTATAAAAGGTTGTGTCAGAATTAGAGATGTTATAGCTAATTTCAAACCAGACATTG
TACACAGTCATATGTTTCATGCAAACATTATCACTAGATTGTCTGTAATTGGAATCAAAAACAGACCTGGT
ATTATATCAACTGCACATAATAAAAATGAAGGTGGGTATTTCAGAATGCTCACATATAGAATAACCGATTG
TTTAAGTGATTGTTGTACAAATGTTAGCAAAGAAGCAGTGGATGAGTTTTTACGGATAAAAGCCTTTAATC
CCGCTAAAGCAATTACTATGTATAATGGGATAGATACCAATAAATTTAAATTTGATTTATTGGCAAGGAGG
GAAATTCGAGACGGTATTAATATAAAAAATGATGATATATTATTACTTGCTGCAGGTCGTTTAACGTTAGC
TAAAGATTATCCTAATTTATTGAATGCAATGACTCTGCTTCCTGAACACTTTAAACTTATTATTATTGGTG
ATGGTGAATTGCGTGACGAAATTAATATGCTTATAAAAAAATTGCAATTATCTAATAGGGTGTCCTTGTTG
GGAGTTAAAAAAAATATTGCTCCCTATTTTTCTGCATGTGATATTTTTGTTCTCTCTTCTCGTTGGGAAGG
ATTTGGATTAGTCGTGGCAGAAGCTATGTCATGTGAGCGAATTGTTGTTGGCACGGATTCAGGGGGAGTAA
GAGAAGTTATTGGTGACGATGATTTTCTTGTACCCATATCTGATTCAACACAACTTGCAAGCAAAATTGAA
AAATTGTCTTTGAGCCAGATACGTGATCACATTGGTTTTCGGAATCGTGAGCGTATTTTAAAAAATTTCTC
AATAGATACTATTATTATGCAGTGGCAAGAACTCTATGGAACTATAATTTGCTCAAACATGAAAGGTAGA
TTTATATTTGGAACGTGTCTTTTGTTTGAATTTAATTCAATCTCAATTGAGATTTTGTATTTCAAAAATA
CCATCATAGCTAACGATGATTGGTATTTATTTTAAGATGCTTTCTATAAATATATTGACGTTTTTAATGCG
CCGAAACGATTGGGCTGGGAACAGAGAAGTAAAACTGTTTTGAGAATGAAGAGTTTTTGAGATGTTTATGG
ATATTAAAAATTGATCCAGTGAATTAATTATTTATAATAAATCAAGATTTAATGTTAATAAATGATAATCT
TTTCTGACACTCATATTAATTATGAGTGGTACGTTTGGTAAACGGTAAACTATTATATGACAGCTAGAACA
ACTAAAGTTTTGCACTTACAATTACTCCCACTCTTAAGTGGCGTTCAAAGGGTAACATTAAACGAAATTAG
TGCGTTATATACTGATTATGATTATACACTAGTTTGCTCAAAAAAAGGTCCACTAACAAAAGCATTGCTGG
AATATGATGTCGATTGTCATTGTATCCCCGAACTTACGAGAGAAATTACCGTAAAGAATGATTTTAAAGCA
TTGTTCAAGCTTTATAAGTTCATAAAAAAAGAAAAATTTGACATTGTGCATACACATTCTTCAAAAACAGG
TATTTTGGGGCGAGTTGCTGCCAAATTAGCACGTGTTGGAAAGGTGATCCACACTGTACATGGTTTTTCTT
TTCCAGCCGCATCTAGTAAAAAAGTTATTACCTTTATTTTTTCATGAATGGATAGCAAAGTTCTTTACG
GATAAGTTAATCGTCTTGAATGTAGATGATGAATATATAGCAATAAACAAATTAAAATTCAAGCGGGATAA
AGTTTTTTTAATTCCTAATGGAGTAGACACTGATAAGTTTTCTCCTTTAGAAAATAAAATTTATAGTAGCA
CCTTGAATCTAGTAATGGTTGGTAGATTATCCAAGCAAAAAGATCTGTAGAAGCATTATTGCTTGCTGTTGAA
AAACTGCTGAATGAAAATGTTAATGTTAAGCTGACACTTGTAGGAGATGGTGAACTAAAAGAACAGTTAGA
AAGCAGGTTCAAACGGCAAGATGGACGTATAATTTTTCATGGATGGTCAGATAACATTGTTAATATTTTAA
AAGTTAATGATCTTTTTATATTACCTTCTCTTTGGGAGGGTATGCCATTAGCAATTTTAGAAGCATTGAGC
TGTGGACTTCCATGTATAGTCACTAATATTCCAGGTAATAATAGCTTAATAGAAGATGGCTATAATGGTTG
TTTGTTTGAAATTAGAGATTGTCAGTTATTATCTCAAAAAATCATGTCATATGTTGGTAAGCCAGAACTGA
TTGCACAGCAATCTACCAATGCACGATCATTTATTCTGAAAAATTATGGATTAGTTAAAAGAAATAATAAG
GTCAGACAGCTATATGATAATTAAGAGCTCGGTACCCGGGCCTAGGGTGTAGGCTGGAGCTGCTTCGAAGT
TCCTATACTTTCTAGAGAATAGGAACTTCGGAATAGGAACTAAGGAGGATATTCATATCCGTCGACGGCGG
CCGCCCTGCAGGCATGCAAGCTTGATCCATATGGATCGCTAGCTTAATTAAATAAAGCCGTAAGCATATAA
GCATGGATAAGCTATTTATACTTTAATAAGTACTTTGTATACTTATTTGCGAACATTCCAGGCCGCGAGCA
TTCAGCGCGGTGATCACACCTGACAGGAGTATGTAATGTCCAAGCAACAGATCGGCGTAGTCGGTATGGCA
GTGATGGGACGCAACCTTGCGCTCAACATCGAAAGCCGTGGTTATACCGTCTCTATTTTCAACCGTTCCCG
TGAGAAGACGGAAGAAGTGATTGCCGAAAATCCAGGCAAGAACTGGTTCCTTACTATACGGTGAAAGAGT
TTGTCGAATCTCTGGAAACGCCTCGTCGCATCCTGTTAATGGTGAAAGCAGGTGCAGGCACGGATGCTGCT
ATTGATTCCCTCAAACCATATCTCGATAAGGAGACATCATCATTGATGGTGGTAACACCTTCTTCCAGGA
CACTATTCGTCGTAATCGTGAGCTTTCAGCAGAGGGCTTTAACTTCATCGGTACCGGTGTTTCTGGCGGTG
AAGAGGGGGCGCTGAAAGGTCTTCTCTATTATGCCTGGTGGCCAGAAAAGAAGCCTATGAATTGGTAGCACCG
ATCCTGACCAAAATCGCCGCCGTAGCTGAAGACGGTGAACCATGCGTTACCTATATTGGTGCCGATGGCGC
AGGTCACTATGTGAAGATGGTTCACAACGGTATTGAATACGGCGATATGCAGCTGATTGCTGAAGCCTATT
CTCTGCTTAAAGGTGGCCTGAACCTCACCAACGAAGAACTGGCGCAGACCTTTACCGAGTGGAATAACGGT
GAACTGAGCAGTTACCTGATCGACATCACCAAAGATATCTTCACCAAAAAGATGAAGACGGTAACTACCT
GGTTGATGTGATCCTGGATGAAGCGGCTAACAAAGGTACGGGTAAATGGACCAGCAGAGCGCGCTGGATC
TCGGCGAACCGCTGTCGCTGATTACCGAGTCTGTGTTTGCACGTTATATCTCTTCTGAAAGATCAGCGT
GTTGCCGCATCTAAAGTTCTCTCTGGTCCGCAAGCACAGCCAGCAGGCGACAAGGCTGAGTTCATCGAAAA
AGTTCGTCGTCGCGCTGTATCTGGGCAAAATCGTTTCTTACGCCAGGCTTCTCTCAGCTGCGTGCTGCGT
CTGAAGAGTACAACTGGGATCTGAACTACGGCGAAATCGCGAAGATTTTCCGTGCTGGCTGCATCATCCGT
GCGCAGTTCCTGCAAAAAATCACCGATGCTTATGCCGAAAATCCACAGATCGCTAACCTGTTGCTGGCTCC
GTACTTCAAGCAAATTGCCGATGACTACCAGCAGGCGCTGCGTGATGTCGTTGCTTATGCAGTACAGAACG
GTATTCCGGTTCCGACCTTCTCCGCAGCGGTTGCCTATTACGACAGCTACCGTGCTGCTGTTCTGCCTGCG
AACCTGATCCAGGCACAGCGTGACTATTTTGGTGCGCATACTTATAAGCGTATTGATAAAGAAGGTGTGTT
CCATACCGAATGGCTGGATTAA |

SEQ ID NO: 18 (example O25B rfb locus nucleotide sequence - O25B-EPA production strain stGVXN4459)
ATGACGAATTTAAAAGCAGTTATTCCTGTAGCGGGTCTCGGGATGCATATGTTGCCTGCCACTAAGGCGAT
ACCCAAAGAGATGCTACCAATCGTCGACAAGCCAATGATTCAGTACATTGTTGACGAGATTGTGGCTGCAG
GGATCAAAGAAATCCTCCTGGTAACTCACGCGTCCAAGAACGCGGTCGAAAACCACTTCGACACCTCTTAT
GAGTTAGAATCACTCCTTGAGCAGCGCGTGAAGCGTCAACTGCTGGCGGAAGTACAGTCCATCTGTCCGCC
GGGCGTGACCATTATGAACGTGCGTCAGGGCGAACCTTTAGGTTTAGGCCACTCCATTTTGTGTGCGCGAC
CTGCCATTGGTGACAACCCATTTGTCGTGGTACTGCCAGACGTTGTGATCGACGATGCCAGCGCCGACCCG
CTACGTTACAACCTTGCTGCCATGATTGCACGTTTCAACGAAACGGGCCGCAGCAGGTGCTGGCAAAACG

| SEQUENCES |
|---|
| TATGCCGGGTGACCTCTCTGAATACTCCGTCATCCAGACTAAAGAGCCGCTGGACCGTGAGGGTAAAGTCA |
| GCCGCATTGTTGAATTTATCGAAAAACCGGATCAGCCGCAGACGCTGGACTCAGACATCATGGCCGTAGGT |
| CGCTATGTGCTTTCTGCCGATATTTGGCCGGAACTGGAACGTACTCAGCCTGGTGCATGGGGACGTATTCA |
| GCTGACTGATGCTATTGCCGAGCTGGCGAAAAAACAATCCGTTGATGCAATGCTGATGACCGGCGACAGTT |
| ACGACTGCGGCAAAAAAATGGGCTATATGCAGGCGTTTGTGAAGTATGGCCTACGCAACCTGAAAGAAGGG |
| GCGAAGTTCCGTAAAGGTATTGAGAAGCTGTTAAGCGAATAATGAAAATCTGACCGGATGTAACGGTTGAT |
| AAGAAAATTATAACGGCAGTGAAAATTCGCAGCAAAAGTAATTTGTTGCGAATCTTCCTGCCGTTGTTTTA |
| TATAAACCATCAGAATAACAACGAGTTAGCAGTAGGGTTTTATTCAAAGTTTTCCAGGATTTTCCTTGTTT |
| CCAGAGCGGATTGGTAAGACAATTAGCGTTTGAATTTTTCGGGTTTAGCGCGAGTGGGTAACGCTCGTCAC |
| ATCATAGGCATGCATGCAGTGCTCTGGTAGCTGTAAAGCCAGGGGCGGTAGCGTGCATTAATACCTCTATT |
| AATCAAACTGAGAGCCGCTTATTTCACAGCATGCTCTGAAGTAATATGGAATAAATTAAGCTAGCAGTGAA |
| GATACTTGTTACTGGTGGCGCAGGATTTATTGGTTCTGCTGTTGTTCGTCACATAATAAATAATACGCAAG |
| ATAGTGTTGTTAATGTCGATAAATTAACATACGCCGGAAACCTGGAATCACTTGCAGATGTTTCTGATTCT |
| GAACGCTATTTCTTTGAACATGCGGATATTTGTGATGCAGCTGCAATGGCACGGATTTTGCTCAGCATCA |
| GCCGGATGCAGTGATGCACCTGGCAGCTGAAAGCCATGTTGACCGTTCAATTACAGGCCCTGCGGCATTTA |
| TTGAAACCAATATTGTGGGTACTTATGTCCTTTTAGAAGCGGCTCGGAATTATTGGTCTGGTCTGGATGAT |
| GAAAAGAAAAAAACTTCCGTTTTCATCATATTTCTACTGATGAGGTGTATGGTGACTTACCCCATCCGGA |
| TGAAGTAAATAGCAATGAAACGTTGCCGCTATTTACGGAAACGACAGCATACGCGCCAAGTAGTCCATATT |
| CTGCTTCTAAAGCTTCCAGCGATCATTTGGTTCGCGCATGGAAACGTACTTATGGTTTACCGACCATTGTG |
| ACTAATTGCTCGAACAACTATGGTCCTTATCATTTCCCGAGAAAGCTTATTCCACTGGTTATTCTTAATTC |
| ACTGGAAGGTAAGGCATTACCTATTTATGGCAAAGGAGATCAGATCCGCGACTGGTTGTATGTAGAGGATC |
| ATGCTCGAGCGTTATATACCGTCGTAACCGAAGGTAAAGCGGGCGAAACTTATAACATTGGTGGACACAAC |
| GAAAAGAAAAACATCGACGTAGTGTTCACTATTTGTGATTGTTGGATGAGATAGTCCCGAAAGAGAAATC |
| TTACCGCGAGCAAATTACTTATGTTACCGATCGTCCGGGACACGATCGCCGTTATGCGATTGATGCTGAGA |
| AGATTGGTCGCGAATTGGGATGGAAACCACAGGAAACGTTTGAGAGTGGGATTCGTAAAACGGTGGAATGG |
| TACCTGTCCAATACAAAATGGGTTGATAATGTGAAAAGTGGTGCCTATCAATCGTGGATTGAACAGAACTA |
| TGAGGGCCGCCAGTAATGAATATCCTCCTTTTTGGCAAAACAGGGCAGGTAGGTTGGGAACTACAGCGTGC |
| TCTGGCACCTCTGGGTAATTTGATTGCTCTTGATGTTCACTCCACTGATTACTGTGGTGATTTTAGTAATC |
| CTGAAGGTGTAGCTGAAACCGTAAGAAGCATTCGGCCTGATATTATTGTCAACGCAGCCGCTCACACCGCA |
| GTAGACAAAGCAGAATCAGAACCGAAGTTTGCACAATTACTGAACGCGACGAGTGTCGAAGCGATCGCGAA |
| AGCAGCCAATGAAGTCGGCGCCTGGGTTATTCACTACTCTACTGACTACGTATTTCCGGGGACCGGTGAAA |
| TACCATGGCAGGAGGAGGATGCAACCGCACCGCTAAATGTTTACGGTGAAACCAAGTTAGCGGGAGAAAAA |
| GCATTACAAGAGCATTGTGCGAAGCACCCTTATTTTCCGGACCAGCTGGGTCTATGCAGGTAAAGGAAATAA |
| CTTCGCCAAAACAATGTTGCGTCTGGCAAAGAGCGTGAAGAATTAGCCGTTATTAATGATCAGTTTGGTG |
| CGCCAACTGGCGCAGAGTTACTGGCTGATTGTACGGCACATGCTATTCGTGTGGCACTGAATAAACCGGAA |
| GTCGCAGGCTTGTACCATCTGGTAGCTAGTGGTACCACAACGTGGCACGATTATGCTGCGCGTGGTTTTGA |
| AGAGGCGCGCAAAGCAGGCATTCCCCTTGCACTCAACAAGCTCAACGCAGTACCAACAACAGCCTATCCTA |
| CACCAGCTCGTCGTCCACATAACTCTCGCCTTAATACAGAAAAATTTCAGCAGAACTTTGCGCTTGTCTTG |
| CCTGACTGGCAGGTTGGCGTGAAACGAATGCTTAACGAATTATTTACGACTACAGCAATTTAATAGTTTTT |
| GCATCTTGTTCGTAATGGTGGAGCAAGATGTATTAAAAGGAATGATGAAATGAAAACGCGTAAAGGTATTA |
| TTTTGGCGGGTGGTTCTGGTACTCGTCTTTATCCTGTGACGATGGCCGTCAGTAAACAGCTGTTACCGATT |
| TATGATAAACCGATGATCTATTACCCGCTCTCTACACTGATGTTAGCGGGTATTCGCGATATTCTGATTAT |
| CAGTACACCACAGGATACTCCTCGTTTTCAACAACTGCTGGGTGACGGGAGCCAGTGGGGCCTGAATCTTC |
| AGTACAAAGTGCAACCGAGTCCGGATGGTCTTGCGCAGGCGTTTATTATCGGTGAAGAGTTTATTGGTGGT |
| GATGATTGTGCTTTGGTACTTTGGTGATAATATCTTCTACGGCCACGACCTGCCGAAGTTAATGGACGTAGC |
| TGTTAACAAAGAAAGTGGTGCAACGGTATTTGCCTATCACGTTAATGATCCTGAACGTTATGGTGTCGTGG |
| AGTTTGATAATAACGGTACTGCAATTAGCCTGGAAGAAAAACCGCTGGAACCAAAAGTAACTATGCGGTT |
| ACTGGGCTTTATTTCTATGACAATGACGTTGTGGAAATGGCGAAAAACCTTAAGCCTTCTGCCCGAGGTGA |
| ACTGGAAATTACCGATATTAACCGTATTTATATGGAACAAGGACGTTTGTCTGTCGCTATGATGGGGCGTG |
| GCTATGCATGGCTGGATACAGGGACGCATCAAAGTCTTATTGAAGCAAGCAACTTCATTGCCACCATTGAA |
| GAGCGCCAGGGACTAAAGGTTTCCTGTCCGGAAGAAATTGCTTATCGTAAAGGGTTTATTGATGCTGAGCA |
| GGTAAAAGTATTAGCCGAACCGTTGAAGAAAAATGCTTATGGTCAGTATCTGCTCAAAATGATTAAAGGTT |
| ATTAATAAGATGAACGTAATTAAAACTGAAATTCCTGATGTGCTGATTTTTGAACCAAAAGTTTTTGGGAA |
| TGAACGTGGCTTCTTTTTTGAGAGTTTTAATCAGAGGATTTTTGAAGAAGCAGTAGGTCGTAAGGTTGAGT |
| TTGTTCAGGATAACCATTCTAAGTCCAGTAAAGGTGTTTTACGTGGTCTTCATTATCAGTTAGAACCTTAT |
| GCTCAAGGAAAACTGGTGCGCTGTGTTGTTGGCGAGGTTTTTGATGTTGCGGTTGATATTCGTAAATCGTC |
| ACCTACATTTGGGAAATGGGTTGGGGTGAATTTGTCTGCTGAGAATAAGCGTCAGTTGTGGATTCCTGAGG |
| GATTTGCACATGGTTTTTTGGTGCTGAGTGATTTAGCAGAAGTTTTATATAAAACGAATCAATATTATGCT |
| CCATCACATGAAAAAAATATTATATGGAATGACCTCTTGCTTAATATTAAATGGCCGAGCACAGCACTGAT |
| CACTCTGTCTGATAAGGATGCAAATGGGGAAAGATTTGAACTAAGTGAGTTTTGAAATGTCTCTCTTAAAA |
| CATAGTATATGGAATGTTGCGGGCTACTTTATACCAACATTAATTGCAATTCCCGCCTTTGGATTAATTGC |
| GAGGAAAATTGGTGTAGAACTATTTGGTTTGTATACGTTAGCAATGATTTTTATAGGGTATGCAAGTATAT |
| TTGATGCTGGGTTAACAAGAGCTGTTGTGCGTGAAATAGCATTACTAAAAAACAGAGTGGACGATTGTAAT |
| ACGATAATAGTAACTTCTATTATCGCTGTGATATTTTTAGGGTTTATCGGAGGCGGGGAGTGTTTCTGCT |
| TAAAGGCGATATTATTGAACTGTTAAATATCTCACCAATATATTACGCCGATTCGATAAAGTCTCTAGTAT |
| TATTATCATCTCTGATACCTGTATTCTTAGTCACGCAAATACTATTGCAGAGCTTGAGGGTCGGGAATAA |
| TTTGGGATTCTAAATATACAAAAAAGTGTAGGGAATTCTTTAATTGCAGGGATTACCTGCATTATTTGTTT |
| AATTAATCAAACGCTTTTTTCTGCAATTATTGGTGTAGCGATTGCAAGAGTTATATGCTTGTGGTTAAGCT |
| ACATTATGAGCAGGGAAAGAATAACTATCGATATCTCATTTTTTTCAATAACTGTTTTAAAGCGGTTATTT |
| AGATATGGCGGGTGGGTAACTATAAGTAACATAATATCTCCTATATTAGCGAGTATGGATAGATTTATTCT |
| ATCCCATATCCAGGGAGCATCAAAAATCATTCTATACAGTCCTAATGAGCTGGTAACTAGGCTTGGAA |
| TAGTTCCAGGCTCTCTTGGGAAAGCTGTTTTTCCAAAATTAAGTCATGCAAGGAATTTTACAGCGTCATAT |
| GCAGAGCAAAAAAAAGCTTATATATTAATGACTGTCATTGTAATGCCTTTGGTTTTATTTGTATATTATTA |
| CGCAAAGTTTATTTTAACATTGTGGATGGGGCTGAGTATGCAGGGATTTCGGTCGAAATATTACGGATTA |
| TGCTTATAGGGTATATTTTAACTGTTATTCACAAATCTCTTTTGCCAACATACAGGCCTTTGGAAAAGCA |
| AAATACACTGCATACATCCATATGATGGAATTTATTCCTTATTTGATAATGTTATATAATTTCAAAGGA |
| ATATGGGGTTATTGGTGTTGCGTGGTTATGGACAATTCGAGTAATAATTGATTTTTTGATGCTTTTATATA |

| SEQUENCES |
|---|
| TGAGTTATCGTTGTAATAATCTTATGAAAAAGGGTAGCCTGATGATATATATTGTGGTATTAAATTGGAA |
| TGGGGCTATAGATACCATTAATTGTGTTAAAAGTTTAATGGATTTAAATGTTAGCGATTATAAAATTATCA |
| TTGTTGATAACTGTTCTATGGATAACTCATATGATACTATAAAAGAAAATCTTAATTCATTATATATTGCT |
| GATAAAAGTATCATTGAGGTGAAGTATGAGGATAGAAATAAATATAAAACCTTAGAAAACGATAAAATCAT |
| ATTAATACAATCTCCGCAAAATAATGGGTACGCAAGTGGTAATAATATTGGCATAGAGTTCGCTCTTAATC |
| AGGAGAATATGAAATACGTCTGGGTTCTGAATAATGATACTGAAGTGGATAAAGAGGCTTTAACTCATTTA |
| ATTAGTAAATGTGATTCAGATAAAAGTATAGGGATTTGCGGTTCTCGTTTAGTCTATTTTGCCGACAGAGA |
| GATGCAGCAAGGACTAGGTGGGGTGCATAACAAATGGTTATGCACTACAAAAAATTATGAAATGGGAAGAT |
| TAGTTTCCAAAAAATATGATGATGAAGTCATTAGTAATGATATAGATTATATAATTGGCGCATCGATGTTT |
| TTCTCTAGAGAATGTTTGGAAACAGTTGGATTGATGAATGAAGAATATTTTTTATACTATGAAGAGTTAGA |
| TATTTGCCTCAGAGCAAAAGCAAAGAACTTTAAATTAGGTATTTGCTCAGAAAGTTTGGTTTATCATAAAA |
| TAGGTGCAAGTACTGATGGGGGAAAGAGCATGATGGCTGATCTTTGCTCAATAAAAAATAGGCTGGTCATT |
| ACAGAAAGGTTTTATCCCCAATATTATTGGACGGTATGGTTGTCACTTTTTGTTGTAGCATTTAACCGTGC |
| TAGAAGAGGTGAGTTTAATAAGATGAAAAGATGTTTGAATGTTATGTTTAACTTCAAACGAAACAAAGGTA |
| GCAAATGCCATTAGAATATGCACTTAATCATGGTGTTAATAAATCTATAGTTTGATATGTTATTAAAGGGT |
| ATTTAATGAAAGTGGCTTTTTTATCTGCTTATGATCCACTATCTACATCCAGTTGGTCTGGCACACCTTAT |
| TATATGCTAAAGGCATTATCGAAGAGAAATATTTCCATTGAAATATTAGGACCGGTAAATAGCTATATGAT |
| ATACATGTTAAAAGTATATAAATTAATATTAAGGTGTTTCGGAAAAGAATATGATTATAGTCATTCGAAGT |
| TGCTTTCCAGGTATTACGGTAGAATATTCGGTAGGAAATTAAAAAAAAATTGATGGTTTGGATTTTATTATC |
| GCACCTGCAGGTTCCTCACAAATTGCTTTTTTAAAAACAACCATACCAATAATATATCTATCGGATACAAC |
| ATATGATCAATTAAAAAGCTATTATCCGAATTTAAATAAAAAAACAATTATAAATGATGAGGATGCAAGTT |
| TAATCGAACGCAAGGCTATTGAAAAAGCAACAGTAGTATCTTTCCCATCTAAATGGGCAATGGATTTTTGC |
| AGGAATTATTACAGATTAGATTTTGATAAATTAGTTGAAATACCATGGGGGGCTAATTTATTTGATGATAT |
| TCACTTTGCTAATAAAAATATAATTCAAAAGAATAGTTATACTTGTCTTTTCTTGGGAGTTGATTGGGAAA |
| GAAAAGGTGGGAAAACAGCCTTGAAAGCAATTGAATATGTAAGGCAGTTATATGGGATCGATGTTAGACTA |
| AAAATTTGTGGATGTACTCCGAATCAAAAGATTTTACCTACTTGGGTTGAATTAATTGATAAAGTAGATAA |
| AAATAACGTTGACGAATATCAGAAATTCATCGATGTGTTATCTAACGCTGATATACTTCTTTTACCAACCA |
| TTGCTGAATGTTATGGAATGGTATTTTGTGAAGCTGCTGCTTTTGTGGTTATGTTCTGAAGAAATACTTAAG |
| GGTGGAGTCAGTTCTATAGTTATCAACGAAAGGACGGGGATATTAATTAAAGACCCGTTAGACTATAAGCA |
| CTTTGGAAATGCAATTCATAAAATAATTAGTTCCGTAGAGACTTATCAAAACTACTCCCAAAACGCAAGAA |
| TTAGATATAATAATATATTGCATTGGGACAATTGGGCTAAAAAGATAATTGAGATTATGTATGAGCATAAG |
| AATAGAAGAATCAAATAGCACAAAAAGAATTATATGTTTATTTATACTTTTTCTTGTTTTCCCTGATTTTT |
| TGTTTTATACATTAGGGGTTGATAATTTTAGCATTTCAACGATAATCTCAATTACATTGCTTTTTGTTTTT |
| TTAAGAGCTAAAATATTTGCAAAGATAATTTTCTAATAATAGTAGCGTTATTCATATTGTTGTGTTTTAA |
| CTGTTTGTTAAGTATGCTATTTAATATTGAACAGGCTTTAACATTTAAAGTTGTACTTTCAATATATAGCA |
| TCTTAATAATGGCATACGTCTCCTCTTGTTATGCACAGACGTTGTGGTTATGTTCTGAAGAAATACTTAAG |
| AGATCCGTCTTTTATTTGTTCGCATTTCTTTGCCTTATTGGCATTATAAGTATTCTTTTACAGAAGACTGA |
| GATTATACATGATAAAAGTATGATTCTTTTTCCTGAACCATCAGCATTTGCATTGGTTTTTATACCTATCT |
| TTTCATTTTGTTTATACTATACAAGAGGGGGGGGGCTACTATTGCTCTATATATTATCTTTGGGTATTGCG |
| TTAGGTATCCAGAATTTAACAATGTTGGTAGGCATTGTGATTAGTGTTTTTGTGATGAAAAAATACTAT |
| AAGGCAAACTATTGTTATACTTTTGGGGGCATGGATTTTTTCCATGATATTAAGTGATTTAGACATTTCTT |
| ACTATACATCGCGGCTTGATTTTAAAAATACTACGAACCTATCAGTGCTTGTATATCTTTCAGGAATTGAA |
| AGAGCTTTCTTGAATTTTATTACAAGTTATGGTCTTGGTATTGGTTTTCAACAAATGGGAGTGAATGGGGA |
| GATAGGAATATATCAACAAATTTTAGCTGAACTTGATGCCCCTATGTTAAATATATACGATGGCTCATTTA |
| TTTCTTCTAAGTTAATATCTGAGTTTGGGGTTATTGGTGCATTAATGTGTATTTTCTATTTTTTTATTTT |
| TCCCGATTTTATCTGCGTTTCAAAAAAAGTAAGAGATATTCACCGCAGTATATTTTAGCATATAGCTTCTA |
| CATGTGTTTCTTCATCCCTCTTTTTATACGTGGTGCTGGTTATATAAACCCCTATGTGTTTATGTTATTTT |
| CATCAATATTTTGTGCAAATATCACGCTAAAAATATCTTGATGAAATCTAATGTCCAGATAGCTATATAA |
| TAGTAGATTATATTATCATTATGCACGTAAATTACATATTAATAGCATATATGATAACTAGGACATAAATAA |
| TGTGCATTAAAAAAAAAACTTAAGTTAATTAAACGATATGGCCTTTATGGTGGTCTTAGGCTTCTTAAAGAT |
| ATATTCTTAACAAAATTTTATTTTGTTCAAATGTTAGGATTATTAGATTTCCATGTTATATTAGAAAAGA |
| TGGAAGTGTTAGTTTTGGAAAAGGTTTTACATCAGGTGTAGGATTACGAGTTGATGCATTTATGGATGCCG |
| TAGTTTCCATTGGAGAAAATGTTCAAATTAATGACTATGTTCACATCGCGGCTATTAATAATGTCATTATT |
| GGTAGAGATACATTAATAGCAAGTAAAGTATTTATTAGTGATCATAATCATGGTATTTTTCTAAATCCGA |
| TATCCATAGTTCACCAACTATTATTCCTTCGTCTAGGCCCCTTGAATCTGCACCTGTGTATATTGGAGAGC |
| GTGTGTGGATTGGCGAAAATGTGACAATATTACCAGGTGCGTGTATAGGTAATGGTGTAGTTATTGGCGCA |
| AACAGTGTTGTTCGTGGTGAGATTCCTAATAATGTGATCATTGCTGGTGTTCCAGCTAAAATTGTTAAAAA |
| ATATAACTATGAGCGTATGCAATGGGAAAGAATATAGTTGTAATATCGGCTGTTAATTTTACAACCGGAGG |
| CCCCTTTACCGTACTAAAAAATGTGCTTACAGCAACTAAAGATAGAGCCGAATGTAAATTTATTGCACTGG |
| TTCATAGCTCTGCTGAACTAATGGAATTATTTCCGTGGGTTGAATTTATAGAGTATCCAGAAGTCAAGTCT |
| TCGTGGGTTAAAAGATTATATTTCGAATATATAACTTGCAATAGATTATCTAAGGTGATTAAGGCAACTCA |
| TTGGGTATGCTTACATGATATTACAGCAAATGTTAGTGTACCCTATAGATTTGTTTATTGCCACAATCCTG |
| CACCGTTCTATAAATATTTAAGCTATCGAGATATTATAGGAGAACCTAAATTTTATCTTTTTATCTTTTT |
| TATGGGCTTTTATACAATATCAATATAAAAAGAACACAGCAGTTTTTGTTCAGCAGCAGTGGCTAAAAAA |
| AGAATTCGAAAAAAATATAAGTTAAAGAATGTTGTTGTTAGTCGCCCTGAAGATATTTGCCCTTTTGAAA |
| GTGATGGTTTGGTAAGAAATAATAATAAAAAGGATGTGAGGATATTTTACCCAGCAGTGCCCGTATATTT |
| AAAAACTTTGAAGTTATCATACGTGCTGCACAAATATTACAAGATAAAAATATTCATTTTTATCTTACTTT |
| TGATGGTACTGAAAATAAGTATGCAAAAGAATATATAAATTAGCTTCCGAACTGAAAAATGTACATTTCC |
| TCGGTTACCTTAATGCAACCGAGATGGTTAACTTTTATCAAGATTCAGATATTATTTGTTTCCCATCGAAA |
| CTAGAAACGTGGGGATTACCATTATCAGAAGCTAAAACATACAAAAAATGGATATTTGCGGCAGACTTACC |
| TTATGCTCATGAAGTTTTATATAACTATTCAAAAACTAGATATTTTCCATTTGACGATGAGAAAATACTTG |
| TTCGCTACATATTAGAGTACACAAGTAAAAATATGCATGAAGATATAAAAAATAGTAGGGTGAATTTTAAT |
| AATGATGCATTGACTGGTTTTGAACAGTTTATTGAATATATCCTCAAGGGGAACTGACGTGGTTTATATTA |
| TAATCGTTTCACATGGCCATGATGACTATATAGAAAATCTTTTATTAAATTTAAAGTTGCCCTCTGGAAGA |
| TTTAAAATAATAGTTCGTGATAACAAAAGTTCAATGGTTTTAAAAAAAACATGCGAAAAAATTGCGTAAC |
| CTATTTGCATGGAGGGCAATATGGATTTGGACATAATAATAACATAGCAGTGTCATATATAATTAATAACT |
| TCATGATTATGAATAATGATTATTTTCTCTTTCTTAACCCCGATGTATTCATAACCAGTGAAAGTTTGATT |

| SEQUENCES |
|---|
| AATTATGTTGATTATATAATTAGTAATGATTATAAGTTTAGCACATTATGTCTTTATCGAGATTTTACTAA |
| AAGCAAACATGATTATTCAATACGGAGTTTTCCAACTTTATATGATTTTCTTTGTTCTTTTTTATTGGGGG |
| TGAATAAAAGTAAAATTAAGAAGGAAAATATACTTTCTGATACTGTAGTTGATTGGTGTGCTGGCTCATTT |
| ATGCTTATTCATGCTTTAAGTTTCTTAAATGTGAATGGTTTTGATCAAAAATATTTTATGTATTGTGAAGA |
| TATTGACCTTTGTATGCGTTTAAAATTAAGTGGAGTAGATCTTTACTATACTCCCCATTTTGATGCTATTC |
| ATTATGCGCAGCATGAAAATAGAAGAATATTTACTAAAGCATTTCGATGGCATATAAGGAGTATTACGCGC |
| TACATATTACGGAAACCAATTCTTTCTTATAAAAACTATAGAAAAATTACATCCGAACTGGTAAAGTGATT |
| AAGGATCCGTGTAGGCTGGAGCTGCTTCGAAGTTCCTATACTTTCTAGAGAATAGGAACTTCGGAATAGGA |
| ACTAAGGAGGATATTCATATGGATAAAGCCGTAAGCATATAAGCATGGATAAGCTATTTATACTTTAATAA |
| GTACTTTGTATACTTATTTGCGAACATTCCAGGCCGCGAGCATTCAGCGCGGTGATCACACCTGACAGGAG |
| TATGTAATGTCCAAGCAACAGATCGGCGTAGTCGGTATGGCAGTGATGGGACGCAACCTTGCGCTCAACAT |
| CGAAAGCCGTGGTTATACCGTCTCTATTTTCAACCGTTCCCGTGAGAAGACGGAAGAAGTGATTGCCGAAA |
| ATCCAGGCAAGAAACTGGTTCCTTACTATACGGTGAAAGAGTTTGTCGAATCTCTGGAAACGCCTCGTCGC |
| ATCCTGTTAATGGTGAAAGCAGGTGCAGGCACGGATGCTGCTATTGATTCCCTCAAACCATATCTCGATAA |
| AGGAGACATCATCATTGATGGTGGTAACACCTTCTTCCAGGACACTATTCGTCGTAATCGTGAGCTTTCAG |
| CAGAGGGCTTTAACTTCATCGGTACCGGTGTTTCTGGCGGTGAAGAGGGGGCGCTGAAAGGTCCTTCTATT |
| ATGCCTGGTGGCCAGAAAGAAGCCTATGAATTGGTAGCACCGATCCTGACCAAAATCGCCGCCGTAGCTGA |
| AGACGGTGAACCATGCGTTACCTATATTGGTGCCGATGGCGCAGGTCACTATGTGAAGATGGTTCACAACG |
| GTATTGAATACGGCGATATGCAGCTGATTGCTGAAGCCTATTCTCTGCTTAAAGGTGGCCTGAACCTCACC |
| AACGAAGAACTGGCGCAGACCTTTACCGAGTGGAATAACGAGTAAGCGCAGTTACCTGATCGACATCAC |
| CAAAGATATCTTCACCAAAAAAGATGAAGACGGTAACTACCTGGTTGATGTGATCCTGGATGAAGCGGCTA |
| ACAAAGGTACCGGTAAATGGACCAGCCAGAGCGCGCTGGATCTCGGCGAACCGCTGTCGCTGATTACCGAG |
| TCTGTGTTTGCACGTTATATCTCTTCTCTGAAAGATCAGCGTGTTGCCGCATCTAAAGTTCTCTCTGGTCC |
| GCAAGCACAGCCAGCAGGCGACAAGGCTGAGTTCATCGAAAAAGTTCGTCGTGCGCTGTATCTGGGCAAAA |
| TCGTTTCTTACGCCCAGGGCTTCTCTCAGCTGCGTGCTGCGTCTGAAGAGTACAACTGGGATCTGAACTAC |
| GGCGAAATCGCGAAGATTTTCCGTGCTGGCTGCATCATCCGTGCGCAGTTCCTGCAGAAAATCACCGATGC |
| TTATGCCGAAATCCACAGATCGCTAACCTGTTGCTGGCTCCGTACTTCAAGCAAATTGCCGATGACTACC |
| AGCAGGCGCTGCGTGATGTCGTTGCTTATGCAGTACAGAACGGTATTCCGGTTCCGACCTTCTCCGCAGCG |
| GTTGCCTATTACGACAGCTACCGTGCTGCTGTTCTGCCTGCGAACCTGATCCAGGCACAGCGTGACTATTT |
| TGGTGCGCATACTTATAAGCGTATTGATAAAGAAGGTGTGTTCCATACCGAATGGCTGGATTAA |

SEQ ID NO: 19 (example O75 rfb locus nucleotide sequence - O75-EPA production strain stLMTB11737)
| |
|---|
| ATGACGAATTTAAAAGCAGTTATTCCTGTAGCGGGTCTCGGGATGCATATGTTGCCTGCCACTAAGGCGAT |
| ACCCAAAGAGATGCTACCAATCGTCGACAAGCCAATGATTCAGTACATTGTTGACGAGATTGTGGCTGCAG |
| GGATCAAAGATAACCTCCTGGTAACTCACGCGTCCAAGAACGCGTCGCGAAAACCACTTCGACACCTCTTAT |
| GAGTTAGAATCACTCCTTGAGCAGCGCGTGAAGCGTCAACTGCTGGCGGAAGTACAGTCCATCTGTCCGCC |
| GGGCGTGACCATTATGAACGTGCGTCAGGGCGAACCTTTAGGTTTAGGCCACTCCATTTTGTGTGCGCGAC |
| CTGCCATTGGTGACAACCCATTTGTCGTGGTACTGCCAGACGTTGTGATCGACGATGCCAGCGCCGACCCG |
| CTACGTTACAACCTTGCTGCCATGATTGCACGTTTCAACGAAACGGGCCGCAGCCAGGTGCTGGCAAAACG |
| TATGCCGGGTGACCTCTCTGAATACTCCGTCATCCAGATCTAAAGAGCCGCTGGACGTGAGGGTAAAGTCA |
| GCCGCATTGTTGAATTTATCGAAAAACCGGATCAGCCGCAGACGCTGGACTCAGACATCATGGCCGTAGGT |
| CGCTATGTGCTTTCTGCCGATATTTGGCCGGAACTGGAACGTACTCAGCCTGGTGCATGGGGACGTATTCA |
| GCTGACTGATGCTATTGCCGAGCTGGCGAAAAACAATCCGTTGATGCAATGCTGATGACCGGCGACAGTT |
| ACGACTGCGGCAAAAAAATGGGCTATATGCAGGCGTTTGTGAAGTATGCCTACGCAACCTGAAAGAAGGG |
| GCGAAGTTCCGTAAAGGTATTGAGAAGCTGTTAAGCGAATAATGAAAATCTGACCGGATGTAACGGTTGAT |
| AAGAAAATTATAACGGCAGTGAAATTCGCAGCAAAGTAATTTGTTGCGAATCTTCCTGCCGTTGTTTTA |
| TATAAACCATCAGAATAACAACGAGTTAGCAGTAGGGTTTTATTCAAAGTTTTCCAGGATTTTCCTTGTTT |
| CCAGAGCGGATTGGTAAGACAATTAGCGTTTGAATTTTTCGGGTTTAGCGCGAGTGGGTAACGCTCGTCAC |
| ATCATAGGCATGCATGCAGTGCTCTGGTAGCTGTAAAGCCAGGGGCGGTAGCGTGCATTAATACCTCTATT |
| AATCAAACTGAGAGCCGCTTATTTCACAGCATGCTCTGAAGTAATATGGAATAAATTAAGCTAGCAGTGAA |
| GATACTTGTTACTGGTGGCGCAGGATTTATTGGTTCTGCTGTTGTTCGTCACATAATAAATAATACGCAAG |
| ATAGTGTTGTTAATGTCGATAAATTAACATACGCCGGAAACCTGGAATCGCTCGCTGAAATTTCTGATTCT |
| GAACGTTATTCATTTGAGCATGCAGATATCTGCGATGCCGAAGCGATGGCTCGTATTTTCGCACAGCACCA |
| GCCAGACGCGGTGATGCACCTGGCAGCAGAGAGCCACGTTGACCGCTCAATAACTGGCCCTGCGGCATTTA |
| TTGAAACCAATATTGTGGGTACTTATGTTCTTTTAGAAGCGGCGCGCAATTATTGGTCTGGTCTGGATGAT |
| GAAAAGAAAAAAAACTTCCGCTTTCATCATATTTCTACTGATGAGGTGTATGGTGACTTACCCCATCCGGA |
| TGAAGTAAATAGCAATGAAACGTTGCCGCTATTTACGGAAATGACAGCATACGCGCCAAGTAGTCCATATT |
| CTGCTTCTAAAGCTTCCAGCGATCATTTGGTTCGCGCATGGAAACGTACTTATGGTTTACCGACCATTGTG |
| ACTAATTGCTCGAACAACTATGGTCCTTATCATTTCCCGGAAAAGCTTATTCCACTGGTTATTCTTAATGC |
| ACTGGAAGGTAAGGCATTACCTATTTATGGCAAAGGAGATCAGATCCGCGACTGGTTGTATGTAGAGGATC |
| ATGCTCGAGCGTTATATACCGTCGTAACCGAAGGTAAAGCGGGCGAAACTTATAACATTGGTGGACACAAC |
| GAAAAGAAAAACATCGACGTAGTGTTCACTATTTGTGATTGTTGGATGAGATAGTCCCGAAAGAGAAATC |
| TTATCGTGAGCAAATTACCTATGTTGCTGATCGCCCAGGGCATGATCGCCGTTATGCAATTGATGCCGATA |
| AAAATTAGCCGCGAATTGGGCTGGAAACCACAGGAAACGTTTGAGAGCGGGATTCGTAAAACTGTGGAATGG |
| TATCTGTCCAATACAAAATGGGTTGATAATGTGAAAAGTGGTGCCTATCAATCGTGGATTGAACAGAACTA |
| TGGGGGCCGCCACTAATGAATATCCTCCTTTTTGGCAAAACAGGGCAGGTTGGTTGGGAACTACAGCGTGC |
| TCTGGCACCTCTGGGTAATTTGATTGCTCTTGATGTTCACTCCACTGATTACTGTGGTGATTTTAGTAACC |
| CTGAAGGTGTGGCTGAAACCGTTAGAAGCATTCGGCCTGATATTATTGTCAACGCAGCCGCTCACACCGCA |
| GTAGACAAAGCAGAATCAGAACCGGAGTTTGCACAATTACTGAACGCGACGAGTGTCGAAGCGATCGCGAA |
| AGCAGCCAATGAAGTCGGCGCTTGGGTTATTCACTACTCTACTGACTACGTATTTCCGGGGACCGGTGAAA |
| TACCATGGCAGGAGGAGGATGCAACCGCACCGCTAAATGTTTACGGTGAAACCAAGTTAGCAGGAGAAAA |
| GCATTACAAGAGCATTGTGCGAAGCACCCTTATTTTCCGGACCAGCTGGGTCTATGCAGGTAAAGGAAATAA |
| CTTCGCCAAAACGATGTTGCGTCTGGCAAAGAGCGTGAAGAATTAGCCGTTATTAATGATCAGTTTGGTG |
| CGCCAACTGGCGCAGAGTTGCTGGCTGATTGTACGGCACATGCCATTCGTGTGGCACTGAATAAACCGGAA |
| GTCGCAGGTTTGTACCATCTGGTAGCAGTGGTACCACAACCTGGCACGATTATGCTGCGCTGGTTTTGA |
| AGAGGCGCGCAAAGCAGGCATTCCCCTTGCACTCAACAAGCTCAACGCAGTACCAACAACAGTCTATCCTA |

| SEQUENCES |
|---|
| CACCAGCTCGTCGTCCACATAACTCTCGCCTTAATACAGAAAAATTTCAGCAGAACTTTGCGCTTGTCTTG |
| CCTGACTGGCAGGTTGGTGTGAAACGCATGCTCAACGAATTATTTACGACTACAGCAATTTAATAGTTTTT |
| GCATCTTGTTCGTGATGGTGGAACAAGATGAATTAAAAGGAATGATGGAATGAATACGCGTAAAGGTATTA |
| TTTTAGCGGGTGGTTCTGGTACACGTCTTTATCCTGTGACTATGGCTGTCAGTAAACAGCTGTTACCGATT |
| TATGATAAACCGATGATCTATTACCCGCTCTCTACACTGATGTTGGCGGGTATTCGCGATATTTTGATTAT |
| CAGCACGCCACAGGATACTCCTCGTTTTCAACAACTGCTGGGTGATGGGAGCCAGTGGGGCTAAATCTTC |
| ACTACAAAGTGCAACCGAGTCCGGATGGTCTTGCGCAGGCATTTATCATCGGTGAAGAGTTTATCGGTGGT |
| GATGATTGTGCTTTGGTACTTGGTGATAATATCTTCTACGGTCACGACCTGCCTAAGTTAATGGATGCCGC |
| TGTTAACAAAGAAAGTGGTGCAACGGTATTTGCCTATCACGTTAATGATCCTGAACGCTATGGTGTCGTTG |
| AGTTTGATAAAAACGGTACTGCAATCAGCCTGGAAGAAAAACCGTTACAACCAAAAGTAATTATGCGGTA |
| ACCGGGCTTTATTTCTATGATAACTACGTTGTGGAAATGGCGAAAAATCTTAAGCCTTCTGCCCGCGGTGA |
| ACTGGAAATTACCGATATTAACCGTATCTATATGGAACAGGGGCATTTATCTGTTGCCATGATGGGACGTG |
| GATATGCCTGGCTGGACACGGGGACACATCAAAGTCTTATTGAAGCAAGCAACTTCATTGCCACCATTGAA |
| GAGCGCCAGGGCTTGAAAGTTTCCTGCCCGGAAGAAATTGCTTACCGTAAAGGGTTTATTGATGCTGAGCA |
| GGTGAAGTATTAGCTAAACCGCTGAAAAAAAATGCTTATGGTCAGTATCTGCTAAAAATGATTAAAGGTT |
| ATTAATAAAATGAATGTTATTAAAACAGAAATTCCAGATGTACTGATTTTTGAACCGAAAGTTTTTGGTGA |
| TGAGCGTGGTTTCTTTATGGAAAGCTTTAATCAGAAAGTTTTCGAAGAGGCTGTAGGGCGGAAGGTTGAAT |
| TTGTTCAGGATAATCATTCTAAATCGTGTAAAGGTGTACTTAGAGGTTTACACTTTCAGCTTCCTCCCTTT |
| GAGCAGGCAAAATTAGTAAGGTGTATAGTTGGCGAGGTATTTGATGTTGCAGTAGACATTAGACCTAATTC |
| TGAAACATTTGGTTCATGGGTTGGAGTAACTCTTTCGTCAGAAAATAAAAGGCAGCTATGGATTCCAGAAG |
| GATTCGCCCATGGTTTTTTAACTTTAAGTGATATTGCAGAGTTTGTTTATAAAACTAACAACTATTATTCT |
| TTAAATCATGAAAGGGGAGTCATTTGGAACGATGAGGAAATTAACATTGCCTGGCCCTCTCAATCAGAGAA |
| GATTCTGTCACAGAAAGATATTAATTTACCATCATTTAGATTTGTTCAAATGTTTAGCAAGTAGTGTTATC |
| TTTACACTGCACATAGTCATCATTTTTTATGCTTTAAGTAAATTATATTGCACATCTATAACACAAAGCGC |
| AATAATATTTCGACCTGATGAAGGTTTGTGGTTATTTATCTTTCTAGGCGTTTTTTATGACTAAAATAGTT |
| GTGGTTTCTACAGCTCCAATATTCCCGACAAATAATGGGTACAAAAGTTCTGTATTAGGAAGAATTGATGA |
| GTTATTAAATGAGGATAATGAGGTCGTTTGATTGAAATAAACCTTGAAAATGTTACGGAAAAGAAAGATG |
| AATTAATACCAACAAGATTTAATAATATTCAAAGATATGAAGTAAAAAAATATCTAGATCATTTATTGCC |
| GAGTTACAAATATTATTTGATATCAGAACTCGGTATGAACAATTATTTTCTTCTGCTGACATTAGAGATAA |
| CATAAAAAAGATAATTGATTTAGAAAAACCTTCTATTATTATTGCTGAGTCTATATGGGCGTTGCAAGCAT |
| TGCCTATTGAAATTAGTGCGAGAATACACTGTGTTATTCATGATGTGGCAACTGATTTCTTTAAAGAAATG |
| TTTGTATCTCATAATGAGGTTGTACGAAAAATTTTGTTTTTTAATGATTACCTAAAGTTGAAAATTACTGA |
| AGAAATATTATCAAACGTTTGAGAGTTGAGCAATTTATCTTTCTGACAGAAGAAGATAAATGTTGGTATA |
| AAACAAGATACAATATTGATGAGGGTTGTTGTTCCTTAGCGAGCAATCATCTTTATGTAGAAAAGATTAAG |
| AGAACTATCAATTTCCAAACCCCTTTCCTGCTTATTCCCGGTAGCATTGAATTTCACAAAATTTTTACGG |
| CTTAAATTGGTTTATAAAAAATATATATCCTGGATTAAATAGGAAAATAAGAATTAGTTGTAACAGGAAAGG |
| CATCAGATAAAAAAATAAAGATGTTAAACTGTGGAGAGGAAATTACCTTTACGGGAGAGCTTGACTTTTCC |
| ACATATATAATAAACTTAGCTCAACATGCTTGTGTGTTATTGCACCGATTACAACGGGCACTGGAATTAAAT |
| AAAAATATTAGAAGCTGTACAAAAAGGTATTCCTGTACTTACAACAAAATTTGCTTCAAAAGGAATATGTT |
| CCGATTTATGTTTTTATTGCGAGGAGGATACTGACACAAACTTTGTCAATTTAATTAACAGTTTTCTTGAA |
| ACGACATTAAGAGTCCAAGAATGAATTTATTGCTTTTTTCAGTCCTTTGCGTTTGGTTTAATATTGGCTTTG |
| GCCCATAATAATAAAGTGGAGATATTAACGCATACTTAATGTTTTTTCTCGTGGTCCTAATGGTATTAAT |
| ATCAGGGCTGCGTATGAATGATAGTGATTATATCGAATACAGGAAAATGTATAATGAAGTGCCTATTTTAT |
| GTGACTTTAGTCTCGCATCTATAAGAGATATACATGGGGAGGTAGGCTATCTATTCTTATCATCAATCTTT |
| AAAACTTTATGCTTGCCATTTCAATTATTTCTTTTTTTATTGCTCACTCCTGCTTACATATTT |
| TTCATTCAGAAAAATAAGTTTAATACCGATACTATCGTTAGTTTTTTATTTAAGCCATGCTTTTATAGTTA |
| GAGATTTGATTCAAATTAGGGCAGGATTAGCTGTTAGCATATCATTATATTCAATAATTAAATTTAAAGGA |
| AATAAAAGTATAATTACAGGAGTTTTATTTGCTTCTTTGATTCATTCTGGGGCGCTTATTATTGCTCTTTG |
| TTATCTGTTTTTCAAAAAAAAATACATACATTAAAAATGATGTTGTTTTTATTTTTAGTGTGCAATTATTT |
| TTCTTATTTGAATGGGCTTAATTTATCGATACAACTCTTATCTCAATATAGTTTGCTTCCAACTGCAATT |
| TCGAATTATGTTGGTTGGGAAGAATATGATTATCGGGTGAGTATATTTACTAATCCGGTTTTTATTAAAGG |
| TGTTTTTTTAATTGTCTTAATGCACAAATATGTACTTTCAGATATTAAAAATGAGAAATTATAGTGCTTT |
| ATAACTTATATGTTTAGGTGTATTAGCTATGGTTGCATTGAGTGGATGGTCTATTCTTTCAGGCCGTCTT |
| TCATCCTTTCTGACACTAGGTGAAAGCATTTTAATTGTATATGCTCGTTCTACAAAAGAAATACACCTCT |
| GGCGTTTCTAATTTTTTCTTTTTTAACAATTGTGCAATTAGGATATGATCTATTTATTTCTAATGTGCATC |
| CTGAGCTTACTCTGATTATATTTGGGTGAATCTAAGTGAAAAATAATAAAATAGGCATACTTATCTCTAAA |
| ATACAAAATCTTGGACCTGTGAATGTATGACGAGGATTGATAAAGAAAATAAAAAATATGCTTTTACTGT |
| TTTTGTTTAACAAATAGCGTAGATAAAAATATATATGATGAGTTATGCTGTTTAGGAGCCAAGGTTATAT |
| TAATACCAGATGGTACTTGGTTCAGCAAAATTTTATTTGTGAGAAGTTTTTTAAAGGAACATCCACATAAT |
| ATCTTACATTCACATGGGATCACGGCCGATATGTTTTCTTACTTTCTGAATGGCGTGAAAATATCTACTAT |
| TCACAATAGACTAGATGAGGATTATATCCATTATTTGGCGCGGTTAAAGGGAATGCTATATATTATCTTC |
| ATCGTTTTATATTACGAAGATTTAATCATATCGTTGCTTGCTCAGCAGCGGTCCAATCAAAACTGAAACAA |
| TCGAAAGTAAAACTAAAATAACCACCATCCAGAATGGGATTGATATAACTAGGTTAAGACACTTGAGTC |
| TGATAAAAAAAATTATTGAGGGAAAAACACGGATTTGATAGTGAAAAAAGAATATTTATATATTGTGGCT |
| CGTTATCATTAAGGAAAATATTGCTTACCTCTTGGAACACTTAGCCATCGAAGAAATGATATATTTTA |
| ATTCTAGGTGATGGTGAACTTTTTAGATATTGTAAGGATAAATATTCTAAAGATTTACGGTATATATTTAT |
| GGGGAAAGTTGAATGCCCTCTTGAATATTATCAATTATCAGATATTTTGTTTCCGCTTCTTTATCGGAAG |
| GGCTCCCCTTGGCACTATTAGAAGCTGCCTCTACTGGGTGCTATTTATATGTTAGCGATATAGAGCCCCAT |
| AGAGAAATTGCATCTCTATTAGGAGAGGAAATATTTCTATGTTAAAATTAAGGATGGATCATATAATTA |
| TTTGCAACCTAAATAAAAAAGCTGACTATAACGCTCTTTCTGACGATAAACTTTACAATATATCCGATA |
| AAAAAATGTCAAATCTTTATGACAAACTTTTTGTTTCTTTATTAGAGCAGGACTACTAATATAATGATTTA |
| TGTTTCGGTAATTTCTCATGGTCATTTCAAAACTCTTAAGGAATTAGGAGCAGTATCAAAATTAAATAATC |
| ACAGCAGAATTAAAGTTATCATCAAAGATAATTTAGGAGAGAGCGAGCTTTGGATTTTGTCAGGAAAAC |
| AAAATAACTTATTTAAGGTCTAAAGAGAAAAAGGATTTGGAGAGAATAATAATGAAGTTTTTTCCTCTAT |
| ATCCTCCTTAATTACTAAGGAAGATTTTTTTGTGGTTATGAATCCTGATATATATATTGAGTGCTCTGATC |
| TATTAGATGTCGTAGATGAGTGTGGTTCAGCGAATGTTAATCTAGCAACGATAAATTTATACAGGGATTTT |
| GATAAAAAAACATATGATAACTCAGTAAGGAAATTTCCCTCGGCAATTGATTTTTTATGTCATTTTTATT |

| SEQUENCES |
|---|
| TAAGAAAAATGACTGTGTAGTAAATAAGAACAAAATAACGAAACCAACATATGTTGATTGGGCTGCAGGTT<br>CTTTTCTAATATTTAATGCCTTCTTTTATTCAAAACTCAACGGATTCAACGAAAAGTATTTTATGTATTGC<br>GAAGATATTGATATATGTTGGCGAGCTAAAAAACACTTCAATACTTCAGTTTTATACTATCCATGCTATGC<br>AGCAATTCATTTGGCACAATTTAACAATCGTAGGATTTTTAGTAGACATTTCATTTGGCATATAAAAGTA<br>TTATCCTTTTTTATTATATAAAAATGGTATGCTGCGTTCTAGTAAGTTGCTTTAATGCTAATATTCTTTT<br>AAGAGGTGAGAATGATACCTGTTATTTTGGCTGGTGGTTCGGGAAGTCGCTTGTGGCCACTTTCACGAGAA<br>AAGTTCCCCAAGCAGTTTTTAAAGTTGACTGGCAGTTTGACAATGTTGCAGTCAACATTGTCACGTCTTAA<br>TAATTTAAATGCTGATGATTCAATAGTTATATGCAACGAAGAGCATAGATTTATTGTTGCAGAACAATTAA<br>GAGAGTTAGGCAAACTTTCAAATAACATTATTCTTGAACCCAAAGGTCGTAATACAGCCCCTGCTATAACA<br>CTCGCAGCATTAGCAGCAAAAAGAAAATTCGCTGATGAAGATCCATTGATTCTTATTTTAGCTGCAGATCA<br>CAACATCCAAGACGAACATGTTTTCTGTGAGGCAATTAATAAGGCGTCATCTTTAGCTAGTTATGGAAAAC<br>TAGTGACTTTTGGTATCGTTCCATTCAAACCTGAAACTGGGTATGGCTATATTCGTCGCGGTGATGAAGTG<br>CCTGTAGATGAGCAGCATGCGGTGGCCTTTGAAGTGGCGCAGTTTGTCGAAAAACCGAATCTGGAAACCGC<br>GCAGGCCTATGTGGCAAGCGGCGAATATTACTGGAACAGCGGTATGTTCCTGTTCCGTGCCGGACGCTATC<br>TCGAAGAACTGAAAAAGTATCGTCCGGATATTCTCGATGCCTGTGAAAAAGCGATGAGCGCCGTCGATCCG<br>GATCTCGATTTTATTCGTGTGGATGAAGAGGCGTTTCTCGCTTGTCCGGAAGAGTCGGTGGATTACGCGGT<br>CATGGAATGCACGGCAGATGCCGTTGTGGTGCCGATGGATGCGGGCTGGAGCGATGTCGGTTCCTGGTCTT<br>CATTATGGGAGATCAGCGCCCACACCGCCGAGGGCAACGTTTGCCACGGCGATGTGATTAATCACAAACT<br>GAAAACAGCTATGTGTACGCCGAATCTGGCCTGGTCACCACCGTCGGGGTGAAAGATTTGGTGGTAGTGCA<br>GACCAAAGATGCAGTGCTGATTGCCGACCGTAATGCGGTGCAGGATGTGAAGAAAGTGGTCGAGCAGATCA<br>AAGCTGATGGTCGCCATGAGCATCGGGTGCATCGCGAAGTGTATCGTCCGTGGGCAAATATGACTCTATC<br>GACGCGGGCGACCGCTACCAGGTGAAACGCATCACCGTGAAACCGGGCGAAGGTTTGTCGGTACAGATGCA<br>TTATCATCGCGCGGAACACTGGGTGGTTGTCGCGGGAACGGCAAAAGTCACTATCAACGGTGATATCAAAC<br>TGCTTGGTGAAAACGAGTCCATTTATATTCCGCTGGGGGCGATGCACTGCCTGGAAAACCCGGGGAAAATA<br>GATTTAGAATTAATTGAAGTTCGCTCTGGTGCATATCTTGAAGAAGATGATGTTATTAGATGTTATGATCG<br>CTATGGACGAAAGTAATATATAATAATTATTTCAGAATTAGAAATGATAATTATAAGTTTTCGTCTGGATA<br>AACAATAGATAGTATGGTTGGAAAATATGAGTTCTTTAACTTGTTTTAAAGCTTACGACATTCGCGGGAA<br>ATTAGGTGAAGAACTGAATGAAGATATCGCCTGGCGCATTGGTCGCGCCTATGGCGAATTTCTCAAACCGA<br>AAACCATTGTGTTAGGCGGTGATGTCCGTCTCACCAGCGAAACCTTAAAACTGGCGCTGGCAAAAGGTTTA<br>CAGGATGCGGGCGTCGATGTGCTGGATATTGGCATGTCCGGCACCGAAGAGATTTATTTCGCCACGTTCCA<br>TCTCGGCGTGGATGGCGGCATTGAAGTTACCGCCAGCCATAATCCGATGGATTACAACGGCATGAAGCTGG<br>TGCGCGAAGGGGCTCGCCCGATCGGCGGTGATACCGGACTGCGCGACGTCCAGCGTCTGGCAGAAGCTAAC<br>GACTTTCCTCCCGTCGATGAAACCAAACGCGGTCGCTATCAGCAAATCAATCTGCGTGACGCTTACGTTGA<br>TCACCTGTTCGGTTATATCAATGTCAAAAACCTTACGCCGCTCAAGCTGGTGATCAACTCCGGGAATGGCG<br>CAGCGGGTCCGGTGGTGGACGCTATCGAAGCCCGCTTTAAAGCCCTCGGCGCACCGGTGGAGTTAATCAAA<br>GTGCATAACACGCCGGACGGCAATTTCCCAACGGTATTCCTAACCGTTGCTGCCGGAATGTCGCGACGA<br>CACCCGCAATGCGGTCATCAAACACGGCGCGGATATGGGCATTGCCTTTGATGGCGATTTTGACCGCTGTT<br>TCCTGTTTGACGAAAAAGGGCAGTTTATTGAGGGCTACTACATTGTCGGCCTGCTGGCAGAAGCGTTCCTC<br>GAAAAAAATCCCGGCGCGAAGATCATCCACGATCCACGTCTCTCCTGGAACACCATTGATGTGGTGACGGC<br>CGCGGGCGGCACGCCGGTGATGTCGAAAACAGGACACGCGCTTTATTAAAGAACGTATGCGCAAGGAAGACG<br>CCATCTACGGTGGCGAAATGAGCGCTCACCATTACTTCCGCGATTTCGCTTACTGTGACAGCGGCATGATC<br>CCGTGGCTGCTGGTCGCCGAACTGGTGTGCCTGAAAGGAAAAACGCTGGGCGAACTGGTGCGCGACCGGAT<br>GGCGGCGTTTCCGGCAAGCGGTGAGATCAACAGAAAACTGGCGCACCCTGTTGAGGCGATTAACCGCGTGG<br>AACAGCATTTTAGCCGTGAGGTGCTGGCGGTGGATCGCACCGATGGCATCAGCATGACCTTTGCCGACTGG<br>CGCTTTAACCTGCGCTCTTCCAACACCGAACCGGTGGTGCGCCTGAATGTGGAATCTCGCGGTGATGTTCA<br>GGTTATGGTAATCCATACTCAAGAAATATTATCAATTTTGACGTCATAAAGAATAAGCCCTGACAAGTTAG<br>GGCTTAATTAATATATATTTTTTTGAATTGGGGATTTGTGGTAAGATTTTTAATATGTTATTTAATGTGG<br>TTGAATTAATGTTGACTGGAAAATAATAATGAGAACGAAAAAAGCATTACACAACTTTAAAGTTGATTTAT<br>TAATTACTTTTTTATTGGTTTTGCTAGGGTTTTATATTCGAATCTGTTTTTTGTTTCAAAAATGGGAAGTGAT<br>ATTACTGGAGTGATGTTACTATTCACACAGTTGACAGCATATCTCAATTTGGCAGAATTAGGTATTGGAAT<br>TGCAGCTGCCAGCGTATTATATAAACCGCTCAGCGAGAATGAATACAATAAAATAACTTACATAATATCTT<br>TGCTCTCAGTCATATACAAATATATATTTGTGTTTGTTTTGATTCTTGGCGTTGTTATAGGTATCTGTATT<br>TATTACTTTATTGATTCTGTAAAGGTTTGTAAATGGCGTTTTTTAATCTGTTTTTTGTTTCGTTTTTTAATAC<br>ATCGTTGACATATAGTTATGCTAAATACTCCACATTATTAACTGCTAATCAGCGGTACTCAGCAGTAAGAA<br>AAATTCAAGGTGGCGGAAAAGTTATAATAATTGTATTTCAGATATTAATTTTGTGCTTTACGCAAAGTTTC<br>ATACTTTATTTGTTAGTTGAGACTTTAGGTATTTTTTCTCAATATTTGATTTTAAAAAAATAATTGGGAA<br>CGGAAATCAATATCTCAGTAATGAGGTTTTACTTATTGAAAGCATAACTTTTGATAAAAAAGAATTAA<br>AAATAAGAATAAAAAATATGTTCTTCCATAAAATAGGTGCTGTGCTTGTCCTTAATACAGACTACCTGCTT<br>GTATCAAAGTTTCTGACATTAAGTTATGTGACAATTTTTGGCAGCTATATGATGGTATTTCAGATAGTAAC<br>TGTTTTGATGTCAAGTTTTGTTAATGCTATTACTGCAGGAATGGGTAATTACTTAATTAATAAAAGTAATT<br>TAGAAATTAAGGAAATTACACGTCAATTTTATGTGATATTTATCGCCTTTGCAACATTCATATCACTAAAT<br>ATGTTTTTTCTTGTTAATGATTTTATCGCAAAATGGATAGGTGTTAATTATACATTAAGTAACACCCTAGT<br>TGCATTAATGATTGTTAACGTATTCATTAGTGTTGTCAGGGTACCTTCTGATATATTAAAAAACGCAAGTG<br>GACATTTTGGTGATATTTATTATCCATTATTAGAAGGTGTGCTGAATATTACGATATCCATCATTTTGGCT<br>ATCATTATTGGATTACCTGGCATTATTATAGGGACAATAGTATCTAACTTAATAGTAATAATGCTTGCGAA<br>ACCATTATATCTTTACTCTAAGTTATTTAATCTTAGAAATCCGACAGGTTTATTTTGAAGTTTATTTCTC<br>GGCCTATGTTATATTCATTATGTGTGATTGGGGTGAGCTATTTATTGCGCGATGAAATATATTCATTTAAA<br>GTAAGTACATGGTTGGATTTTATTAACAAGCTACTCTTAGTCTCTACTCCTAGCATATTGGTAATATGTGC<br>TATTTTCTCTACGGATAGTGACTTTAGATTATTTTTCAGAAAAATTATATATGTGATTATGAAGAAATAAA<br>AATTTCGAAAATGTATTAATCGAAATTATGCAACGAGCTTTATTTTTATAAATGATATGTGATCTTTTCGC<br>GAATAGGATAAGGATCCGTGTAGGCTGGAGCTGCTTCGAAGTTCCTATACTTTCTAGAGATAGGAACTT<br>CGGAATAGGAACTAAGGAGGATATTCATATGGATAAAACCGTAAGCATATAAGCATGGATAAGCTATTTAT<br>ACTTTAATAAGTACTTTGTATACTTATTTGCAACATTCCAGGCCGCGAGCATTCAGCGCGGTGATCACAC<br>CTGACAGGAGTATGTAATGTCCAAGCAACAGATCGGCGTAGTCGGTATGGCAGTGATGGGACGCAACCTTG<br>CGCTCAACATCGAAAGCCGTGGTTATACCGTCTCTATTTTCAACCGTTCCCGTGAGAAGACGGAAGAAGTG<br>ATTGCCGAAAATCCAGGCAAGAAACTGGTTCCTTACTATACGGTGAAAGAGTTTGTCGAATCTCTGGAAAC<br>GCCTCGTCGCATCCTGTTAATGGTGAAAGCAGGTGCAGGCACGGATGCTGCTATTGATTCCCTCAAACCAT |

SEQUENCES

```
ATCTCGATAAAGGAGACATCATCATTGATGGTGGTAACACCTTCTTCCAGGACACTATTCGTCGTAATCGT
GAGCTTTCAGCAGAGGGCTTTAACTTCATCGGTACCGGTGTTTCTGGCGGTGAAGAGGGGGCGCTGAAAGG
TCCTTCTATTATGCCTGGTGGCCAGAAAGAAGCCTATGAATTGGTAGCACCGATCCTGACCAAAATCGCCG
CCGTAGCTGAAGACGGTGAACCATGCGTTACCTATATTGGTGCCGATGGCGCAGGTCACTATGTGAAGATG
GTTCACAACGGTATTGAATACGGCGATATGCAGCTGATTGCTGAAGCCTATTCTCTGCTTAAAGGTGGCCT
GAACCCTCACCAACGAAGAACTGGCGCAGACCTTTACCGAGTGGAATAACGGTGAACTGAGCAGTTACCTGA
TCGACATCACCAAAGATATCTTCACCAAAAAAGATGAAGACGGTAACTACCTGGTTGATGTGATCCTGGAT
GAAGCGGCTAACAAAGGTACCGGTAAATGGACCAGCCAGAGCGCGCTGGATCTCGGCGAACCGCTGTCGCT
GATTACCGAGTCTGTGTTTGCACGTTATATCTCTTCTCTGAAAGATCAGCGTGTTGCCGCATCTAAAGTTC
TCTCTGGTCCGCAAGCACAGCCAGCAGGCGACAAGGCTGAGTTCATCGAAAAAGTTCGTCGTGCGCTGTAT
CTGGGCAAAATCGTTTCTTACGCCCAGGGCTTCTCTCAGCTGCGTGCTGCGTCTGAAGAGTACAACTGGGA
TCTGAACTACGGCGAAATCGCGAAGATTTTCCGTGCTGGCTGCATCATCCGTGCGCAGTTCCTGCAGAAAA
TCACCGATGCTTATGCCGAAAATCCACAGATCGCTAACCTGTTGCTGGCTCCGTACTTCAAGCAAATTGCC
GATGACTACCAGCAGGCGCTGCGTGATGTCGTTGCTTATGCAGTACAGAACGGTATTCCGGTTCCGACCTT
CTCCGCAGCGGTTGCCTATTACGACAGCTACCGTGCTGCTGTTCTGCCTGCGAACCTGATCCAGGCACAGC
GTGACTATTTTGGTGCGCATACTTATAAGCGTATTGATAAAGAAGGTGTGTTCCATACCGAATGGCTGGAT
TAA
```

The invention claimed is:

1. A recombinant host cell for preparing a bioconjugate of an *E. coli* Ox-antigen polysaccharide covalently linked to a carrier protein, the recombinant host cell comprising:
   (a) a nucleotide sequence of an rfb gene cluster for the Ox-antigen polysaccharide;
   (b) a nucleotide sequence encoding the carrier protein comprising at least one glycosylation site comprising a glycosylation consensus sequence having SEQ ID NO: 1; and
   (c) a nucleotide sequence encoding an oligosaccharyl transferase PglBy, wherein the PglBy comprises the amino acid substitution N311V relative to a wild-type PglB having the amino acid sequence of SEQ ID NO: 6, wherein the *E. coli* Ox-antigen polysaccharide is the O1A antigen polysaccharide comprising the structure:

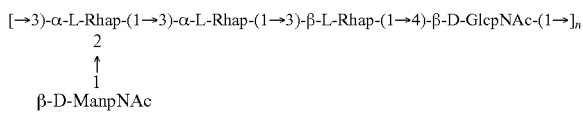

wherein n is independently an integer of 3 to 50.

2. The recombinant host cell of claim 1, wherein the PglB$_y$ comprises the amino acid mutations of N311V, K482R, D483H, and A669V relative to the wild-type PglB.

3. The recombinant host cell of claim 1, wherein the host cell is a prokaryotic host cell.

4. The recombinant host cell of claim 3, wherein the host cell is *E. coli*.

5. The recombinant host cell of claim 1, wherein the carrier protein is selected from the group consisting of detoxified Exotoxin A of *P. aeruginosa* (EPA), *E. coli* flagellin (FliC), CRM197, maltose binding protein (MBP), Diphtheria toxoid, Tetanus toxoid, detoxified hemolysin A of *S. aureus*, clumping factor A, clumping factor B, *E. coli* heat labile enterotoxin, detoxified *E. coli* heat labile enterotoxin, cholera toxin B subunit (CTB), cholera toxin, detoxified cholera toxin, *E. coli* Sat protein, the passenger domain of *E. coli* Sat protein, *Streptococcus pneumoniae* Pneumolysin, Keyhole limpet hemocyanin (KLH), *P. aeruginosa* PcrV, outer membrane protein of *Neisseria meningitidis* (OMPC), and protein D from non-typeable *Haemophilus influenzae*.

6. The recombinant host cell of claim 1, wherein the carrier protein comprises SEQ ID NO: 3.

7. The recombinant host cell of claim 1, wherein the PglBy comprises the amino acid sequence of SEQ ID NO: 6 with the N311V substitution, the host cell is *E. coli* and the carrier protein comprises the amino acid sequence of SEQ ID NO: 3.

8. The recombinant host cell of claim 1, wherein the PglBy comprises the amino acid sequence of SEQ ID NO: 6 with the N311V, K482R, D483H and A669V substitutions, the host cell is *E. coli* and the carrier protein comprises the amino acid sequence of SEQ ID NO: 3.

\* \* \* \* \*

SEQUENCE LISTING

Sequence total quantity: 19

SEQ ID NO: 1           moltype =    length =
SEQUENCE: 1
000

SEQ ID NO: 2           moltype =    length =
SEQUENCE: 2
000

SEQ ID NO: 3           moltype = AA  length = 652
FEATURE                Location/Qualifiers
source                 1..652
                        mol_type = protein
                        organism = synthetic construct
SEQUENCE: 3
```
GSGGGDQNAT GSGGGKLAEE AFDLWNECAK ACVLDLKDGV RSSRMSVDPA IADTNGQGVL   60
HYSMVLEGGN DALKLAIDNA LSITSDGLTI RLEGGVEPNK PVRYSYTRQA RGSWSLNWLV  120
PIGHEKPSNI KVFIHELNAG NQLSHMSPIY TIEMGDELLA KLARDATFFV RAHESNEMQP  180
TLAISHAGVS VVMAQAQPRR EKRWSEWASG KVLCLLDPLD GVYNYLAQQR CNLDDTWEGK  240
IYRVLAGNPA KHDLDIKDNN NSTPTVISHR LHFPEGGSLA ALTAHQACHL PLEAFTRHRQ  300
PRGWEQLEQC GYPVQRLVAL YLAARLSWNQ VDQVIRNALA SPGSGGDLGE AIREQPEQAR  360
LALTLAAAES ERFVRQGTGN DEAGAASADV VSLTCPVAKD QNRTKGECAG PADSGDALLE  420
RNYPTGAEFL GDGGDVSFST RGTQNWTVER LLQAHRQLEE RGYVFVGYHG TFLEAAQSIV  480
FGGVRARSQD LDAIWRGFYI AGDPALAYGY AQDQEPDARG RIRNGALLRV YVPRWSLPGF  540
YRTGLTLAAP EAAGEVERLI GHPLPLRLDA ITGPEEEGGR VTILGWPLAE RTVVIPSAIP  600
TDPRNVGGDL DPSSIPDKEQ AISALPDYAS QPGKPPREDL KLGSGGGDQN AT          652
```

SEQ ID NO: 4           moltype = AA  length = 421
FEATURE                Location/Qualifiers
source                 1..421
                        mol_type = protein
                        organism = synthetic construct
SEQUENCE: 4
```
MNNLIMNNWC KLSIFIIAFI LLWLRRPDIL TNAQFWAEDS VFWYKDAYEN GFLSSLTTPR   60
NGYFQTVSTF IVGLTALLNP DYAPFVSNFF GIMIRSVIIW FLFTERFNFL TLTTRIFLSI  120
YFLCMPGLDE VHANITNAHW YLSLYVSMIL IARNPSSKSW RFHDIFFILL SGLSGPFIIF  180
ILAASCFKFI NNCKDHISVR SFINFYLRQP YALMIVCALI QGTSIILTFN GTRSSAPLGF  240
SFDVISSIIS SNIFLFTFVP WDIAKAGWDN LLLSYFLSVS ILSCAAFVFV KGTWRMKVFA  300
TLPLLIIIFS MAKPQLTDSA PQLPTLINGQ GSRYFVNIHI AIFSLLCVYL LECVRGKVAT  360
LFSKIYLTIL LFVMGCLNFV ITPLPNMNWR EGATLINNAK TGDVISIQVL PPGLTLELRK  420
K                                                                421
```

SEQ ID NO: 5           moltype = DNA length = 1266
FEATURE                Location/Qualifiers
source                 1..1266
                        mol_type = other DNA
                        organism = synthetic construct
SEQUENCE: 5
```
atgaataatt taattatgaa taactggtgt aaattatcta tatttattat tgcatttatt   60
ttgctatggc ttagaaggcc ggatatactc acaaacgcac aatttttggc agaagattcc  120
gttttctggt ataaggacgc ctatgagaac ggattcttaa gttcactaac aacgcctagg  180
aatgggtatt tccagactgt ttctacattt atagttggtc tgactgcttt attaaatcca  240
gattatgcac cttttgtttc taattttttt ggcataatga ttcgctcagt aattatatgg  300
```

```
tttttattta cagaaagatt caacttcctc acattgacta ctaggatttt cttatctatt  360
tattttctat gcatgcctgg attggatgaa gttcatgcaa atataacaaa tgcacattgg  420
tatttgtcat tatatgtatc aatgatcctg atagctcgca atccaagttc aaaatcatgg  480
aggtttcatg atatattctt tatcttgcta tccgggctca gtggcccatt tataattttc  540
attttagcag cttcatgctt taaatttata aataattgta aagatcatat tagtgtaaga  600
tctttcataa atttctactt gcgtcagcca tacgcattaa tgattgtttg cgctttaatt  660
caaggaactt ctataattct aactttcaat ggcacacgtt cctcagcacc gctaggattc  720
agttttgatg tgatttcgtc tattatatca tcgaatattt ttttatttac atttgtccca  780
tgggatattg caaaggctgg gtgggataat ttactgttat cttattttt gtctgtttcg  840
attttgtcgt gtgcggcctt tgttttttgtt aaaggtacgt ggcgaatgaa agtatttgca  900
acttaccat tgctaattat aatatttca atggcaaaac cacaattgac agactcggca  960
cctcaattgc caacacttat taatgggcaa ggttcaagat acttcgtaaa tatacatatt 1020
gcgatattct ctttgctatg tgtttactta cttgagtgcg tcaggggaa agtggcaact 1080
ttattttcca aaatatactt aacaattttg ctattcgtga tgggatgttt gaatttttgtt 1140
atcaccccac tcccaaacat gaactggagg gaaggtgcta ctttgattaa taatgcaaaa 1200
actggtgatg tcatttcgat tcaagtgcta ccacctggcc taacacttga actaaggaaa 1260
aaataa                                                              1266

SEQ ID NO: 6            moltype = AA  length = 713
FEATURE                 Location/Qualifiers
source                  1..713
                        mol_type = protein
                        organism = synthetic construct
SEQUENCE: 6
MLKKEYLKNP YLVLFAMIIL AYVFSVFCRF YWVWWASEFN EYFFNNQLMI ISNDGYAFAE   60
GARDMIAGFH QPNDLSYYGS SLSALTYWLY KITPFSFESI ILYMSTFLSS LVVIPTILLA  120
NEYKRPLMGF VAALLASIAN SYYNRTMSGY YDTDMLVIVL PMFILFFMVR MILKKDFFSL  180
IALPLFIGIY LWWYPSSYTL NVALIGLFLI YTLIFHRKEK IFYIAVILSS LTLSNIAWFY  240
QSAIIVILFA LFALEQKRLN FMIIGILGSA TLIFLILSGG VDPILYQLKF YIFRSDESAN  300
LTQGFMYFNV NQTIQEVENV DLSEFMRRIS GSEIVFLFSL FGFVWLLRKH KSMIMALPIL  360
VLGFLALKGG LRFTIYSVPV MALGFGFLLS EFKAIMVKKY SQLTSNVCIV FATILTLAPV  420
FIHIYNYKAP TVFSQNEASL LNQLKNIANR EDYVVTWWDY GYPVRYYSDV KTLVDGGKHL  480
GKDNFFPSFA LSKDEQAAAN MARLSVEYTE KSFYAPQNDI LKTDILQAMM KDYNQSNVDL  540
FLASLSKPDF KIDTPKTRDI YLYMPARMSL IFSTVASFSF INLDTGVLDK PFTFSTAYPL  600
DVKNGEIYLS NGVVLSDDFR SFKIGDNVVS VNSIVEINSI KQGEYKITPI DDKAQFYIFY  660
LKDSAIPYAQ FILMDKTMFN SAYVQMFFLG NYDKNLFDLV INSRDAKVFK LKI         713

SEQ ID NO: 7            moltype = AA  length = 120
FEATURE                 Location/Qualifiers
source                  1..120
                        mol_type = protein
                        organism = Escherichia coli
SEQUENCE: 7
MLKLFAKYTS IGVLNTLIHW VVFGVCIYVA HTNQALANFA GFVVAVSFSF FANAKFTFKA   60
STTTMRYMLY VGFMGTLSAT VGWAADRCAL PPMITLVTFS AISLVCGFVY SKFIVFRDAK  120

SEQ ID NO: 8            moltype = AA  length = 306
FEATURE                 Location/Qualifiers
source                  1..306
                        mol_type = protein
                        organism = Escherichia coli
SEQUENCE: 8
MKISLVVPVF NEEEAIPIFY KTVREFEELK SYEVEIVFIN DGSKDATESI INALAVSDPL   60
VVPLSFTRNF GKEPALFAGL DHATGDAIIP IDVDLQDPIE VIPHLIEKWQ AGADMVLAKR  120
SDRSTDGRLK RKTAEWFYKL HNKISNPKIE ENVGDFRLMS RDVVENIKLM PERNLFMKGI  180
LSWVGGKTDI VEYVRAERIA GDTKFNGWKL WNLALEGITS FSTFPLRIWT YIGLVVASVA  240
FIYGAWMILD TIIFGNAVRG YPSLLVSILF LGGIQMIGIG VLGEYIGRTY IETKKRPKYI  300
IKRVKK                                                              306

SEQ ID NO: 9            moltype = DNA  length = 14440
FEATURE                 Location/Qualifiers
source                  1..14440
                        mol_type = other DNA
                        organism = synthetic construct
SEQUENCE: 9
atgacgaatt taaaagcagt tattcctgta gcgggtctcg ggatgcatat gttgcctgcc   60
actaaggcga tacccaaaga gatgctacca atcgtcgaca agccaatgat tcagtacatt  120
gttgacgaga ttgtggctgc agggatcaaa gaaatcctcc tggtaactca cgctgtccaa  180
aacgcggtcg aaaaccactt cgacacctct tatgagttag aatcactcgt tgagcagcga  240
gtgaagcgtc aactgctggc ggaagtacga tccatctgtc cgccgggcgt gaccattatg  300
aacgtgcgtc agggcgaacc tttaggttta ggccactcca ttttgtgtgc gcgacctgcc  360
attggtgaca acccatttgt cgtggtactg ccagacgttg tgatcgacga tgccagcgcc  420
gacccgctac gttacaacct tgctgccatg attgcacgtt tcaacgaaac gggccgcagc  480
caggtgctga caaacgtat gccgggtgac ctctctgata actccgtcat ccagactaaa  540
gagccgctga accgtgaggg taaagtcagc cgcattgttg aatttatcga aaaaccggat  600
cagccgcaga cgctggactc agacatcatg gcgtaggtc gctatgtgct ttctgccgat  660
atttggccgg aactggaacg tactcagcct ggtgcatggg gacgtattca gctgactgat  720
gctattgccg agctggcgaa aaaacaatcc gttgatgcaa tgctgatgac cggcgacagt  780
tacgactgcg gcaaaaaaat gggctatatg caggcgtttg tgaagtatgg cctacgcaac  840
```

```
ctgaaagaag gggcgaagtt ccgtaaaggt attgagaagc tgttaagcga ataatgaaaa    900
tctgaccgga tgtaacggtt gataagaaaa ttataacggc agtgaaaatt cgcagcaaaa    960
gtaatttgtt gcgaatcttc ctgccgttgt tttatataaa ccatcagaat aacaacgagt   1020
tagcagtagg gttttattca aagttttcca ggattttcct tgtttccaga gcggattggt   1080
aagacaatta gcgtttgaat ttttcgggtt tagcgcgagt gggtaacgct cgtcacatca   1140
taggcatgca tgcagtgctc tggtagctgt aaagccaggg gcggtagcgt gcattaatac   1200
ctctattaat caaactgaga gccgcttatt tcacagcatg ctctgaagta atatggaata   1260
aattaagtga aatacttgt tactggtggc gcaggattta ttggttcagc tgtagttcgt   1320
cacattataa ataatacgca ggatagtgtt gttaatgtcg ataaattaac gtacgccgga   1380
aaccgggaat cacttgctga tgtttctgat tctgaacgct atgttttga acatgcggat   1440
atttgcgatg cacctgcaat ggcacggatt tttgctcagc atcagccgga tgcagtgatg   1500
cacctggctg ctgaaagcca tgttaccgt tcaattacag gccctgcggc atttattgaa   1560
accaatattg ttggtactta tgtcctttg gaagccgctc gcaattactg gtctgctctt   1620
gatagcgaca agaaaaatag cttccgtttt catcatattt ctactgacga agtatatggt   1680
gatttgcctc atcctgacga ggtaaataat acagaagaat tacccttatt tactgagaca   1740
acagcttacg cgccaagcag ccctttattcc gcatccaaag catccagcga tcatttagtc   1800
cgcgcgtgga aacgtaccta tggtttaccg accattgtga ctaattgctc taacaattat   1860
ggtccttatc atttcccgga aaaattgatt ccattggtta ttctcaatgc tctgaaggt   1920
aaagcattac ctatttatgg taaaggggat caaattcgcg actggctgta tgttgaagat   1980
catgcgcgtg cgttatatac cgtcgtaacc aaggtaaag cgggtgaaac ttataacatt   2040
ggtgggcaca acgaaaagaa aaacatagat gtagtgctca ctatttgtga tttgctggat   2100
gagattgtac cgaaagagaa aatcttatcgt gagcaaatca cttatgttgc cgatcgtccg   2160
ggacacgatc gccgttatgc gattgatgct gagaatattg gtcgcgaatt gggatggaaa   2220
ccacaggaaa cgtttgagag cgggattcgg aagacagtgg aatggtatct gtccaataca   2280
aaatgggttg ataatgtgaa aagtggtgcc tatcaatcgt ggattgaaga aactatgag   2340
ggccgccagt aatgaaatatc ctccttttg gcaaaacagg gatgtaggt tgggaactac   2400
agcgtgctct ggcacctctg ggtaacttga ttgctcttga tgttcattcc actgattatt   2460
gtggcgattt cagtaacccc gaaggtgtgg ctgaaaccgt caaaaaaatt cgcccagatg   2520
ttattgttaa tgctgctgct cataccgcgt tagataaggc tgagtcagaa ccagaatttg   2580
cacaattact caatgcgacc agcgttgaag caattgcaaa agcggctaat gaagttgggg   2640
cttgggtaat tcattactca actgactacg tcttccctgg aaatggcgac atgccatggc   2700
tcgagactga tgtaaccgct ccgctcaatg tttatggcaa aaccaaattg gctggagaaa   2760
gagcattaca agaacattgc gcaaagcatc ttatttccg taccagctgg gtatatgcag   2820
gtaaaggaaa taactttgcc aaaacaatgt tacgtctggc aaaagagcgc gaagaactgg   2880
ctgtgataaa cgatcagttt ggcgcaccaa caggtgctga attgctggct gattgcaccg   2940
ctcatgccat tcgcgtggca ttaaaaaaac cagaagttgc tggcttgtac catctggtag   3000
caaatggcac aacaacctgg cacgattacg ccgcgctagt attcgaagaa gcccgtaaag   3060
cagggattga ccttgcactt aacaaactca acgccgtacc aacaacgcgt tatcctactc   3120
cagcccgccg tcctcataat tctcgcctca ataccgaaca gtttcagcag aactttcgc   3180
ttgtcttgcc tgactggcag gtgggcgtga acgtatgct caacgaatta tttacgacta   3240
cggcaattta acaaattttt gcatctcgct catgatgcca gagcgggatg aattaaaagg   3300
aatggtgaaa tgaaaacgcg taaggtatt attctggctg gtggttccgg cactcgtctt   3360
tatcctgtga cgatggcagt gagtaaacaa ctgctgccaa tttatgataa gccgatgatt   3420
tattatccgc tttcaacgct tatgttagcg ggtattcgcg atattcttat tatcagtacg   3480
ccacaggata caccgcgttt ccaacaattg ttggggacg ggagtcagtg ggggcttaat   3540
ctacagtata aagtacaacc gagtccggat ggcctggcgc aagcgtttat tattggtgaa   3600
gactttattg gtggtgatga ttgtgcactc gtacttggcg ataatatctt ctatggacac   3660
gacttgccga aattaatgga agctgctgtt aacaaagaaa tcggtgcaac ggtatttgct   3720
tatcacgtca atgatcctga acgttatggt gtcgtggagt ttgataataa cggtactgca   3780
attagcctga agaaaaaacc gctggaacca aaaagtaact atgcggttac tgggctttat   3840
ttctatgaca atgatgttgt agaaatggcg aaaaaccttta agccttctgc ccgtggcgaa   3900
ctggaaatta ccgatattaa ccgtatttat atggagcagg gacgtttgtc tgtcgctatg   3960
atggggcgtg gttatgcctg gttggatact ggtacacatc aaagtcttat tgaagcaagt   4020
aacttcattg ccaccattga agagcgtcag ggattaaagg tatcttgccc ggaagagatt   4080
gcttaccgta aagggtttat tgatgctgag caggtgaaaa tattagccga accgctgaag   4140
aaaaatgatt atggtcagta tctgctaaaa atgattaaag gttattaata aaatgaacgt   4200
aattaaaact gaaattcctg atgtgctgat ttttgaacca aaagttttg gtgatgaacg   4260
tggcttcttt tttgagagtt ttaaccagaa agtatttgaa gaagctgtag gacggaaggt   4320
tgaatttgtt caggataacc attctaagtc taaaataaat gtattgcgtg ggatgcatta   4380
tcaaacacaa aatactcaag gaaaactggt tcgggtaatt tctggttcag tatatgatgt   4440
tgccgtagat ttaagagaaa aatcaaagac atttggcaaa tgggtgggtg tagaattatc   4500
tgggaataat aaaagacaat tgtggatccc cgaaggtttt gcccatggtt tttatgtgtt   4560
ggaggagaat accgaatttg tttataaatg taccgtaact tataaccctg ctcatgaaca   4620
cacattgcta tggaatgatc caactatcaa tataagttgg ccaatcatac aaaactgcaa   4680
gccaattatt tctgaaaaag atgctaatgg acatctttt tcacataaaa cctatttctg   4740
aaatgcaata ttatgagttt aattagaaac agtttctata atattgctgg ttttgctgtg   4800
ccgacattag ttgcagtccc tgctttgggg attcttgcca ggctgcttgg accggagaat   4860
tttggacttt tcacactagc attcgctttg ataggatatg caagtatttc cgacgccggg   4920
attagtcgag ctgtaatcag agaaatcgct ctttatcgaa aaagtgaaaa agacaaata   4980
caaattattt cgacagcaag tgtaatcgta ctattcttag gggtggttgc agctttgtta   5040
ctttatttta gtagtaataa agttgttgag ttattgaatg ttagttccgt ttatattgaa   5100
acagcagtgc gtgcattctc tgttatttca tttataatac ctgtgtatct gattaaccag   5160
atttggcttg gttatctgga agggctagaa aaatttgcaa atataaatgt tcagagaatg   5220
atttacaaa caagttggc tatattacca gtgatatttt gttattacaa tccctcgttg   5280
ctttatgcta tgtatgggtt ggtggttggg cgtgtgattt cattttttgat tagcgcaata   5340
atttgtcgag atattattct taaaagtaaa ctttacttta atgtggcaac ttgcaatcgt   5400
cttatctctt ttggtggatg gataacagtt agtaatatca taagcccaat catggcatat   5460
ttcgaccgct ttatcatctc tcatattatg ggggcttcga gaattgcatt ttatacacgc   5520
ccctcagagg gtgtatcaag gttaattaat atcccatatg ctttggcaag agctctattt   5580
```

```
cctaaattgg catatagcaa taatgatgat gaacgaaaaa aattacaact acagagctac  5640
gcaattataa gcattgtatg tctacccata gttgttattg gtgtcatttt tgcctcattc  5700
ataatgacaa catggatggg acctgattat gccttagaag cagcaactat catgaaaata  5760
cttcttgctg gttttttctt taactcttta gcgcaaatac cttatgcata cttgcaatct  5820
atcggaaagt caaaaattac cgcatttgtg catctcatag aacttgcgcc atacttatta  5880
ttattgtatt acttcacaat gcatttcggt ataattggca cggcaatcgc ttggtcactt  5940
agaacatttt gtgattttgt tatactactt tcgatatcga gaagaaaatg attgcggttg  6000
atattgcgct tgcaacctac aatggtgcta attttattcg gcaacagatt gaatctatcc  6060
agaaacaaac ttatagaaat tggcgtctta taataagtga tgataactcg agtgatgata  6120
ctgttgatat tattaaggat atgatgtcta acgacagtcg tatctatttg gtaggaaata  6180
aaagacaagg aggggttatt cagaacttta attatgctct ttcacaaact acatctgaaa  6240
ttgtgttact atgtgaccag gatgacattt ggccggagga gcgtctggaa attcttatag  6300
ataaatttaa ggccttgcag cgtaatgatt ttgttccggc aatgatgttt actgatttga  6360
aattagtaga cgaaaataat tgtttgattg cagaaagttt ttatcgaacg aataattta  6420
atccacaaga taatctgaaa aataataatc ttctctggcg ttcaacggta tatggctgta  6480
cttgcatcat gaataagaaa cttgttgata ttgcattgcc tatacctaca tatgcacata  6540
tgcatgatca atggttggca ttattagcga agcaatatgg taacattttt tatttcgact  6600
atgcgtctgt tcgttatagg caacattcta caaatgttgt tggtggtaga aataaaacgc  6660
catttcaaaa atttaattcc atacaaaaaa acctaaaaag gattaaattg ctagtggata  6720
gaactgttgc tttaattaaa tcaaataacg atttctatcc agggaataaa atggaaaata  6780
aaattgatta cttaaaattt ggagtgaatg aagtattacc ttatcttttt aaaggaaaca  6840
agaaagtttt ttcacttgt gtattaatta gtttggcatt acaaaaatga tatatttatt  6900
atttttttt gcactgttta tgatctgtac gtttttaaca cacaggcgac aggcattata  6960
tgttgtatct gcgttagtat ttctttttt ggctttaacc tatccatcag gaggggactg  7020
gataggttat tttctccatt atgactgcat ggttaatgag cagtgtaata atggttttat  7080
aatgtttgaa cctggatatg aattaattgt ttccttattt ggatatttgg gatttcagac  7140
aattattatt tttatagccg ctgtaaatgt aattctaata ttaaattttg caaagcatt  7200
tgaaaacgga agtttgtta ttgttgcgat aatgtgcatg ttcctttgga gtgtttatgt  7260
tgaggcgatt agacaggctc tggccttatc tatagttata tttgggattc attctctttt  7320
tttgggtaga aaaaggaaat ttataacatt agtattattt gcgtcaactt tccatataac  7380
tgctttgatt tgttttcttc taatgactcc tctattttca aagaaattaa gcaagataat  7440
aagttatagc ctattaattt tcagtagctt ctttttcgct ttttctgaaa ccatattaag  7500
tgcactcctt gcaattttgc cagaaggatc cattgccagt gaaaaattaa gttttttactt  7560
agcaaccgag caatacaggc cacagttatc tattgggagt ggcactattc ttgacattat  7620
acttattttt ctgatatgtg taagttttaa acgaataaag aaatatatgc tcgctaatta  7680
taatgctgca aatgagatat tgcttattgg ttgctgtctt tatatttctt tcggtatttt  7740
tatcgggaaa atgatgccag ttatgactcg cattggttgg tatggttttc catttgttat  7800
agtacttctt tatattaact tgggttattc agaatatttt aagaggtata taaataaaag  7860
agggtgttga tatagcaaat tattaattgc ttttatttt ttgctacaaa ttttgcgacc  7920
attaacatat gattatagct attataatat aatgcaccag gatactttgc tgaataggtt  7980
tgatgcatta gatgatgcat cattaagaca atcagcgaag agaaaatgtt tcgatttggg  8040
aaagatagga tatggtttct tatgtagtat ataatatcct gcattcattc ggataatttc  8100
ctatggaagt gtcctttgct ctgtctgtcc tcatttgttg aaattttatg ttaataagaa  8160
gctttagata accacttagg aactgtatgt ttgatctgtc caaaaattat attattgtaa  8220
gtgcgacggc gctggcttcc ggaggtgcat taactatatt aaagcaattt ataaaacatg  8280
catcacaaaa ttcaaatgac tatattatgt ttgtatctgc gggattggag ttgccggtct  8340
gtgataacat catttacata gaaaacacac caaaggatg gttgaaaaga atatattggg  8400
attggttcgg ttgtcggaag tttatctcgg aacataagat taacgttaag aaagtaaattt  8460
ctctacaaaa ttccagtttg aatgttcctt acgaacagat tatttacttg caccagccaa  8520
ttcctttag taaagttgat tctttttaa aaaatatcac atccgataac gtaaagcttt  8580
tttatataa aaagttttat tcctattta tatttaaata tgtgaatgcc aatacaacca  8640
tcgtagtgca aacgaattgg atgaaaaaag gagtgctgga gcaatgtgat aaaattagta  8700
ccgaaagggt ccttgttata aaacctgata tcaaagcatt taataatact aattttgatg  8760
tagatatgga tgtatctgca aaaacactct tatatccagc gacaccactt acctataaaa  8820
atcatttggt cattctgaag gcgttggtta tttttaaagaa aaagtatttt atagatgatc  8880
tgaaattcca agtgacttt gaaaagaata ggtacaaaaa ttttgataag tttgtgcaat  8940
taaataactt aagcaaaaac gttgattatc tcggcgttct ttcatactcg aacttgcaaa  9000
aaaaatatat ggcggcatct ttaatcgttt ttcctagcta tatcgaatca tatgggttac  9060
cactcatcga agctgctagt ttaggaaaaa aaatcattag tgttgatctt ccttatgccc  9120
gggatgtttt aaaggattat agcggctag attttgtaat ttacaataat gaagatggct  9180
gggctaaggc gttgtttaat gtttaaatg gcaattcgaa gctcaattt aggccttatg  9240
aaaaagatag tcgttcatct tggccacagt tcttctctat tttgaaataa ggtgtattat  9300
gtttaatggt aaaatattgt taattactgg tggtacgggg tctttcggta atgctgttct  9360
aagacgtttt cttgacactg atatcaaaga aatacgtatt tttcccggg atgaaaaaa  9420
acaagatgac atgaggaaaa aatataataa tccgaaactt aagttctata taggtgatgt  9480
tcgcgactat tcgagtatcc tcaatgcttc tcgaggtgtt gatttatttt atcatgctgc  9540
agctctgaag caagtacctt cctgcgaatt ccacccaatg gaagctgtaa aaacgaatgt  9600
tttaggtacg gaaaacgtac tggaagcggc aatagctaat ggagttaggc gaattgtatg  9660
tttgagtaca gataaagctg tatatcctat caatgcaatg ggtatttcca aagcgatgat  9720
ggaaaaagta atggtagcaa atcgcgcaa tgttgactgc tctaaaacgg ttatttgcgg  9780
tacacgttat ggcaatgtaa tggcatctcg tggttcagtt atcccattat ttgtcgatct  9840
gattaaatca ggtagaccaa tgacgataac agaccctaat atgactcgtt tcatgatgac  9900
tctcgaagac gctgttgatt tggttcttta cgcatttgaa catggcaata atggtgatat  9960
ttttgtccaa aaggcacctg cggctaccat gctattgcac tcaaagaatt  10020
acttaatgta aaccaacacc ctgtaaatat aatcggcacc cgacacgggg aaaaactgta  10080
cgaagcgtta ttgagccgag aggaaatgat tgcagcggag gatatgggtg attattatcg  10140
tgttccacca gatctccgcg atttgaacta tggaaaatat gtggacatg gtgaccgtcg  10200
tatctcggaa gtggaagatt ataactctca taatactgat aggttagatg ttgagggaat  10260
gaaaaaatta ctgctaaaac ttccttttat ccgggcactt cggtctggtg aagattatga  10320
```

```
gttggattca taatatgaaa attttagtta ctggcgctgc agggtttatc ggtcgaaatt    10380
tggtattccg gcttaaggaa gctggatata cgaactcat tacgatagat cgtaactctt     10440
ctttggcgga tttagagcag ggacttaagc aggcagattt tattttttcac cttgctgggg   10500
taaatcgtcc cgtgaaggag tgtgaatttg aagagggaaa tagtaatcta actcaacaga   10560
ttgttgatat cctgaaaaaa aacaataaaa atactcctat catgctgagt tcttccatcc   10620
aggctgaatg tgataacgct tatggaaaga gtaaagcagc tgcggaaaaa atcattcagc   10680
agtatgggga aacgacaaac gctaaatatt atatttatcg cttgccgaat gtattcggta   10740
agtggtgtcg accaaattat aactcctta tagcaacttt ctgccatcgc attgcaaatg    10800
atgaagctat tacaattaat gatccttcag cagttgtaaa tctggtgtat atagatgact   10860
tttgttctga catattaaag ctattagaag gagcgaacga aactggttac aggacatttg   10920
gtccaattta ttctgttact gttggtgaag tggcacaatt aatttaccgg tttaaagaaa   10980
gtcgccaaac attaatcacc gaagatgtag gtaatggatt tacacgtgca ttgtactcaa   11040
catggttaag ttacctgtct cctgaacagt ttgcgtatac ggttccttct tatagtgatg   11100
acagaggggt attctgtgaa gtattgaaaa cgaaaaacgc gggccagttt tcgttcttta   11160
ctgcgcatcc aggaattact cggggtggtc attatcatca ttccaaaaat gagaaattta   11220
ttgtcatccg aggaagtgct tgtttcaaat ttgaaaatat tgtcacgagt gaacgatatg   11280
aacttaatgt ttcctctgat gattttaaaa ttgttgaaac agttccggga tggacgcata   11340
acattactaa taatggctcg gatgacgctag ttgttatgct ttgggcaaat gaaatattta   11400
atcgttctga accagatact atagcgagag ttttatcgtg aaaaaattga agtcatgtc    11460
ggttgttggg actcgtccag aaattattcg actctcgcgt gtccttgcaa aattagatga   11520
atattgtgac caccttattg ttcataccgg gcaaaactac gattatgaac tgaatgaagt   11580
ttttttcaaa gatttgggtg ttcgcaaacc tgattatttt cttaatgccg caggtaaaaa   11640
tgcagcagag actattggac aagttatcat taaagttgat gaggtccttg aacaggaaaa   11700
accagaagcc atgttagtac ttggcgatac taactcctgt atttcagcaa taccagcaaa   11760
gcgtcgaaga attccgatct tccatatgga ggctgggaat cgttgttttg accaacgcgt   11820
accggaagaa actaacagaa aaatagttga tcataccgtc gatatcaata tgacatatag   11880
tgatatcgcg cgtgaatatc ttctggctga aggtgtacca gccgatgaaa ttattaaaac   11940
cggtagccca atgtttgaag tactcactca ttatatgccg cagattgatg gttccgatgt   12000
actttctcgc ctgaatttaa cacctgggaa tttctttgtg gtaagtgccc acagagaaga   12060
aaatgttgat acccctaaac aacttgtgaa actggcgaat actaaata ccgtggctga    12120
aaaatatgat gtcccggtag ttgtttctac tcatcctcgc actcgtaacc gcatcaacga   12180
aaacggtatt caattccata aaaatatctt gcttcttaag ccattaggat ttcacgatta   12240
caaccatctg caaaaaatg cacgtgctgt tttatcggat agtgggacta ttacagaaga    12300
gtcctccatt atgaacttcc ctgcactcaa tatacgagaa gcgcacgaac gcccggaagg   12360
cttcgaagaa ggggcagtaa tgatggtcgg tcttgaatct gatcgcgttt tacaggcatt   12420
agaaattatt gcaacacagc ctcgtggaga agtacgctta cttcgtcagg ttagtgacta   12480
tagcatgcca aatgtttcag ataaagttct gcgtattatc cattcatata ctgactacgt   12540
taaacggatt gtctggaagc aatactaatg aaacttgcat taatcattga tgattatttg   12600
ccccatagca cacgcgttgg ggctaaaatg tttcatgagt taggccttga attactgagc   12660
agaggccatg atgtaactgt aattacgcct gacatctcat tacaagcaat ttattctatt   12720
agtatgattg atggtataaa ggtttggcgt tcaaaagtg gacctttaaa ggatgtaggt    12780
aaggctaaac gtgccataaa tgaaactctt ttatcttttc gcgcatggcg cgcatttaag   12840
cacctcattc aacatgatac atttgatggt atcgtttatt atccccctc tattttttg    12900
ggcgacttgg ttaaaaaaat aaaacaacga tgccagtgcc caagctatct gatcctaagg   12960
gatatgtttc cacagtgggt cattgatgca ggtatgttga agccggttc accaattgaa   13020
aaatatttta ggtatttga aaaaaagtca tatcagcagg ctggccggat aggggtaatg   13080
tctgataaga atcttgagat atttcgccag accaataaga gttatccgtg tgaagtttta   13140
cgtaattggg cctcaatgac tcctgtgtct gccagcgatg attatcattc acttcgtcaa   13200
aaatacgatc taaaagataa agtcattttt ttctatggcg gtaatattgg gcatgctcag   13260
gatatggcaa acttaatgcg ccttgcgcgt aatatgatgc gttatcatga tgctcatttc   13320
ctgtttatag ggcagggtga tgaagttgag ctgataaaat ctcttgctgc agaatggaat   13380
ttaactaatt tcactcatct accttcagtg aaccaggaag agtttaaatt aatttttatct   13440
gaagttgatg tcggcctgtt ctcccttca tctcgccatt cttcacataa tttccccgga    13500
aaattactag ggtatatggt tcaatcaatc ccgatccttg ggagtgtgaa tggcggcaat   13560
gatttaatgg atgtaattaa taagcacaga gccggtttca ttcatgttaa tggtgaagat   13620
gataaactgt ttgaatctgc acaattgctt cttagtgatt cagttttaag aaaacagcta   13680
ggtcagaacg ctaatgtgtt gttaaagtct caatttcgg ttgaatcggc ggcacatact    13740
atcgaagtcc gactggaggc tggagaatgc gtttagttga tgacaatatt ctggatgaac   13800
tttttcgcac tgcagcaaat tctgaacgtt tgcgcgctca ttatttattg cacgcatctc   13860
atcaggagaa ggttcaacgt ttacttattg catttgtacg cgacagctat gttgaacccc   13920
attggcatga gttaccgcat cagtgggaaa tgtttgtcgt catgcaaggg caattagaag   13980
tttgtttgta tgagcaaaat ggtgagatcc aaaaacagtt tgttgttgga gacggtacgg   14040
gaataagcgt cgtggaattt tccccaggag atatacatag tgtcaaatgc ctgtcaccaa   14100
aagcccttat gttggagata aaggagggc catttgaccc actcaaagct aaggcttttt   14160
ctaagtggtt ataggggcgat acaccaccgt ttattcttct atcttattct atacatgctg   14220
ggttaccatc ttagcttctt caagccgcgc aaccccgcgg tgaccacccc tgacaggagt   14280
agctagcatt tgaccacccc tgacaggatt agctagcata tgagctcgag gatatctact   14340
gtgggtaccc gggatccgtg taggctggag ctgcttcgaa gttcctatac tttctagaga   14400
ataggaactt cggaatagga actaaggagg atattcatat                         14440

SEQ ID NO: 10         moltype = AA   length = 19
FEATURE               Location/Qualifiers
source                1..19
                      mol_type = protein
                      organism = synthetic construct
SEQUENCE: 10
MKKIWLALAG LVLAFSASA                                                 19

SEQ ID NO: 11         moltype = DNA  length = 13043
```

```
FEATURE              Location/Qualifiers
source               1..13043
                     mol_type = other DNA
                     organism = synthetic construct
SEQUENCE: 11
atgacgaatt taaaagcagt tattcctgta gcgggtctcg ggatgcatat gttgcctgcc    60
actaaggcga tacccaaaga gatgctacca atcgtcgaca agccaatgat tcagtacatt   120
gttgacgaga ttgtggctgc agggatcaaa gaaatcctcc tggtaactca cgcgtccaag   180
aacgcggtcg aaaaccactt cgacacctct tatgagttag aatcactcct tgagcagcga   240
gtgaagcgtc aactgctggc ggaagtacag tccatctgtc cgccgggcgt gaccattatg   300
aacgtgcgtc agggcgaacc tttaggttta ggccactcca ttttgtgtgc gcgacctgcc   360
attggtgaca acccatttgt cgtggtactg ccagacgttg tgatcgacga tgccagcgcc   420
gacccgctac gttacaacct tgctgccatg attgcacgtt tcaacgaaac gggccgcagc   480
caggtgctgg caaaacgtat gccgggtgac ctctctgaat actccgtcat ccagactaaa   540
gagccgctgg accgtgaggg taaagtcagc cgcattgttg aatttatcga aaaaccggat   600
cagccgcaga cgctggactc agacatcatg gccgtaggtc gctatgtgct ttctgccgat   660
atttggccgg aactggaacg tactcagcct ggtgcatggg gacgtattca gctgactgat   720
gctattgccg agctggctga aaaacaatcc gttgatgcac tgctgatgac cggcgacagt   780
tacgactgcg gcaaaaaaat gggctatatg caggcgtttg tgaagtatgg cctacgcaac   840
ctgaaagaag gggcgaagtt ccgtaaaggt attgagaagc tgttaagcga ataatgaaaa   900
tctgaccgga tgtaacggtt gataagaaaa ttataacggc agtgaaaatt cgcagcaaaa   960
gtaatttgtt gcgaatcttc ctgccgttgt tttatataaa ccatcagaat aacaacgagt  1020
tagcagtagg gttttattca aagttttcca ggatttcct tgtttccaga gcggattggt  1080
aagacaatta gcgtttgaat ttttcgggtt tagcgcgagt gggtaacgct cgtcacatca  1140
taggcatgca tgcagtgctc tggtagctgt aaagccaggg gcggtagcgt gcattaatac  1200
ctctattaat caaactgaga gccgcttatt tcacagcatg ctctgaagta atatgaaata  1260
aattaagcta gcgtgaagat acttgttact aggggcgcag gatttattgg ttctgctgta  1320
gttcgtcaca ttataaataa tacgcaggat agtgttgtta atgtcgataa attaacgtac  1380
gccggaaacc tggaatcact tgctgatgtt tctgactctg aacgctatgt ttttgaacat  1440
gcggatattt gcgatgctgc tgcaatggcg cggattttg ctcagcatca gccggatgca  1500
gtgatgcacc tggctgctga aagccatgtg gatcgttcaa ttacaggccc tgcggcatt  1560
attgaaacca atattgttgg tacttatgtc cttttggaag cggctcgcaa ttactggtct  1620
gctcttgatg gcgacaagaa aaatagcttc cgttttcatc atatttctac tgacgaagtc  1680
tatggtgatt tgcctcatcc tgacgaagta aataataaag aacaattacc cctctttact  1740
gagacgacag cttacgcgcc tagtagtcct tattccgcat caaaagcatc cagcgatcat  1800
ttagtccgcg cgtggaaacg tacctatggt ttaccgacta ttgtgactaa ctgttcgaat  1860
aactacggtc cttatcactt tccggaaaaa ttgattccac tagtaattct taatgctctg  1920
gaaggtaagg cattacctat ttatggcaaa ggggatcaaa ttcgtgactg gctgtatgtt  1980
gaagatcatg cgcgtgcgtt atataccgta gttacctgaa gtcaagcggg tgaaacctat  2040
aacattggcg gacacaacga aaagaaaaac atcgatgttg tgctgactat ttgtgatttg  2100
ttggacgaga tagtcccgaa agagaaatct tatcgtgagc aaaattactta tgttgctgat  2160
cgcccagggc atgatcgccg ttatgcgatt gatgctgaga agattggtcg cgaattggga  2220
tggaaaccac aggaaacgtt tgagagtggg attcgtaaaa cggtggaatg gtatttggct  2280
aatgcaaaat gggttgataa tgtgaaaagt ggtgcctatc aatcgtggat tgaacagaac  2340
tatgagggcc gccagtaatg aatatcctcc tttttggcaa aacagggcag gtaggttggg  2400
aactacagcg tgctctggca cctctgggta atttgattgc tcttgatgtt cactccactg  2460
attactgtgg tgattttagt aaccctgaag gtgtggctga aacagtcaaa agaattcgac  2520
ctgatgttat tgttaatgct gcggctcaca ccgcagtaga taaggctgag tcagaacccg  2580
aatttgcaca attactcaat gcgactagcg ttgaatcaat tgcaaaagcg gcaaatgaag  2640
ttgggggctg ggtaattcat tactcaactg actacgtatt ccctgaaat ggcgacacgc  2700
catggctgga gatggatgca accgcaccgc taaatgttta cggtgaaacc aagttagctg  2760
gagaaaaagc attacaagag cattgtgcga agcacctaat tttccgtacc agctgggtct  2820
atgcaggtaa aggaaataat ttcgccaaaa cgatgttgcg tctggcaaaa gagcgtgaag  2880
aactagccgt tattaatgat cagtttggtg cgccaacagg tgctgaactg ctggctgatt  2940
gtacggcaca tgccattcgt gtcgcactga ataaaccgga tgtcgcagge ttgtaccatt  3000
tggtagccag tggtaccaca acctggtacg attatgctgc gctggttttt gaagaggcgc  3060
gcaatgcagg cattcctctt gcactcaaca agctcaacgc agtaccaaca actgcctatc  3120
ctacaccagc tcgtcgtcca cataactctc gccttaatac agaaaatttt cagcagaatt  3180
ttgcgcttgt attgcctgac tggcaggttg gtgtgaaacg catgctcaac gaattattta  3240
cgactacagc aatttaatag tttttgcatc ttgttcgtga tggtggagca agatgaatta  3300
aaaggaatga tgaaatgaaa acgcgtaaag gtattatttt agcggtggt tctggtactc  3360
gtctttatcc tgtgactatg gtcgtcagta aacagctatt acctatatat gataaaccga  3420
tgatctatta tccgctttct acactgatgt tagcgggtat tcgcgatatt ctgattatta  3480
gtacgccaca ggatactcct cgttttcaac aactgctgga tgacgggtac cagtggggcc  3540
tgaatcttca gtacaaagtg caaccgagtc cggatggtct tgcgcaggca tttattatcg  3600
gtgaagagtt tattggtggt gatgattgtg ctttggtact tggtgataat atcttctacg  3660
gtcacgacct gcctaagtta atggatgccg ctgttaacaa agaaagtggt gcaacggtat  3720
ttgcctatca cgttaatgat cctgaacgct atggtgtcgt tgagtttgat aaaaacggtc  3780
cggcgatcag cctggaagaa aaaccgctac aaccaaaaag taattatgcg gtaaccgggc  3840
tttatttta tgataacgac gttgtcgaaa tggcgaaaaa tcttaagcct ctgcccgcg  3900
gtgaactgga aattaccgat attaaccgta tctatatgga acaagggcgt ttatctgttg  3960
ccatgatggg gcgtggttat gcgtggtag acacggggac acatcagagc tgattgagg  4020
caagcaactt tattgcaaca attgaagagc gtcagggcgt gaaagttcc tgcccggaag  4080
aaattgctta tcgctaaaggg tttgttgatg ctgagcaggt gaaagtatta gctgaaccct  4140
tgaaaaaaaa tgcttatggt cagtatctgc tgaaaatgat taaaggttat taataaaatg  4200
aacgtaatta aaacagaaat tcctgatgta ctgattttg aaccgaaagt ttttggtgat  4260
gagcgtggtt ctttttttga gagctttaac cagaaggttt tgaggaagc tgtaggccgc  4320
aaagttgaat tgttcagga taaccattcg aagtctagta aggtgtttt acgcgggctg  4380
cattatcagt tggaacctta tgcacaagga aaattggtgc gttgcgttgt cggtgaagtt  4440
```

```
tttgacgtag ctgttgatat tcgtaaatcg tcatcgactt ttggcaaatg ggttggggtg  4500
aatttatctg ctgagaataa gcggcaattg tggattcctg agggatttgc acatggtttt  4560
ttagtgctga gtgagacggc ggagtttttg tataagacga caaattatta tcatcctcag  4620
agtgatagag gaataaaatg ggatgatcca agcatcaata tttcatggcc agtcgattca  4680
caagtgctgc tatcagctaa agataataag catcctccat taacaaagat tgaaatgtat  4740
agttaagatc acgataaatc ttggaagggt tgcaaaattg aataaaatag tgagcaaaag  4800
tgaaataagg aacgtaatcc acaatgctgg ctatatgatg attactcaga tagctttata  4860
tgttgcacca ttatttatac tgagttatct gttaaaaaca ctgggggttg cacagtttgg  4920
taattatgcc ttaatactat caatcgttgc atatttacag attataacgg attatggttt  4980
ttcttttagt gcaagtcgtg cgatctcaca gaatagagag gacaaagaat atatatcaaa  5040
aatttatctg tcaactatga ctatcaagtt ggcgatatgc gctttcttat tcttattgct  5100
catgctattt ttaaatcttt tgcctgtgca agctgaatta aaacaaggaa tattatatgg  5160
atatcttctt gtaataggaa atactttcca accacaatgg tttttccaag gtatcgaaaa  5220
attaaaaatc atagccctt ctaatgttat atcaagatgc gccgcgtgtt tacttgtatt  5280
tatctatgtg aggaatagcg aggatttaca aaaagcactt ttagtacagt cacttccatt  5340
agtaatttct gcgattggat taaatatatt tatattgaaa tatatcaata ttattttttcc  5400
ggaaaaaaaa ttatttaagg taattttaaa agaaggtaag gatttttttc ttgcatcact  5460
ttattctgtt attctcaata atagtggcat ttttctatta gggattttta ctaatcctgt  5520
tattgttggt gtatatgccg ccgctgaaaa gatagtcaag gccgtattgt cgctatttac  5580
accactgacg caagctatat atccttataa ttgtcgtaag ttttcactat ccgtatttga  5640
cggcattgag gcagcaaaaa aaactggtat accaattata atttttagcat ttatagctgc  5700
tgttatcgtt gcaattacct tacctgttgc aatcgactat cttaattttc caaaagaaac  5760
aattttttgta ggtcaaatat taagtgcatg gatcttttttt ggtgttctta ataatgtatt  5820
cggcattcag atattgagtg catcaggaag aagtaaaata tatagtagga tggtattcgt  5880
atcagcgctt ataacattac ttttgattac tctattattg cagttttgta acgccactgg  5940
agtggcatgt gcaatattat tgggtgaaat gttcttatca atattgttac ttaagcgata  6000
taaaaaaata atttaaggaa tagttatgaa gaagttatta ttagtgttcg gtactaggcc  6060
tgaagcaata aagatggcct ctatcattga attattaaaa aaagattgta gattcgaata  6120
taaaatatgt gtgacaggcc aacataaaga gatgcttgat caagttatgc aagtatttga  6180
tgttaaacct gattataatt tacggattat gcagcctggg caaacattag tatctatagc  6240
aacaaatata ctctcacggt taagtgaagt tttaattata gaaaagccag atattatact  6300
tgtgcatggg gatacaacga ctaccettgc tgctacttta gctgggtatt accaccaaat  6360
aaaagtttgt catgtggaag caggattaag aacaggggga atttactctc cttggcctga  6420
agagggcaat cgtaaagtta caggggcatt agcatgtatt catttcgccc caacagagag  6480
atcaaaagat aatctcctga gggagggggt caaagtaaat aatatatttg taacgggtaa  6540
taccgtcatc gactctttat ttattgcaaa agatatcata gataatgacc ctaatataaa  6600
gaacgcttta cataataaat ttaattttct tgataaaagc cgacgagtag tacttataac  6660
aggtcatcga agagaaaatt tcgggaaagg ttttgaagat atatgctttg caataaagga  6720
attgctttc attatcctta atgtagattt tatttatccg gtgcatctta atcccaatgt  6780
aatggaacca gtcatcgta tattagataa tatatgtaat atttacctta ttgagcccctt  6840
ggattatttg ccttttgttt atttaatgaa tgagtcatat ttaatattga ctgattcagg  6900
ggggatacaa gaagaagcgc cttcgttagg taaaccggtt ttggttatgc gtgatactac  6960
tgaacgccct gaggcggttg aggctggtac tgttgtatta gtggggactt ctaagataaa  7020
aatagtaaat aaagtaacgg agctattaaa caatgctgat atctacaatg ctatgtctct  7080
gttacataat ccatatggcg atggaacagc tgctcaaaaa attcttaatg tgctcgccca  7140
agagctaatt taatttaagc taaaaatatg ttattaatta ttgctgatta tccaaacgaa  7200
atgaatatgc gcgagggagc tatgcaacga atagatgcga tagactctct cattcgagat  7260
cgcaagcgag tgtatttgaa tatttcattc aaaaagcatc tagttcgctc aaatagttcc  7320
tttaataatg ttatagttga aaatctaaat gcaattattc acagaaacat cataaaacag  7380
tacatgcaaa aatcaacaac tatatatgtt cattctgttt ataatttatt aaaggttata  7440
acgctcattg atctaaaaaa aacaattctt gatatacatg gtgttgtacc ggaagaactt  7500
ttggcagata ataaaaaatt acttagtaaa gtatataaca tggtggaaaa aaaaggtgtc  7560
cttggatgca aaaaattaat acacgtcagt acagaaatgc aaaaacacta tgaagcaaaa  7620
tatggagtaa acttggctga aaggtcaata gtgctcccga ttttttgaata taaaaatata  7680
acccaatcgc aaaacaaatg gacagaaaat aaaatacgaa gtatctatct tggaggatta  7740
caaacatggc aaaatattga taaaatgatt caagttgtg atgacacagt gataaacaat  7800
gaagcaggta agtatgaatt caactttttc atcccacaga gtaacttgga agggtttata  7860
gataaatatt cgttaaaatt acataatatc aatgctaatg catctacgct atcacgtgat  7920
gaagtaattc cctttctaaa agaatgtcat attggttttg tattcgcga tgatataata  7980
gtaaacagag ttgcgtgccc tacaaaattg gttgaatatt tagagtgtgg tgtcgttcca  8040
gttgtgctct ccccacttat aggtgatttt tattcgatgg gatatcaata cattactaca  8100
gaggaaatgc ctaacagaag tataagtttg ttggatcttg aaaaaatggc tgcacataat  8160
ttacaaattt tgacttctta tcagaagaga acctacaagg cacagaaaga acttattgct  8220
caactgtgct gaattttta catatataaa attatgtaag catatcgcgg gtcaggtaat  8280
tgtatgcgta tcaaatataa agataacggt tatatattat gttttctatt atgtttcatt  8340
ttgagctact tagttttact caaatctgac tactttcctg ctgattttct gccatataca  8400
gaaatatacg atgggacata cggagaaatc aataatattg agcctgcctt tttatattta  8460
acacggttgt ttcattttt aaatttcccc tatatatttt ttgcaatgtt agtttgtgcc  8520
ttatgtttaa gttggaaaat aaaatatgca agaaaaataa ttaaagatag ttatatatat  8580
ttgttcttgt atgtatatgt atcatttta gtgttttgc atgaaatgac tcaattgcgc  8640
atagcaattg cagtcactat gtgctatgtg tcggttatt attacttttta taaaaattgt  8700
attaaacatg cactgccatg gatggtgttg gctattttgt ttcattacag cgccttgctt  8760
ttatttatgt cattatttat atacagttat aggaggttat taatagtaat tatagggttt  8820
gtaatatgta tgagctttta aaacgtgtat gcagatacaa ttgcactata tttgccaaat  8880
gaaaaaatag taaattattt atatagtatt tcatcatcat tagacaatag aaatgatttg  8940
gcaatattca acctgaataa tataaatttt ttatcaatat ttattttgat cttttatctt  9000
agccgatata taaaattaaa tgataatgag gcgaagttta ttaagtatgt gcaatgttca  9060
ggaatattag ccttttgtat tttctttctg gctagtggag tcccggtcat tgcttatcga  9120
actgcagagt tgctgcgaat atttttatccg atggctttag tattaatcct ttcgcatata  9180
```

```
aaaaataata atatgcgtta ttttattgca gtcattatag ttatcctttc aggcttaatg    9240
ttgtttataa cactaagggc tgtatcaata gttggtcaag gattataaaa tgaatgttgc    9300
tatttttgttg tctacgtata atggcgaaaa atatttagag gaacaactgg attcattgct   9360
gcttcaaagt tatcaggatt ttgtagtgta tatccgtgat gacggatcat ctgatagaac    9420
tgtaaatata ataaaccaat acgtaatgaa agataacaga tttattaacg tgggtaattc    9480
agaaaatctt ggttgtgctg cttcgtttat taatttatta agaaatgctt cagccgatat    9540
ttatatgttt tgtgaccaag atgattattg gcttccgaat aaattacagc gtgctgtgga    9600
ttatttttcg gctattgatc ctttacaacc taccttgtat cattgcgatc taagcgttgc    9660
tgatgaaaaa cttaatatta tacaaaattc attttgcag catcagaaaa tgtcagcgta    9720
tgattcaatg agaaaaaata atcttttcat acaaaatttt gttgttggtt gttcatgtgc    9780
tgttaatgct tcacttgcgg aatttgttct ttcgcgaatt ggagagcagc atgtaaaaat    9840
gatagctatg catgactggt ggttagccgt gactgcaaaa cttttttggtc gaatccattt   9900
tgataatact caaacgattc tttatcgaca acatcagggc aatgtattag gtgcaaaatc    9960
atcaggtatg atgcgtttta ttcgattagg attaaatggg caagggattt cgcgagtagt   10020
atcttttaga aaaaaagttt gtgcgcaaaa taagcttctt ttagatgtct atgataaaga   10080
tttaaatctt gagcaaaaaa aatctatcag gcttgtaatt gagggccta aagagaactc    10140
ttcaattgct gacctttttaa aatgtttcta tcatggtagc tatatgcaag gttttaaacg   10200
taatccttgcc ttaatatatt cagttcttta cacaaaaaaa agaagatagt gtatccttat  10260
gaaaaaaatt gctattatcg gtactgttgg cataccagca tcatatggcg gatttgaaac   10320
attagttgaa aatttaacaa gatacaattc ctcggggagtt gaatataatg ttttttgttc  10380
atcgtttcac tacaaatccc accaaaaaaaa acataatggg gcccgtttaa tttatattcc  10440
gcttaaagcc aatggatggc agagcattgc gtatgacata atttcgttag catattctat   10500
tttttttgaag cctgatgtga ttctgatttt aggggtttct ggttgttcat ttttgccttt  10560
cttcaaactc ttaacacgcg ctaagtttat tactaatatt gatggcctgg aatggcgaag   10620
agataaatgg aattcaaaag tgaaacgttt cttaaaattt tcagaaaaaa tcgcagttca   10680
atattcggat gtcgttatta cggataatga ggcaatttct gagtacgttt ttaacgagta   10740
taataaagat agccgagtta ttgcctatgg aggggatcat gcatggttaa atactgagga   10800
tgtatttaca acaagaaatt ataaaagcga ttactacctt tctgtatgtc gtatcgaacc   10860
cgaaacaat gtagaattaa ttttaaaaac attttcaaag ctaaatata aaataaaatt     10920
tattggaaat tggaatggca gcgagtttgg aaagaaactt aggctgcatt attctaacta   10980
tccaaatatt gaaatgattg atccgattta tgatcttcaa caattattc acttacgaaa    11040
taattgcata ggatatatac atggtcattc ggctggagga acaaaccctt ctttagtcga   11100
ggcaatgcat tttagtaaac ctatatttgc atatgattgt aagtttaata ggtacactac   11160
tgaaaatgaa gcatgttatt tttctaatga atctgacctc gcagagaaaa tcataatgca   11220
ttgtgagcta tcattaggtg tctctggcac gaaaatgaaa gaaattgcta accagaaata   11280
cacttggaga cgaatagcag aaatgtatga ggattgctat taactctgtt aaacttcaaa   11340
tcttttacaa tatatggcat gactataagc gcattaattg ttttttcaagc cgctctcgcg   11400
gtgaccaccc cctgacaggg gatccgtgta ggctggagct gcttcgaagt tcctatactt   11460
tctagagaat aggaacttcg gaatagggaac taaggaggat attcatatgg ataaagccgt   11520
aagcatataa gcatggataa gctatttata ctttaataag tactttgtat acttatttgc   11580
gaacattcca ggccgcgagc attcagcgcg gtgatcacac ctgacaggag tatgtaatgt   11640
ccaagcaaca gatcggcgta gtcggtatgg cagtgatggg acgcaacctt gcgctcaaca   11700
tcgaaagccg tggttatacc gtctctattt tcaaccgttc ccgtgagaag acggaagaag   11760
tgattgccga aaatccaggc aagaaactgg ttccttacta tacggtgaaa gagtttgtcg   11820
aatctctgga aacgcctcgt cgcatcctgt taatggtgaa agcaggtgca ggcacggatg   11880
ctgctattga ttccctcaaa ccatatctcg ataaggaga catcatcatt gatggtggta   11940
acacctttctt ccaggacact attcgtcgta atcgtgcgt ttcagcagag ggctttaact   12000
tcatcggtac cggtgtttct ggcggtgaag aggggggcgct gaaaggtcct tctattatgc   12060
ctggtggcca gaaagaagcc tatgaattgg tagcaccgat cctgaccaaa atcgccgccg   12120
tagctgaaga cggtgaacca tgcgttacct atattggtgc cgatgcgca ggtcactatg    12180
tgaagatggt tcacaacggt attgaatacg gcgatatgca gctgattgct gaagcctatt   12240
ctctgcttaa aggtggcctg aacctcacca acgaagaact ggcgcagacc tttaccgagt   12300
ggaataacgg tgaactgagc agttacctga tcgacatcac caaagatatc ttcaccaaaa   12360
aagatgaaga cggtaactac ctggttgatg tgatcctgga tgaagcggct aacaaaggta   12420
ccggtaaatg gaccagccag agcgcgctgg atctcggcga accgctgtcg ctgattaccg   12480
agtctgtgtt tgcacgttat atctcttctc tgaaagatca gcgtgttgcc gcatctaaag   12540
ttctctctgg tccgcaagca cagccagcag gcgacaaggc tgagttcatc gaaaaagttc   12600
gtcgtgcgct gtatctgggc aaaatcgttt cttacgccca gggcttctct cagctgcgtg   12660
ctgcgtctga agagtacaac tgggatctga actacgcga aatcgcgaag atttccgtcg   12720
ctggctgcat catccgtgcg cagttcctgc agaaaatcac cgatgcttat gccgaaaatc   12780
cacagatcgc taacctgttg ctggctccgt acttcaagca aattgccgat gactaccagc   12840
aggcgctgcg tgatgtcgtt gcttatcgag tacagaacgg tattccggtt ccgacctttct  12900
ccgcagcggt tgcctattac gacagctacc gtgctgctgt tctgcctgcg aacctgatcc   12960
aggcacacgc tgactatttt ggtgcgcata cttataagcg tatcgataaa gaaggtgtgt   13020
tccataccga atggctggat taa                                            13043
SEQ ID NO: 12          moltype = DNA  length = 13790
FEATURE                Location/Qualifiers
source                 1..13790
                       mol_type = other DNA
                       organism = synthetic construct
SEQUENCE: 12
atgacgaatt taaaagcagt tattcctgta gcgggtctcg ggatgcatat gttgcctgcc     60
actaaggcga tacccaaaga gatgctacca atcgtcgtga agccaatgat tcagtacatt    120
gttgacgaga ttgtggctgc agggatcaaa gaaatcctcc tggtaactca cgcgtccaag    180
aacgcggtcg aaaaccactt cgacacctct tatgagttag aatcactcct tgagcagcgc    240
gtgaagcgtc aactgctggc ggaagtacag tccatctgtc cgccgggcgt gaccattatg    300
aacgtgcgtc agggcgaacc tttaggttta ggccactcca ttttgtgtgc gcgacctgcc    360
attggtgaca acccatttgt cgtggtactg ccagacgttg tgatcgacga tgccagcgcc    420
```

-continued

```
gacccgctac gttacaacct tgctgccatg attgcacgtt tcaacgaaac gggccgcagc  480
caggtgctgg caaaacgtat gccgggtgac ctctctgaat actccgtcat ccagactaaa  540
gagccgctgg accgtgaggg taaagtcagc cgcattgttg aatttatcga aaaaccggat  600
cagccgcaga cgctggactc agacatcatg gccgtaggtc gctatgtgct ttctgccgat  660
atttggccgg aactggaacg tactcagcct ggtgcatgga gacgtattca gctgactgat  720
gctattgccg agctggcgaa aaaacaatcc gttgatgcaa tgctgatgac cggcgacagt  780
tacgactgcg gcaaaaaaat gggctatatg caggcgtttg tgaagtatgg cctacgcaac  840
ctgaaagaag gggcgaagtt ccgtaaaggt attgagaagc tgttaagcga ataatgaaaa  900
tctgaccgga tgtaacggtt gataagaaaa ttataacggc agtgaaaatt cgcagcaaaa  960
gtaatttgtt gcgaatcttc ctgccgttgt tttatataaa ccatcagaat aacaacgagt 1020
tagcagtagg gttttattca aagttttcca ggattttcct tgtttccaga gcggattggt 1080
aagacaatta gcgtttgaat ttttcgggtt tagcgcgagt gggtaacgct cgtcacatca 1140
taggcatgca tgcagtgctc tggtagctgt aaagccaggg gcggtagcgt gcattaatac 1200
ctctattaat caaactgaga gccgcttatt tcacagcatc ctctgaagta atatgaaata 1260
aattaagtga aaatacttgt tactggtggc gcaggattta ttggttcagc tgtagttcgt 1320
cacattataa ataatacgca ggatagtgtt gttaatgtcg ataaattaac gtacgccgga 1380
aaccgggaat cacttgctga tgtttctgat tctgaacgct atgttttgta acatgcggat 1440
atttgcgatg cacctgcaat ggcacggatt tttgctcagc atcagccgga tgcagtgatg 1500
cacctggctg ctgaaagcca tgttgaccgt tcaattacag gccctgcggc atttattgaa 1560
accaatattg ttggtactta tgtccttttg gaagccgctc gcaattactg gtctgctctt 1620
gatagcgaca agaaaaatag cttccgtttt catcatattt ctactgacga agtctatggt 1680
gatttgcctc atccagatga agtaaataat acagaagaat tacccttatt tactgagacg 1740
acagcttacg cgccaagcag ccccttattcc gcatccaaag catccagcga tcatttagtc 1800
cgcgcatgga aacgtacgta tggtttaccg accattgtga ctaattgctc gaacaactat 1860
ggtccgtatc acttcccgga aaagcttatt ccattggtta ttcttaatgc actggaaggt 1920
aaggcattac ctatttatgg caaagggat caaattcgac actggttgta tgtagaggat 1980
catgctcgtg cgttatatac cgtcgtaacc gaaggtaaag cgggtgaaac ttataacatt 2040
ggcggacaca acgaaaagaa aaacatcgat gttgtgctga ctatttgtga tttgttggat 2100
gagattgtac cgaaagagaa atcttatcgt gagcaaatta cttatgttgc tgatcgccca 2160
gggcatgatc gccgttatgc aattgatgcc gataaaatta gccgcgaatt gggctggaaa 2220
ccacaggaaa cgtttgagag cgggattcgc aaaacggtgg aatggtatct ggctaataca 2280
aattgggttg agaatgtgaa aagcggtgct tatcagtcat ggatcgaaca aaactatgag 2340
ggccgtcagt aatgaatatc ctgcttttcg gcaaaacagg gcaggtgggt tgggaactgc 2400
agcgtgctct ggcgccgctg ggtaatctga tcgctcttga tgttcactcc actaattatt 2460
gtggagattt cagcaacccc gaaggtgtgg cagaaaccgt caaaaaaatt cgtcctgacg 2520
ttattgttaa tgctgctgct cacactgcag tagataaagc agaatcagaa ccggatttcg 2580
cacaattact taacgcgaca agcgtcgaag cgattgcaaa agctgctaat gaagtcgggg 2640
cctgggttat acactactct actgattatg ttttcccagg cagtggtgac gcgccatggc 2700
tggaaacgga tgcaacagca ccgctaaatg tttacggtga aacaaaatta gctggggaaa 2760
aggcattaca agaacattgc gcaaagcatc ttatttccg taccagctgg gtatacgctg 2820
gtaaaggaaa taactttgct aaaacgatgt tgcgtttggc aaaagaacgc gaagaactgg 2880
ctgtgataaa cgatcagttt ggcgcaccaa caggtgctga attgctggct gattgcaccg 2940
ctcatgccat tcgcgtggca ttaaaaaaac cagaagtcgc tggcttgtac catctggtag 3000
caagtggcac aacaacctgg cacgattatg ctgcgctgtt ttttgaagag gcgcgcaaag 3060
cagggattaa tcttgcactt aacaaactta acgccgtgcc aacaacggcc tatcccacac 3120
cagcccgtcg accccataac tctcgcctca atacagaaaa gtttcagcag aactttgcgc 3180
ttgtcttgcc tgactggcag gtgggcgtga aacgtatgct caacgaatta tttacgacta 3240
cggcaattta acaaattttt gcatctcgct catgatgcca gagcgggatg aattaaaagg 3300
aatggtgaaa tgaaaacgcg taaaggtatt atttctggctg gtggttccgg cactcgtctt 3360
tatcctgtga cgatggcagt gagtaaacaa ttgctgccga tttatgataa gccgatgatt 3420
tattatccgc tttcaacgct tatgttagcg ggtattcgcg atattcttat tattagtacg 3480
ccacaggata caccgcgttt ccaacaatta ttggggacg ggagccagtg gggtcttaat 3540
ctacagtata aagtacaacc gagtccggat ggcctggcgc aagcgtttat tattggcgaa 3600
gactttattg gtggtgatga ttgtgcactc gtacttggcg ataatatctt ctatggacac 3660
gacttgccga aattgatgga agctgctgtt aacaaagaaa gcggtgcaac ggtatttgct 3720
tatcacgtta atgatcctga acgctatggt gtcgtggagt ttgataataa cggtacggca 3780
attagcctgg aagaaaaacc gctggagcca aaaagcaact atgcggttac tgggcttttat 3840
ttctatgaca atgacgttgt ggaaatggct aaaaaccta gccttctgc ccgtggcgaa 3900
ctggaaatta ccgatattaa ccgtatttat atggaacaag gacgtttgtc tgtagccagt 3960
atggggcgtg gctatgcatg gttggataca gggacgcatc aaagccttat tgaagcaagt 4020
aacttcattg caacaattga agagcgtcag ggattaaagg tatcttgccc ggaagagatt 4080
gcttaccgta aagggtttat tgatgccgag caggtgaaag tattagccga accgcttatc 4140
aagaatcaat atggtcaata tttgctgaaa atgatcagcg aatagtatat gggaactcaa 4200
tgatggatat taaattaatc tctttgcaaa aacatgggta tgagcgcggt gcattaattg 4260
ctcttgaaga gcaacgaaat ataccttcg aagtcaaaag aatatattac atacttgaga 4320
ctcttaatgg agtaagacgc ggattcatg cgcacaagt tactcgtcag ttagctattg 4380
tagtcaaggg agcttgtaaa tttcatctgg ataatggtaa agaacaaag caggtggaac 4440
ttaatgatcc aacaattgcg ttgctgatag aaccctatat atggcatgaa atgtatgatt 4500
ttagtgataa ttgtgtgctg cttgtaattg cggatgattt ctataaagag tctgattata 4560
tccgcaatta tgatgatttt attagaagag taaattcaat tgagaattca taagctaagt 4620
gacgtccaga caacatcaat tggtgatgga acaactatct ggcagtttgt tgtgatacta 4680
aaaggtgcta taattggtaa taattgcaac atctgtgcaa ataccttaat tgaaaataac 4740
gttgtaattg gtaacaatgt cacagtcaaa agcggtgtgt atatttggga tggcgttaaa 4800
atagaggata atgtttttat tgtgtccttgt gtactgttta caaatgataa gtatcctcgc 4860
tctaaagtct atcctgatga attttttgcaa acaataatac gcaaaggagc atcaataggt 4920
gctaacgcaa ccatcctgcc aggaattgaa attggtgaaa aagcaatcgt tggtgcgggg 4980
agtgttgtaa ccaaaaatgt accgccatgc gcaatagtaa taggtaatcc agctcgatttt 5040
attaaatggg tagaggataa tgaataaaat tgattttta gatcttttg caattaacca 5100
gcgacagcac aaagaattag tctctgcgtt tagtagggtg ctagattctg gttggtatat 5160
```

```
catgggcgaa gaacttgagc agttcgagaa agagttcgca gaatactgtg gagtttaagta   5220
ttgcattggt gtagcaaatg gccttgatgc gttgatacta gtattgaggg catgaaagaa    5280
acttggctat cttgaagacg gtgacgaggt attagtaccg gcaaatacat atattgcttc    5340
tattcttgct ataacagaga acaaacttgt tcctgttctt gttgaaccag atatagaaac    5400
ttataatatt aatcctgctt taattgaaaa ttacattacg gaaaaaacta aagcaatatt    5460
accggttcac ttatatggtc tattgtgcaa tatgccagaa attagtgcaa tcgccagaaa    5520
atataatctg ttgattcttg aagattgtgc acaagcacat ggtgcaatac gtgatggtcg    5580
caaagctgga gcttgggggg atgctgcagg atttagtttt tatccaggaa aaaaccttgg    5640
agctttgggg gatgcgggag ctgttactac aaataatgca gaattatcct caactataaa    5700
agctttgcga aattatgggt cacataagaa atatgaaaat atttatcagg gattgaatag    5760
tcgattggat gaactgcaag cagccttatt gcgtgtaaaa atccatacat taccggaaga    5820
tactgcgatt cggcaaagga ttgctgaaaa atatattcgt gaaataaaaa accctgcgat    5880
tacgttacca gtgtacgaag gccaaggtgc gcatgtttgg catttatttg tagtaagaat    5940
cgctaatcgt gaaaaattcc agtcatactt attagagaag ggtatcaaaa ccttaattca    6000
ctatccatta ccaccccata agcagcaagc atatcaaaat atgtctagcc ttagccttcc    6060
aattactgag caaattcatg atgaagtcat ttctttacct ataagtccgg taatgagtga    6120
agatgatgtc aattatgtaa tcaaaatggt caatgattac aagtaatgaa aaaatttctt    6180
caggtaacta tattatccgc tatctataca ttcattaaaa tgattgcggg ttttatcatc    6240
ggtaaggtag tagcaattta tacagggcca tcaggggtag caatgcttgg ccaagtgcaa    6300
agtttaatca caatagttgc aggtactacc tctgcacctg taagcacagg ccttgttcga    6360
tatactgcgg aaaattggca agaaggacaa gaagcatgcg cgccatggtg gcgcgcatgc    6420
ttaagggtta ctctgttttt attcttgctt attattccgg ttgttattat attgtcgaaa    6480
aatattagtg agttacttt tagcgatgga caatacacat ggttaatcat tttcgcatgt     6540
tgtatattgc cattctccat tataaataca ttgatcgctt cagttttaaa tggtcaacaa    6600
ttttataagc aatatatatt ggttgggatg ttttctgtat tcatttctac tatgtttatg    6660
attttgttga ttgtagctta taatcttaaa ggtgcattga ttgccacagc tataaatagt    6720
gctattgctg gtcttgtatt ggttttattt tgtctcaata aatcttggtt tagatttaaa    6780
tattggtggg gtaaaacgga taaagacaaa attataaaaa ttattcatta tactctgatg    6840
gctctggttt ctgttatctc catgcctaca gcattgatgt gtattagaaa aatattgatt    6900
gctaaaactg gttgggagga tgcaggggcaa tggcaggccg tatggaagat atctgaggtt    6960
tatcttggtg ttgtgacaat tgctttgtca acatatttct taccaagatt gacaattata    7020
aaaacaagtt tccttataaa aaaagaagta aatagtacta tattatacat aatatctatt    7080
acttcattca tggcgttgag tatctatta ttccgcgatt tggtaataac agttttattt     7140
actgaacagt ttcgctcagc tcgtgaatta tttttattac aacttatagg ggatgtaata    7200
aaaattgctg ggtttctta tgcatacccc cttcaaagtc aggggcatac taaactattc     7260
atcagttcag aagtgatttt ttctatgctc tttatcatta ccacctatat ttttgttgta    7320
aattatggag tacatggtgc taacataagt tatgtcatta catatagttt atattttgtg    7380
tttgcatttg tgtttactaa ttttattaat gttagaagaa ataattaaaa acagaggttg    7440
aattttgaaa ataattatac ctgtcttagg atttggcagg gctggtggtg aaagagttct    7500
ttctaagctg gcaactgaat tgatgaatta tggacatgat gtaagttttg ttgttccaga    7560
taatagaact aatccatatt atgctaccac agcaaaaatt gtcacgagta aatcagtca     7620
aaaccgtgta aaaatattga gaatcattaa aaattactat aatctgtggc gtaaatgcat    7680
agagttaaat cctgatgctg tagttgctag tttttcattg actgcctatc ttgtcgcatt    7740
attaccaatc acccgtcgta agaaatatta ttatattcag gcgtatgaag ttaattttt     7800
tgataatata atatggaaat taatagcggg ttaacatat tatttaccgc ttaaaaaaat     7860
actaaatagt cctaattgc ttcctcataa acatgatgat tttataggag tagttcctgc     7920
aggagtagat ttaaacgttt tctatccgaa accatcaaat aggttattaa atggtcacac    7980
atcaataggg attattggta gaaaagagaa gcacaaagga actagcgaaa ttatttcagt    8040
attgtgttca ctggaaaaata aagctggaat tataatcaat attgcgatct atcttgaaga    8100
agttgataag cagcgtttaa tcgctgccgg gtttcaggtt aatttttttc cgattacttc    8160
tgatttagaa ttggcatcct tttatcgaag caatgacatc atgattgctg ttgggttaat    8220
tgaagatggc gctttccatt atccttgtgc tgaatcaatg gcttgtggtt gtcttgttat    8280
ttcaaattat gcgccactta ctgaaactaa cagtgtactt aaattagtca agtttgatgc    8340
ttgcaaactt ggtgaagcaa ttaatctttg tctcaatctt gacctagaag aaaaaagcaa    8400
agaaatccaa tctaatattt ctgtgttaaa taaatatgac tggaaaattg ttggtgaaac    8460
tttcaatagt ttattgttag atgcaaataa atagtatacg ttgatgggga aaatatgaat    8520
attgttaaaa ctgatattcc agatctgatc gttcttgaac caaaagtgtt tagtgatgaa    8580
cgcggctttt ttatggagag ttataatcag attgaatttg agaaggcaat aggaaggcac    8640
gtaaattttg ttcaggataa tcattcaaaa tctagtaaag gcgtactacg tgggttgcat    8700
tatcaattag caccgtatgc acaggctaaa ttagttcgat gtgttgtagg tcaggtattt    8760
gatgttgctg ttgatcttag aaaaaattca ccaacgttca aaaatggtt tggaataacc     8820
ctttccgcag aaaataaacg acaattatgg atacccgaag gatttgctca tggtttcttg    8880
gtgaccagtg atgaagctga gttcatttat aagacaacta actactatgc tcctggtcat    8940
cagcaagcaa ttatttacaa tgatcctatt ttaaacattg gccttt ctgcagtgt         9000
gctctgtcat tatcacaaaa agatcaagaa gcaaaattat tttcagaatt attggacagt    9060
gaactgttct aataaagtgt gccaccttat ccgtctgaag gataggtggt tgcttatatt    9120
tttttgagta tgtttgtata atgacagaaa atagtccgaa atataaacac gataaaagct    9180
taataagttt tatctactta ttttttatat ttacacttat tgtaggcttt attatcgcaa    9240
atacccagtt tttggggcga agtagagact atgataatta tatacagatc ttttctggta    9300
aagaagggga gggggttctt gaattatttt atcgcggatt gatgttaata acgaccagct    9360
atgaaactat catttttata attttaacat gttcttttttt tataaggca aggtttctcg    9420
ctaactattc gcgtaatttt tcaggcttga ccttattctt tatttattat gcaagcgttg    9480
cactttgggt tttagattat actcaattca gaaatggtct atgtatttcc attttaatgt    9540
tttccgtata ctatttattt ataaatataaac cgacttattt ttatttcctcg gtattatgtg   9600
caattgcaac tcattggtct gctttgcctt ttttgctttt atatccttt gtctattcaa     9660
caaaaataag acgccttggt tatttttgtt tcagtattct tgtttgatt gcgatctcag     9720
gagaaggaaa agagatcata tctttttataa gaaattttgg agtgggacaa aaaataggaa    9780
atgaagctgg tgtaaattta ataaattcat tatccccttac cgctatttcc tggtttatta    9840
ttagttacat atcaagcatt ggaaatgaaa ggagaaattt aaggctttc ttttgttatg      9900
```

```
gtgtcatgca atacgtgact tttagccttt tctctctacc tgttatggct ttccgtattt   9960
tggaaatgta tttttttcctt atgctaacca ttggggtgtt tattaagcaa aaaaagaatt  10020
attattttat tttttgcaaa gtgttaattt tattgtatct aacatactat tatcatatgg  10080
tctttggagt gattaatgtg taaggctaag gtgttggcta taattgttac ttacaacccg  10140
gaaattattc gattgacgga atgtattaac tctttagccc cacaagttga gagaataatt  10200
cttgtagata atggctcaaa taatagtgat ttgataaaaa atatcagtat taataacctt  10260
gaaattattt tactttcgga aaacaaaggc attgcatttg ctcagaacca tggtgttaag  10320
aagggcctgg aagcaaaaga gtttgactat ttattttttct cagatcagga tacttgcttt  10380
cctagcgttg ttattgaaaa acttaagagt acatttacga aaaataataa aaaaggtaaa  10440
aatgttgctt gtgcttctcc ttttttttaaa gaccatcgtt caaattatat gcatccgtca  10500
gtcagcctaa atatttttac gagtacaaaa gttatatgta gtgaagtaga cgatgatctt  10560
tatccctcgc atgttattgc ttctgggatg ttaatgtctc gtgaagcatg gcgcgtcgtc  10620
ggaccatttt gtgaaaaact ctttatagac tgggttgata cagaatggtg ttggcgtgca  10680
ttagctaata atatgattat tgttcagaca ccatcagtca tcatttctca tgaacttggg  10740
tatgggcaga aaattttttgc tggtcgatct gttacaatac ataattcttt cagaaatttt  10800
tataaaatac gcaatgcaat atacttaatg ctgcattcaa attatagctt caagtatcgt  10860
tatcatgctt tttttcatgc gacaaagaat gttgtatttg aaattttata ttcgaaagaa  10920
aaattaaatt cactgaaggt ttgttttaaa gctgtacgtg atggtatgtt caataatttt  10980
taatacgaaa atagttaggc tcaaggtgtt taaatggaag aaaataatat gaagacggtc  11040
gctgtagttg gcacagtggg tgttcctgct tgttatggtg ggttcgaatc acttgttcag  11100
aatctaattg attatcaatc tgatggtata caatatcaga tattttgctc ttcaaaaaaa  11160
tatgataaaa aatttaaaaa ttataaaaat gcagaattaa tctatttgcc gataaatgcc  11220
aatgcgtct ctagcataat ttatgatatt atgtgtttaa ttatttgttt attcaaaagg  11280
ccagatgttg ttttaatatt gggggtgtct ggttgtttat ttctaccaat ttataaacta  11340
ttttcaaaat caaagattat tgtcaatatt gatgggcttg aatggcgtag aaataaatgg  11400
ggaactgtttg ctaagaaatt tcttaaaata tctgaggcga tatctattag aaatagctgat  11460
attatcattt cagataatca agcaatagct gattatgtgg aaaataagta caagaaaaaa  11520
agtgtagtta tagcttatgg cggagatcat gccactaatc ttagtacacc gatagacaat  11580
gatcaaaaaa aagaaggtta ttatttgggg ctttgtagga tagagcctga gaataatata  11640
gaaatgattc tgaatgcctt cattaataca gataaaaaaa ttaaatttat gggtaattgg  11700
gataacagcg agtatggacg ccagctaaaa aaatattatt caaactatcc aaatatcacc  11760
ctactagaac ctaactataa tattgaagag ctttataaac taagaaaaaa ttgtcttgca  11820
tacattcatg gacactcggc tggtggaaca aaccccttctt tagttgaagc gatgcatttt  11880
aatattccta tttttttgcttt cgattgtgac tttaatcgtt acacaactaa caatttagct  11940
cattactttta atgattctga acaacttagc ttattagcag aaagtttgtc ttttggaaat  12000
cttaaatgtc gagtattaga tttaaaaat tatgctgaag atatgtataa ctggaggcat  12060
atagctgcta tgtatgaatc tatttattaa acgcattaac aataatataa ttgacccttat  12120
atagcaggga aagatcacgt aacgctgcgg cgcgccgatc cccatatgaa tatcctcctt  12180
agttcctatt ccgaagttcc tattctttct agagaatagg aacttcggaa taggaactaa  12240
ggaggatatt catatggata aagccgtaag catataagca tggataagct atttatactt  12300
taataagtac tttgtatact tatttgcgaa cattccaggc cgcgagcatt cagcgcggtg  12360
atcacacctg acaggagtat gtaatgtcca agcaacagat cggcgtagtc ggtatggcag  12420
tgatgggacg caaccttgcg ctcaacatcg aaagccgtgg ttataccgtc tctattttca  12480
accgttcccg tgagaagacg gaagaagtga ttgccgaaaa tccaggcaag aaactggttc  12540
cttactatac ggtgaaagag tttgtcgaat ctctggaaac gcctcgtcgc atcctgttaa  12600
tggtgaaagc aggtgcaggc acggatgctg ctattgattc cctcaaacca tatctcgata  12660
aaggagacat catcattgat ggtggtaaca ccttcttcca gacactatt gtcgtaatc  12720
gtgagctttc agcagagggc tttaacttca tcggtaccgg tgtttctggc ggtgaagagg  12780
gggcgctgaa aggtccttct attatgcctg gtgccagaa agaagccatt gaattggtag  12840
caccgatcct gaccaaaatc gccgcgtag ctgaagacgg tgaaccatgc gttacctata  12900
ttggtgccga tggcgcaggt cactatgtga agatggttca caacggtatt gaatacggcg  12960
atatgcagct gattgctgaa gcctattctc tgcttaaagg tggcctgaac ctcaccaacg  13020
aagaactggc gcagaccttt accgagtgga ataacgtga actgagcagt tacctgatcg  13080
acatcaccaa agatatcttc accaaaaag atgaagacgg taactacctg ttgatgtga  13140
tcctggatga agcggctaac aaaggtaccg gtaaatgaca cagccagcgc ggctggatc  13200
tcggcgaacc gctgtcgctg attaccgagt ctgtgtttgc acgttatatc tcttctctga  13260
aagatcagcg tgttgccgca tctaaagttc tctctggtcc gcaagcacag ccagcaggcg  13320
acaaggctga gttcatcgaa aaagttcgtc gtgcgctgta tctgggcaaa atcgtttctt  13380
acgcccaggg cttcctcag ctgcgtgctg cgtctgaaga gtacaactgg gatctgaact  13440
acggcgaaat cgcgaagatt ttccgtgctg gctgcatcat ccgtgcgcgt ttcctgcaga  13500
aaatcaccga tgcttatgcc gaaaatccac agatcgctaa cctgttctgg gctccgtact  13560
tcaagcaaat tgccgatgac taccagcagg cgctgcgtga tgtcgttgct tatgcagtac  13620
agaacggtat tccggttccg accttctccg cagcggttgc ctattcgac agctaccgtg  13680
ctgctgttct gcctgcgaac ctgatccagg cacagcgtga ctatttttgg gcgcatactt  13740
ataagcgtat cgataaagaa ggtgtgttcc ataccgaatg gctggattaa               13790

SEQ ID NO: 13        moltype = DNA   length = 13777
FEATURE              Location/Qualifiers
source               1..13777
                     mol_type = other DNA
                     organism = synthetic construct
SEQUENCE: 13
atgacgaatt taaaagcagt tattcctgta gcgggtctcg ggatgcatat gttgcctgcc   60
actaaggcga tacccaaaga gatgctacca atcgtcgaca agcaatgat tcagtacatt   120
gttgacgaga ttgtggctgc agggatcaaa gaaatcctcc tggtaactca cgcgtccaag   180
aacgcggtcg aaaaccactt cgacacctct tatgagttag aatcactcct tgagcagcgc   240
gtgaagcgtc aactgctggc ggaagtacag tccatttgcc cgccgggcgt gacaattatg   300
aacgtgcgtc agggcgaacc tttaggtttg gccactcca ttttatgtgc acgacctgcc   360
attggtgaca atccatttgt cgtggtgctg ccagacgttg tgatcgacga cgccagcgcc   420
```

-continued

```
gacccgctgc gctacaacct tgctgccatg attgcgcgct tcaacgaaac gggccgcagc  480
caggtgctgg caaaacgtat gccgggtgac ctctctgaat actctgtcat ccagaccaaa  540
gagccgctgg accgcgaagg taaagtcagc cgcattgttg aattcatcga aaaaccggat  600
cagccgcaga cgctggactc agacatcatg gccgttggtc gctatgtgct ttctgccgat  660
atttggccgg aacttgaacg cactcagcct ggtgcatggg ggcgtattca gctgactgat  720
gccattgccg aactggcgaa aaaacagtcc gttgatgcca tgctgatgac cggcgacagc  780
tacgactgcg gtaaaaaaat gggttatatg caagcgttcg tgaagtatgg actacgcaac  840
ctcaaagaag gggcgaagtt ccgtaaaggg attgagaagc tgttaagcga ataatgaaaa  900
tctgaccgga tgtaacggtt gataagaaaa ttataacggc agtgaagatt agcggcgaaa  960
gtaatttgtt gcgaattttc ctgccgttgt tttatataaa caatcagaat aacaacgact 1020
tagcaatagg attttcgtca aagttttcca ggattttcct tgtttccaga gcggattggt 1080
aagacaatta gcatttgaat tttacgggtt tagcgcgagt gggtaacgct cgtcacatcg 1140
tagacatgca tgcagtgctc tggtagctgt aaagccaggg cggtagcgt gctgaaatta 1200
taaagtcatt cttatagaac atcgcatttc aataataaa ttacacctaa atgaatagga 1260
tacaacgtgt gcacaattat ttaaggctta aagataaaat aaaaaacgta tttttagggt 1320
tgtatatatt gcagttattt aatttatatcg cgccattggt aattatccct atcctgataa 1380
aatatattgg gttgggggaa tatggggaat tggtctatat tacatctatt tatcaaatag 1440
tggctttgat tattgatttt ggctttactt acacaggacc tgtgggttgct gcgagacata 1500
gatgtgagac ccaaaattta cagcgctatt actcaatagt tgttcttta aaatcattgc 1560
tttttataat tgcattaaca tgtgtatttt tattgtgcag attaaatata gtccacttgt 1620
cattttttgg gttttttgtca attttttctat gcactattgg taatatatta tcgcccaatt 1680
ggttttttgca ggggattggt gattttaaaa aactttcata ctcacaagta atagtgagaa 1740
taacattgtt tatcatactt cttgtttatg tctgtagtgg cggagataat gttttatcc 1800
taagtttttt gcaaaatgca acattactca tatgctgtat atacttatgg ccaaatattc 1860
atattagcca tgttgttcat cttaaaccta atgaatgcat tgtggaattt aagaaggcag 1920
gaaatgtttt tattggcgta ataggtacga ttggttacaa tggtctcaatt cctgtgttaa 1980
ttggaaacct ttgcggtaat acgagtcttg gtgtttttc aatcgttcaa aaaatgacaa 2040
cagcatgtca aagtctaatt aatccaatat cacagtatat gttatctcaa gtttcagaaa 2100
ttaaacctca agataaactg ttttattata gaattaaaaa aagttttttt gtgcatttaa 2160
caattagcat aattgcatgt ttatgttata tgggggttagg gcaatatgtg gcgacttttta 2220
taggtaaagt tgacgtttca tttgttatta ttttatttgc gtcaataatt accattttt  2280
catctttaaa taatgtcctt ggtatacagt ttcttatacc gacagataat gtaaaaatac 2340
tacgaagtat aaatgttatg gcgggaatta ttgttgttag tttgtcctgg ctgttaatat 2400
cacgctttga catctgggg ggggttttat taaacctaat tggtgagttt cttgtattca 2460
gtatgctagc ttttattgcc catcgaaagt ggggagcgag agtataatga aagtgaaggc 2520
ggttcctgct attacattct atttaagttt aatgctgaca attttagtgt tactgtttgg 2580
taatgaacca aataaatcac aatatatcct tgttatagca acgataacag tttttttatat 2640
cgcatatatc actaataaaa taacttctcc ggccagcctt tcgttatat catcttttgt 2700
gttttaggt tgtcgccctt tattatcttt gtttgcaaac tatgattata ggattgccga 2760
ttggtttatt gaaggatata tggatgacga tgtgattttg gctaactatg ctataacact 2820
aatgtattat ggttatacat tgggactaat tctatgcaaa aatactgaaa aattttatcc 2880
gcatggtcct tatcctgaaa aacaattgct aaaaataaag tttctttga cttattttt 2940
tctgggttcg ataggtatgg ttgtaaaagg gatattcttt ttaacttta tagaatctaa 3000
tagttatgtt gatatttatc aatcaaatat aacaacgcca ataggttatg attttctatc 3060
ttatttattt tattgttctt ttttccttat atgtgcgttt catatacagt tcagaacaaa 3120
taaaaattt ctttttattg cgatatgcat tgctgcattt agcaccttga agggtagtcg 3180
tagtgaagct ataacgtttc tattttaacggt tacatgtata tatttttatg aagtaaagac 3240
aagaaactta cgtctgctga ttacaatgat ttttgttttt agcgtcattt ttgtgattag 3300
tgaatttatc tcaatgtggc gcactggagg gagttttttt caattaatgc agggtaataa 3360
tcctgttata aactttgtat acggcatggg agtatcatat ctttccattt atcaatcagt 3420
aaaactacaa ctattgtcag ggggatataa tgttacctat ctattcagcc agttaataat 3480
aacttgctcg tcaatatttta atgtcaaatt gagcttgccg gaaataagct atagccatt  3540
ggcctcatac acagcaaacc cagaactata taatcttggg ttcggacttg ggggagtta  3600
tttagcagaa tcgtttttag catttggtct gattggatgt ttcattatac ccttttact  3660
tttacttaat ttaaatgtat tggaaaaata tacaaaaaac aaaccaatta tatatttgt  3720
ttattatagt gtgttgccac ctatattatt cacaccaaga gagactttgt tctatttcttt 3780
cccctatctt gtcaaaagta tatttgttgc ttttttagtt acattataca tccagtataa 3840
aaaggattga ccaaatgtc agaaaaaat gtcagcataa taatcccaag ttataacagg 3900
gctcatattc ttaaggaggt cataccaagt tattttcagg atgagactt agaggttata 3960
gttatcaatg atggatcaac agataataca aatagtgtat tagctgaact gaaggaaaaa 4020
tattctcagt tagttatttt agaaaatgaa acgaataaaa aacagatgta ttctaaaaac 4080
cgagggattg aaatagccaa agggaaatat atttttttg gtgatgatga ctcttacctc 4140
ttacccggtg ttatatctcg gttattggct acaaatatg agacaggcgc tgatgtaatc 4200
ggcgcaagaa tactttatat gaataataac gagaaaacaa ttgaagattg cataatcga  4260
cataaaaag aggggcgttt tgttagtgat ctaaatagat tggattttag ttatacatgt 4320
gatttggacc atccgattga atgttttat gcacagcctt tgttctagc tgaaagggaa 4380
ctaatatcga aatatcgatt tgatatatct tatacgggaa actgctatcg tgaggaaact 4440
gatttcatgc tatctctatt tattaaaaat aaaaaattta tatatgattc aaaggctttg 4500
ttaataaatt tacctccaag aaaagcgacg ggaggggcaa gaacagctaa tcgattaaaa 4560
tatcattacg aaagttgcat aaataattat agattttaa aaaaatataa tgataattg  4620
aatcttcttt caggacaaaa gcatgctata ttttaccgac agtgtcaatt cgttctgcta 4680
aaaatgaagt cgtttatcgg gaagttttta aaatgattat atatatcgcc gcgtataatg 4740
gttcaggagg gcaaggtggg gtggaaaggg tgttgcccaa acaatgtaac attcttaaaa 4800
atttggggt taaagtcatt tacttgtata aaacatcct caaaatttct aacaaaattc 4860
gtaacaaaaa aatacaagta gcactttatc caatattagt ttctctttat ttaaccttac 4920
aaaaattacg tggcgtgacg tttaaagtta ttgcacatgg ctattgttct ccttttata  4980
ggaatgcact cttaatagct catggcaata tgaaatgtta tttttcaaaca gtcatgaata 5040
aaaaacctaa tcggttgtct ggcagtggtc tttttatcttt ctatgagcgt tgggctggag 5100
cattttcaaa aaatatctgg gctgtttcaa ataaggttaa aagtgaatgg aatgagcttt 5160
```

```
acaatattaa ttcacataaa atcaaagttg ttcgaaattt tataaatctt gcacaatttg   5220
attacactga tgttaatgaa gcagaatatg tgacatttgt cgggcgattg gaaaaaggaa   5280
aaggaataga tgatctgtat tacatatgta aaaatctgcc agatacttcc ttccatttag   5340
tttcaagtat tcccgcccca caaaattttg cttcgctaaa taatgttctg accagcattg   5400
ctgtcccccta tgcgaaaatg ccagaaatat ttaagaactg cagagtactt atttttaccgt  5460
cctattatga aggatatgag ctggttacta ttgaagcgct atgctgtggt tgccctgtga   5520
taggctataa tgttggtgca attagagagt tgtatgcaga aagttttcct ggcgtattta   5580
ttgccaataa taaagaagat ttagcacaag tagcctacaa attaattagt cttgataatg   5640
aaaaatatta tcatttgaga caaactattt atagcaagcg tgagcttttt tctgaagaga   5700
gatatgcgga aattttaacg gcggcattta atgaaaaaaa ataagaaact ctgtctcatt   5760
tcaattaact catataatga acttaccgga ggaggagtat atttacgtac gcttgttagt   5820
tttctacaaa aacagaatgt taatttaaca cttattgata aaaaatcctc aggtaaacta   5880
ttcgaagaca atacttttca acatatatca tttattaaag gtaaacgtca ggatataata   5940
tccaggcttt tttttatacc atcattttat gtccctatta ttttctcaat aattaaaatt   6000
ttacggaagc aagatattct tgcttttcac aactctcggc ttggattgtt atgtctgctt   6060
tttagaaatac tcatgcccca caaaaagatc atattgttta cggataactt cgaatatgac   6120
ttaataagac aaaaagataa aaacataact acttttattg aaaaattaat tgtttatctc   6180
aatgaattta tcgggcttaa gaattcagat ttagttagct atattacccg gcaagataaa   6240
aatgcaatgg ataaatttta tgggattaaa aaaagcagaa atttaattct ccctgtgata   6300
tttagtagag aaaaaccaac tgatgtattg tcagctcact ttattaatga gtataatcga   6360
ttgaataatg ataataggaa aaaagtagta tttactgcat cttttgattt ttttccaaat   6420
atagatgctg ccaactatgt tttaaatgca gcaaagtcta ataatgatta ttgctatatt   6480
ttggcaggta ggaaaagtac tactttgaat cttcctgatt tggataattt attttttttc   6540
gataatctat ctaatagtga aatgtcatat ttattatctg cttgtgatgt tttttattct   6600
cctatagttt taggaagtgg aatgaaaaca aaaattgcag aagcactatc atatggatta   6660
tatatttatg cgacagagca ttccttaatc ggctatgtag aaattataca caataaggag   6720
tgtgttaaaa aaatctcaca tttgatgag gaatttccta aagatttcaa gatgaaaagt  6780
atcaataaac agctaataat gtcttatcag caaaaatatt attcacatta tcggtttaat   6840
ggccatgaac ttgatataat aaattttgac gattagttag tggagatata atatgaacat   6900
attagtaact ggtggtgctg gatatatcgg atctcatacg gctattgaat tactgaatgc   6960
aggtcatgag attatcgttc tggacaattt cagtaatgct tcatacaagt gtatcgaaaa   7020
aataaaagaa attactcgac gtgatttttat aacaattact ggagatgctg ggtgtaggaa   7080
gacactctcc gctatttcg agaaacacgc catagatata gttattcatt ttgctggctt   7140
taaatctgtt tcagagtcta aaagtgaacc cttaaagtat taccagaata atgttggagt   7200
gaccattact ttattacagg taatggaaga gtacagaatt aaaaaaattta tctttagttc   7260
atctgcgaca gtctatggtg aaccagagat aattccaatt ccagaaacag ctaaaattgg   7320
aggaactacg aatccatatg gcacatcgaa gtattttgtt gaaaaaattc tagaggatgt   7380
tagttccacg ggaaaactgg atataaattttg cttgagatat tttaatcctg tcggtgctca   7440
ttctagtggt aaaataggtg aggctccatc tggtatccct aataatcttg ttccttattt   7500
attggatgtt gcgagtggta aacgtgataa attatttatt tatgggcaatg attacccctac  7560
taatgatgga acaggtgtaa gggatttttat tcatgttgtt gacttagcga aaggtcattt   7620
ggctgcaatg aattatttaa gtatcaattc gggatataat atctttaatc ttggtacagg   7680
aaaaggttat tcggtacttg aattaatcac tacatttgaa gataaaacaa acattaaggt   7740
caataaatct tttatagaga gaagggcagg ggatgttgcg tcttgttggg ctgatgcaga   7800
taaagctaat tctttattgg actggcaagc cgaacaaact ctagaacaga tgttattgga   7860
ctcgtggcgt tggaaaaaaaa attatccaga cggattctga atataaaagg tttcagttt    7920
atgaatcaat cagagcagag aaaaaaaaata ctggttctta cacctcgctt tccctaccct  7980
gtcattggag gggatagatt aagagtctat atgttatgta aagaactttc caaaaaatat   8040
gatcttattc ttctgagctt atgtgatcaa ccactagaac ttgaaataaa tataaatgac   8100
tcggtcttca aagaaattca tcgtgtctat ctaccaaaat ataaatcata ttataatgta   8160
ttaaaagctt tggttacgca aaaaccgttg caaattgctt attatcaatc ggacacattt   8220
aagaataaat acaataaatt aattaaacaa tgcgatgcag tattttgtca tctgataaga   8280
gttgctgatt atgttaagga tacagacaag ttcaaaattc ttgatatgac agatgcaata   8340
tctttgaatt acagtcgcgt taaaaaatta gcaagtaaaa aagtttgcg tgcaattatt   8400
tattctctgg aacaaaaaag attagaatca tatgaacgtt ctgtggcgaa tcttttttgat  8460
ttgaccactt ttatttcatc cgtagaccgt gactatctct accctaatct gggcagtaat   8520
atccatatag tcaataatgg ggttgataca tcagccttga gatatataaa aagagaaata   8580
aaaatcgata agcctgtgga acttatattt atcggaaata tgtattcttt acaaaatatg   8640
gatgctgcaa aacatttttgc taagaatatt ttaccttgct tgtatgatga gtttaatatt   8700
attttaaaag tgattggtaa gatctcagaa actaataaaa atatattaaa ttcatttaaa   8760
aatacaattg cttttaggtac tgttgatgat atcaattctt ccgcttctac agggcatata   8820
ggtatatgtc ctgttcgtct tggagcaggc gtacaaaata aaattcttga atacatggct   8880
ttaggtttac catgtattac atctagcatt ggttatgaag gtattaatgc aaaatcaggt   8940
agcgaaattt ttgttgcaga tacagtagag caatataaa acgtactaag agaaataatt   9000
tacgattata atcgttatac tgaagtggct gaaaatgccc gtagttttgt agaaaataat   9060
ttttcttggg aatcaaaagt tgccaattta atgaatacat tagatgagaa attatatgaa   9120
caataataaa attattacac ctatcattat ggctggtggt tcaggcagtc ggttgtggcc   9180
actatcaaga attctctatc cgaaacaatt tcttagccta atcggtagtc ataccatgct   9240
tcaaacaacg gctaatcgtc tggatggttt ggattgtacc aaccccttatg tcatttgtaa   9300
tgaacaatac cgctttatag ttgctgaaca gcttagaaaa atcgatagat tgacttcaaa   9360
gaatatcatc cttgagcctg ttgggcgtaa cactgcccct gcaattgcat tagcggcgtt   9420
gctgatgtct aagtctgata aaagtgcaga tgatcttatg ctcgtactgg ctgcagatca   9480
cgttatacac gatgaagaaa aatttgtaa cgctgttaga tcggcaattc catacgctgc   9540
tgatgggaaa ttggtaacat ttggtataat tccagacaaa cgaaactg gttatgttta   9600
tatacatcga ggacaatata ttaatcagga agattcggat gcatttatag tgtcatcatt   9660
tgttgaaaag ccaaatcatg agacagccac taaatatctt gcttccggtg agtattattg   9720
gaatagcggg atgtttttgt ttagtgcaaa tcgttatata gaggaactta acaatttcg   9780
gcctgatatt ttatccgctt gtgaaaaagc aattgcttca gcgaactttg accttgattt   9840
tgtgcgttta gatgaaagtt cttctctaa gtgccctgaa gaatcaattg attacgctgt   9900
```

```
aatggaaaaa acaaaagacg caattgttat tccaatggat gctggctgga gtgatgtcgg    9960
ttcatggtct tctctttggg aaattaatga taaagactca gacggcaacg taatagttgg   10020
ggatattttc tctcatgaaa caaagaattc tttcatatat gccgaatcgg gaattgttgc   10080
tacagttgga gtggaaaatt tagttgttgt ccaaacaaag gatgctgttc ttgtctcaga   10140
gagaaataaa gttcaggatg taaagaaaat agtagaacaa attaaaaatt caggtcgtag   10200
cgagcattat gttcatcgcg aagtatatcg tccttggggt aaatatgatt ccattgacac   10260
aggggagcgt tatcaggtca aacgtataac agtaaatcct ggtgaaggac tttctttaca   10320
aatgcaccat catagggcag aacattggat catagtttct ggaactgcaa gggtgactat   10380
aggttctgaa actaagattc ttagcgaaaa tgaatctgat tacataccct ttggtgtaat   10440
acactgcttg gaaaatccag ggaaaattcc tcttgattta attgaagttc gttctggatc   10500
ttatttagaa gaagacgatg ttatccgttt tcaggaccga tatggtcgta gctaaatttt   10560
tgataatgta acgttagtag aagagcgcta atatttttag ttaatctgta ataagtatta   10620
tttgtttaag gtatatcatg tcgagtttac cctgctttaa agcctatgat attcgcggga   10680
aattaggcga agaactgaat gaagatattg cctggcgcat tggtcgcgct tatggcgaat   10740
ttctcaaacc gaaaaccatt gtgttaggcg gtgacgtccg actcaccagc gaaaccttaa   10800
aactggcgct ggcgaagggg ttacaggatg cgggcgtcga tgtgctggat attggcatgt   10860
ccggcaccga agagatctat ttcgccacgt tccatctcgg cgtggatggc ggcatcgaag   10920
ttaccgccag ccataacccg atggattaca acggcatgaa actggtgcgc gaaggggctc   10980
gcccgatcag cggtgatacc ggactgcgcg acatccagcg tctggcagaa gccaacgact   11040
ttcctcccgt tgatgaaacc aaacgcggtc gctatcagca aatcaatctg cgtgacgctt   11100
acgttgatca cctgttcggt tatatcaacg tcaaaaacct cacgccgctc aagctggtga   11160
ttaactcggg gaacggcgcg gcggttccgg tggtggacga cattgaagcc cgctttaaag   11220
ccctcggcgc acccgtggaa ttaatcaaag tgcacaacac gccggacggc aatttcccca   11280
acggtattcc taacccgcta ctgccggaat gtcgcgacga cacccgcaat gcggtcatca   11340
aacacgcgc ggatatgggc attgcctttg atggcgattt tgaccgctgt ttcctgtttg   11400
acgaaaaagg gcagttt att gagggctact acattgtcgg cctgctggca gaagcgttcc   11460
tcgaaaaaaa tcccgcgcg aagatcatcc acgatccacg tctctcctgg aacaccgttg   11520
atgtggtgac tgccgcaggc ggcacccgg taatgtcgaa aaccggacac gcctttatta   11580
aagaacgtat gcgcaaggaa gacgctatct acggtgcga aatgagcgcc caccattact   11640
tccgtgattt cgcttactgc gacagcggca tgatcccgtg gctgctggtc gccgaactgg   11700
tgtgcctgaa aggaaaaacg ctgggcgaac tggtcgcgca ccggatggca gcgtttccgg   11760
caagcggtga gatcaacagc aaactggcac accccgttga ggcgattaac cgcgtggaac   11820
agcactttag ccgcgaggcg ctggcggtgg atcgcaccga tggcatcagc atgacctttg   11880
ccgactggcg ctttaacctg cgctcctcta acaccgaacc ggtggtgcgg ttgaatgtgg   11940
aatcgcgcgg cgatgtaccg ctgatggaag aaaagacaaa acttatcctt gagttactga   12000
acaagtaatt cagtaatttc atataaatgg gttttaaaaa acggaaaaga tgagatatcc   12060
ggtgtggtat atccaaggta atgctattca gtatctctat gagtgagtta acatctatac   12120
cacatttaag ccgcacactt cgggatcccc atatgaatat cctccttagt tcctattccg   12180
aagttcctat tctttctaga gaataggaac ttcggaatag gaactaagga ggatattcat   12240
atggataaag ccgtaagcat ataagcatgg ataagctatt tatactttaa taagtacttt   12300
gtatacttat ttgcgaacat tccaggccgc gagcattcag cgcggtgatc acacctgaca   12360
ggagtatgta atgtccaagc aacagatcgg cgtagtcggt atggcagtga tgggacgcaa   12420
ccttgcgctc aacatcgaaa gccgtggtta taccgtctct attttcaacc gttcccgtga   12480
gaagacggaa gaagtgattg ccgaaaatcc aggcaagaaa ctggttcctt actatacggt   12540
gaaagagttt gtcgaatctc tggaaacgcc tcgtcgcatc ctgttaatgg tgaaagcagg   12600
tgcaggcacg gatgctgcta ttgattccct caaaccatat ctcgataaag gagacatcat   12660
cattgatggt ggtaacaccc tcttccagga cactattcgt cgtaatcgtg agctttcagc   12720
agagggcttt aacttcatcg gtaccggtgt ttctggcggt gaagaggggg cgctgaaagg   12780
tccttctatt atgcctggtg gccagaaaga agcctatgaa ttggtagcac cgatcctgac   12840
caaaatcgcc gccgtagctg aagacggtga accatgcgtt acctatattg gtgccgatgg   12900
cgcaggtcac tatgtgaaga tggttcacaa cggtattgaa tacgccgata tgcagctgat   12960
tgctgaagcc tattctctgc ttaaaggtgg cctgaacctc accaacgaag aactggcgca   13020
gacctttacc gagtggaata acggtgaact gagcagttac ctgatcgaca tcaccaaaga   13080
tatcttcacc aaaaaagatg aagacggtaa ctacctggtt gatgtgatcc tggatgaagc   13140
ggctaacaaa ggtaccggta aatggaccag ccagagccgg ctggatctcg gcgaaccgct   13200
gtcgctgatt accgagtctg tgtttgcacg ttatatctct tctctgaaag atcagcgtgt   13260
tgccgcatct aaagttctct ctggtccgca agcacagcca gcaggcgaca aggctgagtt   13320
catcgaaaaa gttcgtcgtg cgctgtatct gggcaaaatc gtttcttacg cccagggctt   13380
ctctcagctg cgtgctgcgt ctgaagagta caactgggat ctgaactacg gcgaaatcgc   13440
gaagatttc cgtgctggct gcatcatccg tgcgcagttc ctgcagaaaa tcaccgatgc   13500
ttatgccgaa aatccacaga tcgctaacct gttgctggct ccgtacttca gcaaattgc   13560
cgatgactac cagcaggcgc tgcgtgatgt cgttgcttat gcagtacaga acggtattcc   13620
ggttccgacc ttctccgcag cggttgccta ttacgacagc taccgtgctg ctgttctgcc   13680
tgcgaacctg atccaggcac agcgtgacta ttttggtgcg catacttata agcgtatcga   13740
taaagaaggt gtgttccata ccgaatggct ggattaa                            13777

SEQ ID NO: 14             moltype = DNA    length = 15027
FEATURE                   Location/Qualifiers
source                    1..15027
                          mol_type = other DNA
                          organism = synthetic construct
SEQUENCE: 14
atgacgaatt taaaagcagt tattcctgta gcgggtctcg ggatgcatat gttgcctgcc     60
actaaggcga tacccaaaga gatgctacca atcgtcgaca agccaatgat tcagtacatt    120
gttgacgaga ttgtggctgc agggatcaaa gaaatcctcc tggtaactca cgcgtccaag    180
aacgcggtcg aaaaccactt cgacacctct tatgagttag aatcactcct tgagcagcgc    240
gtgaagcgtc aactgctggc ggaagtacag tccatctgtc cgccgggcgt gaccattatg    300
aacgtgcgtc agggcgaacc tttaggttta ggccactcca ttttgtgtgc gcgacctgcc    360
attggtgaca acccatttgt cgtggtactg ccagacgttg tgatcgacga tgccagcgcc    420
```

```
gacccgctac gttacaacct tgctgccatg attgcacgtt tcaacgaaac gggccgcagc    480
caggtgctgg caaaacgtat gccgggtgac ctctctgaat actccgtcat ccagactaaa    540
gagccgctgg accgtgaggg taaagtcagc cgcattgttg aatttatcga aaaaccggat    600
cagccgcaga cgctggactc agacatcatg gccgtaggtc gctatgtgct ttctgccgat    660
atttggccgg aactgaaacg tactcagcct ggtgcatggg gacgtattca gctgactgat    720
gctattgccg agctggcgaa aaaacaatcc gttgatgcaa tgctgatgac cggcgacagt    780
tacgactgcg gcaaaaaaat gggctatatg caggcgtttg tgaagtatgg cctacgcaac    840
ctgaaagaag gggcgaagtt ccgtaaaggt attgagaagc tgttaagcga ataatgaaaa    900
tctgaccgga tgtaacggtt gataagaaaa ttataacggc agtgaaaatt cgcagcaaaa    960
gtaatttgtt gcgaatcttc ctgccgttgt tttatataaa ccatcagaat aacaacgagt   1020
tagcagtagg gttttattca aagttttcca ggattttcct tgtttccaga gcggattggt   1080
aagacaatta gcgtttgaat ttttcgggtt tagcgcgagt gggtaacgct cgtcacatca   1140
taggcatgca tgcagtgctc tggtagctgt aaagccaggg gcggtagcgt gcattaatac   1200
ctctattaat caaactgaga gccgcttatt tcacagcatg ctctgaagta atatgaaata   1260
aattaagcta gcgatcgctt aagatctagg atttcattat gttacttcct gtaattatgg   1320
ctggtggtac cggcagtcgt ctctggccga tgtcacgcga gctttatccg aaacagttcc   1380
tccgcctgtt cgggcagaac tccatgctgc aggaaaccat cacccgactc tcgggccttg   1440
aaatccatga accgatggtc atctgtaacg aagagcaccg cttcctggtg gctgaacagc   1500
tacgccagct caataagctg tcgaataata ttattcttga gccggtcggg cgcaacaccg   1560
ccccggccat cgccctggca gcccttcagg ccacccgcga cggcgacgac ccgctgatgc   1620
tggttctcgc cgctgaccat atcatcaata accagtcggc cttccacgac gccatccggg   1680
tcgccgagca gtatgctgat gaaggtcatc tggtcacctt cggtatcgtg ccgaatgccc   1740
cggaaactgg ctacgttac attcagcgcg gcgtggcgct caccgatagt gcccattccg   1800
cgtaccaggt ggcccgcttt gtggagaagc cggatcgcga gcgcgccgag gcttacctcg   1860
cctccgggga gtactactgg aacagcggca tgtttatgtt ccgcgccaag aaatacctca   1920
tcgagctggc caaataccgt ccggatatcc tggaagcctg ccaggctgtg gtgaatgccg   1980
ccgataatgg cagcgatttc atcaatatcc cgcatgatat tttctgcgag tgcccggatg   2040
agtccgtgga ctatgccgtt atggagaaaa ccgccgatgc ggtggtggtc ggtctcgatg   2100
ctgactggag cgacgtcggc tcctggtccg cactatggga ggtcagcccg aaagacgagc   2160
agggcaatgt cctcagcggt gacgcgtggg tacacaacag cgaaaactgc tacatccgca   2220
gcgacgagaa gctagtggcg gccattggcg tagagaatct ggtgattgtc agcactaagg   2280
acgccgtgct ggtgatgaat cgcgagcgtt cccaggacgt gaagaaggcg gtcgagttcc   2340
tcaagcagaa ccagcgcagc gagtacaagc gccaccgtga gatttaccgc ccctggggcc   2400
gttgcgacgt agtggtccag acccccgcgt tcaacgtcac ccgcatcacg gtgaaaccga   2460
gcggtgcctt ctcgatgcag atgcaccacc atcgcgccga gcattgggtt attctcgccg   2520
gcaccggtca ggtgactgtc aacggtaagc agttcctgtt gtccgagaac cagtccacct   2580
ttattccgat tggcgccgag cactgcctgg aaaaccctgg ctgtattccg ctggaagtgc   2640
tggagatcca gtcggggggcg taccttggcg aggacgacat tattcgtatt aaagaccagt   2700
atggtcgttg ctaattattt tcgggacaag acgcagaatg acacagttaa cttgttttaa   2760
agcttatgac atccgtggtg aactgggtga ggaactgaac gaggacatcg cctaccgtat   2820
cggtcgcgcc tacggcgaat ttctgaaacc cgggaagata gtggtggggg gcgatgtgcg   2880
cctcacaagc gagtcgctga agctggcgct ggcccgcggg ttaatggacg ccggtaccga   2940
cgtgctggac atcggcctga gcggtaccga agagatttac tttgccacct tccaccttgg   3000
ggtagatggt ggcatcgagg tgaccgcgag ccacaatcct atgaactaca acggcatgaa   3060
gctggtgcgc gagaatgcga agcccatcag cggcgacacc ggcctgcggg atatccagcg   3120
cctggcgag gaaaaccagt tcccgccagt ggacccggcg cgtcgcggga ccctgagcaa   3180
gatatcggta ctgaaggagt atgttgacca tctgatgacc tacgtggact tctcgaactt   3240
cacccgtcca ctgaagttgg tggtgaactc cggaaacggg gctgcggggc acgtgattga   3300
tgaggtggag aaaacgcttc gcggcggctgg ggtgccggta acctttatca aggtgcatca   3360
ccagccggat ggccatttcc ctaacggtat cccgaatccg ctgctgccgg agtgccgcca   3420
ggataccgcc gacgcggtgc gcgagcatca ggccgacatg ggattgcct ttgacggcgg   3480
cttcgatcgc tgcttcctgt tcgatgacga agcttcgttt atcgaggggt attacattgt   3540
cggcctgctg gctgaggcgt tcctgcagaa gcagccggga gcgaaaatca ttcacgaccc   3600
gcgcttgacg tggaacacgg tagacatcgt gacccgcaac ggcggccagc cggtgatgtc   3660
gaagacgggg catgcgttca tcaaggagcg gatgcgtcag gaagacgcta tctacggcgg   3720
ggagatgagt gcgcaccatt acttccgcga tttcgcctac tgcgatagcg ggatgatccc   3780
gtggctgctg gtggcggagc tgctgtgtct gaagaacagc tcgctgaaat cgctggtggc   3840
ggaccgccag aaggcgttcc ctgcgtcggg agagatcaac cgcaagctaa gtaatgctgc   3900
tgaggcgatc gcccgcatcc gggcgcagta tgagccggcg gctgcacaca tcgacacaac   3960
ggacgggatc agtattgaat accctgaatg gcgctttaac ctgcgcacgt ctaaccccga   4020
gccggtggtg cgtctgaacg ttgagtccag agctgatgtg gcgcttatga atgaaaaaac   4080
gaccgagctg ttacacctgt taagcgggga ataaggtgag agatttacta acgacgattt   4140
atcgttatcg gggatttatc tggagcagtg ttaaacgtga ttttcaggca cgctatcaaa   4200
ctagtatgct gggcgcacta tggctcgttt tacaaccgct ctctatgatt ctggtctata   4260
ccctggtttt ttccgaggtg atgaaggcaa gaatgcccga taataccggg tcgtttgcct   4320
atagtattta tctctgttcc ggggtactga cctgggatt atttactgag atgctggata   4380
aaggtcagag cgtatttatt aacaatgcta atctgatcaa gaaactcagt tttccgaaaa   4440
tctgtctgcc gatcatcgtg acgttatcgg cggtgctaaa tttgcgatt atttttcagtc   4500
tgtttctaat ttttatcatt gtcaccggta acttcccccg ctggctcttt ctctcggtta   4560
taccggtcct gcttttgcag atcctgtttg ccggtgggct ggggatgatc cttggtgtca   4620
tgaacgtctt tttcagggat gtggggcaac tggttgcgt tgcgctgcaa ttctggtttt   4680
ggttcacacc cattgtttat gtactgaatt cattacctgc atgggcaaaa aatctgatga   4740
tgtataaccc gatgactcgg atcatgcaat cttatcagtc catcttcgcc tatcatctcg   4800
ccccaactg cgtattcgta tggccagtat tggctcatcg cattatttc tgcgtcatcg   4860
gtttcaggat gttccgcaag catgcggcgg atatggtgga tgaattataa tgagttatat   4920
cagagtaaat aatgtcggta aggcgtatcg ccagtatcac tcaaagaccg ggagactgat   4980
cgaatggtta tccctctga ataccaaacg ccataaattg aaatggatcc tccgcgatat   5040
taatttcgaa gtcgctccgg gcgaggctgt cggtattatc ggtatcaacg gtgcaggcaa   5100
gagtaccctg cttaaaactca taaccgggac gtccaggccg acgactggag aaattgaaat   5160
```

```
ctccggacgt gtcgctgcat tactcgaatt ggggatgggg tttcattctg atttcactgg 5220
tcggcagaat gtttatatgt ctgggcaact gttggggtta tcgtcagaga aaataactga 5280
actgatgccg caaattgaag agtttgctga gattggggac tatatcgatc aacctgtgcg 5340
cgtctactcc agtgggatgc aagttcgatt agcttttagt gtagcgacgg ctatccgtcc 5400
tgatgtgcta attatcgatg aggcattatc tgttggggat gcatatttcc agcataaaag 5460
ctttgagcgt attcgaaaat ttcgtcagga agggaccacg ctgttgctgg tatcccatga 5520
taaacaagcg atccaaagca tttgcgaccg ggccatttta ttgaataaag gccaaattga 5580
aatgaaggt gaacctgaag cagtgatgga ttattacaat gctcttctgg ccgataaaca 5640
aaatcagtcc attaaacaag ttgagcataa tggtaaaacg caaactgttt caggcactgg 5700
tgaggtgact atctctgagg ttcatcttct cgatgaacag ggcaatgtga ctgaatttgt 5760
ttcggtaggg catcgtgtca gcttgcaggt caacgttgag gtcaaggacg atattcctga 5820
gcttgttgtc ggatatatga ttaaggatcg acttgggcag ccgattttcg ggaccaatac 5880
gtaccatctc aatcagacac tcacctccct gaaaaaagga gaaaagcgtt cgttcttatt 5940
tcctttcgat gcgagattgg gggttggctc ctattctgtc gctgtcgcgt tgcatacttc 6000
cagtacgcac ctcggcaaaa actatgaatg cgcgatctg gccgtggtat tcaacgtcgt 6060
taacacggaa caacaagagt ttgtcggcgt gtcctggttg ccgcctgaac tggagatttc 6120
ttaatgggtt cgtcgtttta tcgttcattt gaagaacgac acagaggttc ggttgaagaa 6180
atcaagcgcc gcttgagttt ttatttaccct tttcttgcag gtctgaagga catttatcct 6240
gatggcgtga ttgcggatat tggttgcgga cgtggcgaat ggttggagat cctgactgaa 6300
aatggcattg cgaacatcgg cgtcgatctc gatgatggca tgctggcgcg cgccagggag 6360
gccggactga atgtgcagaa aatggattgt ctgcagtttt tgcaaagtca ggcggatcag 6420
agcctgatag cgttgaccgg ttttcatatt gctgagcatt tgccgtttga ggtcctgcag 6480
caactcgcca tgcatacct acgggtgctg aaaccaggtg gtttgctgat cctcgaaacg 6540
ccgaacccgg agaatgtaag cgtcggcacc tgttcatttt atatggatcc aacgcataat 6600
catcctctgc caccgccact gcttgagttt ttacctattc attatggttt tacccgagca 6660
attaccgttc gtctgcagga aaaagaggtt cttcaatctc cggatgcagc cgttaatttg 6720
gtcgatgtac tcaaaggggt gagccccgac tacagcatca ttgctcagaa agcagccgca 6780
acagatattc ttgaacgctt tgacaccctg tttacccagc agtacggtct gacgctggat 6840
gctctgagca accgttacga tgcgattttt cgccaacagt tttcgtccgt tgtctcacgg 6900
ctggacgt tgaaccaaac ctatatgcaa cagataagcc aaatgtcaga gactattcag 6960
acgttgcaag gtgaggttga cgatctgagt catgtcatcg atcagaacca tcagcttcat 7020
cagcaaatgg cggatttaca taacagtcgt tcatggcgta ttactcaacc actacgctgg 7080
ttgtctttgc aacgtcaatt attacgtcag gaaggggcta aagtgcgagc ccgtagggct 7140
gggaaaaaaa tattgcgcaa agggatggcg ctctcgctgg tcttttttcca tcgttacccct 7200
aagtctaagg tttatctgtt taaggttctg agaaaaactg gctgctatac attgctacaa 7260
cgtttgttcc aacgcgtaat gctggtgcaa tctgacacga tgatgatgca gtccagaaga 7320
tatgatgtgg gtactgaaga aatgacaagt cgcgcgatga gtatttataa cgaattaaaa 7380
aataaaaata cggagaaata acgatgcgta ttgtcataga tttacaaggc gcacagacgg 7440
aaagccgctt tcgtcggcatc ggtcgttata gtatcgcaat cgccagagcc ataatcagaa 7500
ataacagccg gcatgagatt ttcatcgcgc tatccgccat gctggatgag tcgattgcaa 7560
atattaaggc gcaatttgcc gatctcctgc cggcagaaaa tatagtcgta tggcatgccg 7620
taggccctgt tcgtgcgatg gaccaaggta atgaatggcg tcgggagagc gcagaactga 7680
ttcgggaagc gttcttgaa tcattgtgtc cagatgtcgt tttcattacg agtttgtttg 7740
aaggtcatgt cgacgatgcg gctacatcgg tacacaaatt tagtcgtcag tataaagtag 7800
ccgtactgca ccacgatctt atcccccctcg tgcaggcgga aacctatctg caggacgatg 7860
tatacaaacc ctactattta cagaaagttg agtggtaaa aaacgctgac cttttgttga 7920
ctaactctgc ttataccgca caggaagcga tcgagcatct gcatttacag ggcgatcatg 7980
tgcagaatat tgcagccgca gtcgattctc agttttgtat ggcggaggtg gcagcgagcg 8040
aaaaagagac cgtccttggc cattacggta ttcagcgcga gttcatgttg tatgcgcccg 8100
gaggatttga ctcaaggaaa aactttaaac ggttgattga ggcctatgcc gggctcagtg 8160
atgccttacg tcgcagtcat caactggtca tcgtcagtaa gctttccatc ggtgatcgtc 8220
agtatctgga atcccttgcg tcaggtaatg gtttacagca gggcgaactg gtactcactg 8280
gttatgtgcc ggaagatgag ctgatccagc tctatcgcct atgtaagctg ttcatctttg 8340
cttcactaca tgaaggtttt gggttgccgg ttctggaagc aatgtcgtgc ggtgcgccgg 8400
tgattggctc aaatgtcacc agtattcctg aagtcatcgg taatcctgag gcattattcg 8460
acccgtattc tgtctcttcc atgagggata agatcgcgca atgtttgact gatgataccct 8520
tcctcgcgcg tctgaaagaa atggcgcagc agcaagcgcg taatttctct tgggataaag 8580
ctgcggtgac tgctctggaa gctttcgaaa agatcgcggt agaagacacc ggtactgcgc 8640
aggttttgcc tgaagctttg attcagaaga tccttgctat ctcacaaggg cagccagatg 8700
accgcgatct gcgcttgtgc gcaacggcca ttgattacaa tctgaaaacg gcagaacttt 8760
atcaaatcga cgataaatcg ctgaactggc gtgtggaagg cccattcgat agctcatata 8820
gtctggcgtt ggtcaaccgc gaatttgccc gggcactctc agccgatggt gtagaggttt 8880
tattgcattc cactgaagga ccaggtgatt ttgcccagatgcctcgttt atggcacagt 8940
cggaaaatag tgatcttctg gcattttata atcaatgtca gaccccgcaag agtaacgaaa 9000
agatagatat tattagcaga aatatctatc caccgcgggt taccaaaatg gatgccaaag 9060
taaaattcct tcattgttat gcttgggaag aaacgggctt tccgcaaccg tggatcaatg 9120
aatttaatcg ggaacttgac ggagtgctgt gtacttcgga acatgttcgt aaaatactga 9180
ttgataacgg actgaatgtg cccgcatttg ttgttgacaa tggctgtgac cattggctca 9240
atatcccagc cgagacgaca aaagatgtgg atcacggaac attccgtttc ctgcacgtct 9300
cttcttgttt cccacgcaaa gggatacagg caatgcttca ggcttggggg aaggcgttca 9360
ctcgtcgtga caatgttatc ttaatcatta agacttttaa caatccgcac aatgaaattg 9420
acgcatggct ggctcaggcc caggctcaat tcatagacta tcccaaagtt gaagtgatca 9480
aagaggatat gtcagccacc gagcttaaag gctttatga aagctgtgat gttttggttg 9540
ctccaggttg cgctgaaggc tttggtttac ctattgctga agcaatgctg agtgggctac 9600
cggctatcgt caccaattgg agcgggcaac ttgattttgt taattcacaa aattcatggc 9660
tggttgacta tcagttcact cgggtaaaaa cgcacttggg tctgtttcc tcagcctggg 9720
ccagtgtgga tattgacaac ttaacagatg cattaaaagc ggcagcctca accgataaat 9780
cagtgctgcg tgacatggcc aatgctggtc gcgagcttca tctgcagcag tttacctgga 9840
aagcggtggc tgatcgttct tgccaggcgg tcaagactct gcgtgcgcat attgatattg 9900
```

```
cacagcatcg ggcgcgcatt ggctgggtga cgacctggaa cacgaaatgt gggatcgcaa   9960
cctattccca gcatctggtg gaaagcgcac ctcatggcgc ggatgttgtt tttgctcccc  10020
aggtcagcgc tggcgatctt gtgtgtgcag acgaagagtt tgtacttcgc aactggattg  10080
taggtaaaga gagcaactat ctggaaaacc tccagccaca cattgatgct ctgagactcg  10140
atgtcattgt gatccaattc aactatggat tctttaatca tcgagaactg tcggcgttta  10200
ttcgtcgcca gcatgacgcc ggtcgttcag ttgttatgac gatgcactca actgtggatc  10260
cgctggaaaa agagccgagc tggaatttcc gtcttgctga aatgaaagag gcgctggcac  10320
tttgcgaccg gttgttggtg cattcgattg ccgatatgaa ccgccttaaa gatttaggct  10380
taactgcgaa tgttgcttta ttcccgcacg gtgttatcaa ctactccgca gcgagcgtca  10440
cacgtcaaca gcagtctttta ccgctaattg cgagctatgg cttctgctta ccgcataagg  10500
gcctgatgga actagtagaa tccgtccata gactcaagca agccggtaaa ccggttcgtt  10560
tacgactggt gaacgcagag tatcctgttg gggagtcacg cgatctggtg gcagagctta  10620
aagctgctgc tcagcggtta ggtgttaccg atctgattga gatgcataat gatttcctac  10680
ctgatgcgga gagtctgcgg ttgctttcag aagccgatct tctgattttt gcttatcaga  10740
atactgggga gtctgctagc ggggcggtac gttatggtat ggcgactcaa aaacctgttg  10800
cggtaacgcc cctggcgata tttgatgatt tggacgatgc cgtctttaaa tttgatggat  10860
gcagcgtcga tgatatcagt caggggattg accggatcct gaattccatc cgtgaacaga  10920
actcttgggc aaccaggact caacaacgtg ccgatgcatg agagtgtctg cggtactgc  10980
aagctgtttc acgccgtctg gttaatatgt gtcaaggctt agctaaagct aaatatttta  11040
aataaaaata tctctcttgt attttttgcc tttgaataca agaggggtta gataatgtgt  11100
catttattat gaaaattatt tttgctactg agccaattaa ataccatta acgggcatcg  11160
gtcggtattc cctggagctg gttaagcggc tggcggtcgc ccgcgaaatt gaagaattaa  11220
agctatttca cggtgcgtcg tttatagaac agatcccttt ggtggagaat aaaagcgata  11280
ccaaagccag caatcatggt cgtctgtcgg cgtttctacg ccgacagacg ctgttgattg  11340
aggcttatcg cttgctgcat ccgcggcgcc aggcgtgggc attgcgcgac tataaggatt  11400
atatctacca tggcccccaat ttttatctgc cgcataaact ggaacgcgcc gtgaccacgt  11460
ttcatgacat atccatttttt acctgcccgg aatatcatcc aaaagatcgg ttcgctata  11520
tggagaagtc cctgcatgag agtctggatt cggcaaagct gatcctgacc gtttctgatt  11580
tctcgcgcag tgaaattatc cgcttgttca actatccggc ggagcggatc gtaaccacca  11640
agctagcctg cagcagtgac tatatcccac gcagccccgc agagtgtctg ccggtactgc  11700
agaaatatca gctggcgtgg caggcctacg cgctatatat cggcactatg gagccacgta  11760
aaaatatccg aggcctgctg catgcctatc agctgctacc gatggagatc cgcatgcgct  11820
atccgctaat ccttagcggc tatcgcggct gggaagacga tgtgctgtgg cagttagtcg  11880
agcgcggtac tcgggaaggc tggatccgtt acctcggata tgttccggat gaagacctgc  11940
cgtatctgca cgcagcggcc agagtctttg tttatccctc cttctacgag ggattcggtt  12000
tacctattct tgaagcgatg tcttgcggtg tgccggtagt atgctccaat gtcacctctt  12060
tgcctgaggt tgttggcgat gccggcctcg ttgccgatcc taatgatata gacgcgatta  12120
gcgcgcaaat tttgcagagc ctgcaagatg atagctggcg ggaaatcgcc accgcgcgcg  12180
gtcttgctca ggcgaaacag ttttcgtggg agaactgtgc gacacagacc attaacgcct  12240
ataaattact ctaagggtgt cagttgagag ttctacacgt ctataagact tactatcccg  12300
atacctacgg cggtattgag caggtcattt atcagctaag tcagggctgc gcccgccggg  12360
gaatcgcagc cgatgttttc acttttagcc cggacaaaga tacaggtcct gtcgcttacg  12420
aagatcatcg ggtcatttat aataaacagc ttttttgaat tgcctccacg ccgttttcga  12480
tgaaagcgtt aaagcgtttt aagctgatta aagatgacta cgatatcatc aactaccatt  12540
ttccgtttcc ctttatggat atgctgcatc tttcggcgcg gcctgacgcc aggactgtgg  12600
tgacctatca ctctgatata gtgaaacaaa acggttaat gaagctgtac cagccgctgc  12660
aggagcgatt tctcagcggc gtagattgca tcgttgcctc gtcgcccaat tacgtggctt  12720
ccagccagac cctgaaaaaa tatctggata aaacggtggt gatcccgttt ggtctggagc  12780
agcaggacgt gcagcacgat ccgcagaggg tcgcgcactg gcgggaaact gtcggcgata  12840
agttcttctt cttcgtcggc actttccgct actacaaagg gctgcatatt ctgatggatg  12900
ccgctgagcg tagccgactg ccagtggtgg ttgtaggggg cgggccgctg gaatcggaag  12960
tgcggcgtga agcgcagcag cgcgggctga gcaatgtgat gtttaccggc atgctcaacg  13020
acgaagataa gtacattctc ttccagctct gccggggcgt ggtattcccc tcgcatctgc  13080
gctctgaggc gtttggcatt acgttattgg aaggcgcacg ctttgcaagg ccgctgatct  13140
cttgcagat cggtacaggt acctctttca ttaaccagga caaagtggtt ggttgcgtga  13200
ttccgccgaa tgatagccag gcgctggtgg aggcgatgaa tgagctctgg aataacgagg  13260
aaaacctcca accgctatgg cgaaaactcgc gtcgtcgttt tgaagagatg tttactgccg  13320
accatatgat tgacgccta gtcaatctct acactacatt gctggaaagc aaatcctgag  13380
cggccgcgag ctcgtcgact cgaggatccg tgtaggctgg agctgcttcg aagttcctat  13440
actttctaga gaataggaac ttcggaatag gaactaagga ggatattcat atggataaag  13500
ccgtaagcat ataagcatgg ataagctatt tatactttaa taagtacttt gtatacttat  13560
ttgcaacat tccaggccgc gagcattcag cgcggtgatc acacctgaca ggagtatgta  13620
atgtccaagc aacagatcgg cgtagtcggt atggcagtga tgggacgcaa ccttgcgctc  13680
aacatcgaaa gccgtggtta taccgtctct attttcaacc gttcccgtga gaagcggaa  13740
gaagtgattg ccgaaaatcc aggcaagaaa ctggttcctt actatacggt gaaagagttt  13800
gtcgaatctc tggaaacgcc tcgtcgcatc ctgttaatgg tgaaagcagg tgcaggcacg  13860
gatgctgcta ttgattccct caaaccatat ctcgataaag gagacatcat cattgatggt  13920
ggtaacacct tcttccagga cactattcgt cgtaatcgtg agctttcagc agagggctat  13980
aacttcatcg gtaccggtgt ttctggcggt gaagagggg cgctgaaagt gtccttctat  14040
atgcctggtg gccagaaaga agcctatgaa ttggtagcac cgatcctgac caaaatcgcc  14100
gccgtagctg aagacggtga accatgcgtt acctatattg tgccgatggg cgcaggtcac  14160
tatgtgaaga tggttcacaa cggtattgaa tacggcgata tgcagctgat tgctgaagcc  14220
tattctctgc ttaaaggtgg cctgaacctc accaacgaag aactggcgca gacctttacc  14280
gagtgaata acggtgaact gagcagttac ctgatcgaca tcaccaaaga tatcttcacc  14340
aaaaaagatg aagacggtaa ctacctggtt gatgtgatcc tggatgaagc ggctaacaaa  14400
ggtaccggta aatggaccag ccagagcgcg ctggatctcg cgaaccgct gtcgctgatt  14460
accgagtctg tgtttgcacg ttatatctct tctctgaaag atcagcgtgt tgccgcatct  14520
aaagttctct ctggtccgca agcacagcca gcaggcgaca aggctgagtt catcgaaaaa  14580
gttcgtcgtg cgctgtatct gggcaaaatc gtttcttacg cccagggctt ctctcagctg  14640
```

```
cgtgctgcgt ctgaagagta caactgggat ctgaactacg gcgaaatcgc gaagattttc   14700
cgtgctggct gcatcatccg tgcgcagttc ctgcagaaaa tcaccgatgc ttatgccgaa   14760
aatccacaga tcgctaacct gttgctggct ccgtacttca agcaaattgc cgatgactac   14820
cagcaggcgc tgcgtgatgt cgttgcttat gcagtacaga acggtattcc ggttccgacc   14880
ttctccgcag cggttgccta ttacgacagc taccgtgctg ctgttctgcc tgcgaacctg   14940
atccaggcac agcgtgacta ttttggtgcg catacttata agcgtattga taaagaaggt   15000
gtgttccata ccgaatggct ggattaa                                      15027

SEQ ID NO: 15         moltype = DNA  length = 11283
FEATURE               Location/Qualifiers
source                1..11283
                      mol_type = other DNA
                      organism = synthetic construct
SEQUENCE: 15
atgacgaatt taaaagcagt tattcctgta gcgggtctcg ggatgcatat gttgcctgcc     60
actaaggcga tacccaaaga gatgctacca atcgtcgaca agccaatgat tcagtacatt    120
gttgacgaga ttgtggctgc agggatcaaa gaaatcctcc tggtaactca cgcgtccaag    180
aacgcggtcg aaaaccactt cgacacctct tatgagttag aatcactcct tgagcagcgc    240
gtgaagcgtc aactgctggc ggaagtacag tccatctgtc cgccgggcgt gaccattatg    300
aacgtgcgtc agggcgaacc tttaggttta ggccactcca ttttgtgtgc gcgacctgcc    360
attggtgaca acccatttgt cgtggtactg ccagacgttg tgatcgacga tgccagcgcc    420
gacccgctac gttacaacct tgctgccatg attgcacgtt tcaacgaaac gggccgcaac    480
caggtgctgg caaaacgtat gccgggtgac ctctctgaat actccgtcat ccagactaaa    540
gagccgctgg accgtgaggg taaagtcagc gcattgttg aatttatcga aaaaccggat     600
cagccgcaga cgctggactc agacatcatg gccgtaggtc gctatgtgct ttctgccgat    660
atttggccgg aactggaacg tactcagcct ggtgcatgga gacgtattca gctgactgat    720
gctattgccg agctggcgaa aaaacaatcc gttgatgcaa tgctgatgac cggcgacagt    780
tacgactgcg gcaaaaaaat gggctatatg caggcgtttg tgaagtatgg cctacgcaac    840
ctgaaagaag gggcgaagtt ccgtaaaggt attgagaagc tgttaagcga ataatgaaaa    900
tctgaccgga tgtaacggtt gataagaaaa ttataacgac agtgaaaatt cgcagcaaaa    960
gtaatttgtt gcgaatcttc ctgccgttgt tttatataaa ccatcagaat aacaacgagt   1020
tagcagtagg gttttattca aagttttcca ggattttcct tgtttccaga gcggattggt   1080
aagacaatta gcgtttgaat tttcgggtt tagcgcgagt gggtaacgct cgtcacatca    1140
taggcatgca tgcagtgctc tggtagctgt aaagccaggg gcggtagcgt gcattaaatac   1200
ctctattaat caaactagga gccgcttatt tcacagcatc ctctgaagta atatggaata   1260
aattaagcta gcatgagcaa aactaaacta aatgttcttt accttgcaat aagtcagggt   1320
gccaattacc tactgccatt attaattttt ccttatcttg ttagagtcat tggtgtatcg   1380
aattttggtg atctgagttt tcattgata actatacaag tgttgttaat ggttgttgaa   1440
tatggttttg datatagtgg gacaagagaa atagcactaa ataacgataa aaaataccat   1500
tctgaattttt tttgcggtgt ggtgcttgct cgttttatat taatgctaat tgcagctata   1560
atactcataa tactctgttt tttttatgtt tttaacgacg ttaagtcttt gttatgtgtt   1620
ggttttctgt ccgtaattgc aggtgttttc aatccaaatt ggttttttgca aggtaaggaa   1680
atgatgagtg tgatggctgt gctgtcacta ttttcacgag gcatagcagt cgttgcagtt   1740
tatctaatta taaaacccgc aacgccgatg tacatcagtg ccttattatt gagcatgcca   1800
tatattttgt attcattctg tggcgttgcc tacttactta ttatcaagga gatttttta   1860
tgtaggccac cgataaagaa aattcaagta atttttaaaa atggatttca ttttttttgt   1920
tcaacacttg cgactagtgc atacacaatg ttgaccccctc ttgtattggg tggcgtatct   1980
ggaaagtttg atgtaggcat cttttaactca gctaacatga tcaaacaagg tttggctgga   2040
cttgcatcac cattagtcca agcttttttat ccaagaatta acattttgca aagagagaat   2100
ccatatattg caaacttaaa atctagaatg attcttaaat acttgcttgt tttttacatg   2160
gctttagcaa taccatttt actttttgcc aaccaattat cattattaat attcggcatg   2220
aaaggtgaag taattgcagg tgcaatgcaa ttaatgacat tgcttcctat attcataggt   2280
tttaatacag ttgtcgggtt acttgtatta gtacctaatg ggatgcaaaa acagtatttc   2340
aaatctattt tcctaggaac tattacttgt ttaagcatag tttatccagc atgtaaatat   2400
tatggagcaa cgggtgcgat tgtgagtctt atttgtagctg aaattttcgt tggcatggga   2460
atgcttaaac aattcattaa agtaaataaa accgtatgta ggcctcataa attatgaata   2520
tctcggtaat aatatctgtt tggaaacgcc cagttcaatt agaattgatt ctctctgagc   2580
tcgattctca ggctaaagac aatagtctac acctagaagt aattgtttcc gatagtcata   2640
gtggtaaaga aattgatgat gtagttgctg ataattatca taaaagaaa aattattaata   2700
ttatccatca acatactaaa aatatactct ccgctaagcg caatttcgga gcatccctag   2760
cccatgggga ttatttaata tttcttgatg atgattgtat acccgcaagt ggatatatat   2820
catcgttgct gaactattta aaaaaaatga atagtaaaag cgtttatgt ggggaagtta    2880
gattcgaaaa tgaactcatt gagaccagca attactatcg ctacaggaac tctttacacc   2940
ctaagtttag tgatagtcct gatatctcta tgaatgcctg gactttttgtc gcaatgaatt   3000
gtgttcttga tagaaaggca tttttcatcag gtatagtttc atataatgaa aatttttattg   3060
gttatggttg tgaagatcat gagtttgggt ggcaacttga aaaaaatgac ttcaaaatta   3120
tttttgctga ttttaaaata ttacatcacg aatacagtgg cgatatagaa ggatatacaa   3180
aaaaaattcg tgctacagca cgtgatggta tgaatgtatt aagcaaagta aggcctgaaa   3240
tgttttctac taataaaaaa ttattcctag ttgagaaaat atttagtaaa cacaaaacgt   3300
ttagtaaaat atgccaatca atattttca ataaatttat ttttaaaaaa ataatcaat    3360
ttttaaaaaa aacagatgca aataaaaaac tctatttccc aattcttac agatatgtgt    3420
tgatttcggc atatatacat ggtattggag agcgtggcac ctcaaaaaca gatgatttgc   3480
ttaagaactg gtatatatag atgatgctat cttcattttat taagcatttt gtatggaagg   3540
taaaaaacaa tgaagtataa tgcattgatg tgcttttttat tatttttttgt tgttttttt    3600
agattgtcgc tgataatacc tttcttatat ttggcatttat ttcctgcatt ttttggtatt   3660
atgtatttag tgcgtaattt tatgattact atgggcaatg gattggtatc tatagatcgt   3720
aaaaatttgt tgctgttatc tatattcata attattttt tattttgttt ggttttcgat    3780
ttgtttcaaa aaagccattc ttttcaaagt tattttaccg ttagattatt tatgttgttt   3840
ttattttcat ttgttcctgc gtattattta gtaaatagat tcataaaggg tgacttgaaa   3900
```

```
ttaatggagc gaatattagt gtattctctc tgggttcaaa tagttatttt ttttggtatg  3960
tatataagtc cagagttaaa aagattgtta tatactttct ttggtatgtc tgactctgtt  4020
aatctttggg aacaaaatgc taaagtaaga ggatttgggt tgtcgggtga aataaatttc  4080
atgcaccat ttttgatgat ctatatgtca ttttttatga tgaaaaggcg ttatgcttta  4140
attactttaa tttgtctgac tcaaatcgta aattctaaca tggctgtgat tgcagccatt  4200
attggtatcg gttgctctag acttaatatt aatataaaaa ttgcaacagt attgattttg  4260
ggagttttag tttatagctt aggagcggtg ttcttcctc gattttatga tgagttcgtt  4320
tctggagatg gcacaagaac tctggatatc ttattacagc aacatgtgtt tgttgtaggt  4380
aatttagatt tttttaatat tatatttgga ttacagcaaa acatatcttc atcaatcccc  4440
gatattaaac aaagttcgga tatgggctgg gttatactgt ttaattacgg tgggttaaca  4500
tttattacac tcttttttatt tttaatcttt actatttcta ttgcgacatt tggaatgaca  4560
tatcaagcaa ttatatggat gttaattggg ataattttca ataccaaagg tttagttta  4620
ggatctaacg gctatttctt tctatctttt atatatatgt ttttgaatag agtaacactt  4680
agtggacaga gttcaattac taataagtta ggtcaagtaa gtaaatagct tccagagtat  4740
atttgtcaat gatttgaggt tcggttatta tgttttcatc taaaacactg ttaattactg  4800
gtggtactgg ctcttcgggg aatgctgtat taaatagatt tcttgataca gatattgcag  4860
aaatccgtat atttagtcgt gatgaaaaaa aacaagatga tatgcggaaa aatacaata  4920
atcaaaaatt aaagttctat attggtgatg tcagagatta ccgtagtatt ttgaatgcga  4980
ctcgcggtgt tgattttata tatcatgcag cggcacttaa gcaagttcca tcatgtgaat  5040
ttcatcctat ggaagccgtt aaaactaata tccttggtac ggaaaatgtt cttgaagcag  5100
ctatagcgaa tgaagtgaag agggttgtat gcctaagtac tgataaagct gtatacccga  5160
ttaacgcaat gggtatttca aaagctatga tggaaaaggt catggtcgcg aaatcccgta  5220
atgttgatcg caataaaaca gtaatatgtg gtacccgtta tgggaatgtt atggcatctc  5280
gcggttcagt tattccatta tttgttgatc ttattagagc gggcaagcca ctcacaataa  5340
ctgatcctaa tatgacccgc tttatgatga ctcttgagga tgcggtagat ttagttcttt  5400
atgcgtttga acatggtaat aatgqtgata tctttgtgca aaaagcacct gcagcaacta  5460
ttgacacatt agctattgct ttaaaggaat tactaaatgt tcctgaccat ccggtaaatg  5520
tcattggaac gcgtcatggc gagaaattat atgaagctct acttagtcgt gaggaaatga  5580
tcgctgctat agatatgggc gattattacc gtgtcccgcc agatcttcgt gaccttaatt  5640
atggcaaata tgttgagcaa ggtgatagcc gaatatctga aatagaagat tataactctc  5700
ataatactca acggttagat gttgaaggca tgaagagct cttgctaaaa ttagccttta  5760
ttcgagcaat tcgtgctggt gaaaaatata atctggattc atgatatgaa aatattagtt  5820
actggtgcaa atggttttat tggtcgtaat ttatgtttga ggcttgagga acttggttat  5880
aaagatctta ttagaattga tcgagaatca acgaagcaag atcttgaaca aggcttacag  5940
gatgccgatt ttatttatca cttagctggt atcaatagac ctaagactga tgatgagttt  6000
atttctggaa acagtgattt aacaaagcat atagttgagt atctcctttc tattggtaag  6060
aatacaccaa ttatgctaag ttcttcgata caagctgaac ttaataatgc ttatggggtt  6120
agcaaagctg tagctgaaag ctatgtcgaa aaatatgctg ctgctagtgg ttcttcgtat  6180
tatattttca gatatccaaa cgttttttggt aaatggtgta agccaaacta taattctttt  6240
atagcaactt tttgctacaa tatttccaat gatattgaga ttactatcaa tgatgcagca  6300
gcgccagtca atctggtcta tattgatgat gttttgtactg atgctatagc tcttctctct  6360
gggacggttg aaagtggata taaagttgtt gcaccaattt attcaacaac agttggtgaa  6420
gttgcagaat taatttatag cttcaaaaat agccgttcca ccctgatcac agagctgtc  6480
ggggcgggat ttacccgtgc attgtattct acatggctga gttatttacc agcagagaag  6540
tttgcgtaca aggtaccttt ttatggggat gcccgcggag tcttttgtga gatgttgaaa  6600
acgccttcag cggggcagtt ttcatttttt actgctcacc ctggtattac gcgtggcgga  6660
cattaccatc acagtaaaaa tgagaagttt ttggtcattc gaggtcaggc atgcttttaaa  6720
tttgaacatg tgattaccgg tgagcgatat gaactgaaag tttcatcggg tgagtttaag  6780
attgttgaaa cagttcctgg ttggacacat gacattacaa atattggaac tgatgaatta  6840
atagtcatgc tctgggcaaa tgaaattttc aaccgtgatg agcccgatac tattgcgaga  6900
cctctataat gaaaaaatta aaagttatgt ctgttgttgg aacccgtcct gagattatcg  6960
gtttgtcgag ggttcttgct aagtttgatg aatactgcga gcatattatt gtccatactg  7020
gtcaaaatta tgattacgaa ttaaatgaag tgttcttcaa tgacttgggt gttcgaaaac  7080
ctgattattt tttaaatgca gcgggtaaaa atgcggcgga aaccattggt caggttatta  7140
ttaaggtaga tgaagtataa gaaatcgaaa aacctgaagc aatactgta ttgggcgata  7200
cgaattcatg tatttctgcc attccggcca aacgccgtaa agtgcctata tttcatatgg  7260
aagcaggtaa ccgttgtttc gatcaacgcg tgcctgaaga aaccaacaga cgtattgttg  7320
accatacggc tgatatcaat atgacctaca gtgatattgc tcgtgaatat ctcttggctg  7380
aaggtatccc agctgatcgg atcataaaaa ctggtagccc tatgtttgag gttctttcat  7440
attatatgcc ccaaattgat ggttcagatg tgctatcgcg tttgaatcta cagtctggtt  7500
agttttttgt agtaagtgcg catcgtgaag agaatgttga ttctccaaaa cagctcgtaa  7560
agcttgcgaa cattctaaat actgttgctg aaaaatataa tcttccagtt attgtctcca  7620
cacacccaag gacacgtaac cgaatccgtg agcaaggaat tgaatttcat tcaaatataa  7680
atctactgaa accattgggt ttccatgatt ataaccactt gcagaagaac tcacgagctg  7740
tgctttcaga tagcggtact atcactgaag agtcatccat catgaatttc ccagcggtaa  7800
acatccggga agcgcatgag cgtccggaag gctttgagga agcatccgtc atgatggtgg  7860
ggttagagtg tgaacgcgta ttacaagcgc tggatattct ggcaacacaa ccgcgaggtg  7920
aagtccgtct tttacgtcag gttagtgatt acagcatgcc aaatgtgtcg gataaagttg  7980
tcagaattgt tcactcttac acagattatg ttaagagagt cgtctggaaa gaatattgat  8040
gaaacttgct ttaatcatag atgattacct gcccaacagt actcgtgttg gtgcaaaaat  8100
gtttcatgaa cttgctcaag aatttatcca gcgtgggcac gatgttacgg taattactcc  8160
tggtacgggc atgcaagaag agatttcttt tgatacctt caggggtaa aaacatggcg  8220
ttttaaaagc gggccgctca aggatgtaag taaaattcag cgagcggtca atgaaacgct  8280
tttgtcctat cgggcgtgga aagccatcaa aaaatgggta aaaagaga cctttgaggg  8340
ggtgatttat tattcacctt ccatattctg ggggccttta gttaaaaaaa ttaaagctcg  8400
ttgccaatgt cctgctatc ttatttaag agatatgtt ccacaatggg taattgatgc  8460
aggaatgctt aatgctggtt ccccaataga acgctacttt cgtcttttttg aaaaaatatc  8520
ttatcgtcag gcaaatcgta ttggacttat gtctgataag aatcttgatg ttttttcggaa  8580
agataataaa ggctatccgt gcgaagtttt gcgtaattgg gcatccctaa caccaacgat  8640
```

```
cataccccaag gattatatac cactacgtaa gcgacttggc ctagaggata aaaccatttt  8700
cttctatggt ggaaacatag gtcatgcaca ggacatgaca aacttgatgc gacttgtgag  8760
aaacatggca gcatatcctc aagctcattt cctatttatt ggccagggg atgaagttga  8820
attaattaat tcattagcat ctgagtgggc attgacgaat tcacctatt tgccctcggt  8880
taaccaagat gaatttaagt tcattttgtc ggaaatggat atcggcttgt tttctctttc  8940
cgctagacac tcttcccata atttttcctgg taagttatta ggctatatgg ttcagtcgct  9000
acctatttta ggtagcgtaa atgccggaaa tgatttgctc gacattgtca atcaaaataa  9060
tgcgggatta atccatgtca atggtgagga cgataaatta tgtcaatctg cgctattaat  9120
gttgcatgat attgatgtgc gccggcaact tggttcgggg gcgaatatat tgttgaaaga  9180
acaattctcc gttgagtctg cggcacagac gatagaaatg aggttggagg catgcaatgc  9240
gattaattga taatgaccaa ctcgacgaat tatatgatca agccgggcaa tcggaacgtt  9300
tacgttccca cctatgatg cacggctcgc atcaagaaaa ggtacagcgt ttacttattg  9360
cattagtaaa gggcagctat gttgaaccgc attatcacga acttcctcat cagtgggaaa  9420
tgttcattgt tatggagggg caacttcagg tttgtttgta tggtagaaat ggtgaggtta  9480
taaagcaatt tatagcagga gataatactg gaatgagcat tgtggagttt tctccgggcg  9540
atatacacag tgtcgaatgc ctatctccgc gtgctcttat ggtggaagtt aaggaggggc  9600
catttgaccc ttcttttgca aaatcgttcg tgtgagcggc cgcgagctcg tcgactcgag  9660
gatccgtgta ggctggagct gcttcgaagt tcctatactt tctagagaat aggaacttcg  9720
gaataggaac taaggaggat attcatatgg ataaagccgt aagcatataa gcatggataa  9780
gctatttata ctttaataag tactttgtat acttatttgc gaacattcca ggccgcgagc  9840
attcagcgcg tgatcacac ctgacaggag tatgtaatgt ccaagcaaca gatcggcgta  9900
gtcggtatgg cagtgatggg acgcaaacctt gcgctcaaca tcgaaagccg tggttatacc  9960
gtctctattt tcaaccgttc ccgtgagaag acgaagaag tgattgccga aaatccaggc  10020
aagaaactgg ttccttacta tacggtgaaa gagtttgtcg aatctctgga aacgcctcgt  10080
cgcatcctgt taatggtgaa agcaggtgca ggcacggatg ctgctattga ttccctcaaa  10140
ccatatctcg ataaaggaga catcatcatt gatggtgta acaccttctt ccaggacact  10200
attcgtcgta atcgtgagct ttcagcagag ggctttaact tcatcggtac cggtgttttct  10260
ggcggtgaag agggggcgct gaaaggtcct tctattatgc ctggtggcca gaaagaagcc  10320
tatgaattgg tagcaccgat cctgaccaaa atcgccgccg tagctgaaga cggtgaacca  10380
tgcgttacct atattgtgc cgatggcgca ggtcactatg tgaagatggt tcacaacgt  10440
attgaatacg gcgatatgca gctgattgct gaagcctatt ctctgcttaa aggtggcctg  10500
aacctcacca acgaagaact ggcgcagacc tttaccgagt ggaataacgg tgaactgagc  10560
agttacctga tcgacatcac caaagatatc ttcaccaaaa aagatgaaga cggtaactac  10620
ctggttgatg tgatcctgga tgaagcggct aacaaaggta ccggtaaatg gaccagccag  10680
agcgcgctgg atctcggcga accgctgtcg ctgattaccg agtctgtgtt tgcacgttat  10740
atctcttctc tgaaagatca gcgtgttgcc gcatctaaag ttctctctgg tccgcaagca  10800
cagccagcag gcgacaaggc tgagttcatc gaaaaagttc gtcgtgcgct gtatctgggc  10860
aaaatcgttt cttacgccca gggcttctct cagctgcgtg ctgcgtctga agagtacaac  10920
tgggatctga actacggcga aatcgcgaag attttccgtg ctggctgcat catccgtgcg  10980
cagttcctgc agaaaatcac cgatgcttat gccgaaaatc cacagatcgc taacctgttg  11040
ctggctccgt acttcaagca aattgccgat gactaccagc aggcgctgcg tgatgtcgtt  11100
gcttatgcag tacagaacgg tattccggtt ccgacctct ccgcagcggt tgcctattac  11160
gacagctacc gtgctgctgt tctgcctgcg aacctgatcc aggcacagcg tgactatttt  11220
ggtgcgcata cttataagcg tattgataaa gaaggtgtgt ccataccga atggctggat  11280
taa                                                                11283

SEQ ID NO: 16          moltype = DNA   length = 13435
FEATURE                Location/Qualifiers
source                 1..13435
                       mol_type = other DNA
                       organism = synthetic construct
SEQUENCE: 16
atgacgaatt taaaagcagt tattcctgta gcgggtctcg ggatgcatat gttgcctgcc   60
actaaggcga tacccaaaga gatgctacca atcgtcgaca agccaatgat tcagtacatt  120
gttgcagaa ttgtggctgc agggatcaaa gaaatcctcc tggtaactca cgcgtccaag  180
aacgcggtcg aaaaccactt cgacacctct tatgagttag aatcactcct tgagcagcgc  240
gtgaagcgtc aactgctggc ggaagtacag tccatctgtc cgccgggcgt gaccattatg  300
aacgtgcgtc agggcgaacc tttaggttta ggccactcca ttttgtgtgc gcgacctgcc  360
attggtgaca acccatttgt cgtggtactg ccagacgttg tgatcgacga tgccagcgcc  420
gacccgctac gttacaacct tgctgccatg attgcacgtt tcaacgaaac gggccgcagc  480
caggtgctgg caaaacgtat gccgggtgac ctctctgaat actccgtcat ccagactaaa  540
gagccgctgg accgtgaggg taaagtcagc cgcattgttg aatttatcga aaaaccggat  600
cagccgcaga cgctggactc agacatcatg gccgtaggtc gctatgtgct ttctgccgat  660
atttgctcgg aactgaacg tactcagcct ggtcatggg gacgtattca gctgattcat  720
gctattgccg agctggcgaa aaaacaatcc gttgatgcaa tgctgatgac cggcgacagt  780
tacgactgcg gcaaaaaaat gggctatatg caggcgtttg tgaagtatgg cctacgcaac  840
ctgaagaag gggcgaagtt ccgtaaaggt attgagaagc tgttaagcga ataatgaaaa  900
tctgaccgga tgtaacggtt gataagaaaa ttataacggc agtgaaaatt cgcagcaaaa  960
gtaattgtt gcgaatcttc ctgccgttgt tttatataa ccatcagaat aacaacgagt 1020
tagcagtagg gttttattca aagttttcca ggatttcct tgtttccaga gcggattggt 1080
aagacaatta gcgtttgaat ttttcgggtt tagcgcgagt gggtaacgct cgtcacatca 1140
taggcatgca tgcagtgctc tggtagctgt aaagccaggg gcggtagcgt gcattaatac 1200
ctctattaat caaactgaga gccgcttatt tcacagcatg ctctgaagta atatggaata 1260
aattaagtga aaatacttgt tactggtggc gcaggattta ttggttcagc tgtagttcgt 1320
cacattataa ataatacgca ggatagtgtt gttaatgtcg ataaattaac gtacgccgga 1380
aaccgggaat cacttgctga tgtttctgat tctgaacgct atgtttttga acatgcggat 1440
atttgcgatg cacctgcaat ggcacggatt tttgctcagc atcagccgga tgcagtgatg 1500
cacctggctg ctgaaagcca tgttgaccgt tcaattacag gccctgcggc atttattgaa 1560
accaatattg ttggtactta tgtcctttg gaagccgctc gcaattactg gtctgctctt 1620
```

```
gatagcgaca agaaaaatag cttccgtttt catcatattt ctactgacga agtctatggt    1680
gatttgcctc atccagatga agtaaataat acagaagaat tacccttatt tactgagacg    1740
acagcttacg cgccaagcag cccttattcc gcatccaaag catccagcga tcatttagtc    1800
cgcgcgtgga aacgtacata tggtttaccg acaattgtga ctaattgctc gaacaactat    1860
ggtccttatc atttcccgga aaagcttatt ccactggtta ttcttaatgc actggaaggt    1920
aaggcattac ctatttatgg caaaggagat cagatccgcg actggttgta tgttgaagat    1980
catgcgcgtg cgttatatac cgtcgtaacc gaaggtaaag cgggtgaaac ttataacatt    2040
ggtgggcaca acgaaaagaa aaacatcgat gtagtgctca ctatttgtga tttgctggat    2100
gagattgtac cgaaagagaa atcttatcgt gagcaaatca cttatgttgc tgatcgtccg    2160
ggacacgatc gccgctatgc tattgatgct gagaagattg tcgcgcatt gggatggaaa     2220
ccacaggaaa cgtttgagag cgggattcgt aaaacggtgg aatggtacct gtccaataca    2280
aaatgggttg ataatgtgaa aagtggtgcc tatcaatcgt ggattgaaca gaactatgag    2340
ggccgccagt aatgaatatc ctccttttg gcaaaacagg gcaggtaggt tgggaactac      2400
agcgtgctct ggcacctttg ggtaatttga ttgcttttga tgttcactct actgattatt    2460
gcggtgattt tagtaatcct gaaggtgtag ctgaaaccgt aagaagcatt cggccggata    2520
ttattgtcaa tgcagccgct cacaccgcag tagacaaagc agaatcagaa ccggagtttg    2580
cacaattaat taacgcaaca agtgtcgaag cgattgcgaa agcagcaaat gaagttggag    2640
cctgggttat ccattactcg actgattacg tcttccctgg aaatggcgat atgccatggc    2700
tggagacgga tgcaaccgca ccactaaatg tttacggtga aaccaagtta gccggagaaa    2760
aagcgttaca ggaatattgc gcgaagcatc ttattttccg gaccagctgg gtctatgcag    2820
gaaaaggaaa taacttcgcc aaaacgatgt tacgtctggc aaaagagcgt gaagaattag    2880
cggttattaa cgatcagttt ggtgcgccaa caggtcgtgc actgctggct gattgtacag    2940
cacatgccat tcgtgtcgca ctgaataaac cggatgtcgc aggcttgtac catttggtag    3000
ccagtggtac cacaacctgg tacgattatg ctgcgctggt ttttgaagag gcgcgcaaag    3060
caggcattcc ccttgcactc aacaagctca acgcagtacc aacaacagcc tatcctacac    3120
cagctcgtcg tccacataac tctcgccta atacagaaaa atttcagcag aacttttgcgc   3180
ttgtcttgcc tgactggcag gttgcgtga aacgaatgct caatgaatta tttacgacta     3240
cagcaattta atagtttttg catcttgttc gtgatggtgg agcaagatga attaaaagga    3300
atgatgaaat gaaaatgcgt aaaggtatta ttttagcggg tggttctggt acacgtcttt    3360
atcctgtgac tatggctgtc agtaaacagc tattacctat ttatgataaa ccgatgatct    3420
attacccgct ctcacactg atgttggcg gtattcgcga tattttgatt atcagtacac        3480
ctcaggatac tcctcgtttt caacaattgc tgggtgacgg tagccagtgg ggcctgaatc    3540
ttcagtacaa agtgcaacct agcccagatg gcctcgcgca ggcatttatc atcggtgaag    3600
agtttattgg tggtgatgat tgtgcttttgg ttcttggtga taatatcttt tacggtcacg   3660
atctgccgaa gctaatggag gccgctgtta acaaagaaag tggtgcaacg gtatttgcct    3720
atcacgttaa tgatccagaa cgctatggtg tcgttgagtt tgataaaaac ggtacggcaa    3780
tcagtctgga agaaaaaccg ttagaaccaa agagtaatta cgccgttaca ggtctgtact    3840
tttatgataa cgacgtggtt cagatggcga aaaacttgaa gccgtctgca cgtggtgagt    3900
tagaaattac agatattaac cgtatttatc ttgagcaggg acgtctgtct gtcgcgatga    3960
tggggcgtgg ctacgcgtgg ctggacacgg ggactcatca gagtctgata gaagcaagta    4020
atttttattgc gacaattgaa gagcgccagg gattgaaggt ttcctgtcct gaagagattg    4080
catttcgtaa aggttttatt gatgttgagc aagtaagaaa attagctgta ccactaataa    4140
agaataatta tgggcagtat ctttataaaa tgacgaagga ttcaaattaa tgaatgtgat    4200
tagaactgaa attgaagatg tgctaattct ggagccaaga gtatttggtg atgatagagg    4260
tttctttat gagagcttta atcaatcagc atttgaacat attctaggct atccggtcag    4320
cttttgttcaa gacaatcact cacgttcatc aaaaaatgta ctcagaggcc ttcactttca    4380
acgcgcggag tacgcacaag ataaacttgt acgctgcact catggagcag tttttgatgt    4440
tgctgttgat attcgaccca attcggtatc ctttggtaaa tgggtggtg ttctgcttc       4500
agctgataat aagcagcagt tgtggatacc aaaaggggttt gctcatggct ttttggttct    4560
gtctgatatc gctgaatttc aatataaaac tacaaactat tatcatcctg aaagcgattg    4620
tggaatatgt tggaatgatg aacgcattgc aattgattgg ccccaaacat cagggttaat    4680
cctttcgcca aaagatgaaa ggctcttac gttagatgag cttatcagat taaaattaat     4740
tgcatgaata cgaatgaaatt tctttaaga gaaacgttaa tatatctggc tgtcgttcaa    4800
ggtagcaatt atctttttacc attgcttaca tttccatatc ttgtaagaac acttggtcct    4860
gaaaaatttcg gtatattcgg tttttgccaa gcgactatgc tatatatgat aatgtttgtt    4920
gaatatggtt tcaatctcac agcaactcag agtattgcca aagcagcaga tagtaaagat    4980
aaagtaacgt ctatttttttg ggcggtgata ttttcaaaaa tagttcttat cgtcattaca    5040
ttgatttttct taacgtcgat gaccttgctt gttcctgaat ataacaagca tgccgtaatt    5100
atatggtcgt ttgttcctgc attagtcggg aatttaatct accctatctg gctgtttcag    5160
ggaaaagaaa aaatgaaatg gctgacttta agtagtattt tatcccgctt ggctattatc    5220
cctctaacat ttattttttgt gaacacaaag tcagatatag caattgccgg ttttattcag    5280
tcaagtgcaa atctggttgc tggaattatt gcactagcta tcgttgttca tgaaggttgg    5340
attggtaaag ttacgctatc attacataat gtgcgtcgat ctttagcaga cggttttcat    5400
gttttattt ccacatctgc tattagttta tattctacgg atagttat tatcctggga       5460
tttatatctg gaccaacgtc cgtagggaat tttaatgcgg ccaatactat aagaaacgcg    5520
cttcaagggc tattaaatcc tatcacccaa gcaatatacc caagaatatc aagtacgctt    5580
gttcttaatc gtgtgaaggg tgtgattta attaaaaaat cattgacctg cttgagtttg     5640
attggtggtg cttttcatt aattctgctc ttgggtgcat ctatactagt aaaaataagt    5700
ataggccgg gatatgataa tgcagtgatt gtgcatagta ttatatcgcc tctgcctttt    5760
cttatttcat taagtaatgt ctatggcatt caagttatgc tgacccataa ttataagaaa    5820
gaattcagta agattttaat cgctgcgggt tgttgagtt tgttgttgat ttttccgcta     5880
acaactcttt ttaaagagat tggtgcagca ataacattgc ttgcaacaga gtgcttagtt    5940
acgtcactca tgctgatgtt cgtaagaaat aataaattac tggtttgctg aggatttat     6000
gtacgattat tcattgttg gttctggttt gtttggtgcg gttgttgcga atgagtttaa     6060
aaagctaaac aaaaaagttt tagtgattga gaaaagaaat catatcggtg gaaatgcgta    6120
cacagaggac tgtgagggta tccagattca taaaatggtt gcacatattt ttcataccaa    6180
tgataaaat atatgggatt acgttaatga tttagtagaa tttaatcgtt ttactaattc     6240
tccactggcg atttataaag acaaattatt caaccttcct tttaatatga atactttcca    6300
ccaaatgtgg ggagttaaag atcctcaaga agctcaaaat atcattaatg ctcagaaaaa    6360
```

```
aaagtatggt gacaaggtac ctgaaaattt ggaggagcag gcgatttcat tagttgggga   6420
ggacttatac caagcattga taaagggtta tacggagaag cagtgggaa gaagtgcaaa    6480
agaattgcct gcatttatta ttaagcgaat cccagtgaga tttacgtttg ataacaatta   6540
tttttccgat cgctatcaag gtattccggt gggaggctac actaagctta ttgaaaaaat   6600
gcttgaaggt gtggacgtaa aattaggcat tgatttttg aaagacaaag attctctagc    6660
gagtaaagcc catagaatca tctacactgg acccattgat cagtacttcg actatatggt   6720
tggagcgtta gaatatcgct cttttaaaatt tgagacggaa cgccatgaat ttccaaactt   6780
ccaagggaat gcagtaataa atttcactga tgctaatgta ccatatacca gaataattga   6840
gcataaacat tttgactatg ttgagacaaa gcatacggtt gttacaaaag aatatccatt   6900
agagtggaaa gttggcgacg aaccctacta tccagttaat gataataaaa acatggagct   6960
ttttaagaaa tatagagagt tagctagcag agaagacaag gttatatttg gcgggcgttt   7020
ggccgagtat aaatattatg atatgcatca agtgatatct gccgctcttt atcaagtgaa   7080
aaatataatg agtacggatt aatgatctat cttgtaatta gtgtctttct cattacagca   7140
tttatctgtt tatatcttaa gaaggatata ttttatccag ccgtatgcgt taatatcatc   7200
ttcgcactgg tcttattggg atatgaaata acgtcagata tatatgcttt tcagttaaat   7260
gacgctacgt tgattttct actttgcaat gttttgacat ttaccctgtc atgtttattg    7320
acggaaagtg tattagatct aaatatcaga aaagtcaata atgctattta tagcatacca   7380
tcgaagaaag tgcataatgt aggcttgtta gttatttctt tttcgatgat atatatatgc   7440
atgaggttaa gtaactacca gttcgggact agcttactta gctatatgaa tttgataaga   7500
gatgctgatg ttgaagacac atcaagaaat ttctcagcat acatgcagcc aatcattcta   7560
actactttg ctttatttat ttggtctaaa aaatttacta atacaaaggt aagtaaaaca    7620
tttactttac ttgttttat tgtattcatc tttgcaatta tactgaatac tggtaagcaa    7680
attgtcttta tggttatcat ctcttatgca ttcatcgtag gtgttaatag agtaaaacat   7740
tatgtttatc ttattacagc tgtaggtgtt ctattctcct tgtatatgct cttttacgt    7800
ggactgcctg gggggatggc atattatcta tccatgtatt tggtcagccc tataatcgcg   7860
tttcaggagt tttattttca gcaagtatct aactctgcca gttctcatgt cttttggttt   7920
tttgaaaggc tgatggggct attaacaggt ggagtctcta tgtcgttgca taaagaattt   7980
gtgtgggtgg gtttgccaac aaatgtttat actgcttttt cggattatgt ttatatttcc   8040
gcggagctaa gctatttgat gatggttatt catggctgta tttcaggtgt tttatggaga   8100
ttgtctcgaa attacatatc tgtgaaaata tttttattcat atttatta tacctttct    8160
ttcattttt atcatgaaag cttcatgact aatattagca gttggataca aataactctt   8220
tgtatcatag tattctctca atttcttaag gcccagaaaa taaagtgaaa atgtattttt   8280
tgaatgattt aaatttctct agacgcgatg ctggatttaa agcaagaaaa gatgcactgg   8340
acattgcttc agattatgaa aacatttctg ttgttaacat tcctctatgg ggtggagtga   8400
tccagagaat tattagttct gttaagctta gtacatttct ctgcggtctt gaaaataaag   8460
atgtttaat tttcaatttc ccgatggcca aaccatttg gcatatattg tcattcttc     8520
accgccttct aaaatttaga atagtacctc tgattcatga tattgatgaa ttaagaggag   8580
gaggggtag tgattctgtg cggcttgcta cctgtgatat ggtcataagt cacaatccac    8640
aaatgcaaa gtaccttagt aaatatatgt ctcaggataa aatcaaagac ataaaaatat    8700
ttgattacct cgtctcatct gatgtggagc atcgagatgt tacggataag caacgaggg    8760
tcatatatgc tggcaacctt tctaggcata atgttctttt catatatact gaaggatgcg   8820
attttactct ctttggtgtc aactatgaaa ataaagataa tcctaaatat cttggaagtt   8880
ttgatgctca atctccggaa aagattaacc tcccaggcat gcaatttgga ctcatttggg   8940
atggagattc tgtcgaaacc tgtagtggtg cctttggcga ctatttaaag tttaataacc   9000
ctcataagac atctctttat ctttcaatgg aacttccagt atttatatgg gataaagccg   9060
cccttgcgga tttcattgta gataatagaa taggatatgc agtgggatca atcaaagaaa   9120
tgcaagagat tgttgactcc atgacaatag aaacttataa gcaaatttagt gagaatacaa   9180
aaattatttc tcagaaaatt cgaacaggaa gttacttcag gatgttctt gaagaggtga    9240
tcgatgatct taaaactcgc taaacgatat ggtctctgtg gttttattcg gcttgttaga   9300
gatgtcttat tgactcgtgt attttaccgg aactgtagaa ttattcgatt tccctgctat   9360
attcgcaatg atggtagcat taattttggt gaaaattca caagtgggat cggtctcagg    9420
ctggatgcat ttggacgtgg cgtgatttt ttttccgata atgtgcaagt taacgactat    9480
gttcatatcg cctcaattga gagcgttacg ataggtcggg atacgcttat tgcaagtaaa   9540
gtatttatta ccgatcataa tcacggttcc tttaagcact ctgatccaat gagttcgcca   9600
aatataccc cagacatgcg cacgttgaa tcttcagctg ttgtaattgg ccagagggtt    9660
tggttgggtg agaatgtgac ggttttgcct ggaacaatta ttggtaatgg agtcgtagtc   9720
ggcgccaatt ctgttgttag aggttctatt cccgaaaata ctgtcattgc gggagtacca   9780
gcaaaaatca taaagaaata caatcatgag accaaattat gggaaaaagc atagtcgttg   9840
tttctgcggt caattttacc actggcggtc catttaccat tttgaaaaaa tttttggcag   9900
caactaataa taaagaaaat gtcagtttta tcgcattagt ccattctgct aaagagttaa   9960
aagaaagtta tccatgggtt aaattcattg agtttcctga ggttaaaggg tcgtggctaa   10020
aacgtttgca ctttgaatat gtagtttgta aaaaactttc aaaagagctg aatgctacgc   10080
attggatttg tctgcatgat attacggcca atgtcgtcac taaaaaaaga tatgtgtatt   10140
gtcataaccc tgccccttt tataaaggaa tttattccg tgaaattctt atggagccta    10200
gcttttctt atttaaaatg ctatacgggc tgatatataa aataaacatt aaaaaaaata   10260
ctgcagtgtt tgttcaacaa ttctggatga agaaaaatt tatcaagaaa tattctataa   10320
ataacatcat tgtcagtcgg ccagaaatta aattatctga taaaagccaa cttactgatg   10380
atgattctca atttaagaat aacccttctg agttgacaat atttaccct gctgttccac    10440
gagtatttaa aaattacgag cttattatta gtgcagcaag gaaattgaaa gaacaatcca   10500
atattaaatt tctgcttact atcagtggta cagaaaatgc gtatgcaaaa tatattatca   10560
gtcttgcaga aggactggat aatgttcatt tcctcgggta cttggataaa gaaaaaatcg   10620
atcattgtta taatatttca gatatagttt gttttccctc taggttagaa acatgggat    10680
tgccgttgtc tgaggctaaa gagcgaggta agtgggtatt agcatcagat ttcccattta   10740
ctagagaaac tcttggtagt tatgaaaaga aagcttttt tgattctaat aacgatgaca   10800
tgttagttaa acttattatt gacttcaaaa aaggtaacct caaaaaagat atctctgatg   10860
caaatttcat ttatcgtaat gaaaatgtat tagttgggtt tgatgaacta gttaattta    10920
ttactgaaga acattgaaat ggtatatata ataatcgttt cccacggaca tgaagactac   10980
atcaaaaaat tactcgaaaa tcttaatgct gacgatgagc actacaagat tatcgtacgc   11040
gacaacaaag actctctatt attgaaacaa atatgccagc attatgcagg cctggactat   11100
```

```
attagtggag gtgtatacgg cttttggtcat aataataata ttgcggtggc gtatgtaaag 11160
gaaaaatata gacccgcaga tgatgattac attttgtttt tgaatcccga tatcatcatg 11220
aagcatgatg atttgctgac atatattaaa tatgtcgaaa gtaagcgtta tgcttttagt 11280
acattatgcc tgttccgaga tgaagcgaaa tctttacatg attattccgt aagaaaattt 11340
cctgtgcttt ctgattttat tgtgtcattt atgttaggga ttaataaaac aaaaattcct 11400
aaagaaagta tctattctga tacggttgtt gattggtgcg caggatcatt tatgctggta 11460
cgttttcag attttgtgcg tgtaaatggc ttcgatcaag gttactttat gtactgtgaa 11520
gatattgacc tgtgcttgag gcttagcctg gctggtgtca gacttcatta tgttcccgct 11580
tttcatgcga tacattatgc tcatcatgac aatcgaagtt tttttcaaa agccttcaga 11640
tggcacttaa aaagtacttt tagatattta gccagaaaac gtattttatc aaatcgcaac 11700
tttgatcgaa tttcatcagt ttttcacccg taagagctcg gtacccgggc ctagggtgta 11760
ggctggagct gcttcgaagt tcctatactt tctagagaat aggaacttcg gaataggaac 11820
taaggaggat attcatatcc gtcgacggcg ccgccctgc aggcatgcaa gcttgatcca 11880
tatggatcgc tagcttaatt aaataaagcc gtaagcatat aagcattat aagctattta 11940
tactttaata agtactttgt atacttattt gcgaacattc caggccgcga gcattcagcg 12000
cggtgatcac acctgacagg agtatgtaat gtccaagcaa cagatcggcg tagtcggtat 12060
ggcagtgatg ggacgcaacc ttgcgctcaa catcgaaagc cgtggttata ccgtctctat 12120
tttcaaccgt tcccgtgaga agacgaaga agtgattgcc gaaaatccag gcaagaaact 12180
ggttccttac tatacggtga aagagtttgt cgaatctctg gaaacgcctc gtcgcatcct 12240
gttaatggtg aaagcaggtg caggcacgga tgctgctatt gattccctca aaccatatct 12300
cgataaagga gacatcatca ttgatggtgg taacaccttc ttccaggaca ctattcgtcg 12360
taatcgtgag ctttcagcag agggctttaa cttcatcggt acggtgttt ctggcggtga 12420
agaggggcg ctgaaaggtc cttctattat gcctggtggc cagaagaag cctatgaatt 12480
ggtagcaccg atcctgacca aaatcgccgc cgtagctgaa gacggtgaac catgcgttac 12540
ctatattggt gccgatggcg caggtcacta tgtgaagatg gttcacaacg gtattgaata 12600
cggcgatatg cagctgattg ctgaagccta ttctctgctt aaaggtggcc tgaacctcac 12660
caacgaagaa ctggcgcaga cctttaccga gtgaataac ggtgaactga gcagttacct 12720
gatcgacatc accaaagata tcttcaccaa aaaagatgaa gacggtaact acctggttga 12780
tgtgatcctg gatgaagcgg ctaacaaagg tacgggtaaa tggaccagcc agagcgcgct 12840
ggatctcggc gaaccgctgt cgctgattac cgagtctgtc tttgcacgtt atatctcttc 12900
tctgaaagat cagcgtgttg ccgcatctaa agttctctct ggtccgcaag cacagccagc 12960
aggcgacaag gctgagttca tcgaaaaagt tcgtcgtgcg ctgtatctgg caaaatcgt 13020
ttcttacgcc cagggcttct ctcagctgcg tgctgcgtct gaagagtaca actgggatct 13080
gaactacggc gaaatcgcga agattttccg tgctggctgc atcatccgtg cgcagttcct 13140
gcaaaaaatc accgatgctt atgccgaaaa tccacagatc gctaacctgt tgctggctcc 13200
gtacttcaag caaattgccg atgactacca gcaggcgctg cgtgatgtcg ttgcttatgc 13260
agtacagaac ggtattccgg ttccgacctt ctccgcagcg gttgcctatt acgacagcta 13320
ccgtgctgct gttctgcctg cgaacctgat ccaggcacag cgtgactatt ttggtgcgca 13380
tacttataag cgtattgata agaaggtgt gttccatacc gaatggctgg attaa 13435
```

SEQ ID NO: 17         moltype = DNA  length = 13228
FEATURE            Location/Qualifiers
source             1..13228
                       mol_type = other DNA
                       organism = synthetic construct
SEQUENCE: 17

```
atgacgaatt taaaagcagt tattcctgta gcgggtctcg ggatgcatat gttgcctgcc 60
actaaggcga tacccaaaga gatgctacca atcgtcgaca agccaatgat tcagtacatt 120
gttgacgaga ttgtggctgc agggatcaaa gaaatcctcc tggtaactca cgcgtccaag 180
aacgcggtcg aaaaccactt cgacacctct tatgagttag aatcactcct tgagcagcgc 240
gtgaagctcc aactgctggc ggaagtacag tccatctgtc cgccggggcgt gaccattagt 300
aacgtgcgtc agggcgaacc tttaggttta ggccactcca ttttgtgtgc gcgacctgcc 360
attggtgaca acccatttgt cgtggtactg ccagacgttg tgatcgacga tgccagcgcc 420
gacccgctac gttacaacct tgctgccatg attgcacgtt tcaacgaaac gggccgcagc 480
caggtgctcg caaaacgtat gccgggtgac ctctctgaat actccgtcat ccagactaaa 540
gagccgctgg accgtgaggg taaagtcagc cgcattgttg aatttatcga aaaaccggat 600
cagccgcaga cgctggactc agacatcatg gccgtaggtc gctatgtgct ttctgccgat 660
atttggccga aactggaacg tactcagcct ggtgcatggg gacgtattca gctgactgat 720
gctattgccg agctggcgaa aaacaatcc gttgatgaa tgctgatgac cggcgacagt 780
tacgactgcg gcaaaaaat gggctatatg caggcgtttg tgaagtatgg cctacgcaac 840
ctgaaagaag gggcgaagtt ccgtaaaggt attgagaagc tgttaagcga ataatgaaaa 900
tctgaccgga tgtaacgtt gataagaaaa ttataacggc agtgaaaatt cgcagcaaaa 960
gtaatttgtt gcgaatcttc ctgccgttgt tttatataaa ccatcagaat aacaacgagt 1020
tagcagtagg gttttattca aagttttcca ggatttttct tgtttccaga gcggattggg 1080
aagacaatta gcgtttgaat ttttcgggtt tagcgcgagt gggtaacgct cgtcacatca 1140
taggcatgca tgcagtgctc tggtagctgt aaagccaggg gcgtagcgt gcattaatac 1200
ctctattaat caaactgaga gccgcttatt tcacagcatg ctctgaagta atgaggaata 1260
aattaagtga aaatacttgt tactggtggc gcaggattta ttggttcagc tgtagttcgt 1320
cacattataa ataatacgca ggatagtgtt gttaatgtcg ataaattaac gtacgccgga 1380
aaccgggaat cacttgctga tgtttctgat tctgaacgct atgttttga acatgcggat 1440
atttgcgatg cacctgcaat ggcacggatt tttgctcagc atcagccgga tgcagtgatg 1500
cacctggctg ctgaaagcca tgttgaccgt tcaattacag gccctgcggc atttattgaa 1560
accaatattg ttggtactta tgtccttttg gaagccgctc gcaattactg gtctgctctt 1620
gatagcgaca agaaaaatag cttccgtttt catcatattt ctactgacga agtctatggt 1680
gatttgcctc atccagatga agtaaataat acagaagaat tacccttatt tactgagacg 1740
acagcttacg cgccaagcag cccttattcc gcatccaaag catccagcga tcatttagtc 1800
cgcgcgtgga aacgtacata tggtttaccg acaattgtga ctaattgctc gaacaactat 1860
ggtccttatc atttcccgga aaagcttatt ccactggtta ttcttaatgc actggaaggt 1920
aaggcattac ctatttatgg caaggagat cagatccgcg actggttgta tgttgaagat 1980
```

```
catgcgcgtg cgttatatac cgtcgtaacc gaaggtaaag cggggtgaaac ttataacatt  2040
ggtgggcaca acgaaaagaa aaacatcgat gtagtgctca ctatttgtga tttgctggat  2100
gagattgtac cgaaagagaa atcttatcgt gagcaaatca cttatgttgc tgatcgtccg  2160
ggacacgatc gccgctatgc tattgatgct gagaagattg gtcgcgcatt gggatggaaa  2220
ccacaggaaa cgtttgagag cgggattcgt aaaacggttg aatggtacct gtccaataca  2280
aaatgggttg ataatgtgaa aagtggtgcc tatcaatcgt ggattgaaca gaactatgag  2340
ggccgccagt aatgaatatc ctccttttg gcaaaacagg gcaggtaggt tgggaactac  2400
agcgtgctct ggcacctttg ggtaatttga ttgcttttga tgttcactct actgattatt  2460
gcggtgattt tagtaatcct gaaggtgtag ctgaaaccgt aagaagcatt cggccggata  2520
ttattgtcaa tgcagccgct cacaccgcag tagacaaagc agaatcagaa ccggagtttg  2580
cacaattaat taacgcaaca agtgtcgaag cgattgcgaa agcagcaaat gaagttggag  2640
cctgggttat ccattactcg actgattacg tcttccctgg aaatgcgat atgccatggc   2700
tggagacgga tgcaaccgca ccactaaatg tttacggtga aaccaagtta gccggagaaa  2760
aagcgttaca ggaatattgc gcgaagcatc ttattttccg gaccagctgg gtctatgcag  2820
gaaaaggaaa taacttcgcc aaaacgatgt tacgtctgcg aaaaagagcgt gaagaattag  2880
cggttattaa cgatcagttt ggtgcgccaa caggtgctga actgctggct gattgtacag  2940
cacatgccat tcgtgtcgca ctgaataaac cggatgtcgc aggcttgtac catttggtag  3000
ccagtggtac cacaacctgg tacgattatg ctgcgcgtgt ttttgaagag gcgcgcaaag  3060
caggcattcc ccttgcactc aacaagctca acgcagtacc aacaacagcc tatcctacac  3120
cagctcgtcg tccacataac tctcgcctta atacagaaaa atttcagcag aactttgcgc  3180
ttgtcttgcc tgactggcag gttggcgtga acgaatgct caatgaatta tttacgacta   3240
cagcaattta atagtttttg catcttgttc gtgatggtgg agcaagatga attaaaagga  3300
atgatgaaat gaaaatgcgt aaaggtatta tttagcggg tggttctggt acacgtcttt   3360
atcctgtgac tatggctgtc agtaaacagc tattacctat ttatgataaa ccgatgatct  3420
attacccgct ctctacactg atgttggcgg gtattcgcga tattttgatt atcagtacac  3480
ctcaggatac tcctcgtttt caacaattgc tgggtgacga tagccagtgg ggcctgaatc  3540
ttcagtacaa agtgcaacct agcccagatg gcctcgcgca ggcatttatc atcggtgaag  3600
agtttattgg tggtgatgat tgtgctttgg ttcttggtga taatatcttt tacggtcacg  3660
atctgccgaa gctaatggag gccgctgtta acaaagaaag tggtgcaacg gtatttgcct  3720
atcacgttaa tgatccagaa cgctatgtg tcgttgagtt tgataaaaac ggtacggcaa    3780
tcagtctgga agaaaaaccg ttagaaccaa agagtaatta cgccgttaca ggtctgtact  3840
tttatgataa cgacgtggtt cagatggcga aaaacttgaa gccgtctgca cgtggtgagt  3900
tagaaattac agatattaac cgtatttatc ttgagcaggg acgtctgtct gtcgcgatga  3960
tggggcgtgg ctacgcgtgg ctggacacgg ggactcatca gagtcgtgata gaagcaagta  4020
atttttattgc gacaattgaa gagcgccagg gattgaaggt ttcctgtcct gaagagattg  4080
catttcgtaa aggttttatt gatgttgagc aagtaagaaa attagctgta ccactaataa  4140
agaataatta tgggcagtat ctttataaaa tgacgaagga ttcaaattaa tgaatgtgat  4200
tagaactgaa attgaagatg tgctaattct ggagccaaga gtatttggtg atgatagagg  4260
tttctttat gagagcttta atcaatcagc atttgaacat attctaggct atccggtcag  4320
ctttgttcaa gacaatcact cacgttcatc aaaaaatgta ctcagaggcc ttcactttca  4380
acgcggcgag tacgcacaag ataaacttgt acgctgcact catggagcag ttttttgatgt  4440
tgctgttgat attcgaccca attcggtatc ctttggtaaa tgggttggtg ttctgctttc  4500
agctgataat aagcagcagt tgtggatacc aaaagggttt gctcatgget ttttggtttc   4560
gtctgatatc gctgaattc aatataaaac tacaaactat tatcatcctg aaagcgattg   4620
tggaatatgt tggaatgatg aacgcattgc aattgattgg ccccaaacat cagggttaat  4680
cctttcgcca aagatgaaa ggctcttac gttagatgag cttatcagat taaaattaat    4740
tgcatgaggc cggccttaag gaggactagt cccggccgc catgagttta atcaaaaaca   4800
gtttttggaa cctttgcggg tatgtacttc cagctattgt gacactacca gctttggta   4860
ttatggggcg aaaattaggc ccagaattat ttggtgtatt cactttggca ttagctgttg  4920
tgggttatgc aagcattttt gatgcaggcc ttactcgcgc agtgatacga gaagtcgcaa  4980
ttgaaaaaga taatgaagaa aataagttga aaattatttc ttcagcgaca gttgtaatta  5040
tttatttgag tttggccgcc tcactcttat tattttttt tagtggtcat atcgcattgc   5100
tactgaacat tagtgagact tttttcata atgtaagtgt ctcgcttaaa attctcgcag   5160
catccatacc attattttg attactcaaa tatggttgtc aattttagaa ggtgaagaaa   5220
gatttggttt acttaatatc tacaaatcaa ttacgggagt gatattagca atctcaccgg  5280
cattatttat acttattaaa ccctctttga tgtatgcgat aataggctta gttctagcaa  5340
ggttttatg ttttattttg gctttataa tttgtcacga taagtgctt aaagctaaac    5400
taacaatcga tataccaaca attaaaagat tgtttatgtt cggtggttgg attacagtaa   5460
gtaatatcat cagccctgtg ctatcatatt ttgataggtt tattgtttca aatcaacttg   5520
gggctgctaa tgttgcttt tatactgcac catcagaaat tatttctcgg cttagtataa    5580
ttccaggtgc gttttcaaga gccttatttc caagattagc taatgcaaat aattccgctg   5640
aaagatataa aacgaaaaga ttaattacaa tttcactttt aataatcatc acccctattt   5700
tttgtattgg cgtgttattt tcagagaaga taatggtttt atggatgggg gcatcatttt   5760
ttggtgagcc tggtttggta ttatcaatat tactgattgg ctttatttt aatggattgg    5820
cacaagtacc atttgccagt attcaatccc gaggtcatgc taagataact agcatttgttc  5880
atctcttaga gttgttcct tatttattac tttatttta cctcataaaa gcacatgggg     5940
ttgttggcgc gggtattgcg tggtcagtga ggatgatagt agattatata gcattaagtc   6000
ttttggacgg taagtatatt aaataataaa attcaaaatg caagttaata actcatggct   6060
ttatttgggt aggtgacaat ttataatgat atatatatta actttaactc ttcttctagt   6120
tatagccata atgtttctc ttctcggcac aaaaagtagg atcacatctc cattacctt    6180
gcatttttta ccatggttac taactttaat tgtcgggata agtaattacg atcaatttta   6240
cgagtttaat gaaagaagct tttactcttt gttgatttgg tttacagtta tttttatat    6300
ttatttcata ggggaactgg ttaattataa acgtgaaaat ataatgttt attatggtct   6360
ttcacatatt aaatatgaat gtaaaaaata ttgagtcatt gtcatcccaa tttcattata    6420
taccatttc gaaatatata tggttggtat ggggggagca gatggattct ttctcaattt   6480
acgtcttgca aatacattgg agggctatac gggtaaaaaa tttatcttaa tgcctgctgt   6540
atatcctcta atgatggcta tgttcgcaat tgtttgtcta acaaaaactt ccaaattaaa   6600
taaatactcc atttattct ggatgttttt gtattgtatt ggcacaatgg gaaaatttc     6660
aatattaacg ccaatattga catatttaat tatttatgac ttcaaacata gattaaaagt   6720
```

```
aaaaaaaaca ataaagttta cattgttgat aattatatta gctttaactt tgcattttac   6780
acgtatggct gagaatgacc actcaacatt tttatctatt ttagggctct atatttattc   6840
accaataatt gctttaggcc agttgaatga agtaaatagt agtcattttg gtgagtatac   6900
gtttagattc atatatgcta taactaataa aattggcctt attaaagaat tgccagtaaa   6960
tactattctt gactattcat acgttcctgt accaacaaat atatactg cacttcaacc     7020
attttaccag gattttggtt atactggcat catatttgga gcagtattat acggactaat   7080
atatgtgagt ttatacacgg ccggtgttcg tggaaataat acacaggcat tactgattta   7140
cgcattgttt tcagttagca gtgcaacggc tttcttcgct gaaacgctag taacgaattt   7200
agctggaaat gtgatgttag tattatgtac catcttacta tggcgattta cagtaatatg   7260
caaaccagta cagtaaccat tctaatggcc acctacaatg gcgaggcctt catcaaaaat   7320
cagattttgt cactacaaca acaaacattt tctaactggc ggttatttat tcaggatgat   7380
gggtctacag acaatactat atctataata aaaaacttcc aaaaatctga ctccagaatt   7440
cggctagttg atgataattt gaaaggtcaa ggtgcaggaa aaaattttt atcgctgata    7500
aagtacagcg agacagatta tacaatttat tgtgaccaag atgatatttg gttagaaaac   7560
aaaatatttg aattagtaaa gtatgcaaat gaaattaaat tgaatgtatc agatgcgcct   7620
tcgctagttt atgctgatgg ctatgcttat atggatggtg agggtacaat cgattttct    7680
gggatatcta acaatcatgc tgatcaatta aaggattttc tttttttaa tggtggatac    7740
caaggatgtt ctattatgtt caatcgtgca atgaccaaat ttcttctgaa ttatcgagga   7800
tttgtatatc tacatgacga tatcacaaca ttagctgcat acgctcttgg taaagtttat   7860
tttctcccga aataccttat gttatataga cagcacacga atgcggtaac tggtatcaaa   7920
acattccgca atgattgac ttctaaattt aaatcaccag taaactatct tttatcacga    7980
aaacattatc aggtaaaaaa atctttttt gaatgtaaca gctctatctt atcagagacg    8040
aataaaaaag ttttttttgga ttttatttca ttttgtgaat caaataataa atttacagat   8100
ttttttaagt tatggcgagg tgggtttaga ttaaataaca gtagaactaa attattatta   8160
aaaattcttaa tacggagaaa atttagcgaa tgatttcaat acttacacct acttttaatc   8220
ggcaacatac tttatcaagg ctattcaatt ctcttatatt acaaactgat aaagattttg   8280
agtggataat aattgatgat ggtagtatag atgcaacagc ggtacttgta gaagatttta   8340
gaaaaaaatg tgattttgac ttgatttatt gctatcagga aaataatggt aagcccatgg   8400
cttttaaacgc tggtgttaaa gcttgtagag gcgattatat ctttattgtt gacagtgatg   8460
atgcactaac tcccgatgcc ataaaattaa ttaaagaatc aatacatgat tgcttatctg   8520
agaaggaaag tttcagcgga gtcggttttta gaaaagcata tataaagggg gggattattg   8580
gtaatgattt aaataattct tcagaacata tatactattt aaatgcgact gagattagca   8640
atttaataaa tggtgatgtt gcatattgtt ttaaaaaga agtttggta aaaaatccat      8700
tccccgtat agaagatgaa aaatttgttc cagaattata tatttggaat aaaaataactg    8760
acaaggcgaa gattcgattt aacataagca aagttatata tctttgtgag tatcttgatg    8820
atggtctttc taaaaatttc cataaccagc ttaaaaaata cccaaagggg tttaagattt    8880
attacaaaga tcaagaaaa cgagagaaaa cttatataaa aaaaacaaag atgctaatta    8940
gatatttgca atgtgttat tatgagaaaa taaaatgaaa atactatttg tcattacagg     9000
tttaggccttt ggaggtgctg agaagcaggt ttgtctttta gctgataaat taagtttaag   9060
cgggcaccat gtaaagatta tttcacttgg acatatgtct aataataaag tctttcctag    9120
cgaaaataat gttaatgtca ttaatgtaaa tatgtcaaaa aacatttctg gagttataaa    9180
aggttgtgtc agaattagag atgttatagc taatttcaaa ccagacattg tacacagtca    9240
tatgtttcat gcaaacatta tcactagatt gtctgtaatt ggaatcaaaa acagacctgg    9300
tattatatca actgcacata ataaaaatga aggtgggtat ttcagaatgc tcacatatag    9360
aataaccgat tgtttaagtg attgttgtac aaatgttagc aaagaagcag tggatgagtt    9420
tttacggata aaagccttta atcccgctaa agcaattact atgtataatg ggatagatac    9480
caataaattt aaatttgatt tattggcaag gagggaaatt cgagacggta ttaatataaa    9540
aaatgatgat atattattac ttgctgcagg tcgtttaacg ttagctaaag attatcctaa    9600
tttattgaat gcaatgactc tgcttcctga acacttaaaa cttattatta ttggtgatgg    9660
tgaattgcgt gacgaaatta atatgcttat aaaaaaattg caattatcta ataggtgtc    9720
cttgttggga gttaaaaaaa atattgctcc ctatttttct gcatgtgata tttttgttct   9780
ctcttctcgt tgggaaggat ttggattagt cgtggcagaa gctatgtcat gtgagcgaat    9840
tgttgttggc acggattcag ggggagtaag agaagttatt ggtgacgatg attttcttgt    9900
acccatatct gattcaacac aacttgcaag caaaattgaa aaattgtctt tgagccagat    9960
acgtgatcac attggttttc ggaatcgtga gcgtatttta aaaaatttct caatagatac   10020
tattattatg cagtggcaag aactctatgg aactataatt tgctcaaaac atgaaaggta   10080
gatttatatt tggaacgtgt cttttgttg aatttaattc aatctcaatt gagattttg     10140
tatttcaaaa ataccatcat agctaacgat gattggtatt tattttaaga tgctttctat   10200
aaatatattg acgtttttaa tgcgccgaaa cgattgggct gggaacagag aagtaaaact   10260
gttttgagaa tgaagagttt ttgagatgtt tatgatatt aaaaattgat ccagtgaatt    10320
aattatttat aataaatcaa gatttaatgt taataaatga taatcttttc tgacactcat   10380
attaattatg agtggtacgt ttggtaaacg gtaaactatt atatgacagc tagaacaact   10440
aaagttttgc acttacaatt actcccactc ttaagtggcg ttcaaagggt aacattaaac   10500
gaaattagtg cgttatatac tgattatgat tatacactag tttgctcaaa aaaaggtcca   10560
ctaacaaaag cattgctgga atatgatgtc gattgtcatt gtatccccga acttacgaga   10620
gaaattaccg taaagaatga ttttaaagca ttgttcaagc tttataagtt cataaaaaaa   10680
gaaaaatttg acattgtgca tacacattct tcaaaaacag gtattttggg gcgagttgct   10740
gccaaattag cacgtgttgg aaaggtgatc cacactgtac atggttttttc ttttccagcc   10800
gcatctagta aaaaaagtta ttacctttat tttttcatgg aatggatagc aaagttcttt   10860
acggataagt taatcgtctt gaatgtgat gatgaatata tagcaataaa caaattaaaa    10920
ttcaagcggg ataaagtttt tttaattcct aatggagtag acactgataa gttttctcct   10980
ttagaaaata aaatttatag tagcaccttg aatctagtaa tggttggtag attatccaag   11040
caaaaagatc ctgagacatt attgcttgct gttgaaaaac tgctgaatga aatgttaat    11100
gttaagctga cacttgtagg agatggtgaa ctaaaagaac agttagaaag caggttcaaa   11160
cggcaagatg gacgtataat ttttcatgga tggtcagata acattgttaa tattttaaaa   11220
gttaatgatc ttttttatatt accttctctt tgggagggta tgccattagc aattttagaa   11280
gcattgagct gtggacttcc atgtatagtc actaatattc caggtaataa tagcttaata   11340
gaagatggct ataatggttg tttgtttgaa attagagatt gtcagttatt atctcaaaaa   11400
atcatgtcat atgttggtaa gccagaactg attgcacagc aatctaccaa tgcacgatca   11460
```

```
tttattctga aaaattatgg attagttaaa agaaataata aggtcagaca gctatatgat   11520
aattaagagc tcggtacccg ggcctagggt gtaggctgga gctgcttcga agttcctata   11580
cttctagag aataggaact tcggaatagg aactaaggag gatattcata tccgtcgacg    11640
gcggccgccc tgcaggcatg caagcttgat ccatatggat cgctagctta attaaataaa   11700
gccgtaagca tataagcatg gataagctat ttatacttta ataagtactt tgtatactta   11760
tttgcgaaca ttccaggccg cgagcattca gcgcggtgat cacacctgac aggagtatgt   11820
aatgtccaag caacagatcg gcgtagtcgg tatggcagtg atgggacgca accttgcgct   11880
caacatcgaa agccgtggtt ataccgtctc tattttcaac cgttcccgtg agaagacgga   11940
agaagtgatt gccgaaaatc caggcaagaa actggttcct tactatacgg tgaaagagtt   12000
tgtcgaatct ctggaaacgc ctcgtcgcat cctgttaatg gtgaaagcag gtgcaggcac   12060
ggatgctgct attgattccc tcaaaccata tctcgataaa ggagacatca tcattgatgg   12120
tggtaacacc ttcttccagg acactattcg tcgtaatcgt gagctttcag cagagggctt   12180
taacttcatc ggtaccggtg tttctggcgg tgaagagggg gcgctgaaag gtccttctat   12240
tatgcctggt ggccagaaag aagcctatga attggtagca ccgatcctga ccaaaatcgc   12300
cgccgtagct gaagacggtg aaccatgcgt tacctatatt ggtgccgatg gcgcaggtca   12360
ctatgtgaag atggttcaca acggtattga atacggcgat atgcagctga ttgctgaagc   12420
ctattctctg cttaaaggtg gcctgaacct caccaacgaa gaactggcgc agacctttac   12480
cgagtggaat aacggtgaac tgagcagtta cctgatcgac atcaccaaag atatctttac   12540
caaaaaagat gaagacggta actacctggt tgatgtgatc ctggatgaag cggctaacaa   12600
aggtacgggg aaatggacca gccagagcgc gctggatctc ggcgaaccgc tgtcgctgat   12660
taccgagtct gtgtttgcac gttatatctc ttctctgaaa gatcagcgtg ttgccgcatc   12720
taaagttctc tctggtccgc aagcacagcc agcaggcgac aaggctgagt tcatcgaaaa   12780
agttcgtcgt gcgctgtatc tgggcaaaat cgttcttac gcccagggct tctctcagct    12840
gcgtgctgcg tctgaagagt acaactggga tctgaactac ggcgaaatcg cgaagatttt   12900
ccgtgctggc tgcatcatcc gtgcgcagtt cctgcaaaaa atcaccgatg cttatgccga   12960
aaatccacag atcgctaacc tgttgctggc tccgtacttc aagcaaattg ccgatgacta   13020
ccagcaggcg ctgcgtgatg tcgttgctta tgcagtacag aacggtattc cggttccgac   13080
cttctccgca gcggttgcct attacgacag ctaccgtgct gctgttctgc ctgcgaacct   13140
gatccaggca cagcgtgact attttggtgc gcatacttat aagcgtattg ataaagaagg   13200
tgtgttccat accgaatggc tggattaa                                     13228

SEQ ID NO: 18           moltype = DNA   length = 13554
FEATURE                 Location/Qualifiers
source                  1..13554
                        mol_type = other DNA
                        organism = synthetic construct
SEQUENCE: 18
atgacgaatt taaaagcagt tattcctgta gcgggtctcg ggatgcatat gttgcctgcc   60
actaaggcga tacccaaaga gatgctacca atcgtcgaca agccaatgat tcagtacatt   120
gttgacgaga ttgtggctgc agggatcaaa gaaatcctcc tggtaactca cgcgtccaag   180
aacgcggtcg aaaaccactt cgacacctct tatgagttag aatcactcct tgagcagcgc   240
gtgaagcgtc aactgctggc ggaagtacag tccatctgtc cgccgggcgt gaccattatg   300
aacgtgcgtc agggcgaacc tttaggttta ggccactcca ttttgtgtgc gcagacctgc   360
attggtgaca acccatttgt cgtggtactg ccagacgttg tgatcgacga tgccagcgcc   420
gacccgctac gttacaacct tgctgccatg attgcacgtt tcaacgaaac gggccgcagc   480
caggtgctgg caaaacgtat gccgggtgac ctctctgaat actccgtcat ccagactaaa   540
gagccgctgg accgtgaggg taaagtcagc gcattgttg aattatcga aaaaccggat    600
cagccgcaga cgctggactc agacatcatg gccgtaggtc gctatgtgct ttctgccgat   660
atttggccgg aactggaacg tactcagcct ggtgcatggg gacgtattca gctgactgat   720
gctattgccg agctggcgaa aaaacaatcc gttgatgcaa tgctgatgac cggcgacagt   780
tacgactgcg gcaaaaaaat gggctatatg caggcgtttg tgaagtatgg cctacgcaac   840
ctgaaagaag gggcgaagtt ccgtaaaggt attgagaagc tgttaagcga ataatgaaaa   900
tctgaccgga tgtaacggtt gataagaaaa ttataacggc agtgaaaatt cgcagcaaaa   960
gtaatttgtt gcgaatcttc ctgccgttgt tttatataaa ccatcagaat aacaacgagt   1020
tagcagtagg gttttattca aagttttcca ggattttcct tgtttccaga gcggattggt   1080
aagacaatta gcgtttgaat ttttcggggtt tagcgcgagt gggtaacgct cgtcacatca   1140
taggcatgca tgcagtgctc tggtagctgt aaagccaggg gcgtagcgt gcattaatac    1200
ctctattaat caaactgaga gccgcttatt tcacagcatg ctctgaagta atatggaata   1260
aattaagcta gcagtgaaga tacttgttac tggtggcgca ggatttattg gttctgctgt   1320
tgttcgtcac ataataaata atacgcaaga tagtgttgtt aatgtcgata aattaacata   1380
cgccggaaac ctggaatcac ttgcagatgt ttctgattct gaacgctatt tctttgaaca   1440
tgcggatatt tgtgatcagc tgcaatggc acggatttt gctcagcatc agccggatgc     1500
agtgatgcac ctggcagctg aaagccatgt tgaccgttca attacaggcc ctgcggcatt   1560
tattgaaacc aatattgtgg gtacttatgt ccttttagaa gcggcctcgga attattgtc    1620
tggtctggat gatgaaaaga aaaaaaactt ccgttttcat catatttcta ctgatgaggt   1680
gtatggtgac ttaccccatc cggatgaagt aaatagcaat gaaacgttgc cgctatttac   1740
ggaaacgaca gcatacgcgc caagtagtcc atattctgct tctaaagctt ccagcgatca   1800
tttggttcgc gcatggaaac gtacttatgg tttaccgacc attgtgacta attgctcgaa   1860
caactatggt cccttatcatt tcccggaaaa gcttattcca ctgttattc ttaattcact    1920
ggaaggtaag gcattaccta tttatggcaa aggagatcag atccgcgact ggttgtatgt   1980
agaggatcat gctcgagcgt tatataccgt cgtaaccgaa ggtaaagcgg cgaaacttta   2040
taacattggt ggacacaacg aaaagaaaaa catcgacgta gtgttcacta tttgtgattt   2100
gttggatgag atagtcccga aagagaaatc ttaccgcgca caattactt atgttaccga    2160
tcgtccggga cacgatcgcc gttatgcgat tgatgcggga aagattgctg gcgaattgga   2220
atggaaacca caggaaacgt tgagagtgg gattcgtaaa acggtggaat ggtacctgtc    2280
caatacaaaa tgggttgata atgtgaaaag tggtgcctat caatcgtgga ttgaacagaa   2340
ctatgagggc cgccagtaat gaatatcctc ttttttggca aaacagggca ggtaggttgg   2400
gaactacagc gtgctctggc acctctgggt aatttgattg ctcttgatgt tcactccact   2460
gattactgtg gtgattttag taatcctgaa ggtgtagctg aaaccgtaag aagcattcgg   2520
```

```
cctgatatta ttgtcaacgc agccgctcac accgcagtag acaaagcaga atcagaaccg  2580
aagtttgcac aattactgaa cgcgacgagt gtcgaagcga tcgcgaaagc agccaatgaa  2640
gtcggcgcct gggttattca ctactctact gactacgtat ttccggggac cggtgaaata  2700
ccatggcagg aggaggatgc aaccgcaccg ctaaatgttt acggtgaaac caagttagcg  2760
ggagaaaaag cattacaaga gcattgtgcg aagcaccttt tttccggacg cagctgggtc  2820
tatgcaggta aaggaaataa cttcgccaaa acaatgttgc gtctggcaaa agagcgtgaa  2880
gaattagccg ttattaatga tcagtttggt gcgccaactg gcgcagagtt actggctgat  2940
tgtacgcac atgctattcg tgtggcactg aataaaccgg aagtcgcagg cttgtaccat  3000
ctggtagcta gtggtaccac aacgtggcac gattatgctg cgctggtttt tgaagaggcg  3060
cgcaaagcag gcattcccct tgcactcaac aagctcaacg cagtaccaac aacagcctat  3120
cctacaccag ctcgtcgtcc acataactct cgccttaata cagaaaaatt tcagcagaac  3180
tttgcgcttg tcttgcctga ctggcaggtt ggcgtgaaac gaatgcttaa cgaattattt  3240
acgactacag caatttaata gttttttgcat cttgttcgta atggtggagc aagatgtatt  3300
aaaaggaatg atgaaatgaa aacgcgtaaa ggtattattt tggcgggtgg ttctggtact  3360
cgtctttatc ctgtgacgat ggccgtcagt aaacagctgt taccgattta tgataaaccg  3420
atgatctatt acccgctctc tacactgatg ttagcgggta ttcgcgatat tctgattatc  3480
agtacaccac aggatactcc tcgttttcaa caactgctgg gtgacgggag ccagtgggc  3540
ctgaatcttc agtacaaagt gcaaccgagt ccggatgtc ttcgcaggc gtttattatc  3600
ggtgaagagt ttattggtgg tgatgattgt gctttggtac ttggtgataa tatcttctac  3660
ggccacgacc tgccgaagtt aatgacgta gctgttaaca aagaaagtgg tgcaacggta  3720
tttgcctatc acgttaatga tcctgaacgt tatggtgtcg tggagtttga taataacggt  3780
actgcaatta gcctggaaga aaaaccgctg gaaccaatga gtaactatgc ggttactggg  3840
ctttatttct atgacaatga cgttgtggaa atggcgaaaa accttaagcc ttctgcccga  3900
ggtgaactgg aaattaccga tattaaccgt atttatatgg aacaaggacg tttgtctgtc  3960
gctatgatgg ggcgtggcta tgcatggctg gatacagga cgcatcaaag tcttattgaa  4020
gcaagcaact tcattgccac cattgaagag cgccaggac taaaggtttc ctgtccgata  4080
gaaattgctt atcgtaaagg gtttattgat gctgagcagg taaaagtatt agccgaaccg  4140
ttgaagaaaa atgcttatgg tcagtatctg ctcaaaatga ttaaaggtta ttaataagat  4200
gaacgtaatt aaaactgaaa ttcctgatgt gctgattttt gaaccaaaag ttttgggga  4260
tgaacgtggc ttcttttttg agagttttaa tcagaggatt tttgaagaag cagtaggtcg  4320
taaggttgag tttgttcagg ataaccattc taagtccagt aaaggtgttt tacgtggtct  4380
tcattatcag ttagaacctt atgctcaagg aaaactggtg cgctgtgttg ttggcgaggt  4440
ttttgatgtt gcgttgata ttcgtaaatc gtcacctaca tttgggaaat gggttggggt  4500
gaatttgtct gctgagaata agcgtcagtt gtggattcct gagggatttg cacatggttt  4560
tttggtgctg agtgatttag cagaagtttt atataaaacg aatcaatatt atgctccatc  4620
acatgaaaaa aatattatat ggaatgacct cttgcttaat attaaatggc cgagcacagc  4680
actgatcact ctgtctgata aggatgcaaa tggggaaaga tttgaactaa gtgagttttg  4740
aaatgtctct cttaaaacat agtatatgga atgttgcggg ctactttata ccaacattaa  4800
ttgcaattcc cgcctttgga ttaattgcga ggaaaattgg tgtagaacta tttggtttgt  4860
atacgttagc aatgatttt ataggtatg caagtatatt tgatgctggg ttaacaagag  4920
ctgttgtgcg tgaaatagca ttactaaaaa acagagtgga cgattgtaat acgataaag  4980
taacttctat tatcgctgtg atattttag ggttatcgg aggcggggga gtgtttctgc  5040
ttaaaggcga tattattgaa ctgttaaata tctcaccaat atattacgcc gattcgataa  5100
agtctctagt attattatca tctctgatac ctgtattctt agtcacgcaa atactattag  5160
cagagcttga gggtcgggaa tattttggga ttctaaatat acaaaaaagt gtagggaatt  5220
cttttaattgc agggttacct gcattatttg ttttaattaa tcaaacgctt ttttctgcaa  5280
ttattggtgt agcgattgca agagttatat gcttgtggtt aagctacatt atgagcaggg  5340
aaagaataac tatcgatatc tcattttttt caataactgt tttaaagcgg ttatttagat  5400
atggcgggtg ggtaactata agtaacataa tatctcctat attagcgagt atggatagat  5460
ttattctatc ccatatccag ggagcatcaa aaatatcatt ctatacagtc cctaatgagc  5520
tggtaactag gcttggaata gttccaggct ctcttggaa agctgttttt ccaaaattaa  5580
gtcatgcaag gaattttaca gcgtcatatg cagagcaaaa aaaagcttat atattaatga  5640
ctgtcattgt aatgccttg gttttatttg tatattatta cgcaaagttt attttaacat  5700
tgtggatggg ggctgagtat gcagggattt cggtcgaaat attacggatt atgcttatag  5760
ggtatatttt taactgttat tcacaaatct cttttgccaa catacaggcc tttggaaaag  5820
caaaatacac tgcatacatc catatgatgg aatttattcc ttatttgata atgttatata  5880
taatttcaaa ggaatatggg gttattggtg ttgcgtggtt atggacaatt cgagtaataa  5940
ttgattttt gatgctttta tatatgagtt atcgttgtaa taatcttatg aaaaagggt  6000
agcctgatga tatatattgt ggtattaaat tggatgggg ctatagatac cattaattgt  6060
gttaaaagtt taatggattt aaatgttagc gattataaaa ttatcattgt tgataactgt  6120
tctatggata actcatatga tactataaaa gaaaatctta attcattata tattgctgat  6180
aaagtcatat tgaggtgaa gtatgaggat agaaataaat ataaaccttt agaaaacgat  6240
aaaatcatat taatacaatc tccgcaaaat aatgggtacg caagtggtaa taatattggc  6300
atagagttcg ctcttaatca ggagaatatg aaatacgtct gggttctgaa taatgatact  6360
gaagtggata aagaggcttt aactcattta attagtaaat gtgattcaga taaaagtata  6420
gggatttgcg gttctcgttt agtctatttt gccgacagag agatgcagca aggactaggg  6480
ggggtgcata acaaatggtt atgcactaca aaaaattatg aatgggaag attagtttcc  6540
aaaaaatatg atgatgaagt cattagtaat gatatagatt ataaattgg cgcatcgatg  6600
tttttctcta gagaatgttt ggaaacagtt ggattgatga atgaagaata ttttttatac  6660
tatgaagagt tagatatttg cctcagagca aaagcaaaga actttaaatt aggtatttgc  6720
tcagaaagtt tggtttatca taaaataggt gcaagtactg atgggggaaa gagcatgatg  6780
gctgatcttt gctcaataaa aaataggctg tcattacag aaaggttta tccccaatat  6840
tattggacgt tatggttgtc actttttgtt gtagcattta accgtgctag aagaggtgag  6900
tttaataaga tgaaaagatg tttgaatgtt atgtttaact tcaaacgaaa caaaggtagc  6960
aaatgccatt agaatatgca cttaatcatg tgtgttaataa atctatagtt tgatatgtta  7020
ttaaaggta tttaatgaaa gtggcttttt tatctgctta tgatccacta tctacatcca  7080
gttggtctgg cacaccttat tatatgctaa aggcattatc gaagagaaat atttccattg  7140
aaatattagg accggtaaat agctatatga tatacatgtt aaaagtatat aaattaatat  7200
taaggtgttt cggaaaagaa tatgattata gtcattcgaa gttgctttcc aggattacg  7260
```

```
gtagaatatt cggtaggaaa ttaaaaaaaa ttgatggttt ggattttatt atcgcacctg    7320
caggttcctc acaaattgct tttttaaaaa caaccatacc aataatatat ctatcggata    7380
caacatatga tcaattaaaa agctattatc cgaatttaaa taaaaaaaca attataaatg    7440
atgaggatgc aagtttaatc gaacgcaagg ctattgaaaa agcaacagta gtatctttcc    7500
catctaaatg ggcaatggat ttttgcagga attattacag attagatttt gataaattag    7560
ttgaaatacc atgggggggct aatttatttg atgatattca ctttgctaat aaaaatataa    7620
ttcaaaagaa tagttatact tgtctttttct tgggagttga ttgggaaaga aaaggtggga    7680
aaacagcctt gaaagcaatt gaatatgtaa ggcagttata tgggatcgat gttagactaa    7740
aaatttgtgg atgtactccg aatcaaaaga ttttacctac ttgggttgaa ttaattgata    7800
aagtagataa aaataacgtt gacgaatatc agaaattcat cgatgtgtta tctaacgctg    7860
atatacttct tttaccaacc attgctgaat gttatggaat ggtatttttgt gaagctgctg    7920
cttttggatt gcctgttgtc gctacagata caggtggagt cagttctata gttatcaacg    7980
aaaggacggg gatattaatt aaagacccgt tagactataa gcactttgga aatgcaattc    8040
ataaaaataat tagttccgta gagacttatc aaaactactc ccaaaacgca agaattagat    8100
ataataatat attgcattgg gacaattggg ctaaaaagat aattgagatt atgtatgagc    8160
ataagaatag aagaatcaaa tagcacaaaa agaattatat gtttatttat acttttctt    8220
gttttccctg atttttttgtt ttatacatta ggggttgata attttagcat ttcaacgata    8280
atctcaatta cattgctttt tgttttttta agagctaaaa atatttgcaa agataatttt    8340
ctaataatag tagcgttatt catattgttg tgttttaact gtttgttaag tatgctattt    8400
aatattgaac aggctttaac atttaaagtt gtactttcaa tatatagcat cttaataatg    8460
gcatacgtct cctcttgtta tgcacagacg ttgtggttat gttctgaaga aatacttaag    8520
agatccgtct tttatttgtt cgcatttctt tgccttattg cgcattataag tattcttta    8580
cagaagactg agattataca tgataaaagt atgattcttt ttcctgaacc atcagcatttt    8640
gcattggttt ttataccctat cttttcatttt tgtttatact atacaagagg gggggggcta    8700
ctattgctct atatattatc tttgggtatt gcgttaggta tccagaattt aacaatgttg    8760
gtaggcattg tgattagtgt ttttgtgatg aaaaaaataa ctataaggca aactattgtt    8820
atacttttgg gggcatggat ttttttccatg atattaagtg atttagacat ttccttactat    8880
acatcgcggc ttgattttaa aaatactacg aacctatcag tgcttgtata tcttttcagga    8940
attgaaaagag ctttcttgaa ttttattaca agttatggtc ttggtattgg ttttcaacaa    9000
atgggagtga atggggagat aggaaatatat caacaaattt tagctgaact tgatgcccct    9060
atgttaaaata tatacgatgg ctcatttatt tcttctaagt taatatctga gtttgggggtt    9120
attggtgcat taatgtgtat tttctatttt tttttatttt cccgatttta tctgcgtttc    9180
aaaaaaagta agagatattc accgcagtat attttagcat atagcttcta catgtgtttc    9240
ttcatccctc tttttatacg tggtgctggt tatataaacc cctatgtgtt tatgttatt    9300
tcatcaatat tttttgtgcaa atatcacgct aaaaatatct tgatgaaatc taatgtccaa    9360
atagctatat aatagtagat tatattatca ttatcacgta aattacatat taatagcata    9420
tatgataact aggacataaa taatgtgcat taaaaaaaaa cttaagttaa ttaaacgata    9480
tggccttttat ggtggtctta ggcttcttaa agatatattc ttaacaaaat tttatttttg    9540
ttcaaatgtt aggattatta gatttccatg ttatattaga aaagatggaa gtgttagttt    9600
tggaaaaggt tttacatcag gtgtaggatt acgagttgat gcatttatgg atgccgtagt    9660
ttccattgga gaaaatgttc aaattaatga ctatgttcac atcgcggcta ttaataatgt    9720
cattattggt agagatacat taatagcaag taaagtattt attagtgatc ataatcatgg    9780
tatttttttct aaatccgata tccatagttc accaactatt attccttcgt ctaggcccct    9840
tgaatctgca cctgtgtata ttggagagcg tgtgtggatt ggcgaaaatg tgacaatatt    9900
accaggtgcg tgtataggta atggtgtagt tattggcgca aacagtgttg ttcgtggtga    9960
gattcctaat aatgtgatca ttgctggtgt tccagctaaa attgttaaaa aatataacta    10020
tgagcgtatg caatgggaaa gaatatagtt gtaatatcgc ctgttaattt tacaaccgga    10080
ggcccctttta ccgtactaaa aaatgtgctt acagcaacta aagatagagc cgaatgtaaa    10140
tttattgcac tggttcatag ctctgctgaa ctaatggaat tatttcgtgt ggttgaattt    10200
atagagtatc cagaagtcaa gtcttcgtgg gttaaaagat tatatttcga atatataact    10260
tgcaatagat tatctaaggt gattaaggca actcattggg tatgcttaca tgatattaca    10320
gcaaatgtta gtgtacccta tagatttgtt tattgccaca atcctgcacc gttctataaa    10380
tatttaagct atcgagatat tataggagaa cctaaatttt atcttttttta tctttttttat    10440
gggctttttat acaatatcaa tataaaaaag aacacagcag tttttgttca gcagcagtgg    10500
ctaaaaaaag aattcgaaaa aaaatataag ttaaagaatg ttgttgttag tcgccctgaa    10560
gatatttgcc cttttgaaag tgatggtttg gtaagaaata ataataaaaa ggatgtgagg    10620
atattttacc cagcagtgcc ccgtatattt aaaaactttg aagttatcat acgtgctgca    10680
caaatattac aagataaaaa tattcatttt tatcttactt ttgatggtac tgaaaataag    10740
tatgcaaaaa gaatatataa attagcttcc gaactgaaaa atgtacattt cctcggttac    10800
cttaatgcaa ccgagatggt taactttttat caagattcag atattatttg ttcccatcg    10860
aaactagaaa cgtggggatt accattatca gaagctaaaa catacaaaaa atggatatttt    10920
gcggcagact tacctatatgc tcatgaagtt ttatataact attcaaaaac tagatatttt    10980
ccattttgacg atgagaaaat acttgttcgc tacatattag agtacacaag taaaaatatg    11040
catgaagata taaaaaatag tagggtgaat tttaataatg atgcattgac tggttttgaa    11100
cagtttattg aatatatcct caaggggaac tgacgtggtt tatattataa tcgtttcaca    11160
tggccatgat gactatatag aaaatctttt attaaattta aagttgccct ctggaagatt    11220
taaaataata gttcgtgata acaaaagttc aatggtttta aaaaaacat gcgaaaaaaa    11280
ttgcgtaacc tatttgcatg gagggcaata tggatttgga cataataata acatagcagt    11340
gtcatatata attaataact tcatgattat gaatatgatt ttcttctct ttcttaaccc    11400
cgatgtattc ataaccagtg aaagtttgat taattatgtt gattatataa ttagtaatga    11460
ttataagttt agcacattat gtctttatcg agattttact aaaaagcaaac atgattattc    11520
aatacggagt tttccaactt tatatgattt tctttgttct tttttattgg gggtgaataa    11580
aagtaaaatt aagaaggaaa atatactttc tgatactgta gttgattggt gtgctggctc    11640
atttatgttt attcatgctt taagtttctt aaatgtgaat ggttttgatc aaaaatttt    11700
tatgtattgt gaagatattg acctttgtat gcgtttaaaa ttaagtggag tagatctttta    11760
ctatactccc catttttgatg ctattcatta tgcgcagcat gaaaatagaa gaatatttac    11820
taaagcattt cgatgcata taaggagtat tacgcgctac atattacgga aaccaattct    11880
ttcttataaa aactatagaa aaattacatc cgaactggta aagtgattaa ggatccgtgt    11940
aggctggagc tgcttcgaag ttcctatact ttctagagaa taggaacttc ggaataggaa    12000
```

```
ctaaggagga tattcatatg gataaagccg taagcatata agcatggata agctatttat   12060
actttaataa gtactttgta tacttatttg cgaacattcc aggccgcgag cattcagcgc   12120
ggtgatcaca cctgacagga gtatgtaatg tccaagcaac agatcggcgt agtcggtatg   12180
gcagtgatgg gacgcaacct tgcgctcaac atcgaaagcc gtggttatac cgtctctatt   12240
ttcaaccgtt cccgtgagaa gacggaagaa gtgattgccg aaaatccagg caagaaactg   12300
gttccttact atacggtgaa agagtttgtc gaatctctgg aaacgcctcg tcgcatcctg   12360
ttaatggtga aagcaggtgc aggcacggat gctgctattg attccctcaa accatatctc   12420
gataaaggag acatcatcat tgatggtggt aacaccttct tccaggacac tattcgtcgt   12480
aatcgtgagc tttcagcaga gggctttaac ttcatcggta ccggtgtttc tggcggtgaa   12540
gaggggggcg ctgaaaggtcc ttctattatg cctggtggcc agaaagaagc ctatgaattg   12600
gtagcaccga tcctgaccaa aatcgccgcc gtagctgaag acggtgaacc atgcgttacc   12660
tatattggtg ccgatggcgc aggtcactat gtgaagatgg ttcacaacgg tattgaatac   12720
ggcgatatgc agctgattgc tgaagcctat tctctgctta aaggtggcct gaacctcacc   12780
aacgaagaac tggcgcagac ctttaccgag tggaataacg gtgaactgag cagttacctg   12840
atcgacatca ccaaagatat cttcaccaaa aaagatgaag acgtaacta cctggttgat   12900
gtgatcctgg atgaagcggc taacaaaggt accgtaaat ggaccagcca gagcgcgctg   12960
gatctcggcg aaccgctgtc gctgattacc gagtctgtgt ttgcacgtta tctcttct   13020
ctgaaagatc agcgtgttgc cgcatctaaa gttctctctg tccgcaagc acagccagca   13080
ggcgacaagg ctgagttcat cgaaaaagtt cgtcgtcgc tgtatctgga caaaatcgtt   13140
tcttacgccc agggcttctc tcagctgcgt gctgcgtctg aagagtacaa ctgggatctg   13200
aactacggcg aaatcgcgaa gattttccgt gctggctgca tcatccgtgc gcagttcctg   13260
cagaaaatca ccgatgctta tgccgaaaat ccacagatcg ctaacctgtt gctggctccg   13320
tacttcaagc aaattgccga tgactaccag caggcgctgc gtgatgtcgt tgcttatgca   13380
gtacagaacg gtattccggt tccgaccttc tccgcagcg ttgccttatta cgacagctac   13440
cgtgctgctg ttctgcctgc gaacctgatc caggcacagc gtgactattt tggtgcgcat   13500
acttataagc gtattgataa agaaggtgtg ttccataccg aatggctgga ttaa          13554

SEQ ID NO: 19           moltype = DNA  length = 15197
FEATURE                 Location/Qualifiers
source                  1..15197
                        mol_type = other DNA
                        organism = synthetic construct
SEQUENCE: 19
atgacgaatt taaaagcagt tattcctgta gcgggtctcg ggatgcatat gttgcctgcc   60
actaaggcga tacccaaaga gatgctacca atcgtcgaca agccaatgat tcagtacatt   120
gttgacgaga ttgtggctgc agggatcaaa gaaatcctcc tggtaactca cgcgtccaag   180
aacgcggtcg aaaaccactt cgacacctct tatgagttag aatcactcct tgagcagcgc   240
gtgaagcgtc aactgctggc ggaagtacag tccatctgtc cgccgggcgt gaccattatg   300
aacgtgcgtc agggcgaacc tttaggttta ggccactcca ttttgtgtgc gcgacctgcc   360
attggtgaca acccattgt cgtggtactg ccagacgttg tgatcgacga tgccagcgac   420
gacccgctac gttacaacct tgctgccatg attgcacgtt tcaacgaaac gggccgcagc   480
caggtgctgg caaaacgtat gccgggtgac ctctctgaat actccgtcat ccagactaaa   540
gagccgctga ccgtgaggg taaagtcagc cgcattgttg aatttatcga aaaccggat   600
cagccgcaga cgctggactc agacatcatg gccgtaggtc gctatgtgct ttctgccgat   660
atttggcggg aactggaacg tactcagcct ggtcatgggg gacgtattca gctgactgat   720
gctattgccg agctggcgaa aaaacaatcc gttgatgcaa tgctgatgac cggcgacagt   780
tacgactgcg gcaaaaaaat gggctatatg caggcgtttg tgaagtatgg cctacgcaac   840
tgaaagaag gggcgaagtt ccgtaaaggt attgagaagc tgttaagcga ataatgaaaa   900
tctgaccgga tgtaacggtt gataagaaaa ttataacggc agtgaaaatt cgcagcaaaa   960
gtaatttgtt gcgaatcttc ctgccgttgt tttatataaa ccatcagaat caacagagt   1020
tagcagtagg gttttattca aagttttcca ggattttcct tgtttccaga gcggattggt   1080
aagacaatta gcgtttgaat ttttcggggtt tagcgcgagt gggtaacgct cgtcacatca   1140
taggcatgca tgcagtgctc tggtagctgt aaagccaggg gcggtagcgt gcattaatac   1200
ctctattaat caaactgaga gccgcttatt tcacagcatg ctctgaagta atatggaata   1260
aattaagcta gcagtgaaga tacttgttac tggtggcgca ggatttattg gttctgctgt   1320
tgttcgtcac ataataaata atacgcaaga tagtgttgtt aatgtcgata aattaacata   1380
cgccggaaac ctggaatcgc tcgctgaaat ttctgattct gaacgttatt catttgagca   1440
tgcagatatc tgccgatgccg aagcgatggc tcgtattttc gcacagcacc agccagacgc   1500
ggtgatgcac ctgcagcag agagccacgt tgaccgctca ataactggcc ctgcggcatt   1560
tattgaaacc aatattgtgg gtacttatgt tctttttagaa gcggcgcgca attattggtc   1620
tggtctggat gatgaaaaga aaaaaaactt ccgctttcat catatttcta ctgatgaggt   1680
gtatggtgac ttaccccatc cggatgaagt aaatagcaat gaaacgttgc cgctatttac   1740
ggaaatgaca gcatacgcgc caagtagtcc atattctgct tctaaagctt ccagcgatca   1800
tttggttcgc gcatggaaac gtacttatgg tttaccgacc attgtgacta attgctgaa   1860
caactatggt ccttatcatt tcccggaaaa gcttattcca ctggttattc ttaatgcact   1920
ggaaggtaag gcattaccta tttatggcaa aggagatcca atccgcgact ggttgtatgt   1980
agaggatcat gctcgagcgt tatataccgt cgtaaccgaa ggtaaagcgg gcgaaactta   2040
taacattggt ggacacaacg aaaagaaaaa catcgacgta gtgttcacta tttgtgattt   2100
gttggatgag atagtcccga aagagaaatc ttatcgtgag caattaccta tgttgctgaa   2160
tcgcccaggg catgatcgcc gttatgcaat tgatgccgat aaaattagcc gcgaattggg   2220
ctggaaacca caggaaacgt ttgaggaggg gattcgtaaa actgtggaat ggtatctgaa   2280
caatacaaaa tgggttgata atgtgaaaag tggtgcctat caatcgtgga ttgaacagaa   2340
ctatgggggc cgccactaat gaatatcctc cttttggca aaacagggca ggttggttgg   2400
gaactacagc gtgctctggc acctctgggt aatttgattg ctcttgatgt tcactccact   2460
gattactgtg gtgattttag taaccctgaa ggtgtggctg aaaccgttag aagcattcgg   2520
cctgatatta ttgtcaacgc agccgctcac accgcagtag acaaagcaga atcagaaccg   2580
```

```
gagtttgcac aattactgaa cgcgacgagt gtcgaagcga tcgcgaaagc agccaatgaa    2640
gtcggcgctt gggttattca ctactctact gactacgtat ttccggggac cggtgaaata    2700
ccatggcagg aggaggatgc aaccgcaccg ctaaatgttt acggtgaaac caagttagca    2760
ggagaaaaag cattacaaga gcattgtgcg aagcacctta ttttccggac cagctgggtc    2820
tatgcaggta aaggaaataa cttcgccaaa acgatgttgc gtctggcaaa agagcgtgaa    2880
gaattagccg ttattaatga tcagtttggt gcgccaactg gcgcagagtt gctggctgat    2940
tgtacggcac atgccattcg tgtggcactg aataaaccgg aagtcgcagg tttgtaccat    3000
ctggtagcca gtggtaccac aacctggcac gattatgctg cgctggtttt tgaagaggcg    3060
cgcaaagcag gcattcccct tgcactcaac aagctcaacg cagtaccaac aacagtctat    3120
cctacaccag ctcgtcgtcc acataactct cgccttaata cagaaaaatt tcagcagaac    3180
tttgcgcttg tcttgcctga ctggcaggtt ggtgtgaaac gcatgctcaa cgaattattt    3240
acgactacag caatttaata gtttttgcat cttgttcgtg atggtggaac aagatgaatt    3300
aaaaggaatg atggaatgaa tacgcgtaaa ggtattattt tagcgggtgg ttctggtaca    3360
cgtctttatc ctgtgactat ggctgtcagt aaacagctgt taccgattta tgataaaccg    3420
atgatctatt acccgctctc tacactgatg ttggcgggta ttcgcgatat tttgattatc    3480
agcacgccac aggatactcc tcgttttcaa caactgctgg gtgatgggag ccagtggggg    3540
ctaaatcttc actacaaagt gcaaccgagt ccggatggtc ttgcgcaggc atttatcatc    3600
ggtgaagagt ttatcggtgg tgatgattgt gcttggtac ttggtgataa tatcttctac    3660
ggtcacgacc tgcctaagtt aatgatgcc gctgttaaca aagaaagtgg tgcaacggta    3720
tttgcctatc acgttaatga tcctgaacgc tatggtgtcg ttgagtttga taaaaacggt    3780
actgcaatca gcctggaaga aaaaccgtta caaccaaaaa gtaattatgc ggtaaccggg    3840
cttatttct atgataacta cgttgtggaa atggcgaaaa tcttaagcc ttctgcccgc    3900
ggtgaactgg aaattaccga tattaaccgt atctatatgg aacaggggca tttatctgtt    3960
gccatgatgg gacgtggata tgcctggctg gacacgggga cacatcaaag tcttattgaa    4020
gcaagcaact tcattgccac cattgaagag cgccagggct tgaaagtttc ctgcccggaa    4080
gaaattgctt accgtaaagg gtttattgat gctgagcagg tgaaagtatt agctaaaccg    4140
ctgaaaaaaa atgcttatgg tcagtatctg ctaaaaatga ttaaaggtta ttaataaaat    4200
gaatgttatt aaaacagaaa ttccagatgt actgattttt gaaccgaaag ttttttggtga    4260
tgagcgtggt ttcttttatgg aaagctttaa tcagaaagtt ttcgaagagg tgtagggcg    4320
gaaggttgaa tttgttcagg ataatcattc taaatcgtgt aaaggtgtac ttagaggttt    4380
acactttcag cttcctccct tgagcaggc aaaattagta aggtgtatag ttggcgaggt    4440
atttgatgtt gcagtagaca ttagacctaa ttctgaaaca tttggttcat gggttggagt    4500
aactctttcg tcagaaaata aaaggcagct atggattcca aaggattcg cccatggttt    4560
tttaacttta agtgatattg cagagtttgt ttataaaact aacaactatt attcttaaa    4620
tcatgaaagg ggagtcattt ggaacgatga ggaaattaac attgcctggc cctctcaatc    4680
agagaagatt ctgtcacaga aagatattaa tttaccatca tttagatttg ttcaaatgtt    4740
tagcaagtag tgttatcttt acactgcaca tagtcatcat ttttatgct ttaagtaaat    4800
tatattgcac atctataaca caaagcgcaa taatatttcg acctgatgaa ggtttgtggt    4860
tatttatctt tctaggcgtt ttttatgact aaaatagttg tggtttctac agctccaata    4920
ttcccgacaa ataatgggta caaaagttct gtattaggaa gaattgatga gttattaaat    4980
gaggataatg aggtcgtttt gattgaaata aaccttgaaa atgttacgga aaagaaagat    5040
gaattaatac caacaagatt taataatatt caaagatatg aagtaaaaa aatatctaga    5100
tcatttattg ccgagttaca aatatttttt gatatcagaa ctcggtatga caattattt    5160
tcttctgctg acattagaga taacataaaa aagataattg atttagaaaa accttctatt    5220
attattgctg agtctatatg ggcgttgcaa gcattgccta ttgaaattag tgcgagaata    5280
cactgtgtta ttcatgatgt ggcaactgat ttctttaaag aaatgtttgt atctcataat    5340
gaggttgtac gaaaaatttt gttttttaat gattacctaa agttgaaaat tactgaagaa    5400
aatattatca aacgtttgag agttgagcaa tttatctttc tgacagaaga agataaatgt    5460
tggtataaaa caagatacaa tattgatgag ggttgttgtt ccttagcgag caatcatctt    5520
tatgtagaaa agattaagag aactatcaat ttccaaaccc ctttcctgct tattcccggt    5580
agcattgaat tttcacaaaa ttttttacggc ttaaattggt ttataaaaaa tatatatcct    5640
ggattaaata ggaaaataag aatagttgta acaggaaagg catcagataa aaaaataaag    5700
atgttaaact gtggagagga aattcccttt acgggagagc ttgacttttc cacatataat    5760
aaacttagct caacatgctt gtgtgttatt gcaccgatta caacgggcac tggaattaaa    5820
ataaaaatat tagaagctgt acaaaaaggt attcctgtac ttacaacaaa attgcttca    5880
aaaggaatat gttccgattt atgttttttat tgcgaggagg atactgacac aaactttgtc    5940
aatttaatta acagttttct tgaaacgaca ttaagagtcc aagatgaatt ttattgcttt    6000
tttcagtcct tgcgtttggt ttaatattgg ctttggccca taataataaa agtggagata    6060
ttaacgcata cttaatgttt tttctcgtgg tcctaatggt attaatatca gggctgcgta    6120
tgaatgatag tgattatatc gaatacagga aaatgtataa tgaagtgcct attttatgtg    6180
actttagtct cgcatctata agagatatac atggggaggt aggctatcta ttcttatcat    6240
caatctttaa aacttatgc ttgccatttc aattattttct ttttttatt gcttttttat    6300
cactcctgct tacatatttt tcattcagaa aaataagttt aataccgata ctatcgttag    6360
tttttatttt aagccatgct tttatagtta gagatttgat tcaaattagg gcaggattag    6420
ctgttagcat atcattatat tcaataatta aatttaaagg aaataaaagt ataattacag    6480
gagttttatt tgcttctttg attcattctg ggggcgcttat tattgctctt tgttatcctt    6540
tttttcaaaaa aaaatacata acattaaaa tgatgttgtt tttattttta gtgtcaatta    6600
ttttttctta tttgaatggg cttaatttat cgatacaact cttatctcaa tatagtttgc    6660
ttccaactgc aatttcgaat tatgttggtt gggaagaata tgattatcgg gtgagtatat    6720
ttactaatcc ggttttatt aaaggtgttt ttttaattgc cttaatgcac aaatatgtac    6780
tatatat aaaatgag aaaattatag tgcttttata cttatatgtt ttaggtgtaa    6840
tagctatggt tgcattgagt gggatggcta tctttcaggg ccgtctttca tcctttctga    6900
cactaggtga agcattttta attgtatatg ctctgttcta caaaagaaat acacctctgg    6960
cgttctaat ttttttctttt ttaacaattg tgcaattagg atatgatcta ttatttcta    7020
atgtgcatcc tgagccttact ctgattatat ttgggtgaat ctaagtgaaa aataataaaa    7080
taggcatact tatctctaaa atacaaaatc ttggacctgt gaatgtagta cgaggattga    7140
```

```
taaaagaaaa taaaaaatat gcttttactg ttttttgttt aacaaatagc gtagataaaa   7200
atatatatga tgagttatgc tgtttaggag ccaaggttat attaatacca gatggtactt   7260
ggttcagcaa aatttattt gtgagaagtt ttttaaagga acatccacat aatatcttac    7320
attcacatgg gatcacggcc gatatgtttt cttactttct gaatggcgtg aaaatatcta   7380
ctattcacaa tagactagat gaggattaa tcccattatt tggcgcggtt aaagggaatg    7440
ctatatatta tcttcatcgt tttatattac gaagatttaa tcatatcgtt gcttgctcag   7500
cagcggtcca atcaaaactg aaacaatcga aagtaaaaac taaataacc accatccaga    7560
atgggattga tataactagg tttaagacac ttgagtctga taaaaaaaaa ttattgaggg   7620
aaaaacacgg atttgatagt gaaaaaagaa tatttatata ttgtggctcg ttatcattaa   7680
ggaaaaatat tgcttacctc ttggaacact tagccatcga agaaaatgat atatttttaa   7740
ttctaggtga tggtgaactt tttagatatt gtaaggataa atattctaaa gatttacggt   7800
atatatttat ggggaaagtt gaatgccctc ttgaatatta tcaattatca gatattttg    7860
tttccgcttc tttatcggaa gggctcccct tggcactatt agaagctgcc tctactgggt   7920
gctatttata tgttagcgat atagagcccc atagagaaat tgcatctcta ttaggagagg   7980
aaaatatttc tatgtttaaa attaaggatg gatcatataa ttatttgcaa cctaaaataa   8040
aaaaagctga ctaacgct cttctgacg ataactttta caatatatcc gataaaaaaa     8100
tgtcaaatct ttatgacaaa cttttgtt ctttattaga gcagaggcac taatataatg    8160
atttatgttt cggtaatttc tcatggtcat ttcaaaactc ttaaggaatt aggagcagta   8220
tcaaaattaa ataatcacag cagaattaaa gttatcatca aagataattt aggagagagc   8280
gagcttttgg attttttgtca ggaaaacaaa ataacttatt taaggtctaa agagaaaaaa  8340
ggatttggag agaataataa tgaagttttt cctctatat cctccttaat tactaaggaa    8400
gatttttttg tggttatgaa tcctgatata tatattgagt gctctgatct attagatgtc   8460
gtagatgagt gtggttcagc gaatgttaat ctagcaacga taaatttata cagggatttt   8520
gataaaaaaa catatgataa ctcagtaagg aaatttccct cggcaattga ttttttttag  8580
tcatttttat ttaagaaaaa tgactgtgta gtaaataaga acaaaataac gaaaccaaca   8640
tatgttgatt gggctgcagg ttctttttcta atatttaatg ccttcttta ttcaaaactc   8700
aacggattca acgaaaagta ttttatgtat tgcgaagata ttgatatatg ttggcgagct   8760
aaaaaacact tcaatacttc agttttatac tatccatgct atgcagcaat tcatttggca   8820
caatttaaca atcgtaggat ttttagtaga catttcattt ggcatataaa aagtattatc   8880
cttttttat tatataaaaa tggtatgctg cgttctagta agttgcttta atgctaatat    8940
tcttttaaga ggtgagaatg ataacctgtta ttttggctgg tggttcggga agtcgcttgt  9000
ggccactttc acgagaaaag ttccccaagc agttttttaaa gttgactggc agtttgacaa  9060
tgttgcagtc aacattgtca cgtcttaata atttaaatgc tgatgattca atagttatat   9120
gcaacgaaga gcatagattt attgttgcag aacaattaag agagttaggc aaactttcaa   9180
ataacattat tcttgaaccc aaaggtcgta atacagcccc tgctataaca ctcgcagcat   9240
tagcagcaaa aagaaaattc gctgatgaag atccattgat tcttatttta gctgcagatc   9300
acaacatcca agacgaacat gttttctgtg aggcaattaa taaggcgtca tctttagcta   9360
gttatgaaa actagtgact tttggtatcg ttccattcaa acctgaaact gggtatggct    9420
atattcgtcg cggtgatgaa gtgcctgtag atgagcagca tgcgctggcc tttgaagtgg   9480
tgcagtttgt cgaaaaaccg aatctggaaa ccgcgcaggc ctatgtggca agcggcgaat   9540
attactggaa cagcggtatg ttcctgttcc gtgccggacg ctatctcgaa gaactgaaaa   9600
agtatcgtcc ggatattctc gatgcctgtg aaaaagcgat gagcgccgtc gatccggatc   9660
tcgattttat tcgtgtggat gaagaggcgt ttctcgcttg tccggaagag tcggtggatt   9720
acgcggtcat ggaatgcacg gcagatgccg ttgtggtgcc gatggatgcg ggctggagcg   9780
atgtcggttc ctggtcttca ttatgggaga tcagcgccga caccgccgcg ggcaacgttt   9840
gccacggcga tgtgattaat cacaaaactg aaaacagcta tgtgtacgcc gaatctggcc   9900
tggtcaccac cgtcggggtg aaagatttgg tggtagtgca gaccaaagat gcagtgctga   9960
ttgccgaccg taatgcggtg caggatgtga agaaagtggt cgagcagatc aaagctgatg  10020
gtcgccatga gcatcgggtg catcgcgaag tgtatcgtcc gtgggcaaa tatgactcta   10080
tcgacgcggg cgacccgctac caggtgaaac gcatccaccgt gaaaccgggc gaaggtttgt  10140
cggtacagat gcattatcat cgcgcggaac actgggtggt tgtcgcggga acggcaaaag   10200
tcactatcaa cggtgatatc aaactgcttg gtgaaaacga gtccatttat attccgctgg   10260
gggcgatgca ctgcctggaa acccggggaa aaatagattt agaattaatt gaagttcgct   10320
ctggtgcata tcttgaagaa gatgatgtta ttagatgtta tgatcgctat ggacgaaagt   10380
aatataataa aattatttca gaattagaaa tgataattat aagttttcgt ctggataaac   10440
aatagatagt atgggttgga aaatatgagt tctttaactt gttttaaagc ttacgacatt   10500
cgcgggaaat taggtgaaga actgaatgaa gatatcgcct ggcgcattgg tcgcgcctat   10560
ggcgaatttc tcaaaccgaa aaccattgtg ttaggcggtg atgtccgtct caccagcgaa   10620
accttaaaac tggcgctggc aaaaggttta caggatgcgg gcgtcgatgt gctggatatt   10680
ggcatgtccg gcaccgaaga gatttatttc gccacgttcc atctcggcgt ggatggcggc   10740
attgaagtta ccgccagcca taatccgatg gattacaacg gcatgaagct ggtgcgcgaa   10800
ggggctcgcc cgatcagcgg tgataccgga ctgcgcgacg tccagcgtct ggcagaagct   10860
aacgactttc ctcccgtcga tgaaaccaaa cgcggtcgct atcagcaaat caatctgcgt   10920
gacgcttacg ttgatcacct gttcggttat atcaatgtca aaaaccttac gccgctcaag   10980
ctggtgatca actccgggaa tggcgcagcg ggtccggtgg tggacgctat cgaagcccgc  11040
tttaaagccc tcggcgcacc ggtggagtta atcaaagtgc ataacacgcc ggacggcaat   11100
ttccccaacg gtattcctaa cccgttgctc ccggaatgtc gcgacgacac ccgcaatgcg   11160
gtcatcaaac acgggcggga tgggcatt gcctttgatg gcgattttga ccgctgtttc    11220
ctgtttgacg aaaaagggca gtttattgag ggctactaca ttgtcggcct gctggcagaa   11280
gcgttcctga aaaaaatcc cggcgcgaag atcatccacg atccacgtct ctcctggaac   11340
accattgatg tggtgaccgc cgcggggcgg acgcggtgta gtcgaaaac aggacacgcc   11400
tttattaaag aacgtatgcg caaggaagac gccatctacg gtggcgaaat gagcgctcac   11460
cattacttcc gcgatttcgc ttactgtgac agcggcatga tcccgtggct gctggtcgcc   11520
gaactggtgt gcctgaaagg aaaaacgctg ggcgaactgg tgcgcgaccg gatggcggcg   11580
tttccggcaa gcggtgagat caacagaaaa ctggcgcacc ctgttgaggc gattaaccgc   11640
gtggaacagc attttagccg tgaggtgctg gcggtggatc gcaccgatgg catcagcatg   11700
```